US011608506B2

(12) United States Patent
Voytas et al.

(10) Patent No.: US 11,608,506 B2
(45) Date of Patent: Mar. 21, 2023

(54) DELIVERY OF DEVELOPMENTAL REGULATORS TO PLANTS FOR THE INDUCTION OF MERISTEMATIC TISSUE WITH GENETIC ALTERATIONS

(71) Applicant: Regents of the University of Minnesota, Minneapolis, MN (US)

(72) Inventors: Daniel F. Voytas, Falcon Heights, MN (US); Ryan A. Nasti, Minneapolis, MN (US); Michael F. Maher, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/255,305

(22) PCT Filed: Jun. 26, 2019

(86) PCT No.: PCT/US2019/039297
§ 371 (c)(1),
(2) Date: Dec. 22, 2020

(87) PCT Pub. No.: WO2020/006112
PCT Pub. Date: Jan. 2, 2020

(65) Prior Publication Data

US 2021/0269813 A1 Sep. 2, 2021

Related U.S. Application Data

(60) Provisional application No. 62/690,165, filed on Jun. 26, 2018.

(51) Int. Cl.
*C12N 15/82* (2006.01)
*A01H 4/00* (2006.01)
*C12Q 1/6895* (2018.01)

(52) U.S. Cl.
CPC ......... *C12N 15/8229* (2013.01); *A01H 4/008* (2013.01); *C12N 15/8213* (2013.01); *C12Q 1/6895* (2013.01); *C12Q 2600/13* (2013.01)

(58) Field of Classification Search
CPC .................................................. C12N 15/8229
See application file for complete search history.

(56) References Cited

U.S. PATENT DOCUMENTS

| | | | |
|---|---|---|---|
| 7,473,822 | B1 | 1/2009 | Paz et al. |
| 8,586,363 | B2 | 11/2013 | Voytas et al. |
| 2011/0145940 | A1 | 6/2011 | Voytas et al. |
| 2014/0157453 | A1 | 6/2014 | Gordon-Kamm et al. |
| 2015/0059010 | A1 | 2/2015 | Cigan et al. |
| 2015/0166980 | A1 | 6/2015 | Liu et al. |
| 2015/0166981 | A1 | 6/2015 | Liu et al. |
| 2015/0167000 | A1 | 6/2015 | Voytas et al. |
| 2016/0237451 | A1 | 8/2016 | Voytas et al. |
| 2017/0121722 | A1 | 5/2017 | Anand et al. |
| 2018/0051267 | A1 | 2/2018 | Voytas et al. |
| 2019/0177740 | A1 | 6/2019 | Gou et al. |
| 2019/0249183 | A1 | 8/2019 | Humanes et al. |
| 2021/0047652 | A1 | 2/2021 | Zhang et al. |
| 2021/0054389 | A1 | 2/2021 | Cho et al. |

FOREIGN PATENT DOCUMENTS

| | | |
|---|---|---|
| WO | WO 2002004649 | 1/2002 |
| WO | WO 2017112006 | 6/2017 |
| WO | WO 2017123772 | 7/2017 |
| WO | WO 2018080389 | 5/2018 |

OTHER PUBLICATIONS

Gallois et al., 2002, Combined SHOOT MERISTEMLESS and WUSCHEL trigger ectopic organogenesis in *Arabidopsis*, Development 129: 3207-3217.*
Mishra and Zhao, 2018, Genome editing technologies and their applications in crop improvement, Plant Biotechnology Reports, 12: 57-68.*
Rodríguez-Leal et al., 2017, Engineering Quantitative Trait Variation for Crop Improvement by Genome Editing, Cell 171: 470-480.*
Li et al., 2016, Generation of Targeted Point Mutations in Rice bya Modified CRISPR/Cas9 System, Molecular Plant 10: 526-529.*
Liu et al., 2018, Phenotypic novelty by CRISPR in plants, Developmental Biology 435: 170-175.*
Gallois, J.L. et al, Development (2002) vol. 129, pp. 3207-3217. (Year: 2002).*
Altpeter et al., "Advancing Crop Transformation in the Era of Genome Editing," Plant Cell, 28(7):1510-1520, Jul. 2016.
Altschul et al., "Gapped BLAST and PSI-BLAST: a new generation of protein database search programs," Nucl. Acids Research, 25(17):3389-3402, Sep. 1997.
Bairu et al., "Somaclonal variation in plants: causes and detection methods," Plant Growth Regulation, 63(2):147-173, Mar. 2011.
Banakar et al., "High-frequency random DNA insertions upon co-delivery of CRISPR-Cas9 ribonucleoprotein and selectable marker plasmid in rice," Sci. Reports, 9:19902, Dec. 2019, 13 pages.
Barton, "Twenty years on: The inner workings of the shoot apical meristem, a developmental dynamo," Dev. Biology, 341(1):95-113, May 2010.
Butler et al., "Crop improvement using genome editing," Plant Breeding Reviews, 41:55-101, Jan. 26, 2018.
Campbell et al., "Functional analysis and development of a CRISPR/Cas9 allelic series for a CPR5 ortholog necessary for proper growth of soybean trichomes," Sci. Reports, 9:14757, Oct. 14, 2019, 11 pages.
Čermák et al., "A Multipurpose Toolkit to Enable Advanced Genome Engineering in Plants," Plant Cell, 29(6):1196-1217, Jun. 2017.

(Continued)

*Primary Examiner* — Russell Kallis
(74) *Attorney, Agent, or Firm* — Fish & Richardson P.C.

(57) ABSTRACT

Materials and methods for inducing genetic alterations in meristematic plant tissue are provided herein.

20 Claims, 50 Drawing Sheets

Specification includes a Sequence Listing.

(56) References Cited

OTHER PUBLICATIONS

Christian et al., "Targeting DNA Double-Strand Breaks with TAL Effector Nucleases," Genetics, 186(2):757-761, Oct. 2010.
Ckurshumova et al., "Irrepressible MONOPTEROS/ARF5 promotes de novo shoot formation," New Phytologist, 204(3):556-566, Nov. 2014.
Cong et al., "Multiplex Genome Engineering Using CRISPR/Cas Systems," Science, 339(6121):819-823, Feb. 15, 2013.
Curtin et al., "CRISPR/Cas9 and TALENs generate heritable mutations for genes involved in small RNA processing of Glycine max and Medicago truncatula," Plant Biotechnol. Journal, 16(6):1125-1137, Jun. 2018.
Curtin et al., "Genome Engineering of Crops with Designer Nucleases," Plant Genome, 5(2):42-50, Jul. 2012.
Curtin et al., "MicroRNA Maturation and MicroRNA Target Gene Expression Regulation Are Severely Disrupted in Soybean dicer-like1 Double Mutants," G3 (Bethesda), 6(2):423-433, Feb. 2016.
Curtin et al., "Targeted Mutagenesis for Functional Analysis of Gene Duplication in Legumes," Methods Mol. Biology, 1069:25-42, Aug. 2013.
Curtin et al., "Targeted Mutagenesis of Duplicated Genes in Soybean with Zinc-Finger Nucleases," Plant Physiology, 156(2):466-473, Jun. 2011.
Curtin et al., "Validating Genome-Wide Association Candidates Controlling Quantitative Variation in Nodulation," Plant Physiology, 173(2):921-931, Feb. 2017.
Demorest et al., "Direct stacking of sequence-specific nuclease-induced mutations to produce high oleic and low linolenic soybean oil," BMC Plant Biology, 6:225, Oct. 13, 2016, 8 pages.
Gallois et al., "Combined SHOOT MERISTEMLESS and WUSCHEL trigger ectopic organogenesis in *Arabidopsis*," Development, 129(13):3207-3217, Jul. 2002.
Gasiunas et al., "Cas9-crRNA ribonucleoprotein complex mediates specific DNA cleavage for adaptive immunity in bacteria," Proc. Natl. Acad. Sci. USA, 109(39):E2579-E2586, Sep. 4, 2012.
Gelvin, "Agrobacterium-Mediated Plant Transformation: the Biology behind the 'Gene-Jockeying' Tool," Microbiol. Mol. Biol. Reviews, 67(1):16-37, Mar. 2003.
Graham et al., "Plant Genome Editing and the Relevance of Off-Target Changes," Plant Physiology, 183(4):1453-1471, Aug. 2020.
Groß-Hardt et al., "Stem cell regulation in the shoot meristem," J. Cell Science, 116(9):1659-1666, May 2003.
Haun et al. , "Improved soybean oil quality by targeted mutagenesis of the fatty acid desaturase 2 gene family," Plant Biotechnology Journal 12(7):934-940, Sep. 2014.
Heidstra et al., "Plant and animal stem cells: similar yet different," Nat. Rev. Mol. Cell Biology, 15(5):301-312, May 2014.
Jacoby et al., "Expanding LAGLIDADG endonuclease scaffold diversity by rapidly surveying evolutionary sequence space," Nucl. Acids Research, 40(11):4954-4964, Feb. 14, 2012.
Jinek et al., "A Programmable Dual-RNA-Guided DNA Endonuclease in Adaptive Bacterial Immunity," Science, 337(6096):816-821, Aug. 17, 2012.
Komor et al., "Programmable editing of a target base in genomic DNA without double-stranded DNA cleavage," Nature, 533(7603):420-424, May 19, 2016.
Kumaran et al., "YABBY Polarity Genes Mediate the Repression of KNOX Homeobox Genes in *Arabidopsis*," Plant Cell, 14(11):2761-2770, Nov. 2002.
Kunkel et al., "Inducible isopentenyl transferase as a high efficiency marker for plant transformation," Nat. Biotechnology, 17(9):916-919, Sep. 1999.
Lee et al., "An Overview of Genetic Transformation of Soybean, A Comprehensive Survey of International Soybean Research," Genetics, Physiology, Agronomy and Nitrogen Relationships, Chapter 23, Jan. 2, 2013, 18 pages.
Liang et al., "Genome editing of bread wheat using biolistic delivery of CRISPR/Cas9 in vitro transcripts or ribonucleoproteins," Nat. Protocols, 13(3):413-430, Mar. 2018.
Liu et al., "Genome Editing in Soybean with CRISPR/Cas9," Methods Mol. Biology, 1917:217-234, Jan. 2019.
Lowe et al., "Morphogenic Regulators Baby boom and Wuschel Improve Monocot Transformation," Plant Cell, 28(9):1998-2015, Sep. 2016.
Makarova et al., "Evolution and classification of the CRISPR-Cas systems," Nat. Rev. Microbiology, 9(6):467-477, Jun. 2011.
Mali et al., "CAS9 transcriptional activators for target specificity screening and paired nickases for cooperative genome engineering," Nat. Biotechnology, 31:833-838, Aug. 2013.
Mali et al., "RNA-Guided Human Genome Engineering via Cas9," Science, 339(6121):823-826, Feb. 15, 2013.
Michno et al., "CRISPR/Cas mutagenesis of soybean and Medicago truncatula using a new web-tool and a modified Cas9 enzyme," GM Crops Food, 6(4):243-252, Mar. 1, 2016.
Mookkan et al., "Selectable marker independent transformation of recalcitrant maize inbred B73 and sorghum P898012 mediated by morphogenic regulators BABY BOOM and WUSCHEL2," Plant Cell Reports, 36(9):1477-1491, Sep. 2017.
PCT International Preliminary Report on Patentability in International Appln. No. PCT/US2019/039297, dated Dec. 29, 2020, 7 pages.
PCT International Search Report and Written Opinion in International Appln. No. PCT/US2019/039297, dated Oct. 9, 2019, 10 pages.
Qin et al., "Disruption of phytoene desaturase gene results in albino and dwarf phenotypes in *Arabidopsis* by impairing chlorophyll, carotenoid, and gibberellin biosynthesis," Cell Research, 17(5):471-482, May 2007.
Sander et al., "Selection-free zinc-finger-nuclease engineering by context-dependent assembly (CoDA)," Nat. Methods, 8(1):67-69, Jan. 2011.
Schmidt et al., "Towards normalization of soybean somatic embryo maturation," Plant Cell Reports, 24(7):383-391, Sep. 2005.
Somers et al., "Recent Advances in Legume Transformation," Plant Physiology, 131(3):892-899, Mar. 2003.
Southern et al., "Luciferases as Reporter Genes," Methods Mol. Biol. *Arabidopsis* Protocols, 323:293-305, 2006.
Stupar et al., "All in the Family: Understanding soybean gene redundancies through genome engineering," Presented at Proceedings of Crops 2015 Conference, Huntsville, AL, May 18-21, 2015, 29 pages.
Stupar et al., "Building a better mutant: Challenges and opportunities for understanding and utilizing gene functions in soybean," Presented at Proceedings of the Université Laval Institute for Integrative and Systems Biology Seminar Series, Quebec City, Canada, Oct. 4-8, 2017, 41 pages.
Stupar et al., "Comparison of genomic structural variation associated with cultivars, mutagenized, and transgenic soybeans," Presented at Proceedings of the Plant and Animal Genome Conference, San Diego, CA, Jan. 10-14, 2015, 22 pages.
Stupar et al., "Identification of Functional Variants in Soybean Using Fast Neutron and CRISPR-Based Mutagenesis," Presented at Proceedings of the Plant and Animal Genome Conference, San Diego, CA, Jan. 13-18, 2017, 27 pages.
Stupar, "All in the Family: Understanding soybean gene redundancies through genome engineering," Presented at Proceedings of the Iowa State University Genome Editing: Foundations and Applications Meeting, Ames, IA, Apr. 9-11, 2015, 39 pages.
Stupar, "Applications of engineered nucleases," Presented at Proceedings of the Soybean Precision Genomics Workshop 2013, Columbia, MO, Jul. 7-10, 2013, 4 pages.
Stupar, "Cloudy with a chance of mutations: Gene editing and functional analyses in soybean," Presented at Proceedings of the 17th Biennial Molecular and Cellular Biology of the Soybean Conference, Athens, GA, Aug. 26-29, 2018, 20 pages.
Stupar, "Cloudy with a chance of mutations: Gene editing and functional analyses in soybean," Presented at Proceedings of the Plant and Animal Genome Conference, San Diego, CA, Jan. 12-16, 2019, 5 pages.

(56) References Cited

OTHER PUBLICATIONS

Stupar, "CRISPR/Cas-9 overview, applications and case studies," Presented at Proceedings of the Soybean Precision Genomics and Mutant Finder Workshops 2016, Columbia, MO, Aug. 3-4, 2016, 28 pages.
Stupar, "Gene Editing for Crop Improvement," Presented at Proceedings of the ASA-CSSA-SSSA 2015 International Annual Meetings Symposium, Minneapolis, MN, Nov. 15-18, 2015, 23 pages.
Stupar, "Inheritance patterns of transgenes and targeted mutations in a soybean CRISPR-based system," Presented at Proceedings of the 16th Biennial Molecular and Cellular Biology of the Soybean Conference, Columbus, OH, Aug. 7-10, 2016, 19 pages.
Stupar, "Old mutations and new biotechnology: expanding and understanding the genetic resources of soybean," Presented at Proceedings of the University of York Genomics Seminar, York, UK, Mar. 22, 2016, 63 pages.
Stupar, "Opportunities and obstacles for candidate gene validation using CRISPR/Cas in soybean," Presented at Proceedings of the ASA-CSSA-SSSA 2016 International Annual Meetings Svmposium, Phoenix, AZ, Nov. 6-9, 2016, 21 pages.
Stupar, "Opportunities and Obstacles for CRISPR in Soybean: Lessons Learned from the Inheritance of Transgenes and Targeted Mutations," Presented at Proceedings of the Banbury Center Genomics-enabled Accelerated Crop Breeding Meeting, Long Island, NY, Oct. 16-19, 2016, 31 pages.
Stupar, "Opportunities and Obstacles for CRISPR in Soybean: Lessons Learned from the Inheritance of Transgenes and Targeted Mutations," Presented at Proceedings of the Donald Danforth Plant Sciences Center 18th Annual Fall Symposium, St. Louis, MO, Sep. 28-30, 2016, 30 pages.
Stupar, "Opportunities and Obstacles for CRISPR in Soybean: Lessons Learned from the Inheritance of Transgenes and Targeted Mutations," Presented at Proceedings of the National Association of Plant Breeders Annual Meeting, Raleigh, NC, Aug. 15-18, 2016, 6 pages.
Stupar, "Overcoming the bottleneck: Understanding and expanding soybean genetic diversity," Presented at the Institute of Crop Science, Chinese Academy of Agricultural Sciences, Beijing, China, Feb. 16-25, 2014, 42 pages.
Stupar, "Soybean breeding with genome-editing technology," Presented at Proceedings of the 2019 Soybean Breeders Workshop, St. Louis, MO, Feb. 11-13, 2019, 6 pages.
Stupar, "Soybean precision genomics," Presented at Proceedings of the Soybean Precision Genomics Workshop 2012, St. Paul, MN, Jul. 18-20, 2012, 23 pages.
Stupar, "The CRISPR x Genome interaction: Challenges and opportunities for understanding gene function in soybean," Presented at Proceedings of Biotechnology Havana 2017, Havana, Cuba, Dec. 3-6, 2017, 29 pages.
Stupar, "USDA-BRAG: Genomic variation associated with different soybean germplasm sources," Presented to the U.S. Department of Agriculture—Animal and Plant Health Inspection Service, Washington, DC, Sep. 2016, 23 pages.
UniProt Accession No. Q03JI6, "CRISPR-associated endonuclease Cas9 2," dated May 23, 2018, 3 pages.
UniProt Accession No. Q99ZW2, "CRISPR-associated endonuclease Cas9/Csn1," dated Jun. 20, 2018, 11 pages.
Veena et al., "Agrobacterium rhizogenes: recent developments and promising applications," In Vitro Cell. Dev. Biol.—Plant, 43(5):383-403, Nov. 2007.
Virdi et al., "Similar Seed Composition Phenotypes Are Observed From CRISPR-Generated In-Frame and Knockout Alleles of a Soybean KASI Ortholog," Front. Plant Science, 11:1005, Jul. 2020, 11 pages.
Voytas, "Genome Editing and Plant Agriculture: Expression of Developmental Regulators for Accelerated Plant Gene Editing," Presentation at the Federation of American Societies for Experimental Biology Science Research Conference—Genome Engineering: Cutting Edge Research and Applications, Florence, Italy, Jun. 24-28, 2017, 26 pages.
Wu et al., "AGROBEST: an efficient Agrobacterium-mediated transient expression method for versatile gene function analyses in *Arabidopsis* seedlings," Plant Methods, 10:19, Jun. 2014, 16 pages.
Zeng et al., "Refined glufosinate selection in Agrobacterium mediated transformation of soybean [*Glycine max* (L.) Merrill]," Plant Cell Reports, 22(7):478-482, Feb. 2004.
U.S. Appl. No. 16/913,478, filed Jun. 26, 2020, Feng Zhang, Published as U.S. 2021/0047652.
Boehm (2014) (Masters Theses, Univ. Tenn.) "Molecular Marker Assisted Backcross Development and Evaluation of an Environmentally Friendly, Commercially Acceptable Low Seed Phytate Soybean."

* cited by examiner

FIG. 3A
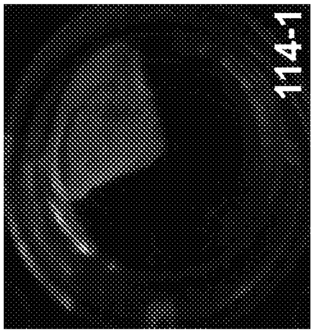
FIG. 3B
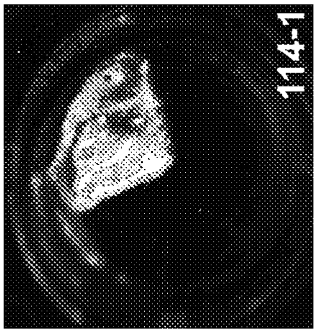
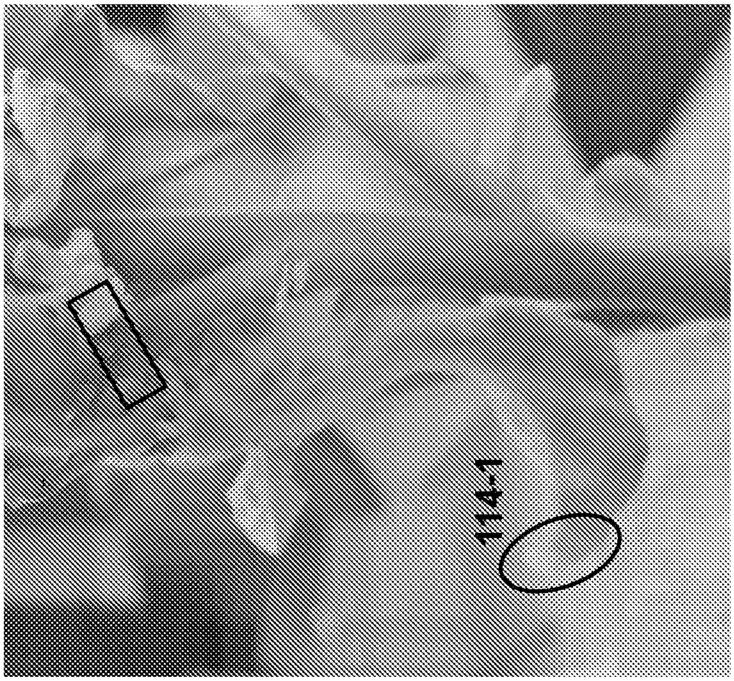
FIG. 3C
FIG. 3D
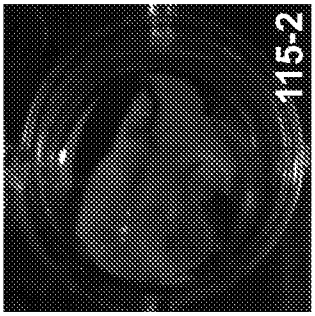
FIG. 3E
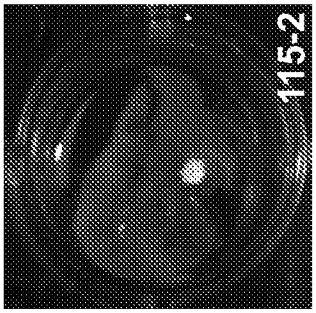
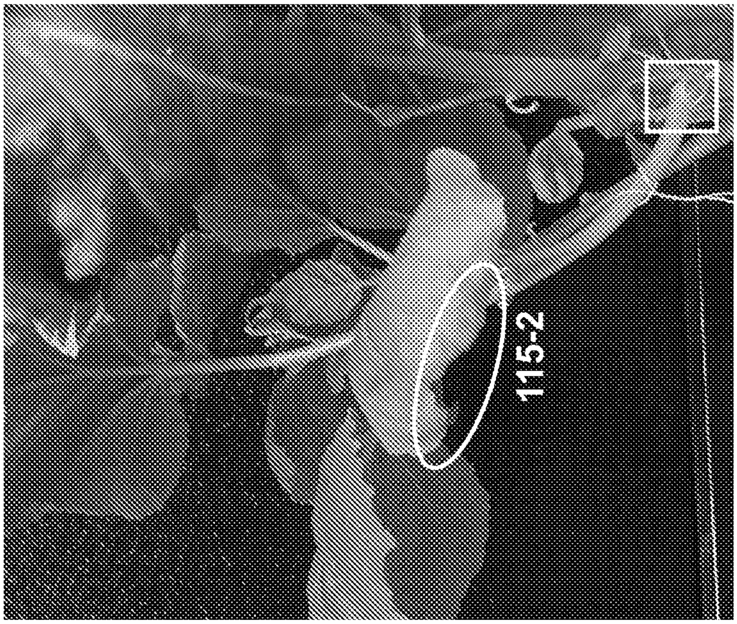
FIG. 3F

Split STM & WUS

GTTTGGTAGTAGCCGACTCCATGGGGCATAAGGTTTAGAAT Reference
GTTTGGTAGTAGCCGACT-CATGGGGCATAAGGTTTAGAAT 93.43% (14997 reads)
TTTTGGTAGTAGCCGACTCCCATGGGGCATAAGGTTTAGAAT 4.60% (739 reads)
GTTTGGTAGTAGCCGACTCC-ATGGGGCATAAGGTTTAGAAT 0.21% (34 reads)

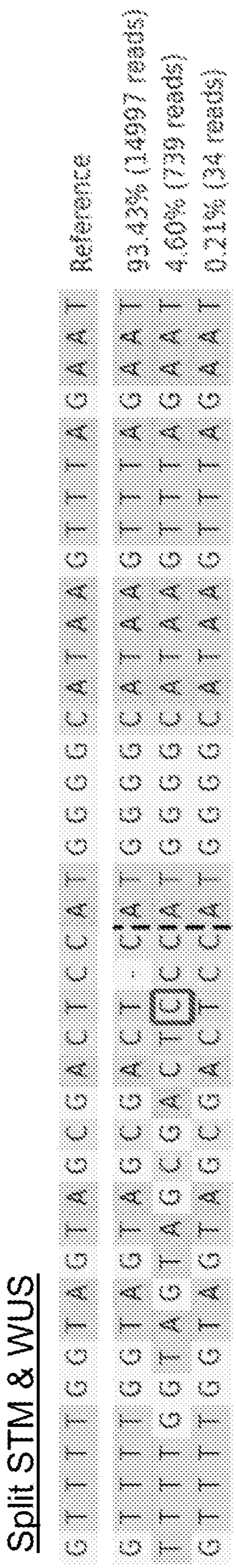

FIG. 4F

WUS & IPT

GTTTGGTAGTAGCCGACTCCATGGGCATAAGGTTTAGAAT Reference
TTTTGGTAGTAGCCGACTCCCATGGGCATAAGGTTTAGAAT 96.92% (2488 reads)
GTTTGGTAGTAGCCGACT-CATGGGCATAAGGTTTAGAAT 1.52% (39 reads)

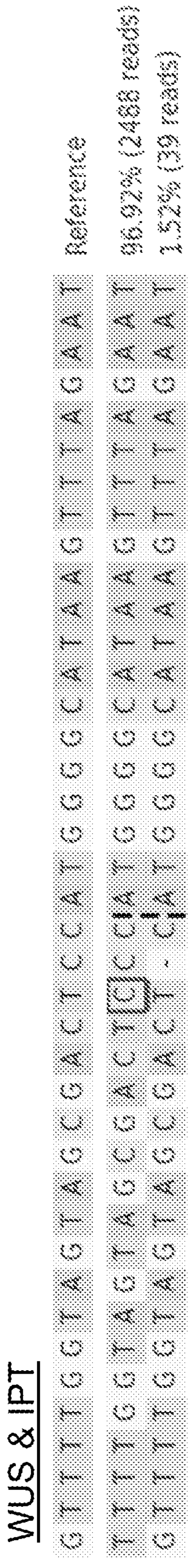

| Construct | Plant designator | Sequences analyzed | Insertions | Deletions | Indel frequency | Observed mutations | Seed produced? |
|---|---|---|---|---|---|---|---|
| WUS/STM | 5-13-3-12 | 1628 | 0 | 821 | 821 (50.4%) | -1bp & WT | No |
| WUS/IPT | 7-19-2-11** | 1089 | 0 | 1072 | 1072 (98.4%) | -10bp & -29bp | No |
| WUS/IPT | 7-19-2-12** | 2431 | 0 | 2399 | 2399 (98.7%) | -10bp & -29bp | No |
| WUS/IPT | 7-19-2-13** | 528 | 0 | 493 | 493 (93.4%) | -10bp & -29bp | No |
| All Combo | 5-14-1-08 | 258 | 0 | 104 | 104 (40.3%) | -3bp & WT | Yes |
| All Combo | 1-1-5 | 1057 | 111 | 892 | 1003 (94.9%) | Chimeric: spectrum of +1bp, -3bp, -1bp or larger | No |

** Shoots derived from the same injection site had the same mutation profile, suggesting they were derived from common, edited progenitor cells.

FIG. 5B

```
                                                                                   (SEQ ID NO:)
WT:          GGAATTTGTTATGTTTTGGTAGTAGCGACTC-CATGGGGCATAAGTTTAGAATTCGTACTCCC     (99)
5-13-3-12:   GGAATTTGTTATGTTTTGGTAGTAGCGACT--CATGGGGCATAAGTTTAGAATTCGTACTCCC    (100)
             GGAATTTGTTATGTTTTGGTAGTAGCGACTC-CATGGGGCATAAGTTTAGAATTCGTACTCCC     (99)

7-19-2-11:   GGAATTTGTTATGTTTTGGTAG-----------ATGGGGCATAAGTTTAGAATTCGTACTCCC    (101)
             GGAATTTGTTATGTTTTGGTAGTAGCG------------------------------ACTCCC    (102)

7-19-2-12:   GGAATTTGTTATGTTTTGGTAG-----------ATGGGGCATAAGTTTAGAATTCGTACTCCC    (101)
             GGAATTTGTTATGTTTTGGTAGTAGCG------------------------------ACTCCC    (102)

7-19-2-13:   GGAATTTGTTATGTTTTGGTAG-----------ATGGGGCATAAGTTTAGAATTCGTACTCCC    (101)
             GGAATTTGTTATGTTTTGGTAGTAGCG------------------------------ACTCCC    (102)

5-14-1-08:   GGAATTTGTTATGTTTTGGTAGTAGCGA----CATGGGGCATAAGTTTAGAATTCGTACTCCC    (103)
             GGAATTTGTTATGTTTTGGTAGTAGCGACTC-CATGGGGCATAAGTTTAGAATTCGTACTCCC     (99)

1-1-5 #1:    GGAATTTGTTATGTTTTGGTAGTAGCGA----CATGGGGCATAAGTTTAGAATTCGTACTCCC    (104)
1-1-5 #2:    GGAATTTGTTATGTTTTGGTAGTAGCGACT--CATGGGGCATAAGTTTAGAATTCGTACTCCC    (100)
1-1-5 #3:    GGAATTTGTTATGTTTTGGTAGTAGCGACTCCCATGGGGCATAAGTTTAGAATTCGTACTCCC    (105)
1-1-5 #4:    GGAATTTGTTATGTTTTGGTAGTAGCGACTC-CATGGGGCATAAGTTTAGAATTCGTACTCCC     (99)
1-1-5 #5:    GGAATTTGTTATGTTTTGGTAGTAGCGA-----ATGGGGCATAAGTTTAGAATTCGTACTCCC    (106)
1-1-5 #6:    GGAATTTGTTATGTTTTGGTAGTAG-------CATGGGGCATAAGTTTAGAATTCGTACTCCC    (107)
1-1-5 #7:    GGAATTTGTTATGTTTTGGTAGTAGCG------------------------------ACTCCC    (108)
1-1-5 #8:    GGAATTTGTTATGTTTTGGT-------------ATGGGGCATAAGTTTAGAATTCGTACTCCC    (109)
1-1-5 #9:    GGAATTTGTTATGTTTTGGTAGT----------ATGGGGCATAAGTTTAGAATTCGTACTCCC    (110)
1-1-5 #10:   GGAATTTGTTATGTTTTGGTAGTAG--------ATGGGGCATAAGTTTAGAATTCGTACTCCC    (111)
1-1-5 #11:   GGAATTTGTTATGTTTTGGTAGTA------------GGGCATAAGTTTAGAATTCGTACTCCC    (112)
1-1-5 #12:   ---------------------------------ATGGGGCATAAGTTTAGAATTCGTACTCCC    (113)
1-1-5 #13:   ---------------------------------------------------------------
```

FIG. 8A

| Sample | Phenotype | PDS1* | PDS2* |
|---|---|---|---|
| Parental white tissue | White | +1 (18%) / -1 (34%)<br>-2 (21%) / -3 (16%) | -48 / +1 / -1 |
| Seedling 1 | White | +1 (42%) / -2 (49%) | -1 (98%) |
| Seedling 2 | White | +1 (43%) / -2 (48%) | -1 (96%) |
| Seedling 3 | White | +1 (39%) / -2 (51%) | +1 (44%) / -1 (46%) |
| Seedling 4 | White | -2 (95%) | +1 (49%) / -1 (37%) |
| Seedling 5 | White | +1 (46%) / -2 (46%) | +1 (99%) |
| Seedling 6 | White | +1 (51%) / -1 (41%) | +1 (42%) / -1 (45%) |
| Seedling 7 | White | No data | +1 (58%) / -1 (35%) |
| Seedling 8 | White | +1 (55%) / -2 (35%) | +1 (36%) / -1 (35%) |
| Seedling 9 | White | +1 (100%) | +1 (49%) / -1 (42%) |
| Seedling 10 | White | +1 (41%) / -2 (48%) | +1 (98%) |

FIG. 10A

| Sample | Phenotype | PDS1* | PDS2* |
|---|---|---|---|
| Parental green tissue | Green | -1bp (100%) | Heterozygous -48/-1 |
| Seedling 1 | Green | -1 (99%) | Heterozygous -48/-1 |
| Seedling 2 | Green | -1 (99%) | Homozygous -48 |
| Seedling 3 | Green | -1 (100%) | Heterozygous -48/-1 |
| Seedling 4 | Green | No data | No data |
| Seedling 5 | Green | -1 (100%) | Heterozygous -48/-1 |
| Seedling 6 | Green | -1 (100%) | Heterozygous -48/-1 |
| Seedling 7 | Green | -1 (100%) | Heterozygous -48 |
| Seedling 8 | Green | -1 (98%) | Heterozygous -1/-48 |
| Seedling 9 | Green | -1 (100%) | Homozygous -48 |
| Seedling 10 | Green | -1 (100%) | Heterozygous -48/-1 |
| Seedling 28 | White | -1 (100%) | Homozygous -1 |
| Seedling 29 | White | -1 (100%) | Homozygous -1 |
| Seedling 30 | White | -1 (100%) | Homozygous -1 |
| Seedling 31 | White | -1 (100%) | Homozygous -1 |
| Seedling 32 | White | -1 (100%) | Homozygous -1 |

FIG. 11

| Seedling Number | Phenotype | PDS1* | PDS2* |
|---|---|---|---|
| Parental tissue | WT | -3bp, WT | WT (100%) |
| S1 | WT | WT (100%) | WT (100%) |
| S3 | WT | WT (100%) | WT (100%) |
| S5 | WT | WT (48%), -3bp (46%) | WT (98%) |
| S7 | WT | WT (48%), -3bp (45%) | WT (99%) |
| S9 | WT | WT (100%) | WT (96%) |
| S11 | WT | WT (46%), -3bp (48%) | WT (99%) |
| S13 | WT | -3bp (99.6%) | WT (99%) |
| S15 | WT | WT (43%), -3bp (55%) | WT (97%) |
| S17 | WT | -3bp (99.4%) | WT (100%) |
| S19 | WT | -3bp (99%) | WT (98%) |

pRN119 (Nos-WUS & 35S-STM, BeYDV Replicon), P1 #7

Initial Luciferase Fluorescence pRN114 (Nos-WUS & CmYLCV-STM, BeYDV Replicon), P1 #2

Initial Luciferase Fluorescence pRN119 (Nos-WUS & 35S-STM, BeYDV Replicon), P1 #7

24 Days Post Imaging pRN114 (Nos-WUS & CmYLCV-STM, BeYDV Replicon), P1 #2

24 Days Post Imaging pRN120-1-3

Original Growth pRN119-4-5

Original Growth pRN120-1-3

Regenerated Plantlets pRN119-4-5

Regenerated Plantlets

FIG. 19A

| Developmental regulator combinations | Constructs co-cultured | Starting # seedlings | Total # growths | # shoot-like growths | # white shoot-like growths | Full plants formed | # edited plants | # plants with developmental abnormalities |
|---|---|---|---|---|---|---|---|---|
| BBM | pMM146 | 24 | 0 | 0 | 0 | 0 | 0 | 0 |
| IPT | pMM134 | 24 | 0 | 0 | 0 | 0 | 0 | 0 |
| MPΔ | pMM136 | 24 | 0 | 0 | 0 | 0 | 0 | 0 |
| STM | pMM131 | 24 | 0 | 0 | 0 | 0 | 0 | 0 |
| WUS | pMM135 | 24 | 20 | 4 | 0 | 1 | 1 | 1 |
| All | pMM131, 134, 135, 136, 146 | 30 | 17 | 4 | 0 | 1 | 0 | 1 |
| BBM & IPT | pMM134, 146 | 36 | 0 | 0 | 0 | 0 | 0 | 0 |
| BBM & WUS | pMM135, 146 | 31 | 12 | 4 | 0 | 3 | 0 | 0 |
| IPT & MPΔ | pMM134, 136 | 34 | 0 | 0 | 0 | 0 | 0 | 0 |
| STM & MPΔ | pMM131, 136 | 29 | 0 | 0 | 0 | 0 | 0 | 0 |
| WUS & IPT | pMM134, 135 | 27 | 46 | 23 | 3.5 | 11 | 2 | 0 |
| WUS & STM | pMM131, 135 | 36 | 29 | 17 | 3 | 11 | 2 | 7 |

FIG. 21B

| | | | | (SEQ ID NO:) |
|---|---|---|---|---|
| **PDS1** | WT: | | GGAATTTGTTATGTTTTGGTAGTAGCGACTC\|CATGGGGCA | (114) |
| | F4: | #5- | GGAATTTGTTATGTTTTGGTAGTAGCGACTCC\|CATGGGGCA | (115) |
| | | | GGAATTTGTTATGTTTTGGTAGTAGCGAC\|CATGGGGCA | (116) |
| | F4: | #6- | GGAATTTGTTATGTTTTGGTAGTAGCGACTCC\|CATGGGGCA | (115) |
| | | | GGAATTTGTTATGTTTTGGTAGTAGCGAC\|CATGGGGCA | (116) |
| | F6: | #9- | GGAATTTGTTATGTTTTGGTAGTAGCGACTCC\|CATGGGGCA | (115) |
| | | | GGAATTTGTTATGTTTTGGTAGTAGCGACTCC\|CATGGGGCA | (115) |
| | F6: | #10- | GGAATTTGTTATGTTTTGGTAGTAGCGACTCC\|CATGGGGCA | (115) |
| | | | GGAATTTGTTATGTTTTGGTAGTAGCGAC\|CATGGGGCA | (116) |
| **PDS2** | WT: | | GGAATTTGTTATGTTTTGGTAGTAGCGACTC\|CATGGGGCA | (114) |
| | F4: | #5- | GGAATTTGTTATGTTTTGGTAGTAGCGACTCC\|CATGGGGCA | (115) |
| | | | GGAATTTGTTATGTTTTGGTAGTAGCGACT\|CATGGGGCA | (117) |
| | F4: | #6- | GGAATTTGTTATGTTTTGGTAGTAGCGACT\|CATGGGGCA | (117) |
| | | | GGAATTTGTTATGTTTTGGTAGTAGCGACT\|CATGGGGCA | (117) |
| | F6: | #9- | GGAATTTGTTATGTTTTGGTAGTAGCGACTCC\|CATGGGGCA | (115) |
| | | | GGAATTTGTTATGTTTTGGTAGTAGCGACT\|CATGGGGCA | (117) |
| | F6: | #10- | GGAATTTGTTATGTTTTGGTAGTAGCGACT\|CATGGGGCA | (117) |
| | | | GGAATTTGTTATGTTTTGGTAGTAGCGACT\|CATGGGGCA | (117) |

FIG. 22C

| Developmental Regulators | Total Seedlings | Number w/ Callus-like Growths | Number w/ Shoot-like Growths |
|---|---|---|---|
| Nos:WUS/CmYLCV:STM | 24 | 4 | 0 |
| Nos:WUS/35S:IPT | 41 | 15 | 3 |
| Nos:WUS/35S:STM | 24 | 7 | 0 |

FIG. 22J

| Constructs and DR combinations | Expt. | Starting # of seedlings | # of growths | Avg. growths per plant | # Shoot-like growths | Luc + shoot-like growths |
|---|---|---|---|---|---|---|
| WUS/IPT (MKV57) | 1<br>2 | 6<br>18 | 9<br>44 | 1.5<br>2.444444 | 0<br>3 | 0<br>3 |
| WUS & IPT (MKV58 & MKV59) | 1<br>2 | 6<br>18 | 20<br>46 | 3.333333<br>2.555556 | 4<br>7 | 1<br>3 |
| No DRs (MKV60) | 1<br>2 | 5<br>18 | 8<br>18 | 1.6<br>1 | 0<br>1 | 0<br>0 |

SEQUENCE LISTING

```
<160> NUMBER OF SEQ ID NOS: 122

<210> SEQ ID NO 1
<211> LENGTH: 842
<212> TYPE: DNA
<213> ORGANISM: Cauliflower mosaic virus

<400> SEQUENCE: 1
```

-continued

```
agatttgcct tttcaatttc agaaagaatg ctaacccaca gatggttaga gaggcttacg      60

cagcaggtat catcaagacg atctacccga gcaataatct ccaggaaatc aaataccttc     120

ccaagaaggt taaagatgca gtcaaaagat tcaggactaa ctgcatcaag aacacagaga     180

aagatatatt tctcaagatc agaagtacta ttccagtatg gacgattcaa ggcttgcttc     240

acaaaccaag gcaagtaata gagattggag tctctaaaaa ggtagttccc actgaatcaa     300

aggccatgga gtcaaagatt caaatagagg acctaacaga actcgccgta aagactggcg     360

aacagttcat acagagtctc ttacgactca atgacaagaa gaaaatcttc gtcaacatgg     420

tggagcacga cacacttgtc tactccaaaa atatcaaaga tacagtctca gaagaccaaa     480

gggcaattga gacttttcaa caaagggtaa tatccggaaa cctcctcgga ttccattgcc     540

cagctatctg tcactttatt gtgaagatag tggaaaagga aggtggctcc tacaaatgcc     600

atcattgcga taaaggaaag gccatcgttg aagatgcctc tgccgacagt ggtcccaaag     660

atggaccccc acccacgagg agcatcgtgg aaaaagaaga cgttccaacc acgtcttcaa     720

agcaagtgga ttgatgtgat atctccactg acgtaaggga tgacgcacaa tcccactatc     780

cttcgcaaga cccttcctct atataaggaa gttcatttca tttggagaga acacggggga     840

ct                                                                    842
```

<210> SEQ ID NO 2
<211> LENGTH: 1327
<212> TYPE: DNA
<213> ORGANISM: Arabidopsis thaliana

<400> SEQUENCE: 2

```
gtcgagctgc aggtcaacgg atcaggatat tcttgtttaa gatgttgaac tctatggagg      60

tttgtatgaa ctgatgatct aggaccggat aagttccctt cttcatagcg aacttattca     120

aagaatgttt tgtgtatcat tcttgttaca ttgttattaa tgaaaaaata ttattggtca     180

ttggactgaa cacgagtgtt aaatatggac caggccccaa ataagatcca ttgatatatg     240

aattaaataa caagaataaa tcgagtcacc aaaccacttg cctttttttaa cgagacttgt     300

tcaccaactt gatacaaaag tcattatcct atgcaaatca ataatcatac aaaaatatcc     360

aataacacta aaaaattaaa agaaatggat aatttcacaa tatgttatac gataaagaag     420

ttacttttcc aagaaattca ctgattttat aagcccactt gcattagata aatggcaaaa     480

aaaaacaaaa aggaaaagaa ataaagcacg aagaattcta gaaaatacga aatacgcttc     540

aatgcagtgg gacccacggt tcaattattg ccaattttca gctccaccgt atatttaaaa     600

aataaaacga taatgctaaa aaaatataaa tcgtaacgat cgttaaatct caacggctgg     660

atcttatgac gaccgttaga aattgtggtt gtcgacgagt cagtaataaa cggcgtcaaa     720

gtggttgcag ccggcacaca cgagtcgtgt ttatcaactc aaagcacaaa tacttttcct     780

caacctaaaa ataaggcaat tagccaaaaa caactttgcg tgtaaacaac gctcaataca     840

cgtgtcattt tattattagc tattgcttca ccgccttagc tttctcgtga cctagtcgtc     900

ctcgtctttt cttcttcttc ttctataaaa caatacccaa agagctcttc ttcttcacaa     960

ttcagatttc aatttctcaa aatcttaaaa actttctctc aattctctct accgtgatca    1020

aggtaaattt ctgtgttcct tattctctca aaatcttcga ttttgttttc gttcgatccc    1080

aatttcgtat atgttctttg gtttagattc tgttaatctt agatcgaaca cgattttctg    1140

ggtttgatcg ttagatatca tcttaattct cgattagggt ttcatagata tcatccgatt    1200

tgttcaaata atttgagttt tgtcgaataa ttactcttcg atttgtgatt tctatctaga    1260
```

```
tctggtgtta gtttctagtt tgtgcgatcg aatttgtcga ttaatctgag tttttctgat   1320

taacagg                                                             1327


<210> SEQ ID NO 3
<211> LENGTH: 465
<212> TYPE: DNA
<213> ORGANISM: Cestrum yellow leaf curling virus

<400> SEQUENCE: 3

tggcagacat actgtcccac aaatgaagat ggaatctgta aaagaaaacg cgtgaaataa     60

tgcgtctgac aaaggttagg tcggctgcct ttaatcaata ccaaagtggt ccctaccacg    120

atggaaaaac tgtgcagtcg gtttggcttt ttctgacgaa caaataagat tcgtggccga    180

caggtggggg tccaccatgt gaaggcatct tcagactcca ataatggagc aatgacgtaa    240

gggcttacga aataagtaag ggtagtttgg gaaatgtcca ctcacccgtc agtctataaa    300

tacttagccc ctccctcatt gttaagggag caaaatctca gagagatagt cctagagaga    360

gaaagagagc aagtagccta gaagtagtca aggcggcgaa gtattcaggc acgtggccag    420

gaagaagaaa agccaagacg acgaaaacag gtaagagcta agctt                    465


<210> SEQ ID NO 4
<211> LENGTH: 445
<212> TYPE: DNA
<213> ORGANISM: Arabidopsis thaliana

<400> SEQUENCE: 4

cttcgttgaa caacggaaac tcgacttgcc ttccgcacaa tacatcattt cttcttagct     60

ttttttcttc ttcttcgttc atacagtttt tttttgttta tcagcttaca ttttcttgaa    120

ccgtagcttt cgttttcttc tttttaactt tccattcgga gtttttgtat cttgtttcat    180

agtttgtccc aggattagaa tgattaggca tcgaaccttc aagaatttga ttgaataaaa    240

catcttcatt cttaagatat gaagataatc ttcaaaaggc ccctgggaat ctgaaagaag    300

agaagcaggc ccatttatat gggaaagaac aatagtattt cttatatagg cccatttaag    360

ttgaaaacaa tcttcaaaag tcccacatcg cttagataag aaaacgaagc tgagtttata    420

tacagctaga gtcgaagtag tgatt                                          445


<210> SEQ ID NO 5
<211> LENGTH: 304
<212> TYPE: DNA
<213> ORGANISM: Agrobacterium tumefaciens

<400> SEQUENCE: 5

gatcatgagc ggagaattaa gggagtcacg ttatgacccc cgccgatgac gcgggacaag     60

ccgttttacg tttggaactg acagaaccgc aacgttgaag gagccactca gccgcgggtt    120

tctggagttt aatgagctaa gcacatacgt cagaaaccat tattgcgcgt tcaaaagtcg    180

cctaaggtca ctatcagcta gcaaatattt cttgtcaaaa atgctccact gacgttccat    240

aaattcccct cggtatccaa ttagagtctc atattcactc tcaatccaaa taatctgcac    300

cgta                                                                 304


<210> SEQ ID NO 6
<211> LENGTH: 909
<212> TYPE: DNA
<213> ORGANISM: Zea maize
```

-continued

<400> SEQUENCE: 6
atggcggcca atgcgggcgg cggtggagcg ggaggaggca gcggcagcgg cagcgtggct 60
gcgccggcgg tgtgccgccc cagcggctcg cggtggacgc cgacgccgga gcagatcagg 120
atgctgaagg agctgtacta cggctgcggc atccggtcgc ccagctcgga gcagatccag 180
cgcatcaccg ccatgctgcg gcagcacggc aagatcgagg gcaagaacgt cttctactgg 240
ttccagaacc acaaggcccg cgagcgccag aagcgccgcc tcaccagcct cgacgtgaac 300
gtgcccgccg ccggcgcggc cgacgccacc accagccaac tcggcgtcct ctcgctgtcg 360
tcgccgccgc cttcaggcgc ggcgcctccc tcgcccaccc tcggcttcta cgccgccggc 420
aatggcggcg gatcggctgt gctgctggac acgagttccg actggggcag cagcggcgct 480
gcgatggcca ccgagacatg cttcctccag gactacatgg gcgtgacgga cacgggcagc 540
tcgtcgcagt ggccacgctt ctcgtcgtcg gacacgataa tggcggcggc cgcggcgcgg 600
gcggcgacga cgcgggcgcc cgagactctc cctctcttcc cgacctgcgg cgacgacggc 660
ggcagcggta gcagcagcta cttgccgttc tggggtgccg cgtccacaac tgccggcgcc 720
acttcttccg ttgcgatcca gcagcaacac cagctgcagg agcagtacag cttttacagc 780
aacagcaaca gcacccagct ggccggcacc ggcaaccaag acgtatcggc aacagcagca 840
gcagccgccg ccctggagct gagcctcagc tcatggtgct cccccttaccc tgctgcaggg 900
agtatgtga 909

<210> SEQ ID NO 7
<211> LENGTH: 1149
<212> TYPE: DNA
<213> ORGANISM: Arabidopsis thaliana

<400> SEQUENCE: 7
atggagagtg gttccaacag cacttcttgt ccaatggctt ttgccgggga taatagtgat 60
ggtccgatgt gtcctatgat gatgatgatg ccgcccatca tgacatcaca tcaacatcat 120
ggtcatgatc atcaacatca acaacaagaa catgatggtt atgcatatca gtcacaccac 180
caacaaagta gttccctttt tcttcaatca ctagctcctc cccaaggaac taagaacaaa 240
gttgcttctt cttcttctcc ttcctcttgt gctcctgcct attctctaat ggagatccat 300
cataacgaaa tcgttgcagg aggaatcaac ccttgctcct cttcctcttc ttcagcctct 360
gtcaaggcca agatcatggc tcatcctcac taccaccgcc tcttggccgc ttatgtcaat 420
tgtcagaagg ttggagcacc accggaggtt gtggcgaggc tagaggaggc atgctcgtct 480
gccgcagccg ctgccgcatc tatgggacca acaggatgtc taggtgaaga tccagggctt 540
gatcaattca tggaagctta ctgtgaaatg ctcgttaagt atgagcaaga gctctccaaa 600
cctttcaagg aagctatggt cttccttcaa cgtgtcgagt gtcaattcaa atccctctct 660
ctatcctcac cttcctcttt ctccggttat ggagagacag caattgatag gaacaataat 720
gggtcatccg aggaagaagt cgatatgaac aatgaatttg tagatccaca agctgaggat 780
agagagctta aaggacagct cttgcgcaag tacagtggtt acttagggag cctcaagcaa 840
gagttcatga agaagaggaa gaaaggaaag ctccctaaag aagctcgtca acaactgctt 900
gattggtgga gccgtcacta caaatggcct tacccttcgg agcaacaaaa gctcgccctt 960
gcggaatcaa cggggctgga ccagaaacag ataaacaatt ggttcataaa ccagaggaaa 1020
cggcattgga agccgtcgga ggacatgcag tttgtagtaa tggacgcaac acatcctcac 1080
cattacttca tggataatgt cttgggcaat cctttcccaa tggatcacat ctcctccacc 1140
atgctttga 1149

<210> SEQ ID NO 8
<211> LENGTH: 1245
<212> TYPE: DNA
<213> ORGANISM: Arabidopsis thaliana

<400> SEQUENCE: 8
atgatggctt cattgtcttg tgttgaagac aagatgaaaa caagttgttt ggttaatggt 60
ggaggaacta taacaacaac aacatctcaa tctaccttgc ttgaagagat gaagctgttg 120
aaagaccagt caggtacaag aaagccggta ataaactcgg agctatggca cgcttgtgca 180 ggcccctttgg tgtgtctccc tcaagttggg agcttagtgt attacttctc acaaggtcat 240
agcgagcagg ttgctgtttc aaccagaaga tcagcaacaa cacaagttcc taattatccg 300
aaccttccat ctcagttgat gtgtcaagtc cataatgtta ctcttcatgc tgacaaagac 360
agtgacgaaa tctatgctca gatgagtctt caacctgttc actctgagag agatgtgttc 420
cctgtaccag actttggaat gctgagagga agtaagcacc cgactgagtt tttctgcaaa 480
acacttactg caagtgacac aagcacacat ggaggtttct cagtgccacg tagagctgca 540
gagaagctat ttccaccatt ggactactca gcacagccgc caacgcaaga gcttgtagtt 600
cgagatcttc atgagaatac ttggacattt cgccatatct accgagggca accaaagaga 660
catctcctaa ctacaggatg gagtttgttc gttggatcga agagattgag agctggggat 720
tctgttttgt tcatcaggga tgagaagtca caacttatgg tcggtgttag gcgtgccaat 780
cgccaacaaa cagcacttcc ttcatcagtt ctctcagcgg atagtatgca catcggtgtt 840
cttgctgctg ctgctcacgc aaccgccaac cgtactcctt ttttgatatt ctataatcca 900
agagcttgtc cagcagagtt cgtgatccct ctagctaagt accgtaaggc gatatgcggg 960
tctcagctct cagttggtat gagatttgga atgatgtttg aaactgaaga ttccgggaaa 1020
cgaaggtaca tgggaactat tgttggaatc agcgatttgg atccgttgag atggcctggt 1080
tctaagtggc gtaaccttca ggtagaatgg gatgagcctg gatgtaatga taaacctact 1140
cgggtcagtc catgggatat cgaaacacct gaaagtctct tcatttttcc ttctctgacc 1200
tcaggactca aacgtcagct ccatccatct tactttgctg gtgaa 1245

<210> SEQ ID NO 9
<211> LENGTH: 2133
<212> TYPE: DNA
<213> ORGANISM: Zea maize

<400> SEQUENCE: 9
atggccactg tgaacaactg gctcgctttc tccctctccc cgcaggagct gccgccctcc 60
cagacgacgg actccacact catctcggcc gccaccgccg accatgtctc cggcgatgtc 120
tgcttcaaca tcccccaaga ttggagcatg aggggatcag agctttcggc gctcgtcgcg 180
gagccgaagc tggaggactt cctcggcggc atctccttct ccgagcagca tcacaaggcc 240
aactgcaaca tgatacccag cactagcagc acagtttgct acgccagctc aggtgctagc 300
accggctacc atcaccagct gtaccaccag cccaccagct cagcgctcca cttcgcggac 360
tccgtaatgg tggcctcctc ggccggtgtc cacgacggcg gtgccatgct cagcgcggcc 420
gccgctaacg gtgtcgctgg cgctgccagt gccaacggcg gcggcatcgg gctgtccatg 480
attaagaact ggctgcggag ccaaccggcg cccatgcagc cgagggtggc ggcggctgag 540

-continued

```
ggcgcgcagg ggctctcttt gtccatgaac atggcgggga cgacccaagg cgctgctggc    600

atgccacttc tcgctggaga gcgcgcacgg gcgcccgaga gtgtatccac gtcagcacag    660

ggtggagccg tcgtcgtcac ggcgccgaag gaggatagcg gtggcagcgg tgttgccggc    720

gctctagtag ccgtgagcac ggacacgggt ggcagcggcg gcgcgtcggc tgacaacacg    780

gcaaggaaga cggtggacac gttcgggcag cgcacgtcga tttaccgtgg cgtgacaagg    840

catagatgga ctgggagata tgaggcacat ctttgggata acagttgcag aagggaaggg    900

caaactcgta agggtcgtca agtctattta ggtggctatg ataaagagga gaaagctgct    960

agggcttatg atcttgctgc tctgaagtac tggggtgcca caacaacaac aaattttcca   1020

gtgagtaact acgaaaagga gctggaggac atgaagcaca tgacaaggca ggagtttgta   1080

gcgcctctga gaaggaagtc cagtggtttc tccagaggtg catccattta caggggagtg   1140

actaggcatc accaacatgg aagatggcaa gcacggattg gacgagttgc agggaacaag   1200

gatctttact tgggcacctt cagcacccag gaggaggcag cggaggcgta cgacatcgcg   1260

gcgatcaagt tccgcggcct caacgccgtc accaacttcg acatgagccg ctacgacgtg   1320

aagtccatcc tggacagcag cgccctcccc atcggcagcg ccgccaagcg cctcaaggag   1380

gccgaggccg cagcgtccgc gcagcaccac catgcgggtg tcgtttccta tgacgttggg   1440

aggattgcca gccaactggg agatggcggt gccctcgctg cggcctatgg tgctcactat   1500

cacggtgccg cgtggccaac gattgcattc cagccgggcg cggcgtccac cggactgtac   1560

catccttacg cgcagcagcc tatgcgcggc ggtggatggt gtaaacaaga gcaagatcac   1620

gctgtgatag cagcggcaca ctccttgcag gatcttcatc atttgaatct cggagccgcc   1680

ggggcccacg actttttctc ggcagggcag caggccgccg ccgctgcgat gcacggcctg   1740

ggtagcatcg acagtgcgtc gctggagcac agcaccggct ccaactccgt cgtctacaac   1800

ggcggggtcg gcgacagcaa cggcgccagc gccgtcggcg gcagtggcgg tggctacatg   1860

atgccgatga gcgctgccgg agcaaccact acatcggcaa tggtgagcca cgagcaggtc   1920

catgcacggg cctacgacga agccaagcag gctgctcaga tggggtacga gagctacctg   1980

gtgaacgcgg agaacaatgg tggcggaagg atgtctgcat gggggactgt cgtgtctgca   2040

gccgcggcgg cagcagcaag cagcaacgac aacatggccg ccgacgtggg ccacggcggc   2100

gcgcagctgt tcagtgtctg gaacgacact taa                                2133
```

<210> SEQ ID NO 10
<211> LENGTH: 1007
<212> TYPE: DNA
<213> ORGANISM: Arabidopsis thaliana

<400> SEQUENCE: 10

```
atgaactcga tgaataactg gttaggcttc tctctctctc ctcatgatca aaatcatcac     60

cgtacggatg ttgactcctc caccaccaga accgccgtag atgttgccgg agggtactgt    120

tttgatctgg ccgctccctc cgatgaatct tctgccgttc aaacatcttt tctttctcct    180

ttcggtgtca ccctcgaagc tttcaccaga gacaataata gtcactcccg agattgggac    240

atcaatggtg gtgcatgcaa taacattaac aataacgaac aaaatggacc aaagcttgag    300

aatttcctcg gccgcaccac cacgatttac aataccaacg agaccgttgt agatggaaat    360

ggcgattgtg gaggaggaga cggtggtggt ggcggctcac taggcctttc gatgataaaa    420

acatggctga gtaatcattc ggttgctaat gctaatcatc aagacaatgg taacggtgca    480

cgaggcttgt ccctctctat gaattcatct actagtgata gcaacaacta caacaacaat    540
```

-continued

```
gatgatgtcg tccaagagaa gactattgtt gatgtcgtag aaactacacc gaagaaaact    600

attgagagtt ttggacaaag gacgtctata taccgcggtg ttacaaggca tcggtggaca    660

ggtagatacg aggcacattt atgggacaat agttgcaaaa gagaaggcca gactcgcaaa    720

ggaagacaag tttatctggg aggttatgac aaagaagaaa aagcagctag ggcttacgat    780

ttagccgcac taaagtattg gggaaccacc actactacta acttcccctt gagtgaatat    840

gagaaagagg tagaagagat gaagcacatg acgaggcaag agtatgttgc ctctctgcgc    900

aggaaaagta gtggtttctc tcgtggtgca tcgatttatc gaggagtaac aaggcatcac    960

caacatggaa ggtggcaagc taggatcgga agagtcgccg gtaacaa                 1007
```

<210> SEQ ID NO 11
<211> LENGTH: 723
<212> TYPE: DNA
<213> ORGANISM: Agrobacterium tumefaciens

<400> SEQUENCE: 11

```
atggatctgc gtctaatttt cggtccaact tgcacaggaa agacgtcgac cgcgatacgt     60

cttgcccagc agactggcct tccagtcctt tcgctcgatc gggtccaatg ctgtcctcaa    120

ctgtcaaccg gaagcggacg accaacagtg gaagaactga aaggaacgac ccgtctatac    180

cttgaagatc ggcctctggt gaagggtatc atcgcagcca agcaagctca cgaaaggctg    240

atcggggaag tgtacaatta tgaggcccac ggcgggctta ttcttgaggg aggatctatc    300

tcgttgctca ggtgcatggc gcaaagcagt tattggagta ccgattttcg ttggcatatt    360

attcgccaca agttagcaga cgaggagaca ttcatgaacg cggccaaggc cagagttagg    420

cagatgttgc gccctgctgt aggcccatct attattcaag agttggttca tctttggaat    480

gagcctcggc tgaggcccat actgaaagag atcgacggat atcgatatgc catgttattt    540

gctagccaga accagatcac acccgatatg ctattgcagc ttgacccaga tatggagggt    600

gagttgattc atggaatcgc tcaggagtat ctcatccatg cgcgccggca ggagcaggaa    660

ttccctccag tgagcgtggt cgctttcgaa ggattcgaag gtccaccgtt cggaatgtgc    720

tag                                                                  723
```

<210> SEQ ID NO 12
<211> LENGTH: 20
<212> TYPE: DNA
<213> ORGANISM: artificial
<220> FEATURE:
<223> OTHER INFORMATION: synthetic oligonucleotide

<400> SEQUENCE: 12

```
ttggtagtag cgactccatg                                                 20
```

<210> SEQ ID NO 13
<211> LENGTH: 20
<212> TYPE: DNA
<213> ORGANISM: artificial
<220> FEATURE:
<223> OTHER INFORMATION: synthetic oligonucleotide

<400> SEQUENCE: 13

```
ccattggaga ttgttattgc                                                 20
```

<210> SEQ ID NO 14
<211> LENGTH: 1457
<212> TYPE: DNA

<213> ORGANISM: artificial
<220> FEATURE:
<223> OTHER INFORMATION: synthetic oligonucleotide

<400> SEQUENCE: 14
atggaagacg ccaaaaacat aaagaaaggc ccggcgccat tctatccgct ggaagatgga 60
accgctggag agcaactgca taaggctatg aagagatacg ccctggttcc tggaacaatt 120
gcttttacag atgcacatat cgaggtggac atcacttacg ctgagtactt cgaaatgtcc 180
gttcggtata acgtggcgta agtgaaacta agctttcgaa cgtgacatag tccaccgttc 240
ggttggcaga agctatgaaa cgatatgggc tgaatacaaa tcacagaatc gtcgtatgca 300
gtgaaaactc tcttcaattc tttatgccgg tgttgggcgc gttatttatc ggagttgcag 360
ttgcgcccgc gaacgacatt tataatgaac gtgaattgct caacagtatg ggcatttcgc 420
agcctaccgt ggtgttcgtt tccaaaaagg ggttgcaaaa aattttgaac gtgcaaaaaa 480
agctcccaat catccaaaaa attattatca tggattctaa aacggattac cagggatttc 540
agtcgatgta cacgttcgtc acatctcatc tacctcccgg ttttaatgaa tacgattttg 600
tgccagagtc cttcgatagg gacaagacaa ttgcactgat catgaactcc tctggatcta 660
ctggtctgcc taaaggtgtc gctctgcctc atagaactgc ctgcgtgaga ttctcgcatg 720
ccagagatcc tatttttggc aatcaaatca ttccggatac tgcgatttta agtgttgttc 780
cattccatca cggttttgga atgtttacta cactcggata tttgatatgt ggatttcgag 840
tcgtcttaat gtatagattt gaagaagagc tgtttctgag gagccttcag gattacaaga 900
ttcaaagtgc gctgctggtg ccaaccctat tctccttctt cgccaaaagc actctgattg 960
acaaatacga tttatctaat ttacacgaaa ttgcttctgg tggcgctccc ctctctaagg 1020
aagtcgggga agcggttgcc aagaggttcc atctgccagg tatcaggcaa ggatatgggc 1080
tcactgagac tacatcagct attctgatta cacccgaggg ggatgataaa ccgggcgcgg 1140
tcggtaaagt tgttccattt tttgaagcga aggttgtgga tctggatacc gggaaaacgc 1200
tgggcgttaa tcaaagaggc gaactgtgtg tgagaggtcc tatgattatg tccggttatg 1260
taaacaatcc ggaagcgacc aacgccttga ttgacaagga tggatggcta cattctggag 1320
acatagctta ctgggacgaa gacgaacact tcttcatcgt tgaccgcctg aagtctctga 1380
ttaagtacaa aggctatcag gtggctcccg ctgaattgga atccatcttg ctccaacacc 1440
ccaacatctt cgacgct 1457

<210> SEQ ID NO 15
<211> LENGTH: 720
<212> TYPE: DNA
<213> ORGANISM: artificial
<220> FEATURE:
<223> OTHER INFORMATION: synthetic oligonucleotide

<400> SEQUENCE: 15
atggtgagta aaggagaaga acttttcact ggagttgtcc caattcttgt tgaattagat 60
ggtgatgtta atgggcacaa attttctgtc agtggagagg gtgaaggtga tgcaacatac 120
ggaaaactta cccttaaatt tatttgcact actggaaaac tacctgttcc atggccaacc 180
ctggtcacca ccctgaccta cggcgtgcag tgcttctccc gttaccctga tcatatgaag 240
cggcacgact tcttcaagag cgccatgcct gagggatacg tgcaggagag gaccatcttc 300
ttcaaggacg acgggaacta caagacacgt gctgaagtca agtttgaggg agacaccctc 360
gtcaacagga tcgagcttaa gggaatcgat ttcaaggagg acggaaacat cctcggccac 420
aagttggaat acaactacaa ctcccacaac gtatacatca tggccgacaa gcaaaagaac 480
ggcatcaaag ccaacttcaa gacccgccac aacatcgaag acggcggcgt gcaactcgct 540
gatcattatc aacaaaatac tccaattggc gatggccctg tccttttacc agacaaccat 600
tacctgtcca cacaatctgc cctttcgaaa gatcccaacg aaaagagaga ccacatggtc 660
cttcttgagt ttgtaacagc tgctgggatt acacatggca tggatgaact atacaaataa 720

<210> SEQ ID NO 16
<211> LENGTH: 8895
<212> TYPE: DNA
<213> ORGANISM: Nicotiana benthamiana
<220> FEATURE:
<221> NAME/KEY: misc_feature
<223> OTHER INFORMATION: N=A, C, G, or T
<220> FEATURE:
<221> NAME/KEY: misc_feature
<222> LOCATION: (2763)..(3070)
<223> OTHER INFORMATION: n is a, c, g, or t
<220> FEATURE:
<221> NAME/KEY: misc_feature
<222> LOCATION: (4364)..(4364)
<223> OTHER INFORMATION: n is a, c, g, or t
<220> FEATURE:
<221> NAME/KEY: misc_feature
<222> LOCATION: (5293)..(5293)
<223> OTHER INFORMATION: n is a, c, g, or t
<220> FEATURE:
<221> NAME/KEY: misc_feature
<222> LOCATION: (5675)..(6605)
<223> OTHER INFORMATION: n is a, c, g, or t

<400> SEQUENCE: 16
cctcaatgac ccagtaaccc aagtgggaga tgtgtgcaaa gtggtcaaat cttagaagga 60
atgagcaaag caagaaatta aaaagagaga cagagaggtg ttatccatca aatgtggcta 120
tggtcggaat agccaatggt gggacagtct agccaaacat aaaggccggt ccagtgcgag 180
ttgctgcaaa ttgagttgga gtaaaaaatt aagataccat atttccagct aaatagcaaa 240
caaatgaccc accattaacg gaagtggcca aaccaccaaa ttcaggcatc tccaccaaaa 300
attagttttt tatacacgaa agattcaaca attagtattt ctttaagcct tcctaattct 360
ttgtcagggg tatctttttg tgggtaacag ccaaaccacc acaaattttc agttcccact 420
cttaactctt tttaacttca acacaacaaa ttttttgctt ttccttcttt gtttatcttg 480
tgcataacga tttcctacaa ctttagcata atcttggttt gtaatccaca acgtgaaaca 540
catcacctag gcggtttcat accgaggtaa caaatgattt tggtttcttt ggttacatca 600
gctgaatgct ttacttgaga aaagctttct ccttttcccg tttaggatct tgtttatttg 660
ctttcgtttt tctactcgtt aaaattttaa cttgattttg tgggtgaatt ataactttac 720
tcatagtgcg agaacaagtt tcgtatggac tgtaaaagct agaatctttt ttacttttgc 780
atataaattt gtgtaataaa tgcttaagaa ccagaatatt gaaaaaacaa aggaattcta 840
catagtattt aggttcacaa gtgggacaat cttcttacag tgaaatatct ttatgtcagg 900
cttaatttac tgctattttg ttcagtaaaa tgccccaaat tggacttgtt tctgccgtta 960
atttgagagt ccaaggtaat tcagcttatc tttggagctc gaggtcttct ttgggaactg 1020
aaagtcaaga tggtcgcttg caaaggaatt tgttatgttt tggtagtagc gactccatgg 1080
ggcataagtt tagaattcgt actcccagtg ccatgaccag aagattgaca aaggacttca 1140
atcctttaaa ggtttgtttt gaatgcgaaa gtgtgatgct gaatttatga tcacgagcat 1200
atattctcta aaataagata tcttgccatt caggtagtct gcattgatta tccaagaccg 1260

-continued

```
gagctagaca atacagttaa ctatttggag gcggcgttat catcatcatc atttcgtact   1320
tcctcacgcc caacaaaacc attggagatt gttattgctg gtgcaggtga ttttttccag   1380
tcatctatat ttgtagtctt catttttctt tctttggaag gaagatcatt ctattagttg   1440
tattatcact agaacattta ttgtgcattc ttttcttatt aactgttttg gaccgcaaaa   1500
ttttaagttc ttacttcttc gcctcccaac tgattagatt aggagtgatt tgaaaattag   1560
tttgttttga gctatttttg ccgtcactca tatactgttg agttgtccca catcggtgag   1620
atttgaagtc cttggtctca cctcataagt tagcttttgg ggttgagtta ggcccaatat   1680
ccatttatca tagtacgaga gccaggccca tcccagttat tgttaccaat gtcgggctcc   1740
tatttatgtt gtccacgctc cagtttgcaa gcctaggcgt gggggagggg ggtgttgagt   1800
tgtcccacat ccgtgggatt tgaggtactt ggtctcctta tatggtcttg gacaatccat   1860
aagctagctt ttggggttga gttcggccca atgttcattt atcatatata tatatatata   1920
tatatatgtc tattctctct taccatctga gccatgataa gcgggtgaac gtgctgtcta   1980
ttggatggca tgtccgatgg atcattccga aatattggag gcagatgaac caataccttg   2040
tgcaagattg atatcactat acctataatc agagtactta gagttccaaa aatttgcaga   2100
acccattgaa aagtcaaaca agttacatat aggggttgca ctcttctaag gcttgcaatc   2160
tgtgagaaaa agatgagaag gagatcttca tatttcatct ttattaggct ggaccattga   2220
ccggttagca gttttgaact tgttcttcaa cttggcttgc atagtactgt gccgatcatt   2280
tcttttgtat tgtcatcaac tggttgatta tttgagtacc taaagaaaga atgttatgca   2340
tgatacattg tgctgtacta taaaagatat aataaagaat gctagccgag gtactacatg   2400
gccttttcag acaaatagaa gctgtagcat gattctaatt cgatttgttt tgaaatatca   2460
ggtttgggtg gcttgtctac agcaaaatat ctggcagatg ctggtcacaa accgatattg   2520
ctggaggcaa gagatgtcct aggtggaaag gtgaagaata tccaatcttt cctttaattt   2580
tattcctttt tcttctgtgt ccttgcctat tggtagtccc tgttcaggaa ggcttctgtt   2640
tgttttattt aaaatcattt ttcatactct ttaaacattc agttgctcaa acaattgcaa   2700
gggtgttcac tattcctatt tttgactgtc ttactttctc tcagtttagt tttattcccc   2760
tcnnnnnnnn nnnnnnnnnn nnnnnnnnnn nnnnnnnnnn nnnnnnnnnn nnnnnnnnnn   2820
nnnnnnnnnn nnnnnnnnnn nnnnnnnnnn nnnnnnnnnn nnnnnnnnnn nnnnnnnnnn   2880
nnnnnnnnnn nnnnnnnnnn nnnnnnnnnn nnnnnnnnnn nnnnnnnnnn nnnnnnnnnn   2940
nnnnnnnnnn nnnnnnnnnn nnnnnnnnnn nnnnnnnnnn nnnnnnnnnn nnnnnnnnnn   3000
nnnnnnnnnn nnnnnnnnnn nnnnnnnnnn nnnnnnnnnn nnnnnnnnnn nnnnnnnnnn   3060
nnnnnnnnnn cccccccccct gtctctctct ctctctctgt ttttggagga aatagatctg   3120
tcctaaaaac ttccagcttt actactaata gtgttaattg tcgagaaaat attacagcat   3180
attaggtata tggaaagtat attattattc tctattattt taagattgag tcaattttac   3240
ccgtcctgtt ggttgcattt ctcacataaa cagtcttttc tgtgagatgc tatgttaatt   3300
agctgatgtt tttggtatag agcactatgt tagttttatc tttactgaag cagtcaccaa   3360
gaatctagtt gtataggcta aaagattgaa ttagcattaa tctttatgtg ttttgcacct   3420
gaatacctat acctaccttt taggtagctg catggaaaga tgatgatgga gattggtacg   3480
agactgggtt gcacatattc tgtaagtttg actcctcaag aatgcatact ttaatcttct   3540
aatacaacag tttctttcaa gatctctttt ctctattaat cagatagata tcgctgtttg   3600
```

-continued tgttttgtct tttgcaaata gccaattttt gtcagtcgat ctgtattctg ccttgcctat 3660
ctttttttat ctgttaattt catatggtga ctcatacaag ttggtgcatc ccctttaagt 3720
tggggcttac ccaaatatgc agaacctgtt tggagaacta gggattaacg atcggttgca 3780
gtggaaggaa cattcgatga tatttgcgat gcctaacaag ccgggggagt tcagccgctt 3840 tgatttttcct gaagctcttc ctgcgccatt aaatggttag tacttaatca tgatttctcc 3900
cttctgcatt gattatccaa taaggtatga aattgattag tccattgacc attaatactc 3960
tggcacattg ctaacatcaa aagaacataa aggttcatta tgtcttgatc agaatttctg 4020
catgtagcta aagtgattga gtgtctgtgt atatttttat acattgcaag cataagccag 4080
ttatgttatc tcttattttc atttctctat cgatgcgtta ttacttctac aggaatttta 4140
gccatactaa agaacaacga aatgcttaca tggcccgaaa aaatcaaatt tgctattgga 4200
ctcttgccag caatgcttgg agggcaatct tatgttgaag ctcaagacgg tttaagtgtt 4260
aaggactgga tgagaaagca agtatgtgat cgttttatct tattctttaa agttcataac 4320
cttgaggaca tagttgactt gcatgttgtt gatttaacat gttnatgtga tcgttttatc 4380
ttactcttta aagttcataa ccttgaggac atagttgact tgcatgttgt tgatttaaca 4440
tgttagaatt gtctacctgc ctttcttttt ttaacaacat acatcttaca aatctcagca 4500
gcagctattt gcttaattgc ttttcagggt gtgcctgata gggtgacaga tgaggtgttc 4560
attgccatgt caaaggcact taacttcata aaccctgacg agctttcgat gcagtgcatt 4620
ttgattgctt tgaacagatt tcttcaggtt agaatcctga tccaccctca aaacaaaaag 4680
agagaaaggg atataatccg accaagctgt aaatcatgtt agggacctga catattggtg 4740
caggaaactt atttgtgaac ttttccactc tgtttaactt ttctgatata tttgaattat 4800
taatctgcag gagaaacatg gttcaaaaat ggcctttttta gatggtaatc ctcctgagag 4860
actttgcatg ccaattgttg aacatattga gtcaaaaggt ggccaagtca gactaaactc 4920
acgaataaaa aagattgagc tgaatgagga tggaagtgtc aaatgtttta tactgaataa 4980
tggcagtaca attaaaggag atgcttttgt gtttgccact ccaggtataa tatccattat 5040
actagtatcg atgcttccag ttttcacatt tttaatatga atgtataatt ttttgctgac 5100
ttttcattat ccgattagtg gatatcttca agcttctttt gcctgaagac tggaaagaga 5160
tcccatattt ccaaaagttg gagaagctag tgggagttcc tgtgataaat gtccatatat 5220
ggttagtgat gaaaattttg cttttcagtg tttggtcttc ctctagcata tctatgtatg 5280
tgcatgttaa tgnacttttc agtgtttgtt cttcctctag catatctatg tatgtgcctg 5340
ttaatgtcta tacatacatg tttatgtggt cctccggtat tgtgttaact tcccttgagc 5400
gaggaactta tggatctacg cttttccaaa actttgattg cacacattgc aattgtctgt 5460
tcaactttga tgagcagaac taccattgtt tagctattag tggctgagat tcctgctgaa 5520
aagatttgta taaatttaat tgcaggtttg acagaaaact gaagaacaca tctgataatc 5580
tgctcttcag caggttcatt tttgatcaat tttattgttc cagagcagtt tctgcgtgtc 5640
catgactaca ttctcatatt agctcccccc ccccnnnnnn nnnnnnnnnn nnnnnnnnnn 5700
nnnnnnnnnn nnnnnnnnnn nnnnnnnnnn nnnnnnnnnn nnnnnnnnnn nnnnnnnnnn 5760
nnnnnnnnnn nnnnnnnnnn nnnnnnnnnn nnnnnnnnnn nnnnnnnnnn nnnnnnnnnn 5820
nnnnnnnnnn nnnnnnnnnn nnnnnnnnnn nnnnnnnnnn nnnnnnnnnn nnnnnnnnnn 5880
nnnnnnnnnn nnnnnnnnnn nnnnnnnnnn nnnnnnnnnn nnnnnnnnnn nnnnnnnnnn 5940
nnnnnnnnnn nnnnnnnnnn nnnnnnnnnn nnnnnnnnnn nnnnnnnnnn nnnnnnnnnn 6000

-continued

```
nnnnnnnnnn nnnnnnnnnn nnnnnnnnnn nnnnnnnnnn nnnnnnnnnn nnnnnnnnnn   6060
nnnnnnnnnn nnnnnnnnnn nnnnnnnnnn nnnnnnnnnn nnnnnnnnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnnnnnnnnn nnnnnnnnnn nnnnnnnnnn   6240
nnnnnnnnnn nnnnnnnnnn nnnnnnnnnn nnnnnnnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnacatg ttatgatgac catttctcca aggcatttta tccatgccac gtttcatcag   6660
ctacatgttg actatgttcc cctacttttt aaatggcacc attgttggtg gagaaagatt   6720
atagatgttc ctgatacttg tatgggttcc cttgctcaat ctctctttta cttcatgcag   6780
aagcccattg ctcagtgtgt atgctgacat gtctgttaca tgtaaggtat tgactcgtct   6840
gtaccattca tactggtcta atctgttgga tatgagttgc tggtaaattg cataatgctt   6900
gttggatttg tgtgtgagtt gctgctagat ctgtgtcctg ctatatttat gtatgagttg   6960
ctgctattgt aatcttcatt taggatgctt aatgatatag gttctgtatg tatggaatag   7020
tcaggacaat gctcctgtct gtgcacaggg gctctacagg aagcaacttt cgaaggagaa   7080
gtaaagaaag tgtgatgaac agggaaagta gtttccttta gctaccttaa ttcagtgtta   7140
cctgcaatgt tcagtgtttg gagagaggcg ataagcctac ttcttaattt tgttagaaaa   7200
tgcgtacaaa atataaatca gtagttacta aaaagttgga gaagtagtgg gatcttttcg   7260
ctatttttaa cccagaataa gacagctatg ccatatagct ttgattatcc gttaacgttc   7320
tgtatataaa tagataattc ataataatgt cgtaatacta aagcctggag atcagactgc   7380
tttaactatc ctgagatgat tacttttact cttggattag cttaggcgag ccacaagact   7440
acattgaatc tttagaaatg agaacataaa aagggtgcag aagtggggaa gtggctgaac   7500
gatatgcata tgggagtgag tggggagtaa aattatttcc tttacttggg tacaatcaag   7560
aatgaatgac aacttagccc actatatccg ttcatgtgtt ctttagggcc ctctgatata   7620
attggtctct ctgcaggaat attacaaccc caatcagtct atgttggaat tggtatttgc   7680
acctgcagaa gagtggataa atcgtagtga ctcagaaatt attgatgcta caatgaagga   7740
actagcaaag cttttccctg acgaaatttc ggcagatcag agcaaagcaa aaatattgaa   7800
gtatcatgtt gtcaaaactc caaggccagt aatcatttgc tttcatactt gtgcaatata   7860
cgagaactgc agtccacgtg gaatctattc ctattctgaa tcctgattaa tctgcttttt   7920
ttctctcagg tctgtttata aaactgtgcc aggttgtgaa ccctgtcggc ccttgcaaag   7980
atctcctatt gaggggtttt atttagctgg cgactacaca aaacagaaat acttggcttc   8040
aatggaaggt gctgtcttat caggaaagct ttgtgcccaa gctattgtac aggttagttc   8100
tcacagttgt ttttgtccac taatagtata tttgatcaaa ttttgtcatc tttgctgcgg   8160
tagagaattt ttgaagcatg gacgtcaagc atgcctctta cttataattg ctaatttgcg   8220
gaatagttct ccaaccaata tagtgttaaa ccaaaaaaat aaaattgtgc acacagatca   8280
cagagttgct caggatatct gcatttttgg agcctcagta gtagcatgat aaaatgcaga   8340
```

```
aggttatgtt tttttcattc tttattaaat ttatatctct atattttgca ggattacgag   8400

ttacttcttg gccggagcca gaagaagttg gcagaagcaa gcgtagttta gcatggtgaa   8460

ctaaaatgtt gcttctctac actaaattta agatgaaggt ggccacactg aattagcgtt   8520

gtagacaaca catacaagga cagtacaaca tttaacccaa atacgagaaa tgttacacaa   8580

atatgtgctc tgctttccct ccgatttagt tcgcaagtta ctaattataa gatggaattg   8640

aatgaaacca aagacggata aagaccctaa actataagat aagtaagcct ctccagacca   8700

tacaagtgcg cgtcgagccc atgcgaaggg tttggttaag atatgccaga ttccaccaag   8760

tatacaaatg aaacctaacc atacatgtcc tccgattata taatgcaaat tgattcattc   8820

aaactaaact tttaagcgtc acagttatac tagcaaatac ctttaagaca ttaagcttca   8880

cgtcttaaaa catca                                                    8895


<210> SEQ ID NO 17
<211> LENGTH: 7951
<212> TYPE: DNA
<213> ORGANISM: Nicotiana benthamiana
<220> FEATURE:
<221> NAME/KEY: misc_feature
<223> OTHER INFORMATION: N=A, C, G, or T
<220> FEATURE:
<221> NAME/KEY: misc_feature
<222> LOCATION: (5069)..(5130)
<223> OTHER INFORMATION: n is a, c, g, or t
<220> FEATURE:
<221> NAME/KEY: misc_feature
<222> LOCATION: (6277)..(6653)
<223> OTHER INFORMATION: n is a, c, g, or t

<400> SEQUENCE: 17

gaatgagcaa agcaagaaat taaaaagaga gagaggtgct ttatccatca aatgtggcta     60

tggtaggaag agccaatggt gggacatttt tggagtgtag ccaaaaacata aaggaaggtc   120

cagtgcgagt tactgcaaat tgagttggga gtgaggatta aagaagatag taacatattt    180

ctagctaaat agcaaacaaa tgatccgtta acagaagtgg ccaaaccacc aaattcaggc    240

atctccacca aatattagtt ttttatacac aaaagattca acacaaacag ttaagtactt    300

ctttaatcgt tcctaattct ttgttcaggg gtatcttttt gtgggtaacg gccaaaccac    360

cacaaatttt cagttcccac tcttaactct ttcaacttca acacaacaaa ttagtatttg    420

cttttccttc tttgcttatc tagtgcataa cgattttcta caactttagc atagtccaca    480

acgtgaaaca caactccttg gcggtttata ccgaggtaag aaatgatttt ggtttctttg    540

gttacatcag ctgaatgctt tgcttgagaa aagctctctt tttcccgttt aggatcttgt    600

ttatttgctt tcgtttttct actcgtttga attttaactt gattttgtgg gtgaaggcta    660

atttttctca tagtgtaaga acaagtttca tatgtactgt aaaagctaga atcttttttta   720

cttttgcata taaatttgtg taataaatgc ttaagaacca gaatatttga aaaagataag    780

gaattttgca tagtatttag gttcacaagt gggacaatct tcttacactg aaatatcttt    840

atgtcaggct taatttactg ctatcttgtt caataaaatg ccccaaattg gacttgtttc    900

tgccgttaat ttgagagtcc aaggtaattc agcttatctt tggagctcga ggtcttcgtt    960

gggaactgaa agtcaagatg tttgcttgca aaggaatttg ttatgttttg gtagtagcga   1020

ctccatgggg cataagttaa ggattcgtac tccaagtgcc acgacccgaa gattgacaaa   1080

ggactttaat cctttaaagg tttgttttga atgcgaaagt gtgatgctgg atttatgatc   1140

gtgggcatat atcctctaaa ataagagatg tatatcttgc cattcaggta gtctgcattg   1200
```

-continued

```
attatccaag accagagcta gacaatacag ttaactattt ggaggcggcg ttattatcat   1260
catcgtttcg tacttcctca cgcccaacta aaccattgga gattgttatt gctggtgcag   1320
gtgatttttt ccagccatct atatttgtag ttttcatttt tctttctttg gaaggaagat   1380
cattctatta gttatattat cactagaata tttacctgta cattcttttc tgattaactg   1440
ttttggaccg caaaatttta ggttcttact tcttcgccat tttgcaacta atcagcaatt   1500
wrdaggagcg gtttgaaaac tagtttgttt tgaactattt ttgccgtcac tctatttata   1560
tactgttgaa ttgtcccaaa tcggtggaat ttgaggtcct tggtctcatc tcataagcta   1620
gcttttgggg ttgagttacc acatcggtgg gatttgaggt ccttcgtctc cttatatgtt   1680
cttggacaag cttcacctca taagctagct tttggggtta gagttaggcc caaggtccat   1740
ttatcatatg cttgtctatt ctctcttatc atctgagcca tgataagcgg gtgaacgtgc   1800
tgtctattgg gtggcatgtc caaaggatca ttctgaaata ttggaggcaa atgaaccaat   1860
accttgtgca agattgatct cactatacct ataatcagag tactgagttc caaaaatttc   1920
aaaacccatt gaaaagtcaa acgagttaca tataggggtt gcactcttct acggcttgca   1980
atatgtgaga aaaagatgag aagtcgatct tcatatttca tctttactag gctggaccat   2040
tgactggtta gcagttttga acttgttctt caacttggct tgcatggtac tgtgccgatc   2100
atttcttttg tattgtcatc agctggttga ttatctgagt acctaaagaa agaatgttat   2160
atgcatgata tattctactg tactataaaa gatataataa agaatgctag ccgaggtact   2220
gcatggcctt ttcagataaa tagaagctgt agcatgattc taattcaatt tttttgggaa   2280
tatcaggttt gggtggtttg tctacagcaa aatatctggc agatgctggt cacaaaccga   2340
tattgctgga ggcaagagat gtcctaggtg ggaaggtgaa gaatatccaa tctttccttt   2400
aattttattc ctttttcttt tgtgtccttc cctattgata gtccctttc aggaaggctt    2460
ctgtttgttt tatttgaaat catttttcat actctttaag cattcagttg ctcaaacaat   2520
tgcaaggata ttcactattc ctaattttga ccgtcttctt ttctctcagt ttagttttat   2580
tcccctctct ttttgaagga aatagatctg tcctaaaaat ttccagcttt actactaata   2640
gtgttaattg tcgataaaat agtacatcat attaggtaaa agatatggac tgtatattat   2700
tatcattctc tattatttta aactgagtca attttaaccg tcctgttggg tgcatttctc   2760
atataaacag tcttttctgt gagatgctat gtgaattagc tgattgtttt ggtatagagc   2820
actatgttag tcagttttat cttactgaag cagtcaccaa gagtctagtt gtataggcta   2880
gaagattgaa ttagcattaa tctttatgtg ttctgcacct gaatacttgt acctcccttt   2940
taggtagctg catggaaaga tgatgatgga gattggtacg agactgggtt gcacatattc   3000
tgtaagtttg actcctcaag aatgctactt taatcttcta atacagtcat agcaatttct   3060
ttcaagatct cttttattaa tcagatagct atccctgttt gtcttttgtc ttttgcaaat   3120
agccaatttt tgtcagtcga tctgtattct gccttgcctc tctttattta tctgctaact   3180
cgtatggtga ctcatacaag ttggtgcatc tcctttaagt tggggcttac ccaaatatgc   3240
agaacctgtt tggagaacta gggattgatg atcggttgca gtggaaggaa cattcaatga   3300
tatttgcgat gcctaacaag ccaggggagt tcagccgctt tgattttcct gaagctcttc   3360
ctgcgccatt aaatggtaag tacttaatca tgagtaaatt tctcccttca gcgttgatta   3420
tgcaaacttc cccaataagg tatgaaattg attagtctta ataccctggc acattgctaa   3480
catcaaaaga acataaaggt tcattacgtc ttgatcagaa tttctgcatg tagctaaagt   3540
gaatgagtgt ctgtatagat ttttacacat tgcaagcata agcctgttat gttatctctt   3600
```

-continued

```
tttttcattt ctctacctgt atctcttatt ctcatttctc tatctatgcg ttattacttc   3660
tacaggaatt ttggccatac taaagaacaa cgaaatgctt acgtggcccg agaaagtcaa   3720
atttgctatt ggactcttgc cagcaatgct tggagggcaa tcttatgttg aagctcaaga   3780
cggtttaagt gttaaggact ggatgagaaa gcaagtgcgt gatcgtttta tcttattctt   3840
taaagttcat aaccttgagg acatagttga cttgcatatt gttgatttaa catgttcgaa   3900
ttgtctacct gcctttcttt ttctaacaac atagatctta caatctcagc agcagctatt   3960
tgcttaatgc ttttcagggt gtgcctgata gggtgacaga tgaggtgttc attgccatgt   4020
caaaggcact taacttcata aaccctgacg agctttcgat gcagtgcatt ttgattgctt   4080
tgaacagatt tcttcaggtt agaatcctga tccaccctca aaacaaaaag agagaaaggg   4140
atataatcct accaaagctg taaatcatgt tagggacctg acatatcggt gcaggaaact   4200
tatgagtgaa cttgtccact ctgtttaact tttctgatat atttgaatta ttaatctgca   4260
ggagaaacat ggttcaaaaa tggccttttt agatggtaac cctcctgaga gactttgcat   4320
gccgattgtg gaacatattg agtcaaaagg tggccaagtc agactaaact cacgaataaa   4380
aaagatcgag ctgaatgagg atggaagtgt caaatgtttt atactgaata atggcagtac   4440
aattaaagga gatgcttttg tgtttgccac tccaggtata atatccatta tactagtatg   4500
acgcttccag ttttcacatt ttaatatgaa tttatagttt tttgctgact tttgattatc   4560
caattagtgg atatcttgaa gcttcttttg cctgaagact ggaaagagat cccatatttc   4620
caaaagttgg agaagctagt gggagttcct gtgataaatg tccatatatg gttagtgatg   4680
aaaattttgc ttttcagtgt ttggtcttcc tctagcatat ctatgtatgt gcatgttaat   4740
gtctatacgt acatgtttat gtggtcctcc cgtattgtgt ttacttccct tgaatgagga   4800
acttatggat gtacgctttt ccaactttga ttgtacacat tgcaattgtc tgttcaactt   4860
tgaggagcag aacttccatt gtttagctat tagtggctga gattcctgct gaaaagattt   4920
gtataaattt aatttgcagg tttgacagaa aactgaagaa cacatctgat aatctgctct   4980
tcagcaggtt catttttgat caattttatt gttccagacc agtttctgcg tgtccatgac   5040
tacattctca tattagctcc ccccccccnn nnnnnnnnnn nnnnnnnnnn nnnnnnnnnn   5100
nnnnnnnnnn nnnnnnnnnn nnnnnnnnnn cccccccccc ccggtctctt ttttgccatt   5160
taaatgagac cttacaattt gtttagtact ctaccatagt tttttaatca ataagccaaa   5220
ggggaaaaac taataaaagt gtataaaatt tcttcctgta ttagtccaat tctttcgcaa   5280
cttatattgt taattattat ttatcttttg gattgaaatg gattttgtat atctaataat   5340
ataaacaaat atatctcttc ctcttataag atttttcacc atagaaaaat gctcccataa   5400
ggtcagtcat tctggctaaa tatcccacac ttcaaccatt gagatatttt gttctttgca   5460
tccaggaata catttggcat caatagatag gaatcaatga agatatatta tcaatttcct   5520
gcaagtttct tggcactaga aacattagat ccatatcatg taaattgcct ttgttaaatt   5580
gaaggtctat gaaatttggg ttggtttgaa aaccttttgt ttttcccccc cacatcccta   5640
atcgtttatt tagtcaaggt cagacctgac atgttatgat gaccatttct ccaaggcatt   5700
tataatggac tggagtatcc atgccacatt tcatcagcta catgtcgatt atgttcccct   5760
acttttaaat ggcaccattg ttggtggagc aagattatag attttcctga tacttgtatg   5820
ggttcccttg ctcaatctct cttttacttc atgcagaagc ccgttgctca gtgtgtacgc   5880
tgacatgtct gttacatgta aggtattgac tcgtctgtac cattatactg gtctaatctg   5940
```

-continued

```
ttgggtatga gttgctggta aattgcataa tgcttgttgg atttgtgtgt gagttgctgc   6000
tagatctatg tcctgctata tttatgtatg agttgctgtt gttgcaatct tcatttcgaa   6060
tgcataatga tataggttct gtatgtacgg aatagtcagg acaatgctcc tgtctgtgca   6120
cgggggctct acaggaagca actttcggag gagaagtaca gaaagtgtga tgaatcttaa   6180
ggcggttaaa gtagtttctt ttagctaaat tttgaaataa tttgaaggag gggaaaacgc   6240
tctctcagtc tgtggttgca ttggttgtgg ggggggnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnntggaggg   6660
accttaattc agtgttacct gcatataaat cagactaaag cctggagatc agacgttctg   6720
catataaata gataattaat aatgatctcg taatactcta aagcctggag atcagactgt   6780
tttaactatc ctgagatgat tacttttact ctcggattag cttaggcgag ctgcaagact   6840
acatcgaatc tttagaaatg ggaacataaa aaaggtgcga agtggggaag tggctgaaca   6900
ataggcatat gtgagtgagt ggggagtaaa attacttcct ttacttgggt acagtcaaga   6960
atggatgaca gcttagccca ctatatctgt tcatgtgttc tttagggtcc tctgatataa   7020
ctggtctctc tgcaggaata ttacaacccc aatcagtcta tgttggaatt ggtatttgca   7080
cccgcagaag agtggataaa tcgtagtgac tcagaaatta ttgatgctac aatgaaggaa   7140
ctagcgaagc ttttccctga tgaaatttcg gcagatcaga gcaaagcaaa aatattgaag   7200
tatcatgttg tcaaaacccc aaggtcagta atcattttgc tttcatagtt gtgtagtatg   7260
cgagaattac tgtccacgtg gaatctattc ctgttatgaa tcctgattaa tctgcttttt   7320
actttcaggt ctgtttataa aactgtgcca ggttgtgaac cctgtcggcc cttgcaaaga   7380
tcccctatag agggttttta tttagctggt gactacacga aacagaagta cttggcttca   7440
atggaaggtg ctgtcttatc aggaaagctt tgtgccgaag ctattgtaca ggttagctct   7500
cacatttttt tcccttccat tgatagtgta tttgattata ttttgtcatc tttgctgcgg   7560
tagagaattt tagaagcatt tctcagacat tagttagcag agttactcag gatatctgca   7620
gttttggagc ttcagtagta gcatgataaa atgcagagga ttgtgttttt tcattcttta   7680
ttaaaccttg tgccaaaggt cttttggaaa caacctctct accccgaggt aggggtaagg   7740
tctgcgtaca tattaccctc cccataccc atgcgtggga ttatactggg tggttgttgt   7800
ataaacctat atctctataa tttgcaggat tacgagttac ttcttggccg gagccagaag   7860
atgttggcag aagcaagcgt agttagcata gtgaactaaa atgttaattc tgtacacaaa   7920
atttaagatg aaggcggcca cgctgaatta g                                  7951
```

<210> SEQ ID NO 18
<211> LENGTH: 10145
<212> TYPE: DNA
<213> ORGANISM: artificial
<220> FEATURE:
<223> OTHER INFORMATION: synthetic oligonucleotide

<400> SEQUENCE: 18

```
gtaggcggtg ctacagagtt cttgaagtgg tggcctaact acggctacac tagaaggaca     60
```

-continued

```
gtatttggta tctgcgctct gctgaagcca gttaccttcg gaaaaagagt tggtagctct    120
tgatccggca aacaaaccac cgctggtagc ggtggttttt ttgtttgcaa gcagcagatt    180
acgcgcagaa aaaaaggatc tcaagaagat cctttgatct tttctacggg gtctgacgct    240
cagtggaacg aaaactcacg ttaagggatt ttggtcatgc attctaggta ctaaaacaat    300
tcatccagta aaatataata ttttattttc tcccaatcag gcttgatccc cagtaagtca    360
aaaaatagct cgacatactg ttcttccccg atatcctccc tgatcgaccg gacgcagaag    420
gcaatgtcat accacttgtc cgccctgccg cttctcccaa gatcaataaa gccacttact    480
ttgccatctt tcacaaagat gttgctgtct cccaggtcgc cgtgggaaaa gacaagttcc    540
tcttcgggct tttccgtctt taaaaaatca tacagctcgc gcggatcttt aaatggagtg    600
tcttcttccc agttttcgca atccacatcg gccagatcgt tattcagtaa gtaatccaat    660
tcggctaagc ggctgtctaa gctattcgta tagggacaat ccgatatgtc gatggagtga    720
aagagcctga tgcactccgc atacagctcg ataatctttt cagggctttg ttcatcttca    780
tactcttccg agcaaaggac gccatcggcc tcactcatga gcagattgct ccagccatca    840
tgccgttcaa agtgcaggac ctttggaaca ggcagctttc cttccagcca tagcatcatg    900
tccttttccc gttccacatc ataggtggtc cctttatacc ggctgtccgt catttttaaa    960
tataggtttt cattttctcc caccagctta tataccttag caggagacat tccttccgta   1020
tcttttacgc agcggtattt ttcgatcagt tttttcaatt ccggtgatat tctcatttta   1080
gccatttatt atttccttcc tcttttctac agtatttaaa gataccccaa gaagctaatt   1140
ataacaagac gaactccaat tcactgttcc ttgcattcta aaaccttaaa taccagaaaa   1200
cagctttttc aaagttgttt tcaaagttgg cgtataacat agtatcgacg gagccgattt   1260
tgaaaccgcg gtgatcacag gcagcaacgc tctgtcatcg ttacaatcaa catgctaccc   1320
tccgcgagat catccgtgtt tcaaacccgg cagcttagtt gccgttcttc cgaatagcat   1380
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg   1500
gctggctggt ggcaggatat attgtggtgt aaacaaattg acgcttagac aacttaataa   1560
cacattgcgg acgtttttaa tgtagagctc aaagtttaac gcgttagcag aaggcatgtt   1620
gttgtgactc cgaggggttg cctcaaactc tatcttataa ccggcgtgga ggcatggagg   1680
caggggtatt ttggtcattt taatagatag tggaaaatga cgtggaattt acttaaagac   1740
gaagtctttg cgacaagggg gggcccacgc cgaatttaat attaccggcg tggccccccc   1800
ttatcgcgag tgctttagca cgagcggtcc agatttaaag tagaaaattt cccgcccact   1860
agggttaaag gtgttcacac tataaaagca tatacgatgt gatggtattt gatggagcgt   1920
atattgtatc aggtatttcc gttggatacg aattattcgt acgaccctcg gtaccgatca   1980
aaagcaggtg acaagtttgt acaaaaaagc tgaacgagaa acgtaaaatg atataaatat   2040
caatatatta aattagattt tgcataaaaa acagactaca taatactgta aaacacaaca   2100
tatccagtca ctatggcggc cgcattaggc accccaggct ttacacttta tgcttccggc   2160
tcgtataatg tgtggatttt gagttaggat ccgtcgagat tttcaggagc taaggaagct   2220
aaaatggaga aaaaaatcac tggatatacc accgttgata tatcccaatg gcatcgtaaa   2280
gaacattttg aggcatttca gtcagtcgct caatgtacct ataaccagac cgttcagctg   2340
gatattacgg cctttttaaa gaccgtaaag aaaaataagc acaagtttta tccggccttt   2400
```

-continued

```
attcacattc ttgcccgcct gatgaatgct catccggaat tccgtatggc aatgaaagac   2460
ggtgagctgg tgatatggga tagtgttcac ccttgttaca ccgttttcca tgagcaaact   2520
gaaacgtttt catcgctctg gagtgaatac cacgacgatt tccggcagtt tctacacata   2580
tattcgcaag atgtggcgtg ttacggtgaa aacctggcct atttccctaa agggtttatt   2640
gagaatatgt ttttcgtctc agccaatccc tgggtgagtt tcaccagttt tgatttaaac   2700
gtggccaata tggacaactt cttcgccccc gttttcacca tgggcaaata ttatacgcaa   2760
ggcgacaagg tgctgatgcc gctggcgatt caggttcatc atgccgtttg tgatggcttc   2820
catgtcggca gaatgcttaa tgaattacaa cagtactgcg atgagtggca ggcggggcgt   2880
aatctagagg atccggctta ctaaaagcca gataacagta tgcgtatttg cgcgctgatt   2940
tttgcggtat aagaatatat actgatatgt atacccgaag tatgtcaaaa agaggtatgc   3000
tatgaagcag cgtattacag tgacagttga cagcgacagc tatcagttgc tcaaggcata   3060
tatgatgtca atatctccgg tctggtaagc acaaccatgc agaatgaagc ccgtcgtctg   3120
cgtgccgaac gctggaaagc ggaaaatcag gaagggatgg ctgaggtcgc ccggtttatt   3180
gaaatgaacg gctcttttgc tgacgagaac aggggctggt gaaatgcagt ttaaggttta   3240
cacctataaa agagagagcc gttatcgtct gtttgtggat gtacagagtg atattattga   3300
cacgcccggg cgacggatgg tgatccccct ggccagtgca cgtctgctgt cagataaagt   3360
cccccgtgaa ctttacccgg tggtgcatat cggggatgaa agctggcgca tgatgaccac   3420
cgatatggcc agtgtgccgg tctccgttat cggggaagaa gtggctgatc tcagccaccg   3480
cgaaaatgac atcaaaaacg ccattaacct gatgttctgg ggaatataaa tgtcaggctc   3540
ccttatacac agccagtctg caggtcgacc atagtgactg gatatgttgt gttttacagt   3600
attatgtagt ctgtttttta tgcaaaatct aatttaatat attgatattt atatcatttt   3660
acgtttctcg ttcagctttc ttgtacaaag tggtcacctg caaaaagtgt ttgatcgccg   3720
gcggtaccga gtgtacttca agtcagtggg aaatcaataa aatgattatt ttatgaatat   3780
atttcattgt gcaagtagat agaaattaca tatgttacat aacacacgaa ataaacaaaa   3840
aaagacaatc caaaaacaaa caccccaaaa aaaataatca ctttagataa actcgtatga   3900
ggagaggcac gttcagtgac tcgacgattc ccgagcaaaa aaagtctccc cgtcacacat   3960
gtagtgggtg acgcaattat ctttaaagta atccttctgt tgacttgtca ttgataacat   4020
ccagtcttcg tcaggattgc aaagaattat agaagggatc ccacctttta ttttcttctt   4080
ttttccatat ttagggttga cagtgaaatc agactggcaa cctattaatt gcttccacaa   4140
tgggacgaac ttgaagggga tgtcgtcgat gatattatag gtggcgtgtt catcgtagtt   4200
ggtgaaatcg atggtaccgt tccaatagtt gtgtcgtccg agacttctag cccaggtggt   4260
ctttccggta cgagttggtc cgcagatgta gaggctgggg tgtcggattc cattccttcc   4320
attgtccttg ttaaatcggc catccattca aggtcagatt gagcttgttg gtatgagaca   4380
ggatgtatgt aagtataagc gtctatgctt acatggtata gatgggtttc cctccaggag   4440
tgtagatctt cgtggcagcg aagatctgat tctgtgaagg gcgacacata cggttcaggt   4500
tgtggaggga ataatttgtt ggctgaatat tccagccatt gaagctttgt tgcccattca   4560
tgagggaatt cttccttgat catgtcaaga tattcctcct tagacgttgc agtctggata   4620
atagttctcc atcgtgcgtc agatttgcga ggagaaacct tatgatctcg gaaatctcct   4680
ctggttttaa tatctccgtc ctttgatatg taatcaagga cttgtttaga gtttctagct   4740
ggctggatat tagggtgatt tccttcaaaa tcgaaaaaag aaggatccct aatacaaggt   4800
```

-continued

```
tttttatcaa gctggagaag agcatgatag tgggtagtgc catcttgatg aagctcagaa   4860
gcaacaccaa ggaagaaaat aagaaaaggt gtgagtttct cccagagaaa ctggaataaa   4920
tcatctcttt gagatgagca cttgggatag gtaaggaaaa catatttaga ttggagtctg   4980
aagttcttac tagcagaagg catgttgttg tgactccgag ggttgcctc aaactctatc    5040
ttataaccgg cgtggaggca tggaggcagg ggtattttgg tcattttaat agatagtgga   5100
aaatgacgtg gaatttactt aaagacgaag tctttgcgac aaggggggc ccacgccgaa    5160
tttaatatta ccggcgtggc cccccttat cgcgagtgct ttagcacgag cggtccagat    5220
ttaaagtaga aaatttcccg cccactaggg ttaaaggtgt tcacactata aaagcatata   5280
cgatgtgatg gtatttgatg gagcgtatat tgtatcaggt atttccgttg gatacgaatt   5340
attcgtacga ccctcatagt ttaaactatc agtgtttgac aggatatatt ggcgggtaaa   5400
cctaagagaa aagagcgttt attagaataa cggatattta aaagggcgtg aaaaggttta   5460
tccgttcgtc catttgtatg tgcatgccaa ccacagggtt cccctcggga tcaaagtact   5520
ttgatccaac ccctccgctg ctatagtgca gtcggcttct gacgttcagt gcagccgtct   5580
tctgaaaacg acatgtcgca caagtcctaa gttacgcgac aggctgccgc cctgcccttt   5640
tcctggcgtt ttcttgtcgc gtgttttagt cgcataaagt agaatacttg cgactagaac   5700
cggagacatt acgccatgaa caagagcgcc gccgctggcc tgctgggcta tgcccgcgtc   5760
agcaccgacg accaggactt gaccaaccaa cgggccgaac tgcacgcggc cggctgcacc   5820
aagctgtttt ccgagaagat caccggcacc aggcgcgacc gcccggagct ggccaggatg   5880
cttgaccacc tacgccctgg cgacgttgtg acagtgacca ggctagaccg cctggcccgc   5940
agcacccgcg acctactgga cattgccgag cgcatccagg aggccggcgc gggcctgcgt   6000
agcctggcag agccgtgggc cgacaccacc acgccggccg gccgcatggt gttgaccgtg   6060
ttcgccggca ttgccgagtt cgagcgttcc ctaatcatcg accgcacccg gagcgggcgc   6120
gaggccgcca aggcccgagg cgtgaagttt ggcccccgcc ctaccctcac cccggcacag   6180
atcgcgcacg cccgcgagct gatcgaccag gaaggccgca ccgtgaaaga ggcggctgca   6240
ctgcttggcg tgcatcgctc gaccctgtac cgcgcacttg agcgcagcga ggaagtgacg   6300
cccaccgagg ccaggcggcg cggtgccttc cgtgaggacg cattgaccga ggccgacgcc   6360
ctggcggccg ccgagaatga acgccaagag gaacaagcat gaaaccgcac caggacggcc   6420
aggacgaacc gtttttcatt accgaagaga tcgaggcgga gatgatcgcg gccgggtacg   6480
tgttcgagcc gcccgcgcac ggctcaaccg tgcggctgca tgaaatcctg gccggtttgt   6540
ctgatgccaa gctggcggcc tggccggcca gcttggccgc tgaagaaacc gagcgccgcc   6600
gtctaaaaag gtgatgtgta tttgagtaaa acagcttgcg tcatgcggtc gctgcgtata   6660
tgatgcgatg agtaaataaa caaatacgca aggggaacgc atgaaggtta tcgctgtact   6720
taaccagaaa ggcgggtcag gcaagacgac catcgcaacc catctagccc gcgccctgca   6780
actcgccggg gccgatgttc tgttagtcga ttccgatccc cagggcagtg cccgcgattg   6840
ggcggccgtg cgggaagatc aaccgctaac cgttgtcggc atcgaccgcc cgacgattga   6900
ccgcgacgtg aaggccatcg gccggcgcga cttcgtagtg atcgacggag cgccccaggc   6960
ggcggacttg gctgtgtccg cgatcaaggc agccgacttc gtgctgattc cggtgcagcc   7020
aagcccttac gacatatggg ccaccgccga cctggtggag ctggttaagc agcgcattga   7080
ggtcacggat ggaaggctac aagcggcctt tgtcgtgtcg cgggcgatca aaggcacgcg   7140
```

-continued

```
catcggcggt gaggttgccg aggcgctggc cgggtacgag ctgcccattc ttgagtcccg   7200
tatcacgcag cgcgtgagct acccaggcac tgccgccgcc ggcacaaccg ttcttgaatc   7260
agaacccgag ggcgacgctg cccgcgaggt ccaggcgctg gccgctgaaa ttaaatcaaa   7320
actcatttga gttaatgagg taaagagaaa atgagcaaaa gcacaaacac gctaagtgcc   7380
ggccgtccga gcgcacgcag cagcaaggct gcaacgttgg ccagcctggc agacacgcca   7440
gccatgaagc gggtcaactt tcagttgccg gcggaggatc acaccaagct gaagatgtac   7500
gcggtacgcc aaggcaagac cattaccgag ctgctatctg aatacatcgc gcagctacca   7560
gagtaaatga gcaaatgaat aaatgagtag atgaatttta gcggctaaag gaggcggcat   7620
ggaaaatcaa gaacaaccag gcaccgacgc cgtggaatgc cccatgtgtg gaggaacggg   7680
cggttggcca ggcgtaagcg gctgggttgt ctgccggccc tgcaatggca ctggaacccc   7740
caagcccgag gaatcggcgt gacggtcgca aaccatccgg cccggtacaa atcggcgcgg   7800
cgctgggtga tgacctggtg gagaagttga aggccgcgca ggccgcccag cggcaacgca   7860
tcgaggcaga agcacgcccc ggtgaatcgt ggcaagcggc cgctgatcga atccgcaaag   7920
aatcccggca accgccggca gccggtgcgc cgtcgattag gaagccgccc aagggcgacg   7980
agcaaccaga tttttcgtt ccgatgctct atgacgtggg cacccgcgat agtcgcagca   8040
tcatggacgt ggccgttttc cgtctgtcga agcgtgaccg acgagctggc gaggtgatcc   8100
gctacgagct tccagacggg cacgtagagg tttccgcagg gccggccggc atggccagtg   8160
tgtgggatta cgacctggta ctgatggcgg tttcccatct aaccgaatcc atgaaccgat   8220
accgggaagg gaagggagac aagcccggcc gcgtgttccg tccacacgtt gcggacgtac   8280
tcaagttctg ccggcgagcc gatggcggaa agcagaaaga cgacctggta gaaacctgca   8340
ttcggttaaa caccacgcac gttgccatgc agcgtacgaa gaaggccaag aacggccgcc   8400
tggtgacggt atccgagggt gaagccttga ttagccgcta caagatcgta aagagcgaaa   8460
ccgggcggcc ggagtacatc gagatcgagc tagctgattg gatgtaccgc gagatcacag   8520
aaggcaagaa cccggacgtg ctgacggttc accccgatta ctttttgatc gatcccggca   8580
tcggccgttt tctctaccgc ctggcacgcc gcgccgcagg caaggcagaa gccagatggt   8640
tgttcaagac gatctacgaa cgcagtggca gcgccggaga gttcaagaag ttctgtttca   8700
ccgtgcgcaa gctgatcggg tcaaatgacc tgccggagta cgatttgaag gaggaggcgg   8760
ggcaggctgg cccgatccta gtcatgcgct accgcaacct gatcgagggc gaagcatccg   8820
ccggttccta atgtacggag cagatgctag ggcaaattgc cctagcaggg gaaaaaggtc   8880
gaaaaggcct ctttcctgtg gatagcacgt acattgggaa cccaaagccg tacattggga   8940
accggaaccc gtacattggg aacccaaagc cgtacattgg gaaccggtca cacatgtaag   9000
tgactgatat aaaagagaaa aaaggcgatt tttccgccta aaactcttta aaacttatta   9060
aaactcttaa aacccgcctg gcctgtgcat aactgtctgg ccagcgcaca gccgaagagc   9120
tgcaaaaagc gcctaccctt cggtcgctgc gctccctacg ccccgccgct tcgcgtcggc   9180
ctatcgcggc cgctggccgc tcaaaaatgg ctggcctacg gccaggcaat ctaccagggc   9240
gcggacaagc cgcgccgtcg ccactcgacc gccggcgccc acatcaaggc accctgcctc   9300
gcgcgtttcg gtgatgacgg tgaaaacctc tgacacatgc agctcccgga aacggtcaca   9360
gcttgtctgt aagcggatgc cgggagcaga caagcccgtc agggcgcgtc agcgggtgtt   9420
ggcgggtgtc ggggcgcagc catgacccag tcacgtagcg atagcggagt gtatactggc   9480
ttaactatgc ggcatcagag cagattgtac tgagagtgca ccatatgcgg tgtgaaatac   9540
```

```
cgcacagatg cgtaaggaga aaataccgca tcaggcgctc ttccgcttcc tcgctcactg   9600

actcgctgcg ctcggtcgtt cggctgcggc gagcggtatc agctcactca aaggcggtaa   9660

tacggttatc cacagaatca ggggataacg caggaaagaa catgtgagca aaaggccagc   9720

aaaaggccag gaaccgtaaa aaggccgcgt tgctggcgtt tttccatagg ctccgccccc   9780

ctgacgagca tcacaaaaat cgacgctcaa gtcagaggtg gcgaaacccg acaggactat   9840

aaagatacca ggcgtttccc cctggaagct ccctcgtgcg ctctcctgtt ccgaccctgc   9900

cgcttaccgg atacctgtcc gcctttctcc cttcgggaag cgtggcgctt tctcatagct   9960

cacgctgtag gtatctcagt tcggtgtagg tcgttcgctc caagctgggc tgtgtgcacg  10020

aaccccccgt tcagcccgac cgctgcgcct tatccggtaa ctatcgtctt gagtccaacc  10080

cggtaagaca cgacttatcg ccactggcag cagccactgg taacaggatt agcagagcga  10140

ggtat                                                              10145
```

<210> SEQ ID NO 19
<211> LENGTH: 12261
<212> TYPE: DNA
<213> ORGANISM: artificial
<220> FEATURE:
<223> OTHER INFORMATION: synthetic oligonucleotide

<400> SEQUENCE: 19

```
gtaggcggtg ctacagagtt cttgaagtgg tggcctaact acggctacac tagaaggaca     60

gtatttggta tctgcgctct gctgaagcca gttaccttcg gaaaaagagt tggtagctct    120

tgatccggca aacaaaccac cgctggtagc ggtggttttt ttgtttgcaa gcagcagatt    180

acgcgcagaa aaaaaggatc tcaagaagat cctttgatct tttctacggg gtctgacgct    240

cagtggaacg aaaactcacg ttaagggatt ttggtcatgc attctaggta ctaaaacaat    300

tcatccagta aaatataata ttttattttc tcccaatcag gcttgatccc cagtaagtca    360

aaaaatagct cgacatactg ttcttccccg atatcctccc tgatcgaccg gacgcagaag    420

gcaatgtcat accacttgtc cgccctgccg cttctcccaa gatcaataaa gccacttact    480

ttgccatctt tcacaaagat gttgctgtct cccaggtcgc cgtgggaaaa gacaagttcc    540

tcttcgggct tttccgtctt taaaaaatca tacagctcgc gcggatcttt aaatggagtg    600

tcttcttccc agttttcgca atccacatcg gccagatcgt tattcagtaa gtaatccaat    660

tcggctaagc ggctgtctaa gctattcgta tagggacaat ccgatatgtc gatggagtga    720

aagagcctga tgcactccgc atacagctcg ataatctttt cagggctttg ttcatcttca    780

tactcttccg agcaaaggac gccatcggcc tcactcatga gcagattgct ccagccatca    840

tgccgttcaa agtgcaggac ctttggaaca ggcagctttc cttccagcca tagcatcatg    900

tccttttccc gttccacatc ataggtggtc cctttatacc ggctgtccgt catttttaaa    960

tataggtttt cattttctcc caccagctta tataccttag caggagacat tccttccgta   1020

tcttttacgc agcggtattt ttcgatcagt tttttcaatt ccggtgatat tctcatttta   1080

gccatttatt atttccttcc tcttttctac agtatttaaa gataccccaa gaagctaatt   1140

ataacaagac gaactccaat tcactgttcc ttgcattcta aaaccttaaa taccagaaaa   1200

cagctttttc aaagttgttt tcaaagttgg cgtataacat agtatcgacg gagccgattt   1260

tgaaaccgcg gtgatcacag gcagcaacgc tctgtcatcg ttacaatcaa catgctaccc   1320

tccgcgagat catccgtgtt tcaaacccgg cagcttagtt gccgttcttc cgaatagcat   1380
```

-continued

```
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg   1500
gctggctggt ggcaggatat attgtggtgt aaacaaattg acgcttagac aacttaataa   1560
cacattgcgg acgtttttaa tgtactgaat taacgccgaa ttaattcggg ggatctggat   1620
tttagtactg gattttggtt ttaggaatta gaaattttat tgatagaagt attttacaaa   1680
tacaaataca tactaagggt ttcttatatg ctcaacacat gagcgaaacc ctataggaac   1740
cctaattccc ttatctggga actactcaca cattattatg gagaaactcg agcttgtcga   1800
tcgactctag ctagaggatc gatccgaacc ccagagtccc gctcagaaga actcgtcaag   1860
aaggcgatag aaggcgatgc gctgcgaatc gggagcggcg ataccgtaaa gcacgaggaa   1920
gcggtcagcc cattcgccgc caagttcttc agcaatatca cgggtagcca acgctatgtc   1980
ctgatagcgg tccgccacac ccagccggcc acagtcgatg aatccagaaa agcggccatt   2040
ttccaccatg atattcggca agcaggcatc gccatgtgtc acgacgagat cctcgccgtc   2100
gggcatgcgc gccttgagcc tggcgaacag ttcggctggc gcgagcccct gatgttcttc   2160
gtccagatca tcctgatcga caagaccggc ttccatccga gtacgtgctc gctcgatgcg   2220
atgtttcgct tggtggtcga atgggcaggt agccggatca agcgtatgca gccgccgcat   2280
tgcatcagcc atgatggata ctttctcggc aggagcaagg tgagatgaca ggagatcctg   2340
ccccggcact tcgcccaata gcagccagtc ccttcccgct tcagtgacaa cgtcgagcac   2400
agctgcgcaa ggaacgcccg tcgtggccag ccacgatagc cgcgctgcct cgtcctggag   2460
ttcattcagg gcaccggaca ggtcggtctt gacaaaaaga accgggcgcc cctgcgctga   2520
cagccgaaac acggcggcat cagagcagcc gattgtctgt tgtgcccagt catagccgaa   2580
tagcctctcc acccaagcgg ccggagaacc tgcgtgcaat ccatcttgtt caatccccat   2640
ggtcgatcga cagatctgcg aaagctcgag agagatagat ttgtagagag agactggtga   2700
tttcagcgtg tcctctccaa atgaaatgaa cttccttata tagaggaagg tcttgcgaag   2760
gatagtggga ttgtgcgtca tcccttacgt cagtggagat atcacatcaa tccacttgct   2820
ttgaagacgt ggttggaacg tcttcttttt ccacgatgct cctcgtgggt gggggtccat   2880
ctttgggacc actgtcggca gaggcatctt gaacgatagc ctttccttta tcgcaatgat   2940
ggcatttgta ggtgccacct tccttttcta ctgtcctttt gatgaagtga cagatagctg   3000
ggcaatggaa tccgaggagg tttcccgata ttaccctttg ttgaaaagtc tcaatagccc   3060
tttggtcttc tgagactgta tctttgatat tcttggagta gacgagagtg tcgtgctcca   3120
ccatgttatc acatcaatcc acttgctttg aagacgtggt tggaacgtct tctttttcca   3180
cgatgctcct cgtgggtggg ggtccatctt tgggaccact gtcggcagag gcatcttgaa   3240
cgatagcctt tcctttatcg caatgatggc atttgtaggt gccaccttcc ttttctactg   3300
tccttttgat gaagtgacag atagctgggc aatggaatcc gaggaggttt cccgatatta   3360
ccctttgttg aaaagtctca atagcccttt ggtcttctga gactgtatct ttgatattct   3420
tggagtagac gagagtgtcg tgctccacca tgttggcaag ctgctctagc caatacgcaa   3480
accgcctctc cccgcgcgtt ggccgattca ttaatgcagc tggcacgaca ggtttcccga   3540
ctggaaagcg ggcagtgagc gcaacgcaat taatgtgagt tagctcactc attaggcacc   3600
ccaggcttta cactttatgc ttccggctcg tatgttgtgt ggaattgtga gcggataaca   3660
atttcacaca ggaaacagct atgaccatga ttacgaattc gagctcaaag tttaacgcgt   3720
tagcagaagg catgttgttg tgactccgag ggttgcctc aaactctatc ttataaccgg   3780
```

-continued

```
cgtggaggca tggaggcagg ggtattttgg tcattttaat agatagtgga aaatgacgtg   3840
gaatttactt aaagacgaag tctttgcgac aagggggggc ccacgccgaa tttaatatta   3900
ccggcgtggc cccccctat cgcgagtgct ttagcacgag cggtccagat ttaaagtaga   3960
aaatttcccg cccactaggg ttaaaggtgt tcacactata aaagcatata cgatgtgatg   4020
gtatttgatg gagcgtatat tgtatcaggt atttccgttg gatacgaatt attcgtacga   4080
ccctcggtac cgatcaaaag caggtgacaa gtttgtacaa aaaagctgaa cgagaaacgt   4140
aaaatgatat aaatatcaat atattaaatt agattttgca taaaaaacag actacataat   4200
actgtaaaac acaacatatc cagtcactat ggcggccgca ttaggcaccc caggctttac   4260
actttatgct tccggctcgt ataatgtgtg gattttgagt taggatccgt cgagattttc   4320
aggagctaag gaagctaaaa tggagaaaaa aatcactgga tataccaccg ttgatatatc   4380
ccaatggcat cgtaaagaac attttgaggc atttcagtca gttgctcaat gtacctataa   4440
ccagaccgtt cagctggata ttacggcctt tttaaagacc gtaaagaaaa ataagcacaa   4500
gttttatccg gcctttattc acattcttgc ccgcctgatg aatgctcatc cggaattccg   4560
tatggcaatg aaagacggtg agctggtgat atgggatagt gttcaccctt gttacaccgt   4620
tttccatgag caaactgaaa cgttttcatc gctctggagt gaataccacg acgatttccg   4680
gcagtttcta cacatatatt cgcaagatgt ggcgtgttac ggtgaaaacc tggcctattt   4740
ccctaaaggg tttattgaga atatgttttt cgtctcagcc aatccctggg tgagtttcac   4800
cagttttgat ttaaacgtgg ccaatatgga caacttcttc gcccccgttt tcaccatggg   4860
caaatattat acgcaaggcg acaaggtgct gatgccgctg gcgattcagg ttcatcatgc   4920
cgtttgtgat ggcttccatg tcggcagaat gcttaatgaa ttacaacagt actgcgatga   4980
gtggcaggcg gggcgtaatc tagaggatcc ggcttactaa aagccagata acagtatgcg   5040
tatttgcgcg ctgatttttg cggtataaga atatatactg atatgtatac ccgaagtatg   5100
tcaaaaagag gtatgctatg aagcagcgta ttacagtgac agttgacagc gacagctatc   5160
agttgctcaa ggcatatatg atgtcaatat ctccggtctg gtaagcacaa ccatgcagaa   5220
tgaagcccgt cgtctgcgtg ccgaacgctg gaaagcggaa aatcaggaag ggatggctga   5280
ggtcgcccgg tttattgaaa tgaacggctc ttttgctgac gagaacaggg gctggtgaaa   5340
tgcagtttaa ggtttacacc tataaaagag agagccgtta tcgtctgttt gtggatgtac   5400
agagtgatat tattgacacg cccgggcgac ggatggtgat ccccctggcc agtgcacgtc   5460
tgctgtcaga taaagtcccc cgtgaacttt acccggtggt gcatatcggg gatgaaagct   5520
ggcgcatgat gaccaccgat atggccagtg tgccggtctc cgttatcggg gaagaagtgg   5580
ctgatctcag ccaccgcgaa aatgacatca aaaacgccat taacctgatg ttctggggaa   5640
tataaatgtc aggctccctt atacacagcc agtctgcagg tcgaccatag tgactggata   5700
tgttgtgttt tacagtatta tgtagtctgt tttttatgca aaatctaatt taatatattg   5760
atatttatat cattttacgt ttctcgttca gctttcttgt acaaagtggt cacctgcaaa   5820
aagtgtttga tcgccggcgg taccgagtgt acttcaagtc agtgggaaat caataaaatg   5880
attattttat gaatatattt cattgtgcaa gtagatagaa attacatatg ttacataaca   5940
cacgaaataa acaaaaaaag acaatccaaa aacaaacacc ccaaaaaaaa taatcacttt   6000
agataaactc gtatgaggag aggcacgttc agtgactcga cgattcccga gcaaaaaaag   6060
tctccccgtc acacatgtag tgggtgacgc aattatcttt aaagtaatcc ttctgttgac   6120
```

-continued

```
ttgtcattga taacatccag tcttcgtcag gattgcaaag aattatagaa gggatcccac   6180
cttttatttt cttctttttt ccatatttag ggttgacagt gaaatcagac tggcaaccta   6240
ttaattgctt ccacaatggg acgaacttga aggggatgtc gtcgatgata ttataggtgg   6300
cgtgttcatc gtagttggtg aaatcgatgg taccgttcca atagttgtgt cgtccgagac   6360
ttctagccca ggtggtcttt ccggtacgag ttggtccgca gatgtagagg ctggggtgtc   6420
ggattccatt ccttccattg tccttgttaa atcggccatc cattcaaggt cagattgagc   6480
ttgttggtat gagacaggat gtatgtaagt ataagcgtct atgcttacat ggtatagatg   6540
ggtttccctc caggagtgta gatcttcgtg gcagcgaaga tctgattctg tgaagggcga   6600
cacatacggt tcaggttgtg gagggaataa tttgttggct gaatattcca gccattgaag   6660
ctttgttgcc cattcatgag ggaattcttc cttgatcatg tcaagatatt cctccttaga   6720
cgttgcagtc tggataatag ttctccatcg tgcgtcagat ttgcgaggag aaaccttatg   6780
atctcggaaa tctcctctgg ttttaatatc tccgtccttt gatatgtaat caaggacttg   6840
tttagagttt ctagctggct ggatattagg gtgatttcct tcaaaatcga aaaaagaagg   6900
atccctaata caaggttttt tatcaagctg gagaagagca tgatagtggg tagtgccatc   6960
ttgatgaagc tcagaagcaa caccaaggaa gaaaataaga aaaggtgtga gtttctccca   7020
gagaaactgg aataaatcat ctctttgaga tgagcacttg ggataggtaa ggaaaacata   7080
tttagattgg agtctgaagt tcttactagc agaaggcatg ttgttgtgac tccgaggggt   7140
tgcctcaaac tctatcttat aaccggcgtg gaggcatgga ggcaggggta ttttggtcat   7200
tttaatagat agtggaaaat gacgtggaat ttacttaaag acgaagtctt tgcgacaagg   7260
gggggcccac gccgaattta atattaccgg cgtggccccc ccttatcgcg agtgctttag   7320
cacgagcggt ccagatttaa agtagaaaat ttcccgccca ctagggttaa aggtgttcac   7380
actataaaag catatacgat gtgatggtat ttgatggagc gtatattgta tcaggtattt   7440
ccgttggata cgaattattc gtacgaccct catagtttaa actatcagtg tttgacagga   7500
tatattggcg ggtaaaccta agagaaaaga gcgtttatta gaataacgga tatttaaaag   7560
ggcgtgaaaa ggtttatccg ttcgtccatt tgtatgtgca tgccaaccac agggttcccc   7620
tcgggatcaa agtactttga tccaacccct ccgctgctat agtgcagtcg gcttctgacg   7680
ttcagtgcag ccgtcttctg aaaacgacat gtcgcacaag tcctaagtta cgcgacaggc   7740
tgccgccctg cccttttcct ggcgttttct tgtcgcgtgt tttagtcgca taaagtagaa   7800
tacttgcgac tagaaccgga gacattacgc catgaacaag agcgccgccg ctggcctgct   7860
gggctatgcc cgcgtcagca ccgacgacca ggacttgacc aaccaacggg ccgaactgca   7920
cgcggccggc tgcaccaagc tgttttccga gaagatcacc ggcaccaggc gcgaccgccc   7980
ggagctggcc aggatgcttg accacctacg ccctggcgac gttgtgacag tgaccaggct   8040
agaccgcctg gcccgcagca cccgcgacct actggacatt gccgagcgca tccaggaggc   8100
cggcgcgggc ctgcgtagcc tggcagagcc gtgggccgac accaccacgc cggccggccg   8160
catggtgttg accgtgttcg ccggcattgc cgagttcgag cgttccctaa tcatcgaccg   8220
cacccggagc gggcgcgagg ccgccaaggc ccgaggcgtg aagtttggcc cccgccctac   8280
cctcaccccg gcacagatcg cgcacgcccg cgagctgatc gaccaggaag gccgcaccgt   8340
gaaagaggcg gctgcactgc ttggcgtgca tcgctcgacc ctgtaccgcg cacttgagcg   8400
cagcgaggaa gtgacgccca ccgaggccag gcggcgcggt gccttccgtg aggacgcatt   8460
gaccgaggcc gacgccctgg cggccgccga gaatgaacgc caagaggaac aagcatgaaa   8520
```

-continued

```
ccgcaccagg acggccagga cgaaccgttt ttcattaccg aagagatcga ggcggagatg   8580
atcgcggccg ggtacgtgtt cgagccgccc gcgcacggct caaccgtgcg gctgcatgaa   8640
atcctggccg gtttgtctga tgccaagctg gcggcctggc cggccagctt ggccgctgaa   8700
gaaaccgagc gccgccgtct aaaaaggtga tgtgtatttg agtaaaacag cttgcgtcat   8760
gcggtcgctg cgtatatgat gcgatgagta aataaacaaa tacgcaaggg gaacgcatga   8820
aggttatcgc tgtacttaac cagaaaggcg ggtcaggcaa gacgaccatc gcaacccatc   8880
tagcccgcgc cctgcaactc gccggggccg atgttctgtt agtcgattcc gatccccagg   8940
gcagtgcccg cgattgggcg gccgtgcggg aagatcaacc gctaaccgtt gtcggcatcg   9000
accgcccgac gattgaccgc gacgtgaagg ccatcggccg gcgcgacttc gtagtgatcg   9060
acggagcgcc ccaggcggcg gacttggctg tgtccgcgat caaggcagcc gacttcgtgc   9120
tgattccggt gcagccaagc ccttacgaca tatgggccac cgccgacctg gtggagctgg   9180
ttaagcagcg cattgaggtc acggatggaa ggctacaagc ggcctttgtc gtgtcgcggg   9240
cgatcaaagg cacgcgcatc ggcggtgagg ttgccgaggc gctggccggg tacgagctgc   9300
ccattcttga gtcccgtatc acgcagcgcg tgagctaccc aggcactgcc gccgccggca   9360
caaccgttct tgaatcagaa cccgagggcg acgctgcccg cgaggtccag gcgctggccg   9420
ctgaaattaa atcaaaactc atttgagtta atgaggtaaa gagaaaatga gcaaaagcac   9480
aaacacgcta agtgccggcc gtccgagcgc acgcagcagc aaggctgcaa cgttggccag   9540
cctggcagac acgccagcca tgaagcgggt caactttcag ttgccggcgg aggatcacac   9600
caagctgaag atgtacgcgg tacgccaagg caagaccatt accgagctgc tatctgaata   9660
catcgcgcag ctaccagagt aaatgagcaa atgaataaat gagtagatga attttagcgg   9720
ctaaaggagg cggcatggaa aatcaagaac aaccaggcac cgacgccgtg gaatgcccca   9780
tgtgtggagg aacgggcggt tggccaggcg taagcggctg ggttgtctgc cggccctgca   9840
atggcactgg aacccccaag cccgaggaat cggcgtgacg gtcgcaaacc atccggcccg   9900
gtacaaatcg gcgcggcgct gggtgatgac ctggtggaga agttgaaggc cgcgcaggcc   9960
gcccagcggc aacgcatcga ggcagaagca cgccccggtg aatcgtggca agcggccgct  10020
gatcgaatcc gcaaagaatc ccggcaaccg ccggcagccg gtgcgccgtc gattaggaag  10080
ccgcccaagg gcgacgagca accagatttt ttcgttccga tgctctatga cgtgggcacc  10140
cgcgatagtc gcagcatcat ggacgtggcc gttttccgtc tgtcgaagcg tgaccgacga  10200
gctggcgagg tgatccgcta cgagcttcca gacgggcacg tagaggtttc cgcagggccg  10260
gccggcatgg ccagtgtgtg ggattacgac ctggtactga tggcggtttc ccatctaacc  10320
gaatccatga accgataccg ggaagggaag ggagacaagc ccggccgcgt gttccgtcca  10380
cacgttgcgg acgtactcaa gttctgccgg cgagccgatg gcggaaagca gaaagacgac  10440
ctggtagaaa cctgcattcg gttaaacacc acgcacgttg ccatgcagcg tacgaagaag  10500
gccaagaacg gccgcctggt gacggtatcc gagggtgaag ccttgattag ccgctacaag  10560
atcgtaaaga gcgaaaccgg gcggccggag tacatcgaga tcgagctagc tgattggatg  10620
taccgcgaga tcacagaagg caagaacccg gacgtgctga cggttcaccc cgattacttt  10680
ttgatcgatc ccggcatcgg ccgttttctc taccgcctgg cacgccgcgc cgcaggcaag  10740
gcagaagcca gatggttgtt caagacgatc tacgaacgca gtggcagcgc cggagagttc  10800
aagaagttct gtttcaccgt gcgcaagctg atcgggtcaa atgacctgcc ggagtacgat  10860
```

```
ttgaaggagg aggcggggca ggctggcccg atcctagtca tgcgctaccg caacctgatc  10920

gagggcgaag catccgccgg ttcctaatgt acggagcaga tgctagggca aattgcccta  10980

gcaggggaaa aaggtcgaaa aggcctcttt cctgtggata gcacgtacat tgggaaccca  11040

aagccgtaca ttgggaaccg gaacccgtac attgggaacc caaagccgta cattgggaac  11100

cggtcacaca tgtaagtgac tgatataaaa gagaaaaaag gcgatttttc cgcctaaaac  11160

tctttaaaac ttattaaaac tcttaaaacc cgcctggcct gtgcataact gtctggccag  11220

cgcacagccc aagagctgca aaaagcgcct acccttcggt cgctgcgctc cctacgcccc  11280

gccgcttcgc gtcggcctat cgcggccgct ggccgctcaa aaatggctgg cctacggcca  11340

ggcaatctac cagggcgcgg acaagccgcg ccgtcgccac tcgaccgccg gcgcccacat  11400

caaggcaccc tgcctcgcgc gtttcggtga tgacggtgaa aacctctgac acatgcagct  11460

cccggaaacg gtcacagctt gtctgtaagc ggatgccggg agcagacaag cccgtcaggg  11520

cgcgtcagcg ggtgttggcg ggtgtcgggg cgcagccatg acccagtcac gtagcgatag  11580

cggagtgtat actggcttaa ctatgcggca tcagagcaga ttgtactgag agtgcaccat  11640

atgcggtgtg aaataccgca cagatgcgta aggagaaaat accgcatcag gccctcttcc  11700

gcttcctcgc tcactgactc gctgcgctcg gtcgttcggc tgcggcgagc ggtatcagct  11760

cactcaaagg cggtaatacg gttatccaca gaatcagggg ataacgcagg aaagaacatg  11820

tgagcaaaag gccagcaaaa ggccaggaac cgtaaaaagg ccgcgttgct ggcgtttttc  11880

cataggctcc gcccccctga cgagcatcac aaaaatcgac gctcaagtca gaggtggcga  11940

aacccgacag gactataaag ataccaggcg tttccccctg gaagctccct cgtgcgctct  12000

cctgttccga ccctgccgct taccggatac ctgtccgcct ttctcccttc gggaagcgtg  12060

gcgctttctc atagctcacg ctgtaggtat ctcagttcgg tgtaggtcgt tcgctccaag  12120

ctgggctgtg tgcacgaacc ccccgttcag cccgaccgct gcgccttatc cggtaactat  12180

cgtcttgagt ccaacccggt aagacacgac ttatcgccac tggcagcagc cactggtaac  12240

aggattagca gagcgaggta t                                            12261
```

<210> SEQ ID NO 20
<211> LENGTH: 24
<212> TYPE: DNA
<213> ORGANISM: artificial
<220> FEATURE:
<223> OTHER INFORMATION: synthetic oligonucleotide

<400> SEQUENCE: 20

```
tgggaactga aagtcaagat ggtc                                            24
```

<210> SEQ ID NO 21
<211> LENGTH: 22
<212> TYPE: DNA
<213> ORGANISM: artificial
<220> FEATURE:
<223> OTHER INFORMATION: synthetic oligonucleotide

<400> SEQUENCE: 21

```
acaataaatg ggatgggcct gg                                              22
```

<210> SEQ ID NO 22
<211> LENGTH: 24
<212> TYPE: DNA
<213> ORGANISM: artificial
<220> FEATURE:
<223> OTHER INFORMATION: synthetic oligonucleotide

<400> SEQUENCE: 22
tgggaactga aagtcaagat gttt 24

<210> SEQ ID NO 23
<211> LENGTH: 25
<212> TYPE: DNA
<213> ORGANISM: artificial
<220> FEATURE:
<223> OTHER INFORMATION: synthetic oligonucleotide

<400> SEQUENCE: 23
caaaagctag cttatgaggt gaagc 25

<210> SEQ ID NO 24
<211> LENGTH: 4140
<212> TYPE: DNA
<213> ORGANISM: Streptococcus pyogenes

<400> SEQUENCE: 24
atggataaga agtactctat cggactcgat atcggaacta actctgtggg atgggctgtg 60
atcaccgatg agtacaaggt gccatctaag aagttcaagg ttctcggaaa caccgatagg 120
cactctatca agaaaaacct tatcggtgct ctcctcttcg attctggtga aactgctgag 180
gctaccagac tcaagagaac cgctagaaga aggtacacca gaagaaagaa caggatctgc 240
tacctccaag agatcttctc taacgagatg gctaaagtgg atgattcatt cttccacagg 300
ctcgaagagt cattcctcgt ggaagaagat aagaagcacg agaggcaccc tatcttcgga 360
aacatcgttg atgaggtggc ataccacgag aagtacccta ctatctacca cctcagaaag 420
aagctcgttg attctactga taaggctgat ctcaggctca tctacctcgc tctcgctcac 480
atgatcaagt tcagaggaca cttcctcatc gagggtgatc tcaaccctga taactctgat 540
gtggataagt tgttcatcca gctcgtgcag acctacaacc agcttttcga agagaaccct 600
atcaacgctt caggtgtgga tgctaaggct atcctctctg ctaggctctc taagtcaaga 660
aggcttgaga acctcattgc tcagctccct ggtgagaaga agaacggact tttcggaaac 720
ttgatcgctc tctctctcgg actcacccct aacttcaagt ctaacttcga tctcgctgag 780
gatgcaaagc tccagctctc aaaggatacc tacgatgatg atctcgataa cctcctcgct 840
cagatcggag atcagtacgc tgatttgttc ctcgctgcta agaacctctc tgatgctatc 900
ctcctcagtg atatcctcag agtgaacacc gagatcacca aggctccact ctcagcttct 960
atgatcaaga gatacgatga gcaccaccag gatctcacac ttctcaaggc tcttgttaga 1020
cagcagctcc cagagaagta caaagagatt ttcttcgatc agtctaagaa cggatacgct 1080
ggttacatcg atggtggtgc atctcaagaa gagttctaca agttcatcaa gcctatcctc 1140
gagaagatgg atggaaccga ggaactcctc gtgaagctca atagagagga tcttctcaga 1200
aagcagagga ccttcgataa cggatctatc cctcatcaga tccacctcgg agagttgcac 1260
gctatcctta gaaggcaaga ggatttctac ccattcctca aggataacag ggaaaagatt 1320
gagaagattc tcaccttcag aatcccttac tacgtgggac ctctcgctag aggaaactca 1380
agattcgctt ggatgaccag aaagtctgag gaaaccatca ccccttggaa cttcgaagag 1440
gtggtggata agggtgctag tgctcagtct ttcatcgaga ggatgaccaa cttcgataag 1500
aaccttccaa acgagaaggt gctccctaag cactctttgc tctacgagta cttcaccgtg 1560
tacaacgagt tgaccaaggt taagtacgtg accgagggaa tgaggaagcc tgctttttg 1620 tcaggtgagc aaaagaaggc tatcgttgat ctcttgttca agaccaacag aaaggtgacc 1680
gtgaagcagc tcaaagagga ttacttcaag aaaatcgagt gcttcgattc agttgagatt 1740
tctggtgttg aggataggtt caacgcatct ctcggaacct accacgatct cctcaagatc 1800
attaaggata aggatttctt ggataacgag gaaaacgagg atatcttgga ggatatcgtt 1860
cttaccctca ccctctttga agatagagag atgattgaag aaaggctcaa gacctacgct 1920
catctcttcg atgataaggt gatgaagcag ttgaagagaa gaagatacac tggttgggga 1980
aggctctcaa gaaagctcat taacggaatc agggataagc agtctggaaa gacaatcctt 2040
gatttcctca agtctgatgg attcgctaac agaaacttca tgcagctcat ccacgatgat 2100
tctctcacct ttaaagagga tatccagaag gctcaggttt caggacaggg tgatagtctc 2160
catgagcata tcgctaacct cgctggatct cctgcaatca agaagggaat cctccagact 2220
gtgaaggttg tggatgagtt ggtgaaggtg atgggaaggc ataagcctga gaacatcgtg 2280
atcgaaatgg ctagagagaa ccagaccact cagaagggac agaagaactc tagggaaagg 2340
atgaagagga tcgaggaagg tatcaaagag cttggatctc agatcctcaa agagcaccct 2400
gttgagaaca ctcagctcca gaatgagaag ctctacctct actacctcca gaacggaagg 2460
gatatgtatg tggatcaaga gttggatatc aacaggctct ctgattacga tgttgatcat 2520
atcgtgccac agtcattctt gaaggatgat tctatcgata acaaggtgct caccaggtct 2580
gataagaaca ggggtaagag tgataacgtg ccaagtgaag aggttgtgaa gaaaatgaag 2640
aactattgga ggcagctcct caacgctaag ctcatcactc agagaaagtt cgataacttg 2700
actaaggctg agaggggagg actctctgaa ttggataagg caggattcat caagaggcag 2760
cttgtggaaa ccaggcagat cactaagcac gttgcacaga tcctcgattc taggatgaac 2820
accaagtacg atgagaacga taagttgatc agggaagtga aggttatcac cctcaagtca 2880
aagctcgtgt ctgatttcag aaaggatttc caattctaca aggtgaggga aatcaacaac 2940
taccaccacg ctcacgatgc ttaccttaac gctgttgttg gaaccgctct catcaagaag 3000
tatcctaagc tcgagtcaga gttcgtgtac ggtgattaca aggtgtacga tgtgaggaag 3060
atgatcgcta agtctgagca agagatcgga aaggctaccg ctaagtattt cttctactct 3120
aacatcatga atttcttcaa gaccgagatt accctcgcta acggtgagat cagaaagagg 3180
ccactcatcg agacaaacgg tgaaacaggt gagatcgtgt gggataaggg aagggatttc 3240
gctaccgtta gaaaggtgct ctctatgcca caggtgaaca tcgttaagaa aaccgaggtg 3300
cagaccggtg gattctctaa agagtctatc ctccctaaga ggaactctga taagctcatt 3360
gctaggaaga aggattggga ccctaagaaa tacggtggtt tcgattctcc taccgtggct 3420
tactctgttc tcgttgtggc taaggttgag aagggaaaga gtaagaagct caagtctgtt 3480
aaggaacttc tcggaatcac tatcatggaa aggtcatctt tcgagaagaa cccaatcgat 3540
ttcctcgagg ctaagggata caaagaggtt aagaaggatc tcatcatcaa gctcccaaag 3600
tactcactct tcgaactcga gaacggtaga aagaggatgc tcgcttctgc tggtgagctt 3660
caaaagggaa acgagcttgc tctcccatct aagtacgtta actttcttta cctcgcttct 3720
cactacgaga agttgaaggg atctccagaa gataacgagc agaagcaact tttcgttgag 3780
cagcacaagc actacttgga tgagatcatc gagcagatct ctgagttctc taaaagggtg 3840
atcctcgctg atgcaaacct cgataaggtg ttgtctgctt acaacaagca cagagataag 3900
cctatcaggg aacaggcaga gaacatcatc catctcttca cccttaccaa cctcggtgct 3960
cctgctgctt tcaagtactt cgatacaacc atcgatagga agagatacac ctctaccaaa 4020
gaagtgctcg atgctaccct catccatcag tctatcactg gactctacga gactaggatc 4080
gatctctcac agctcggtgg tgattcaagg gctgatccta agaagaagag gaaggtttga 4140

<210> SEQ ID NO 25
<211> LENGTH: 940
<212> TYPE: DNA
<213> ORGANISM: Agrobacterium tumefaciens

<400> SEQUENCE: 25
ccttttattt tcttcttttt tccatattta gggttgacag tgaaatcaga ctggcaacct 60
attaattgct tccacaatgg gacgaacttg aaggggatgt cgtcgatgat attataggtg 120
gcgtgttcat cgtagttggt gaaatcgatg gtaccgttcc aatagttgtg tcgtccgaga 180
cttctagccc aggtggtctt tccggtacga gttggtccgc agatgtagag gctggggtgt 240
cggattccat tccttccatt gtccttgtta aatcggccat ccattcaagg tcagattgag 300
cttgttggta tgagacagga tgtatgtaag tataagcgtc tatgcttaca tggtatagat 360
gggtttccct ccaggagtgt agatcttcgt ggcagcgaag atctgattct gtgaagggcg 420
acacatacgg ttcaggttgt ggagggaata atttgttggc tgaatattcc agccattgaa 480
gctttgttgc ccattcatga gggaattctt ccttgatcat gtcaagatat tcctccttag 540
acgttgcagt ctggataata gttctccatc gtgcgtcaga tttgcgagga gaaaccttat 600
gatctcggaa atctcctctg gttttaatat ctccgtcctt tgatatgtaa tcaaggactt 660
gtttagagtt tctagctggc tggatattag ggtgatttcc ttcaaaatcg aaaaaagaag 720
gatccctaat acaaggtttt ttatcaagct ggagaagagc atgatagtgg gtagtgccat 780
cttgatgaag ctcagaagca acaccaagga agaaaataag aaaaggtgtg agtttctccc 840
agagaaactg gaataaatca tctctttgag atgagcactt gggataggta aggaaaacat 900
atttagattg gagtctgaag ttcttactag cagaaggcat 940

<210> SEQ ID NO 26
<211> LENGTH: 17275
<212> TYPE: DNA
<213> ORGANISM: artificial
<220> FEATURE:
<223> OTHER INFORMATION: synthetic oligonucleotide

<400> SEQUENCE: 26
gtaggcggtg ctacagagtt cttgaagtgg tggcctaact acggctacac tagaaggaca 60
gtatttggta tctgcgctct gctgaagcca gttaccttcg gaaaaagagt tggtagctct 120
tgatccggca aacaaaccac cgctggtagc ggtggttttt ttgtttgcaa gcagcagatt 180
acgcgcagaa aaaaaggatc tcaagaagat cctttgatct tttctacggg gtctgacgct 240
cagtggaacg aaaactcacg ttaagggatt ttggtcatgc attctaggta ctaaaacaat 300
tcatccagta aaatataata ttttattttc tcccaatcag gcttgatccc cagtaagtca 360
aaaaatagct cgacatactg ttcttccccg atatcctccc tgatcgaccg gacgcagaag 420
gcaatgtcat accacttgtc cgccctgccg cttctcccaa gatcaataaa gccacttact 480
ttgccatctt tcacaaagat gttgctgtct cccaggtcgc cgtgggaaaa gacaagttcc 540
tcttcgggct tttccgtctt taaaaaatca tacagctcgc gcggatcttt aaatggagtg 600
tcttcttccc agttttcgca atccacatcg gccagatcgt tattcagtaa gtaatccaat 660
tcggctaagc ggctgtctaa gctattcgta tagggacaat ccgatatgtc gatggagtga 720

-continued

```
aagagcctga tgcactccgc atacagctcg ataatctttt cagggctttg ttcatcttca    780
tactcttccg agcaaaggac gccatcggcc tcactcatga gcagattgct ccagccatca    840
tgccgttcaa agtgcaggac ctttggaaca ggcagctttc cttccagcca tagcatcatg    900
tccttttccc gttccacatc ataggtggtc cctttatacc ggctgtccgt catttttaaa    960
tataggtttt cattttctcc caccagctta tataccttag caggagacat tccttccgta   1020
tcttttacgc agcggtattt ttcgatcagt tttttcaatt ccggtgatat tctcatttta   1080
gccatttatt atttccttcc tcttttctac agtatttaaa gataccccaa gaagctaatt   1140
ataacaagac gaactccaat tcactgttcc ttgcattcta aaaccttaaa taccagaaaa   1200
cagctttttc aaagttgttt tcaaagttgg cgtataacat agtatcgacg gagccgattt   1260
tgaaaccgcg gtgatcacag gcagcaacgc tctgtcatcg ttacaatcaa catgctaccc   1320
tccgcgagat catccgtgtt tcaaacccgg cagcttagtt gccgttcttc cgaatagcat   1380
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg   1500
gctggctggt ggcaggatat attgtggtgt aaacaaattg acgcttagac aacttaataa   1560
cacattgcgg acgtttttaa tgtactgaat taacgccgaa ttaattcggg ggatctggat   1620
tttagtactg gattttggtt ttaggaatta gaaattttat tgatagaagt attttacaaa   1680
tacaaataca tactaagggt ttcttatatg ctcaacacat gagcgaaacc ctataggaac   1740
cctaattccc ttatctggga actactcaca cattattatg gagaaactcg agcttgtcga   1800
tcgactctag ctagaggatc gatccgaacc ccagagtccc gctcagaaga actcgtcaag   1860
aaggcgatag aaggcgatgc gctgcgaatc gggagcggcg ataccgtaaa gcacgaggaa   1920
gcggtcagcc cattcgccgc caagttcttc agcaatatca cgggtagcca acgctatgtc   1980
ctgatagcgg tccgccacac ccagccggcc acagtcgatg aatccagaaa agcggccatt   2040
ttccaccatg atattcggca agcaggcatc gccatgtgtc acgacgagat cctcgccgtc   2100
gggcatgcgc gccttgagcc tggcgaacag ttcggctggc gcgagcccct gatgttcttc   2160
gtccagatca tcctgatcga caagaccggc ttccatccga gtacgtgctc gctcgatgcg   2220
atgtttcgct tggtggtcga atgggcaggt agccggatca agcgtatgca gccgccgcat   2280
tgcatcagcc atgatggata ctttctcggc aggagcaagg tgagatgaca ggagatcctg   2340
ccccggcact tcgcccaata gcagccagtc ccttcccgct tcagtgacaa cgtcgagcac   2400
agctgcgcaa ggaacgcccg tcgtggccag ccacgatagc cgcgctgcct cgtcctggag   2460
ttcattcagg gcaccggaca ggtcggtctt gacaaaaaga accgggcgcc cctgcgctga   2520
cagccgaaac acggcggcat cagagcagcc gattgtctgt tgtgcccagt catagccgaa   2580
tagcctctcc acccaagcgg ccggagaacc tgcgtgcaat ccatcttgtt caatccccat   2640
ggtcgatcga cagatctgcg aaagctcgag agagatagat ttgtagagag agactggtga   2700
tttcagcgtg tcctctccaa atgaaatgaa cttccttata tagaggaagg tcttgcgaag   2760
gatagtggga ttgtgcgtca tcccttacgt cagtggagat atcacatcaa tccacttgct   2820
ttgaagacgt ggttggaacg tcttcttttt ccacgatgct cctcgtgggt gggggtccat   2880
ctttgggacc actgtcggca gaggcatctt gaacgatagc ctttccttta tcgcaatgat   2940
ggcatttgta ggtgccacct tccttttcta ctgtcctttt gatgaagtga cagatagctg   3000
ggcaatggaa tccgaggagg tttcccgata ttaccctttg ttgaaaagtc tcaatagccc   3060
tttggtcttc tgagactgta tctttgatat tcttggagta gacgagagtg tcgtgctcca   3120
```

-continued

```
ccatgttatc acatcaatcc acttgctttg aagacgtggt tggaacgtct tctttttcca   3180
cgatgctcct cgtgggtggg ggtccatctt tgggaccact gtcggcagag gcatcttgaa   3240
cgatagcctt tcctttatcg caatgatggc atttgtaggt gccaccttcc ttttctactg   3300
tccttttgat gaagtgacag atagctgggc aatggaatcc gaggaggttt cccgatatta   3360
ccctttgttg aaaagtctca atagcccttt ggtcttctga gactgtatct ttgatattct   3420
tggagtagac gagagtgtcg tgctccacca tgttggcaag ctgctctagc caatacgcaa   3480
accgcctctc cccgcgcgtt ggccgattca ttaatgcagc tggcacgaca ggtttcccga   3540
ctggaaagcg ggcagtgagc gcaacgcaat taatgtgagt tagctcactc attaggcacc   3600
ccaggcttta cactttatgc ttccggctcg tatgttgtgt ggaattgtga gcggataaca   3660
atttcacaca ggaaacagct atgaccatga ttacgaattc gagctcaaag tttaacgcgt   3720
tagcagaagg catgttgttg tgactccgag ggttgcctc aaactctatc ttataaccgg   3780
cgtggaggca tggaggcagg ggtattttgg tcattttaat agatagtgga aaatgacgtg   3840
gaatttactt aaagacgaag tctttgcgac aagggggggc ccacgccgaa tttaatatta   3900
ccggcgtggc ccccccttat cgcgagtgct ttagcacgag cggtccagat ttaaagtaga   3960
aaatttcccg cccactaggg ttaaaggtgt tcacactata aaagcatata cgatgtgatg   4020
gtatttgatg gagcgtatat tgtatcaggt atttccgttg gatacgaatt attcgtacga   4080
ccctcggtac cgatcaaaag caggtgtggc gcgccagatt tgccttttca atttcagaaa   4140
gaatgctaac ccacagatgg ttagagaggc ttacgcagca ggtatcatca agacgatcta   4200
cccgagcaat aatctccagg aaatcaaata ccttcccaag aaggttaaag atgcagtcaa   4260
aagattcagg actaactgca tcaagaacac agagaaagat atatttctca agatcagaag   4320
tactattcca gtatggacga ttcaaggctt gcttcacaaa ccaaggcaag taatagagat   4380
tggagtctct aaaaaggtag ttcccactga atcaaaggcc atggagtcaa agattcaaat   4440
agaggaccta acagaactcg ccgtaaagac tggcgaacag ttcatacaga gtctcttacg   4500
actcaatgac aagaagaaaa tcttcgtcaa catggtggag cacgacacac ttgtctactc   4560
caaaaatatc aaagatacag tctcagaaga ccaaagggca attgagactt ttcaacaaag   4620
ggtaatatcc ggaaacctcc tcggattcca ttgcccagct atctgtcact ttattgtgaa   4680
gatagtggaa aaggaaggtg gctcctacaa atgccatcat tgcgataaag gaaaggccat   4740
cgttgaagat gcctctgccg acagtggtcc caaagatgga cccccaccca cgaggagcat   4800
cgtggaaaaa gaagacgttc caaccacgtc ttcaaagcaa gtggattgat gtgatatctc   4860
cactgacgta agggatgacg cacaatccca ctatccttcg caagaccctt cctctatata   4920
aggaagttca tttcatttgg agagaacacg ggggactcct gcaggatgga agacgccaaa   4980
aacataaaga aaggcccggc gccattctat ccgctggaag atggaaccgc tggagagcaa   5040
ctgcataagg ctatgaagag atacgccctg gttcctggaa caattgcttt tacagatgca   5100
catatcgagg tggacatcac ttacgctgag tacttcgaaa tgtccgttcg gttggcagaa   5160
gctatgaaac gatatgggct gaatacaaat cacagaatcg tcgtatgcag tgaaaactct   5220
cttcaattct ttatgccggt gttgggcgcg ttatttatcg gagttgcagt tgcgcccgcg   5280
aacgacattt ataatgaacg tgaattgctc aacagtatgg gcatttcgca gcctaccgtg   5340
gtgttcgttt ccaaaaaggg gttgcaaaaa attttgaacg tgcaaaaaaa gctcccaatc   5400
atccaaaaaa ttattatcat ggattctaaa acggattacc agggatttca gtcgatgtac   5460
```

-continued

```
acgttcgtca catctcatct acctcccggt tttaatgaat acgattttgt gccagagtcc   5520
ttcgataggg acaagacaat tgcactgatc atgaactcct ctggatctac tggtctgcct   5580
aaaggtgtcg ctctgcctca tagaactgcc tgcgtgagat tctcgcatgc cagagatcct   5640
atttttggca atcaaatcat tccggatact gcgattttaa gtgttgttcc attccatcac   5700
ggttttggaa tgtttactac actcggatat ttgatatgtg gatttcgagt cgtcttaatg   5760
tatagatttg aagaagagct gtttctgagg agccttcagg attacaagat tcaaagtgcg   5820
ctgctggtgc caaccctatt ctccttcttc gccaaaagca ctctgattga caaatacgat   5880
ttatctaatt tacacgaaat tgcttctggt ggcgctcccc tctctaagga agtcggggaa   5940
gcggttgcca agaggttcca tctgccaggt atcaggcaag gatatgggct cactgagact   6000
acatcagcta ttctgattac acccgagggg gatgataaac cgggcgcggt cggtaaagtt   6060
gttccatttt ttgaagcgaa ggttgtggat ctggataccg ggaaaacgct gggcgttaat   6120
caaagaggcg aactgtgtgt gagaggtcct atgattatgt ccggttatgt aaacaatccg   6180
gaagcgacca acgccttgat tgacaaggat ggatggctac attctggaga catagcttac   6240
tgggacgaag acgaacactt cttcatcgtt gaccgcctga agtctctgat taagtacaaa   6300
ggctatcagg tggctcccgc tgaattggaa tccatcttgc tccaacaccc caacatcttc   6360
gacgctggtg tcgcaggtct tcccgacgat gacgccggtg aacttcccgc cgccgttgtt   6420
gttttggagc acggaaagac gatgacggaa aaagagatcg tggattacgt cgccagtcaa   6480
gtaacaaccg cgaaaaagtt gcgcggagga gttgtgtttg tggacgaagt accgaaaggt   6540
cttaccggaa aactcgacgc aagaaaaatc agagagatcc tcataaaggc caagaagggc   6600
ggaaagatcg ccgtgtgacg tcgacgatat gaagatgaag atgaaatatt tggtgtgtca   6660
aataaaaagc ttgtgtgctt aagtttgtgt ttttttcttg gcttgttgtg ttatgaattt   6720
gtggcttttt ctaatattaa atgaatgtaa gatcacatta taatgaataa acaaatgttt   6780
ctataatcca ttgtgaatgt tttgttggat ctcttctgca gcatataact actgtatgtg   6840
ctatggtatg gactatggaa tatgattaaa gataagccag agctctggtg acggacggcg   6900
cgactagttt tacgtacgtt aattaacccg ggcgcgccga tcatgagcgg agaattaagg   6960
gagtcacgtt atgacccccg ccgatgacgc gggacaagcc gttttacgtt tggaactgac   7020
agaaccgcaa cgttgaagga gccactcagc cgcgggtttc tggagtttaa tgagctaagc   7080
acatacgtca gaaaccatta ttgcgcgttc aaaagtcgcc taaggtcact atcagctagc   7140
aaatatttct tgtcaaaaat gctccactga cgttccataa attcccctcg gtatccaatt   7200
agagtctcat attcactctc aatccaaata atctgcaccg tacctgcagg gtccgagcta   7260
ggtcacagaa gcgctcagga aggccgctga gatagaggca tggcggccaa tgcgggcggc   7320
ggtggagcgg gaggaggcag cggcagcggc agcgtggctg cgccggcggt gtgccgcccc   7380
agcggctcgc ggtggacgcc gacgccggag cagatcagga tgctgaagga gctgtactac   7440
ggctgcggca tccggtcgcc cagctcggag cagatccagc gcatcaccgc catgctgcgg   7500
cagcacggca agatcgaggg caagaacgtc ttctactggt tccagaacca caaggcccgc   7560
gagcgccaga agcgccgcct caccagcctc gacgtgaacg tgcccgccgc cggcgcggcc   7620
gacgccacca ccagccaact cggcgtcctc tcgctgtcgt cgccgccgcc ttcaggcgcg   7680
gcgcctccct cgcccaccct cggcttctac gccgccggca atggcggcgg atcggctgtg   7740
ctgctggaca cgagttccga ctggggcagc agcggcgctg cgatggccac cgagacatgc   7800
ttcctccagg actacatggg cgtgacggac acgggcagct cgtcgcagtg gccacgcttc   7860
```

tcgtcgtcgg acacgataat ggcggcggcc gcggcgcggg cggcgacgac gcgggcgccc 7920
gagactctcc ctctcttccc gacctgcggc gacgacggcg gcagcggtag cagcagctac 7980
ttgccgttct ggggtgccgc gtccacaact gccggcgcca cttcttccgt tgcgatccag 8040
cagcaacacc agctgcagga gcagtacagc ttttacagca acagcaacag cacccagctg 8100
gccggcaccg gcaaccaaga cgtatcggca acagcagcag cagccgccgc cctggagctg 8160
agcctcagct catggtgctc cccttaccct gctgcaggga gtatgtgaga gcaacgcgag 8220
ctgccactgc tcttcactta tgtctctgga atggaaggag gaggaagtga gcatagcgtt 8280
ggtgcgttgc tgtcattgtc ctaggttagt agctagtgcc agttactagt aagcatcagg 8340
cataggagta tgtagtagaa gcatgcacgt tgccggccag ccaggcttta gacgggaaaa 8400
gaatttggtg cagccggctg caaaacagga tgtttacagc cccccctcg agccctagac 8460
ttgtccatct tctggattgg ccaagttaat taatgtatga aataaaagga tgcacacata 8520
gtgacatgct aatcactata atgtgggcat caaagttgtg tgttatgtgt aattactaat 8580
tatctgaata agagaaagag atcatccata tttcttatcc taaatgaatg tcacgtgtct 8640
ttataattct ttgatgaacc agatgcattt tattaaccaa ttccatatac atataaatat 8700
taatcatata taattaatat caattgggtt agcaaaacaa atctagtcta ggtgtgtttt 8760
gctaattatt gggggatagt gcaaaaagaa atctacgttc tcaataattc agatagaaaa 8820
cttaataaag tgagataatt tacatagatt gcttttatcc tttgatatat gtgaaaccat 8880
gcatgatata aggaaaatag atagagaaat aattttttac atcgttgaat atgtaaacaa 8940
tttaattcaa gaagctagga atataaatat tgaggagttt atgattagag ctctcccact 9000
aaacgtcccg ctggcagaca tactgtccca caaatgaaga tggaatctgt aaaagaaaac 9060
gcgtgaaata atgcgtctga caaaggttag gtcggctgcc tttaatcaat accaaagtgg 9120
tccctaccac gatggaaaaa ctgtgcagtc ggtttggctt tttctgacga acaaataaga 9180
ttcgtggccg acaggtgggg gtccaccatg tgaaggcatc ttcagactcc aataatggag 9240
caatgacgta agggcttacg aaataagtaa gggtagtttg ggaaatgtcc actcacccgt 9300
cagtctataa atacttagcc cctccctcat tgttaaggga gcaaaatctc agagagatag 9360
tcctagagag agaaagagag caagtagcct agaagtagtc aaggcggcga agtattcagg 9420
cacgtggcca ggaagaagaa aagccaagac gacgaaaaca ggtaagagct aagcttatgg 9480
agagtggttc caacagcact tcttgtccaa tggcttttgc cggggataat agtgatggtc 9540
cgatgtgtcc tatgatgatg atgatgccgc ccatcatgac atcacatcaa catcatggtc 9600
atgatcatca acatcaacaa caagaacatg atggttatgc atatcagtca caccaccaac 9660
aaagtagttc cctttttctt caatcactag ctcctcccca aggaactaag aacaaagttg 9720
cttcttcttc ttctccttcc tcttgtgctc ctgcctattc tctaatggag atccatcata 9780
acgaaatcgt tgcaggagga atcaaccctt gctcctcttc ctcttcttca gcctctgtca 9840
aggccaagat catggctcat cctcactacc accgcctctt ggccgcttat gtcaattgtc 9900
agaaggttgg agcaccaccg gaggttgtgg cgaggctaga ggaggcatgc tcgtctgccg 9960
cagccgctgc cgcatctatg ggaccaacag gatgtctagg tgaagatcca gggcttgatc 10020
aattcatgga agcttactgt gaaatgctcg ttaagtatga gcaagagctc tccaaacctt 10080
tcaaggaagc tatggtcttc cttcaacgtg tcgagtgtca attcaaatcc ctctctctat 10140
cctcaccttc ctctttctcc ggttatggag agacagcaat tgataggaac aataatgggt 10200

-continued

```
catccgagga agaagtcgat atgaacaatg aatttgtaga tccacaagct gaggatagag  10260
agcttaaagg acagctcttg cgcaagtaca gtggttactt agggagcctc aagcaagagt  10320
tcatgaagaa gaggaagaaa ggaaagctcc ctaaagaagc tcgtcaacaa ctgcttgatt  10380
ggtggagccg tcactacaaa tggccttacc cttcggagca acaaaagctc gcccttgcgg  10440
aatcaacggg gctggaccag aaacagataa acaattggtt cataaaccag aggaaacggc  10500
attggaagcc gtcggaggac atgcagtttg tagtaatgga cgcaacacat cctcaccatt  10560
acttcatgga taatgtcttg ggcaatcctt tcccaatgga tcacatctcc tccaccatgc  10620
tttgactcga gtttctccat aataatgtgt gagtagttcc cagataaggg aattagggtt  10680
cctatagggt ttcgctcatg tgttgagcat ataagaaacc cttagtatgt atttgtattt  10740
gtaaaatact tctatcaata aaatttctaa ttcctaaaac caaaatccag tactaaaatc  10800
cagatccccc gaattaagtg actacacctg caaaaagtgt ttgatcgccg gcggtaccga  10860
gtgtacttca agtcagtggg aaatcaataa aatgattatt ttatgaatat atttcattgt  10920
gcaagtagat agaaattaca tatgttacat aacacacgaa ataaacaaaa aaagacaatc  10980
caaaaacaaa caccccaaaa aaaataatca ctttagataa actcgtatga ggagaggcac  11040
gttcagtgac tcgacgattc ccgagcaaaa aaagtctccc cgtcacacat gtagtgggtg  11100
acgcaattat ctttaaagta atccttctgt tgacttgtca ttgataacat ccagtcttcg  11160
tcaggattgc aaagaattat agaagggatc ccacctttta ttttcttctt ttttccatat  11220
ttagggttga cagtgaaatc agactggcaa cctattaatt gcttccacaa tgggacgaac  11280
ttgaagggga tgtcgtcgat gatattatag gtggcgtgtt catcgtagtt ggtgaaatcg  11340
atggtaccgt tccaatagtt gtgtcgtccg agacttctag cccaggtggt ctttccggta  11400
cgagttggtc cgcagatgta gaggctgggg tgtcggattc cattccttcc attgtccttg  11460
ttaaatcggc catccattca aggtcagatt gagcttgttg gtatgagaca ggatgtatgt  11520
aagtataagc gtctatgctt acatggtata gatgggtttc cctccaggag tgtagatctt  11580
cgtggcagcg aagatctgat tctgtgaagg gcgacacata cggttcaggt tgtggaggga  11640
ataatttgtt ggctgaatat tccagccatt gaagctttgt tgcccattca tgagggaatt  11700
cttccttgat catgtcaaga tattcctcct tagacgttgc agtctggata atagttctcc  11760
atcgtgcgtc agatttgcga ggagaaacct tatgatctcg gaaatctcct ctggttttaa  11820
tatctccgtc ctttgatatg taatcaagga cttgtttaga gtttctagct ggctggatat  11880
tagggtgatt tccttcaaaa tcgaaaaaag aaggatccct aatacaaggt tttttatcaa  11940
gctggagaag agcatgatag tgggtagtgc catcttgatg aagctcagaa gcaacaccaa  12000
ggaagaaaat aagaaaaggt gtgagtttct cccagagaaa ctggaataaa tcatctcttt  12060
gagatgagca cttgggatag gtaaggaaaa catatttaga ttggagtctg aagttcttac  12120
tagcagaagg catgttgttg tgactccgag gggttgcctc aaactctatc ttataaccgg  12180
cgtggaggca tggaggcagg ggtattttgg tcattttaat agatagtgga aaatgacgtg  12240
gaatttactt aaagacgaag tctttgcgac aagggggggc ccacgccgaa tttaatatta  12300
ccggcgtggc cccccttat cgcgagtgct ttagcacgag cggtccagat ttaaagtaga  12360
aaatttcccg cccactaggg ttaaaggtgt tcacactata aaagcatata cgatgtgatg  12420
gtatttgatg gagcgtatat tgtatcaggt atttccgttg gatacgaatt attcgtacga  12480
ccctcatagt ttaaactatc agtgtttgac aggatatatt ggcgggtaaa cctaagagaa  12540
aagagcgttt attagaataa cggatattta aaagggcgtg aaaaggttta tccgttcgtc  12600
```

```
catttgtatg tgcatgccaa ccacagggtt cccctcggga tcaaagtact ttgatccaac  12660
ccctccgctg ctatagtgca gtcggcttct gacgttcagt gcagccgtct tctgaaaacg  12720
acatgtcgca caagtcctaa gttacgcgac aggctgccgc cctgcccttt tcctggcgtt  12780
ttcttgtcgc gtgttttagt cgcataaagt agaatacttg cgactagaac cggagacatt  12840
acgccatgaa caagagcgcc gccgctggcc tgctgggcta tgcccgcgtc agcaccgacg  12900
accaggactt gaccaaccaa cgggccgaac tgcacgcggc cggctgcacc aagctgtttt  12960
ccgagaagat caccggcacc aggcgcgacc gcccggagct ggccaggatg cttgaccacc  13020
tacgccctgg cgacgttgtg acagtgacca ggctagaccg cctggcccgc agcacccgcg  13080
acctactgga cattgccgag cgcatccagg aggccggcgc gggcctgcgt agcctggcag  13140
agccgtgggc cgacaccacc acgccggccg gccgcatggt gttgaccgtg ttcgccggca  13200
ttgccgagtt cgagcgttcc ctaatcatcg accgcacccg gagcgggcgc gaggccgcca  13260
aggcccgagg cgtgaagttt ggcccccgcc ctaccctcac cccggcacag atcgcgcacg  13320
cccgcgagct gatcgaccag gaaggccgca ccgtgaaaga ggcggctgca ctgcttggcg  13380
tgcatcgctc gaccctgtac cgcgcacttg agcgcagcga ggaagtgacg cccaccgagg  13440
ccaggcggcg cggtgccttc cgtgaggacg cattgaccga ggccgacgcc ctggcggccg  13500
ccgagaatga acgccaagag gaacaagcat gaaaccgcac caggacggcc aggacgaacc  13560
gtttttcatt accgaagaga tcgaggcgga gatgatcgcg gccgggtacg tgttcgagcc  13620
gcccgcgcac ggctcaaccg tgcggctgca tgaaatcctg gccggtttgt ctgatgccaa  13680
gctggcggcc tggccggcca gcttggccgc tgaagaaacc gagcgccgcc gtctaaaaag  13740
gtgatgtgta tttgagtaaa acagcttgcg tcatgcggtc gctgcgtata tgatgcgatg  13800
agtaaataaa caaatacgca aggggaacgc atgaaggtta tcgctgtact taaccagaaa  13860
ggcgggtcag gcaagacgac catcgcaacc catctagccc gcgccctgca actcgccggg  13920
gccgatgttc tgttagtcga ttccgatccc cagggcagtg cccgcgattg ggcggccgtg  13980
cgggaagatc aaccgctaac cgttgtcggc atcgaccgcc cgacgattga ccgcgacgtg  14040
aaggccatcg gccggcgcga cttcgtagtg atcgacggag cgccccaggc ggcggacttg  14100
gctgtgtccg cgatcaaggc agccgacttc gtgctgattc cggtgcagcc aagcccttac  14160
gacatatggg ccaccgccga cctggtggag ctggttaagc agcgcattga ggtcacggat  14220
ggaaggctac aagcggcctt tgtcgtgtcg cgggcgatca aaggcacgcg catcggcggt  14280
gaggttgccg aggcgctggc cgggtacgag ctgcccattc ttgagtcccg tatcacgcag  14340
cgcgtgagct acccaggcac tgccgccgcc ggcacaaccg ttcttgaatc agaacccgag  14400
ggcgacgctg cccgcgaggt ccaggcgctg gccgctgaaa ttaaatcaaa actcatttga  14460
gttaatgagg taaagagaaa atgagcaaaa gcacaaacac gctaagtgcc ggccgtccga  14520
gcgcacgcag cagcaaggct gcaacgttgg ccagcctggc agacacgcca gccatgaagc  14580
gggtcaactt tcagttgccg gcggaggatc acaccaagct gaagatgtac gcggtacgcc  14640
aaggcaagac cattaccgag ctgctatctg aatacatcgc gcagctacca gagtaaatga  14700
gcaaatgaat aaatgagtag atgaatttta gcggctaaag gaggcggcat ggaaaatcaa  14760
gaacaaccag gcaccgacgc cgtggaatgc cccatgtgtg gaggaacggg cggttggcca  14820
ggcgtaagcg gctgggttgt ctgccggccc tgcaatggca ctggaacccc caagcccgag  14880
gaatcggcgt gacggtcgca aaccatccgg cccggtacaa atcggcgcgg cgctgggtga  14940
```

-continued

```
tgacctggtg gagaagttga aggccgcgca ggccgcccag cggcaacgca tcgaggcaga  15000
agcacgcccc ggtgaatcgt ggcaagcggc cgctgatcga atccgcaaag aatcccggca  15060
accgccggca gccggtgcgc cgtcgattag gaagccgccc aagggcgacg agcaaccaga  15120
tttttcgtt ccgatgctct atgacgtggg cacccgcgat agtcgcagca tcatggacgt  15180
ggccgttttc cgtctgtcga agcgtgaccg acgagctggc gaggtgatcc gctacgagct  15240
tccagacggg cacgtagagg tttccgcagg gccggccggc atggccagtg tgtgggatta  15300
cgacctggta ctgatggcgg tttcccatct aaccgaatcc atgaaccgat accgggaagg  15360
gaagggagac aagcccggcc gcgtgttccg tccacacgtt gcggacgtac tcaagttctg  15420
ccggcgagcc gatggcggaa agcagaaaga cgacctggta gaaacctgca ttcggttaaa  15480
caccacgcac gttgccatgc agcgtacgaa gaaggccaag aacggccgcc tggtgacggt  15540
atccgagggt gaagccttga ttagccgcta caagatcgta aagagcgaaa ccgggcggcc  15600
ggagtacatc gagatcgagc tagctgattg gatgtaccgc gagatcacag aaggcaagaa  15660
cccggacgtg ctgacggttc accccgatta ctttttgatc gatcccggca tcggccgttt  15720
tctctaccgc ctggcacgcc gcgccgcagg caaggcagaa gccagatggt tgttcaagac  15780
gatctacgaa cgcagtggca gcgccggaga gttcaagaag ttctgtttca ccgtgcgcaa  15840
gctgatcggg tcaaatgacc tgccggagta cgatttgaag gaggaggcgg ggcaggctgg  15900
cccgatccta gtcatgcgct accgcaacct gatcgagggc gaagcatccg ccggttccta  15960
atgtacggag cagatgctag ggcaaattgc cctagcaggg gaaaaaggtc gaaaaggcct  16020
ctttcctgtg gatagcacgt acattgggaa cccaaagccg tacattggga accggaaccc  16080
gtacattggg aacccaaagc cgtacattgg gaaccggtca cacatgtaag tgactgatat  16140
aaaagagaaa aaaggcgatt tttccgccta aaactcttta aaacttatta aaactcttaa  16200
aacccgcctg gcctgtgcat aactgtctgg ccagcgcaca gcccaagagc tgcaaaaagc  16260
gcctaccctt cggtcgctgc gctccctacg ccccgccgct tcgcgtcggc ctatcgcggc  16320
cgctggccgc tcaaaaatgg ctggcctacg gccaggcaat ctaccagggc gcggacaagc  16380
cgcgccgtcg ccactcgacc gccggcgccc acatcaaggc accctgcctc gcgcgtttcg  16440
gtgatgacgg tgaaaacctc tgacacatgc agctcccgga aacggtcaca gcttgtctgt  16500
aagcggatgc cgggagcaga caagcccgtc agggcgcgtc agcgggtgtt ggcgggtgtc  16560
ggggcgcagc catgacccag tcacgtagcg atagcggagt gtatactggc ttaactatgc  16620
ggcatcagag cagattgtac tgagagtgca ccatatgcgg tgtgaaatac cgcacagatg  16680
cgtaaggaga aaataccgca tcaggccctc ttccgcttcc tcgctcactg actcgctgcg  16740
ctcggtcgtt cggctgcggc gagcggtatc agctcactca aaggcggtaa tacggttatc  16800
cacagaatca ggggataacg caggaaagaa catgtgagca aaaggccagc aaaaggccag  16860
gaaccgtaaa aaggccgcgt tgctggcgtt tttccatagg ctccgccccc ctgacgagca  16920
tcacaaaaat cgacgctcaa gtcagaggtg gcgaaacccg acaggactat aaagatacca  16980
ggcgtttccc cctggaagct ccctcgtgcg ctctcctgtt ccgaccctgc cgcttaccgg  17040
atacctgtcc gcctttctcc cttcgggaag cgtggcgctt tctcatagct cacgctgtag  17100
gtatctcagt tcggtgtagg tcgttcgctc caagctgggc tgtgtgcacg aaccccccgt  17160
tcagcccgac cgctgcgcct tatccggtaa ctatcgtctt gagtccaacc cggtaagaca  17220
cgacttatcg ccactggcag cagccactgg taacaggatt agcagagcga ggtat       17275
```

<210> SEQ ID NO 27
<211> LENGTH: 17263
<212> TYPE: DNA
<213> ORGANISM: artificial
<220> FEATURE:
<223> OTHER INFORMATION: synthetic oligonucleotide

<400> SEQUENCE: 27

```
gtaggcggtg ctacagagtt cttgaagtgg tggcctaact acggctacac tagaaggaca     60

gtatttggta tctgcgctct gctgaagcca gttaccttcg gaaaaagagt tggtagctct    120

tgatccggca aacaaaccac cgctggtagc ggtggttttt ttgtttgcaa gcagcagatt    180

acgcgcagaa aaaaaggatc tcaagaagat cctttgatct tttctacggg gtctgacgct    240

cagtggaacg aaaactcacg ttaagggatt ttggtcatgc attctaggta ctaaaacaat    300

tcatccagta aaatataata ttttattttc tcccaatcag gcttgatccc cagtaagtca    360

aaaaatagct cgacatactg ttcttccccg atatcctccc tgatcgaccg gacgcagaag    420

gcaatgtcat accacttgtc cgccctgccg cttctcccaa gatcaataaa gccacttact    480

ttgccatctt tcacaaagat gttgctgtct cccaggtcgc cgtgggaaaa gacaagttcc    540

tcttcgggct tttccgtctt taaaaaatca tacagctcgc gcggatcttt aaatggagtg    600

tcttcttccc agttttcgca atccacatcg gccagatcgt tattcagtaa gtaatccaat    660

tcggctaagc ggctgtctaa gctattcgta tagggacaat ccgatatgtc gatggagtga    720

aagagcctga tgcactccgc atacagctcg ataatctttt cagggctttg ttcatcttca    780

tactcttccg agcaaaggac gccatcggcc tcactcatga gcagattgct ccagccatca    840

tgccgttcaa agtgcaggac ctttggaaca ggcagctttc cttccagcca tagcatcatg    900

tccttttccc gttccacatc ataggtggtc cctttatacc ggctgtccgt catttttaaa    960

tataggtttt cattttctcc caccagctta tataccttag caggagacat tccttccgta   1020

tcttttacgc agcggtattt ttcgatcagt tttttcaatt ccggtgatat tctcatttta   1080

gccatttatt atttccttcc tcttttctac agtatttaaa gataccccaa gaagctaatt   1140

ataacaagac gaactccaat tcactgttcc ttgcattcta aaaccttaaa taccagaaaa   1200

cagcttttc aaagttgttt tcaaagttgg cgtataacat agtatcgacg gagccgattt   1260

tgaaaccgcg gtgatcacag gcagcaacgc tctgtcatcg ttacaatcaa catgctaccc   1320

tccgcgagat catccgtgtt tcaaacccgg cagcttagtt gccgttcttc cgaatagcat   1380

cggtaacatg agcaaagtct gccgccttac aacggctctc ccgctgacgc cgtcccggac   1440

tgatgggctg cctgtatcga gtggtgattt tgtgccgagc tgccggtcgg ggagctgttg   1500

gctggctggt ggcaggatat attgtggtgt aaacaaattg acgcttagac aacttaataa   1560

cacattgcgg acgtttttaa tgtactgaat taacgccgaa ttaattcggg ggatctggat   1620

tttagtactg gattttggtt ttaggaatta gaaattttat tgatagaagt attttacaaa   1680

tacaaataca tactaagggt ttcttatatg ctcaacacat gagcgaaacc ctataggaac   1740

cctaattccc ttatctggga actactcaca cattattatg gagaaactcg agcttgtcga   1800

tcgactctag ctagaggatc gatccgaacc ccagagtccc gctcagaaga actcgtcaag   1860

aaggcgatag aaggcgatgc gctgcgaatc gggagcggcg ataccgtaaa gcacgaggaa   1920

gcggtcagcc cattcgccgc caagttcttc agcaatatca cgggtagcca acgctatgtc   1980

ctgatagcgg tccgccacac ccagccggcc acagtcgatg aatccagaaa agcggccatt   2040

ttccaccatg atattcggca agcaggcatc gccatgtgtc acgacgagat cctcgccgtc   2100
```

gggcatgcgc gccttgagcc tggcgaacag ttcggctggc gcgagcccct gatgttcttc 2160
gtccagatca tcctgatcga caagaccggc ttccatccga gtacgtgctc gctcgatgcg 2220
atgtttcgct tggtggtcga atgggcaggt agccggatca agcgtatgca gccgccgcat 2280
tgcatcagcc atgatggata ctttctcggc aggagcaagg tgagatgaca ggagatcctg 2340
ccccggcact tcgcccaata gcagccagtc ccttcccgct tcagtgacaa cgtcgagcac 2400
agctgcgcaa ggaacgcccg tcgtggccag ccacgatagc cgcgctgcct cgtcctggag 2460
ttcattcagg gcaccggaca ggtcggtctt gacaaaaaga accgggcgcc cctgcgctga 2520
cagccgaaac acggcggcat cagagcagcc gattgtctgt tgtgcccagt catagccgaa 2580
tagcctctcc acccaagcgg ccggagaacc tgcgtgcaat ccatcttgtt caatccccat 2640
ggtcgatcga cagatctgcg aaagctcgag agagatagat ttgtagagag agactggtga 2700
tttcagcgtg tcctctccaa atgaaatgaa cttccttata tagaggaagg tcttgcgaag 2760
gatagtggga ttgtgcgtca tcccttacgt cagtggagat atcacatcaa tccacttgct 2820
ttgaagacgt ggttggaacg tcttcttttt ccacgatgct cctcgtgggt gggggtccat 2880
ctttgggacc actgtcggca gaggcatctt gaacgatagc ctttccttta tcgcaatgat 2940
ggcatttgta ggtgccacct tccttttcta ctgtcctttt gatgaagtga cagatagctg 3000
ggcaatggaa tccgaggagg tttcccgata ttaccctttg ttgaaaagtc tcaatagccc 3060
tttggtcttc tgagactgta tctttgatat tcttggagta gacgagagtg tcgtgctcca 3120
ccatgttatc acatcaatcc acttgctttg aagacgtggt tggaacgtct tctttttcca 3180
cgatgctcct cgtgggtggg ggtccatctt tgggaccact gtcggcagag gcatcttgaa 3240
cgatagcctt tcctttatcg caatgatggc atttgtaggt gccaccttcc ttttctactg 3300
tccttttgat gaagtgacag atagctgggc aatggaatcc gaggaggttt cccgatatta 3360
ccctttgttg aaaagtctca atagcccttt ggtcttctga gactgtatct ttgatattct 3420
tggagtagac gagagtgtcg tgctccacca tgttggcaag ctgctctagc caatacgcaa 3480
accgcctctc cccgcgcgtt ggccgattca ttaatgcagc tggcacgaca ggtttcccga 3540
ctggaaagcg ggcagtgagc gcaacgcaat taatgtgagt tagctcactc attaggcacc 3600
ccaggcttta cactttatgc ttccggctcg tatgttgtgt ggaattgtga gcggataaca 3660
atttcacaca ggaaacagct atgaccatga ttacgaattc gagctcaaag tttaacgcgt 3720
tagcagaagg catgttgttg tgactccgag gggttgcctc aaactctatc ttataaccgg 3780
cgtggaggca tggaggcagg ggtattttgg tcattttaat agatagtgga aaatgacgtg 3840
gaatttactt aaagacgaag tctttgcgac aaggggggc ccacgccgaa tttaatatta 3900
ccggcgtggc cccccttat cgcgagtgct ttagcacgag cggtccagat ttaaagtaga 3960
aaatttcccg cccactaggg ttaaaggtgt tcacactata aaagcatata cgatgtgatg 4020
gtatttgatg gagcgtatat tgtatcaggt atttccgttg gatacgaatt attcgtacga 4080
ccctcggtac cgatcaaaag caggtgtcat gatcggcgcg cctggcagac atactgtccc 4140
acaaatgaag atggaatctg taaaagaaaa cgcgtgaaat aatgcgtctg acaaaggtta 4200
ggtcggctgc ctttaatcaa taccaaagtg gtccctacca cgatggaaaa actgtgcagt 4260
cggtttggct ttttctgacg aacaaataag attcgtggcc gacaggtggg ggtccaccat 4320
gtgaaggcat cttcagactc caataatgga gcaatgacgt aagggcttac gaaataagta 4380
agggtagttt gggaaatgtc cactcacccg tcagtctata aatacttagc ccctccctca 4440
ttgttaaggg agcaaaatct cagagagata gtcctagaga gagaaagaga gcaagtagcc 4500
tagaagtagt caaggcggcg aagtattcag gcacgtggcc aggaagaaga aaagccaaga 4560
cgacgaaaac aggtaagagc taagcttcct gcaggatgga agacgccaaa aacataaaga 4620
aaggcccggc gccattctat ccgctggaag atggaaccgc tggagagcaa ctgcataagg 4680
ctatgaagag atacgccctg gttcctggaa caattgcttt tacagatgca catatcgagg 4740
tggacatcac ttacgctgag tacttcgaaa tgtccgttcg gttggcagaa gctatgaaac 4800
gatatgggct gaatacaaat cacagaatcg tcgtatgcag tgaaaactct cttcaattct 4860
ttatgccggt gttgggcgcg ttatttatcg gagttgcagt tgcgcccgcg aacgacattt 4920
ataatgaacg tgaattgctc aacagtatgg gcatttcgca gcctaccgtg gtgttcgttt 4980
ccaaaaaggg gttgcaaaaa attttgaacg tgcaaaaaaa gctcccaatc atccaaaaaa 5040
ttattatcat ggattctaaa acggattacc agggatttca gtcgatgtac acgttcgtca 5100
catctcatct acctcccggt tttaatgaat acgattttgt gccagagtcc ttcgataggg 5160
acaagacaat tgcactgatc atgaactcct ctggatctac tggtctgcct aaaggtgtcg 5220
ctctgcctca tagaactgcc tgcgtgagat tctcgcatgc cagagatcct atttttggca 5280
atcaaatcat tccggatact gcgattttaa gtgttgttcc attccatcac ggttttggaa 5340
tgtttactac actcggatat ttgatatgtg gatttcgagt cgtcttaatg tatagatttg 5400
aagaagagct gtttctgagg agccttcagg attacaagat tcaaagtgcg ctgctggtgc 5460
caaccctatt ctccttcttc gccaaaagca ctctgattga caaatacgat ttatctaatt 5520
tacacgaaat tgcttctggt ggcgctcccc tctctaagga agtcggggaa gcggttgcca 5580
agaggttcca tctgccaggt atcaggcaag gatatgggct cactgagact acatcagcta 5640
ttctgattac acccgagggg gatgataaac cgggcgcggt cggtaaagtt gttccatttt 5700
ttgaagcgaa ggttgtggat ctggataccg ggaaaacgct gggcgttaat caaagaggcg 5760
aactgtgtgt gagaggtcct atgattatgt ccggttatgt aaacaatccg gaagcgacca 5820
acgccttgat tgacaaggat ggatggctac attctggaga catagcttac tgggacgaag 5880
acgaacactt cttcatcgtt gaccgcctga agtctctgat taagtacaaa ggctatcagg 5940
tggctcccgc tgaattggaa tccatcttgc tccaacaccc caacatcttc gacgctggtg 6000
tcgcaggtct tcccgacgat gacgccggtg aacttcccgc cgccgttgtt gttttggagc 6060
acggaaagac gatgacggaa aaagagatcg tggattacgt cgccagtcaa gtaacaaccg 6120
cgaaaaagtt gcgcggagga gttgtgtttg tggacgaagt accgaaaggt cttaccggaa 6180
aactcgacgc aagaaaaatc agagagatcc tcataaaggc caagaagggc ggaaagatcg 6240
ccgtgtgacg tcgacgatat gaagatgaag atgaaatatt tggtgtgtca aataaaaagc 6300
ttgtgtgctt aagtttgtgt ttttttcttg gcttgttgtg ttatgaattt gtggcttttt 6360
ctaatattaa atgaatgtaa gatcacatta taatgaataa acaaatgttt ctataatcca 6420
ttgtgaatgt tttgttggat ctcttctgca gcatataact actgtatgtg ctatggtatg 6480
gactatggaa tatgattaaa gataagccag agctctggtg acggacggcg cgactagttt 6540
tacgtacgtt aattaacccg ggcgcgccga tcatgagcgg agaattaagg gagtcacgtt 6600
atgacccccg ccgatgacgc gggacaagcc gttttacgtt tggaactgac agaaccgcaa 6660
cgttgaagga gccactcagc cgcgggtttc tggagtttaa tgagctaagc acatacgtca 6720
gaaaccatta ttgcgcgttc aaaagtcgcc taaggtcact atcagctagc aaatatttct 6780
tgtcaaaaat gctccactga cgttccataa attcccctcg gtatccaatt agagtctcat 6840

-continued

```
attcactctc aatccaaata atctgcaccg tacctgcagg gtccgagcta ggtcacagaa   6900
gcgctcagga aggccgctga gatagaggca tggcggccaa tgcgggcggc ggtggagcgg   6960
gaggaggcag cggcagcggc agcgtggctg cgccggcggt gtgccgcccc agcggctcgc   7020
ggtggacgcc gacgccggag cagatcagga tgctgaagga gctgtactac ggctgcggca   7080
tccggtcgcc cagctcggag cagatccagc gcatcaccgc catgctgcgg cagcacggca   7140
agatcgaggg caagaacgtc ttctactggt tccagaacca caaggcccgc gagcgccaga   7200
agcgccgcct caccagcctc gacgtgaacg tgcccgccgc cggcgcggcc gacgccacca   7260
ccagccaact cggcgtcctc tcgctgtcgt cgccgccgcc ttcaggcgcg gcgcctccct   7320
cgcccaccct cggcttctac gccgccggca atggcggcgg atcggctgtg ctgctggaca   7380
cgagttccga ctggggcagc agcggcgctg cgatggccac cgagacatgc ttcctccagg   7440
actacatggg cgtgacggac acgggcagct cgtcgcagtg gccacgcttc tcgtcgtcgg   7500
acacgataat ggcggcggcc gcggcgcggg cggcgacgac gcgggcgccc gagactctcc   7560
ctctcttccc gacctgcggc gacgacggcg gcagcggtag cagcagctac ttgccgttct   7620
ggggtgccgc gtccacaact gccggcgcca cttcttccgt tgcgatccag cagcaacacc   7680
agctgcagga gcagtacagc ttttacagca acagcaacag cacccagctg gccggcaccg   7740
gcaaccaaga cgtatcggca acagcagcag cagccgccgc cctggagctg agcctcagct   7800
catggtgctc cccttaccct gctgcaggga gtatgtgaga gcaacgcgag ctgccactgc   7860
tcttcactta tgtctctgga atggaaggag gaggaagtga gcatagcgtt ggtgcgttgc   7920
tgtcattgtc ctaggttagt agctagtgcc agttactagt aagcatcagg cataggagta   7980
tgtagtagaa gcatgcacgt tgccggccag ccaggcttta gacgggaaaa gaatttggtg   8040
cagccggctg caaaacagga tgtttacagc ccccccctcg agccctagac ttgtccatct   8100
tctggattgg ccaagttaat taatgtatga aataaaagga tgcacacata gtgacatgct   8160
aatcactata atgtgggcat caaagttgtg tgttatgtgt aattactaat tatctgaata   8220
agagaaagag atcatccata tttcttatcc taaatgaatg tcacgtgtct ttataattct   8280
ttgatgaacc agatgcattt tattaaccaa ttccatatac atataaatat taatcatata   8340
taattaatat caattgggtt agcaaaacaa atctagtcta ggtgtgtttt gctaattatt   8400
gggggatagt gcaaaaagaa atctacgttc tcaataattc agatagaaaa cttaataaag   8460
tgagataatt tacatagatt gcttttatcc tttgatatat gtgaaaccat gcatgatata   8520
aggaaaatag atagagaaat aattttttac atcgttgaat atgtaaacaa tttaattcaa   8580
gaagctagga atataaatat tgaggagttt atgattagag ctctcccact aaacgtcccg   8640
cagatttgcc ttttcaattt cagaaagaat gctaacccac agatggttag agaggcttac   8700
gcagcaggta tcatcaagac gatctacccg agcaataatc tccaggaaat caaatacctt   8760
cccaagaagg ttaaagatgc agtcaaaaga ttcaggacta actgcatcaa gaacacagag   8820
aaagatatat ttctcaagat cagaagtact attccagtat ggacgattca aggcttgctt   8880
cacaaaccaa ggcaagtaat agagattgga gtctctaaaa aggtagttcc cactgaatca   8940
aaggccatgg agtcaaagat tcaaatagag gacctaacag aactcgccgt aaagactggc   9000
gaacagttca tacagagtct cttacgactc aatgacaaga agaaaatctt cgtcaacatg   9060
gtggagcacg acacacttgt ctactccaaa aatatcaaag atacagtctc agaagaccaa   9120
agggcaattg agacttttca acaaagggta atatccggaa acctcctcgg attccattgc   9180
ccagctatct gtcactttat tgtgaagata gtggaaaagg aaggtggctc ctacaaatgc   9240
```

-continued

```
catcattgcg ataaaggaaa ggccatcgtt gaagatgcct ctgccgacag tggtcccaaa    9300
gatggacccc cacccacgag gagcatcgtg gaaaaagaag acgttccaac cacgtcttca    9360
aagcaagtgg attgatgtga tatctccact gacgtaaggg atgacgcaca atcccactat    9420
ccttcgcaag acccttcctc tatataagga agttcatttc atttggagag aacacggggg    9480
actatggaga gtggttccaa cagcacttct tgtccaatgg cttttgccgg ggataatagt    9540
gatggtccga tgtgtcctat gatgatgatg atgccgccca tcatgacatc acatcaacat    9600
catggtcatg atcatcaaca tcaacaacaa gaacatgatg gttatgcata tcagtcacac    9660
caccaacaaa gtagttccct ttttcttcaa tcactagctc ctccccaagg aactaagaac    9720
aaagttgctt cttcttcttc tccttcctct tgtgctcctg cctattctct aatggagatc    9780
catcataacg aaatcgttgc aggaggaatc aacccttgct cctcttcctc ttcttcagcc    9840
tctgtcaagg ccaagatcat ggctcatcct cactaccacc gcctcttggc cgcttatgtc    9900
aattgtcaga aggttggagc accaccggag gttgtggcga ggctagagga ggcatgctcg    9960
tctgccgcag ccgctgccgc atctatggga ccaacaggat gtctaggtga agatccaggg   10020
cttgatcaat tcatggaagc ttactgtgaa atgctcgtta agtatgagca agagctctcc   10080
aaacctttca aggaagctat ggtcttcctt caacgtgtcg agtgtcaatt caaatccctc   10140
tctctatcct caccttcctc tttctccggt tatggagaga cagcaattga taggaacaat   10200
aatgggtcat ccgaggaaga agtcgatatg aacaatgaat ttgtagatcc acaagctgag   10260
gatagagagc ttaaaggaca gctcttgcgc aagtacagtg gttacttagg gagcctcaag   10320
caagagttca tgaagaagag gaagaaagga aagctcccta aagaagctcg tcaacaactg   10380
cttgattggt ggagccgtca ctacaaatgg ccttaccctt cggagcaaca aaagctcgcc   10440
cttgcggaat caacggggct ggaccagaaa cagataaaca attggttcat aaaccagagg   10500
aaacggcatt ggaagccgtc ggaggacatg cagtttgtag taatggacgc aacacatcct   10560
caccattact tcatggataa tgtcttgggc aatcctttcc caatggatca catctcctcc   10620
accatgcttt gactcgagtt tctccataat aatgtgtgag tagttcccag ataagggaat   10680
tagggttcct atagggtttc gctcatgtgt tgagcatata agaaaccctt agtatgtatt   10740
tgtatttgta aaatacttct atcaataaaa tttctaattc ctaaaaccaa aatccagtac   10800
taaaatccag atcccccgaa ttaagtgttt gatcgccggc ggtaccgagt gtacttcaag   10860
tcagtgggaa atcaataaaa tgattatttt atgaatatat ttcattgtgc aagtagatag   10920
aaattacata tgttacataa cacacgaaat aaacaaaaaa agacaatcca aaaacaaaca   10980
ccccaaaaaa aataatcact ttagataaac tcgtatgagg agaggcacgt tcagtgactc   11040
gacgattccc gagcaaaaaa agtctccccg tcacacatgt agtgggtgac gcaattatct   11100
ttaaagtaat ccttctgttg acttgtcatt gataacatcc agtcttcgtc aggattgcaa   11160
agaattatag aagggatccc accttttatt ttcttctttt ttccatattt agggttgaca   11220
gtgaaatcag actggcaacc tattaattgc ttccacaatg ggacgaactt gaaggggatg   11280
tcgtcgatga tattataggt ggcgtgttca tcgtagttgg tgaaatcgat ggtaccgttc   11340
caatagttgt gtcgtccgag acttctagcc caggtggtct ttccggtacg agttggtccg   11400
cagatgtaga ggctggggtg tcggattcca ttccttccat tgtccttgtt aaatcggcca   11460
tccattcaag gtcagattga gcttgttggt atgagacagg atgtatgtaa gtataagcgt   11520
ctatgcttac atggtataga tgggtttccc tccaggagtg tagatcttcg tggcagcgaa   11580
```

-continued gatctgattc tgtgaagggc gacacatacg gttcaggttg tggagggaat aatttgttgg 11640
ctgaatattc cagccattga agctttgttg cccattcatg agggaattct tccttgatca 11700
tgtcaagata ttcctcctta gacgttgcag tctggataat agttctccat cgtgcgtcag 11760
atttgcgagg agaaacctta tgatctcgga aatctcctct ggttttaata tctccgtcct 11820
ttgatatgta atcaaggact tgtttagagt ttctagctgg ctggatatta gggtgatttc 11880
cttcaaaatc gaaaaaagaa ggatccctaa tacaaggttt tttatcaagc tggagaagag 11940
catgatagtg ggtagtgcca tcttgatgaa gctcagaagc aacaccaagg aagaaaataa 12000
gaaaaggtgt gagtttctcc cagagaaact ggaataaatc atctctttga gatgagcact 12060
tgggataggt aaggaaaaca tatttagatt ggagtctgaa gttcttacta gcagaaggca 12120
tgttgttgtg actccgaggg gttgcctcaa actctatctt ataaccggcg tggaggcatg 12180
gaggcagggg tattttggtc attttaatag atagtggaaa atgacgtgga atttacttaa 12240
agacgaagtc tttgcgacaa ggggggggcc acgccgaatt taatattacc ggcgtggccc 12300
ccccttatcg cgagtgcttt agcacgagcg gtccagattt aaagtagaaa atttcccgcc 12360
cactagggtt aaaggtgttc acactataaa agcatatacg atgtgatggt atttgatgga 12420
gcgtatattg tatcaggtat ttccgttgga tacgaattat tcgtacgacc ctcatagttt 12480
aaactatcag tgtttgacag gatatattgg cgggtaaacc taagagaaaa gagcgtttat 12540
tagaataacg gatatttaaa agggcgtgaa aaggtttatc cgttcgtcca tttgtatgtg 12600
catgccaacc acagggttcc cctcgggatc aaagtacttt gatccaaccc ctccgctgct 12660
atagtgcagt cggcttctga cgttcagtgc agccgtcttc tgaaaacgac atgtcgcaca 12720
agtcctaagt tacgcgacag gctgccgccc tgcccttttc ctggcgtttt cttgtcgcgt 12780
gttttagtcg cataaagtag aatacttgcg actagaaccg gagacattac gccatgaaca 12840
agagcgccgc cgctggcctg ctgggctatg cccgcgtcag caccgacgac caggacttga 12900
ccaaccaacg ggccgaactg cacgcggccg gctgcaccaa gctgttttcc gagaagatca 12960
ccggcaccag gcgcgaccgc ccggagctgg ccaggatgct tgaccaccta cgccctggcg 13020
acgttgtgac agtgaccagg ctagaccgcc tggcccgcag cacccgcgac ctactggaca 13080
ttgccgagcg catccaggag gccggcgcgg gcctgcgtag cctggcagag ccgtgggccg 13140
acaccaccac gccggccggc cgcatggtgt tgaccgtgtt cgccggcatt gccgagttcg 13200
agcgttccct aatcatcgac cgcacccgga gcgggcgcga ggccgccaag gcccgaggcg 13260
tgaagtttgg cccccgccct accctcaccc cggcacagat cgcgcacgcc cgcgagctga 13320
tcgaccagga aggccgcacc gtgaaagagg cggctgcact gcttggcgtg catcgctcga 13380
ccctgtaccg cgcacttgag cgcagcgagg aagtgacgcc caccgaggcc aggcggcgcg 13440
gtgccttccg tgaggacgca ttgaccgagg ccgacgccct ggcggccgcc gagaatgaac 13500
gccaagagga acaagcatga aaccgcacca ggacggccag gacgaaccgt ttttcattac 13560
cgaagagatc gaggcggaga tgatcgcggc cgggtacgtg ttcgagccgc ccgcgcacgg 13620
ctcaaccgtg cggctgcatg aaatcctggc cggtttgtct gatgccaagc tggcggcctg 13680
gccggccagc ttggccgctg aagaaaccga gcgccgccgt ctaaaaaggt gatgtgtatt 13740
tgagtaaaac agcttgcgtc atgcggtcgc tgcgtatatg atgcgatgag taaataaaca 13800
aatacgcaag gggaacgcat gaaggttatc gctgtactta accagaaagg cgggtcaggc 13860
aagacgacca tcgcaaccca tctagcccgc gccctgcaac tcgccggggc cgatgttctg 13920
ttagtcgatt ccgatcccca gggcagtgcc cgcgattggg cggccgtgcg ggaagatcaa 13980

-continued

```
ccgctaaccg ttgtcggcat cgaccgcccg acgattgacc gcgacgtgaa ggccatcggc  14040
cggcgcgact tcgtagtgat cgacggagcg ccccaggcgg cggacttggc tgtgtccgcg  14100
atcaaggcag ccgacttcgt gctgattccg gtgcagccaa gcccttacga catatgggcc  14160
accgccgacc tggtggagct ggttaagcag cgcattgagg tcacggatgg aaggctacaa  14220
gcggcctttg tcgtgtcgcg ggcgatcaaa ggcacgcgca tcggcggtga ggttgccgag  14280
gcgctggccg ggtacgagct gcccattctt gagtcccgta tcacgcagcg cgtgagctac  14340
ccaggcactg ccgccgccgg cacaaccgtt cttgaatcag aacccgaggg cgacgctgcc  14400
cgcgaggtcc aggcgctggc cgctgaaatt aaatcaaaac tcatttgagt taatgaggta  14460
aagagaaaat gagcaaaagc acaaacacgc taagtgccgg ccgtccgagc gcacgcagca  14520
gcaaggctgc aacgttggcc agcctggcag acacgccagc catgaagcgg gtcaactttc  14580
agttgccggc ggaggatcac accaagctga agatgtacgc ggtacgccaa ggcaagacca  14640
ttaccgagct gctatctgaa tacatcgcgc agctaccaga gtaaatgagc aaatgaataa  14700
atgagtagat gaattttagc ggctaaagga ggcggcatgg aaaatcaaga acaaccaggc  14760
accgacgccg tggaatgccc catgtgtgga ggaacgggcg gttggccagg cgtaagcggc  14820
tgggttgtct gccggccctg caatggcact ggaacccccca agcccgagga atcggcgtga  14880
cggtcgcaaa ccatccggcc cggtacaaat cggcgcggcg ctgggtgatg acctggtgga  14940
gaagttgaag gccgcgcagg ccgcccagcg gcaacgcatc gaggcagaag cacgccccgg  15000
tgaatcgtgg caagcggccg ctgatcgaat ccgcaaagaa tcccggcaac cgccggcagc  15060
cggtgcgccg tcgattagga agccgcccaa gggcgacgag caaccagatt ttttcgttcc  15120
gatgctctat gacgtgggca cccgcgatag tcgcagcatc atggacgtgg ccgttttccg  15180
tctgtcgaag cgtgaccgac gagctggcga ggtgatccgc tacgagcttc cagacgggca  15240
cgtagaggtt tccgcagggc cggccggcat ggccagtgtg tgggattacg acctggtact  15300
gatggcggtt tcccatctaa ccgaatccat gaaccgatac cgggaaggga agggagacaa  15360
gcccggccgc gtgttccgtc cacacgttgc ggacgtactc aagttctgcc ggcgagccga  15420
tggcggaaag cagaaagacg acctggtaga aacctgcatt cggttaaaca ccacgcacgt  15480
tgccatgcag cgtacgaaga aggccaagaa cggccgcctg gtgacggtat ccgagggtga  15540
agccttgatt agccgctaca agatcgtaaa gagcgaaacc gggcggccgg agtacatcga  15600
gatcgagcta gctgattgga tgtaccgcga gatcacagaa ggcaagaacc cggacgtgct  15660
gacggttcac cccgattact ttttgatcga tcccggcatc ggccgttttc tctaccgcct  15720
ggcacgccgc gccgcaggca aggcagaagc cagatggttg ttcaagacga tctacgaacg  15780
cagtggcagc gccggagagt tcaagaagtt ctgtttcacc gtgcgcaagc tgatcgggtc  15840
aaatgacctg ccggagtacg atttgaagga ggaggcgggg caggctggcc cgatcctagt  15900
catgcgctac cgcaacctga tcgagggcga agcatccgcc ggttcctaat gtacggagca  15960
gatgctaggg caaattgccc tagcagggga aaaaggtcga aaaggcctct ttcctgtgga  16020
tagcacgtac attgggaacc caaagccgta cattgggaac cggaacccgt acattgggaa  16080
cccaaagccg tacattggga accggtcaca catgtaagtg actgatataa aagagaaaaa  16140
aggcgatttt tccgcctaaa actctttaaa acttattaaa actcttaaaa cccgcctggc  16200
ctgtgcataa ctgtctggcc agcgcacagc ccaagagctg caaaaagcgc ctacccttcg  16260
gtcgctgcgc tccctacgcc ccgccgcttc gcgtcggcct atcgcggccg ctggccgctc  16320
```

-continued

```
aaaaatggct ggcctacggc caggcaatct accagggcgc ggacaagccg cgccgtcgcc  16380
actcgaccgc cggcgcccac atcaaggcac cctgcctcgc gcgtttcggt gatgacggtg  16440
aaaacctctg acacatgcag ctcccggaaa cggtcacagc ttgtctgtaa gcggatgccg  16500
ggagcagaca agcccgtcag ggcgcgtcag cgggtgttgg cgggtgtcgg ggcgcagcca  16560
tgacccagtc acgtagcgat agcggagtgt atactggctt aactatgcgg catcagagca  16620
gattgtactg agagtgcacc atatgcggtg tgaaataccg cacagatgcg taaggagaaa  16680
ataccgcatc aggccctctt ccgcttcctc gctcactgac tcgctgcgct cggtcgttcg  16740
gctgcggcga gcggtatcag ctcactcaaa ggcggtaata cggttatcca cagaatcagg  16800
ggataacgca ggaaagaaca tgtgagcaaa aggccagcaa aaggccagga accgtaaaaa  16860
ggccgcgttg ctggcgtttt tccataggct ccgcccccct gacgagcatc acaaaaatcg  16920
acgctcaagt cagaggtggc gaaacccgac aggactataa agataccagg cgtttccccc  16980
tggaagctcc ctcgtgcgct ctcctgttcc gaccctgccg cttaccggat acctgtccgc  17040
ctttctccct tcgggaagcg tggcgctttc tcatagctca cgctgtaggt atctcagttc  17100
ggtgtaggtc gttcgctcca agctgggctg tgtgcacgaa ccccccgttc agcccgaccg  17160
ctgcgcctta tccggtaact atcgtcttga gtccaacccg gtaagacacg acttatcgcc  17220
actggcagca gccactggta acaggattag cagagcgagg tat                    17263
```

<210> SEQ ID NO 28
<211> LENGTH: 17767
<212> TYPE: DNA
<213> ORGANISM: artificial
<220> FEATURE:
<223> OTHER INFORMATION: synthetic oligonucleotide

<400> SEQUENCE: 28

```
gtaggcggtg ctacagagtt cttgaagtgg tggcctaact acggctacac tagaaggaca     60
gtatttggta tctgcgctct gctgaagcca gttaccttcg gaaaaagagt tggtagctct    120
tgatccggca aacaaaccac cgctggtagc ggtggttttt ttgtttgcaa gcagcagatt    180
acgcgcagaa aaaaaggatc tcaagaagat cctttgatct tttctacggg gtctgacgct    240
cagtggaacg aaaactcacg ttaagggatt ttggtcatgc attctaggta ctaaaacaat    300
tcatccagta aaatataata ttttattttc tcccaatcag gcttgatccc cagtaagtca    360
aaaaatagct cgacatactg ttcttccccg atatcctccc tgatcgaccg gacgcagaag    420
gcaatgtcat accacttgtc cgccctgccg cttctcccaa gatcaataaa gccacttact    480
ttgccatctt tcacaaagat gttgctgtct cccaggtcgc cgtgggaaaa gacaagttcc    540
tcttcgggct tttccgtctt taaaaaatca tacagctcgc gcggatcttt aaatggagtg    600
tcttcttccc agttttcgca atccacatcg gccagatcgt tattcagtaa gtaatccaat    660
tcggctaagc ggctgtctaa gctattcgta tagggacaat ccgatatgtc gatggagtga    720
aagagcctga tgcactccgc atacagctcg ataatctttt cagggctttg ttcatcttca    780
tactcttccg agcaaaggac gccatcggcc tcactcatga gcagattgct ccagccatca    840
tgccgttcaa agtgcaggac ctttggaaca ggcagctttc cttccagcca tagcatcatg    900
tccttttccc gttccacatc ataggtggtc cctttatacc ggctgtccgt catttttaaa    960
tataggtttt cattttctcc caccagctta tataccttag caggagacat tccttccgta   1020
tcttttacgc agcggtattt ttcgatcagt tttttcaatt ccggtgatat tctcatttta   1080
gccatttatt atttccttcc tcttttctac agtatttaaa gataccccaa gaagctaatt   1140
```

-continued

```
ataacaagac gaactccaat tcactgttcc ttgcattcta aaaccttaaa taccagaaaa   1200
cagctttttc aaagttgttt tcaaagttgg cgtataacat agtatcgacg gagccgattt   1260
tgaaaccgcg gtgatcacag gcagcaacgc tctgtcatcg ttacaatcaa catgctaccc   1320
tccgcgagat catccgtgtt tcaaacccgg cagcttagtt gccgttcttc cgaatagcat   1380
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg   1500
gctggctggt ggcaggatat attgtggtgt aaacaaattg acgcttagac aacttaataa   1560
cacattgcgg acgtttttaa tgtactgaat taacgccgaa ttaattcggg ggatctggat   1620
tttagtactg gattttggtt ttaggaatta gaaattttat tgatagaagt attttacaaa   1680
tacaaataca tactaagggt ttcttatatg ctcaacacat gagcgaaacc ctataggaac   1740
cctaattccc ttatctggga actactcaca cattattatg gagaaactcg agcttgtcga   1800
tcgactctag ctagaggatc gatccgaacc ccagagtccc gctcagaaga actcgtcaag   1860
aaggcgatag aaggcgatgc gctgcgaatc gggagcggcg ataccgtaaa gcacgaggaa   1920
gcggtcagcc cattcgccgc caagttcttc agcaatatca cgggtagcca acgctatgtc   1980
ctgatagcgg tccgccacac ccagccggcc acagtcgatg aatccagaaa agcggccatt   2040
ttccaccatg atattcggca agcaggcatc gccatgtgtc acgacgagat cctcgccgtc   2100
gggcatgcgc gccttgagcc tggcgaacag ttcggctggc gcgagcccct gatgttcttc   2160
gtccagatca tcctgatcga caagaccggc ttccatccga gtacgtgctc gctcgatgcg   2220
atgtttcgct tggtggtcga atgggcaggt agccggatca agcgtatgca gccgccgcat   2280
tgcatcagcc atgatggata ctttctcggc aggagcaagg tgagatgaca ggagatcctg   2340
ccccggcact tcgcccaata gcagccagtc ccttcccgct tcagtgacaa cgtcgagcac   2400
agctgcgcaa ggaacgcccg tcgtggccag ccacgatagc cgcgctgcct cgtcctggag   2460
ttcattcagg gcaccggaca ggtcggtctt gacaaaaaga accgggcgcc cctgcgctga   2520
cagccgaaac acggcggcat cagagcagcc gattgtctgt tgtgcccagt catagccgaa   2580
tagcctctcc acccaagcgg ccggagaacc tgcgtgcaat ccatcttgtt caatccccat   2640
ggtcgatcga cagatctgcg aaagctcgag agagatagat ttgtagagag agactggtga   2700
tttcagcgtg tcctctccaa atgaaatgaa cttccttata tagaggaagg tcttgcgaag   2760
gatagtggga ttgtgcgtca tcccttacgt cagtggagat atcacatcaa tccacttgct   2820
ttgaagacgt ggttggaacg tcttcttttt ccacgatgct cctcgtgggt gggggtccat   2880
ctttgggacc actgtcggca gaggcatctt gaacgatagc ctttccttta tcgcaatgat   2940
ggcatttgta ggtgccacct tccttttcta ctgtcctttt gatgaagtga cagatagctg   3000
ggcaatggaa tccgaggagg tttcccgata ttaccctttg ttgaaaagtc tcaatagccc   3060
tttggtcttc tgagactgta tctttgatat tcttggagta gacgagagtg tcgtgctcca   3120
ccatgttatc acatcaatcc acttgctttg aagacgtggt tggaacgtct tctttttcca   3180
cgatgctcct cgtgggtggg ggtccatctt tgggaccact gtcggcagag gcatcttgaa   3240
cgatagcctt tcctttatcg caatgatggc atttgtaggt gccaccttcc ttttctactg   3300
tccttttgat gaagtgacag atagctgggc aatggaatcc gaggaggttt cccgatatta   3360
ccctttgttg aaaagtctca atagcccttt ggtcttctga gactgtatct ttgatattct   3420
tggagtagac gagagtgtcg tgctccacca tgttggcaag ctgctctagc caatacgcaa   3480
```

-continued

```
accgcctctc cccgcgcgtt ggccgattca ttaatgcagc tggcacgaca ggtttcccga   3540
ctggaaagcg ggcagtgagc gcaacgcaat taatgtgagt tagctcactc attaggcacc   3600
ccaggcttta cactttatgc ttccggctcg tatgttgtgt ggaattgtga gcggataaca   3660
atttcacaca ggaaacagct atgaccatga ttacgaattc gagctcaaag tttaacgcgt   3720
tagcagaagg catgttgttg tgactccgag gggttgcctc aaactctatc ttataaccgg   3780
cgtggaggca tggaggcagg ggtattttgg tcattttaat agatagtgga aaatgacgtg   3840
gaatttactt aaagacgaag tctttgcgac aagggggggc ccacgccgaa tttaatatta   3900
ccggcgtggc ccccccttat cgcgagtgct ttagcacgag cggtccagat ttaaagtaga   3960
aaatttcccg cccactaggg ttaaaggtgt tcacactata aaagcatata cgatgtgatg   4020
gtatttgatg gagcgtatat tgtatcaggt atttccgttg gatacgaatt attcgtacga   4080
ccctcggtac cgatcaaaag caggtgtcat gatcggcgcg cctggcagac atactgtccc   4140
acaaatgaag atggaatctg taaaagaaaa cgcgtgaaat aatgcgtctg acaaaggtta   4200
ggtcggctgc ctttaatcaa taccaaagtg gtccctacca cgatggaaaa actgtgcagt   4260
cggtttggct ttttctgacg aacaaataag attcgtggcc gacaggtggg ggtccaccat   4320
gtgaaggcat cttcagactc caataatgga gcaatgacgt aagggcttac gaaataagta   4380
agggtagttt gggaaatgtc cactcacccg tcagtctata aatacttagc ccctccctca   4440
ttgttaaggg agcaaaatct cagagagata gtcctagaga gagaaagaga gcaagtagcc   4500
tagaagtagt caaggcggcg aagtattcag gcacgtggcc aggaagaaga aaagccaaga   4560
cgacgaaaac aggtaagagc taagcttcct gcaggatgga agacgccaaa aacataaaga   4620
aaggcccggc gccattctat ccgctggaag atggaaccgc tggagagcaa ctgcataagg   4680
ctatgaagag atacgccctg gttcctggaa caattgcttt tacagatgca catatcgagg   4740
tggacatcac ttacgctgag tacttcgaaa tgtccgttcg gttggcagaa gctatgaaac   4800
gatatgggct gaatacaaat cacagaatcg tcgtatgcag tgaaaactct cttcaattct   4860
ttatgccggt gttgggcgcg ttatttatcg gagttgcagt tgcgcccgcg aacgacattt   4920
ataatgaacg tgaattgctc aacagtatgg gcatttcgca gcctaccgtg gtgttcgttt   4980
ccaaaaaggg gttgcaaaaa attttgaacg tgcaaaaaaa gctcccaatc atccaaaaaa   5040
ttattatcat ggattctaaa acggattacc agggatttca gtcgatgtac acgttcgtca   5100
catctcatct acctcccggt tttaatgaat acgattttgt gccagagtcc ttcgataggg   5160
acaagacaat tgcactgatc atgaactcct ctggatctac tggtctgcct aaaggtgtcg   5220
ctctgcctca tagaactgcc tgcgtgagat tctcgcatgc cagagatcct atttttggca   5280
atcaaatcat tccggatact gcgattttaa gtgttgttcc attccatcac ggttttggaa   5340
tgtttactac actcggatat ttgatatgtg gatttcgagt cgtcttaatg tatagatttg   5400
aagaagagct gtttctgagg agccttcagg attacaagat tcaaagtgcg ctgctggtgc   5460
caaccctatt ctccttcttc gccaaaagca ctctgattga caaatacgat ttatctaatt   5520
tacacgaaat tgcttctggt ggcgctcccc tctctaagga agtcggggaa gcggttgcca   5580
agaggttcca tctgccaggt atcaggcaag gatatgggct cactgagact acatcagcta   5640
ttctgattac acccgagggg gatgataaac cgggcgcggt cggtaaagtt gttccatttt   5700
ttgaagcgaa ggttgtggat ctggataccg ggaaaacgct gggcgttaat caaagaggcg   5760
aactgtgtgt gagaggtcct atgattatgt ccggttatgt aaacaatccg gaagcgacca   5820
acgccttgat tgacaaggat ggatggctac attctggaga catagcttac tgggacgaag   5880
```

-continued acgaacactt cttcatcgtt gaccgcctga agtctctgat taagtacaaa ggctatcagg 5940
tggctcccgc tgaattggaa tccatcttgc tccaacaccc caacatcttc gacgctggtg 6000
tcgcaggtct tcccgacgat gacgccggtg aacttcccgc cgccgttgtt gttttggagc 6060
acggaaagac gatgacggaa aaagagatcg tggattacgt cgccagtcaa gtaacaaccg 6120
cgaaaaagtt gcgcggagga gttgtgtttg tggacgaagt accgaaaggt cttaccggaa 6180
aactcgacgc aagaaaaatc agagagatcc tcataaaggc caagaagggc ggaaagatcg 6240
ccgtgtgacg tcgacgatat gaagatgaag atgaaatatt tggtgtgtca aataaaaagc 6300
ttgtgtgctt aagtttgtgt ttttttcttg gcttgttgtg ttatgaattt gtggcttttt 6360
ctaatattaa atgaatgtaa gatcacatta taatgaataa acaaatgttt ctataatcca 6420
ttgtgaatgt tttgttggat ctcttctgca gcatataact actgtatgtg ctatggtatg 6480
gactatggaa tatgattaaa gataagccag agctctggtg acggacggcg cgactagttt 6540
tacgtacgtt aattaacccg ggcgcgccga tcatgagcgg agaattaagg gagtcacgtt 6600
atgacccccg ccgatgacgc gggacaagcc gttttacgtt tggaactgac agaaccgcaa 6660
cgttgaagga gccactcagc cgcgggtttc tggagtttaa tgagctaagc acatacgtca 6720
gaaaccatta ttgcgcgttc aaaagtcgcc taaggtcact atcagctagc aaatatttct 6780
tgtcaaaaat gctccactga cgttccataa attcccctcg gtatccaatt agagtctcat 6840
attcactctc aatccaaata atctgcaccg tacctgcagg gtccgagcta ggtcacagaa 6900
gcgctcagga aggccgctga gatagaggca tggcggccaa tgcgggcggc ggtggagcgg 6960
gaggaggcag cggcagcggc agcgtggctg cgccggcggt gtgccgcccc agcggctcgc 7020
ggtggacgcc gacgccggag cagatcagga tgctgaagga gctgtactac ggctgcggca 7080
tccggtcgcc cagctcggag cagatccagc gcatcaccgc catgctgcgg cagcacggca 7140
agatcgaggg caagaacgtc ttctactggt tccagaacca caaggcccgc gagcgccaga 7200
agcgccgcct caccagcctc gacgtgaacg tgcccgccgc cggcgcggcc gacgccacca 7260
ccagccaact cggcgtcctc tcgctgtcgt cgccgccgcc ttcaggcgcg gcgcctccct 7320
cgcccaccct cggcttctac gccgccggca atggcggcgg atcggctgtg ctgctggaca 7380
cgagttccga ctggggcagc agcggcgctg cgatggccac cgagacatgc ttcctccagg 7440
actacatggg cgtgacggac acgggcagct cgtcgcagtg gccacgcttc tcgtcgtcgg 7500
acacgataat ggcggcggcc gcggcgcggg cggcgacgac gcgggcgccc gagactctcc 7560
ctctcttccc gacctgcggc gacgacggcg gcagcggtag cagcagctac ttgccgttct 7620
ggggtgccgc gtccacaact gccggcgcca cttcttccgt tgcgatccag cagcaacacc 7680
agctgcagga gcagtacagc ttttacagca acagcaacag cacccagctg gccggcaccg 7740
gcaaccaaga cgtatcggca acagcagcag cagccgccgc cctggagctg agcctcagct 7800
catggtgctc cccttaccct gctgcaggga gtatgtgaga gcaacgcgag ctgccactgc 7860
tcttcactta tgtctctgga atggaaggag gaggaagtga gcatagcgtt ggtgcgttgc 7920
tgtcattgtc ctaggttagt agctagtgcc agttactagt aagcatcagg cataggagta 7980
tgtagtagaa gcatgcacgt tgccggccag ccaggcttta gacgggaaaa gaatttggtg 8040
cagccggctg caaaacagga tgtttacagc cccccccctcg agccctagac ttgtccatct 8100
tctggattgg ccaagttaat taatgtatga aataaaagga tgcacacata gtgacatgct 8160
aatcactata atgtgggcat caaagttgtg tgttatgtgt aattactaat tatctgaata 8220

-continued

```
agagaaagag atcatccata tttcttatcc taaatgaatg tcacgtgtct ttataattct   8280
ttgatgaacc agatgcattt tattaaccaa ttccatatac atataaatat taatcatata   8340
taattaatat caattgggtt agcaaaacaa atctagtcta ggtgtgtttt gctaattatt   8400
gggggatagt gcaaaaagaa atctacgttc tcaataattc agatagaaaa cttaataaag   8460
tgagataatt tacatagatt gcttttatcc tttgatatat gtgaaaccat gcatgatata   8520
aggaaaatag atagagaaat aatttttac atcgttgaat atgtaaacaa tttaattcaa   8580
gaagctagga atataaatat tgaggagttt atgattagag ctctcccact aaacgtcccg   8640
cgtcgagctg caggtcaacg gatcaggata ttcttgttta agatgttgaa ctctatggag   8700
gtttgtatga actgatgatc taggaccgga taagttccct tcttcatagc gaacttattc   8760
aaagaatgtt ttgtgtatca ttcttgttac attgttatta atgaaaaaat attattggtc   8820
attggactga acacgagtgt taaatatgga ccaggcccca aataagatcc attgatatat   8880
gaattaaata acaagaataa atcgagtcac caaaccactt gccttttttta acgagacttg   8940
ttcaccaact tgatacaaaa gtcattatcc tatgcaaatc aataatcata caaaaatatc   9000
caataacact aaaaaattaa aagaaatgga taatttcaca atatgttata cgataaagaa   9060
gttacttttc caagaaattc actgatttta taagcccact tgcattagat aaatggcaaa   9120
aaaaaacaaa aaggaaaaga aataaagcac gaagaattct agaaaatacg aaatacgctt   9180
caatgcagtg ggacccacgg ttcaattatt gccaattttc agctccaccg tatatttaaa   9240
aaataaaacg ataatgctaa aaaaatataa atcgtaacga tcgttaaatc tcaacggctg   9300
gatcttatga cgaccgttag aaattgtggt tgtcgacgag tcagtaataa acggcgtcaa   9360
agtggttgca gccggcacac acgagtcgtg tttatcaact caaagcacaa atacttttcc   9420
tcaacctaaa aataaggcaa ttagccaaaa acaactttgc gtgtaaacaa cgctcaatac   9480
acgtgtcatt ttattattag ctattgcttc accgccttag ctttctcgtg acctagtcgt   9540
cctcgtcttt tcttcttctt cttctataaa acaataccca aagagctctt cttcttcaca   9600
attcagattt caatttctca aaatcttaaa aactttctct caattctctc taccgtgatc   9660
aaggtaaatt tctgtgttcc ttattctctc aaaatcttcg attttgtttt cgttcgatcc   9720
caatttcgta tatgttcttt ggtttagatt ctgttaatct tagatcgaac acgattttct   9780
gggtttgatc gttagatatc atcttaattc tcgattaggg tttcatagat atcatccgat   9840
ttgttcaaat aatttgagtt ttgtcgaata attactcttc gatttgtgat ttctatctag   9900
atctggtgtt agtttctagt ttgtgcgatc gaatttgtcg attaatctga gtttttctga   9960
ttaacaggat ggagagtggt tccaacagca cttcttgtcc aatggctttt gccggggata  10020
atagtgatgg tccgatgtgt cctatgatga tgatgatgcc gcccatcatg acatcacatc  10080
aacatcatgg tcatgatcat caacatcaac aacaagaaca tgatggttat gcatatcagt  10140
cacaccacca acaaagtagt tccctttttc ttcaatcact agctcctccc caaggaacta  10200
agaacaaagt tgcttcttct tcttctcctt cctcttgtgc tcctgcctat tctctaatgg  10260
agatccatca taacgaaatc gttgcaggag gaatcaaccc ttgctcctct tcctcttctt  10320
cagcctctgt caaggccaag atcatggctc atcctcacta ccaccgcctc ttggccgctt  10380
atgtcaattg tcagaaggtt ggagcaccac cggaggttgt ggcgaggcta gaggaggcat  10440
gctcgtctgc cgcagccgct gccgcatcta tgggaccaac aggatgtcta ggtgaagatc  10500
cagggcttga tcaattcatg gaagcttact gtgaaatgct cgttaagtat gagcaagagc  10560
tctccaaacc tttcaaggaa gctatggtct tccttcaacg tgtcgagtgt caattcaaat  10620
```

```
ccctctctct atcctcacct tcctctttct ccggttatgg agagacagca attgatagga  10680
acaataatgg gtcatccgag gaagaagtcg atatgaacaa tgaatttgta gatccacaag  10740
ctgaggatag agagcttaaa ggacagctct tgcgcaagta cagtggttac ttagggagcc  10800
tcaagcaaga gttcatgaag aagaggaaga aaggaaagct ccctaaagaa gctcgtcaac  10860
aactgcttga ttggtggagc cgtcactaca aatggcctta cccttcggag caacaaaagc  10920
tcgcccttgc ggaatcaacg gggctggacc agaaacagat aaacaattgg ttcataaacc  10980
agaggaaacg gcattggaag ccgtcggagg acatgcagtt tgtagtaatg gacgcaacac  11040
atcctcacca ttacttcatg gataatgtct tgggcaatcc tttcccaatg gatcacatct  11100
cctccaccat gctttgactc gagtttctcc ataataatgt gtgagtagtt cccagataag  11160
ggaattaggg ttcctatagg gtttcgctca tgtgttgagc atataagaaa cccttagtat  11220
gtatttgtat ttgtaaaata cttctatcaa taaaatttct aattcctaaa accaaaatcc  11280
agtactaaaa tccagatccc ccgaattaag tgactacacc tgcaaaaagt gtttgatcgc  11340
cggcggtacc gagtgtactt caagtcagtg ggaaatcaat aaaatgatta ttttatgaat  11400
atatttcatt gtgcaagtag atagaaatta catatgttac ataacacacg aaataaacaa  11460
aaaaagacaa tccaaaaaca aacaccccaa aaaaaataat cactttagat aaactcgtat  11520
gaggagaggc acgttcagtg actcgacgat tcccgagcaa aaaaagtctc cccgtcacac  11580
atgtagtggg tgacgcaatt atctttaaag taatccttct gttgacttgt cattgataac  11640
atccagtctt cgtcaggatt gcaaagaatt atagaaggga tcccaccttt tattttcttc  11700
ttttttccat atttagggtt gacagtgaaa tcagactggc aacctattaa ttgcttccac  11760
aatgggacga acttgaaggg gatgtcgtcg atgatattat aggtggcgtg ttcatcgtag  11820
ttggtgaaat cgatggtacc gttccaatag ttgtgtcgtc cgagacttct agcccaggtg  11880
gtctttccgg tacgagttgg tccgcagatg tagaggctgg ggtgtcggat tccattcctt  11940
ccattgtcct tgttaaatcg gccatccatt caaggtcaga ttgagcttgt tggtatgaga  12000
caggatgtat gtaagtataa gcgtctatgc ttacatggta tagatgggtt tccctccagg  12060
agtgtagatc ttcgtggcag cgaagatctg attctgtgaa gggcgacaca tacggttcag  12120
gttgtggagg gaataatttg ttggctgaat attccagcca ttgaagcttt gttgcccatt  12180
catgagggaa ttcttccttg atcatgtcaa gatattcctc cttagacgtt gcagtctgga  12240
taatagttct ccatcgtgcg tcagatttgc gaggagaaac cttatgatct cggaaatctc  12300
ctctggtttt aatatctccg tcctttgata tgtaatcaag gacttgttta gagtttctag  12360
ctggctggat attagggtga tttccttcaa aatcgaaaaa agaaggatcc ctaatacaag  12420
gttttttatc aagctggaga agagcatgat agtgggtagt gccatcttga tgaagctcag  12480
aagcaacacc aaggaagaaa ataagaaaag gtgtgagttt ctcccagaga aactggaata  12540
aatcatctct ttgagatgag cacttgggat aggtaaggaa aacatattta gattggagtc  12600
tgaagttctt actagcagaa ggcatgttgt tgtgactccg aggggttgcc tcaaactcta  12660
tcttataacc ggcgtggagg catggaggca ggggtatttt ggtcatttta atagatagtg  12720
gaaaatgacg tggaatttac ttaaagacga agtctttgcg acaagggggg gcccacgccg  12780
aatttaatat taccggcgtg gcccccccctt atcgcgagtg ctttagcacg agcggtccag  12840
atttaaagta gaaaatttcc cgcccactag ggttaaaggt gttcacacta taaaagcata  12900
tacgatgtga tggtatttga tggagcgtat attgtatcag gtatttccgt tggatacgaa  12960
```

-continued

```
ttattcgtac gaccctcata gtttaaacta tcagtgtttg acaggatata ttggcgggta  13020
aacctaagag aaaagagcgt ttattagaat aacggatatt taaaagggcg tgaaaaggtt  13080
tatccgttcg tccatttgta tgtgcatgcc aaccacaggg ttcccctcgg gatcaaagta  13140
ctttgatcca acccctccgc tgctatagtg cagtcggctt ctgacgttca gtgcagccgt  13200
cttctgaaaa cgacatgtcg cacaagtcct aagttacgcg acaggctgcc gccctgccct  13260
tttcctggcg ttttcttgtc gcgtgtttta gtcgcataaa gtagaatact tgcgactaga  13320
accggagaca ttacgccatg aacaagagcg ccgccgctgg cctgctgggc tatgcccgcg  13380
tcagcaccga cgaccaggac ttgaccaacc aacgggccga actgcacgcg gccggctgca  13440
ccaagctgtt ttccgagaag atcaccggca ccaggcgcga ccgcccggag ctggccagga  13500
tgcttgacca cctacgccct ggcgacgttg tgacagtgac caggctagac cgcctggccc  13560
gcagcacccg cgacctactg gacattgccg agcgcatcca ggaggccggc gcgggcctgc  13620
gtagcctggc agagccgtgg gccgacacca ccacgccggc cggccgcatg gtgttgaccg  13680
tgttcgccgg cattgccgag ttcgagcgtt ccctaatcat cgaccgcacc cggagcgggc  13740
gcgaggccgc caaggcccga ggcgtgaagt ttggcccccg ccctaccctc accccggcac  13800
agatcgcgca cgcccgcgag ctgatcgacc aggaaggccg caccgtgaaa gaggcggctg  13860
cactgcttgg cgtgcatcgc tcgaccctgt accgcgcact tgagcgcagc gaggaagtga  13920
cgcccaccga ggccaggcgg cgcggtgcct tccgtgagga cgcattgacc gaggccgacg  13980
ccctggcggc cgccgagaat gaacgccaag aggaacaagc atgaaaccgc accaggacgg  14040
ccaggacgaa ccgtttttca ttaccgaaga gatcgaggcg gagatgatcg cggccgggta  14100
cgtgttcgag ccgcccgcgc acggctcaac cgtgcggctg catgaaatcc tggccggttt  14160
gtctgatgcc aagctggcgg cctggccggc cagcttggcc gctgaagaaa ccgagcgccg  14220
ccgtctaaaa aggtgatgtg tatttgagta aaacagcttg cgtcatgcgg tcgctgcgta  14280
tatgatgcga tgagtaaata aacaaatacg caaggggaac gcatgaaggt tatcgctgta  14340
cttaaccaga aaggcgggtc aggcaagacg accatcgcaa cccatctagc ccgcgccctg  14400
caactcgccg gggccgatgt tctgttagtc gattccgatc cccagggcag tgcccgcgat  14460
tgggcggccg tgcgggaaga tcaaccgcta accgttgtcg gcatcgaccg cccgacgatt  14520
gaccgcgacg tgaaggccat cggccggcgc gacttcgtag tgatcgacgg agcgccccag  14580
gcggcggact tggctgtgtc cgcgatcaag gcagccgact tcgtgctgat tccggtgcag  14640
ccaagccctt acgacatatg ggccaccgcc gacctggtgg agctggttaa gcagcgcatt  14700
gaggtcacgg atggaaggct acaagcggcc tttgtcgtgt cgcgggcgat caaaggcacg  14760
cgcatcggcg gtgaggttgc cgaggcgctg gccgggtacg agctgcccat tcttgagtcc  14820
cgtatcacgc agcgcgtgag ctacccaggc actgccgccg ccggcacaac cgttcttgaa  14880
tcagaacccg agggcgacgc tgcccgcgag gtccaggcgc tggccgctga aattaaatca  14940
aaactcattt gagttaatga ggtaaagaga aaatgagcaa aagcacaaac acgctaagtg  15000
ccggccgtcc gagcgcacgc agcagcaagg ctgcaacgtt ggccagcctg gcagacacgc  15060
cagccatgaa gcgggtcaac tttcagttgc cggcggagga tcacaccaag ctgaagatgt  15120
acgcggtacg ccaaggcaag accattaccg agctgctatc tgaatacatc gcgcagctac  15180
cagagtaaat gagcaaatga ataaatgagt agatgaattt tagcggctaa aggaggcggc  15240
atggaaaatc aagaacaacc aggcaccgac gccgtggaat gccccatgtg tggaggaacg  15300
ggcggttggc caggcgtaag cggctgggtt gtctgccggc cctgcaatgg cactggaacc  15360
```

```
cccaagcccg aggaatcggc gtgacggtcg caaaccatcc ggcccggtac aaatcggcgc  15420
ggcgctgggt gatgacctgg tggagaagtt gaaggccgcg caggccgccc agcggcaacg  15480
catcgaggca gaagcacgcc ccggtgaatc gtggcaagcg gccgctgatc gaatccgcaa  15540
agaatcccgg caaccgccgg cagccggtgc gccgtcgatt aggaagccgc ccaagggcga  15600
cgagcaacca gatttttttcg ttccgatgct ctatgacgtg ggcacccgcg atagtcgcag  15660
catcatggac gtggccgttt tccgtctgtc gaagcgtgac cgacgagctg gcgaggtgat  15720
ccgctacgag cttccagacg ggcacgtaga ggtttccgca gggccggccg gcatggccag  15780
tgtgtgggat tacgacctgg tactgatggc ggtttcccat ctaaccgaat ccatgaaccg  15840
ataccgggaa gggaagggag acaagcccgg ccgcgtgttc cgtccacacg ttgcggacgt  15900
actcaagttc tgccggcgag ccgatggcgg aaagcagaaa gacgacctgg tagaaacctg  15960
cattcggtta aacaccacgc acgttgccat gcagcgtacg aagaaggcca agaacggccg  16020
cctggtgacg gtatccgagg gtgaagcctt gattagccgc tacaagatcg taaagagcga  16080
aaccgggcgg ccggagtaca tcgagatcga gctagctgat tggatgtacc gcgagatcac  16140
agaaggcaag aacccggacg tgctgacggt tcaccccgat tactttttga tcgatcccgg  16200
catcggccgt tttctctacc gcctggcacg ccgcgccgca ggcaaggcag aagccagatg  16260
gttgttcaag acgatctacg aacgcagtgg cagcgccgga gagttcaaga agttctgttt  16320
caccgtgcgc aagctgatcg ggtcaaatga cctgccggag tacgatttga aggaggaggc  16380
ggggcaggct ggcccgatcc tagtcatgcg ctaccgcaac ctgatcgagg gcgaagcatc  16440
cgccggttcc taatgtacgg agcagatgct agggcaaatt gccctagcag gggaaaaagg  16500
tcgaaaaggc ctctttcctg tggatagcac gtacattggg aacccaaagc cgtacattgg  16560
gaaccggaac ccgtacattg ggaacccaaa gccgtacatt gggaaccggt cacacatgta  16620
agtgactgat ataaaagaga aaaaaggcga tttttccgcc taaaactctt taaaacttat  16680
taaaactctt aaaacccgcc tggcctgtgc ataactgtct ggccagcgca cagcccaaga  16740
gctgcaaaaa gcgcctaccc ttcggtcgct gcgctcccta cgccccgccg cttcgcgtcg  16800
gcctatcgcg gccgctggcc gctcaaaaat ggctggccta cggccaggca atctaccagg  16860
gcgcggacaa gccgcgccgt cgccactcga ccgccggcgc ccacatcaag gcaccctgcc  16920
tcgcgcgttt cggtgatgac ggtgaaaacc tctgacacat gcagctcccg gaaacggtca  16980
cagcttgtct gtaagcggat gccgggagca gacaagcccg tcagggcgcg tcagcgggtg  17040
ttggcgggtg tcggggcgca gccatgaccc agtcacgtag cgatagcgga gtgtatactg  17100
gcttaactat gcggcatcag agcagattgt actgagagtg caccatatgc ggtgtgaaat  17160
accgcacaga tgcgtaagga gaaaataccg catcaggccc tcttccgctt cctcgctcac  17220
tgactcgctg cgctcggtcg ttcggctgcg gcgagcggta tcagctcact caaaggcggt  17280
aatacggtta tccacagaat caggggataa cgcaggaaag aacatgtgag caaaaggcca  17340
gcaaaaggcc aggaaccgta aaaaggccgc gttgctggcg tttttccata ggctccgccc  17400
ccctgacgag catcacaaaa atcgacgctc aagtcagagg tggcgaaacc cgacaggact  17460
ataaagatac caggcgtttc cccctggaag ctccctcgtg cgctctcctg ttccgaccct  17520
gccgcttacc ggatacctgt ccgcctttct cccttcggga agcgtggcgc tttctcatag  17580
ctcacgctgt aggtatctca gttcggtgta ggtcgttcgc tccaagctgg gctgtgtgca  17640
cgaacccccc gttcagcccg accgctgcgc cttatccggt aactatcgtc ttgagtccaa  17700
```

cccggtaaga cacgacttat cgccactggc agcagccact ggtaacagga ttagcagagc 17760
gaggtat 17767

<210> SEQ ID NO 29
<211> LENGTH: 20340
<212> TYPE: DNA
<213> ORGANISM: artificial
<220> FEATURE:
<223> OTHER INFORMATION: synthetic oligonucleotide

<400> SEQUENCE: 29
gtaggcggtg ctacagagtt cttgaagtgg tggcctaact acggctacac tagaaggaca 60
gtatttggta tctgcgctct gctgaagcca gttaccttcg gaaaaagagt tggtagctct 120
tgatccggca aacaaaccac cgctggtagc ggtggttttt ttgtttgcaa gcagcagatt 180
acgcgcagaa aaaaaggatc tcaagaagat cctttgatct tttctacggg gtctgacgct 240
cagtggaacg aaaactcacg ttaagggatt ttggtcatgc attctaggta ctaaaacaat 300
tcatccagta aaatataata ttttattttc tcccaatcag gcttgatccc cagtaagtca 360
aaaaatagct cgacatactg ttcttccccg atatcctccc tgatcgaccg gacgcagaag 420
gcaatgtcat accacttgtc cgccctgccg cttctcccaa gatcaataaa gccacttact 480
ttgccatctt tcacaaagat gttgctgtct cccaggtcgc cgtgggaaaa gacaagttcc 540
tcttcgggct tttccgtctt taaaaaatca tacagctcgc gcggatcttt aaatggagtg 600
tcttcttccc agttttcgca atccacatcg gccagatcgt tattcagtaa gtaatccaat 660
tcggctaagc ggctgtctaa gctattcgta tagggacaat ccgatatgtc gatggagtga 720
aagagcctga tgcactccgc atacagctcg ataatctttt cagggctttg ttcatcttca 780
tactcttccg agcaaaggac gccatcggcc tcactcatga gcagattgct ccagccatca 840
tgccgttcaa agtgcaggac ctttggaaca ggcagctttc cttccagcca tagcatcatg 900
tccttttccc gttccacatc ataggtggtc cctttatacc ggctgtccgt catttttaaa 960
tataggtttt cattttctcc caccagctta tataccttag caggagacat tccttccgta 1020
tcttttacgc agcggtattt ttcgatcagt tttttcaatt ccggtgatat tctcatttta 1080
gccatttatt atttccttcc tcttttctac agtatttaaa gataccccaa gaagctaatt 1140
ataacaagac gaactccaat tcactgttcc ttgcattcta aaaccttaaa taccagaaaa 1200 cagcttttc aaagttgttt tcaaagttgg cgtataacat agtatcgacg gagccgattt 1260
tgaaaccgcg gtgatcacag gcagcaacgc tctgtcatcg ttacaatcaa catgctaccc 1320
tccgcgagat catccgtgtt tcaaacccgg cagcttagtt gccgttcttc cgaatagcat 1380
cggtaacatg agcaaagtct gccgccttac aacggctctc ccgctgacgc cgtcccggac 1440
tgatgggctg cctgtatcga gtggtgattt tgtgccgagc tgccggtcgg ggagctgttg 1500
gctggctggt ggcaggatat attgtggtgt aaacaaattg acgcttagac aacttaataa 1560
cacattgcgg acgtttttaa tgtactgaat taacgccgaa ttaattcggg ggatctggat 1620
tttagtactg gattttggtt ttaggaatta gaaattttat tgatagaagt attttacaaa 1680
tacaaataca tactaagggt ttcttatatg ctcaacacat gagcgaaacc ctataggaac 1740
cctaattccc ttatctggga actactcaca cattattatg gagaaactcg agcttgtcga 1800
tcgactctag ctagaggatc gatccgaacc ccagagtccc gctcagaaga actcgtcaag 1860
aaggcgatag aaggcgatgc gctgcgaatc gggagcggcg ataccgtaaa gcacgaggaa 1920
gcggtcagcc cattcgccgc caagttcttc agcaatatca cgggtagcca acgctatgtc 1980
ctgatagcgg tccgccacac ccagccggcc acagtcgatg aatccagaaa agcggccatt 2040
ttccaccatg atattcggca agcaggcatc gccatgtgtc acgacgagat cctcgccgtc 2100
gggcatgcgc gccttgagcc tggcgaacag ttcggctggc gcgagcccct gatgttcttc 2160
gtccagatca tcctgatcga caagaccggc ttccatccga gtacgtgctc gctcgatgcg 2220
atgtttcgct tggtggtcga atgggcaggt agccggatca agcgtatgca gccgccgcat 2280
tgcatcagcc atgatggata ctttctcggc aggagcaagg tgagatgaca ggagatcctg 2340
ccccggcact tcgcccaata gcagccagtc ccttcccgct tcagtgacaa cgtcgagcac 2400
agctgcgcaa ggaacgcccg tcgtggccag ccacgatagc cgcgctgcct cgtcctggag 2460
ttcattcagg gcaccggaca ggtcggtctt gacaaaaaga accgggcgcc cctgcgctga 2520
cagccgaaac acggcggcat cagagcagcc gattgtctgt tgtgcccagt catagccgaa 2580
tagcctctcc acccaagcgg ccggagaacc tgcgtgcaat ccatcttgtt caatccccat 2640
ggtcgatcga cagatctgcg aaagctcgag agagatagat ttgtagagag agactggtga 2700
tttcagcgtg tcctctccaa atgaaatgaa cttccttata tagaggaagg tcttgcgaag 2760
gatagtggga ttgtgcgtca tcccttacgt cagtggagat atcacatcaa tccacttgct 2820
ttgaagacgt ggttggaacg tcttcttttt ccacgatgct cctcgtgggt gggggtccat 2880
ctttgggacc actgtcggca gaggcatctt gaacgatagc ctttccttta tcgcaatgat 2940
ggcatttgta ggtgccacct tccttttcta ctgtcctttt gatgaagtga cagatagctg 3000
ggcaatggaa tccgaggagg tttcccgata ttaccctttg ttgaaaagtc tcaatagccc 3060
tttggtcttc tgagactgta tctttgatat tcttggagta gacgagagtg tcgtgctcca 3120
ccatgttatc acatcaatcc acttgctttg aagacgtggt tggaacgtct tctttttcca 3180
cgatgctcct cgtgggtggg ggtccatctt tgggaccact gtcggcagag gcatcttgaa 3240
cgatagcctt tcctttatcg caatgatggc atttgtaggt gccaccttcc ttttctactg 3300
tccttttgat gaagtgacag atagctgggc aatggaatcc gaggaggttt cccgatatta 3360
ccctttgttg aaaagtctca atagcccttt ggtcttctga gactgtatct ttgatattct 3420
tggagtagac gagagtgtcg tgctccacca tgttggcaag ctgctctagc caatacgcaa 3480
accgcctctc cccgcgcgtt ggccgattca ttaatgcagc tggcacgaca ggtttcccga 3540
ctggaaagcg ggcagtgagc gcaacgcaat taatgtgagt tagctcactc attaggcacc 3600
ccaggcttta cactttatgc ttccggctcg tatgttgtgt ggaattgtga gcggataaca 3660
atttcacaca ggaaacagct atgaccatga ttacgaattc gagctcaaag tttaacgcgt 3720
tagcagaagg catgttgttg tgactccgag gggttgcctc aaactctatc ttataaccgg 3780
cgtggaggca tggaggcagg ggtattttgg tcattttaat agatagtgga aaatgacgtg 3840
gaatttactt aaagacgaag tctttgcgac aaggggggc ccacgccgaa tttaatatta 3900
ccggcgtggc ccccccttat cgcgagtgct ttagcacgag cggtccagat ttaaagtaga 3960
aaatttcccg cccactaggg ttaaaggtgt tcacactata aaagcatata cgatgtgatg 4020
gtatttgatg gagcgtatat tgtatcaggt atttccgttg gatacgaatt attcgtacga 4080
ccctcggtac cgatcaaaat catgatcggc gcgccagatt tgccttttca atttcagaaa 4140
gaatgctaac ccacagatgg ttagagaggc ttacgcagca ggtatcatca agacgatcta 4200
cccgagcaat aatctccagg aaatcaaata ccttcccaag aaggttaaag atgcagtcaa 4260
aagattcagg actaactgca tcaagaacac agagaaagat atatttctca agatcagaag 4320

```
tactattcca gtatggacga ttcaaggctt gcttcacaaa ccaaggcaag taatagagat   4380
tggagtctct aaaaaggtag ttcccactga atcaaaggcc atggagtcaa agattcaaat   4440
agaggaccta acagaactcg ccgtaaagac tggcgaacag ttcatacaga gtctcttacg   4500
actcaatgac aagaagaaaa tcttcgtcaa catggtggag cacgacacac ttgtctactc   4560
caaaaatatc aaagatacag tctcagaaga ccaaagggca attgagactt ttcaacaaag   4620
ggtaatatcc ggaaacctcc tcggattcca ttgcccagct atctgtcact ttattgtgaa   4680
gatagtggaa aaggaaggtg gctcctacaa atgccatcat tgcgataaag gaaaggccat   4740
cgttgaagat gcctctgccg acagtggtcc caaagatgga cccccaccca cgaggagcat   4800
cgtggaaaaa gaagacgttc caaccacgtc ttcaaagcaa gtggattgat gtgatatctc   4860
cactgacgta agggatgacg cacaatccca ctatccttcg caagaccctt cctctatata   4920
aggaagttca tttcatttgg agagaacacg ggggactcct gcaggtagat cgctcgtcga   4980
catggataag aagtactcta tcggactcga tatcggaact aactctgtgg gatgggctgt   5040
gatcaccgat gagtacaagg tgccatctaa gaagttcaag gttctcggaa acaccgatag   5100
gcactctatc aagaaaaacc ttatcggtgc tctcctcttc gattctggtg aaactgctga   5160
ggctaccaga ctcaagagaa ccgctagaag aaggtacacc agaagaaaga acaggatctg   5220
ctacctccaa gagatcttct ctaacgagat ggctaaagtg gatgattcat tcttccacag   5280
gctcgaagag tcattcctcg tggaagaaga taagaagcac gagaggcacc ctatcttcgg   5340
aaacatcgtt gatgaggtgg cataccacga gaagtaccct actatctacc acctcagaaa   5400
gaagctcgtt gattctactg ataaggctga tctcaggctc atctacctcg ctctcgctca   5460
catgatcaag ttcagaggac acttcctcat cgagggtgat ctcaaccctg ataactctga   5520
tgtggataag ttgttcatcc agctcgtgca gacctacaac cagcttttcg aagagaaccc   5580
tatcaacgct tcaggtgtgg atgctaaggc tatcctctct gctaggctct ctaagtcaag   5640
aaggcttgag aacctcattg ctcagctccc tggtgagaag aagaacggac ttttcggaaa   5700
cttgatcgct ctctctctcg gactcacccc taacttcaag tctaacttcg atctcgctga   5760
ggatgcaaag ctccagctct caaaggatac ctacgatgat gatctcgata acctcctcgc   5820
tcagatcgga gatcagtacg ctgatttgtt cctcgctgct aagaacctct ctgatgctat   5880
cctcctcagt gatatcctca gagtgaacac cgagatcacc aaggctccac tctcagcttc   5940
tatgatcaag agatacgatg agcaccacca ggatctcaca cttctcaagg ctcttgttag   6000
acagcagctc ccagagaagt acaaagagat tttcttcgat cagtctaaga acggatacgc   6060
tggttacatc gatggtggtg catctcaaga agagttctac aagttcatca agcctatcct   6120
cgagaagatg gatggaaccg aggaactcct cgtgaagctc aatagagagg atcttctcag   6180
aaagcagagg accttcgata acggatctat ccctcatcag atccacctcg gagagttgca   6240
cgctatcctt agaaggcaag aggatttcta cccattcctc aaggataaca gggaaaagat   6300
tgagaagatt ctcaccttca gaatccctta ctacgtggga cctctcgcta gaggaaactc   6360
aagattcgct tggatgacca gaaagtctga ggaaaccatc accccttgga acttcgaaga   6420
ggtggtggat aagggtgcta gtgctcagtc tttcatcgag aggatgacca acttcgataa   6480
gaaccttcca aacgagaagg tgctccctaa gcactctttg ctctacgagt acttcaccgt   6540
gtacaacgag ttgaccaagg ttaagtacgt gaccgaggga atgaggaagc ctgctttttt   6600
gtcaggtgag caaaagaagg ctatcgttga tctcttgttc aagaccaaca gaaaggtgac   6660
cgtgaagcag ctcaaagagg attacttcaa gaaaatcgag tgcttcgatt cagttgagat   6720
```

ttctggtgtt gaggataggt tcaacgcatc tctcggaacc taccacgatc tcctcaagat 6780
cattaaggat aaggatttct tggataacga ggaaaacgag gatatcttgg aggatatcgt 6840
tcttaccctc accctctttg aagatagaga gatgattgaa gaaaggctca agacctacgc 6900
tcatctcttc gatgataagg tgatgaagca gttgaagaga agaagataca ctggttgggg 6960
aaggctctca agaaagctca ttaacggaat cagggataag cagtctggaa agacaatcct 7020
tgatttcctc aagtctgatg gattcgctaa cagaaacttc atgcagctca tccacgatga 7080
ttctctcacc tttaaagagg atatccagaa ggctcaggtt tcaggacagg gtgatagtct 7140
ccatgagcat atcgctaacc tcgctggatc tcctgcaatc aagaagggaa tcctccagac 7200
tgtgaaggtt gtggatgagt tggtgaaggt gatgggaagg cataagcctg agaacatcgt 7260
gatcgaaatg gctagagaga accagaccac tcagaaggga cagaagaact ctagggaaag 7320
gatgaagagg atcgaggaag gtatcaaaga gcttggatct cagatcctca aagagcaccc 7380
tgttgagaac actcagctcc agaatgagaa gctctacctc tactacctcc agaacggaag 7440
ggatatgtat gtggatcaag agttggatat caacaggctc tctgattacg atgttgatca 7500
tatcgtgcca cagtcattct tgaaggatga ttctatcgat aacaaggtgc tcaccaggtc 7560
tgataagaac aggggtaaga gtgataacgt gccaagtgaa gaggttgtga agaaaatgaa 7620
gaactattgg aggcagctcc tcaacgctaa gctcatcact cagagaaagt tcgataactt 7680
gactaaggct gagaggggag gactctctga attggataag gcaggattca tcaagaggca 7740
gcttgtggaa accaggcaga tcactaagca cgttgcacag atcctcgatt ctaggatgaa 7800
caccaagtac gatgagaacg ataagttgat cagggaagtg aaggttatca ccctcaagtc 7860
aaagctcgtg tctgatttca gaaaggattt ccaattctac aaggtgaggg aaatcaacaa 7920
ctaccaccac gctcacgatg cttaccttaa cgctgttgtt ggaaccgctc tcatcaagaa 7980
gtatcctaag ctcgagtcag agttcgtgta cggtgattac aaggtgtacg atgtgaggaa 8040
gatgatcgct aagtctgagc aagagatcgg aaaggctacc gctaagtatt tcttctactc 8100
taacatcatg aatttcttca agaccgagat taccctcgct aacggtgaga tcagaaagag 8160
gccactcatc gagacaaacg gtgaaacagg tgagatcgtg tgggataagg gaagggattt 8220
cgctaccgtt agaaaggtgc tctctatgcc acaggtgaac atcgttaaga aaaccgaggt 8280
gcagaccggt ggattctcta aagagtctat cctccctaag aggaactctg ataagctcat 8340
tgctaggaag aaggattggg accctaagaa atacggtggt ttcgattctc ctaccgtggc 8400
ttactctgtt ctcgttgtgg ctaaggttga gaagggaaag agtaagaagc tcaagtctgt 8460
taaggaactt ctcggaatca ctatcatgga aaggtcatct ttcgagaaga acccaatcga 8520
tttcctcgag gctaagggat acaaagaggt taagaaggat ctcatcatca agctcccaaa 8580
gtactcactc ttcgaactcg agaacggtag aaagaggatg ctcgcttctg ctggtgagct 8640
tcaaaaggga aacgagcttg ctctcccatc taagtacgtt aactttcttt acctcgcttc 8700
tcactacgag aagttgaagg gatctccaga agataacgag cagaagcaac ttttcgttga 8760
gcagcacaag cactacttgg atgagatcat cgagcagatc tctgagttct ctaaaagggt 8820
gatcctcgct gatgcaaacc tcgataaggt gttgtctgct tacaacaagc acagagataa 8880
gcctatcagg gaacaggcag agaacatcat ccatctcttc acccttacca acctcggtgc 8940
tcctgctgct ttcaagtact tcgatacaac catcgatagg aagagataca cctctaccaa 9000
agaagtgctc gatgctaccc tcatccatca gtctatcact ggactctacg agactaggat 9060

-continued

```
cgatctctca cagctcggtg gtgattcaag ggctgatcct aagaagaaga ggaaggtttg   9120
acgtcgacga tatgaagatg aagatgaaat atttggtgtg tcaaataaaa agcttgtgtg   9180
cttaagtttg tgttttttc ttggcttgtt gtgttatgaa tttgtggctt tttctaatat   9240
taaatgaatg taagatcaca ttataatgaa taaacaaatg tttctataat ccattgtgaa   9300
tgttttgttg gatctcttct gcagcatata actactgtat gtgctatggt atggactatg   9360
gaatatgatt aaagataagc cagagctctg gtgacggacg tgggcttcgt tgaacaacgg   9420
aaactcgact tgccttccgc acaatacatc atttcttctt agcttttttt cttcttcttc   9480
gttcatacag ttttttttg tttatcagct tacattttct tgaaccgtag ctttcgtttt   9540
cttcttttta actttccatt cggagttttt gtatcttgtt tcatagtttg tcccaggatt   9600
agaatgatta ggcatcgaac cttcaagaat ttgattgaat aaaacatctt cattcttaag   9660
atatgaagat aatcttcaaa aggcccctgg gaatctgaaa gaagagaagc aggcccattt   9720
atatgggaaa gaacaatagt atttcttata taggcccatt taagttgaaa acaatcttca   9780
aaagtcccac atcgcttaga taagaaaacg aagctgagtt tatatacagc tagagtcgaa   9840
gtagtgattg ttggtagtag cgactccatg gttttagagc tagaaatagc aagttaaaat   9900
aaggctagtc cgttatcaac ttgaaaaagt ggcaccgagt cggtgcccag agctctggtg   9960
acggacggcg cgactagttt tacgtacgtt aattaacccg ggcgcgccga tcatgagcgg  10020
agaattaagg gagtcacgtt atgacccccg ccgatgacgc gggacaagcc gttttacgtt  10080
tggaactgac agaaccgcaa cgttgaagga gccactcagc cgcgggtttc tggagtttaa  10140
tgagctaagc acatacgtca gaaaccatta ttgcgcgttc aaaagtcgcc taaggtcact  10200
atcagctagc aaatatttct tgtcaaaaat gctccactga cgttccataa attcccctcg  10260
gtatccaatt agagtctcat attcactctc aatccaaata atctgcaccg tacctgcagg  10320
gtccgagcta ggtcacagaa gcgctcagga aggccgctga gatagaggca tggcggccaa  10380
tgcgggcggc ggtggagcgg gaggaggcag cggcagcggc agcgtggctg cgccggcggt  10440
gtgccgcccc agcggctcgc ggtggacgcc gacgccggag cagatcagga tgctgaagga  10500
gctgtactac ggctgcggca tccggtcgcc cagctcggag cagatccagc gcatcaccgc  10560
catgctgcgg cagcacggca agatcgaggg caagaacgtc ttctactggt tccagaacca  10620
caaggcccgc gagcgccaga agcgccgcct caccagcctc gacgtgaacg tgcccgccgc  10680
cggcgcggcc gacgccacca ccagccaact cggcgtcctc tcgctgtcgt cgccgccgcc  10740
ttcaggcgcg gcgcctccct cgcccaccct cggcttctac gccgccggca atggcggcgg  10800
atcggctgtg ctgctggaca cgagttccga ctggggcagc agcggcgctg cgatggccac  10860
cgagacatgc ttcctccagg actacatggg cgtgacggac acgggcagct cgtcgcagtg  10920
gccacgcttc tcgtcgtcgg acacgataat ggcggcggcc gcggcgcggg cggcgacgac  10980
gcgggcgccc gagactctcc ctctcttccc gacctgcggc gacgacggcg gcagcggtag  11040
cagcagctac ttgccgttct ggggtgccgc gtccacaact gccggcgcca cttcttccgt  11100
tgcgatccag cagcaacacc agctgcagga gcagtacagc ttttacagca acagcaacag  11160
cacccagctg gccggcaccg gcaaccaaga cgtatcggca acagcagcag cagccgccgc  11220
cctggagctg agcctcagct catggtgctc cccttaccct gctgcaggga gtatgtgaga  11280
gcaacgcgag ctgccactgc tcttcactta tgtctctgga atggaaggag gaggaagtga  11340
gcatagcgtt ggtgcgttgc tgtcattgtc ctaggttagt agctagtgcc agttactagt  11400
aagcatcagg cataggagta tgtagtagaa gcatgcacgt tgccggccag ccaggcttta  11460
```

gacgggaaaa gaatttggtg cagccggctg caaaacagga tgtttacagc cccccctcg 11520 agccctagac ttgtccatct tctggattgg ccaagttaat taatgtatga aataaaagga 11580
tgcacacata gtgacatgct aatcactata atgtgggcat caaagttgtg tgttatgtgt 11640
aattactaat tatctgaata agagaaagag atcatccata tttcttatcc taaatgaatg 11700
tcacgtgtct ttataattct ttgatgaacc agatgcattt tattaaccaa ttccatatac 11760
atataaatat taatcatata taattaatat caattgggtt agcaaaacaa atctagtcta 11820
ggtgtgtttt gctaattatt gggggatagt gcaaaaagaa atctacgttc tcaataattc 11880
agatagaaaa cttaataaag tgagataatt tacatagatt gcttttatcc tttgatatat 11940
gtgaaaccat gcatgatata aggaaaatag atagagaaat aattttttac atcgttgaat 12000
atgtaaacaa tttaattcaa gaagctagga atataaatat tgaggagttt atgattagag 12060
ctctcccact aaacgtcccg ctggcagaca tactgtccca caaatgaaga tggaatctgt 12120
aaaagaaaac gcgtgaaata atgcgtctga caaaggttag gtcggctgcc tttaatcaat 12180
accaaagtgg tccctaccac gatggaaaaa ctgtgcagtc ggtttggctt tttctgacga 12240
acaaataaga ttcgtggccg acaggtgggg gtccaccatg tgaaggcatc ttcagactcc 12300
aataatggag caatgacgta agggcttacg aaataagtaa gggtagtttg ggaaatgtcc 12360
actcacccgt cagtctataa atacttagcc cctccctcat tgttaaggga gcaaaatctc 12420
agagagatag tcctagagag agaaagagag caagtagcct agaagtagtc aaggcggcga 12480
agtattcagg cacgtggcca ggaagaagaa aagccaagac gacgaaaaca ggtaagagct 12540
aagcttatgg agagtggttc caacagcact tcttgtccaa tggcttttgc cggggataat 12600
agtgatggtc cgatgtgtcc tatgatgatg atgatgccgc ccatcatgac atcacatcaa 12660
catcatggtc atgatcatca acatcaacaa caagaacatg atggttatgc atatcagtca 12720
caccaccaac aaagtagttc ccttttttctt caatcactag ctcctcccca aggaactaag 12780
aacaaagttg cttcttcttc ttctccttcc tcttgtgctc ctgcctattc tctaatggag 12840
atccatcata acgaaatcgt tgcaggagga atcaaccctt gctcctcttc ctcttcttca 12900
gcctctgtca aggccaagat catggctcat cctcactacc accgcctctt ggccgcttat 12960
gtcaattgtc agaaggttgg agcaccaccg gaggttgtgg cgaggctaga ggaggcatgc 13020
tcgtctgccg cagccgctgc cgcatctatg ggaccaacag gatgtctagg tgaagatcca 13080
gggcttgatc aattcatgga agcttactgt gaaatgctcg ttaagtatga gcaagagctc 13140
tccaaacctt tcaaggaagc tatggtcttc cttcaacgtg tcgagtgtca attcaaatcc 13200
ctctctctat cctcaccttc ctctttctcc ggttatggag agacagcaat tgataggaac 13260
aataatgggt catccgagga agaagtcgat atgaacaatg aatttgtaga tccacaagct 13320
gaggatagag agcttaaagg acagctcttg cgcaagtaca gtggttactt agggagcctc 13380
aagcaagagt tcatgaagaa gaggaagaaa ggaaagctcc ctaaagaagc tcgtcaacaa 13440
ctgcttgatt ggtggagccg tcactacaaa tggcccttacc cttcggagca acaaaagctc 13500
gcccttgcgg aatcaacggg gctggaccag aaacagataa acaattggtt cataaaccag 13560
aggaaacggc attggaagcc gtcggaggac atgcagtttg tagtaatgga cgcaacacat 13620
cctcaccatt acttcatgga taatgtcttg ggcaatcctt tcccaatgga tcacatctcc 13680
tccaccatgc tttgactcga gtttctccat aataatgtgt gagtagttcc cagataaggg 13740
aattagggtt cctatagggt ttcgctcatg tgttgagcat ataagaaacc cttagtatgt 13800

-continued

```
atttgtattt gtaaaatact tctatcaata aaatttctaa ttcctaaaac caaaatccag  13860
tactaaaatc cagatccccc gaattaagtg actacaaaaa agtgtttgat cgccggcggt  13920
accgagtgta cttcaagtca gtgggaaatc aataaaatga ttattttatg aatatatttc  13980
attgtgcaag tagatagaaa ttacatatgt tacataacac acgaaataaa caaaaaaaga  14040
caatccaaaa acaaacaccc caaaaaaaat aatcacttta gataaactcg tatgaggaga  14100
ggcacgttca gtgactcgac gattcccgag caaaaaaagt ctccccgtca cacatgtagt  14160
gggtgacgca attatcttta aagtaatcct tctgttgact tgtcattgat aacatccagt  14220
cttcgtcagg attgcaaaga attatagaag ggatcccacc ttttattttc ttcttttttc  14280
catatttagg gttgacagtg aaatcagact ggcaacctat taattgcttc cacaatggga  14340
cgaacttgaa ggggatgtcg tcgatgatat tataggtggc gtgttcatcg tagttggtga  14400
aatcgatggt accgttccaa tagttgtgtc gtccgagact tctagcccag gtggtctttc  14460
cggtacgagt tggtccgcag atgtagaggc tggggtgtcg gattccattc cttccattgt  14520
ccttgttaaa tcggccatcc attcaaggtc agattgagct tgttggtatg agacaggatg  14580
tatgtaagta taagcgtcta tgcttacatg gtatagatgg gtttccctcc aggagtgtag  14640
atcttcgtgg cagcgaagat ctgattctgt gaagggcgac acatacggtt caggttgtgg  14700
agggaataat ttgttggctg aatattccag ccattgaagc tttgttgccc attcatgagg  14760
gaattcttcc ttgatcatgt caagatattc ctccttagac gttgcagtct ggataatagt  14820
tctccatcgt gcgtcagatt tgcgaggaga aaccttatga tctcggaaat ctcctctggt  14880
tttaatatct ccgtcctttg atatgtaatc aaggacttgt ttagagtttc tagctggctg  14940
gatattaggg tgatttcctt caaaatcgaa aaaagaagga tccctaatac aaggtttttt  15000
atcaagctgg agaagagcat gatagtgggt agtgccatct tgatgaagct cagaagcaac  15060
accaaggaag aaaataagaa aaggtgtgag tttctcccag agaaactgga ataaatcatc  15120
tctttgagat gagcacttgg gataggtaag gaaaacatat ttagattgga gtctgaagtt  15180
cttactagca gaaggcatgt tgttgtgact ccgaggggtt gcctcaaact ctatcttata  15240
accggcgtgg aggcatggag gcaggggtat tttggtcatt ttaatagata gtggaaaatg  15300
acgtggaatt tacttaaaga cgaagtcttt gcgacaaggg ggggcccacg ccgaatttaa  15360
tattaccggc gtggcccccc cttatcgcga gtgctttagc acgagcggtc cagatttaaa  15420
gtagaaaatt tcccgcccac tagggttaaa ggtgttcaca ctataaaagc atatacgatg  15480
tgatggtatt tgatggagcg tatattgtat caggtatttc cgttggatac gaattattcg  15540
tacgaccctc atagtttaaa ctatcagtgt ttgacaggat atattggcgg gtaaacctaa  15600
gagaaaagag cgtttattag aataacggat atttaaaagg gcgtgaaaag gtttatccgt  15660
tcgtccattt gtatgtgcat gccaaccaca gggttcccct cgggatcaaa gtactttgat  15720
ccaacccctc cgctgctata gtgcagtcgg cttctgacgt tcagtgcagc cgtcttctga  15780
aaacgacatg tcgcacaagt cctaagttac gcgacaggct gccgccctgc ccttttcctg  15840
gcgttttctt gtcgcgtgtt ttagtcgcat aaagtagaat acttgcgact agaaccggag  15900
acattacgcc atgaacaaga gcgccgccgc tggcctgctg ggctatgccc gcgtcagcac  15960
cgacgaccag gacttgacca accaacgggc cgaactgcac gcggccggct gcaccaagct  16020
gttttccgag aagatcaccg gcaccaggcg cgaccgcccg gagctggcca ggatgcttga  16080
ccacctacgc cctggcgacg ttgtgacagt gaccaggcta gaccgcctgg cccgcagcac  16140
ccgcgaccta ctggacattg ccgagcgcat ccaggaggcc ggcgcgggcc tgcgtagcct  16200
```

-continued

```
ggcagagccg tgggccgaca ccaccacgcc ggccggccgc atggtgttga ccgtgttcgc  16260
cggcattgcc gagttcgagc gttccctaat catcgaccgc acccggagcg ggcgcgaggc  16320
cgccaaggcc cgaggcgtga agtttggccc ccgccctacc ctcaccccgg cacagatcgc  16380
gcacgcccgc gagctgatcg accaggaagg ccgcaccgtg aaagaggcgg ctgcactgct  16440
tggcgtgcat cgctcgaccc tgtaccgcgc acttgagcgc agcgaggaag tgacgcccac  16500
cgaggccagg cggcgcggtg ccttccgtga ggacgcattg accgaggccg acgccctggc  16560
ggccgccgag aatgaacgcc aagaggaaca agcatgaaac cgcaccagga cggccaggac  16620
gaaccgtttt tcattaccga agagatcgag gcggagatga tcgcggccgg gtacgtgttc  16680
gagccgcccg cgcacggctc aaccgtgcgg ctgcatgaaa tcctggccgg tttgtctgat  16740
gccaagctgg cggcctggcc ggccagcttg gccgctgaag aaaccgagcg ccgccgtcta  16800
aaaaggtgat gtgtatttga gtaaaacagc ttgcgtcatg cggtcgctgc gtatatgatg  16860
cgatgagtaa ataaacaaat acgcaagggg aacgcatgaa ggttatcgct gtacttaacc  16920
agaaaggcgg gtcaggcaag acgaccatcg caacccatct agcccgcgcc ctgcaactcg  16980
ccggggccga tgttctgtta gtcgattccg atccccaggg cagtgcccgc gattgggcgg  17040
ccgtgcggga agatcaaccg ctaaccgttg tcggcatcga ccgcccgacg attgaccgcg  17100
acgtgaaggc catcggccgg cgcgacttcg tagtgatcga cggagcgccc caggcggcgg  17160
acttggctgt gtccgcgatc aaggcagccg acttcgtgct gattccggtg cagccaagcc  17220
cttacgacat atgggccacc gccgacctgg tggagctggt taagcagcgc attgaggtca  17280
cggatggaag gctacaagcg gcctttgtcg tgtcgcgggc gatcaaaggc acgcgcatcg  17340
gcggtgaggt tgccgaggcg ctggccgggt acgagctgcc cattcttgag tcccgtatca  17400
cgcagcgcgt gagctaccca ggcactgccg ccgccggcac aaccgttctt gaatcagaac  17460
ccgagggcga cgctgcccgc gaggtccagg cgctggccgc tgaaattaaa tcaaaactca  17520
tttgagttaa tgaggtaaag agaaaatgag caaaagcaca aacacgctaa gtgccggccg  17580
tccgagcgca cgcagcagca aggctgcaac gttggccagc ctggcagaca cgccagccat  17640
gaagcgggtc aactttcagt tgccggcgga ggatcacacc aagctgaaga tgtacgcggt  17700
acgccaaggc aagaccatta ccgagctgct atctgaatac atcgcgcagc taccagagta  17760
aatgagcaaa tgaataaatg agtagatgaa ttttagcggc taaaggaggc ggcatggaaa  17820
atcaagaaca accaggcacc gacgccgtgg aatgccccat gtgtggagga acgggcggtt  17880
ggccaggcgt aagcggctgg gttgtctgcc ggccctgcaa tggcactgga acccccaagc  17940
ccgaggaatc ggcgtgacgg tcgcaaacca tccggcccgg tacaaatcgg cgcggcgctg  18000
ggtgatgacc tggtggagaa gttgaaggcc gcgcaggccg cccagcggca acgcatcgag  18060
gcagaagcac gccccggtga atcgtggcaa gcggccgctg atcgaatccg caaagaatcc  18120
cggcaaccgc cggcagccgg tgcgccgtcg attaggaagc cgcccaaggg cgacgagcaa  18180
ccagattttt tcgttccgat gctctatgac gtgggcaccc gcgatagtcg cagcatcatg  18240
gacgtggccg ttttccgtct gtcgaagcgt gaccgacgag ctggcgaggt gatccgctac  18300
gagcttccag acgggcacgt agaggtttcc gcagggccgg ccggcatggc cagtgtgtgg  18360
gattacgacc tggtactgat ggcggtttcc catctaaccg aatccatgaa ccgataccgg  18420
gaagggaagg gagacaagcc cggccgcgtg ttccgtccac acgttgcgga cgtactcaag  18480
ttctgccggc gagccgatgg cggaaagcag aaagacgacc tggtagaaac ctgcattcgg  18540
```

ttaaacacca cgcacgttgc catgcagcgt acgaagaagg ccaagaacgg ccgcctggtg 18600
acggtatccg agggtgaagc cttgattagc cgctacaaga tcgtaaagag cgaaaccggg 18660
cggccggagt acatcgagat cgagctagct gattggatgt accgcgagat cacagaaggc 18720
aagaacccgg acgtgctgac ggttcacccc gattactttt tgatcgatcc cggcatcggc 18780
cgttttctct accgcctggc acgccgcgcc gcaggcaagg cagaagccag atggttgttc 18840
aagacgatct acgaacgcag tggcagcgcc ggagagttca agaagttctg tttcaccgtg 18900
cgcaagctga tcgggtcaaa tgacctgccg gagtacgatt tgaaggagga ggcggggcag 18960
gctggcccga tcctagtcat gcgctaccgc aacctgatcg agggcgaagc atccgccggt 19020
tcctaatgta cggagcagat gctagggcaa attgccctag caggggaaaa aggtcgaaaa 19080
ggcctctttc ctgtggatag cacgtacatt gggaacccaa agccgtacat tgggaaccgg 19140
aacccgtaca ttgggaaccc aaagccgtac attgggaacc ggtcacacat gtaagtgact 19200
gatataaaag agaaaaaagg cgatttttcc gcctaaaact ctttaaaact tattaaaact 19260
cttaaaaccc gcctggcctg tgcataactg tctggccagc gcacagccca agagctgcaa 19320
aaagcgccta cccttcggtc gctgcgctcc ctacgccccg ccgcttcgcg tcggcctatc 19380
gcggccgctg gccgctcaaa aatggctggc ctacggccag gcaatctacc agggcgcgga 19440
caagccgcgc cgtcgccact cgaccgccgg cgcccacatc aaggcaccct gcctcgcgcg 19500
tttcggtgat gacggtgaaa acctctgaca catgcagctc ccggaaacgg tcacagcttg 19560
tctgtaagcg gatgccggga gcagacaagc ccgtcagggc gcgtcagcgg gtgttggcgg 19620
gtgtcggggc gcagccatga cccagtcacg tagcgatagc ggagtgtata ctggcttaac 19680
tatgcggcat cagagcagat tgtactgaga gtgcaccata tgcggtgtga aataccgcac 19740
agatgcgtaa ggagaaaata ccgcatcagg ccctcttccg cttcctcgct cactgactcg 19800
ctgcgctcgg tcgttcggct gcggcgagcg gtatcagctc actcaaaggc ggtaatacgg 19860
ttatccacag aatcagggga taacgcagga aagaacatgt gagcaaaagg ccagcaaaag 19920
gccaggaacc gtaaaaaggc cgcgttgctg gcgtttttcc ataggctccg cccccctgac 19980
gagcatcaca aaaatcgacg ctcaagtcag aggtggcgaa acccgacagg actataaaga 20040
taccaggcgt ttccccctgg aagctccctc gtgcgctctc ctgttccgac cctgccgctt 20100
accggatacc tgtccgcctt tctcccttcg ggaagcgtgg cgctttctca tagctcacgc 20160
tgtaggtatc tcagttcggt gtaggtcgtt cgctccaagc tgggctgtgt gcacgaaccc 20220
cccgttcagc ccgaccgctg cgccttatcc ggtaactatc gtcttgagtc caacccggta 20280
agacacgact tatcgccact ggcagcagcc actggtaaca ggattagcag agcgaggtat 20340

<210> SEQ ID NO 30
<211> LENGTH: 15641
<212> TYPE: DNA
<213> ORGANISM: artificial
<220> FEATURE:
<223> OTHER INFORMATION: synthetic oligonucleotide

<400> SEQUENCE: 30
ggcagccggt gcgccgtcga ttaggaagcc gcccaagggc gacgagcaac cagatttttt 60
cgttccgatg ctctatgacg tgggcacccg cgatagtcgc agcatcatgg acgtggccgt 120
tttccgtctg tcgaagcgtg accgacgagc tggcgaggtg atccgctacg agcttccaga 180
cgggcacgta gaggtttccg cagggccggc cggcatggcc agtgtgtggg attacgacct 240
ggtactgatg gcggtttccc atctaaccga atccatgaac cgataccggg aagggaaggg 300

-continued

```
agacaagccc ggccgcgtgt tccgtccaca cgttgcggac gtactcaagt tctgccggcg    360
agccgatggc ggaaagcaga aagacgacct ggtagaaacc tgcattcggt taaacaccac    420
gcacgttgcc atgcagcgta cgaagaaggc caagaacggc cgcctggtga cggtatccga    480
gggtgaagcc ttgattagcc gctacaagat cgtaaagagc gaaaccgggc ggccggagta    540
catcgagatc gagctagctg attggatgta ccgcgagatc acagaaggca agaacccgga    600
cgtgctgacg gttcaccccg attacttttt gatcgatccc ggcatcggcc gttttctcta    660
ccgcctggca cgccgcgccg caggcaaggc agaagccaga tggttgttca agacgatcta    720
cgaacgcagt ggcagcgccg gagagttcaa gaagttctgt ttcaccgtgc gcaagctgat    780
cgggtcaaat gacctgccgg agtacgattt gaaggaggag gcggggcagg ctggcccgat    840
cctagtcatg cgctaccgca acctgatcga gggcgaagca tccgccggtt cctaatgtac    900
ggagcagatg ctagggcaaa ttgccctagc aggggaaaaa ggtcgaaaag gcctctttcc    960
tgtggatagc acgtacattg ggaacccaaa gccgtacatt gggaaccgga acccgtacat   1020
tgggaaccca aagccgtaca ttgggaaccg gtcacacatg taagtgactg atataaaaga   1080
gaaaaaaggc gatttttccg cctaaaactc tttaaaactt attaaaactc ttaaaacccg   1140
cctggcctgt gcataactgt ctggccagcg cacagccgaa gagctgcaaa aagcgcctac   1200
ccttcggtcg ctgcgctccc tacgccccgc cgcttcgcgt cggcctatcg cggccgctgg   1260
ccgctcaaaa atggctggcc tacggccagg caatctacca gggcgcggac aagccgcgcc   1320
gtcgccactc gaccgccggc gcccacatca aggcaccctg cctcgcgcgt ttcggtgatg   1380
acggtgaaaa cctctgacac atgcagctcc cggaaacggt cacagcttgt ctgtaagcgg   1440
atgccgggag cagacaagcc cgtcagggcg cgtcagcggg tgttggcggg tgtcggggcg   1500
cagccatgac ccagtcacgt agcgatagcg gagtgtatac tggcttaact atgcggcatc   1560
agagcagatt gtactgagag tgcaccatat gcggtgtgaa ataccgcaca gatgcgtaag   1620
gagaaaatac cgcatcaggc gctcttccgc ttcctcgctc actgactcgc tgcgctcggt   1680
cgttcggctg cggcgagcgg tatcagctca ctcaaaggcg gtaatacggt tatccacaga   1740
atcaggggat aacgcaggaa agaacatgtg agcaaaaggc cagcaaaagg ccaggaaccg   1800
taaaaaggcc gcgttgctgg cgtttttcca taggctccgc ccccctgacg agcatcacaa   1860
aaatcgacgc tcaagtcaga ggtggcgaaa cccgacagga ctataaagat accaggcgtt   1920
tccccctgga agctccctcg tgcgctctcc tgttccgacc ctgccgctta ccggatacct   1980
gtccgccttt ctcccttcgg gaagcgtggc gctttctcat agctcacgct gtaggtatct   2040
cagttcggtg taggtcgttc gctccaagct gggctgtgtg cacgaacccc ccgttcagcc   2100
cgaccgctgc gccttatccg gtaactatcg tcttgagtcc aacccggtaa gacacgactt   2160
atcgccactg gcagcagcca ctggtaacag gattagcaga gcgaggtatg taggcggtgc   2220
tacagagttc ttgaagtggt ggcctaacta cggctacact agaaggacag tatttggtat   2280
ctgcgctctg ctgaagccag ttaccttcgg aaaaagagtt ggtagctctt gatccggcaa   2340
acaaaccacc gctggtagcg gtggtttttt tgtttgcaag cagcagatta cgcgcagaaa   2400
aaaaggatct caagaagatc ctttgatctt ttctacgggg tctgacgctc agtggaacga   2460
aaactcacgt taagggattt tggtcatgca ttctaggtac taaaacaatt catccagtaa   2520
aatataatat tttattttct cccaatcagg cttgatcccc agtaagtcaa aaaatagctc   2580
gacatactgt tcttccccga tatcctccct gatcgaccgg acgcagaagg caatgtcata   2640
```

-continued

```
ccacttgtcc gccctgccgc ttctcccaag atcaataaag ccacttactt tgccatcttt   2700
cacaaagatg ttgctgtctc ccaggtcgcc gtgggaaaag acaagttcct cttcgggctt   2760
ttccgtcttt aaaaaatcat acagctcgcg cggatcttta aatggagtgt cttcttccca   2820
gttttcgcaa tccacatcgg ccagatcgtt attcagtaag taatccaatt cggctaagcg   2880
gctgtctaag ctattcgtat agggacaatc cgatatgtcg atggagtgaa agagcctgat   2940
gcactccgca tacagctcga taatcttttc agggctttgt tcatcttcat actcttccga   3000
gcaaaggacg ccatcggcct cactcatgag cagattgctc cagccatcat gccgttcaaa   3060
gtgcaggacc tttggaacag gcagctttcc ttccagccat agcatcatgt ccttttcccg   3120
ttccacatca taggtggtcc ctttataccg gctgtccgtc atttttaaat ataggttttc   3180
attttctccc accagcttat ataccttagc aggagacatt ccttccgtat cttttacgca   3240
gcggtatttt tcgatcagtt ttttcaattc cggtgatatt ctcattttag ccatttatta   3300
tttccttcct cttttctaca gtatttaaag ataccccaag aagctaatta taacaagacg   3360
aactccaatt cactgttcct tgcattctaa aaccttaaat accagaaaac agctttttca   3420
aagttgtttt caaagttggc gtataacata gtatcgacgg agccgatttt gaaaccgcgg   3480
tgatcacagg cagcaacgct ctgtcatcgt tacaatcaac atgctaccct ccgcgagatc   3540
atccgtgttt caaacccggc agcttagttg ccgttcttcc gaatagcatc ggtaacatga   3600
gcaaagtctg ccgccttaca acggctctcc cgctgacgcc gtcccggact gatgggctgc   3660
ctgtatcgag tggtgatttt gtgccgagct gccggtcggg gagctgttgg ctggctggtg   3720
gcaggatata ttgtggtgta aacaaattga cgcttagaca acttaataac acattgcgga   3780
cgtttttaat gtagagctca aagtttaacg cgttagcaga aggcatgttg ttgtgactcc   3840
gaggggttgc ctcaaactct atcttataac cggcgtggag gcatggaggc aggggtattt   3900
tggtcatttt aatagatagt ggaaaatgac gtggaattta cttaaagacg aagtctttgc   3960
gacaaggggg ggcccacgcc gaatttaata ttaccggcgt ggcccccccct tatcgcgagt   4020
gctttagcac gagcggtcca gatttaaagt agaaaatttc ccgcccacta gggttaaagg   4080
tgttcacact ataaaagcat atacgatgtg atggtatttg atggagcgta tattgtatca   4140
ggtatttccg ttggatacga attattcgta cgaccctcgg taccgatcgg cgcgccagat   4200
ttgccttttc aatttcagaa agaatgctaa cccacagatg gttagagagg cttacgcagc   4260
aggtatcatc aagacgatct acccgagcaa taatctccag gaaatcaaat accttcccaa   4320
gaaggttaaa gatgcagtca aaagattcag gactaactgc atcaagaaca cagagaaaga   4380
tatatttctc aagatcagaa gtactattcc agtatggacg attcaaggct tgcttcacaa   4440
accaaggcaa gtaatagaga ttggagtctc taaaaaggta gttcccactg aatcaaaggc   4500
catggagtca aagattcaaa tagaggacct aacagaactc gccgtaaaga ctggcgaaca   4560
gttcatacag agtctcttac gactcaatga caagaagaaa atcttcgtca acatggtgga   4620
gcacgacaca cttgtctact ccaaaaatat caaagataca gtctcagaag accaaagggc   4680
aattgagact tttcaacaaa gggtaatatc cggaaacctc ctcggattcc attgcccagc   4740
tatctgtcac tttattgtga agatagtgga aaaggaaggt ggctcctaca aatgccatca   4800
ttgcgataaa ggaaaggcca tcgttgaaga tgcctctgcc gacagtggtc ccaaagatgg   4860
acccccaccc acgaggagca tcgtggaaaa agaagacgtt ccaaccacgt cttcaaagca   4920
agtggattga tgtgatatct ccactgacgt aagggatgac gcacaatccc actatccttc   4980
gcaagaccct tcctctatat aaggaagttc atttcatttg gagagaacac gggggactcc   5040
```

```
tgcaggatgg aagacgccaa aaacataaag aaaggcccgg cgccattcta tccgctggaa   5100
gatggaaccg ctggagagca actgcataag gctatgaaga gatacgccct ggttcctgga   5160
acaattgctt ttacagatgc acatatcgag gtggacatca cttacgctga gtacttcgaa   5220
atgtccgttc ggttggcaga agctatgaaa cgatatgggc tgaatacaaa tcacagaatc   5280
gtcgtatgca gtgaaaactc tcttcaattc tttatgccgg tgttgggcgc gttatttatc   5340
ggagttgcag ttgcgcccgc gaacgacatt tataatgaac gtgaattgct caacagtatg   5400
ggcatttcgc agcctaccgt ggtgttcgtt tccaaaaagg ggttgcaaaa aattttgaac   5460
gtgcaaaaaa agctcccaat catccaaaaa attattatca tggattctaa aacggattac   5520
cagggatttc agtcgatgta cacgttcgtc acatctcatc tacctcccgg ttttaatgaa   5580
tacgattttg tgccagagtc cttcgatagg gacaagacaa ttgcactgat catgaactcc   5640
tctggatcta ctggtctgcc taaaggtgtc gctctgcctc atagaactgc ctgcgtgaga   5700
ttctcgcatg ccagagatcc tatttttggc aatcaaatca ttccggatac tgcgatttta   5760
agtgttgttc cattccatca cggttttgga atgtttacta cactcggata tttgatatgt   5820
ggatttcgag tcgtcttaat gtatagattt gaagaagagc tgtttctgag gagccttcag   5880
gattacaaga ttcaaagtgc gctgctggtg ccaaccctat tctccttctt cgccaaaagc   5940
actctgattg acaaatacga tttatctaat ttacacgaaa ttgcttctgg tggcgctccc   6000
ctctctaagg aagtcgggga agcggttgcc aagaggttcc atctgccagg tatcaggcaa   6060
ggatatgggc tcactgagac tacatcagct attctgatta cacccgaggg ggatgataaa   6120
ccgggcgcgg tcggtaaagt tgttccattt tttgaagcga aggttgtgga tctggatacc   6180
gggaaaacgc tgggcgttaa tcaaagaggc gaactgtgtg tgagaggtcc tatgattatg   6240
tccggttatg taaacaatcc ggaagcgacc aacgccttga ttgacaagga tggatggcta   6300
cattctggag acatagctta ctgggacgaa gacgaacact tcttcatcgt tgaccgcctg   6360
aagtctctga ttaagtacaa aggctatcag gtggctcccg ctgaattgga atccatcttg   6420
ctccaacacc ccaacatctt cgacgctggt gtcgcaggtc ttcccgacga tgacgccggt   6480
gaacttcccg ccgccgttgt tgttttggag cacggaaaga cgatgacgga aaaagagatc   6540
gtggattacg tcgccagtca agtaacaacc gcgaaaaagt tgcgcggagg agttgtgttt   6600
gtggacgaag taccgaaagg tcttaccgga aaactcgacg caagaaaaat cagagagatc   6660
ctcataaagg ccaagaaggg cggaaagatc gccgtgtgac gtcgacgata tgaagatgaa   6720
gatgaaatat ttggtgtgtc aaataaaaag cttgtgtgct taagtttgtg ttttttttctt   6780
ggcttgttgt gttatgaatt tgtggctttt tctaatatta aatgaatgta agatcacatt   6840
ataatgaata aacaaatgtt tctataatcc attgtgaatg ttttgttgga tctcttctgc   6900
agcatataac tactgtatgt gctatggtat ggactatgga atatgattaa agataagcca   6960
gagctctggt gacggaccca tggcttcgtt gaacaacgga aactcgactt gccttccgca   7020
caatacatca tttcttctta gcttttttttc ttcttcttcg ttcatacagt tttttttttgt   7080
ttatcagctt acattttctt gaaccgtagc tttcgttttc ttcttttttaa ctttccattc   7140
ggagtttttg tatcttgttt catagtttgt cccaggatta gaatgattag gcatcgaacc   7200
ttcaagaatt tgattgaata aaacatcttc attcttaaga tatgaagata atcttcaaaa   7260
ggcccctggg aatctgaaag aagagaagca ggcccattta tatgggaaag aacaatagta   7320
tttcttatat aggcccattt aagttgaaaa caatcttcaa aagtcccaca tcgcttagat   7380
```

-continued

```
aagaaaacga agctgagttt atatacagct agagtcgaag tagtgattgt tggtagtagc   7440
gactccatgg ttttagagct agaaatagca agttaaaata aggctagtcc gttatcaact   7500
tgaaaaagtg gcaccgagtc ggtgcttttt ttcccgggcg cgccgatcat gagcggagaa   7560
ttaagggagt cacgttatga cccccgccga tgacgcggga caagccgttt tacgtttgga   7620
actgacagaa ccgcaacgtt gaaggagcca ctcagccgcg ggtttctgga gtttaatgag   7680
ctaagcacat acgtcagaaa ccattattgc gcgttcaaaa gtcgcctaag gtcactatca   7740
gctagcaaat atttcttgtc aaaaatgctc cactgacgtt ccataaattc ccctcggtat   7800
ccaattagag tctcatattc actctcaatc caaataatct gcaccgtacc tgcagggtcc   7860
gagctaggtc acagaagcgc tcaggaaggc cgctgagata gaggcatggc ggccaatgcg   7920
ggcggcggtg gagcgggagg aggcagcggc agcggcagcg tggctgcgcc ggcggtgtgc   7980
cgccccagcg gctcgcggtg gacgccgacg ccggagcaga tcaggatgct gaaggagctg   8040
tactacggct gcggcatccg gtcgcccagc tcggagcaga tccagcgcat caccgccatg   8100
ctgcggcagc acggcaagat cgagggcaag aacgtcttct actggttcca gaaccacaag   8160
gcccgcgagc gccagaagcg ccgcctcacc agcctcgacg tgaacgtgcc cgccgccggc   8220
gcggccgacg ccaccaccag ccaactcggc gtcctctcgc tgtcgtcgcc gccgccttca   8280
ggcgcggcgc ctccctcgcc caccctcggc ttctacgccg ccggcaatgg cggcggatcg   8340
gctgtgctgc tggacacgag ttccgactgg ggcagcagcg gcgctgcgat ggccaccgag   8400
acatgcttcc tccaggacta catgggcgtg acggacacgg gcagctcgtc gcagtggcca   8460
cgcttctcgt cgtcggacac gataatggcg gcggccgcgg cgcgggcggc gacgacgcgg   8520
gcgcccgaga ctctccctct cttcccgacc tgcggcgacg acggcggcag cggtagcagc   8580
agctacttgc cgttctgggg tgccgcgtcc acaactgccg gcgccacttc ttccgttgcg   8640
atccagcagc aacaccagct gcaggagcag tacagctttt acagcaacag caacagcacc   8700
cagctggccg gcaccggcaa ccaagacgta tcggcaacag cagcagcagc cgccgccctg   8760
gagctgagcc tcagctcatg gtgctcccct taccctgctg cagggagtat gtgagagcaa   8820
cgcgagctgc cactgctctt cacttatgtc tctggaatgg aaggaggagg aagtgagcat   8880
agcgttggtg cgttgctgtc attgtcctag gttagtagct agtgccagtt actagtaagc   8940
atcaggcata ggagtatgta gtagaagcat gcacgttgcc ggccagccag gctttagacg   9000
ggaaaagaat ttggtgcagc cggctgcaaa acaggatgtt tacagccccc ccctcgagcc   9060
ctagacttgt ccatcttctg gattggccaa gttaattaat gtatgaaata aaaggatgca   9120
cacatagtga catgctaatc actataatgt gggcatcaaa gttgtgtgtt atgtgtaatt   9180
actaattatc tgaataagag aaagagatca tccatatttc ttatcctaaa tgaatgtcac   9240
gtgtctttat aattctttga tgaaccagat gcattttatt aaccaattcc atatacatat   9300
aaatattaat catatataat taatatcaat tgggttagca aaacaaatct agtctaggtg   9360
tgttttgcta attattgggg gatagtgcaa aaagaaatct acgttctcaa taattcagat   9420
agaaaactta ataaagtgag ataatttaca tagattgctt ttatcctttg atatatgtga   9480
aaccatgcat gatataagga aaatagatag agaaataatt ttttacatcg ttgaatatgt   9540
aaacaattta attcaagaag ctaggaatat aaatattgag gagtttatga ttagagctct   9600
cccgctggca gacatactgt cccacaaatg aagatggaat ctgtaaaaga aaacgcgtga   9660
aataatgcgt ctgacaaagg ttaggtcggc tgcctttaat caataccaaa gtggtcccta   9720
ccacgatgga aaaactgtgc agtcggtttg gctttttctg acgaacaaat aagattcgtg   9780
```

-continued

```
gccgacaggt gggggtccac catgtgaagg catcttcaga ctccaataat ggagcaatga   9840
cgtaagggct tacgaaataa gtaagggtag tttgggaaat gtccactcac ccgtcagtct   9900
ataaatactt agcccctccc tcattgttaa gggagcaaaa tctcagagag atagtcctag   9960
agagagaaag agagcaagta gcctagaagt agtcaaggcg gcgaagtatt caggcacgtg  10020
gccaggaaga agaaaagcca agacgacgaa aacaggtaag agctaagctt atggagagtg  10080
gttccaacag cacttcttgt ccaatggctt ttgccgggga taatagtgat ggtccgatgt  10140
gtcctatgat gatgatgatg ccgcccatca tgacatcaca tcaacatcat ggtcatgatc  10200
atcaacatca acaacaagaa catgatggtt atgcatatca gtcacaccac caacaaagta  10260
gttccctttt tcttcaatca ctagctcctc cccaaggaac taagaacaaa gttgcttctt  10320
cttcttctcc ttcctcttgt gctcctgcct attctctaat ggagatccat cataacgaaa  10380
tcgttgcagg aggaatcaac ccttgctcct cttcctcttc ttcagcctct gtcaaggcca  10440
agatcatggc tcatcctcac taccaccgcc tcttggccgc ttatgtcaat tgtcagaagg  10500
ttggagcacc accggaggtt gtggcgaggc tagaggaggc atgctcgtct gccgcagccg  10560
ctgccgcatc tatgggacca acaggatgtc taggtgaaga tccagggctt gatcaattca  10620
tggaagctta ctgtgaaatg ctcgttaagt atgagcaaga gctctccaaa cctttcaagg  10680
aagctatggt cttccttcaa cgtgtcgagt gtcaattcaa atccctctct ctatcctcac  10740
cttcctcttt ctccggttat ggagagacag caattgatag gaacaataat gggtcatccg  10800
aggaagaagt cgatatgaac aatgaatttg tagatccaca agctgaggat agagagctta  10860
aaggacagct cttgcgcaag tacagtggtt acttagggag cctcaagcaa gagttcatga  10920
agaagaggaa gaaaggaaag ctccctaaag aagctcgtca acaactgctt gattggtgga  10980
gccgtcacta caaatggcct tacccttcgg agcaacaaaa gctcgccctt gcggaatcaa  11040
cggggctgga ccagaaacag ataaacaatt ggttcataaa ccagaggaaa cggcattgga  11100
agccgtcgga ggacatgcag tttgtagtaa tggacgcaac acatcctcac cattacttca  11160
tggataatgt cttgggcaat cctttcccaa tggatcacat ctcctccacc atgctttgac  11220
tcgagtttct ccataataat gtgtgagtag ttcccagata agggaattag ggttcctata  11280
gggtttcgct catgtgttga gcatataaga aacccttagt atgtatttgt atttgtaaaa  11340
tacttctatc aataaaattt ctaattccta aaaccaaaat ccagtactaa aatccagatc  11400
ccccgaatta agtgtttgat cgccggcggt accgagtgta cttcaagtca gtgggaaatc  11460
aataaaatga ttattttatg aatatatttc attgtgcaag tagatagaaa ttacatatgt  11520
tacataacac acgaaataaa caaaaaaaga caatccaaaa acaaacaccc caaaaaaaat  11580
aatcacttta gataaactcg tatgaggaga ggcacgttca gtgactcgac gattcccgag  11640
caaaaaaagt ctccccgtca cacatgtagt gggtgacgca attatcttta aagtaatcct  11700
tctgttgact tgtcattgat aacatccagt cttcgtcagg attgcaaaga attatagaag  11760
ggatcccacc ttttatttc ttcttttttc catatttagg gttgacagtg aaatcagact  11820
ggcaacctat taattgcttc cacaatggga cgaacttgaa ggggatgtcg tcgatgatat  11880
tataggtggc gtgttcatcg tagttggtga aatcgatggt accgttccaa tagttgtgtc  11940
gtccgagact tctagcccag gtggtctttc cggtacgagt tggtccgcag atgtagaggc  12000
tggggtgtcg gattccattc cttccattgt ccttgttaaa tcggccatcc attcaaggtc  12060
agattgagct tgttggtatg agacaggatg tatgtaagta taagcgtcta tgcttacatg  12120
```

-continued

```
gtatagatgg gtttccctcc aggagtgtag atcttcgtgg cagcgaagat ctgattctgt  12180
gaagggcgac acatacggtt caggttgtgg agggaataat ttgttggctg aatattccag  12240
ccattgaagc tttgttgccc attcatgagg gaattcttcc ttgatcatgt caagatattc  12300
ctccttagac gttgcagtct ggataatagt tctccatcgt gcgtcagatt tgcgaggaga  12360
aaccttatga tctcggaaat ctcctctggt tttaatatct ccgtcctttg atatgtaatc  12420
aaggacttgt ttagagtttc tagctggctg gatattaggg tgatttcctt caaaatcgaa  12480
aaaagaagga tccctaatac aaggtttttt atcaagctgg agaagagcat gatagtgggt  12540
agtgccatct tgatgaagct cagaagcaac accaaggaag aaaataagaa aaggtgtgag  12600
tttctcccag agaaactgga ataaatcatc tctttgagat gagcacttgg gataggtaag  12660
gaaaacatat ttagattgga gtctgaagtt cttactagca gaaggcatgt tgttgtgact  12720
ccgaggggtt gcctcaaact ctatcttata accggcgtgg aggcatggag gcaggggtat  12780
tttggtcatt ttaatagata gtggaaaatg acgtggaatt tacttaaaga cgaagtcttt  12840
gcgacaaggg ggggcccacg ccgaatttaa tattaccggc gtggcccccc cttatcgcga  12900
gtgctttagc acgagcggtc cagatttaaa gtagaaaatt tcccgcccac tagggttaaa  12960
ggtgttcaca ctataaaagc atatacgatg tgatggtatt tgatggagcg tatattgtat  13020
caggtatttc cgttggatac gaattattcg tacgaccctc atagtttaaa ctatcagtgt  13080
ttgacaggat atattggcgg gtaaacctaa gagaaaagag cgtttattag aataacggat  13140
atttaaaagg gcgtgaaaag gtttatccgt tcgtccattt gtatgtgcat gccaaccaca  13200
gggttcccct cgggatcaaa gtactttgat ccaacccctc cgctgctata gtgcagtcgg  13260
cttctgacgt tcagtgcagc cgtcttctga aaacgacatg tcgcacaagt cctaagttac  13320
gcgacaggct gccgccctgc ccttttcctg gcgttttctt gtcgcgtgtt ttagtcgcat  13380
aaagtagaat acttgcgact agaaccggag acattacgcc atgaacaaga gcgccgccgc  13440
tggcctgctg ggctatgccc gcgtcagcac cgacgaccag gacttgacca accaacgggc  13500
cgaactgcac gcggccggct gcaccaagct gttttccgag aagatcaccg gcaccaggcg  13560
cgaccgcccg gagctggcca ggatgcttga ccacctacgc cctggcgacg ttgtgacagt  13620
gaccaggcta gaccgcctgg cccgcagcac ccgcgaccta ctggacattg ccgagcgcat  13680
ccaggaggcc ggcgcgggcc tgcgtagcct ggcagagccg tgggccgaca ccaccacgcc  13740
ggccggccgc atggtgttga ccgtgttcgc cggcattgcc gagttcgagc gttccctaat  13800
catcgaccgc acccggagcg ggcgcgaggc cgccaaggcc cgaggcgtga agtttggccc  13860
ccgccctacc ctcaccccgg cacagatcgc gcacgcccgc gagctgatcg accaggaagg  13920
ccgcaccgtg aaagaggcgg ctgcactgct tggcgtgcat cgctcgaccc tgtaccgcgc  13980
acttgagcgc agcgaggaag tgacgcccac cgaggccagg cggcgcggtg ccttccgtga  14040
ggacgcattg accgaggccg acgccctggc ggccgccgag aatgaacgcc aagaggaaca  14100
agcatgaaac cgcaccagga cggccaggac gaaccgtttt tcattaccga agagatcgag  14160
gcggagatga tcgcggccgg gtacgtgttc gagccgcccg cgcacggctc aaccgtgcgg  14220
ctgcatgaaa tcctggccgg tttgtctgat gccaagctgg cggcctggcc ggccagcttg  14280
gccgctgaag aaaccgagcg ccgccgtcta aaaaggtgat gtgtatttga gtaaaacagc  14340
ttgcgtcatg cggtcgctgc gtatatgatg cgatgagtaa ataaacaaat acgcaagggg  14400
aacgcatgaa ggttatcgct gtacttaacc agaaaggcgg gtcaggcaag acgaccatcg  14460
caacccatct agcccgcgcc ctgcaactcg ccggggccga tgttctgtta gtcgattccg  14520
```

```
atccccaggg cagtgcccgc gattgggcgg ccgtgcggga agatcaaccg ctaaccgttg  14580
tcggcatcga ccgcccgacg attgaccgcg acgtgaaggc catcggccgg cgcgacttcg  14640
tagtgatcga cggagcgccc caggcggcgg acttggctgt gtccgcgatc aaggcagccg  14700
acttcgtgct gattccggtg cagccaagcc cttacgacat atgggccacc gccgacctgg  14760
tggagctggt taagcagcgc attgaggtca cggatggaag gctacaagcg gcctttgtcg  14820
tgtcgcgggc gatcaaaggc acgcgcatcg gcggtgaggt tgccgaggcg ctggccgggt  14880
acgagctgcc cattcttgag tcccgtatca cgcagcgcgt gagctaccca ggcactgccg  14940
ccgccggcac aaccgttctt gaatcagaac ccgagggcga cgctgcccgc gaggtccagg  15000
cgctggccgc tgaaattaaa tcaaaactca tttgagttaa tgaggtaaag agaaaatgag  15060
caaaagcaca aacacgctaa gtgccggccg tccgagcgca cgcagcagca aggctgcaac  15120
gttggccagc ctggcagaca cgccagccat gaagcgggtc aactttcagt tgccggcgga  15180
ggatcacacc aagctgaaga tgtacgcggt acgccaaggc aagaccatta ccgagctgct  15240
atctgaatac atcgcgcagc taccagagta aatgagcaaa tgaataaatg agtagatgaa  15300
ttttagcggc taaaggaggc ggcatggaaa atcaagaaca accaggcacc gacgccgtgg  15360
aatgccccat gtgtggagga acgggcggtt ggccaggcgt aagcggctgg gttgtctgcc  15420
ggccctgcaa tggcactgga acccccaagc ccgaggaatc ggcgtgacgg tcgcaaacca  15480
tccggcccgg tacaaatcgg cgcggcgctg ggtgatgacc tggtggagaa gttgaaggcc  15540
gcgcaggccg cccagcggca acgcatcgag gcagaagcac gccccggtga atcgtggcaa  15600
gcggccgctg atcgaatccg caaagaatcc cggcaaccgc c                      15641
```

```
<210> SEQ ID NO 31
<211> LENGTH: 15580
<212> TYPE: DNA
<213> ORGANISM: artificial
<220> FEATURE:
<223> OTHER INFORMATION: synthetic oligonucleotide

<400> SEQUENCE: 31
```

```
cctttattt  tcttcttttt tccatattta gggttgacag tgaaatcaga ctggcaacct     60
attaattgct tccacaatgg gacgaacttg aaggggatgt cgtcgatgat attataggtg    120
gcgtgttcat cgtagttggt gaaatcgatg gtaccgttcc aatagttgtg tcgtccgaga    180
cttctagccc aggtggtctt tccggtacga gttggtccgc agatgtagag gctggggtgt    240
cggattccat tccttccatt gtccttgtta aatcggccat ccattcaagg tcagattgag    300
cttgttggta tgagacagga tgtatgtaag tataagcgtc tatgcttaca tggtatagat    360
gggtttccct ccaggagtgt agatcttcgt ggcagcgaag atctgattct gtgaagggcg    420
acacatacgg ttcaggttgt ggagggaata atttgttggc tgaatattcc agccattgaa    480
gctttgttgc ccattcatga gggaattctt ccttgatcat gtcaagatat tcctccttag    540
acgttgcagt ctggataata gttctccatc gtgcgtcaga tttgcgagga gaaaccttat    600
gatctcggaa atctcctctg gttttaatat ctccgtcctt tgatatgtaa tcaaggactt    660
gtttagagtt tctagctggc tggatattag ggtgatttcc ttcaaaatcg aaaaaagaag    720
gatccctaat acaaggtttt ttatcaagct ggagaagagc atgatagtgg gtagtgccat    780
cttgatgaag ctcagaagca acaccaagga agaaaataag aaaaggtgtg agtttctccc    840
agagaaactg gaataaatca tctctttgag atgagcactt gggataggta aggaaaacat    900
```

-continued

```
atttagattg gagtctgaag ttcttactag cagaaggcat gttgttgtga ctccgagggg    960
ttgcctcaaa ctctatctta taaccggcgt ggaggcatgg aggcaggggt attttggtca   1020
ttttaataga tagtggaaaa tgacgtggaa tttacttaaa gacgaagtct ttgcgacaag   1080
ggggggccca cgccgaattt aatattaccg gcgtggcccc cccttatcgc gagtgcttta   1140
gcacgagcgg tccagattta aagtagaaaa tttcccgccc actagggtta aaggtgttca   1200
cactataaaa gcatatacga tgtgatggta tttgatggag cgtatattgt atcaggtatt   1260
tccgttggat acgaattatt cgtacgaccc tcatagttta aactatcagt gtttgacagg   1320
atatattggc gggtaaacct aagagaaaag agcgtttatt agaataacgg atatttaaaa   1380
gggcgtgaaa aggtttatcc gttcgtccat ttgtatgtgc atgccaacca cagggttccc   1440
ctcgggatca aagtactttg atccaacccc tccgctgcta tagtgcagtc ggcttctgac   1500
gttcagtgca gccgtcttct gaaaacgaca tgtcgcacaa gtcctaagtt acgcgacagg   1560
ctgccgccct gccctttcc tggcgttttc ttgtcgcgtg ttttagtcgc ataaagtaga   1620
atacttgcga ctagaaccgg agacattacg ccatgaacaa gagcgccgcc gctggcctgc   1680
tgggctatgc ccgcgtcagc accgacgacc aggacttgac caaccaacgg gccgaactgc   1740
acgcggccgg ctgcaccaag ctgttttccg agaagatcac cggcaccagg cgcgaccgcc   1800
cggagctggc caggatgctt gaccacctac gccctggcga cgttgtgaca gtgaccaggc   1860
tagaccgcct ggcccgcagc acccgcgacc tactggacat tgccgagcgc atccaggagg   1920
ccggcgcggg cctgcgtagc ctggcagagc cgtgggccga caccaccacg ccggccggcc   1980
gcatggtgtt gaccgtgttc gccggcattg ccgagttcga gcgttcccta atcatcgacc   2040
gcacccggag cgggcgcgag gccgccaagg cccgaggcgt gaagtttggc ccccgcccta   2100
ccctcacccc ggcacagatc gcgcacgccc gcgagctgat cgaccaggaa ggccgcaccg   2160
tgaaagaggc ggctgcactg cttggcgtgc atcgctcgac cctgtaccgc gcacttgagc   2220
gcagcgagga agtgacgccc accgaggcca ggcggcgcgg tgccttccgt gaggacgcat   2280
tgaccgaggc cgacgccctg gcggccgccg agaatgaacg ccaagaggaa caagcatgaa   2340
accgcaccag gacggccagg acgaaccgtt tttcattacc gaagagatcg aggcggagat   2400
gatcgcggcc gggtacgtgt tcgagccgcc cgcgcacggc tcaaccgtgc ggctgcatga   2460
aatcctggcc ggtttgtctg atgccaagct ggcggcctgg ccggccagct tggccgctga   2520
agaaaccgag cgccgccgtc taaaaaggtg atgtgtattt gagtaaaaca gcttgcgtca   2580
tgcggtcgct gcgtatatga tgcgatgagt aaataaacaa atacgcaagg ggaacgcatg   2640
aaggttatcg ctgtacttaa ccagaaaggc gggtcaggca agacgaccat cgcaacccat   2700
ctagcccgcg ccctgcaact cgccggggcc gatgttctgt tagtcgattc cgatccccag   2760
ggcagtgccc gcgattgggc ggccgtgcgg gaagatcaac cgctaaccgt tgtcggcatc   2820
gaccgcccga cgattgaccg cgacgtgaag gccatcggcc ggcgcgactt cgtagtgatc   2880
gacggagcgc cccaggcggc ggacttggct gtgtccgcga tcaaggcagc cgacttcgtg   2940
ctgattccgg tgcagccaag cccttacgac atatgggcca ccgccgacct ggtggagctg   3000
gttaagcagc gcattgaggt cacggatgga aggctacaag cggcctttgt cgtgtcgcgg   3060
gcgatcaaag gcacgcgcat cggcggtgag gttgccgagg cgctggccgg gtacgagctg   3120
cccattcttg agtcccgtat cacgcagcgc gtgagctacc caggcactgc cgccgccggc   3180
acaaccgttc ttgaatcaga acccgagggc gacgctgccc gcgaggtcca ggcgctggcc   3240
gctgaaatta aatcaaaact catttgagtt aatgaggtaa agagaaaatg agcaaaagca   3300
```

-continued

```
caaacacgct aagtgccggc cgtccgagcg cacgcagcag caaggctgca acgttggcca   3360
gcctggcaga cacgccagcc atgaagcggg tcaactttca gttgccggcg gaggatcaca   3420
ccaagctgaa gatgtacgcg gtacgccaag gcaagaccat taccgagctg ctatctgaat   3480
acatcgcgca gctaccagag taaatgagca aatgaataaa tgagtagatg aattttagcg   3540
gctaaaggag gcggcatgga aaatcaagaa caaccaggca ccgacgccgt ggaatgcccc   3600
atgtgtggag gaacgggcgg ttggccaggc gtaagcggct gggttgtctg ccggccctgc   3660
aatggcactg gaacccccaa gcccgaggaa tcggcgtgac ggtcgcaaac catccggccc   3720
ggtacaaatc ggcgcggcgc tgggtgatga cctggtggag aagttgaagg ccgcgcaggc   3780
cgcccagcgg caacgcatcg aggcagaagc acgccccggt gaatcgtggc aagcggccgc   3840
tgatcgaatc cgcaaagaat cccggcaacc gccggcagcc ggtgcgccgt cgattaggaa   3900
gccgcccaag ggcgacgagc aaccagattt tttcgttccg atgctctatg acgtgggcac   3960
ccgcgatagt cgcagcatca tggacgtggc cgttttccgt ctgtcgaagc gtgaccgacg   4020
agctggcgag gtgatccgct acgagcttcc agacgggcac gtagaggttt ccgcagggcc   4080
ggccggcatg gccagtgtgt gggattacga cctggtactg atggcggttt cccatctaac   4140
cgaatccatg aaccgatacc gggaagggaa gggagacaag cccggccgcg tgttccgtcc   4200
acacgttgcg gacgtactca agttctgccg gcgagccgat ggcggaaagc agaaagacga   4260
cctggtagaa acctgcattc ggttaaacac cacgcacgtt gccatgcagc gtacgaagaa   4320
ggccaagaac ggccgcctgg tgacggtatc cgagggtgaa gccttgatta gccgctacaa   4380
gatcgtaaag agcgaaaccg ggcggccgga gtacatcgag atcgagctag ctgattggat   4440
gtaccgcgag atcacagaag gcaagaaccc ggacgtgctg acggttcacc ccgattactt   4500
tttgatcgat cccggcatcg gccgttttct ctaccgcctg gcacgccgcg ccgcaggcaa   4560
ggcagaagcc agatggttgt tcaagacgat ctacgaacgc agtggcagcg ccggagagtt   4620
caagaagttc tgtttcaccg tgcgcaagct gatcgggtca aatgacctgc cggagtacga   4680
tttgaaggag gaggcggggc aggctggccc gatcctagtc atgcgctacc gcaacctgat   4740
cgagggcgaa gcatccgccg gttcctaatg tacggagcag atgctagggc aaattgccct   4800
agcaggggaa aaaggtcgaa aaggcctctt tcctgtggat agcacgtaca ttgggaaccc   4860
aaagccgtac attgggaacc ggaacccgta cattgggaac ccaaagccgt acattgggaa   4920
ccggtcacac atgtaagtga ctgatataaa agagaaaaaa ggcgattttt ccgcctaaaa   4980
ctctttaaaa cttattaaaa ctcttaaaac ccgcctggcc tgtgcataac tgtctggcca   5040
gcgcacagcc gaagagctgc aaaaagcgcc tacccttcgg tcgctgcgct ccctacgccc   5100
cgccgcttcg cgtcggccta tcgcggccgc tggccgctca aaaatggctg gcctacggcc   5160
aggcaatcta ccagggcgcg gacaagccgc gccgtcgcca ctcgaccgcc ggcgcccaca   5220
tcaaggcacc ctgcctcgcg cgtttcggtg atgacggtga aaacctctga cacatgcagc   5280
tcccggaaac ggtcacagct tgtctgtaag cggatgccgg gagcagacaa gcccgtcagg   5340
gcgcgtcagc gggtgttggc gggtgtcggg gcgcagccat gacccagtca cgtagcgata   5400
gcggagtgta tactggctta actatgcggc atcagagcag attgtactga gagtgcacca   5460
tatgcggtgt gaaataccgc acagatgcgt aaggagaaaa taccgcatca ggcgctcttc   5520
cgcttcctcg ctcactgact cgctgcgctc ggtcgttcgg ctgcggcgag cggtatcagc   5580
tcactcaaag gcggtaatac ggttatccac agaatcaggg gataacgcag gaaagaacat   5640
```

-continued

```
gtgagcaaaa ggccagcaaa aggccaggaa ccgtaaaaag gccgcgttgc tggcgttttt   5700
ccataggctc cgcccccctg acgagcatca caaaaatcga cgctcaagtc agaggtggcg   5760
aaacccgaca ggactataaa gataccaggc gtttccccct ggaagctccc tcgtgcgctc   5820
tcctgttccg accctgccgc ttaccggata cctgtccgcc tttctccctt cgggaagcgt   5880
ggcgctttct catagctcac gctgtaggta tctcagttcg gtgtaggtcg ttcgctccaa   5940
gctgggctgt gtgcacgaac cccccgttca gcccgaccgc tgcgccttat ccggtaacta   6000
tcgtcttgag tccaacccgg taagacacga cttatcgcca ctggcagcag ccactggtaa   6060
caggattagc agagcgaggt atgtaggcgg tgctacagag ttcttgaagt ggtggcctaa   6120
ctacggctac actagaagga cagtatttgg tatctgcgct ctgctgaagc cagttacctt   6180
cggaaaaaga gttggtagct cttgatccgg caaacaaacc accgctggta gcggtggttt   6240
ttttgtttgc aagcagcaga ttacgcgcag aaaaaaagga tctcaagaag atcctttgat   6300
cttttctacg gggtctgacg ctcagtggaa cgaaaactca cgttaaggga ttttggtcat   6360
gcattctagg tactaaaaca attcatccag taaaatataa tattttattt tctcccaatc   6420
aggcttgatc cccagtaagt caaaaaatag ctcgacatac tgttcttccc cgatatcctc   6480
cctgatcgac cggacgcaga aggcaatgtc ataccacttg tccgccctgc cgcttctccc   6540
aagatcaata aagccactta ctttgccatc tttcacaaag atgttgctgt ctcccaggtc   6600
gccgtgggaa aagacaagtt cctcttcggg cttttccgtc tttaaaaaat catacagctc   6660
gcgcggatct ttaaatggag tgtcttcttc ccagttttcg caatccacat cggccagatc   6720
gttattcagt aagtaatcca attcggctaa gcggctgtct aagctattcg tatagggaca   6780
atccgatatg tcgatggagt gaaagagcct gatgcactcc gcatacagct cgataatctt   6840
ttcagggctt tgttcatctt catactcttc cgagcaaagg acgccatcgg cctcactcat   6900
gagcagattg ctccagccat catgccgttc aaagtgcagg acctttggaa caggcagctt   6960
tccttccagc catagcatca tgtccttttc ccgttccaca tcataggtgg tccctttata   7020
ccggctgtcc gtcattttta aatataggtt ttcattttct cccaccagct tatatacctt   7080
agcaggagac attccttccg tatcttttac gcagcggtat ttttcgatca gtttttcaa    7140
ttccggtgat attctcattt tagccattta ttatttcctt cctcttttct acagtattta   7200
aagatacccc aagaagctaa ttataacaag acgaactcca attcactgtt ccttgcattc   7260
taaaacctta aataccagaa aacagctttt tcaaagttgt tttcaaagtt ggcgtataac   7320
atagtatcga cggagccgat tttgaaaccg cggtgatcac aggcagcaac gctctgtcat   7380
cgttacaatc aacatgctac cctccgcgag atcatccgtg tttcaaaccc ggcagcttag   7440
ttgccgttct tccgaatagc atcggtaaca tgagcaaagt ctgccgcctt acaacggctc   7500
tcccgctgac gccgtcccgg actgatgggc tgcctgtatc gagtggtgat tttgtgccga   7560
gctgccggtc ggggagctgt tggctggctg gtggcaggat atattgtggt gtaaacaaat   7620
tgacgcttag acaacttaat aacacattgc ggacgttttt aatgtagagc tcaaagttta   7680
acgcgttagc agaaggcatg ttgttgtgac tccgaggggt tgcctcaaac tctatcttat   7740
aaccggcgtg gaggcatgga ggcaggggta ttttggtcat tttaatagat agtggaaaat   7800
gacgtggaat ttacttaaag acgaagtctt tgcgacaagg gggggcccac gccgaattta   7860
atattaccgg cgtggccccc ccttatcgcg agtgctttag cacgagcggt ccagatttaa   7920
agtagaaaat ttcccgccca ctagggttaa aggtgttcac actataaaag catatacgat   7980
gtgatggtat ttgatggagc gtatattgta tcaggtattt ccgttggata cgaattattc   8040
```

-continued

```
gtacgaccct cggtaccgat cggcgcgcct ggcagacata ctgtcccaca aatgaagatg   8100
gaatctgtaa aagaaaacgc gtgaaataat gcgtctgaca aaggttaggt cggctgcctt   8160
taatcaatac caaagtggtc cctaccacga tggaaaaact gtgcagtcgg tttggctttt   8220
tctgacgaac aaataagatt cgtggccgac aggtgggggt ccaccatgtg aaggcatctt   8280
cagactccaa taatggagca atgacgtaag ggcttacgaa ataagtaagg gtagtttggg   8340
aaatgtccac tcacccgtca gtctataaat acttagcccc tccctcattg ttaagggagc   8400
aaaatctcag agagatagtc ctagagagag aaagagagca agtagcctag aagtagtcaa   8460
ggcggcgaag tattcaggca cgtggccagg aagaagaaaa gccaagacga cgaaaacagg   8520
taagagctaa gcttcctgca ccatggaaga cgccaaaaac ataaagaaag gcccggcgcc   8580
attctatccg ctggaagatg gaaccgctgg agagcaactg cataaggcta tgaagagata   8640
cgccctggtt cctggaacaa ttgcttttac agatgcacat atcgaggtgg acatcactta   8700
cgctgagtac ttcgaaatgt ccgttcggtt ggcagaagct atgaaacgat atgggctgaa   8760
tacaaatcac agaatcgtcg tatgcagtga aaactctctt caattcttta tgccggtgtt   8820
gggcgcgtta tttatcggag ttgcagttgc gcccgcgaac gacatttata atgaacgtga   8880
attgctcaac agtatgggca tttcgcagcc taccgtggtg ttcgtttcca aaaaggggtt   8940
gcaaaaaatt ttgaacgtgc aaaaaaagct cccaatcatc caaaaaatta ttatcatgga   9000
ttctaaaacg gattaccagg gatttcagtc gatgtacacg ttcgtcacat ctcatctacc   9060
tcccggtttt aatgaatacg attttgtgcc agagtccttc gatagggaca agacaattgc   9120
actgatcatg aactcctctg gatctactgg tctgcctaaa ggtgtcgctc tgcctcatag   9180
aactgcctgc gtgagattct cgcatgccag agatcctatt tttggcaatc aaatcattcc   9240
ggatactgcg attttaagtg ttgttccatt ccatcacggt tttggaatgt ttactacact   9300
cggatatttg atatgtggat ttcgagtcgt cttaatgtat agatttgaag aagagctgtt   9360
tctgaggagc cttcaggatt acaagattca aagtgcgctg ctggtgccaa ccctattctc   9420
cttcttcgcc aaaagcactc tgattgacaa atacgattta tctaatttac acgaaattgc   9480
ttctggtggc gctcccctct ctaaggaagt cggggaagcg gttgccaaga ggttccatct   9540
gccaggtatc aggcaaggat atgggctcac tgagactaca tcagctattc tgattacacc   9600
cgagggggat gataaaccgg gcgcggtcgg taaagttgtt ccattttttg aagcgaaggt   9660
tgtggatctg gataccggga aaacgctggg cgttaatcaa agaggcgaac tgtgtgtgag   9720
aggtcctatg attatgtccg gttatgtaaa caatccggaa gcgaccaacg ccttgattga   9780
caaggatgga tggctacatt ctggagacat agcttactgg gacgaagacg aacacttctt   9840
catcgttgac cgcctgaagt ctctgattaa gtacaaaggc tatcaggtgg ctcccgctga   9900
attggaatcc atcttgctcc aacaccccaa catcttcgac gctggtgtcg caggtcttcc   9960
cgacgatgac gccggtgaac ttcccgccgc cgttgttgtt ttggagcacg gaaagacgat  10020
gacggaaaaa gagatcgtgg attacgtcgc cagtcaagta acaaccgcga aaaagttgcg  10080
cggaggagtt gtgtttgtgg acgaagtacc gaaaggtctt accggaaaac tcgacgcaag  10140
aaaaatcaga gagatcctca taaaggccaa gaagggcgga aagatcgccg tgtaactcga  10200
gatatgaaga tgaagatgaa atatttggtg tgtcaaataa aaagcttgtg tgcttaagtt  10260
tgtgtttttt tcttggcttg ttgtgttatg aatttgtggc tttttctaat attaaatgaa  10320
tgtaagatca cattataatg aataaacaaa tgtttctata atccattgtg aatgttttgt  10380
```

-continued tggatctctt ctgcagcata taactactgt atgtgctatg gtatggacta tggaatatga 10440
ttaaagataa ggagctccgg tgacggaccc atggcttcgt tgaacaacgg aaactcgact 10500
tgccttccgc acaatacatc atttcttctt agcttttttt cttcttcttc gttcatacag 10560
tttttttttg tttatcagct tacattttct tgaaccgtag ctttcgtttt cttcttttta 10620
actttccatt cggagttttt gtatcttgtt tcatagtttg tcccaggatt agaatgatta 10680
ggcatcgaac cttcaagaat ttgattgaat aaaacatctt cattcttaag atatgaagat 10740
aatcttcaaa aggcccctgg gaatctgaaa gaagagaagc aggcccattt atatgggaaa 10800
gaacaatagt atttcttata taggcccatt taagttgaaa acaatcttca aaagtcccac 10860
atcgcttaga taagaaaacg aagctgagtt tatatacagc tagagtcgaa gtagtgattg 10920
ttggtagtag cgactccatg gttttagagc tagaaatagc aagttaaaat aaggctagtc 10980
cgttatcaac ttgaaaaagt ggcaccgagt cggtgctttt tttcccgggc gcgccgatca 11040
tgagcggaga attaagggag tcacgttatg acccccgccg atgacgcggg acaagccgtt 11100
ttacgtttgg aactgacaga accgcaacgt tgaaggagcc actcagccgc gggtttctgg 11160
agtttaatga gctaagcaca tacgtcagaa accattattg cgcgttcaaa agtcgcctaa 11220
ggtcactatc agctagcaaa tatttcttgt caaaaatgct ccactgacgt tccataaatt 11280
cccctcggta tccaattaga gtctcatatt cactctcaat ccaaataatc tgcaccgtac 11340
ctgcagggtc cgagctaggt cacagaagcg ctcaggaagg ccgctgagat agaggcatgg 11400
cggccaatgc gggcggcggt ggagcgggag gaggcagcgg cagcggcagc gtggctgcgc 11460
cggcggtgtg ccgccccagc ggctcgcggt ggacgccgac gccggagcag atcaggatgc 11520
tgaaggagct gtactacggc tgcggcatcc ggtcgcccag ctcggagcag atccagcgca 11580
tcaccgccat gctgcggcag cacggcaaga tcgagggcaa gaacgtcttc tactggttcc 11640
agaaccacaa ggcccgcgag cgccagaagc gccgcctcac cagcctcgac gtgaacgtgc 11700
ccgccgccgg cgcggccgac gccaccacca gccaactcgg cgtcctctcg ctgtcgtcgc 11760
cgccgccttc aggcgcggcg cctccctcgc ccaccctcgg cttctacgcc gccggcaatg 11820
gcggcggatc ggctgtgctg ctggacacga gttccgactg ggcagcagc ggcgctgcga 11880 tggccaccga gacatgcttc ctccaggact acatgggcgt gacggacacg ggcagctcgt 11940
cgcagtggcc acgcttctcg tcgtcggaca cgataatggc ggcggccgcg gcgcgggcgg 12000
cgacgacgcg ggcgcccgag actctccctc tcttcccgac ctgcggcgac gacggcggca 12060
gcggtagcag cagctacttg ccgttctggg gtgccgcgtc cacaactgcc ggcgccactt 12120
cttccgttgc gatccagcag caacaccagc tgcaggagca gtacagcttt tacagcaaca 12180
gcaacagcac ccagctggcc ggcaccggca accaagacgt atcggcaaca gcagcagcag 12240
ccgccgccct ggagctgagc ctcagctcat ggtgctcccc ttaccctgct gcagggagta 12300
tgtgagagca acgcgagctg ccactgctct tcacttatgt ctctggaatg gaaggaggag 12360
gaagtgagca tagcgttggt gcgttgctgt cattgtccta ggttagtagc tagtgccagt 12420
tactagtaag catcaggcat aggagtatgt agtagaagca tgcacgttgc cggccagcca 12480
ggctttagac gggaaaagaa tttggtgcag ccggctgcaa aacaggatgt ttacagcccc 12540
cccctcgagc cctagacttg tccatcttct ggattggcca agttaattaa tgtatgaaat 12600
aaaaggatgc acacatagtg acatgctaat cactataatg tgggcatcaa agttgtgtgt 12660
tatgtgtaat tactaattat ctgaataaga gaaagagatc atccatattt cttatcctaa 12720
atgaatgtca cgtgtcttta taattctttg atgaaccaga tgcattttat taaccaattc 12780
catatacata taaatattaa tcatatataa ttaatatcaa ttgggttagc aaaacaaatc 12840
tagtctaggt gtgttttgct aattattggg ggatagtgca aaaagaaatc tacgttctca 12900
ataattcaga tagaaaactt aataaagtga gataatttac atagattgct tttatccttt 12960
gatatatgtg aaaccatgca tgatataagg aaaatagata gagaaataat tttttacatc 13020
gttgaatatg taaacaattt aattcaagaa gctaggaata taaatattga ggagtttatg 13080
attagagctc tcccggcgcg ccagatttgc cttttcaatt tcagaaagaa tgctaaccca 13140
cagatggtta gagaggctta cgcagcaggt atcatcaaga cgatctaccc gagcaataat 13200
ctccaggaaa tcaaatacct tcccaagaag gttaaagatg cagtcaaaag attcaggact 13260
aactgcatca agaacacaga gaaagatata tttctcaaga tcagaagtac tattccagta 13320
tggacgattc aaggcttgct tcacaaacca aggcaagtaa tagagattgg agtctctaaa 13380
aaggtagttc ccactgaatc aaaggccatg gagtcaaaga ttcaaataga ggacctaaca 13440
gaactcgccg taaagactgg cgaacagttc atacagagtc tcttacgact caatgacaag 13500
aagaaaatct tcgtcaacat ggtggagcac gacacacttg tctactccaa aaatatcaaa 13560
gatacagtct cagaagacca aagggcaatt gagacttttc aacaaagggt aatatccgga 13620
aacctcctcg gattccattg cccagctatc tgtcacttta ttgtgaagat agtggaaaag 13680
gaaggtggct cctacaaatg ccatcattgc gataaaggaa aggccatcgt tgaagatgcc 13740
tctgccgaca gtggtcccaa agatggaccc ccacccacga ggagcatcgt ggaaaaagaa 13800
gacgttccaa ccacgtcttc aaagcaagtg gattgatgtg atatctccac tgacgtaagg 13860
gatgacgcac aatcccacta tccttcgcaa gacccttcct ctatataagg aagttcattt 13920
catttggaga gaacacgggg gactcctgca ggatggatct gcgtctaatt ttcggtccaa 13980
cttgcacagg aaagacgtcg accgcgatac gtcttgccca gcagactggc cttccagtcc 14040
tttcgctcga tcgggtccaa tgctgtcctc aactgtcaac cggaagcgga cgaccaacag 14100
tggaagaact gaaaggaacg acccgtctat accttgaaga tcggcctctg gtgaagggta 14160
tcatcgcagc caagcaagct cacgaaaggc tgatcgggga agtgtacaat tatgaggccc 14220
acggcgggct tattcttgag ggaggatcta tctcgttgct caggtgcatg gcgcaaagca 14280
gttattggag taccgatttt cgttggcata ttattcgcca caagttagca gacgaggaga 14340
cattcatgaa cgcggccaag gccagagtta ggcagatgtt gcgccctgct gtaggcccat 14400
ctattattca agagttggtt catctttgga atgagcctcg gctgaggccc atactgaaag 14460
agatcgacgg atatcgatat gccatgttat ttgctagcca gaaccagatc acacccgata 14520
tgctattgca gcttgaccca gatatggagg gtgagttgat tcatggaatc gctcaggagt 14580
atctcatcca tgcgcgccgg caggagcagg aattccctcc agtgagcgtg gtcgctttcg 14640
aaggattcga aggtccaccg ttcggaatgt gctagctcga gccctagact tgtccatctt 14700
ctggattggc caagttaatt aatgtatgaa ataaaaggat gcacacatag tgacatgcta 14760
atcactataa tgtgggcatc aaagttgtgt gttatgtgta attactaatt atctgaataa 14820
gagaaagaga tcatccatat ttcttatcct aaatgaatgt cacgtgtctt tataattctt 14880
tgatgaacca gatgcatttt attaaccaat tccatataca tataaatatt aatcatatat 14940
aattaatatc aattgggtta gcaaaacaaa tctagtctag gtgtgttttg ctaattattg 15000
ggggatagtg caaaaagaaa tctacgttct caataattca gatagaaaac ttaataaagt 15060
gagataattt acatagattg cttttatcct ttgatatatg tgaaaccatg catgatataa 15120

-continued

```
ggaaaataga tagagaaata attttttaca tcgttgaata tgtaaacaat ttaattcaag  15180

aagctaggaa tataaatatt gaggagttta tgattagagc tcagtgtttg atcgccggcg  15240

gtaccgagtg tacttcaagt cagtgggaaa tcaataaaat gattatttta tgaatatatt  15300

tcattgtgca agtagataga aattacatat gttacataac acacgaaata aacaaaaaaa  15360

gacaatccaa aaacaaacac cccaaaaaaa ataatcactt tagataaact cgtatgagga  15420

gaggcacgtt cagtgactcg acgattcccg agcaaaaaaa gtctccccgt cacacatgta  15480

gtgggtgacg caattatctt taaagtaatc cttctgttga cttgtcattg ataacatcca  15540

gtcttcgtca ggattgcaaa gaattataga agggatccca                        15580
```

<210> SEQ ID NO 32
<211> LENGTH: 16945
<212> TYPE: DNA
<213> ORGANISM: artificial
<220> FEATURE:
<223> OTHER INFORMATION: synthetic oligonucleotide

<400> SEQUENCE: 32

```
gttgaaggcc gcgcaggccg cccagcggca acgcatcgag gcagaagcac gccccggtga     60

atcgtggcaa gcggccgctg atcgaatccg caaagaatcc cggcaaccgc cggcagccgg    120

tgcgccgtcg attaggaagc cgcccaaggg cgacgagcaa ccagattttt tcgttccgat    180

gctctatgac gtgggcaccc gcgatagtcg cagcatcatg gacgtggccg ttttccgtct    240

gtcgaagcgt gaccgacgag ctggcgaggt gatccgctac gagcttccag acgggcacgt    300

agaggtttcc gcagggccgg ccggcatggc cagtgtgtgg gattacgacc tggtactgat    360

ggcggtttcc catctaaccg aatccatgaa ccgataccgg gaagggaagg gagacaagcc    420

cggccgcgtg ttccgtccac acgttgcgga cgtactcaag ttctgccggc gagccgatgg    480

cggaaagcag aaagacgacc tggtagaaac ctgcattcgg ttaaacacca cgcacgttgc    540

catgcagcgt acgaagaagg ccaagaacgg ccgcctggtg acggtatccg agggtgaagc    600

cttgattagc cgctacaaga tcgtaaagag cgaaaccggg cggccggagt acatcgagat    660

cgagctagct gattggatgt accgcgagat cacagaaggc aagaacccgg acgtgctgac    720

ggttcacccc gattactttt tgatcgatcc cggcatcggc cgttttctct accgcctggc    780

acgccgcgcc gcaggcaagg cagaagccag atggttgttc aagacgatct acgaacgcag    840

tggcagcgcc ggagagttca agaagttctg tttcaccgtg cgcaagctga tcgggtcaaa    900

tgacctgccg gagtacgatt tgaaggagga ggcggggcag gctggcccga tcctagtcat    960

gcgctaccgc aacctgatcg agggcgaagc atccgccggt tcctaatgta cggagcagat   1020

gctagggcaa attgccctag caggggaaaa aggtcgaaaa ggcctctttc ctgtggatag   1080

cacgtacatt gggaacccaa agccgtacat tgggaaccgg aacccgtaca ttgggaaccc   1140

aaagccgtac attgggaacc ggtcacacat gtaagtgact gatataaaag agaaaaaagg   1200

cgatttttcc gcctaaaact ctttaaaact tattaaaact cttaaaaccc gcctggcctg   1260

tgcataactg tctggccagc gcacagccga agagctgcaa aaagcgccta cccttcggtc   1320

gctgcgctcc ctacgccccg ccgcttcgcg tcggcctatc gcggccgctg gccgctcaaa   1380

aatggctggc ctacggccag gcaatctacc agggcgcgga caagccgcgc cgtcgccact   1440

cgaccgccgg cgcccacatc aaggcaccct gcctcgcgcg tttcggtgat gacggtgaaa   1500

acctctgaca catgcagctc ccggaaacgg tcacagcttg tctgtaagcg gatgccggga   1560

gcagacaagc ccgtcagggc gcgtcagcgg gtgttggcgg gtgtcggggc gcagccatga   1620
```

-continued

```
cccagtcacg tagcgatagc ggagtgtata ctggcttaac tatgcggcat cagagcagat   1680
tgtactgaga gtgcaccata tgcggtgtga aataccgcac agatgcgtaa ggagaaaata   1740
ccgcatcagg cgctcttccg cttcctcgct cactgactcg ctgcgctcgg tcgttcggct   1800
gcggcgagcg gtatcagctc actcaaaggc ggtaatacgg ttatccacag aatcagggga   1860
taacgcagga aagaacatgt gagcaaaagg ccagcaaaag gccaggaacc gtaaaaaggc   1920
cgcgttgctg gcgtttttcc ataggctccg cccccctgac gagcatcaca aaaatcgacg   1980
ctcaagtcag aggtggcgaa acccgacagg actataaaga taccaggcgt ttccccctgg   2040
aagctccctc gtgcgctctc ctgttccgac cctgccgctt accggatacc tgtccgcctt   2100
tctcccttcg ggaagcgtgg cgctttctca tagctcacgc tgtaggtatc tcagttcggt   2160
gtaggtcgtt cgctccaagc tgggctgtgt gcacgaaccc cccgttcagc ccgaccgctg   2220
cgccttatcc ggtaactatc gtcttgagtc caacccggta agacacgact tatcgccact   2280
ggcagcagcc actggtaaca ggattagcag agcgaggtat gtaggcggtg ctacagagtt   2340
cttgaagtgg tggcctaact acggctacac tagaaggaca gtatttggta tctgcgctct   2400
gctgaagcca gttaccttcg gaaaaagagt tggtagctct tgatccggca aacaaaccac   2460
cgctggtagc ggtggttttt ttgtttgcaa gcagcagatt acgcgcagaa aaaaaggatc   2520
tcaagaagat cctttgatct tttctacggg gtctgacgct cagtggaacg aaaactcacg   2580
ttaagggatt ttggtcatgc attctaggta ctaaaacaat tcatccagta aaatataata   2640
ttttattttc tcccaatcag gcttgatccc cagtaagtca aaaaatagct cgacatactg   2700
ttcttccccg atatcctccc tgatcgaccg gacgcagaag gcaatgtcat accacttgtc   2760
cgccctgccg cttctcccaa gatcaataaa gccacttact ttgccatctt tcacaaagat   2820
gttgctgtct cccaggtcgc cgtgggaaaa gacaagttcc tcttcgggct tttccgtctt   2880
taaaaaatca tacagctcgc gcggatcttt aaatggagtg tcttcttccc agttttcgca   2940
atccacatcg gccagatcgt tattcagtaa gtaatccaat tcggctaagc ggctgtctaa   3000
gctattcgta tagggacaat ccgatatgtc gatggagtga aagagcctga tgcactccgc   3060
atacagctcg ataatctttt cagggctttg ttcatcttca tactcttccg agcaaaggac   3120
gccatcggcc tcactcatga gcagattgct ccagccatca tgccgttcaa agtgcaggac   3180
ctttggaaca ggcagctttc cttccagcca tagcatcatg tccttttccc gttccacatc   3240
ataggtggtc cctttatacc ggctgtccgt catttttaaa tataggtttt cattttctcc   3300
caccagctta tataccttag caggagacat tccttccgta tcttttacgc agcggtattt   3360
ttcgatcagt tttttcaatt ccggtgatat tctcatttta gccatttatt atttccttcc   3420
tcttttctac agtatttaaa gataccccaa gaagctaatt ataacaagac gaactccaat   3480
tcactgttcc ttgcattcta aaaccttaaa taccagaaaa cagctttttc aaagttgttt   3540
tcaaagttgg cgtataacat agtatcgacg gagccgattt tgaaaccgcg gtgatcacag   3600
gcagcaacgc tctgtcatcg ttacaatcaa catgctaccc tccgcgagat catccgtgtt   3660
tcaaacccgg cagcttagtt gccgttcttc cgaatagcat cggtaacatg agcaaagtct   3720
gccgccttac aacggctctc ccgctgacgc cgtcccggac tgatgggctg cctgtatcga   3780
gtggtgattt tgtgccgagc tgccggtcgg ggagctgttg gctggctggt ggcaggatat   3840
attgtggtgt aaacaaattg acgcttagac aacttaataa cacattgcgg acgtttttaa   3900
tgtagagctc aaagtttaac gcgttagcag aaggcatgtt gttgtgactc cgaggggttg   3960
```

cctcaaactc tatcttataa ccggcgtgga ggcatggagg caggggtatt ttggtcattt 4020
taatagatag tggaaaatga cgtggaattt acttaaagac gaagtctttg cgacaagggg 4080
gggcccacgc cgaatttaat attaccggcg tggccccccc ttatcgcgag tgctttagca 4140
cgagcggtcc agatttaaag tagaaaattt cccgcccact agggttaaag gtgttcacac 4200
tataaaagca tatacgatgt gatggtattt gatggagcgt atattgtatc aggtatttcc 4260
gttggatacg aattattcgt acgaccctcg gtaccgatcg gcgcgcctgg cagacatact 4320
gtcccacaaa tgaagatgga atctgtaaaa gaaaacgcgt gaaataatgc gtctgacaaa 4380
ggttaggtcg gctgccttta atcaatacca aagtggtccc taccacgatg gaaaaactgt 4440
gcagtcggtt tggctttttc tgacgaacaa ataagattcg tggccgacag gtgggggtcc 4500
accatgtgaa ggcatcttca gactccaata atggagcaat gacgtaaggg cttacgaaat 4560
aagtaagggt agtttgggaa atgtccactc acccgtcagt ctataaatac ttagcccctc 4620
cctcattgtt aagggagcaa aatctcagag agatagtcct agagagagaa agagagcaag 4680
tagcctagaa gtagtcaagg cggcgaagta ttcaggcacg tggccaggaa gaagaaaagc 4740
caagacgacg aaaacaggta agagctaagc ttcctgcacc atggaagacg ccaaaaacat 4800
aaagaaaggc ccggcgccat tctatccgct ggaagatgga accgctggag agcaactgca 4860
taaggctatg aagagatacg ccctggttcc tggaacaatt gcttttacag atgcacatat 4920
cgaggtggac atcacttacg ctgagtactt cgaaatgtcc gttcggttgg cagaagctat 4980
gaaacgatat gggctgaata caaatcacag aatcgtcgta tgcagtgaaa actctcttca 5040
attctttatg ccggtgttgg gcgcgttatt tatcggagtt gcagttgcgc ccgcgaacga 5100
catttataat gaacgtgaat tgctcaacag tatgggcatt tcgcagccta ccgtggtgtt 5160
cgtttccaaa aaggggttgc aaaaaatttt gaacgtgcaa aaaaagctcc caatcatcca 5220
aaaaattatt atcatggatt ctaaaacgga ttaccaggga tttcagtcga tgtacacgtt 5280
cgtcacatct catctacctc ccggttttaa tgaatacgat tttgtgccag agtccttcga 5340
tagggacaag acaattgcac tgatcatgaa ctcctctgga tctactggtc tgcctaaagg 5400
tgtcgctctg cctcatagaa ctgcctgcgt gagattctcg catgccagag atcctatttt 5460
tggcaatcaa atcattccgg atactgcgat tttaagtgtt gttccattcc atcacggttt 5520
tggaatgttt actacactcg gatatttgat atgtggattt cgagtcgtct taatgtatag 5580
atttgaagaa gagctgtttc tgaggagcct tcaggattac aagattcaaa gtgcgctgct 5640
ggtgccaacc ctattctcct tcttcgccaa aagcactctg attgacaaat acgatttatc 5700
taatttacac gaaattgctt ctggtggcgc tcccctctct aaggaagtcg gggaagcggt 5760
tgccaagagg ttccatctgc caggtatcag gcaaggatat gggctcactg agactacatc 5820
agctattctg attacacccg agggggatga taaaccgggc gcggtcggta aagttgttcc 5880
attttttgaa gcgaaggttg tggatctgga taccgggaaa acgctgggcg ttaatcaaag 5940
aggcgaactg tgtgtgagag gtcctatgat tatgtccggt tatgtaaaca atccggaagc 6000
gaccaacgcc ttgattgaca aggatggatg gctacattct ggagacatag cttactggga 6060
cgaagacgaa cacttcttca tcgttgaccg cctgaagtct ctgattaagt acaaaggcta 6120
tcaggtggct cccgctgaat tggaatccat cttgctccaa caccccaaca tcttcgacgc 6180
tggtgtcgca ggtcttcccg acgatgacgc cggtgaactt cccgccgccg ttgttgtttt 6240
ggagcacgga aagacgatga cggaaaaaga gatcgtggat tacgtcgcca gtcaagtaac 6300
aaccgcgaaa aagttgcgcg gaggagttgt gtttgtggac gaagtaccga aaggtcttac 6360

```
cggaaaactc gacgcaagaa aaatcagaga gatcctcata aaggccaaga agggcggaaa   6420
gatcgccgtg taactcgaga tatgaagatg aagatgaaat atttggtgtg tcaaataaaa   6480
agcttgtgtg cttaagtttg tgttttttc ttggcttgtt gtgttatgaa tttgtggctt   6540
tttctaatat taaatgaatg taagatcaca ttataatgaa taaacaaatg tttctataat   6600
ccattgtgaa tgttttgttg gatctcttct gcagcatata actactgtat gtgctatggt   6660
atggactatg gaatatgatt aaagataagg agctccggtg acggacccat ggcttcgttg   6720
aacaacggaa actcgacttg ccttccgcac aatacatcat ttcttcttag ctttttttct   6780
tcttcttcgt tcatacagtt ttttttgtt tatcagctta cattttcttg aaccgtagct   6840
ttcgttttct tctttttaac tttccattcg gagtttttgt atcttgtttc atagtttgtc   6900
ccaggattag aatgattagg catcgaacct tcaagaattt gattgaataa aacatcttca   6960
ttcttaagat atgaagataa tcttcaaaag gcccctggga atctgaaaga agagaagcag   7020
gcccatttat atgggaaaga acaatagtat ttcttatata ggcccattta agttgaaaac   7080
aatcttcaaa agtcccacat cgcttagata agaaaacgaa gctgagttta tatacagcta   7140
gagtcgaagt agtgattgtt ggtagtagcg actccatggt tttagagcta gaaatagcaa   7200
gttaaaataa ggctagtccg ttatcaactt gaaaaagtgg caccgagtcg gtgctttttt   7260
tcccggcgta atatggcgcg ccagatttgc cttttcaatt tcagaaagaa tgctaaccca   7320
cagatggtta gagaggctta cgcagcaggt atcatcaaga cgatctaccc gagcaataat   7380
ctccaggaaa tcaaatacct tcccaagaag gttaaagatg cagtcaaaag attcaggact   7440
aactgcatca agaacacaga gaaagatata tttctcaaga tcagaagtac tattccagta   7500
tggacgattc aaggcttgct tcacaaacca aggcaagtaa tagagattgg agtctctaaa   7560
aaggtagttc ccactgaatc aaaggccatg gagtcaaaga ttcaaataga ggacctaaca   7620
gaactcgccg taaagactgg cgaacagttc atacagagtc tcttacgact caatgacaag   7680
aagaaaatct tcgtcaacat ggtggagcac gacacacttg tctactccaa aaatatcaaa   7740
gatacagtct cagaagacca aagggcaatt gagacttttc aacaaagggt aatatccgga   7800
aacctcctcg gattccattg cccagctatc tgtcacttta ttgtgaagat agtggaaaag   7860
gaaggtggct cctacaaatg ccatcattgc gataaaggaa aggccatcgt tgaagatgcc   7920
tctgccgaca gtggtcccaa agatggaccc ccacccacga ggagcatcgt ggaaaaagaa   7980
gacgttccaa ccacgtcttc aaagcaagtg gattgatgtg atatctccac tgacgtaagg   8040
gatgacgcac aatcccacta tccttcgcaa gacccttcct ctatataagg aagttcattt   8100
catttggaga gaacacgggg gactcctgca ggatggatct gcgtctaatt ttcggtccaa   8160
cttgcacagg aaagacgtcg accgcgatac gtcttgccca gcagactggc cttccagtcc   8220
tttcgctcga tcgggtccaa tgctgtcctc aactgtcaac cggaagcgga cgaccaacag   8280
tggaagaact gaaaggaacg acccgtctat accttgaaga tcggcctctg gtgaagggta   8340
tcatcgcagc caagcaagct cacgaaaggc tgatcgggga agtgtacaat tatgaggccc   8400
acggcgggct tattcttgag ggaggatcta tctcgttgct caggtgcatg gcgcaaagca   8460
gttattggag taccgatttt cgttggcata ttattcgcca caagttagca gacgaggaga   8520
cattcatgaa cgcggccaag gccagagtta ggcagatgtt gcgccctgct gtaggcccat   8580
ctattattca agagttggtt catctttgga atgagcctcg gctgaggccc atactgaaag   8640
agatcgacgg atatcgatat gccatgttat ttgctagcca gaaccagatc acacccgata   8700
```

-continued

```
tgctattgca gcttgaccca gatatggagg gtgagttgat tcatggaatc gctcaggagt   8760
atctcatcca tgcgcgccgg caggagcagg aattccctcc agtgagcgtg gtcgctttcg   8820
aaggattcga aggtccaccg ttcggaatgt gctagctcga gccctagact tgtccatctt   8880
ctggattggc caagttaatt aatgtatgaa ataaaaggat gcacacatag tgacatgcta   8940
atcactataa tgtgggcatc aaagttgtgt gttatgtgta attactaatt atctgaataa   9000
gagaaagaga tcatccatat ttcttatcct aaatgaatgt cacgtgtctt tataattctt   9060
tgatgaacca gatgcatttt attaaccaat tccatataca tataaatatt aatcatatat   9120
aattaatatc aattgggtta gcaaaacaaa tctagtctag gtgtgttttg ctaattattg   9180
ggggatagtg caaaaagaaa tctacgttct caataattca gatagaaaac ttaataaagt   9240
gagataattt acatagattg cttttatcct ttgatatatg tgaaaccatg catgatataa   9300
ggaaaataga tagagaaata attttttaca tcgttgaata tgtaaacaat ttaattcaag   9360
aagctaggaa tataaatatt gaggagttta tgattagagc tctcccgcag atttgccttt   9420
tcaatttcag aaagaatgct aacccacaga tggttagaga ggcttacgca gcaggtatca   9480
tcaagacgat ctacccgagc aataatctcc aggaaatcaa ataccttccc aagaaggtta   9540
aagatgcagt caaaagattc aggactaact gcatcaagaa cacagagaaa gatatatttc   9600
tcaagatcag aagtactatt ccagtatgga cgattcaagg cttgcttcac aaaccaaggc   9660
aagtaataga gattggagtc tctaaaaagg tagttcccac tgaatcaaag gccatggagt   9720
caaagattca aatagaggac ctaacagaac tcgccgtaaa gactggcgaa cagttcatac   9780
agagtctctt acgactcaat gacaagaaga aaatcttcgt caacatggtg gagcacgaca   9840
cacttgtcta ctccaaaaat atcaaagata cagtctcaga agaccaaagg gcaattgaga   9900
cttttcaaca aagggtaata tccggaaacc tcctcggatt ccattgccca gctatctgtc   9960
actttattgt gaagatagtg gaaaaggaag gtggctccta caaatgccat cattgcgata  10020
aaggaaaggc catcgttgaa gatgcctctg ccgacagtgg tcccaaagat ggacccccac  10080
ccacgaggag catcgtggaa aaagaagacg ttccaaccac gtcttcaaag caagtggatt  10140
gatgtgatat ctccactgac gtaagggatg acgcacaatc ccactatcct tcgcaagacc  10200
cttcctctat ataaggaagt tcatttcatt tggagagaac acgggggact atgatggctt  10260
cattgtcttg tgttgaagac aagatgaaaa caagttgttt ggttaatggt ggaggaacta  10320
taacaacaac aacatctcaa tctaccttgc ttgaagagat gaagctgttg aaagaccagt  10380
caggtacaag aaagccggta ataaactcgg agctatggca cgcttgtgca ggcccttttgg  10440
tgtgtctccc tcaagttggg agcttagtgt attacttctc acaaggtcat agcgagcagg  10500
ttgctgtttc aaccagaaga tcagcaacaa cacaagttcc taattatccg aaccttccat  10560
ctcagttgat gtgtcaagtc cataatgtta ctcttcatgc tgacaaagac agtgacgaaa  10620
tctatgctca gatgagtctt caacctgttc actctgagag agatgtgttc cctgtaccag  10680
actttggaat gctgagagga agtaagcacc cgactgagtt tttctgcaaa acacttactg  10740
caagtgacac aagcacacat ggaggtttct cagtgccacg tagagctgca gagaagctat  10800
ttccaccatt ggactactca gcacagccgc caacgcaaga gcttgtagtt cgagatcttc  10860
atgagaatac ttggacattt cgccatatct accgagggca accaaagaga catctcctaa  10920
ctacaggatg gagtttgttc gttggatcga agagattgag agctggggat tctgttttgt  10980
tcatcaggga tgagaagtca caacttatgg tcggtgttag gcgtgccaat cgccaacaaa  11040
cagcacttcc ttcatcagtt ctctcagcgg atagtatgca catcggtgtt cttgctgctg  11100
```

ctgctcacgc aaccgccaac cgtactcctt ttttgatatt ctataatcca agagcttgtc 11160
cagcagagtt cgtgatccct ctagctaagt accgtaaggc gatatgcggg tctcagctct 11220
cagttggtat gagatttgga atgatgtttg aaactgaaga ttccgggaaa cgaaggtaca 11280
tgggaactat tgttggaatc agcgatttgg atccgttgag atggcctggt tctaagtggc 11340
gtaaccttca ggtagaatgg gatgagcctg gatgtaatga taaacctact cgggtcagtc 11400
catgggatat cgaaacacct gaaagtctct tcatttttcc ttctctgacc tcaggactca 11460
aacgtcagct ccatccatct tactttgctg gtgaaactga atggggtagc ttgataaaac 11520
ggccacttat acgtgttcct gattccgcga atgggattat gccatatgca tctttcccta 11580
gtatggcttc ggagcagctt atgaaaatga tgatgaggcc tcacaacaac caaaatgtac 11640
catctttcat gtctgagatg cagcagaata ttgtaatggg gaatggaggt ttgctaggag 11700
atatgaagat gcagcaaccc ctgatgatga accagaaatc tgagatggtg cagccacaaa 11760
acaagctaac agtgaaccca tctgcttcta atacgagtgg ccaagaacag aatctttcac 11820
agagtatgag tgctcctgct aaacctgaga actctacact ctctggttgc agctctggta 11880
gagtccaaca tggacttgag cagtcaatgg aacaggcaag ccaggttact acatccacag 11940
tgtgtaatga ggaaaaggtt aatcagctac ttcagaaacc gggtgcttcg tcgcctgtac 12000
aagctgatca atgtcttgac attactcatc agatttacca accacagtct gatccaataa 12060
atggattctc tttcctggaa actgatgagc tgacatcaca agtctcttcc ttccagtctc 12120
ttgccggatc atacaagcaa ccattcattc tatcctccca ggattcttca gctgttgtgt 12180
taccggattc cacaaactca ccgctgtttc atgatgtgtg ggacactcag ttgaacggtc 12240
tcaagtttga ccagttcagt cccttgatgc agcaggacct ttatgctagt cagaatatct 12300
gtatgagtaa tagcacaacc agtaacattc tagatcctcc actctcaaac acagtccttg 12360
atgacttctg tgccatcaaa gacactgatt tccagaacca cccttctggt tgtttggttg 12420
gaaacaacaa cactagcttt gctcaagatg tccagtcgca gatcacatca gctagctttg 12480
cagactcaca ggccttctct cgccaagatt ttccagataa ttctggaggc actggtacat 12540
cttcaagcaa tgttgatttt gatgattgta gtctgcggca aaatagtaaa ggctcatcat 12600
ggcagaaaat tgcgacaccc cgcgtccgaa cctactcgag tttctccata ataatgtgtg 12660
agtagttccc agataaggga attagggttc ctatagggtt tcgctcatgt gttgagcata 12720
taagaaaccc ttagtatgta tttgtatttg taaaatactt ctatcaataa aatttctaat 12780
tcctaaaacc aaaatccagt actaaaatcc agatcccccg aattaagtgt ttgatcgccg 12840
gcggtaccga gtgtacttca agtcagtggg aaatcaataa aatgattatt ttatgaatat 12900
atttcattgt gcaagtagat agaaattaca tatgttacat aacacacgaa ataaacaaaa 12960
aaagacaatc caaaaacaaa caccccaaaa aaaataatca ctttagataa actcgtatga 13020
ggagaggcac gttcagtgac tcgacgattc ccgagcaaaa aaagtctccc cgtcacacat 13080
gtagtgggtg acgcaattat ctttaaagta atccttctgt tgacttgtca ttgataacat 13140
ccagtcttcg tcaggattgc aaagaattat agaagggatc ccacctttta ttttcttctt 13200
ttttccatat ttagggttga cagtgaaatc agactggcaa cctattaatt gcttccacaa 13260
tgggacgaac ttgaagggga tgtcgtcgat gatattatag gtggcgtgtt catcgtagtt 13320
ggtgaaatcg atggtaccgt tccaatagtt gtgtcgtccg agacttctag cccaggtggt 13380
ctttccggta cgagttggtc cgcagatgta gaggctgggg tgtcggattc cattccttcc 13440

-continued

```
attgtccttg ttaaatcggc catccattca aggtcagatt gagcttgttg gtatgagaca  13500
ggatgtatgt aagtataagc gtctatgctt acatggtata gatgggtttc cctccaggag  13560
tgtagatctt cgtggcagcg aagatctgat tctgtgaagg gcgacacata cggttcaggt  13620
tgtggaggga ataatttgtt ggctgaatat tccagccatt gaagctttgt tgcccattca  13680
tgagggaatt cttccttgat catgtcaaga tattcctcct tagacgttgc agtctggata  13740
atagttctcc atcgtgcgtc agatttgcga ggagaaacct tatgatctcg gaaatctcct  13800
ctggttttaa tatctccgtc ctttgatatg taatcaagga cttgtttaga gtttctagct  13860
ggctggatat tagggtgatt tccttcaaaa tcgaaaaaag aaggatccct aatacaaggt  13920
tttttatcaa gctggagaag agcatgatag tgggtagtgc catcttgatg aagctcagaa  13980
gcaacaccaa ggaagaaaat aagaaaaggt gtgagtttct cccagagaaa ctggaataaa  14040
tcatctcttt gagatgagca cttgggatag gtaaggaaaa catatttaga ttggagtctg  14100
aagttcttac tagcagaagg catgttgttg tgactccgag ggttgcctc aaactctatc  14160
ttataaccgg cgtggaggca tggaggcagg ggtattttgg tcattttaat agatagtgga  14220
aaatgacgtg gaatttactt aaagacgaag tctttgcgac aagggggggc ccacgccgaa  14280
tttaatatta ccggcgtggc cccccttat cgcgagtgct ttagcacgag cggtccagat  14340
ttaaagtaga aaatttcccg cccactaggg ttaaaggtgt tcacactata aaagcatata  14400
cgatgtgatg gtatttgatg gagcgtatat tgtatcaggt atttccgttg gatacgaatt  14460
attcgtacga ccctcatagt ttaaactatc agtgtttgac aggatatatt ggcgggtaaa  14520
cctaagagaa aagagcgttt attagaataa cggatattta aaagggcgtg aaaaggttta  14580
tccgttcgtc catttgtatg tgcatgccaa ccacagggtt cccctcggga tcaaagtact  14640
ttgatccaac ccctccgctg ctatagtgca gtcggcttct gacgttcagt gcagccgtct  14700
tctgaaaacg acatgtcgca caagtcctaa gttacgcgac aggctgccgc cctgcccttt  14760
tcctggcgtt ttcttgtcgc gtgttttagt cgcataaagt agaatacttg cgactagaac  14820
cggagacatt acgccatgaa caagagcgcc gccgctggcc tgctgggcta tgcccgcgtc  14880
agcaccgacg accaggactt gaccaaccaa cgggccgaac tgcacgcggc cggctgcacc  14940
aagctgtttt ccgagaagat caccggcacc aggcgcgacc gcccggagct ggccaggatg  15000
cttgaccacc tacgccctgg cgacgttgtg acagtgacca ggctagaccg cctggcccgc  15060
agcacccgcg acctactgga cattgccgag cgcatccagg aggccggcgc gggcctgcgt  15120
agcctggcag agccgtgggc cgacaccacc acgccggccg gccgcatggt gttgaccgtg  15180
ttcgccggca ttgccgagtt cgagcgttcc ctaatcatcg accgcacccg gagcgggcgc  15240
gaggccgcca aggcccgagg cgtgaagttt ggcccccgcc ctaccctcac cccggcacag  15300
atcgcgcacg cccgcgagct gatcgaccag gaaggccgca ccgtgaaaga ggcggctgca  15360
ctgcttggcg tgcatcgctc gaccctgtac cgcgcacttg agcgcagcga ggaagtgacg  15420
cccaccgagg ccaggcggcg cggtgccttc cgtgaggacg cattgaccga ggccgacgcc  15480
ctggcggccg ccgagaatga acgccaagag gaacaagcat gaaaccgcac caggacggcc  15540
aggacgaacc gtttttcatt accgaagaga tcgaggcgga gatgatcgcg gccgggtacg  15600
tgttcgagcc gcccgcgcac ggctcaaccg tgcggctgca tgaaatcctg gccggtttgt  15660
ctgatgccaa gctggcggcc tggccggcca gcttggccgc tgaagaaacc gagcgccgcc  15720
gtctaaaaag gtgatgtgta tttgagtaaa acagcttgcg tcatgcggtc gctgcgtata  15780
tgatgcgatg agtaaataaa caaatacgca aggggaacgc atgaaggtta tcgctgtact  15840
```

taaccagaaa ggcgggtcag gcaagacgac catcgcaacc catctagccc gcgccctgca 15900
actcgccggg gccgatgttc tgttagtcga ttccgatccc cagggcagtg cccgcgattg 15960
ggcggccgtg cgggaagatc aaccgctaac cgttgtcggc atcgaccgcc cgacgattga 16020
ccgcgacgtg aaggccatcg gccggcgcga cttcgtagtg atcgacggag cgccccaggc 16080
ggcggacttg gctgtgtccg cgatcaaggc agccgacttc gtgctgattc cggtgcagcc 16140
aagcccttac gacatatggg ccaccgccga cctggtggag ctggttaagc agcgcattga 16200
ggtcacggat ggaaggctac aagcggcctt tgtcgtgtcg cgggcgatca aaggcacgcg 16260
catcggcggt gaggttgccg aggcgctggc cgggtacgag ctgcccattc ttgagtcccg 16320
tatcacgcag cgcgtgagct acccaggcac tgccgccgcc ggcacaaccg ttcttgaatc 16380
agaacccgag ggcgacgctg cccgcgaggt ccaggcgctg gccgctgaaa ttaaatcaaa 16440
actcatttga gttaatgagg taaagagaaa atgagcaaaa gcacaaacac gctaagtgcc 16500
ggccgtccga gcgcacgcag cagcaaggct gcaacgttgg ccagcctggc agacacgcca 16560
gccatgaagc gggtcaactt tcagttgccg gcggaggatc acaccaagct gaagatgtac 16620
gcggtacgcc aaggcaagac cattaccgag ctgctatctg aatacatcgc gcagctacca 16680
gagtaaatga gcaaatgaat aaatgagtag atgaatttta gcggctaaag gaggcggcat 16740
ggaaaatcaa gaacaaccag gcaccgacgc cgtggaatgc cccatgtgtg gaggaacggg 16800
cggttggcca ggcgtaagcg gctgggttgt ctgccggccc tgcaatggca ctggaacccc 16860
caagcccgag gaatcggcgt gacggtcgca aaccatccgg cccggtacaa atcggcgcgg 16920
cgctgggtga tgacctggtg gagaa 16945

<210> SEQ ID NO 33
<211> LENGTH: 13599
<212> TYPE: DNA
<213> ORGANISM: artificial
<220> FEATURE:
<223> OTHER INFORMATION: synthetic oligonucleotide

<400> SEQUENCE: 33
ccttttattt tcttcttttt tccatattta gggttgacag tgaaatcaga ctggcaacct 60
attaattgct tccacaatgg gacgaacttg aaggggatgt cgtcgatgat attataggtg 120
gcgtgttcat cgtagttggt gaaatcgatg gtaccgttcc aatagttgtg tcgtccgaga 180
cttctagccc aggtggtctt tccggtacga gttggtccgc agatgtagag gctggggtgt 240
cggattccat tccttccatt gtccttgtta aatcggccat ccattcaagg tcagattgag 300
cttgttggta tgagacagga tgtatgtaag tataagcgtc tatgcttaca tggtatagat 360
gggtttccct ccaggagtgt agatcttcgt ggcagcgaag atctgattct gtgaagggcg 420
acacatacgg ttcaggttgt ggagggaata atttgttggc tgaatattcc agccattgaa 480
gctttgttgc ccattcatga gggaattctt ccttgatcat gtcaagatat tcctccttag 540
acgttgcagt ctggataata gttctccatc gtgcgtcaga tttgcgagga gaaaccttat 600
gatctcggaa atctcctctg gttttaatat ctccgtcctt tgatatgtaa tcaaggactt 660
gtttagagtt tctagctggc tggatattag ggtgatttcc ttcaaaatcg aaaaaagaag 720
gatccctaat acaaggtttt ttatcaagct ggagaagagc atgatagtgg gtagtgccat 780
cttgatgaag ctcagaagca acaccaagga agaaaataag aaaaggtgtg agtttctccc 840
agagaaactg gaataaatca tctctttgag atgagcactt gggataggta aggaaaacat 900

-continued

```
atttagattg gagtctgaag ttcttactag cagaaggcat gttgttgtga ctccgagggg    960
ttgcctcaaa ctctatctta taaccggcgt ggaggcatgg aggcaggggt attttggtca   1020
ttttaataga tagtggaaaa tgacgtggaa tttacttaaa gacgaagtct ttgcgacaag   1080
ggggggccca cgccgaattt aatattaccg gcgtggcccc cccttatcgc gagtgcttta   1140
gcacgagcgg tccagattta aagtagaaaa tttcccgccc actagggtta aaggtgttca   1200
cactataaaa gcatatacga tgtgatggta tttgatggag cgtatattgt atcaggtatt   1260
tccgttggat acgaattatt cgtacgaccc tcatagttta aactatcagt gtttgacagg   1320
atatattggc gggtaaacct aagagaaaag agcgtttatt agaataacgg atatttaaaa   1380
gggcgtgaaa aggtttatcc gttcgtccat ttgtatgtgc atgccaacca cagggttccc   1440
ctcgggatca aagtactttg atccaacccc tccgctgcta tagtgcagtc ggcttctgac   1500
gttcagtgca gccgtcttct gaaaacgaca tgtcgcacaa gtcctaagtt acgcgacagg   1560
ctgccgccct gccctttcc tggcgttttc ttgtcgcgtg ttttagtcgc ataaagtaga   1620
atacttgcga ctagaaccgg agacattacg ccatgaacaa gagcgccgcc gctggcctgc   1680
tgggctatgc ccgcgtcagc accgacgacc aggacttgac caaccaacgg gccgaactgc   1740
acgcggccgg ctgcaccaag ctgttttccg agaagatcac cggcaccagg cgcgaccgcc   1800
cggagctggc caggatgctt gaccacctac gccctggcga cgttgtgaca gtgaccaggc   1860
tagaccgcct ggcccgcagc acccgcgacc tactggacat tgccgagcgc atccaggagg   1920
ccggcgcggg cctgcgtagc ctggcagagc cgtgggccga caccaccacg ccggccggcc   1980
gcatggtgtt gaccgtgttc gccggcattg ccgagttcga gcgttcccta atcatcgacc   2040
gcacccggag cgggcgcgag gccgccaagg cccgaggcgt gaagtttggc ccccgcccta   2100
ccctcacccc ggcacagatc gcgcacgccc gcgagctgat cgaccaggaa ggccgcaccg   2160
tgaaagaggc ggctgcactg cttggcgtgc atcgctcgac cctgtaccgc gcacttgagc   2220
gcagcgagga agtgacgccc accgaggcca ggcggcgcgg tgccttccgt gaggacgcat   2280
tgaccgaggc cgacgccctg gcggccgccg agaatgaacg ccaagaggaa caagcatgaa   2340
accgcaccag gacggccagg acgaaccgtt tttcattacc gaagagatcg aggcggagat   2400
gatcgcggcc gggtacgtgt tcgagccgcc cgcgcacggc tcaaccgtgc ggctgcatga   2460
aatcctggcc ggtttgtctg atgccaagct ggcggcctgg ccggccagct tggccgctga   2520
agaaaccgag cgccgccgtc taaaaaggtg atgtgtattt gagtaaaaca gcttgcgtca   2580
tgcggtcgct gcgtatatga tgcgatgagt aaataaacaa atacgcaagg ggaacgcatg   2640
aaggttatcg ctgtacttaa ccagaaaggc gggtcaggca agacgaccat cgcaacccat   2700
ctagcccgcg ccctgcaact cgccggggcc gatgttctgt tagtcgattc cgatccccag   2760
ggcagtgccc gcgattgggc ggccgtgcgg gaagatcaac cgctaaccgt tgtcggcatc   2820
gaccgcccga cgattgaccg cgacgtgaag gccatcggcc ggcgcgactt cgtagtgatc   2880
gacggagcgc cccaggcggc ggacttggct gtgtccgcga tcaaggcagc cgacttcgtg   2940
ctgattccgg tgcagccaag cccttacgac atatgggcca ccgccgacct ggtggagctg   3000
gttaagcagc gcattgaggt cacggatgga aggctacaag cggcctttgt cgtgtcgcgg   3060
gcgatcaaag gcacgcgcat cggcggtgag gttgccgagg cgctggccgg gtacgagctg   3120
cccattcttg agtcccgtat cacgcagcgc gtgagctacc caggcactgc cgccgccggc   3180
acaaccgttc ttgaatcaga acccgagggc gacgctgccc gcgaggtcca ggcgctggcc   3240
gctgaaatta aatcaaaact catttgagtt aatgaggtaa agagaaaatg agcaaaagca   3300
```

-continued

```
caaacacgct aagtgccggc cgtccgagcg cacgcagcag caaggctgca acgttggcca   3360
gcctggcaga cacgccagcc atgaagcggg tcaactttca gttgccggcg gaggatcaca   3420
ccaagctgaa gatgtacgcg gtacgccaag gcaagaccat taccgagctg ctatctgaat   3480
acatcgcgca gctaccagag taaatgagca aatgaataaa tgagtagatg aattttagcg   3540
gctaaaggag gcggcatgga aaatcaagaa caaccaggca ccgacgccgt ggaatgcccc   3600
atgtgtggag gaacgggcgg ttggccaggc gtaagcggct gggttgtctg ccggccctgc   3660
aatggcactg gaacccccaa gcccgaggaa tcggcgtgac ggtcgcaaac catccggccc   3720
ggtacaaatc ggcgcggcgc tgggtgatga cctggtggag aagttgaagg ccgcgcaggc   3780
cgcccagcgg caacgcatcg aggcagaagc acgccccggt gaatcgtggc aagcggccgc   3840
tgatcgaatc cgcaaagaat cccggcaacc gccggcagcc ggtgcgccgt cgattaggaa   3900
gccgcccaag ggcgacgagc aaccagattt tttcgttccg atgctctatg acgtgggcac   3960
ccgcgatagt cgcagcatca tggacgtggc cgttttccgt ctgtcgaagc gtgaccgacg   4020
agctggcgag gtgatccgct acgagcttcc agacgggcac gtagaggttt ccgcagggcc   4080
ggccggcatg gccagtgtgt gggattacga cctggtactg atggcggttt cccatctaac   4140
cgaatccatg aaccgatacc gggaagggaa gggagacaag cccggccgcg tgttccgtcc   4200
acacgttgcg gacgtactca agttctgccg gcgagccgat ggcggaaagc agaaagacga   4260
cctggtagaa acctgcattc ggttaaacac cacgcacgtt gccatgcagc gtacgaagaa   4320
ggccaagaac ggccgcctgg tgacggtatc cgagggtgaa gccttgatta gccgctacaa   4380
gatcgtaaag agcgaaaccg ggcggccgga gtacatcgag atcgagctag ctgattggat   4440
gtaccgcgag atcacagaag gcaagaaccc ggacgtgctg acggttcacc ccgattactt   4500
tttgatcgat cccggcatcg gccgttttct ctaccgcctg gcacgccgcg ccgcaggcaa   4560
ggcagaagcc agatggttgt tcaagacgat ctacgaacgc agtggcagcg ccggagagtt   4620
caagaagttc tgtttcaccg tgcgcaagct gatcgggtca aatgacctgc cggagtacga   4680
tttgaaggag gaggcggggc aggctggccc gatcctagtc atgcgctacc gcaacctgat   4740
cgagggcgaa gcatccgccg gttcctaatg tacggagcag atgctagggc aaattgccct   4800
agcaggggaa aaaggtcgaa aaggcctctt tcctgtggat agcacgtaca ttgggaaccc   4860
aaagccgtac attgggaacc ggaacccgta cattgggaac ccaaagccgt acattgggaa   4920
ccggtcacac atgtaagtga ctgatataaa agagaaaaaa ggcgattttt ccgcctaaaa   4980
ctctttaaaa cttattaaaa ctcttaaaac ccgcctggcc tgtgcataac tgtctggcca   5040
gcgcacagcc gaagagctgc aaaaagcgcc tacccttcgg tcgctgcgct ccctacgccc   5100
cgccgcttcg cgtcggccta tcgcggccgc tggccgctca aaaatggctg gcctacggcc   5160
aggcaatcta ccagggcgcg gacaagccgc gccgtcgcca ctcgaccgcc ggcgcccaca   5220
tcaaggcacc ctgcctcgcg cgtttcggtg atgacggtga aaacctctga cacatgcagc   5280
tcccggaaac ggtcacagct tgtctgtaag cggatgccgg gagcagacaa gcccgtcagg   5340
gcgcgtcagc gggtgttggc gggtgtcggg gcgcagccat gacccagtca cgtagcgata   5400
gcggagtgta tactggctta actatgcggc atcagagcag attgtactga gagtgcacca   5460
tatgcggtgt gaaataccgc acagatgcgt aaggagaaaa taccgcatca ggcgctcttc   5520
cgcttcctcg ctcactgact cgctgcgctc ggtcgttcgg ctgcggcgag cggtatcagc   5580
tcactcaaag gcggtaatac ggttatccac agaatcaggg gataacgcag gaaagaacat   5640
```

-continued

```
gtgagcaaaa ggccagcaaa aggccaggaa ccgtaaaaag gccgcgttgc tggcgttttt   5700
ccataggctc cgcccccctg acgagcatca caaaaatcga cgctcaagtc agaggtggcg   5760
aaacccgaca ggactataaa gataccaggc gtttccccct ggaagctccc tcgtgcgctc   5820
tcctgttccg accctgccgc ttaccggata cctgtccgcc tttctccctt cgggaagcgt   5880
ggcgctttct catagctcac gctgtaggta tctcagttcg gtgtaggtcg ttcgctccaa   5940
gctgggctgt gtgcacgaac cccccgttca gcccgaccgc tgcgccttat ccggtaacta   6000
tcgtcttgag tccaacccgg taagacacga cttatcgcca ctggcagcag ccactggtaa   6060
caggattagc agagcgaggt atgtaggcgg tgctacagag ttcttgaagt ggtggcctaa   6120
ctacggctac actagaagga cagtatttgg tatctgcgct ctgctgaagc cagttacctt   6180
cggaaaaaga gttggtagct cttgatccgg caaacaaacc accgctggta gcggtggttt   6240
ttttgtttgc aagcagcaga ttacgcgcag aaaaaaagga tctcaagaag atcctttgat   6300
cttttctacg gggtctgacg ctcagtggaa cgaaaactca cgttaaggga ttttggtcat   6360
gcattctagg tactaaaaca attcatccag taaaatataa tattttattt tctcccaatc   6420
aggcttgatc cccagtaagt caaaaaatag ctcgacatac tgttcttccc cgatatcctc   6480
cctgatcgac cggacgcaga aggcaatgtc ataccacttg tccgccctgc cgcttctccc   6540
aagatcaata aagccactta ctttgccatc tttcacaaag atgttgctgt ctcccaggtc   6600
gccgtgggaa aagacaagtt cctcttcggg cttttccgtc tttaaaaaat catacagctc   6660
gcgcggatct ttaaatggag tgtcttcttc ccagttttcg caatccacat cggccagatc   6720
gttattcagt aagtaatcca attcggctaa gcggctgtct aagctattcg tatagggaca   6780
atccgatatg tcgatggagt gaaagagcct gatgcactcc gcatacagct cgataatctt   6840
ttcagggctt tgttcatctt catactcttc cgagcaaagg acgccatcgg cctcactcat   6900
gagcagattg ctccagccat catgccgttc aaagtgcagg acctttggaa caggcagctt   6960
tccttccagc catagcatca tgtccttttc ccgttccaca tcataggtgg tccctttata   7020
ccggctgtcc gtcattttta aatataggtt ttcattttct cccaccagct tatatacctt   7080
agcaggagac attccttccg tatcttttac gcagcggtat ttttcgatca gtttttttcaa   7140
ttccggtgat attctcattt tagccattta ttatttcctt cctcttttct acagtattta   7200
aagatacccc aagaagctaa ttataacaag acgaactcca attcactgtt ccttgcattc   7260
taaaacctta aataccagaa aacagctttt tcaaagttgt tttcaaagtt ggcgtataac   7320
atagtatcga cggagccgat tttgaaaccg cggtgatcac aggcagcaac gctctgtcat   7380
cgttacaatc aacatgctac cctccgcgag atcatccgtg tttcaaaccc ggcagcttag   7440
ttgccgttct tccgaatagc atcggtaaca tgagcaaagt ctgccgcctt acaacggctc   7500
tcccgctgac gccgtcccgg actgatgggc tgcctgtatc gagtggtgat tttgtgccga   7560
gctgccggtc ggggagctgt tggctggctg gtggcaggat atattgtggt gtaaacaaat   7620
tgacgcttag acaacttaat aacacattgc ggacgttttt aatgtagagc tcaaagttta   7680
acgcgttagc agaaggcatg ttgttgtgac tccgaggggt tgcctcaaac tctatcttat   7740
aaccggcgtg gaggcatgga ggcaggggta ttttggtcat tttaatagat agtggaaaat   7800
gacgtggaat ttacttaaag acgaagtctt tgcgacaagg gggggcccac gccgaattta   7860
atattaccgg cgtggccccc ccttatcgcg agtgctttag cacgagcggt ccagatttaa   7920
agtagaaaat ttcccgccca ctagggttaa aggtgttcac actataaaag catatacgat   7980
gtgatggtat ttgatggagc gtatattgta tcaggtattt ccgttggata cgaattattc   8040
```

gtacgaccct cggtaccgat cggcgcgcca gatttgcctt ttcaatttca gaaagaatgc 8100
taacccacag atggttagag aggcttacgc agcaggtatc atcaagacga tctacccgag 8160
caataatctc caggaaatca aataccttcc caagaaggtt aaagatgcag tcaaaagatt 8220
caggactaac tgcatcaaga acacagagaa agatatattt ctcaagatca gaagtactat 8280
tccagtatgg acgattcaag gcttgcttca caaaccaagg caagtaatag agattggagt 8340
ctctaaaaag gtagttccca ctgaatcaaa ggccatggag tcaaagattc aaatagagga 8400
cctaacagaa ctcgccgtaa agactggcga acagttcata cagagtctct tacgactcaa 8460
tgacaagaag aaaatcttcg tcaacatggt ggagcacgac acacttgtct actccaaaaa 8520
tatcaaagat acagtctcag aagaccaaag ggcaattgag acttttcaac aaagggtaat 8580
atccggaaac ctcctcggat tccattgccc agctatctgt cactttattg tgaagatagt 8640
ggaaaaggaa ggtggctcct acaaatgcca tcattgcgat aaaggaaagg ccatcgttga 8700
agatgcctct gccgacagtg gtcccaaaga tggaccccca cccacgagga gcatcgtgga 8760
aaaagaagac gttccaacca cgtcttcaaa gcaagtggat tgatgtgata tctccactga 8820
cgtaagggat gacgcacaat cccactatcc ttcgcaagac ccttcctcta tataaggaag 8880
ttcatttcat ttggagagaa cacgggggac tcctgcagga tggaagacgc caaaaacata 8940
aagaaaggcc cggcgccatt ctatccgctg gaagatggaa ccgctggaga gcaactgcat 9000
aaggctatga agagatacgc cctggttcct ggaacaattg cttttacaga tgcacatatc 9060
gaggtggaca tcacttacgc tgagtacttc gaaatgtccg ttcggttggc agaagctatg 9120
aaacgatatg ggctgaatac aaatcacaga atcgtcgtat gcagtgaaaa ctctcttcaa 9180
ttctttatgc cggtgttggg cgcgttattt atcggagttg cagttgcgcc cgcgaacgac 9240
atttataatg aacgtgaatt gctcaacagt atgggcattt cgcagcctac cgtggtgttc 9300
gtttccaaaa aggggttgca aaaaattttg aacgtgcaaa aaaagctccc aatcatccaa 9360
aaaattatta tcatggattc taaaacggat taccagggat ttcagtcgat gtacacgttc 9420
gtcacatctc atctacctcc cggttttaat gaatacgatt ttgtgccaga gtccttcgat 9480
agggacaaga caattgcact gatcatgaac tcctctggat ctactggtct gcctaaaggt 9540
gtcgctctgc ctcatagaac tgcctgcgtg agattctcgc atgccagaga tcctattttt 9600
ggcaatcaaa tcattccgga tactgcgatt ttaagtgttg ttccattcca tcacggtttt 9660
ggaatgttta ctacactcgg atatttgata tgtggatttc gagtcgtctt aatgtataga 9720
tttgaagaag agctgtttct gaggagcctt caggattaca agattcaaag tgcgctgctg 9780
gtgccaaccc tattctcctt cttcgccaaa agcactctga ttgacaaata cgatttatct 9840
aatttacacg aaattgcttc tggtggcgct cccctctcta aggaagtcgg ggaagcggtt 9900
gccaagaggt tccatctgcc aggtatcagg caaggatatg ggctcactga gactacatca 9960
gctattctga ttacacccga gggggatgat aaaccgggcg cggtcggtaa agttgttcca 10020
ttttttgaag cgaaggttgt ggatctggat accgggaaaa cgctgggcgt taatcaaaga 10080
ggcgaactgt gtgtgagagg tcctatgatt atgtccggtt atgtaaacaa tccggaagcg 10140
accaacgcct tgattgacaa ggatggatgg ctacattctg gagacatagc ttactgggac 10200
gaagacgaac acttcttcat cgttgaccgc ctgaagtctc tgattaagta caaaggctat 10260
caggtggctc ccgctgaatt ggaatccatc ttgctccaac accccaacat cttcgacgct 10320
ggtgtcgcag gtcttcccga cgatgacgcc ggtgaacttc ccgccgccgt tgttgttttg 10380

-continued

```
gagcacggaa agacgatgac ggaaaaagag atcgtggatt acgtcgccag tcaagtaaca  10440
accgcgaaaa agttgcgcgg aggagttgtg tttgtggacg aagtaccgaa aggtcttacc  10500
ggaaaactcg acgcaagaaa aatcagagag atcctcataa aggccaagaa gggcggaaag  10560
atcgccgtgt gacgtcgacg atatgaagat gaagatgaaa tatttggtgt gtcaaataaa  10620
aagcttgtgt gcttaagttt gtgttttttt cttggcttgt tgtgttatga atttgtggct  10680
ttttctaata ttaaatgaat gtaagatcac attataatga ataaacaaat gtttctataa  10740
tccattgtga atgttttgtt ggatctcttc tgcagcatat aactactgta tgtgctatgg  10800
tatggactat ggaatatgat taaagataag ccagagctct ggtgacggac ccatggcttc  10860
gttgaacaac ggaaactcga cttgccttcc gcacaataca tcatttcttc ttagcttttt  10920
ttcttcttct tcgttcatac agtttttttt tgtttatcag cttacatttt cttgaaccgt  10980
agctttcgtt ttcttctttt taactttcca ttcggagttt ttgtatcttg tttcatagtt  11040
tgtcccagga ttagaatgat taggcatcga accttcaaga atttgattga ataaaacatc  11100
ttcattctta agatatgaag ataatcttca aaaggcccct gggaatctga aagaagagaa  11160
gcaggcccat ttatatggga aagaacaata gtatttctta tataggccca tttaagttga  11220
aaacaatctt caaaagtccc acatcgctta gataagaaaa cgaagctgag tttatataca  11280
gctagagtcg aagtagtgat tgttggtagt agcgactcca tggttttaga gctagaaata  11340
gcaagttaaa ataaggctag tccgttatca acttgaaaaa gtggcaccga gtcggtgctt  11400
tttttcccgg ggcgcgccga tatcgagctc tcccgctggc agacatactg tcccacaaat  11460
gaagatggaa tctgtaaaag aaaacgcgtg aaataatgcg tctgacaaag gttaggtcgg  11520
ctgcctttaa tcaataccaa agtggtccct accacgatgg aaaaactgtg cagtcggttt  11580
ggctttttct gacgaacaaa taagattcgt ggccgacagg tgggggtcca ccatgtgaag  11640
gcatcttcag actccaataa tggagcaatg acgtaagggc ttacgaaata agtaagggta  11700
gtttgggaaa tgtccactca cccgtcagtc tataaatact tagcccctcc ctcattgtta  11760
agggagcaaa atctcagaga gatagtccta gagagagaaa gagagcaagt agcctagaag  11820
tagtcaaggc ggcgaagtat tcaggcacgt ggccaggaag aagaaaagcc aagacgacga  11880
aaacaggtaa gagctaagct tatggagagt ggttccaaca gcacttcttg tccaatggct  11940
tttgccgggg ataatagtga tggtccgatg tgtcctatga tgatgatgat gccgcccatc  12000
atgacatcac atcaacatca tggtcatgat catcaacatc aacaacaaga acatgatggt  12060
tatgcatatc agtcacacca ccaacaaagt agttcccttt ttcttcaatc actagctcct  12120
ccccaaggaa ctaagaacaa agttgcttct tcttcttctc cttcctcttg tgctcctgcc  12180
tattctctaa tggagatcca tcataacgaa atcgttgcag gaggaatcaa cccttgctcc  12240
tcttcctctt cttcagcctc tgtcaaggcc aagatcatgg ctcatcctca ctaccaccgc  12300
ctcttggccg cttatgtcaa ttgtcagaag gttggagcac caccggaggt tgtggcgagg  12360
ctagaggagg catgctcgtc tgccgcagcc gctgccgcat ctatgggacc aacaggatgt  12420
ctaggtgaag atccagggct tgatcaattc atggaagctt actgtgaaat gctcgttaag  12480
tatgagcaag agctctccaa acctttcaag gaagctatgg tcttccttca acgtgtcgag  12540
tgtcaattca aatccctctc tctatcctca ccttcctctt tctccggtta tggagagaca  12600
gcaattgata ggaacaataa tgggtcatcc gaggaagaag tcgatatgaa caatgaattt  12660
gtagatccac aagctgagga tagagagctt aaaggacagc tcttgcgcaa gtacagtggt  12720
tacttaggga gcctcaagca agagttcatg aagaagagga agaaaggaaa gctccctaaa  12780
```

-continued

```
gaagctcgtc aacaactgct tgattggtgg agccgtcact acaaatggcc ttacccttcg  12840

gagcaacaaa agctcgccct tgcggaatca acggggctgg accagaaaca gataaacaat  12900

tggttcataa accagaggaa acggcattgg aagccgtcgg aggacatgca gtttgtagta  12960

atggacgcaa cacatcctca ccattacttc atggataatg tcttgggcaa tcctttccca  13020

atggatcaca tctcctccac catgctttga ctcgagtttc tccataataa tgtgtgagta  13080

gttcccagat aagggaatta gggttcctat agggtttcgc tcatgtgttg agcatataag  13140

aaacccttag tatgtatttg tatttgtaaa atacttctat caataaaatt tctaattcct  13200

aaaaccaaaa tccagtacta aaatccagat cccccgaatt aagtgtttga tcgccggcgg  13260

taccgagtgt acttcaagtc agtgggaaat caataaaatg attattttat gaatatattt  13320

cattgtgcaa gtagatagaa attacatatg ttacataaca cacgaaataa acaaaaaaag  13380

acaatccaaa aacaaacacc ccaaaaaaaa taatcacttt agataaactc gtatgaggag  13440

aggcacgttc agtgactcga cgattcccga gcaaaaaaag tctccccgtc acacatgtag  13500

tgggtgacgc aattatcttt aaagtaatcc ttctgttgac ttgtcattga taacatccag  13560

tcttcgtcag gattgcaaag aattatagaa gggatccca                         13599
```

<210> SEQ ID NO 34
<211> LENGTH: 13546
<212> TYPE: DNA
<213> ORGANISM: artificial
<220> FEATURE:
<223> OTHER INFORMATION: synthetic oligonucleotide

<400> SEQUENCE: 34

```
tttccgtctg tcgaagcgtg accgacgagc tggcgaggtg atccgctacg agcttccaga     60

cgggcacgta gaggtttccg cagggccggc cggcatggcc agtgtgtggg attacgacct    120

ggtactgatg gcggtttccc atctaaccga atccatgaac cgataccggg aagggaaggg    180

agacaagccc ggccgcgtgt tccgtccaca cgttgcggac gtactcaagt tctgccggcg    240

agccgatggc ggaaagcaga aagacgacct ggtagaaacc tgcattcggt taaacaccac    300

gcacgttgcc atgcagcgta cgaagaaggc caagaacggc cgcctggtga cggtatccga    360

gggtgaagcc ttgattagcc gctacaagat cgtaaagagc gaaaccgggc ggccggagta    420

catcgagatc gagctagctg attggatgta ccgcgagatc acagaaggca agaacccgga    480

cgtgctgacg gttcaccccg attacttttt gatcgatccc ggcatcggcc gttttctcta    540

ccgcctggca cgccgcgccg caggcaaggc agaagccaga tggttgttca agacgatcta    600

cgaacgcagt ggcagcgccg gagagttcaa gaagttctgt ttcaccgtgc gcaagctgat    660

cgggtcaaat gacctgccgg agtacgattt gaaggaggag gcggggcagg ctggcccgat    720

cctagtcatg cgctaccgca acctgatcga gggcgaagca tccgccggtt cctaatgtac    780

ggagcagatg ctagggcaaa ttgccctagc aggggaaaaa ggtcgaaaag gcctctttcc    840

tgtggatagc acgtacattg ggaacccaaa gccgtacatt gggaaccgga acccgtacat    900

tgggaaccca aagccgtaca ttgggaaccg gtcacacatg taagtgactg atataaaaga    960

gaaaaaaggc gatttttccg cctaaaactc tttaaaactt attaaaactc ttaaaacccg   1020

cctggcctgt gcataactgt ctggccagcg cacagccgaa gagctgcaaa aagcgcctac   1080

ccttcggtcg ctgcgctccc tacgccccgc cgcttcgcgt cggcctatcg cggccgctgg   1140

ccgctcaaaa atggctggcc tacggccagg caatctacca gggcgcggac aagccgcgcc   1200
```

-continued

```
gtcgccactc gaccgccggc gcccacatca aggcaccctg cctcgcgcgt ttcggtgatg   1260
acggtgaaaa cctctgacac atgcagctcc cggaaacggt cacagcttgt ctgtaagcgg   1320
atgccgggag cagacaagcc cgtcagggcg cgtcagcggg tgttggcggg tgtcggggcg   1380
cagccatgac ccagtcacgt agcgatagcg gagtgtatac tggcttaact atgcggcatc   1440
agagcagatt gtactgagag tgcaccatat gcggtgtgaa ataccgcaca gatgcgtaag   1500
gagaaaatac cgcatcaggc gctcttccgc ttcctcgctc actgactcgc tgcgctcggt   1560
cgttcggctg cggcgagcgg tatcagctca ctcaaaggcg gtaatacggt tatccacaga   1620
atcaggggat aacgcaggaa agaacatgtg agcaaaaggc cagcaaaagg ccaggaaccg   1680
taaaaaggcc gcgttgctgg cgtttttcca taggctccgc ccccctgacg agcatcacaa   1740
aaatcgacgc tcaagtcaga ggtggcgaaa cccgacagga ctataaagat accaggcgtt   1800
tccccctgga agctccctcg tgcgctctcc tgttccgacc ctgccgctta ccggatacct   1860
gtccgccttt ctcccttcgg gaagcgtggc gctttctcat agctcacgct gtaggtatct   1920
cagttcggtg taggtcgttc gctccaagct gggctgtgtg cacgaacccc ccgttcagcc   1980
cgaccgctgc gccttatccg gtaactatcg tcttgagtcc aacccggtaa gacacgactt   2040
atcgccactg gcagcagcca ctggtaacag gattagcaga gcgaggtatg taggcggtgc   2100
tacagagttc ttgaagtggt ggcctaacta cggctacact agaaggacag tatttggtat   2160
ctgcgctctg ctgaagccag ttaccttcgg aaaaagagtt ggtagctctt gatccggcaa   2220
acaaaccacc gctggtagcg gtggtttttt tgtttgcaag cagcagatta cgcgcagaaa   2280
aaaaggatct caagaagatc ctttgatctt ttctacgggg tctgacgctc agtggaacga   2340
aaactcacgt taagggattt tggtcatgca ttctaggtac taaaacaatt catccagtaa   2400
aatataatat tttattttct cccaatcagg cttgatcccc agtaagtcaa aaaatagctc   2460
gacatactgt tcttccccga tatcctccct gatcgaccgg acgcagaagg caatgtcata   2520
ccacttgtcc gccctgccgc ttctcccaag atcaataaag ccacttactt tgccatcttt   2580
cacaaagatg ttgctgtctc ccaggtcgcc gtgggaaaag acaagttcct cttcgggctt   2640
ttccgtcttt aaaaaatcat acagctcgcg cggatcttta aatggagtgt cttcttccca   2700
gttttcgcaa tccacatcgg ccagatcgtt attcagtaag taatccaatt cggctaagcg   2760
gctgtctaag ctattcgtat agggacaatc cgatatgtcg atggagtgaa agagcctgat   2820
gcactccgca tacagctcga taatcttttc agggctttgt tcatcttcat actcttccga   2880
gcaaaggacg ccatcggcct cactcatgag cagattgctc cagccatcat gccgttcaaa   2940
gtgcaggacc tttggaacag gcagctttcc ttccagccat agcatcatgt ccttttcccg   3000
ttccacatca taggtggtcc ctttataccg gctgtccgtc atttttaaat ataggttttc   3060
attttctccc accagcttat ataccttagc aggagacatt ccttccgtat cttttacgca   3120
gcggtatttt tcgatcagtt ttttcaattc cggtgatatt ctcattttag ccatttatta   3180
tttccttcct cttttctaca gtatttaaag ataccccaag aagctaatta taacaagacg   3240
aactccaatt cactgttcct tgcattctaa aaccttaaat accagaaaac agctttttca   3300
aagttgtttt caaagttggc gtataacata gtatcgacgg agccgatttt gaaaccgcgg   3360
tgatcacagg cagcaacgct ctgtcatcgt tacaatcaac atgctaccct ccgcgagatc   3420
atccgtgttt caaacccggc agcttagttg ccgttcttcc gaatagcatc ggtaacatga   3480
gcaaagtctg ccgccttaca acggctctcc cgctgacgcc gtcccggact gatgggctgc   3540
ctgtatcgag tggtgatttt gtgccgagct gccggtcggg gagctgttgg ctggctggtg   3600
```

-continued gcaggatata ttgtggtgta aacaaattga cgcttagaca acttaataac acattgcgga 3660
cgtttttaat gtagagctca aagtttaacg cgttagcaga aggcatgttg ttgtgactcc 3720
gaggggttgc ctcaaactct atcttataac cggcgtggag gcatggaggc aggggtattt 3780
tggtcatttt aatagatagt ggaaaatgac gtggaattta cttaaagacg aagtctttgc 3840
gacaaggggg ggcccacgcc gaatttaata ttaccggcgt ggcccccccct tatcgcgagt 3900 gctttagcac gagcggtcca gatttaaagt agaaaatttc ccgcccacta gggttaaagg 3960
tgttcacact ataaaagcat atacgatgtg atggtatttg atggagcgta tattgtatca 4020
ggtatttccg ttggatacga attattcgta cgaccctcgg taccgatcgg cgcgcctggc 4080
agacatactg tcccacaaat gaagatggaa tctgtaaaag aaaacgcgtg aaataatgcg 4140
tctgacaaag gttaggtcgg ctgcctttaa tcaataccaa agtggtccct accacgatgg 4200
aaaaactgtg cagtcggttt ggctttttct gacgaacaaa taagattcgt ggccgacagg 4260
tgggggtcca ccatgtgaag gcatcttcag actccaataa tggagcaatg acgtaagggc 4320
ttacgaaata agtaagggta gtttgggaaa tgtccactca cccgtcagtc tataaatact 4380
tagcccctcc ctcattgtta agggagcaaa atctcagaga gatagtccta gagagagaaa 4440
gagagcaagt agcctagaag tagtcaaggc ggcgaagtat tcaggcacgt ggccaggaag 4500
aagaaaagcc aagacgacga aaacaggtaa gagctaagct tcctgcacca tggaagacgc 4560
caaaaacata aagaaaggcc cggcgccatt ctatccgctg gaagatggaa ccgctggaga 4620
gcaactgcat aaggctatga agagatacgc cctggttcct ggaacaattg cttttacaga 4680
tgcacatatc gaggtggaca tcacttacgc tgagtacttc gaaatgtccg ttcggttggc 4740
agaagctatg aaacgatatg ggctgaatac aaatcacaga atcgtcgtat gcagtgaaaa 4800
ctctcttcaa ttctttatgc cggtgttggg cgcgttattt atcggagttg cagttgcgcc 4860
cgcgaacgac atttataatg aacgtgaatt gctcaacagt atgggcattt cgcagcctac 4920
cgtggtgttc gtttccaaaa aggggttgca aaaaattttg aacgtgcaaa aaaagctccc 4980
aatcatccaa aaaattatta tcatggattc taaaacggat taccagggat ttcagtcgat 5040
gtacacgttc gtcacatctc atctacctcc cggttttaat gaatacgatt ttgtgccaga 5100
gtccttcgat agggacaaga caattgcact gatcatgaac tcctctggat ctactggtct 5160
gcctaaaggt gtcgctctgc ctcatagaac tgcctgcgtg agattctcgc atgccagaga 5220
tcctattttt ggcaatcaaa tcattccgga tactgcgatt ttaagtgttg ttccattcca 5280
tcacggtttt ggaatgttta ctacactcgg atatttgata tgtggatttc gagtcgtctt 5340
aatgtataga tttgaagaag agctgtttct gaggagcctt caggattaca agattcaaag 5400
tgcgctgctg gtgccaaccc tattctcctt cttcgccaaa agcactctga ttgacaaata 5460
cgatttatct aatttacacg aaattgcttc tggtggcgct cccctctcta aggaagtcgg 5520
ggaagcggtt gccaagaggt tccatctgcc aggtatcagg caaggatatg ggctcactga 5580
gactacatca gctattctga ttacacccga gggggatgat aaaccgggcg cggtcggtaa 5640
agttgttcca tttttgaag cgaaggttgt ggatctggat accgggaaaa cgctgggcgt 5700
taatcaaaga ggcgaactgt gtgtgagagg tcctatgatt atgtccggtt atgtaaacaa 5760
tccggaagcg accaacgcct tgattgacaa ggatggatgg ctacattctg gagacatagc 5820
ttactgggac gaagacgaac acttcttcat cgttgaccgc ctgaagtctc tgattaagta 5880
caaaggctat caggtggctc ccgctgaatt ggaatccatc ttgctccaac accccaacat 5940

-continued

```
cttcgacgct ggtgtcgcag gtcttcccga cgatgacgcc ggtgaacttc ccgccgccgt   6000
tgttgttttg gagcacggaa agacgatgac ggaaaaagag atcgtggatt acgtcgccag   6060
tcaagtaaca accgcgaaaa agttgcgcgg aggagttgtg tttgtggacg aagtaccgaa   6120
aggtcttacc ggaaaactcg acgcaagaaa aatcagagag atcctcataa aggccaagaa   6180
gggcggaaag atcgccgtgt aactcgagat atgaagatga agatgaaata tttggtgtgt   6240
caaataaaaa gcttgtgtgc ttaagtttgt gttttttct tggcttgttg tgttatgaat   6300
ttgtggcttt ttctaatatt aaatgaatgt aagatcacat tataatgaat aaacaaatgt   6360
ttctataatc cattgtgaat gttttgttgg atctcttctg cagcatataa ctactgtatg   6420
tgctatggta tggactatgg aatatgatta aagataagga gctccggtga cggacccatg   6480
gcttcgttga acaacggaaa ctcgacttgc cttccgcaca atacatcatt tcttcttagc   6540
ttttttctt cttcttcgtt catacagttt ttttttgttt atcagcttac attttcttga   6600
accgtagctt tcgttttctt ctttttaact ttccattcgg agtttttgta tcttgtttca   6660
tagtttgtcc caggattaga atgattaggc atcgaacctt caagaatttg attgaataaa   6720
acatcttcat tcttaagata tgaagataat cttcaaaagg cccctgggaa tctgaaagaa   6780
gagaagcagg cccatttata tgggaaagaa caatagtatt tcttatatag gcccatttaa   6840
gttgaaaaca atcttcaaaa gtcccacatc gcttagataa gaaaacgaag ctgagtttat   6900
atacagctag agtcgaagta gtgattgttg gtagtagcga ctccatggtt ttagagctag   6960
aaatagcaag ttaaaataag gctagtccgt tatcaacttg aaaaagtggc accgagtcgg   7020
tgcttttttt cccggcgtaa tatggcgcgc cagatttgcc ttttcaattt cagaaagaat   7080
gctaacccac agatggttag agaggcttac gcagcaggta tcatcaagac gatctacccg   7140
agcaataatc tccaggaaat caaatacctt cccaagaagg ttaaagatgc agtcaaaaga   7200
ttcaggacta actgcatcaa gaacacagag aaagatatat ttctcaagat cagaagtact   7260
attccagtat ggacgattca aggcttgctt cacaaaccaa ggcaagtaat agagattgga   7320
gtctctaaaa aggtagttcc cactgaatca aaggccatgg agtcaaagat tcaaatagag   7380
gacctaacag aactcgccgt aaagactggc gaacagttca tacagagtct cttacgactc   7440
aatgacaaga agaaaatctt cgtcaacatg gtggagcacg acacacttgt ctactccaaa   7500
aatatcaaag atacagtctc agaagaccaa agggcaattg agacttttca acaaagggta   7560
atatccggaa acctcctcgg attccattgc ccagctatct gtcactttat tgtgaagata   7620
gtggaaaagg aaggtggctc ctacaaatgc catcattgcg ataaaggaaa ggccatcgtt   7680
gaagatgcct ctgccgacag tggtcccaaa gatggacccc cacccacgag gagcatcgtg   7740
gaaaaagaag acgttccaac cacgtcttca aagcaagtgg attgatgtga tatctccact   7800
gacgtaaggg atgacgcaca atcccactat ccttcgcaag acccttcctc tatataagga   7860
agttcatttc atttggagag aacacggggg actcctgcag gatggatctg cgtctaattt   7920
tcggtccaac ttgcacagga aagacgtcga ccgcgatacg tcttgcccag cagactggcc   7980
ttccagtcct ttcgctcgat cgggtccaat gctgtcctca actgtcaacc ggaagcggac   8040
gaccaacagt ggaagaactg aaaggaacga cccgtctata ccttgaagat cggcctctgg   8100
tgaagggtat catcgcagcc aagcaagctc acgaaaggct gatcggggaa gtgtacaatt   8160
atgaggccca cggcgggctt attcttgagg gaggatctat ctcgttgctc aggtgcatgg   8220
cgcaaagcag ttattggagt accgattttc gttggcatat tattcgccac aagttagcag   8280
acgaggagac attcatgaac gcggccaagg ccagagttag gcagatgttg cgccctgctg   8340
```

```
taggcccatc tattattcaa gagttggttc atctttggaa tgagcctcgg ctgaggccca   8400
tactgaaaga gatcgacgga tatcgatatg ccatgttatt tgctagccag aaccagatca   8460
cacccgatat gctattgcag cttgacccag atatggaggg tgagttgatt catggaatcg   8520
ctcaggagta tctcatccat gcgcgccggc aggagcagga attccctcca gtgagcgtgg   8580
tcgctttcga aggattcgaa ggtccaccgt tcggaatgtg ctagctcgag ccctagactt   8640
gtccatcttc tggattggcc aagttaatta atgtatgaaa taaaaggatg cacacatagt   8700
gacatgctaa tcactataat gtgggcatca aagttgtgtg ttatgtgtaa ttactaatta   8760
tctgaataag agaaagagat catccatatt tcttatccta aatgaatgtc acgtgtcttt   8820
ataattcttt gatgaaccag atgcatttta ttaaccaatt ccatatacat ataaatatta   8880
atcatatata attaatatca attgggttag caaaacaaat ctagtctagg tgtgttttgc   8940
taattattgg gggatagtgc aaaaagaaat ctacgttctc aataattcag atagaaaact   9000
taataaagtg agataattta catagattgc ttttatcctt tgatatatgt gaaaccatgc   9060
atgatataag gaaaatagat agagaaataa ttttttacat cgttgaatat gtaaacaatt   9120
taattcaaga agctaggaat ataaatattg aggagtttat gattagagct ctcccggcgc   9180
gccgatatcg agctcagtgt ttgatcgccg gcggtaccga gtgtacttca agtcagtggg   9240
aaatcaataa aatgattatt ttatgaatat atttcattgt gcaagtagat agaaattaca   9300
tatgttacat aacacacgaa ataaacaaaa aaagacaatc caaaaacaaa caccccaaaa   9360
aaaataatca ctttagataa actcgtatga ggagaggcac gttcagtgac tcgacgattc   9420
ccgagcaaaa aaagtctccc cgtcacacat gtagtgggtg acgcaattat ctttaaagta   9480
atccttctgt tgacttgtca ttgataacat ccagtcttcg tcaggattgc aaagaattat   9540
agaagggatc ccacctttta ttttcttctt ttttccatat ttagggttga cagtgaaatc   9600
agactggcaa cctattaatt gcttccacaa tgggacgaac ttgaagggga tgtcgtcgat   9660
gatattatag gtggcgtgtt catcgtagtt ggtgaaatcg atggtaccgt tccaatagtt   9720
gtgtcgtccg agacttctag cccaggtggt ctttccggta cgagttggtc cgcagatgta   9780
gaggctgggg tgtcggattc cattccttcc attgtccttg ttaaatcggc catccattca   9840
aggtcagatt gagcttgttg gtatgagaca ggatgtatgt aagtataagc gtctatgctt   9900
acatggtata gatgggtttc cctccaggag tgtagatctt cgtggcagcg aagatctgat   9960
tctgtgaagg gcgacacata cggttcaggt tgtggaggga ataatttgtt ggctgaatat  10020
tccagccatt gaagctttgt tgcccattca tgagggaatt cttccttgat catgtcaaga  10080
tattcctcct tagacgttgc agtctggata atagttctcc atcgtgcgtc agatttgcga  10140
ggagaaacct tatgatctcg gaaatctcct ctggttttaa tatctccgtc ctttgatatg  10200
taatcaagga cttgtttaga gtttctagct ggctggatat tagggtgatt tccttcaaaa  10260
tcgaaaaaag aaggatccct aatacaaggt tttttatcaa gctggagaag agcatgatag  10320
tgggtagtgc catcttgatg aagctcagaa gcaacaccaa ggaagaaaat aagaaaaggt  10380
gtgagtttct cccagagaaa ctggaataaa tcatctcttt gagatgagca cttgggatag  10440
gtaaggaaaa catatttaga ttggagtctg aagttcttac tagcagaagg catgttgttg  10500
tgactccgag gggttgcctc aaactctatc ttataaccgg cgtggaggca tggaggcagg  10560
ggtattttgg tcattttaat agatagtgga aaatgacgtg gaatttactt aaagacgaag  10620
tctttgcgac aaggggggc ccacgccgaa tttaatatta ccggcgtggc ccccccttat  10680
```

-continued

```
cgcgagtgct ttagcacgag cggtccagat ttaaagtaga aaatttcccg cccactaggg  10740
ttaaaggtgt tcacactata aaagcatata cgatgtgatg gtatttgatg gagcgtatat  10800
tgtatcaggt atttccgttg gatacgaatt attcgtacga ccctcatagt ttaaactatc  10860
agtgtttgac aggatatatt ggcgggtaaa cctaagagaa aagagcgttt attagaataa  10920
cggatattta aaagggcgtg aaaaggttta tccgttcgtc catttgtatg tgcatgccaa  10980
ccacagggtt cccctcggga tcaaagtact ttgatccaac ccctccgctg ctatagtgca  11040
gtcggcttct gacgttcagt gcagccgtct tctgaaaacg acatgtcgca caagtcctaa  11100
gttacgcgac aggctgccgc cctgcccttt tcctggcgtt ttcttgtcgc gtgttttagt  11160
cgcataaagt agaatacttg cgactagaac cggagacatt acgccatgaa caagagcgcc  11220
gccgctggcc tgctgggcta tgcccgcgtc agcaccgacg accaggactt gaccaaccaa  11280
cgggccgaac tgcacgcggc cggctgcacc aagctgtttt ccgagaagat caccggcacc  11340
aggcgcgacc gcccggagct ggccaggatg cttgaccacc tacgccctgg cgacgttgtg  11400
acagtgacca ggctagaccg cctggcccgc agcacccgcg acctactgga cattgccgag  11460
cgcatccagg aggccggcgc gggcctgcgt agcctggcag agccgtgggc cgacaccacc  11520
acgccggccg gccgcatggt gttgaccgtg ttcgccggca ttgccgagtt cgagcgttcc  11580
ctaatcatcg accgcacccg gagcgggcgc gaggccgcca aggcccgagg cgtgaagttt  11640
ggcccccgcc ctaccctcac cccggcacag atcgcgcacg cccgcgagct gatcgaccag  11700
gaaggccgca ccgtgaaaga ggcggctgca ctgcttggcg tgcatcgctc gaccctgtac  11760
cgcgcacttg agcgcagcga ggaagtgacg cccaccgagg ccaggcggcg cggtgccttc  11820
cgtgaggacg cattgaccga ggccgacgcc ctggcggccg ccgagaatga acgccaagag  11880
gaacaagcat gaaaccgcac caggacggcc aggacgaacc gtttttcatt accgaagaga  11940
tcgaggcgga gatgatcgcg gccgggtacg tgttcgagcc gcccgcgcac ggctcaaccg  12000
tgcggctgca tgaaatcctg gccggtttgt ctgatgccaa gctggcggcc tggccggcca  12060
gcttggccgc tgaagaaacc gagcgccgcc gtctaaaaag gtgatgtgta tttgagtaaa  12120
acagcttgcg tcatgcggtc gctgcgtata tgatgcgatg agtaaataaa caaatacgca  12180
aggggaacgc atgaaggtta tcgctgtact taaccagaaa ggcgggtcag gcaagacgac  12240
catcgcaacc catctagccc gcgccctgca actcgccggg gccgatgttc tgttagtcga  12300
ttccgatccc cagggcagtg cccgcgattg ggcggccgtg cgggaagatc aaccgctaac  12360
cgttgtcggc atcgaccgcc cgacgattga ccgcgacgtg aaggccatcg gccggcgcga  12420
cttcgtagtg atcgacggag cgccccaggc ggcggacttg gctgtgtccg cgatcaaggc  12480
agccgacttc gtgctgattc cggtgcagcc aagcccttac gacatatggg ccaccgccga  12540
cctggtggag ctggttaagc agcgcattga ggtcacggat ggaaggctac aagcggcctt  12600
tgtcgtgtcg cgggcgatca aaggcacgcg catcggcggt gaggttgccg aggcgctggc  12660
cgggtacgag ctgcccattc ttgagtcccg tatcacgcag cgcgtgagct acccaggcac  12720
tgccgccgcc ggcacaaccg ttcttgaatc agaacccgag ggcgacgctg cccgcgaggt  12780
ccaggcgctg gccgctgaaa ttaaatcaaa actcatttga gttaatgagg taaagagaaa  12840
atgagcaaaa gcacaaacac gctaagtgcc ggccgtccga gcgcacgcag cagcaaggct  12900
gcaacgttgg ccagcctggc agacacgcca gccatgaagc gggtcaactt tcagttgccg  12960
gcggaggatc acaccaagct gaagatgtac gcggtacgcc aaggcaagac cattaccgag  13020
ctgctatctg aatacatcgc gcagctacca gagtaaatga gcaaatgaat aaatgagtag  13080
```

-continued

```
atgaatttta gcggctaaag gaggcggcat ggaaaatcaa gaacaaccag gcaccgacgc  13140
cgtggaatgc cccatgtgtg gaggaacggg cggttggcca ggcgtaagcg gctgggttgt  13200
ctgccggccc tgcaatggca ctggaacccc caagcccgag gaatcggcgt gacggtcgca  13260
aaccatccgg cccggtacaa atcggcgcgg cgctgggtga tgacctggtg gagaagttga  13320
aggccgcgca ggccgcccag cggcaacgca tcgaggcaga agcacgcccc ggtgaatcgt  13380
ggcaagcggc cgctgatcga atccgcaaag aatcccggca accgccggca gccggtgcgc  13440
cgtcgattag gaagccgccc aagggcgacg agcaaccaga tttttcgtt ccgatgctct  13500
atgacgtggg cacccgcgat agtcgcagca tcatggacgt ggccgt                 13546
```

<210> SEQ ID NO 35
<211> LENGTH: 13472
<212> TYPE: DNA
<213> ORGANISM: artificial
<220> FEATURE:
<223> OTHER INFORMATION: synthetic oligonucleotide

<400> SEQUENCE: 35

```
ttgcgtcatg cggtcgctgc gtatatgatg cgatgagtaa ataaacaaat acgcaagggg     60
aacgcatgaa ggttatcgct gtacttaacc agaaaggcgg gtcaggcaag acgaccatcg    120
caacccatct agcccgcgcc ctgcaactcg ccggggccga tgttctgtta gtcgattccg    180
atccccaggg cagtgcccgc gattgggcgg ccgtgcggga agatcaaccg ctaaccgttg    240
tcggcatcga ccgcccgacg attgaccgcg acgtgaaggc catcggccgg cgcgacttcg    300
tagtgatcga cggagcgccc caggcggcgg acttggctgt gtccgcgatc aaggcagccg    360
acttcgtgct gattccggtg cagccaagcc cttacgacat atgggccacc gccgacctgg    420
tggagctggt taagcagcgc attgaggtca cggatggaag gctacaagcg gcctttgtcg    480
tgtcgcgggc gatcaaaggc acgcgcatcg gcggtgaggt tgccgaggcg ctggccgggt    540
acgagctgcc cattcttgag tcccgtatca cgcagcgcgt gagctaccca ggcactgccg    600
ccgccggcac aaccgttctt gaatcagaac ccgagggcga cgctgcccgc gaggtccagg    660
cgctggccgc tgaaattaaa tcaaaactca tttgagttaa tgaggtaaag agaaaatgag    720
caaaagcaca aacacgctaa gtgccggccg tccgagcgca cgcagcagca aggctgcaac    780
gttggccagc ctggcagaca cgccagccat gaagcgggtc aactttcagt tgccggcgga    840
ggatcacacc aagctgaaga tgtacgcggt acgccaaggc aagaccatta ccgagctgct    900
atctgaatac atcgcgcagc taccagagta aatgagcaaa tgaataaatg agtagatgaa    960
ttttagcggc taaaggaggc ggcatggaaa atcaagaaca accaggcacc gacgccgtgg   1020
aatgccccat gtgtggagga acgggcggtt ggccaggcgt aagcggctgg gttgtctgcc   1080
ggccctgcaa tggcactgga acccccaagc ccgaggaatc ggcgtgacgg tcgcaaacca   1140
tccggcccgg tacaaatcgg cgcggcgctg ggtgatgacc tggtggagaa gttgaaggcc   1200
gcgcaggccg cccagcggca acgcatcgag gcagaagcac gccccggtga atcgtggcaa   1260
gcggccgctg atcgaatccg caaagaatcc cggcaaccgc cggcagccgg tgcgccgtcg   1320
attaggaagc cgcccaaggg cgacgagcaa ccagattttt tcgttccgat gctctatgac   1380
gtgggcaccc gcgatagtcg cagcatcatg gacgtggccg ttttccgtct gtcgaagcgt   1440
gaccgacgag ctggcgaggt gatccgctac gagcttccag acgggcacgt agaggtttcc   1500
gcagggccgg ccggcatggc cagtgtgtgg gattacgacc tggtactgat ggcggtttcc   1560
```

-continued

```
catctaaccg aatccatgaa ccgataccgg gaagggaagg gagacaagcc cggccgcgtg   1620
ttccgtccac acgttgcgga cgtactcaag ttctgccggc gagccgatgg cggaaagcag   1680
aaagacgacc tggtagaaac ctgcattcgg ttaaacacca cgcacgttgc catgcagcgt   1740
acgaagaagg ccaagaacgg ccgcctggtg acggtatccg agggtgaagc cttgattagc   1800
cgctacaaga tcgtaaagag cgaaaccggg cggccggagt acatcgagat cgagctagct   1860
gattggatgt accgcgagat cacagaaggc aagaacccgg acgtgctgac ggttcacccc   1920
gattactttt tgatcgatcc cggcatcggc cgttttctct accgcctggc acgccgcgcc   1980
gcaggcaagg cagaagccag atggttgttc aagacgatct acgaacgcag tggcagcgcc   2040
ggagagttca agaagttctg tttcaccgtg cgcaagctga tcgggtcaaa tgacctgccg   2100
gagtacgatt tgaaggagga ggcggggcag gctggcccga tcctagtcat gcgctaccgc   2160
aacctgatcg agggcgaagc atccgccggt tcctaatgta cggagcagat gctagggcaa   2220
attgccctag caggggaaaa aggtcgaaaa ggcctctttc ctgtggatag cacgtacatt   2280
gggaacccaa agccgtacat tgggaaccgg aacccgtaca ttgggaaccc aaagccgtac   2340
attgggaacc ggtcacacat gtaagtgact gatataaaag agaaaaaagg cgatttttcc   2400
gcctaaaact ctttaaaact tattaaaact cttaaaaccc gcctggcctg tgcataactg   2460
tctggccagc gcacagccga agagctgcaa aaagcgccta cccttcggtc gctgcgctcc   2520
ctacgccccg ccgcttcgcg tcggcctatc gcggccgctg gccgctcaaa aatggctggc   2580
ctacggccag gcaatctacc agggcgcgga caagccgcgc cgtcgccact cgaccgccgg   2640
cgcccacatc aaggcaccct gcctcgcgcg tttcggtgat gacggtgaaa acctctgaca   2700
catgcagctc ccggaaacgg tcacagcttg tctgtaagcg gatgccggga gcagacaagc   2760
ccgtcagggc gcgtcagcgg gtgttggcgg gtgtcggggc gcagccatga cccagtcacg   2820
tagcgatagc ggagtgtata ctggcttaac tatgcggcat cagagcagat tgtactgaga   2880
gtgcaccata tgcggtgtga aataccgcac agatgcgtaa ggagaaaata ccgcatcagg   2940
cgctcttccg cttcctcgct cactgactcg ctgcgctcgg tcgttcggct gcggcgagcg   3000
gtatcagctc actcaaaggc ggtaatacgg ttatccacag aatcagggga taacgcagga   3060
aagaacatgt gagcaaaagg ccagcaaaag gccaggaacc gtaaaaaggc cgcgttgctg   3120
gcgtttttcc ataggctccg cccccctgac gagcatcaca aaaatcgacg ctcaagtcag   3180
aggtggcgaa acccgacagg actataaaga taccaggcgt ttccccctgg aagctccctc   3240
gtgcgctctc ctgttccgac cctgccgctt accggatacc tgtccgcctt tctcccttcg   3300
ggaagcgtgg cgctttctca tagctcacgc tgtaggtatc tcagttcggt gtaggtcgtt   3360
cgctccaagc tgggctgtgt gcacgaaccc cccgttcagc ccgaccgctg cgccttatcc   3420
ggtaactatc gtcttgagtc caacccggta agacacgact tatcgccact ggcagcagcc   3480
actggtaaca ggattagcag agcgaggtat gtaggcggtg ctacagagtt cttgaagtgg   3540
tggcctaact acggctacac tagaaggaca gtatttggta tctgcgctct gctgaagcca   3600
gttaccttcg gaaaaagagt tggtagctct tgatccggca aacaaaccac cgctggtagc   3660
ggtggttttt ttgtttgcaa gcagcagatt acgcgcagaa aaaaaggatc tcaagaagat   3720
cctttgatct tttctacggg gtctgacgct cagtggaacg aaaactcacg ttaagggatt   3780
ttggtcatgc attctaggta ctaaaacaat tcatccagta aaatataata ttttattttc   3840
tcccaatcag gcttgatccc cagtaagtca aaaaatagct cgacatactg ttcttccccg   3900
atatcctccc tgatcgaccg gacgcagaag gcaatgtcat accacttgtc cgccctgccg   3960
```

-continued

```
cttctcccaa gatcaataaa gccacttact ttgccatctt tcacaaagat gttgctgtct   4020
cccaggtcgc cgtgggaaaa gacaagttcc tcttcgggct tttccgtctt taaaaaatca   4080
tacagctcgc gcggatcttt aaatggagtg tcttcttccc agttttcgca atccacatcg   4140
gccagatcgt tattcagtaa gtaatccaat tcggctaagc ggctgtctaa gctattcgta   4200
tagggacaat ccgatatgtc gatggagtga aagagcctga tgcactccgc atacagctcg   4260
ataatctttt cagggctttg ttcatcttca tactcttccg agcaaaggac gccatcggcc   4320
tcactcatga gcagattgct ccagccatca tgccgttcaa agtgcaggac ctttggaaca   4380
ggcagctttc cttccagcca tagcatcatg tccttttccc gttccacatc ataggtggtc   4440
cctttatacc ggctgtccgt catttttaaa tataggtttt cattttctcc caccagctta   4500
tataccttag caggagacat tccttccgta tcttttacgc agcggtattt ttcgatcagt   4560
tttttcaatt ccggtgatat tctcatttta gccatttatt atttccttcc tcttttctac   4620
agtatttaaa gataccccaa gaagctaatt ataacaagac gaactccaat tcactgttcc   4680
ttgcattcta aaaccttaaa taccagaaaa cagctttttc aaagttgttt tcaaagttgg   4740
cgtataacat agtatcgacg gagccgattt tgaaaccgcg gtgatcacag gcagcaacgc   4800
tctgtcatcg ttacaatcaa catgctaccc tccgcgagat catccgtgtt tcaaacccgg   4860
cagcttagtt gccgttcttc cgaatagcat cggtaacatg agcaaagtct gccgccttac   4920
aacggctctc ccgctgacgc cgtcccggac tgatgggctg cctgtatcga gtggtgattt   4980
tgtgccgagc tgccggtcgg ggagctgttg gctggctggt ggcaggatat attgtggtgt   5040
aaacaaattg acgcttagac aacttaataa cacattgcgg acgtttttaa tgtagagctc   5100
aaagtttaac gcgttagcag aaggcatgtt gttgtgactc cgaggggttg cctcaaactc   5160
tatcttataa ccggcgtgga ggcatggagg caggggtatt ttggtcattt taatagatag   5220
tggaaaatga cgtggaattt acttaaagac gaagtctttg cgacaagggg gggcccacgc   5280
cgaatttaat attaccggcg tggccccccc ttatcgcgag tgctttagca cgagcggtcc   5340
agatttaaag tagaaaattt cccgcccact agggttaaag gtgttcacac tataaaagca   5400
tatacgatgt gatggtattt gatggagcgt atattgtatc aggtatttcc gttggatacg   5460
aattattcgt acgaccctcg gtaccgatcg gcgcgcctgg cagacatact gtcccacaaa   5520
tgaagatgga atctgtaaaa gaaaacgcgt gaaataatgc gtctgacaaa ggttaggtcg   5580
gctgccttta atcaatacca aagtggtccc taccacgatg gaaaaactgt gcagtcggtt   5640
tggctttttc tgacgaacaa ataagattcg tggccgacag gtgggggtcc accatgtgaa   5700
ggcatcttca gactccaata atggagcaat gacgtaaggg cttacgaaat aagtaagggt   5760
agtttgggaa atgtccactc acccgtcagt ctataaatac ttagcccctc cctcattgtt   5820
aagggagcaa aatctcagag agatagtcct agagagagaa agagagcaag tagcctagaa   5880
gtagtcaagg cggcgaagta ttcaggcacg tggccaggaa gaagaaaagc caagacgacg   5940
aaaacaggta agagctaagc ttcctgcacc atggaagacg ccaaaaacat aaagaaaggc   6000
ccggcgccat tctatccgct ggaagatgga accgctggag agcaactgca taaggctatg   6060
aagagatacg ccctggttcc tggaacaatt gcttttacag atgcacatat cgaggtggac   6120
atcacttacg ctgagtactt cgaaatgtcc gttcggttgg cagaagctat gaaacgatat   6180
gggctgaata caaatcacag aatcgtcgta tgcagtgaaa actctcttca attctttatg   6240
ccggtgttgg gcgcgttatt tatcggagtt gcagttgcgc ccgcgaacga catttataat   6300
```

gaacgtgaat tgctcaacag tatgggcatt tcgcagccta ccgtggtgtt cgtttccaaa 6360
aaggggttgc aaaaaatttt gaacgtgcaa aaaaagctcc caatcatcca aaaaattatt 6420
atcatggatt ctaaaacgga ttaccaggga tttcagtcga tgtacacgtt cgtcacatct 6480
catctacctc ccggttttaa tgaatacgat tttgtgccag agtccttcga tagggacaag 6540
acaattgcac tgatcatgaa ctcctctgga tctactggtc tgcctaaagg tgtcgctctg 6600
cctcatagaa ctgcctgcgt gagattctcg catgccagag atcctatttt tggcaatcaa 6660
atcattccgg atactgcgat tttaagtgtt gttccattcc atcacggttt tggaatgttt 6720
actacactcg gatatttgat atgtggattt cgagtcgtct taatgtatag atttgaagaa 6780
gagctgtttc tgaggagcct tcaggattac aagattcaaa gtgcgctgct ggtgccaacc 6840
ctattctcct tcttcgccaa aagcactctg attgacaaat acgatttatc taatttacac 6900
gaaattgctt ctggtggcgc tcccctctct aaggaagtcg gggaagcggt tgccaagagg 6960
ttccatctgc caggtatcag gcaaggatat gggctcactg agactacatc agctattctg 7020
attacacccg agggggatga taaaccgggc gcggtcggta aagttgttcc attttttgaa 7080
gcgaaggttg tggatctgga taccgggaaa acgctgggcg ttaatcaaag aggcgaactg 7140
tgtgtgagag gtcctatgat tatgtccggt tatgtaaaca atccggaagc gaccaacgcc 7200
ttgattgaca aggatggatg gctacattct ggagacatag cttactggga cgaagacgaa 7260
cacttcttca tcgttgaccg cctgaagtct ctgattaagt acaaaggcta tcaggtggct 7320
cccgctgaat tggaatccat cttgctccaa caccccaaca tcttcgacgc tggtgtcgca 7380
ggtcttcccg acgatgacgc cggtgaactt cccgccgccg ttgttgtttt ggagcacgga 7440
aagacgatga cggaaaaaga gatcgtggat tacgtcgcca gtcaagtaac aaccgcgaaa 7500
aagttgcgcg gaggagttgt gtttgtggac gaagtaccga aaggtcttac cggaaaactc 7560
gacgcaagaa aaatcagaga gatcctcata aaggccaaga agggcggaaa gatcgccgtg 7620
taactcgaga tatgaagatg aagatgaaat atttggtgtg tcaaataaaa agcttgtgtg 7680
cttaagtttg tgtttttttc ttggcttgtt gtgttatgaa tttgtggctt tttctaatat 7740
taaatgaatg taagatcaca ttataatgaa taaacaaatg tttctataat ccattgtgaa 7800
tgttttgttg gatctcttct gcagcatata actactgtat gtgctatggt atggactatg 7860
gaatatgatt aaagataagg agctccggtg acggacccat ggcttcgttg aacaacggaa 7920
actcgacttg ccttccgcac aatacatcat ttcttcttag ctttttttct tcttcttcgt 7980
tcatacagtt ttttttgtt tatcagctta catttcttg aaccgtagct ttcgttttct 8040
tctttttaac tttccattcg gagtttttgt atcttgtttc atagtttgtc ccaggattag 8100
aatgattagg catcgaacct tcaagaattt gattgaataa aacatcttca ttcttaagat 8160
atgaagataa tcttcaaaag gcccctggga atctgaaaga agagaagcag gcccatttat 8220
atgggaaaga acaatagtat ttcttatata ggcccattta agttgaaaac aatcttcaaa 8280
agtcccacat cgcttagata agaaaacgaa gctgagttta tatacagcta gagtcgaagt 8340
agtgattgtt ggtagtagcg actccatggt tttagagcta gaaatagcaa gttaaaataa 8400
ggctagtccg ttatcaactt gaaaaagtgg caccgagtcg gtgctttttt tcccgggcgc 8460
gccgatcatg agcggagaat taagggagtc acgttatgac cccgccgat gacgcgggac 8520
aagccgtttt acgtttggaa ctgacagaac cgcaacgttg aaggagccac tcagccgcgg 8580
gtttctggag tttaatgagc taagcacata cgtcagaaac cattattgcg cgttcaaaag 8640
tcgcctaagg tcactatcag ctagcaaata tttcttgtca aaaatgctcc actgacgttc 8700

-continued

```
cataaattcc cctcggtatc caattagagt ctcatattca ctctcaatcc aaataatctg    8760
caccgtacct gcagggtccg agctaggtca cagaagcgct caggaaggcc gctgagatag    8820
aggcatggcg gccaatgcgg gcggcggtgg agcgggagga ggcagcggca gcggcagcgt    8880
ggctgcgccg gcggtgtgcc gccccagcgg ctcgcggtgg acgccgacgc cggagcagat    8940
caggatgctg aaggagctgt actacggctg cggcatccgg tcgcccagct cggagcagat    9000
ccagcgcatc accgccatgc tgcggcagca cggcaagatc gagggcaaga acgtcttcta    9060
ctggttccag aaccacaagg cccgcgagcg ccagaagcgc cgcctcacca gcctcgacgt    9120
gaacgtgccc gccgccggcg cggccgacgc caccaccagc caactcggcg tcctctcgct    9180
gtcgtcgccg ccgccttcag gcgcggcgcc tccctcgccc accctcggct tctacgccgc    9240
cggcaatggc ggcggatcgg ctgtgctgct ggacacgagt tccgactggg gcagcagcgg    9300
cgctgcgatg gccaccgaga catgcttcct ccaggactac atgggcgtga cggacacggg    9360
cagctcgtcg cagtggccac gcttctcgtc gtcggacacg ataatggcgg cggccgcggc    9420
gcgggcggcg acgacgcggg cgcccgagac tctccctctc ttcccgacct gcggcgacga    9480
cggcggcagc ggtagcagca gctacttgcc gttctggggt gccgcgtcca caactgccgg    9540
cgccacttct tccgttgcga tccagcagca acaccagctg caggagcagt acagctttta    9600
cagcaacagc aacagcaccc agctggccgg caccggcaac caagacgtat cggcaacagc    9660
agcagcagcc gccgccctgg agctgagcct cagctcatgg tgctcccctt accctgctgc    9720
agggagtatg tgagagcaac gcgagctgcc actgctcttc acttatgtct ctggaatgga    9780
aggaggagga agtgagcata gcgttggtgc gttgctgtca ttgtcctagg ttagtagcta    9840
gtgccagtta ctagtaagca tcaggcatag gagtatgtag tagaagcatg cacgttgccg    9900
gccagccagg ctttagacgg gaaaagaatt tggtgcagcc ggctgcaaaa caggatgttt    9960
acagcccccc cctcgagccc tagacttgtc catcttctgg attggccaag ttaattaatg   10020
tatgaaataa aaggatgcac acatagtgac atgctaatca ctataatgtg ggcatcaaag   10080
ttgtgtgtta tgtgtaatta ctaattatct gaataagaga aagagatcat ccatatttct   10140
tatcctaaat gaatgtcacg tgtctttata attctttgat gaaccagatg cattttatta   10200
accaattcca tatacatata aatattaatc atatataatt aatatcaatt gggttagcaa   10260
aacaaatcta gtctaggtgt gttttgctaa ttattggggg atagtgcaaa aagaaatcta   10320
cgttctcaat aattcagata gaaaacttaa taaagtgaga taatttacat agattgcttt   10380
tatcctttga tatatgtgaa accatgcatg atataaggaa aatagataga gaaataattt   10440
tttacatcgt tgaatatgta aacaatttaa ttcaagaagc taggaatata aatattgagg   10500
agtttatgat tagagctctc ccggcgcgcc gatatcgagc tcagtgtttg atcgccggcg   10560
gtaccgagtg tacttcaagt cagtgggaaa tcaataaaat gattatttta tgaatatatt   10620
tcattgtgca agtagataga aattacatat gttacataac acacgaaata aacaaaaaaa   10680
gacaatccaa aaacaaacac cccaaaaaaa ataatcactt tagataaact cgtatgagga   10740
gaggcacgtt cagtgactcg acgattcccg agcaaaaaaa gtctccccgt cacacatgta   10800
gtgggtgacg caattatctt taaagtaatc cttctgttga cttgtcattg ataacatcca   10860
gtcttcgtca ggattgcaaa gaattataga agggatccca ccttttattt tcttcttttt   10920
tccatattta gggttgacag tgaaatcaga ctggcaacct attaattgct tccacaatgg   10980
gacgaacttg aaggggatgt cgtcgatgat attataggtg gcgtgttcat cgtagttggt   11040
```

gaaatcgatg gtaccgttcc aatagttgtg tcgtccgaga cttctagccc aggtggtctt 11100
tccggtacga gttggtccgc agatgtagag gctggggtgt cggattccat tccttccatt 11160
gtccttgtta aatcggccat ccattcaagg tcagattgag cttgttggta tgagacagga 11220
tgtatgtaag tataagcgtc tatgcttaca tggtatagat gggtttccct ccaggagtgt 11280
agatcttcgt ggcagcgaag atctgattct gtgaagggcg acacatacgg ttcaggttgt 11340
ggagggaata atttgttggc tgaatattcc agccattgaa gctttgttgc ccattcatga 11400
gggaattctt ccttgatcat gtcaagatat tcctccttag acgttgcagt ctggataata 11460
gttctccatc gtgcgtcaga tttgcgagga gaaaccttat gatctcggaa atctcctctg 11520
gttttaatat ctccgtcctt tgatatgtaa tcaaggactt gtttagagtt tctagctggc 11580
tggatattag ggtgatttcc ttcaaaatcg aaaaaagaag gatccctaat acaaggtttt 11640
ttatcaagct ggagaagagc atgatagtgg gtagtgccat cttgatgaag ctcagaagca 11700
acaccaagga agaaaataag aaaaggtgtg agtttctccc agagaaactg gaataaatca 11760
tctctttgag atgagcactt gggataggta aggaaaacat atttagattg gagtctgaag 11820
ttcttactag cagaaggcat gttgttgtga ctccgagggg ttgcctcaaa ctctatctta 11880
taaccggcgt ggaggcatgg aggcaggggt attttggtca ttttaataga tagtggaaaa 11940
tgacgtggaa tttacttaaa gacgaagtct ttgcgacaag ggggggccca cgccgaattt 12000
aatattaccg gcgtggcccc cccttatcgc gagtgcttta gcacgagcgg tccagattta 12060
aagtagaaaa tttcccgccc actagggtta aaggtgttca cactataaaa gcatatacga 12120
tgtgatggta tttgatggag cgtatattgt atcaggtatt tccgttggat acgaattatt 12180
cgtacgaccc tcatagttta aactatcagt gtttgacagg atatattggc gggtaaacct 12240
aagagaaaag agcgtttatt agaataacgg atatttaaaa gggcgtgaaa aggtttatcc 12300
gttcgtccat ttgtatgtgc atgccaacca cagggttccc ctcgggatca aagtactttg 12360
atccaacccc tccgctgcta tagtgcagtc ggcttctgac gttcagtgca gccgtcttct 12420
gaaaacgaca tgtcgcacaa gtcctaagtt acgcgacagg ctgccgccct gccctttcc 12480
tggcgttttc ttgtcgcgtg ttttagtcgc ataaagtaga atacttgcga ctagaaccgg 12540
agacattacg ccatgaacaa gagcgccgcc gctggcctgc tgggctatgc ccgcgtcagc 12600
accgacgacc aggacttgac caaccaacgg gccgaactgc acgcggccgg ctgcaccaag 12660
ctgttttccg agaagatcac cggcaccagg cgcgaccgcc cggagctggc caggatgctt 12720
gaccacctac gccctggcga cgttgtgaca gtgaccaggc tagaccgcct ggcccgcagc 12780
acccgcgacc tactggacat tgccgagcgc atccaggagg ccggcgcggg cctgcgtagc 12840
ctggcagagc cgtgggccga caccaccacg ccggccggcc gcatggtgtt gaccgtgttc 12900
gccggcattg ccgagttcga gcgttcccta atcatcgacc gcacccggag cgggcgcgag 12960
gccgccaagg cccgaggcgt gaagtttggc ccccgcccta ccctcacccc ggcacagatc 13020
gcgcacgccc gcgagctgat cgaccaggaa ggccgcaccg tgaaagaggc ggctgcactg 13080
cttggcgtgc atcgctcgac cctgtaccgc gcacttgagc gcagcgagga agtgacgccc 13140
accgaggcca ggcggcgcgg tgccttccgt gaggacgcat tgaccgaggc cgacgccctg 13200
gcggccgccg agaatgaacg ccaagaggaa caagcatgaa accgcaccag gacggccagg 13260
acgaaccgtt tttcattacc gaagagatcg aggcggagat gatcgcggcc gggtacgtgt 13320
tcgagccgcc cgcgcacggc tcaaccgtgc ggctgcatga aatcctggcc ggtttgtctg 13380
atgccaagct ggcggcctgg ccggccagct tggccgctga agaaaccgag cgccgccgtc 13440
taaaaaggtg atgtgtattt gagtaaaaca gc 13472

<210> SEQ ID NO 36
<211> LENGTH: 14829
<212> TYPE: DNA
<213> ORGANISM: artificial
<220> FEATURE:
<223> OTHER INFORMATION: synthetic oligonucleotide

<400> SEQUENCE: 36
gcagccggtg cgccgtcgat taggaagccg cccaagggcg acgagcaacc agattttttc 60
gttccgatgc tctatgacgt gggcacccgc gatagtcgca gcatcatgga cgtggccgtt 120
ttccgtctgt cgaagcgtga ccgacgagct ggcgaggtga tccgctacga gcttccagac 180
gggcacgtag aggtttccgc agggccggcc ggcatggcca gtgtgtggga ttacgacctg 240
gtactgatgg cggtttccca tctaaccgaa tccatgaacc gataccggga agggaaggga 300
gacaagcccg gccgcgtgtt ccgtccacac gttgcggacg tactcaagtt ctgccggcga 360
gccgatggcg gaaagcagaa agacgacctg gtagaaacct gcattcggtt aaacaccacg 420
cacgttgcca tgcagcgtac gaagaaggcc aagaacggcc gcctggtgac ggtatccgag 480
ggtgaagcct tgattagccg ctacaagatc gtaaagagcg aaaccgggcg gccggagtac 540
atcgagatcg agctagctga ttggatgtac cgcgagatca cagaaggcaa gaacccggac 600
gtgctgacgg ttcaccccga ttactttttg atcgatcccg gcatcggccg ttttctctac 660
cgcctggcac gccgcgccgc aggcaaggca gaagccagat ggttgttcaa gacgatctac 720
gaacgcagtg gcagcgccgg agagttcaag aagttctgtt tcaccgtgcg caagctgatc 780
gggtcaaatg acctgccgga gtacgatttg aaggaggagg cggggcaggc tggcccgatc 840
ctagtcatgc gctaccgcaa cctgatcgag ggcgaagcat ccgccggttc ctaatgtacg 900
gagcagatgc tagggcaaat tgccctagca ggggaaaaag gtcgaaaagg cctctttcct 960
gtggatagca cgtacattgg gaacccaaag ccgtacattg ggaaccggaa cccgtacatt 1020
gggaacccaa agccgtacat tgggaaccgg tcacacatgt aagtgactga tataaaagag 1080
aaaaaaggcg atttttccgc ctaaaactct ttaaaactta ttaaaactct taaaacccgc 1140
ctggcctgtg cataactgtc tggccagcgc acagccgaag agctgcaaaa agcgcctacc 1200
cttcggtcgc tgcgctccct acgccccgcc gcttcgcgtc ggcctatcgc ggccgctggc 1260
cgctcaaaaa tggctggcct acggccaggc aatctaccag ggcgcggaca agccgcgccg 1320
tcgccactcg accgccggcg cccacatcaa ggcaccctgc ctcgcgcgtt tcggtgatga 1380
cggtgaaaac ctctgacaca tgcagctccc ggaaacggtc acagcttgtc tgtaagcgga 1440
tgccgggagc agacaagccc gtcagggcgc gtcagcgggt gttggcgggt gtcggggcgc 1500
agccatgacc cagtcacgta gcgatagcgg agtgtatact ggcttaacta tgcggcatca 1560
gagcagattg tactgagagt gcaccatatg cggtgtgaaa taccgcacag atgcgtaagg 1620
agaaaatacc gcatcaggcg ctcttccgct tcctcgctca ctgactcgct gcgctcggtc 1680
gttcggctgc ggcgagcggt atcagctcac tcaaaggcgg taatacggtt atccacagaa 1740
tcaggggata acgcaggaaa gaacatgtga gcaaaaggcc agcaaaaggc caggaaccgt 1800
aaaaaggccg cgttgctggc gtttttccat aggctccgcc cccctgacga gcatcacaaa 1860
aatcgacgct caagtcagag gtggcgaaac ccgacaggac tataaagata ccaggcgttt 1920
ccccctggaa gctccctcgt gcgctctcct gttccgaccc tgccgcttac cggatacctg 1980

-continued

```
tccgcctttc tcccttcggg aagcgtggcg ctttctcata gctcacgctg taggtatctc   2040
agttcggtgt aggtcgttcg ctccaagctg ggctgtgtgc acgaaccccc cgttcagccc   2100
gaccgctgcg ccttatccgg taactatcgt cttgagtcca acccggtaag acacgactta   2160
tcgccactgg cagcagccac tggtaacagg attagcagag cgaggtatgt aggcggtgct   2220
acagagttct tgaagtggtg gcctaactac ggctacacta gaaggacagt atttggtatc   2280
tgcgctctgc tgaagccagt taccttcgga aaaagagttg gtagctcttg atccggcaaa   2340
caaaccaccg ctggtagcgg tggttttttt gtttgcaagc agcagattac gcgcagaaaa   2400
aaaggatctc aagaagatcc tttgatcttt tctacggggt ctgacgctca gtggaacgaa   2460
aactcacgtt aagggatttt ggtcatgcat tctaggtact aaaacaattc atccagtaaa   2520
atataatatt ttattttctc ccaatcaggc ttgatcccca gtaagtcaaa aaatagctcg   2580
acatactgtt cttccccgat atcctccctg atcgaccgga cgcagaaggc aatgtcatac   2640
cacttgtccg ccctgccgct tctcccaaga tcaataaagc cacttacttt gccatctttc   2700
acaaagatgt tgctgtctcc caggtcgccg tgggaaaaga caagttcctc ttcgggcttt   2760
tccgtcttta aaaaatcata cagctcgcgc ggatctttaa atggagtgtc ttcttcccag   2820
ttttcgcaat ccacatcggc cagatcgtta ttcagtaagt aatccaattc ggctaagcgg   2880
ctgtctaagc tattcgtata gggacaatcc gatatgtcga tggagtgaaa gagcctgatg   2940
cactccgcat acagctcgat aatcttttca gggctttgtt catcttcata ctcttccgag   3000
caaaggacgc catcggcctc actcatgagc agattgctcc agccatcatg ccgttcaaag   3060
tgcaggacct ttggaacagg cagctttcct tccagccata gcatcatgtc cttttcccgt   3120
tccacatcat aggtggtccc tttataccgg ctgtccgtca tttttaaata taggttttca   3180
ttttctccca ccagcttata taccttagca ggagacattc cttccgtatc ttttacgcag   3240
cggtattttt cgatcagttt tttcaattcc ggtgatattc tcattttagc catttattat   3300
ttccttcctc ttttctacag tatttaaaga taccccaaga agctaattat aacaagacga   3360
actccaattc actgttcctt gcattctaaa accttaaata ccagaaaaca gctttttcaa   3420
agttgttttc aaagttggcg tataacatag tatcgacgga gccgattttg aaaccgcggt   3480
gatcacaggc agcaacgctc tgtcatcgtt acaatcaaca tgctaccctc cgcgagatca   3540
tccgtgtttc aaacccggca gcttagttgc cgttcttccg aatagcatcg gtaacatgag   3600
caaagtctgc cgccttacaa cggctctccc gctgacgccg tcccggactg atgggctgcc   3660
tgtatcgagt ggtgattttg tgccgagctg ccggtcgggg agctgttggc tggctggtgg   3720
caggatatat tgtggtgtaa acaaattgac gcttagacaa cttaataaca cattgcggac   3780
gtttttaatg tagagctcaa agtttaacgc gttagcagaa ggcatgttgt tgtgactccg   3840
aggggttgcc tcaaactcta tcttataacc ggcgtggagg catggaggca ggggtatttt   3900
ggtcatttta atagatagtg gaaaatgacg tggaatttac ttaaagacga agtctttgcg   3960
acaagggggg gcccacgccg aatttaatat taccggcgtg gcccccccct atcgcgagtg   4020
ctttagcacg agcggtccag atttaaagta gaaaatttcc cgcccactag ggttaaaggt   4080
gttcacacta taaaagcata tacgatgtga tggtatttga tggagcgtat attgtatcag   4140
gtatttccgt tggatacgaa ttattcgtac gaccctcggt accgatcggc gcgcctggca   4200
gacatactgt cccacaaatg aagatggaat ctgtaaaaga aaacgcgtga aataatgcgt   4260
ctgacaaagg ttaggtcggc tgcctttaat caataccaaa gtggtcccta ccacgatgga   4320
aaaactgtgc agtcggtttg gctttttctg acgaacaaat aagattcgtg gccgacaggt   4380
```

```
gggggtccac catgtgaagg catcttcaga ctccaataat ggagcaatga cgtaagggct   4440
tacgaaataa gtaagggtag tttgggaaat gtccactcac ccgtcagtct ataaatactt   4500
agcccctccc tcattgttaa gggagcaaaa tctcagagag atagtcctag agagagaaag   4560
agagcaagta gcctagaagt agtcaaggcg gcgaagtatt caggcacgtg gccaggaaga   4620
agaaaagcca agacgacgaa aacaggtaag agctaagctt cctgcaccat ggaagacgcc   4680
aaaaacataa agaaaggccc ggcgccattc tatccgctgg aagatggaac cgctggagag   4740
caactgcata aggctatgaa gagatacgcc ctggttcctg gaacaattgc ttttacagat   4800
gcacatatcg aggtggacat cacttacgct gagtacttcg aaatgtccgt tcggttggca   4860
gaagctatga aacgatatgg gctgaataca aatcacagaa tcgtcgtatg cagtgaaaac   4920
tctcttcaat tctttatgcc ggtgttgggc gcgttattta tcggagttgc agttgcgccc   4980
gcgaacgaca tttataatga acgtgaattg ctcaacagta tgggcatttc gcagcctacc   5040
gtggtgttcg tttccaaaaa ggggttgcaa aaaattttga acgtgcaaaa aaagctccca   5100
atcatccaaa aaattattat catggattct aaaacggatt accagggatt tcagtcgatg   5160
tacacgttcg tcacatctca tctacctccc ggttttaatg aatacgattt tgtgccagag   5220
tccttcgata gggacaagac aattgcactg atcatgaact cctctggatc tactggtctg   5280
cctaaaggtg tcgctctgcc tcatagaact gcctgcgtga gattctcgca tgccagagat   5340
cctatttttg gcaatcaaat cattccggat actgcgattt taagtgttgt tccattccat   5400
cacggttttg gaatgtttac tacactcgga tatttgatat gtggatttcg agtcgtctta   5460
atgtatagat ttgaagaaga gctgtttctg aggagccttc aggattacaa gattcaaagt   5520
gcgctgctgg tgccaaccct attctccttc ttcgccaaaa gcactctgat tgacaaatac   5580
gatttatcta atttacacga aattgcttct ggtggcgctc ccctctctaa ggaagtcggg   5640
gaagcggttg ccaagaggtt ccatctgcca ggtatcaggc aaggatatgg gctcactgag   5700
actacatcag ctattctgat tacacccgag ggggatgata aaccgggcgc ggtcggtaaa   5760
gttgttccat tttttgaagc gaaggttgtg gatctggata ccgggaaaac gctgggcgtt   5820
aatcaaagag gcgaactgtg tgtgagaggt cctatgatta tgtccggtta tgtaaacaat   5880
ccggaagcga ccaacgcctt gattgacaag gatggatggc tacattctgg agacatagct   5940
tactgggacg aagacgaaca cttcttcatc gttgaccgcc tgaagtctct gattaagtac   6000
aaaggctatc aggtggctcc cgctgaattg gaatccatct tgctccaaca ccccaacatc   6060
ttcgacgctg gtgtcgcagg tcttcccgac gatgacgccg gtgaacttcc cgccgccgtt   6120
gttgttttgg agcacggaaa gacgatgacg gaaaaagaga tcgtggatta cgtcgccagt   6180
caagtaacaa ccgcgaaaaa gttgcgcgga ggagttgtgt ttgtggacga agtaccgaaa   6240
ggtcttaccg gaaaactcga cgcaagaaaa atcagagaga tcctcataaa ggccaagaag   6300
ggcggaaaga tcgccgtgta actcgagata tgaagatgaa gatgaaatat ttggtgtgtc   6360
aaataaaaag cttgtgtgct taagtttgtg tttttttctt ggcttgttgt gttatgaatt   6420
tgtggctttt tctaatatta aatgaatgta agatcacatt ataatgaata aacaaatgtt   6480
tctataatcc attgtgaatg ttttgttgga tctcttctgc agcatataac tactgtatgt   6540
gctatggtat ggactatgga atatgattaa agataaggag ctccggtgac ggacccatgg   6600
cttcgttgaa caacggaaac tcgacttgcc ttccgcacaa tacatcattt cttcttagct   6660
tttttcttc ttcttcgttc atacagtttt tttttgttta tcagcttaca ttttcttgaa   6720
```

-continued

```
ccgtagcttt cgttttcttc tttttaactt tccattcgga gtttttgtat cttgtttcat   6780
agtttgtccc aggattagaa tgattaggca tcgaaccttc aagaatttga ttgaataaaa   6840
catcttcatt cttaagatat gaagataatc ttcaaaaggc ccctgggaat ctgaaagaag   6900
agaagcaggc ccatttatat gggaaagaac aatagtattt cttatatagg cccatttaag   6960
ttgaaaacaa tcttcaaaag tcccacatcg cttagataag aaaacgaagc tgagtttata   7020
tacagctaga gtcgaagtag tgattgttgg tagtagcgac tccatggttt tagagctaga   7080
aatagcaagt taaaataagg ctagtccgtt atcaacttga aaaagtggca ccgagtcggt   7140
gctttttttc ccggggcgcg ccgatatcga gctctcccgc agatttgcct tttcaatttc   7200
agaaagaatg ctaacccaca gatggttaga gaggcttacg cagcaggtat catcaagacg   7260
atctacccga gcaataatct ccaggaaatc aaataccttc ccaagaaggt taaagatgca   7320
gtcaaaagat tcaggactaa ctgcatcaag aacacagaga aagatatatt tctcaagatc   7380
agaagtacta ttccagtatg gacgattcaa ggcttgcttc acaaaccaag gcaagtaata   7440
gagattggag tctctaaaaa ggtagttccc actgaatcaa aggccatgga gtcaaagatt   7500
caaatagagg acctaacaga actcgccgta aagactggcg aacagttcat acagagtctc   7560
ttacgactca atgacaagaa gaaaatcttc gtcaacatgg tggagcacga cacacttgtc   7620
tactccaaaa atatcaaaga tacagtctca gaagaccaaa gggcaattga gacttttcaa   7680
caaagggtaa tatccggaaa cctcctcgga ttccattgcc cagctatctg tcactttatt   7740
gtgaagatag tggaaaagga aggtggctcc tacaaatgcc atcattgcga taaaggaaag   7800
gccatcgttg aagatgcctc tgccgacagt ggtcccaaag atggaccccc acccacgagg   7860
agcatcgtgg aaaaagaaga cgttccaacc acgtcttcaa agcaagtgga ttgatgtgat   7920
atctccactg acgtaaggga tgacgcacaa tcccactatc cttcgcaaga cccttcctct   7980
atataaggaa gttcatttca tttggagaga acacggggga ctatgatggc ttcattgtct   8040
tgtgttgaag acaagatgaa aacaagttgt ttggttaatg gtggaggaac tataacaaca   8100
acaacatctc aatctacctt gcttgaagag atgaagctgt tgaaagacca gtcaggtaca   8160
agaaagccgg taataaactc ggagctatgg cacgcttgtg caggcccttt ggtgtgtctc   8220
cctcaagttg ggagcttagt gtattacttc tcacaaggtc atagcgagca ggttgctgtt   8280
tcaaccagaa gatcagcaac aacacaagtt cctaattatc cgaaccttcc atctcagttg   8340
atgtgtcaag tccataatgt tactcttcat gctgacaaag acagtgacga aatctatgct   8400
cagatgagtc ttcaacctgt tcactctgag agagatgtgt tccctgtacc agactttgga   8460
atgctgagag gaagtaagca cccgactgag tttttctgca aaacacttac tgcaagtgac   8520
acaagcacac atggaggttt ctcagtgcca cgtagagctg cagagaagct atttccacca   8580
ttggactact cagcacagcc gccaacgcaa gagcttgtag ttcgagatct tcatgagaat   8640
acttggacat ttcgccatat ctaccgaggg caaccaaaga gacatctcct aactacagga   8700
tggagtttgt tcgttggatc gaagagattg agagctgggg attctgtttt gttcatcagg   8760
gatgagaagt cacaacttat ggtcggtgtt aggcgtgcca atcgccaaca aacagcactt   8820
ccttcatcag ttctctcagc ggatagtatg cacatcggtg ttcttgctgc tgctgctcac   8880
gcaaccgcca accgtactcc ttttttgata ttctataatc caagagcttg tccagcagag   8940
ttcgtgatcc ctctagctaa gtaccgtaag gcgatatgcg ggtctcagct ctcagttggt   9000
atgagatttg gaatgatgtt tgaaactgaa gattccggga aacgaaggta catgggaact   9060
attgttggaa tcagcgattt ggatccgttg agatggcctg gttctaagtg gcgtaacctt   9120
```

caggtagaat gggatgagcc tggatgtaat gataaaccta ctcgggtcag tccatgggat 9180
atcgaaacac ctgaaagtct cttcattttt ccttctctga cctcaggact caaacgtcag 9240
ctccatccat cttactttgc tggtgaaact gaatggggta gcttgataaa acggccactt 9300
atacgtgttc ctgattccgc gaatgggatt atgccatatg catctttccc tagtatggct 9360
tcggagcagc ttatgaaaat gatgatgagg cctcacaaca accaaaatgt accatctttc 9420
atgtctgaga tgcagcagaa tattgtaatg gggaatggag gtttgctagg agatatgaag 9480
atgcagcaac ccctgatgat gaaccagaaa tctgagatgg tgcagccaca aaacaagcta 9540
acagtgaacc catctgcttc taatacgagt ggccaagaac agaatctttc acagagtatg 9600
agtgctcctg ctaaacctga gaactctaca ctctctggtt gcagctctgg tagagtccaa 9660
catggacttg agcagtcaat ggaacaggca agccaggtta ctacatccac agtgtgtaat 9720
gaggaaaagg ttaatcagct acttcagaaa ccgggtgctt cgtcgcctgt acaagctgat 9780
caatgtcttg acattactca tcagatttac caaccacagt ctgatccaat aaatggattc 9840
tctttcctgg aaactgatga gctgacatca caagtctctt ccttccagtc tcttgccgga 9900
tcatacaagc aaccattcat tctatcctcc caggattctt cagctgttgt gttaccggat 9960
tccacaaact caccgctgtt tcatgatgtg tgggacactc agttgaacgg tctcaagttt 10020
gaccagttca gtcccttgat gcagcaggac ctttatgcta gtcagaatat ctgtatgagt 10080
aatagcacaa ccagtaacat tctagatcct ccactctcaa acacagtcct tgatgacttc 10140
tgtgccatca aagacactga tttccagaac caccccttctg gttgtttggt tggaaacaac 10200
aacactagct ttgctcaaga tgtccagtcg cagatcacat cagctagctt tgcagactca 10260
caggccttct ctcgccaaga ttttccagat aattctggag gcactggtac atcttcaagc 10320
aatgttgatt ttgatgattg tagtctgcgg caaaatagta aaggctcatc atggcagaaa 10380
attgcgacac cccgcgtccg aacctactcg agtttctcca taataatgtg tgagtagttc 10440
ccagataagg gaattagggt tcctataggg tttcgctcat gtgttgagca tataagaaac 10500
ccttagtatg tatttgtatt tgtaaaatac ttctatcaat aaaatttcta attcctaaaa 10560
ccaaaatcca gtactaaaat ccagatcccc cgaattaagt gtttgatcgc cggcggtacc 10620
gagtgtactt caagtcagtg ggaaatcaat aaaatgatta ttttatgaat atatttcatt 10680
gtgcaagtag atagaaatta catatgttac ataacacacg aaataaacaa aaaaagacaa 10740
tccaaaaaca aacaccccaa aaaaaataat cactttagat aaactcgtat gaggagaggc 10800
acgttcagtg actcgacgat tcccgagcaa aaaaagtctc cccgtcacac atgtagtggg 10860
tgacgcaatt atctttaaag taatccttct gttgacttgt cattgataac atccagtctt 10920
cgtcaggatt gcaaagaatt atagaaggga tcccaccttt tattttcttc tttttccat 10980
atttagggtt gacagtgaaa tcagactggc aacctattaa ttgcttccac aatgggacga 11040
acttgaaggg gatgtcgtcg atgatattat aggtggcgtg ttcatcgtag ttggtgaaat 11100
cgatggtacc gttccaatag ttgtgtcgtc cgagacttct agcccaggtg gtctttccgg 11160
tacgagttgg tccgcagatg tagaggctgg ggtgtcggat tccattcctt ccattgtcct 11220
tgttaaatcg gccatccatt caaggtcaga ttgagcttgt tggtatgaga caggatgtat 11280
gtaagtataa gcgtctatgc ttacatggta tagatgggtt tccctccagg agtgtagatc 11340
ttcgtggcag cgaagatctg attctgtgaa gggcgacaca tacggttcag gttgtggagg 11400
gaataatttg ttggctgaat attccagcca ttgaagcttt gttgcccatt catgagggaa 11460
ttcttccttg atcatgtcaa gatattcctc cttagacgtt gcagtctgga taatagttct 11520
ccatcgtgcg tcagatttgc gaggagaaac cttatgatct cggaaatctc ctctggtttt 11580
aatatctccg tcctttgata tgtaatcaag gacttgttta gagtttctag ctggctggat 11640
attagggtga tttccttcaa aatcgaaaaa agaaggatcc ctaatacaag gtttttttatc 11700 aagctggaga agagcatgat agtgggtagt gccatcttga tgaagctcag aagcaacacc 11760
aaggaagaaa ataagaaaag gtgtgagttt ctcccagaga aactggaata aatcatctct 11820
ttgagatgag cacttgggat aggtaaggaa aacatattta gattggagtc tgaagttctt 11880
actagcagaa ggcatgttgt tgtgactccg aggggttgcc tcaaactcta tcttataacc 11940
ggcgtggagg catggaggca ggggtatttt ggtcatttta atagatagtg gaaaatgacg 12000
tggaatttac ttaaagacga agtctttgcg acaagggggg gcccacgccg aatttaatat 12060
taccggcgtg gcccccccctt atcgcgagtg ctttagcacg agcggtccag atttaaagta 12120
gaaaatttcc cgcccactag ggttaaaggt gttcacacta taaaagcata tacgatgtga 12180
tggtatttga tggagcgtat attgtatcag gtatttccgt tggatacgaa ttattcgtac 12240
gaccctcata gtttaaacta tcagtgtttg acaggatata ttggcgggta aacctaagag 12300
aaaagagcgt ttattagaat aacggatatt taaaagggcg tgaaaaggtt tatccgttcg 12360
tccatttgta tgtgcatgcc aaccacaggg ttcccctcgg gatcaaagta ctttgatcca 12420
acccctccgc tgctatagtg cagtcggctt ctgacgttca gtgcagccgt cttctgaaaa 12480
cgacatgtcg cacaagtcct aagttacgcg acaggctgcc gccctgccct tttcctggcg 12540
ttttcttgtc gcgtgtttta gtcgcataaa gtagaatact tgcgactaga accggagaca 12600
ttacgccatg aacaagagcg ccgccgctgg cctgctgggc tatgcccgcg tcagcaccga 12660
cgaccaggac ttgaccaacc aacgggccga actgcacgcg gccggctgca ccaagctgtt 12720
ttccgagaag atcaccggca ccaggcgcga ccgcccggag ctggccagga tgcttgacca 12780
cctacgccct ggcgacgttg tgacagtgac caggctagac cgcctggccc gcagcacccg 12840
cgacctactg gacattgccg agcgcatcca ggaggccggc gcgggcctgc gtagcctggc 12900
agagccgtgg gccgacacca ccacgccggc cggccgcatg gtgttgaccg tgttcgccgg 12960
cattgccgag ttcgagcgtt ccctaatcat cgaccgcacc cggagcgggc gcgaggccgc 13020
caaggcccga ggcgtgaagt ttggcccccg ccctaccctc accccggcac agatcgcgca 13080
cgcccgcgag ctgatcgacc aggaaggccg caccgtgaaa gaggcggctg cactgcttgg 13140
cgtgcatcgc tcgaccctgt accgcgcact tgagcgcagc gaggaagtga cgcccaccga 13200
ggccaggcgg cgcggtgcct tccgtgagga cgcattgacc gaggccgacg ccctggcggc 13260
cgccgagaat gaacgccaag aggaacaagc atgaaaccgc accaggacgg ccaggacgaa 13320
ccgtttttca ttaccgaaga gatcgaggcg gagatgatcg cggccgggta cgtgttcgag 13380
ccgcccgcgc acggctcaac cgtgcggctg catgaaatcc tggccggttt gtctgatgcc 13440
aagctggcgg cctggccggc cagcttggcc gctgaagaaa ccgagcgccg ccgtctaaaa 13500
aggtgatgtg tatttgagta aaacagcttg cgtcatgcgg tcgctgcgta tatgatgcga 13560
tgagtaaata aacaaatacg caaggggaac gcatgaaggt tatcgctgta cttaaccaga 13620
aaggcgggtc aggcaagacg accatcgcaa cccatctagc ccgcgccctg caactcgccg 13680
gggccgatgt tctgttagtc gattccgatc cccagggcag tgcccgcgat tgggcggccg 13740
tgcgggaaga tcaaccgcta accgttgtcg gcatcgaccg cccgacgatt gaccgcgacg 13800
tgaaggccat cggccggcgc gacttcgtag tgatcgacgg agcgccccag gcggcggact 13860

```
tggctgtgtc cgcgatcaag gcagccgact tcgtgctgat tccggtgcag ccaagccctt  13920
acgacatatg ggccaccgcc gacctggtgg agctggttaa gcagcgcatt gaggtcacgg  13980
atggaaggct acaagcggcc tttgtcgtgt cgcgggcgat caaaggcacg cgcatcggcg  14040
gtgaggttgc cgaggcgctg gccgggtacg agctgcccat tcttgagtcc cgtatcacgc  14100
agcgcgtgag ctacccaggc actgccgccg ccggcacaac cgttcttgaa tcagaacccg  14160
agggcgacgc tgcccgcgag gtccaggcgc tggccgctga aattaaatca aaactcattt  14220
gagttaatga ggtaaagaga aaatgagcaa aagcacaaac acgctaagtg ccggccgtcc  14280
gagcgcacgc agcagcaagg ctgcaacgtt ggccagcctg gcagacacgc cagccatgaa  14340
gcgggtcaac tttcagttgc cggcggagga tcacaccaag ctgaagatgt acgcggtacg  14400
ccaaggcaag accattaccg agctgctatc tgaatacatc gcgcagctac cagagtaaat  14460
gagcaaatga ataaatgagt agatgaattt tagcggctaa aggaggcggc atggaaaatc  14520
aagaacaacc aggcaccgac gccgtggaat gccccatgtg tggaggaacg ggcggttggc  14580
caggcgtaag cggctgggtt gtctgccggc cctgcaatgg cactggaacc cccaagcccg  14640
aggaatcggc gtgacggtcg caaaccatcc ggcccggtac aaatcggcgc ggcgctgggt  14700
gatgacctgg tggagaagtt gaaggccgcg caggccgccc agcggcaacg catcgaggca  14760
gaagcacgcc ccggtgaatc gtggcaagcg gccgctgatc gaatccgcaa agaatcccgg  14820
caaccgccg                                                          14829
```

```
<210> SEQ ID NO 37
<211> LENGTH: 16222
<212> TYPE: DNA
<213> ORGANISM: artificial
<220> FEATURE:
<223> OTHER INFORMATION: synthetic oligonucleotide

<400> SEQUENCE: 37

atggccagtg tgtgggatta cgacctggta ctgatggcgg tttcccatct aaccgaatcc     60
atgaaccgat accgggaagg gaagggagac aagcccggcc gcgtgttccg tccacacgtt    120
gcggacgtac tcaagttctg ccggcgagcc gatggcggaa agcagaaaga cgacctggta    180
gaaacctgca ttcggttaaa caccacgcac gttgccatgc agcgtacgaa gaaggccaag    240
aacggccgcc tggtgacggt atccgagggt gaagccttga ttagccgcta caagatcgta    300
aagagcgaaa ccgggcggcc ggagtacatc gagatcgagc tagctgattg gatgtaccgc    360
gagatcacag aaggcaagaa cccggacgtg ctgacggttc accccgatta ctttttgatc    420
gatcccggca tcggccgttt tctctaccgc ctggcacgcc gcgccgcagg caaggcagaa    480
gccagatggt tgttcaagac gatctacgaa cgcagtggca gcgccggaga gttcaagaag    540
ttctgtttca ccgtgcgcaa gctgatcggg tcaaatgacc tgccggagta cgatttgaag    600
gaggaggcgg ggcaggctgg cccgatccta gtcatgcgct accgcaacct gatcgagggc    660
gaagcatccg ccggttccta atgtacggag cagatgctag ggcaaattgc cctagcaggg    720
gaaaaaggtc gaaaaggcct ctttcctgtg gatagcacgt acattgggaa cccaaagccg    780
tacattggga accggaaccc gtacattggg aacccaaagc cgtacattgg gaaccggtca    840
cacatgtaag tgactgatat aaaagagaaa aaaggcgatt tttccgccta aaactcttta    900
aaacttatta aaactcttaa aacccgcctg gcctgtgcat aactgtctgg ccagcgcaca    960
gccgaagagc tgcaaaaagc gcctaccctt cggtcgctgc gctccctacg ccccgccgct   1020
```

-continued

```
tcgcgtcggc ctatcgcggc cgctggccgc tcaaaaatgg ctggcctacg gccaggcaat   1080
ctaccagggc gcggacaagc cgcgccgtcg ccactcgacc gccggcgccc acatcaaggc   1140
accctgcctc gcgcgtttcg gtgatgacgg tgaaaacctc tgacacatgc agctcccgga   1200
aacggtcaca gcttgtctgt aagcggatgc cgggagcaga caagcccgtc agggcgcgtc   1260
agcgggtgtt ggcgggtgtc ggggcgcagc catgacccag tcacgtagcg atagcggagt   1320
gtatactggc ttaactatgc ggcatcagag cagattgtac tgagagtgca ccatatgcgg   1380
tgtgaaatac cgcacagatg cgtaaggaga aaataccgca tcaggcgctc ttccgcttcc   1440
tcgctcactg actcgctgcg ctcggtcgtt cggctgcggc gagcggtatc agctcactca   1500
aaggcggtaa tacggttatc cacagaatca ggggataacg caggaaagaa catgtgagca   1560
aaaggccagc aaaaggccag gaaccgtaaa aaggccgcgt tgctggcgtt tttccatagg   1620
ctccgccccc ctgacgagca tcacaaaaat cgacgctcaa gtcagaggtg gcgaaacccg   1680
acaggactat aaagatacca ggcgtttccc cctggaagct ccctcgtgcg ctctcctgtt   1740
ccgaccctgc cgcttaccgg atacctgtcc gcctttctcc cttcgggaag cgtggcgctt   1800
tctcatagct cacgctgtag gtatctcagt tcggtgtagg tcgttcgctc caagctgggc   1860
tgtgtgcacg aaccccccgt tcagcccgac cgctgcgcct tatccggtaa ctatcgtctt   1920
gagtccaacc cggtaagaca cgacttatcg ccactggcag cagccactgg taacaggatt   1980
agcagagcga ggtatgtagg cggtgctaca gagttcttga agtggtggcc taactacggc   2040
tacactagaa ggacagtatt tggtatctgc gctctgctga agccagttac cttcggaaaa   2100
agagttggta gctcttgatc cggcaaacaa accaccgctg gtagcggtgg tttttttgtt   2160
tgcaagcagc agattacgcg cagaaaaaaa ggatctcaag aagatccttt gatcttttct   2220
acggggtctg acgctcagtg gaacgaaaac tcacgttaag ggattttggt catgcattct   2280
aggtactaaa acaattcatc cagtaaaata taatatttta ttttctccca atcaggcttg   2340
atccccagta agtcaaaaaa tagctcgaca tactgttctt ccccgatatc ctccctgatc   2400
gaccggacgc agaaggcaat gtcataccac ttgtccgccc tgccgcttct cccaagatca   2460
ataaagccac ttactttgcc atctttcaca aagatgttgc tgtctcccag gtcgccgtgg   2520
gaaaagacaa gttcctcttc gggcttttcc gtctttaaaa aatcatacag ctcgcgcgga   2580
tctttaaatg gagtgtcttc ttcccagttt tcgcaatcca catcggccag atcgttattc   2640
agtaagtaat ccaattcggc taagcggctg tctaagctat tcgtataggg acaatccgat   2700
atgtcgatgg agtgaaagag cctgatgcac tccgcataca gctcgataat cttttcaggg   2760
ctttgttcat cttcatactc ttccgagcaa aggacgccat cggcctcact catgagcaga   2820
ttgctccagc catcatgccg ttcaaagtgc aggacctttg gaacaggcag ctttccttcc   2880
agccatagca tcatgtcctt ttcccgttcc acatcatagg tggtcccttt ataccggctg   2940
tccgtcattt ttaaatatag gttttcattt tctcccacca gcttatatac cttagcagga   3000
gacattcctt ccgtatcttt tacgcagcgg tatttttcga tcagtttttt caattccggt   3060
gatattctca ttttagccat ttattatttc cttcctcttt tctacagtat ttaaagatac   3120
cccaagaagc taattataac aagacgaact ccaattcact gttccttgca ttctaaaacc   3180
ttaaatacca gaaaacagct ttttcaaagt tgttttcaaa gttggcgtat aacatagtat   3240
cgacggagcc gattttgaaa ccgcggtgat cacaggcagc aacgctctgt catcgttaca   3300
atcaacatgc taccctccgc gagatcatcc gtgtttcaaa cccggcagct tagttgccgt   3360
tcttccgaat agcatcggta acatgagcaa agtctgccgc cttacaacgg ctctcccgct   3420
```

gacgccgtcc cggactgatg ggctgcctgt atcgagtggt gattttgtgc cgagctgccg 3480
gtcggggagc tgttggctgg ctggtggcag gatatattgt ggtgtaaaca aattgacgct 3540
tagacaactt aataacacat tgcggacgtt tttaatgtag agctcaaagt ttaacgcgtt 3600
agcagaaggc atgttgttgt gactccgagg ggttgcctca aactctatct tataaccggc 3660
gtggaggcat ggaggcaggg gtattttggt cattttaata gatagtggaa aatgacgtgg 3720
aatttactta aagacgaagt ctttgcgaca aggggggggcc cacgccgaat ttaatattac 3780
cggcgtggcc ccccttatc gcgagtgctt tagcacgagc ggtccagatt taaagtagaa 3840
aatttcccgc ccactagggt taaaggtgtt cacactataa aagcatatac gatgtgatgg 3900
tatttgatgg agcgtatatt gtatcaggta tttccgttgg atacgaatta ttcgtacgac 3960
cctcggtacc gatcggcgcg cctggcagac atactgtccc acaaatgaag atggaatctg 4020
taaaagaaaa cgcgtgaaat aatgcgtctg acaaaggtta ggtcggctgc ctttaatcaa 4080
taccaaagtg gtccctacca cgatggaaaa actgtgcagt cggtttggct ttttctgacg 4140
aacaaataag attcgtggcc gacaggtggg ggtccaccat gtgaaggcat cttcagactc 4200
caataatgga gcaatgacgt aagggcttac gaaataagta agggtagttt gggaaatgtc 4260
cactcacccg tcagtctata aatacttagc ccctccctca ttgttaaggg agcaaaatct 4320
cagagagata gtcctagaga gagaaagaga gcaagtagcc tagaagtagt caaggcggcg 4380
aagtattcag gcacgtggcc aggaagaaga aaagccaaga cgacgaaaac aggtaagagc 4440
taagcttcct gcaccatgga agacgccaaa aacataaaga aaggcccggc gccattctat 4500
ccgctggaag atggaaccgc tggagagcaa ctgcataagg ctatgaagag atacgccctg 4560
gttcctggaa caattgcttt tacagatgca catatcgagg tggacatcac ttacgctgag 4620
tacttcgaaa tgtccgttcg gttggcagaa gctatgaaac gatatgggct gaatacaaat 4680
cacagaatcg tcgtatgcag tgaaaactct cttcaattct ttatgccggt gttgggcgcg 4740
ttatttatcg gagttgcagt tgcgcccgcg aacgacattt ataatgaacg tgaattgctc 4800
aacagtatgg gcatttcgca gcctaccgtg gtgttcgttt ccaaaaaggg gttgcaaaaa 4860
attttgaacg tgcaaaaaaa gctcccaatc atccaaaaaa ttattatcat ggattctaaa 4920
acggattacc agggatttca gtcgatgtac acgttcgtca catctcatct acctcccggt 4980
tttaatgaat acgattttgt gccagagtcc ttcgataggg acaagacaat tgcactgatc 5040
atgaactcct ctggatctac tggtctgcct aaaggtgtcg ctctgcctca tagaactgcc 5100
tgcgtgagat tctcgcatgc cagagatcct atttttggca atcaaatcat tccggatact 5160
gcgattttaa gtgttgttcc attccatcac ggttttggaa tgtttactac actcggatat 5220
ttgatatgtg gatttcgagt cgtcttaatg tatagatttg aagaagagct gtttctgagg 5280
agccttcagg attacaagat tcaaagtgcg ctgctggtgc caaccctatt ctccttcttc 5340
gccaaaagca ctctgattga caaatacgat ttatctaatt tacacgaaat tgcttctggt 5400
ggcgctcccc tctctaagga agtcggggaa gcggttgcca agaggttcca tctgccaggt 5460
atcaggcaag gatatgggct cactgagact acatcagcta ttctgattac acccgagggg 5520
gatgataaac cgggcgcggt cggtaaagtt gttccatttt ttgaagcgaa ggttgtggat 5580
ctggataccg ggaaaacgct gggcgttaat caaagaggcg aactgtgtgt gagaggtcct 5640
atgattatgt ccggttatgt aaacaatccg gaagcgacca acgccttgat tgacaaggat 5700
ggatggctac attctggaga catagcttac tgggacgaag acgaacactt cttcatcgtt 5760

-continued

```
gaccgcctga agtctctgat taagtacaaa ggctatcagg tggctcccgc tgaattggaa   5820
tccatcttgc tccaacaccc caacatcttc gacgctggtg tcgcaggtct tcccgacgat   5880
gacgccggtg aacttcccgc cgccgttgtt gttttggagc acggaaagac gatgacggaa   5940
aaagagatcg tggattacgt cgccagtcaa gtaacaaccg cgaaaaagtt gcgcggagga   6000
gttgtgtttg tggacgaagt accgaaaggt cttaccggaa aactcgacgc aagaaaaatc   6060
agagagatcc tcataaaggc caagaagggc ggaaagatcg ccgtgtaact cgagatatga   6120
agatgaagat gaaatatttg gtgtgtcaaa taaaaagctt gtgtgcttaa gtttgtgttt   6180
ttttcttggc ttgttgtgtt atgaatttgt ggctttttct aatattaaat gaatgtaaga   6240
tcacattata atgaataaac aaatgtttct ataatccatt gtgaatgttt tgttggatct   6300
cttctgcagc atataactac tgtatgtgct atggtatgga ctatggaata tgattaaaga   6360
taaggagctc cggtgacgga cccatggctt cgttgaacaa cggaaactcg acttgccttc   6420
cgcacaatac atcatttctt cttagctttt tttcttcttc ttcgttcata cagttttttt   6480
ttgtttatca gcttacattt tcttgaaccg tagctttcgt tttcttcttt ttaactttcc   6540
attcggagtt tttgtatctt gtttcatagt ttgtcccagg attagaatga ttaggcatcg   6600
aaccttcaag aatttgattg aataaaacat cttcattctt aagatatgaa gataatcttc   6660
aaaaggcccc tgggaatctg aaagaagaga agcaggccca tttatatggg aaagaacaat   6720
agtatttctt atataggccc atttaagttg aaaacaatct tcaaaagtcc cacatcgctt   6780
agataagaaa acgaagctga gtttatatac agctagagtc gaagtagtga ttgttggtag   6840
tagcgactcc atggttttag agctagaaat agcaagttaa aataaggcta gtccgttatc   6900
aacttgaaaa agtggcaccg agtcggtgct ttttttcccg gggcgcgccg atatcgagct   6960
ctcccggcgc gcctgcagtg cagcgtgacc cggtcgtgcc cctctctaga gataatgagc   7020
attgcatgtc taagttataa aaaattacca catatttttt ttgtcacact tgtttgaagt   7080
gcagtttatc tatctttata catatattta aactttactc tacgaataat ataatctata   7140
gtactacaat aatatcagtg ttttagagaa tcatataaat gaacagttag acatggtcta   7200
aaggacaatt gagtattttg acaacaggac tctacagttt tatcttttta gtgtgcatgt   7260
gttctccttt ttttttgcaa atagcttcac ctatataata cttcatccat tttattagta   7320
catccattta gggtttaggg ttaatggttt ttatagacta atttttttag tacatctatt   7380
ttattctatt ttagcctcta aattaagaaa actaaaactc tattttagtt tttttattta   7440
ataatttaga tataaaatag aataaaataa agtgactaaa aattaaacaa ataccctta    7500
agaaattaaa aaaactaagg aaacattttt cttgtttcga gtagataatg ccagcctgtt   7560
aaacgccgtc gacgagtcta acggacacca accagcgaac cagcagcgtc gcgtcgggcc   7620
aagcgaagca gacggcacgg catctctgtc gctgcctctg gacccctctc gagagttccg   7680
ctccaccgtt ggacttgctc cgctgtcggc atccagaaat tgcgtggcgg agcggcagac   7740
gtgagccggc acggcaggcg gcctcctcct cctctcacgg caccggcagc tacgggggat   7800
tcctttccca ccgctccttc gctttccctt cctcgcccgc cgtaataaat agacaccccc   7860
tccacaccct ctttccccaa cctcgtgttg ttcggagcgc acacacacac aaccagatct   7920
cccccaaatc cacccgtcgg cacctccgct tcaaggtacg ccgctcgtcc tccccccccc   7980
ccctctctac cttctctaga tcggcgttcc ggtccatggt tagggcccgg tagttctact   8040
tctgttcatg tttgtgttag atccgtgttt gtgttagatc cgtgctgcta gcgttcgtac   8100
acggatgcga cctgtacgtc agacacgttc tgattgctaa cttgccagtg tttctctttg   8160
```

```
gggaatcctg ggatggctct agccgttccg cagacgggat cgatttcatg attttttttg   8220
tttcgttgca tagggtttgg tttgcccttt tcctttattt caatatatgc cgtgcacttg   8280
tttgtcgggt catcttttca tgcttttttt tgtcttggtt gtgatgatgt ggtctggttg   8340
ggcggtcgtt ctagatcgga gtagaattaa ttctgtttca aactacctgg tggatttatt   8400
aattttggat ctgtatgtgt gtgccataca tattcatagt tacgaattga agatgatgga   8460
tggaaatatc gatctaggat aggtatacat gttgatgcgg gttttactga tgcatataca   8520
gagatgcttt ttgttcgctt ggttgtgatg atgtggtgtg gttgggcggt cgttcattcg   8580
ttctagatcg gagtagaata ctgtttcaaa ctacctggtg tatttattaa ttttggaact   8640
gtatgtgtgt gtcatacatc ttcatagtta cgagtttaag atggatggaa atatcgatct   8700
aggataggta tacatgttga tgtgggtttt actgatgcat atacatgatg gcatatgcag   8760
catctattca tatgctctaa ccttgagtac ctatctatta taataaacaa gtatgtttta   8820
taattatttt gatcttgata tacttggatg atggcatatg cagcagctat atgtggattt   8880
ttttagccct gccttcatac gctatttatt tgcttggtac tgtttctttt gtcgatgctc   8940
accctgttgt ttggtgttac ttcctgcagg cttccctaac ctttgcactg tccaaaatgg   9000
cttcctgatc ccctcacttc ctcgaatcaa tctaagaaga aactcaagcc gcaaccatta   9060
ggggcagatt aattgctgca ctttcagata atcaagcatg gccactgtga acaactggct   9120
cgctttctcc ctctccccgc aggagctgcc gccctcccag acgacggact ccacactcat   9180
ctcggccgcc accgccgacc atgtctccgg cgatgtctgc ttcaacatcc cccaagattg   9240
gagcatgagg ggatcagagc tttcggcgct cgtcgcggag ccgaagctgg aggacttcct   9300
cggcggcatc tccttctccg agcagcatca caaggccaac tgcaacatga tacccagcac   9360
tagcagcaca gtttgctacg ccagctcagg tgctagcacc ggctaccatc accagctgta   9420
ccaccagccc accagctcag cgctccactt cgcggactcc gtaatggtgg cctcctcggc   9480
cggtgtccac gacggcggtg ccatgctcag cgcggccgcc gctaacggtg tcgctggcgc   9540
tgccagtgcc aacggcggcg gcatcgggct gtccatgatt aagaactggc tgcggagcca   9600
accggcgccc atgcagccga gggtggcggc ggctgagggc gcgcaggggc tctctttgtc   9660
catgaacatg gcggggacga cccaaggcgc tgctggcatg ccacttctcg ctggagagcg   9720
cgcacgggcg cccgagagtg tatccacgtc agcacagggt ggagccgtcg tcgtcacggc   9780
gccgaaggag gatagcggtg gcagcggtgt tgccggcgct ctagtagccg tgagcacgga   9840
cacgggtggc agcggcggcg cgtcggctga caacacggca aggaagacgg tggacacgtt   9900
cgggcagcgc acgtcgattt accgtggcgt gacaaggcat agatggactg ggagatatga   9960
ggcacatctt tgggataaca gttgcagaag ggaagggcaa actcgtaagg gtcgtcaagt  10020
ctatttaggt ggctatgata aagaggagaa agctgctagg gcttatgatc ttgctgctct  10080
gaagtactgg ggtgccacaa caacaacaaa ttttccagtg agtaactacg aaaaggagct  10140
ggaggacatg aagcacatga caaggcagga gtttgtagcg cctctgagaa ggaagtccag  10200
tggtttctcc agaggtgcat ccatttacag gggagtgact aggcatcacc aacatggaag  10260
atggcaagca cggattggac gagttgcagg gaacaaggat ctttacttgg gcaccttcag  10320
cacccaggag gaggcagcgg aggcgtacga catcgcggcg atcaagttcc gcggcctcaa  10380
cgccgtcacc aacttcgaca tgagccgcta cgacgtgaag tccatcctgg acagcagcgc  10440
cctccccatc ggcagcgccg ccaagcgcct caaggaggcc gaggccgcag cgtccgcgca  10500
```

-continued

```
gcaccaccat gcgggtgtcg tttcctatga cgttgggagg attgccagcc aactgggaga  10560
tggcggtgcc ctcgctgcgg cctatggtgc tcactatcac ggtgccgcgt ggccaacgat  10620
tgcattccag ccgggcgcgg cgtccaccgg actgtaccat ccttacgcgc agcagcctat  10680
gcgcggcggt ggatggtgta aacaagagca agatcacgct gtgatagcag cggcacactc  10740
cttgcaggat cttcatcatt tgaatctcgg agccgccggg gcccacgact ttttctcggc  10800
agggcagcag gccgccgccg ctgcgatgca cggcctgggt agcatcgaca gtgcgtcgct  10860
ggagcacagc accggctcca actccgtcgt ctacaacggc ggggtcggcg acagcaacgg  10920
cgccagcgcc gtcggcggca gtggcggtgg ctacatgatg ccgatgagcg ctgccggagc  10980
aaccactaca tcggcaatgg tgagccacga gcaggtccat gcacgggcct acgacgaagc  11040
caagcaggct gctcagatgg ggtacgagag ctacctggtg aacgcggaga acaatggtgg  11100
cggaaggatg tctgcatggg ggactgtcgt gtctgcagcc gcggcggcag cagcaagcag  11160
caacgacaac atggccgccg acgtgggcca cggcggcgcg cagctgttca gtgtctggaa  11220
cgacacttaa ctcgagccct agacttgtcc atcttctgga ttggccaagt taattaatgt  11280
atgaaataaa aggatgcaca catagtgaca tgctaatcac tataatgtgg gcatcaaagt  11340
tgtgtgttat gtgtaattac taattatctg aataagagaa agagatcatc catatttctt  11400
atcctaaatg aatgtcacgt gtctttataa ttctttgatg aaccagatgc attttattaa  11460
ccaattccat atacatataa atattaatca tatataatta atatcaattg ggttagcaaa  11520
acaaatctag tctaggtgtg ttttgctaat tattggggga tagtgcaaaa agaaatctac  11580
gttctcaata attcagatag aaaacttaat aaagtgagat aatttacata gattgctttt  11640
atcctttgat atatgtgaaa ccatgcatga tataaggaaa atagatagag aaataatttt  11700
ttacatcgtt gaatatgtaa acaatttaat tcaagaagct aggaatataa atattgagga  11760
gtttatgatt agagctcagt gtttgatcgc cggcggtacc gagtgtactt caagtcagtg  11820
ggaaatcaat aaaatgatta ttttatgaat atatttcatt gtgcaagtag atagaaatta  11880
catatgttac ataacacacg aaataaacaa aaaaagacaa tccaaaaaca aacaccccaa  11940
aaaaaataat cactttagat aaactcgtat gaggagaggc acgttcagtg actcgacgat  12000
tcccgagcaa aaaaagtctc cccgtcacac atgtagtggg tgacgcaatt atctttaaag  12060
taatccttct gttgacttgt cattgataac atccagtctt cgtcaggatt gcaaagaatt  12120
atagaaggga tcccaccttt tattttcttc ttttttccat atttagggtt gacagtgaaa  12180
tcagactggc aacctattaa ttgcttccac aatgggacga acttgaaggg gatgtcgtcg  12240
atgatattat aggtggcgtg ttcatcgtag ttggtgaaat cgatggtacc gttccaatag  12300
ttgtgtcgtc cgagacttct agcccaggtg gtctttccgg tacgagttgg tccgcagatg  12360
tagaggctgg ggtgtcggat tccattcctt ccattgtcct tgttaaatcg gccatccatt  12420
caaggtcaga ttgagcttgt tggtatgaga caggatgtat gtaagtataa gcgtctatgc  12480
ttacatggta tagatgggtt tccctccagg agtgtagatc ttcgtggcag cgaagatctg  12540
attctgtgaa gggcgacaca tacggttcag gttgtggagg gaataatttg ttggctgaat  12600
attccagcca ttgaagcttt gttgcccatt catgagggaa ttcttccttg atcatgtcaa  12660
gatattcctc cttagacgtt gcagtctgga taatagttct ccatcgtgcg tcagatttgc  12720
gaggagaaac cttatgatct cggaaatctc ctctggtttt aatatctccg tcctttgata  12780
tgtaatcaag gacttgttta gagtttctag ctggctggat attagggtga tttccttcaa  12840
aatcgaaaaa agaaggatcc ctaatacaag gttttttatc aagctggaga agagcatgat  12900
```

-continued

```
agtgggtagt gccatcttga tgaagctcag aagcaacacc aaggaagaaa ataagaaaag  12960
gtgtgagttt ctcccagaga aactggaata aatcatctct ttgagatgag cacttgggat  13020
aggtaaggaa aacatattta gattggagtc tgaagttctt actagcagaa ggcatgttgt  13080
tgtgactccg aggggttgcc tcaaactcta tcttataacc ggcgtggagg catggaggca  13140
ggggtatttt ggtcatttta atagatagtg gaaaatgacg tggaatttac ttaaagacga  13200
agtctttgcg acaagggggg gcccacgccg aatttaatat taccggcgtg gcccccccctt  13260
atcgcgagtg ctttagcacg agcggtccag atttaaagta gaaaatttcc cgcccactag  13320
ggttaaaggt gttcacacta taaaagcata tacgatgtga tggtatttga tggagcgtat  13380
attgtatcag gtatttccgt tggatacgaa ttattcgtac gaccctcata gtttaaacta  13440
tcagtgtttg acaggatata ttggcgggta aacctaagag aaaagagcgt ttattagaat  13500
aacggatatt taaaagggcg tgaaaaggtt tatccgttcg tccatttgta tgtgcatgcc  13560
aaccacaggg ttcccctcgg gatcaaagta ctttgatcca acccctccgc tgctatagtg  13620
cagtcggctt ctgacgttca gtgcagccgt cttctgaaaa cgacatgtcg cacaagtcct  13680
aagttacgcg acaggctgcc gccctgccct tttcctggcg ttttcttgtc gcgtgtttta  13740
gtcgcataaa gtagaatact tgcgactaga accggagaca ttacgccatg aacaagagcg  13800
ccgccgctgg cctgctgggc tatgcccgcg tcagcaccga cgaccaggac ttgaccaacc  13860
aacgggccga actgcacgcg gccggctgca ccaagctgtt ttccgagaag atcaccggca  13920
ccaggcgcga ccgcccggag ctggccagga tgcttgacca cctacgccct ggcgacgttg  13980
tgacagtgac caggctagac cgcctggccc gcagcacccg cgacctactg gacattgccg  14040
agcgcatcca ggaggccggc gcgggcctgc gtagcctggc agagccgtgg gccgacacca  14100
ccacgccggc cggccgcatg gtgttgaccg tgttcgccgg cattgccgag ttcgagcgtt  14160
ccctaatcat cgaccgcacc cggagcgggc gcgaggccgc caaggcccga ggcgtgaagt  14220
ttggcccccg ccctaccctc accccggcac agatcgcgca cgcccgcgag ctgatcgacc  14280
aggaaggccg caccgtgaaa gaggcggctg cactgcttgg cgtgcatcgc tcgaccctgt  14340
accgcgcact tgagcgcagc gaggaagtga cgcccaccga ggccaggcgg cgcggtgcct  14400
tccgtgagga cgcattgacc gaggccgacg ccctggcggc cgccgagaat gaacgccaag  14460
aggaacaagc atgaaaccgc accaggacgg ccaggacgaa ccgtttttca ttaccgaaga  14520
gatcgaggcg gagatgatcg cggccgggta cgtgttcgag ccgcccgcgc acggctcaac  14580
cgtgcggctg catgaaatcc tggccggttt gtctgatgcc aagctggcgg cctggccggc  14640
cagcttggcc gctgaagaaa ccgagcgccg ccgtctaaaa aggtgatgtg tatttgagta  14700
aaacagcttg cgtcatgcgg tcgctgcgta tatgatgcga tgagtaaata aacaaatacg  14760
caaggggaac gcatgaaggt tatcgctgta cttaaccaga aaggcgggtc aggcaagacg  14820
accatcgcaa cccatctagc ccgcgccctg caactcgccg gggccgatgt tctgttagtc  14880
gattccgatc cccagggcag tgcccgcgat tgggcggccg tgcgggaaga tcaaccgcta  14940
accgttgtcg gcatcgaccg cccgacgatt gaccgcgacg tgaaggccat cggccggcgc  15000
gacttcgtag tgatcgacgg agcgccccag gcggcggact tggctgtgtc cgcgatcaag  15060
gcagccgact tcgtgctgat tccggtgcag ccaagccctt acgacatatg ggccaccgcc  15120
gacctggtgg agctggttaa gcagcgcatt gaggtcacgg atggaaggct acaagcggcc  15180
tttgtcgtgt cgcgggcgat caaaggcacg cgcatcggcg gtgaggttgc cgaggcgctg  15240
```

-continued gccgggtacg agctgcccat tcttgagtcc cgtatcacgc agcgcgtgag ctacccaggc 15300
actgccgccg ccggcacaac cgttcttgaa tcagaacccg agggcgacgc tgcccgcgag 15360
gtccaggcgc tggccgctga aattaaatca aaactcattt gagttaatga ggtaaagaga 15420
aaatgagcaa aagcacaaac acgctaagtg ccggccgtcc gagcgcacgc agcagcaagg 15480
ctgcaacgtt ggccagcctg gcagacacgc cagccatgaa gcgggtcaac tttcagttgc 15540
cggcggagga tcacaccaag ctgaagatgt acgcggtacg ccaaggcaag accattaccg 15600
agctgctatc tgaatacatc gcgcagctac cagagtaaat gagcaaatga ataaatgagt 15660
agatgaattt tagcggctaa aggaggcggc atggaaaatc aagaacaacc aggcaccgac 15720
gccgtggaat gccccatgtg tggaggaacg ggcggttggc caggcgtaag cggctgggtt 15780
gtctgccggc cctgcaatgg cactggaacc cccaagcccg aggaatcggc gtgacggtcg 15840
caaaccatcc ggcccggtac aaatcggcgc ggcgctgggt gatgacctgg tggagaagtt 15900
gaaggccgcg caggccgccc agcggcaacg catcgaggca gaagcacgcc ccggtgaatc 15960
gtggcaagcg gccgctgatc gaatccgcaa agaatcccgg caaccgccgg cagccggtgc 16020
gccgtcgatt aggaagccgc ccaagggcga cgagcaacca gattttttcg ttccgatgct 16080
ctatgacgtg ggcacccgcg atagtcgcag catcatggac gtggccgttt tccgtctgtc 16140
gaagcgtgac cgacgagctg gcgaggtgat ccgctacgag cttccagacg ggcacgtaga 16200
ggtttccgca gggccggccg gc 16222

<210> SEQ ID NO 38
<211> LENGTH: 40
<212> TYPE: DNA
<213> ORGANISM: Nicotiana benthamiana

<400> SEQUENCE: 38
gttttggtag tagcgactcc atggggcata agtttagaat 40

<210> SEQ ID NO 39
<211> LENGTH: 39
<212> TYPE: DNA
<213> ORGANISM: artificial
<220> FEATURE:
<223> OTHER INFORMATION: synthetic oligonucleotide

<400> SEQUENCE: 39
gttttggtag tagcgactca tggggcataa gtttagaat 39

<210> SEQ ID NO 40
<211> LENGTH: 40
<212> TYPE: DNA
<213> ORGANISM: artificial
<220> FEATURE:
<223> OTHER INFORMATION: synthetic oligonucleotide

<400> SEQUENCE: 40
ttttggtagt agcgactccc atggggcata agtttagaat 40

<210> SEQ ID NO 41
<211> LENGTH: 33
<212> TYPE: DNA
<213> ORGANISM: artificial
<220> FEATURE:
<223> OTHER INFORMATION: synthetic oligonucleotide

<400> SEQUENCE: 41
gttttggtag tagatggggc ataagtttag aat 33

<210> SEQ ID NO 42
<211> LENGTH: 31
<212> TYPE: DNA
<213> ORGANISM: artificial
<220> FEATURE:
<223> OTHER INFORMATION: synthetic oligonucleotide

<400> SEQUENCE: 42
gttttggtag tatggggcat aagtttagaa t 31

<210> SEQ ID NO 43
<211> LENGTH: 38
<212> TYPE: DNA
<213> ORGANISM: artificial
<220> FEATURE:
<223> OTHER INFORMATION: synthetic oligonucleotide

<400> SEQUENCE: 43
gttttggtag tagcgactat ggggcataag tttagaat 38

<210> SEQ ID NO 44
<211> LENGTH: 40
<212> TYPE: DNA
<213> ORGANISM: artificial
<220> FEATURE:
<223> OTHER INFORMATION: synthetic oligonucleotide

<400> SEQUENCE: 44
gttttggtag tagcgactcc aatggggcat aagtttagaa 40

<210> SEQ ID NO 45
<211> LENGTH: 37
<212> TYPE: DNA
<213> ORGANISM: artificial
<220> FEATURE:
<223> OTHER INFORMATION: synthetic oligonucleotide

<400> SEQUENCE: 45
gttttggtag tagcgacatg gggcataagt ttagaat 37

<210> SEQ ID NO 46
<211> LENGTH: 19
<212> TYPE: DNA
<213> ORGANISM: artificial
<220> FEATURE:
<223> OTHER INFORMATION: synthetic oligonucleotide

<400> SEQUENCE: 46
tggggcataa gtttagaat 19

<210> SEQ ID NO 47
<211> LENGTH: 38
<212> TYPE: DNA
<213> ORGANISM: artificial
<220> FEATURE:
<223> OTHER INFORMATION: synthetic oligonucleotide

<400> SEQUENCE: 47
gttttggtag tagcgactct ggggcataag tttagaat 38

<210> SEQ ID NO 48
<211> LENGTH: 36
<212> TYPE: DNA
<213> ORGANISM: artificial
<220> FEATURE:

-continued

<223> OTHER INFORMATION: synthetic oligonucleotide

<400> SEQUENCE: 48
gttttggtag tagcgaatgg ggcataagtt tagaat 36

<210> SEQ ID NO 49
<211> LENGTH: 15
<212> TYPE: DNA
<213> ORGANISM: artificial
<220> FEATURE:
<223> OTHER INFORMATION: synthetic oligonucleotide

<400> SEQUENCE: 49
gttttggtag tagcg 15

<210> SEQ ID NO 50
<211> LENGTH: 34
<212> TYPE: DNA
<213> ORGANISM: artificial
<220> FEATURE:
<223> OTHER INFORMATION: synthetic oligonucleotide

<400> SEQUENCE: 50
gttttggtag tagcatgggg cataagttta gaat 34

<210> SEQ ID NO 51
<211> LENGTH: 20
<212> TYPE: DNA
<213> ORGANISM: artificial
<220> FEATURE:
<223> OTHER INFORMATION: synthetic oligonucleotide

<400> SEQUENCE: 51
gttttggtag tagcgactcc 20

<210> SEQ ID NO 52
<211> LENGTH: 20
<212> TYPE: DNA
<213> ORGANISM: artificial
<220> FEATURE:
<223> OTHER INFORMATION: synthetic oligonucleotide

<400> SEQUENCE: 52
atggggcata agtttagaat 20

<210> SEQ ID NO 53
<211> LENGTH: 28
<212> TYPE: DNA
<213> ORGANISM: artificial
<220> FEATURE:
<223> OTHER INFORMATION: synthetic oligonucleotide

<400> SEQUENCE: 53
gttttggtat ggggcataag tttagaat 28

<210> SEQ ID NO 54
<211> LENGTH: 40
<212> TYPE: DNA
<213> ORGANISM: artificial
<220> FEATURE:
<223> OTHER INFORMATION: synthetic oligonucleotide

<400> SEQUENCE: 54
gttttggtag tagcgactcc tatggggcat aagtttagaa 40

<210> SEQ ID NO 55
<211> LENGTH: 34
<212> TYPE: DNA
<213> ORGANISM: artificial
<220> FEATURE:
<223> OTHER INFORMATION: synthetic oligonucleotide

<400> SEQUENCE: 55
cttctggtca tggcatgggg cataagttta gaat 34

<210> SEQ ID NO 56
<211> LENGTH: 31
<212> TYPE: DNA
<213> ORGANISM: artificial
<220> FEATURE:
<223> OTHER INFORMATION: synthetic oligonucleotide

<400> SEQUENCE: 56
gttttggtag tagcgggcat aagtttagaa t 31

<210> SEQ ID NO 57
<211> LENGTH: 23
<212> TYPE: DNA
<213> ORGANISM: artificial
<220> FEATURE:
<223> OTHER INFORMATION: synthetic oligonucleotide

<400> SEQUENCE: 57
gttttggggc ataagtttag aat 23

<210> SEQ ID NO 58
<211> LENGTH: 39
<212> TYPE: DNA
<213> ORGANISM: artificial
<220> FEATURE:
<223> OTHER INFORMATION: synthetic oligonucleotide

<400> SEQUENCE: 58
tcaatcatag tgcgagaaca tcggtgagat ttgtcatgt 39

<210> SEQ ID NO 59
<211> LENGTH: 21
<212> TYPE: DNA
<213> ORGANISM: artificial
<220> FEATURE:
<223> OTHER INFORMATION: synthetic oligonucleotide

<400> SEQUENCE: 59
catggggcat aagtttagaa t 21

<210> SEQ ID NO 60
<211> LENGTH: 16
<212> TYPE: DNA
<213> ORGANISM: artificial
<220> FEATURE:
<223> OTHER INFORMATION: synthetic oligonucleotide

<400> SEQUENCE: 60
gttttggtag tagaat 16

<210> SEQ ID NO 61
<211> LENGTH: 36
<212> TYPE: DNA
<213> ORGANISM: artificial
<220> FEATURE:
<223> OTHER INFORMATION: synthetic oligonucleotide

<400> SEQUENCE: 61
gttttggtag tagcgcatgg ggcataagtt tagaat 36

<210> SEQ ID NO 62
<211> LENGTH: 13
<212> TYPE: DNA
<213> ORGANISM: artificial
<220> FEATURE:
<223> OTHER INFORMATION: synthetic oligonucleotide

<400> SEQUENCE: 62
gttttggtag aat 13

<210> SEQ ID NO 63
<211> LENGTH: 35
<212> TYPE: DNA
<213> ORGANISM: artificial
<220> FEATURE:
<223> OTHER INFORMATION: synthetic oligonucleotide

<400> SEQUENCE: 63
gttttggtag tagcgatggg gcataagttt agaat 35

<210> SEQ ID NO 64
<211> LENGTH: 34
<212> TYPE: DNA
<213> ORGANISM: artificial
<220> FEATURE:
<223> OTHER INFORMATION: synthetic oligonucleotide

<400> SEQUENCE: 64
gttttggtag tagcgactgg cataagttta gaat 34

<210> SEQ ID NO 65
<211> LENGTH: 39
<212> TYPE: DNA
<213> ORGANISM: artificial
<220> FEATURE:
<223> OTHER INFORMATION: synthetic oligonucleotide

<400> SEQUENCE: 65
gttttggtag tagcgactcc tggggcataa gtttagaat 39

<210> SEQ ID NO 66
<211> LENGTH: 15
<212> TYPE: DNA
<213> ORGANISM: artificial
<220> FEATURE:
<223> OTHER INFORMATION: synthetic oligonucleotide

<400> SEQUENCE: 66
gcataagttt agaat 15

<210> SEQ ID NO 67
<211> LENGTH: 40
<212> TYPE: DNA
<213> ORGANISM: artificial
<220> FEATURE:
<223> OTHER INFORMATION: synthetic oligonucleotide

<400> SEQUENCE: 67
gttttggtag tagcgactct atggggcata agtttagaat 40

<210> SEQ ID NO 68
<211> LENGTH: 40

<212> TYPE: DNA
<213> ORGANISM: artificial
<220> FEATURE:
<223> OTHER INFORMATION: synthetic oligonucleotide

<400> SEQUENCE: 68
ttttggtagt agcgactcac atggggcata agtttagaat 40

<210> SEQ ID NO 69
<211> LENGTH: 30
<212> TYPE: DNA
<213> ORGANISM: artificial
<220> FEATURE:
<223> OTHER INFORMATION: synthetic oligonucleotide

<400> SEQUENCE: 69
gttttggtag tagcgacata agtttagaat 30

<210> SEQ ID NO 70
<211> LENGTH: 40
<212> TYPE: DNA
<213> ORGANISM: artificial
<220> FEATURE:
<223> OTHER INFORMATION: synthetic oligonucleotide

<400> SEQUENCE: 70
gttttggtag tagcgactcc atggggcata agtgtagaat 40

<210> SEQ ID NO 71
<211> LENGTH: 40
<212> TYPE: DNA
<213> ORGANISM: artificial
<220> FEATURE:
<223> OTHER INFORMATION: synthetic oligonucleotide

<400> SEQUENCE: 71
gttttggtag tagcgactcc atggggcata agtttagaag 40

<210> SEQ ID NO 72
<211> LENGTH: 40
<212> TYPE: DNA
<213> ORGANISM: artificial
<220> FEATURE:
<223> OTHER INFORMATION: synthetic oligonucleotide

<400> SEQUENCE: 72
gttttggtag tagcgactcc atggggcata agttgagaat 40

<210> SEQ ID NO 73
<211> LENGTH: 30
<212> TYPE: DNA
<213> ORGANISM: artificial
<220> FEATURE:
<223> OTHER INFORMATION: synthetic oligonucleotide

<400> SEQUENCE: 73
gttttggtag atggggcata agtttagaat 30

<210> SEQ ID NO 74
<211> LENGTH: 40
<212> TYPE: DNA
<213> ORGANISM: artificial
<220> FEATURE:
<223> OTHER INFORMATION: synthetic oligonucleotide

<400> SEQUENCE: 74

-continued gttttggtag tagcgactcc aatagtatgg ccgtatactt 40

<210> SEQ ID NO 75
<211> LENGTH: 23
<212> TYPE: DNA
<213> ORGANISM: artificial
<220> FEATURE:
<223> OTHER INFORMATION: synthetic oligonucleotide

<400> SEQUENCE: 75
gttttggggc ataagtttag aat 23

<210> SEQ ID NO 76
<211> LENGTH: 29
<212> TYPE: DNA
<213> ORGANISM: artificial
<220> FEATURE:
<223> OTHER INFORMATION: synthetic oligonucleotide

<400> SEQUENCE: 76
gttttggtag tagcgactcc gtttagaat 29

<210> SEQ ID NO 77
<211> LENGTH: 40
<212> TYPE: DNA
<213> ORGANISM: artificial
<220> FEATURE:
<223> OTHER INFORMATION: synthetic oligonucleotide

<400> SEQUENCE: 77
gttttggtag tagcgaatcc atggggcata agtttagaat 40

<210> SEQ ID NO 78
<211> LENGTH: 57
<212> TYPE: DNA
<213> ORGANISM: artificial
<220> FEATURE:
<223> OTHER INFORMATION: synthetic oligonucleotide

<400> SEQUENCE: 78
acactctttc cctacacgac gctcttccga tctcaattgc cgttaatttg agagtcc 57

<210> SEQ ID NO 79
<211> LENGTH: 57
<212> TYPE: DNA
<213> ORGANISM: artificial
<220> FEATURE:
<223> OTHER INFORMATION: synthetic oligonucleotide

<400> SEQUENCE: 79
acactctttc cctacacgac gctcttccga tctcgtttgc cgttaatttg agagtcc 57

<210> SEQ ID NO 80
<211> LENGTH: 57
<212> TYPE: DNA
<213> ORGANISM: artificial
<220> FEATURE:
<223> OTHER INFORMATION: synthetic oligonucleotide

<400> SEQUENCE: 80
acactctttc cctacacgac gctcttccga tctttcctgc cgttaatttg agagtcc 57

<210> SEQ ID NO 81
<211> LENGTH: 57
<212> TYPE: DNA
<213> ORGANISM: artificial

<220> FEATURE:
<223> OTHER INFORMATION: synthetic oligonucleotide

<400> SEQUENCE: 81
acactctttc cctacacgac gctcttccga tctgtcgtgc cgttaatttg agagtcc 57

<210> SEQ ID NO 82
<211> LENGTH: 57
<212> TYPE: DNA
<213> ORGANISM: artificial
<220> FEATURE:
<223> OTHER INFORMATION: synthetic oligonucleotide

<400> SEQUENCE: 82
acactctttc cctacacgac gctcttccga tctgatttgc cgttaatttg agagtcc 57

<210> SEQ ID NO 83
<211> LENGTH: 56
<212> TYPE: DNA
<213> ORGANISM: artificial
<220> FEATURE:
<223> OTHER INFORMATION: synthetic oligonucleotide

<400> SEQUENCE: 83
gactggagtt cagacgtgtg ctcttccgat cttgctatgc tcgtgatcat aaattc 56

<210> SEQ ID NO 84
<211> LENGTH: 56
<212> TYPE: DNA
<213> ORGANISM: artificial
<220> FEATURE:
<223> OTHER INFORMATION: synthetic oligonucleotide

<400> SEQUENCE: 84
gactggagtt cagacgtgtg ctcttccgat ctatagatgc tcgtgatcat aaattc 56

<210> SEQ ID NO 85
<211> LENGTH: 56
<212> TYPE: DNA
<213> ORGANISM: artificial
<220> FEATURE:
<223> OTHER INFORMATION: synthetic oligonucleotide

<400> SEQUENCE: 85
gactggagtt cagacgtgtg ctcttccgat ctccccatgc tcgtgatcat aaattc 56

<210> SEQ ID NO 86
<211> LENGTH: 56
<212> TYPE: DNA
<213> ORGANISM: artificial
<220> FEATURE:
<223> OTHER INFORMATION: synthetic oligonucleotide

<400> SEQUENCE: 86
gactggagtt cagacgtgtg ctcttccgat cttgaaatgc tcgtgatcat aaattc 56

<210> SEQ ID NO 87
<211> LENGTH: 56
<212> TYPE: DNA
<213> ORGANISM: artificial
<220> FEATURE:
<223> OTHER INFORMATION: synthetic oligonucleotide

<400> SEQUENCE: 87
gactggagtt cagacgtgtg ctcttccgat ctcgctatgc tcgtgatcat aaattc 56

<210> SEQ ID NO 88
<211> LENGTH: 19658
<212> TYPE: DNA
<213> ORGANISM: artificial
<220> FEATURE:
<223> OTHER INFORMATION: synthetic oligonucleotide

<400> SEQUENCE: 88
ggaaagcaga aagacgacct ggtagaaacc tgcattcggt taaacaccac gcacgttgcc 60
atgcagcgta cgaagaaggc caagaacggc cgcctggtga cggtatccga gggtgaagcc 120
ttgattagcc gctacaagat cgtaaagagc gaaaccgggc ggccggagta catcgagatc 180
gagctagctg attggatgta ccgcgagatc acagaaggca agaacccgga cgtgctgacg 240
gttcaccccg attacttttt gatcgatccc ggcatcggcc gttttctcta ccgcctggca 300
cgccgcgccg caggcaaggc agaagccaga tggttgttca agacgatcta cgaacgcagt 360
ggcagcgccg gagagttcaa gaagttctgt ttcaccgtgc gcaagctgat cgggtcaaat 420
gacctgccgg agtacgattt gaaggaggag gcggggcagg ctggcccgat cctagtcatg 480
cgctaccgca acctgatcga gggcgaagca tccgccggtt cctaatgtac ggagcagatg 540
ctagggcaaa ttgccctagc aggggaaaaa ggtcgaaaag gcctctttcc tgtggatagc 600
acgtacattg ggaacccaaa gccgtacatt gggaaccgga acccgtacat tgggaaccca 660
aagccgtaca ttgggaaccg gtcacacatg taagtgactg atataaaaga gaaaaaaggc 720
gatttttccg cctaaaactc tttaaaactt attaaaactc ttaaaacccg cctggcctgt 780
gcataactgt ctggccagcg cacagccgaa gagctgcaaa aagcgcctac ccttcggtcg 840
ctgcgctccc tacgccccgc cgcttcgcgt cggcctatcg cggccgctgg ccgctcaaaa 900
atggctggcc tacggccagg caatctacca gggcgcggac aagccgcgcc gtcgccactc 960
gaccgccggc gcccacatca aggcaccctg cctcgcgcgt ttcggtgatg acggtgaaaa 1020
cctctgacac atgcagctcc cggaaacggt cacagcttgt ctgtaagcgg atgccgggag 1080
cagacaagcc cgtcagggcg cgtcagcggg tgttggcggg tgtcggggcg cagccatgac 1140
ccagtcacgt agcgatagcg gagtgtatac tggcttaact atgcggcatc agagcagatt 1200
gtactgagag tgcaccatat gcggtgtgaa ataccgcaca gatgcgtaag gagaaaatac 1260
cgcatcaggc gctcttccgc ttcctcgctc actgactcgc tgcgctcggt cgttcggctg 1320
cggcgagcgg tatcagctca ctcaaaggcg gtaatacggt tatccacaga atcaggggat 1380
aacgcaggaa agaacatgtg agcaaaaggc cagcaaaagg ccaggaaccg taaaaaggcc 1440
gcgttgctgg cgtttttcca taggctccgc ccccctgacg agcatcacaa aaatcgacgc 1500
tcaagtcaga ggtggcgaaa cccgacagga ctataaagat accaggcgtt tccccctgga 1560
agctccctcg tgcgctctcc tgttccgacc ctgccgctta ccggatacct gtccgccttt 1620
ctcccttcgg gaagcgtggc gctttctcat agctcacgct gtaggtatct cagttcggtg 1680
taggtcgttc gctccaagct gggctgtgtg cacgaacccc ccgttcagcc cgaccgctgc 1740
gccttatccg gtaactatcg tcttgagtcc aacccggtaa gacacgactt atcgccactg 1800
gcagcagcca ctggtaacag gattagcaga gcgaggtatg taggcggtgc tacagagttc 1860
ttgaagtggt ggcctaacta cggctacact agaaggacag tatttggtat ctgcgctctg 1920
ctgaagccag ttaccttcgg aaaaagagtt ggtagctctt gatccggcaa acaaaccacc 1980
gctggtagcg gtggtttttt tgtttgcaag cagcagatta cgcgcagaaa aaaaggatct 2040
caagaagatc ctttgatctt ttctacgggg tctgacgctc agtggaacga aaactcacgt 2100
taagggattt tggtcatgca ttctaggtac taaaacaatt catccagtaa aatataatat 2160
tttattttct cccaatcagg cttgatcccc agtaagtcaa aaaatagctc gacatactgt 2220
tcttccccga tatcctccct gatcgaccgg acgcagaagg caatgtcata ccacttgtcc 2280
gccctgccgc ttctcccaag atcaataaag ccacttactt tgccatcttt cacaaagatg 2340
ttgctgtctc ccaggtcgcc gtgggaaaag acaagttcct cttcgggctt ttccgtcttt 2400
aaaaaatcat acagctcgcg cggatcttta aatggagtgt cttcttccca gttttcgcaa 2460
tccacatcgg ccagatcgtt attcagtaag taatccaatt cggctaagcg gctgtctaag 2520
ctattcgtat agggacaatc cgatatgtcg atggagtgaa agagcctgat gcactccgca 2580
tacagctcga taatcttttc agggctttgt tcatcttcat actcttccga gcaaaggacg 2640
ccatcggcct cactcatgag cagattgctc cagccatcat gccgttcaaa gtgcaggacc 2700
tttggaacag gcagctttcc ttccagccat agcatcatgt ccttttcccg ttccacatca 2760
taggtggtcc ctttataccg gctgtccgtc atttttaaat ataggttttc attttctccc 2820
accagcttat ataccttagc aggagacatt ccttccgtat cttttacgca gcggtatttt 2880
tcgatcagtt ttttcaattc cggtgatatt ctcattttag ccatttatta tttccttcct 2940
cttttctaca gtatttaaag ataccccaag aagctaatta taacaagacg aactccaatt 3000
cactgttcct tgcattctaa aaccttaaat accagaaaac agctttttca aagttgtttt 3060
caaagttggc gtataacata gtatcgacgg agccgatttt gaaaccgcgg tgatcacagg 3120
cagcaacgct ctgtcatcgt tacaatcaac atgctaccct ccgcgagatc atccgtgttt 3180
caaacccggc agcttagttg ccgttcttcc gaatagcatc ggtaacatga gcaaagtctg 3240
ccgccttaca acggctctcc cgctgacgcc gtcccggact gatgggctgc ctgtatcgag 3300
tggtgatttt gtgccgagct gccggtcggg gagctgttgg ctggctggtg gcaggatata 3360
ttgtggtgta aacaaattga cgcttagaca acttaataac acattgcgga cgtttttaat 3420
gtagagctca aagtttaacg cgttagcaga aggcatgttg ttgtgactcc gaggggttgc 3480
ctcaaactct atcttataac cggcgtggag gcatggaggc aggggtattt tggtcatttt 3540
aatagatagt ggaaaatgac gtggaattta cttaaagacg aagtctttgc gacaaggggg 3600
ggcccacgcc gaatttaata ttaccggcgt ggcccccccct tatcgcgagt gctttagcac 3660
gagcggtcca gatttaaagt agaaaatttc ccgcccacta gggttaaagg tgttcacact 3720
ataaaagcat atacgatgtg atggtatttg atggagcgta tattgtatca ggtatttccg 3780
ttggatacga attattcgta cgaccctcgg taccgatcgg cgcgccagat ttgccttttc 3840
aatttcagaa agaatgctaa cccacagatg gttagagagg cttacgcagc aggtatcatc 3900
aagacgatct acccgagcaa taatctccag gaaatcaaat accttcccaa gaaggttaaa 3960
gatgcagtca aaagattcag gactaactgc atcaagaaca cagagaaaga tatatttctc 4020
aagatcagaa gtactattcc agtatggacg attcaaggct tgcttcacaa accaaggcaa 4080
gtaatagaga ttggagtctc taaaaaggta gttcccactg aatcaaaggc catggagtca 4140
aagattcaaa tagaggacct aacagaactc gccgtaaaga ctggcgaaca gttcatacag 4200
agtctcttac gactcaatga caagaagaaa atcttcgtca acatggtgga gcacgacaca 4260
cttgtctact ccaaaaatat caaagataca gtctcagaag accaaagggc aattgagact 4320
tttcaacaaa gggtaatatc cggaaacctc ctcggattcc attgcccagc tatctgtcac 4380
tttattgtga agatagtgga aaaggaaggt ggctcctaca aatgccatca ttgcgataaa 4440

-continued

```
ggaaaggcca tcgttgaaga tgcctctgcc gacagtggtc ccaaagatgg acccccaccc   4500
acgaggagca tcgtggaaaa agaagacgtt ccaaccacgt cttcaaagca agtggattga   4560
tgtgatatct ccactgacgt aagggatgac gcacaatccc actatccttc gcaagaccct   4620
tcctctatat aaggaagttc atttcatttg gagagaacac gggggactcc tgcaggtaga   4680
tcgctcgtcg acatggataa gaagtactct atcggactcg atatcggaac taactctgtg   4740
ggatgggctg tgatcaccga tgagtacaag gtgccatcta agaagttcaa ggttctcgga   4800
aacaccgata ggcactctat caagaaaaac cttatcggtg ctctcctctt cgattctggt   4860
gaaactgctg aggctaccag actcaagaga accgctagaa gaaggtacac cagaagaaag   4920
aacaggatct gctacctcca agagatcttc tctaacgaga tggctaaagt ggatgattca   4980
ttcttccaca ggctcgaaga gtcattcctc gtggaagaag ataagaagca cgagaggcac   5040
cctatcttcg gaaacatcgt tgatgaggtg gcataccacg agaagtaccc tactatctac   5100
cacctcagaa agaagctcgt tgattctact gataaggctg atctcaggct catctacctc   5160
gctctcgctc acatgatcaa gttcagagga cacttcctca tcgagggtga tctcaaccct   5220
gataactctg atgtggataa gttgttcatc cagctcgtgc agacctacaa ccagcttttc   5280
gaagagaacc ctatcaacgc ttcaggtgtg gatgctaagg ctatcctctc tgctaggctc   5340
tctaagtcaa gaaggcttga gaacctcatt gctcagctcc ctggtgagaa gaagaacgga   5400
cttttcggaa acttgatcgc tctctctctc ggactcaccc ctaacttcaa gtctaacttc   5460
gatctcgctg aggatgcaaa gctccagctc tcaaaggata cctacgatga tgatctcgat   5520
aacctcctcg ctcagatcgg agatcagtac gctgatttgt tcctcgctgc taagaacctc   5580
tctgatgcta tcctcctcag tgatatcctc agagtgaaca ccgagatcac caaggctcca   5640
ctctcagctt ctatgatcaa gagatacgat gagcaccacc aggatctcac acttctcaag   5700
gctcttgtta gacagcagct cccagagaag tacaaagaga ttttcttcga tcagtctaag   5760
aacggatacg ctggttacat cgatggtggt gcatctcaag aagagttcta caagttcatc   5820
aagcctatcc tcgagaagat ggatggaacc gaggaactcc tcgtgaagct caatagagag   5880
gatcttctca gaaagcagag gaccttcgat aacggatcta tccctcatca gatccacctc   5940
ggagagttgc acgctatcct tagaaggcaa gaggatttct acccattcct caaggataac   6000
agggaaaaga ttgagaagat tctcaccttc agaatccctt actacgtggg acctctcgct   6060
agaggaaact caagattcgc ttggatgacc agaaagtctg aggaaaccat caccccttgg   6120
aacttcgaag aggtggtgga taagggtgct agtgctcagt ctttcatcga gaggatgacc   6180
aacttcgata agaaccttcc aaacgagaag gtgctcccta agcactcttt gctctacgag   6240
tacttcaccg tgtacaacga gttgaccaag gttaagtacg tgaccgaggg aatgaggaag   6300
cctgcttttt tgtcaggtga gcaaaagaag gctatcgttg atctcttgtt caagaccaac   6360
agaaaggtga ccgtgaagca gctcaaagag gattacttca agaaaatcga gtgcttcgat   6420
tcagttgaga tttctggtgt tgaggatagg ttcaacgcat ctctcggaac ctaccacgat   6480
ctcctcaaga tcattaagga taaggatttc ttggataacg aggaaaacga ggatatcttg   6540
gaggatatcg ttcttaccct caccctcttt gaagatagag agatgattga agaaaggctc   6600
aagacctacg ctcatctctt cgatgataag gtgatgaagc agttgaagag aagaagatac   6660
actggttggg gaaggctctc aagaaagctc attaacggaa tcagggataa gcagtctgga   6720
aagacaatcc ttgatttcct caagtctgat ggattcgcta acagaaactt catgcagctc   6780
atccacgatg attctctcac ctttaaagag gatatccaga aggctcaggt ttcaggacag   6840
```

-continued ggtgatagtc tccatgagca tatcgctaac ctcgctggat ctcctgcaat caagaaggga 6900
atcctccaga ctgtgaaggt tgtggatgag ttggtgaagg tgatgggaag gcataagcct 6960
gagaacatcg tgatcgaaat ggctagagag aaccagacca ctcagaaggg acagaagaac 7020
tctagggaaa ggatgaagag gatcgaggaa ggtatcaaag agcttggatc tcagatcctc 7080
aaagagcacc ctgttgagaa cactcagctc cagaatgaga agctctacct ctactacctc 7140
cagaacggaa gggatatgta tgtggatcaa gagttggata tcaacaggct ctctgattac 7200
gatgttgatc atatcgtgcc acagtcattc ttgaaggatg attctatcga taacaaggtg 7260
ctcaccaggt ctgataagaa caggggtaag agtgataacg tgccaagtga agaggttgtg 7320
aagaaaatga agaactattg gaggcagctc ctcaacgcta agctcatcac tcagagaaag 7380
ttcgataact tgactaaggc tgagagggga ggactctctg aattggataa ggcaggattc 7440
atcaagaggc agcttgtgga aaccaggcag atcactaagc acgttgcaca gatcctcgat 7500
tctaggatga acaccaagta cgatgagaac gataagttga tcagggaagt gaaggttatc 7560
accctcaagt caaagctcgt gtctgatttc agaaaggatt tccaattcta caaggtgagg 7620
gaaatcaaca actaccacca cgctcacgat gcttacctta acgctgttgt tggaaccgct 7680
ctcatcaaga agtatcctaa gctcgagtca gagttcgtgt acggtgatta caaggtgtac 7740
gatgtgagga agatgatcgc taagtctgag caagagatcg gaaaggctac cgctaagtat 7800
ttcttctact ctaacatcat gaatttcttc aagaccgaga ttaccctcgc taacggtgag 7860
atcagaaaga ggccactcat cgagacaaac ggtgaaacag gtgagatcgt gtgggataag 7920
ggaagggatt tcgctaccgt tagaaaggtg ctctctatgc cacaggtgaa catcgttaag 7980
aaaaccgagg tgcagaccgg tggattctct aaagagtcta tcctccctaa gaggaactct 8040
gataagctca ttgctaggaa gaaggattgg gaccctaaga aatacggtgg tttcgattct 8100
cctaccgtgg cttactctgt tctcgttgtg gctaaggttg agaagggaaa gagtaagaag 8160
ctcaagtctg ttaaggaact tctcggaatc actatcatgg aaaggtcatc tttcgagaag 8220
aacccaatcg atttcctcga ggctaaggga tacaaagagg ttaagaagga tctcatcatc 8280
aagctcccaa agtactcact cttcgaactc gagaacggta gaaagaggat gctcgcttct 8340
gctggtgagc ttcaaaaggg aaacgagctt gctctcccat ctaagtacgt taactttctt 8400
tacctcgctt ctcactacga gaagttgaag ggatctccag aagataacga gcagaagcaa 8460
cttttcgttg agcagcacaa gcactacttg gatgagatca tcgagcagat ctctgagttc 8520
tctaaaaggg tgatcctcgc tgatgcaaac ctcgataagg tgttgtctgc ttacaacaag 8580
cacagagata agcctatcag ggaacaggca gagaacatca tccatctctt cacccttacc 8640
aacctcggtg ctcctgctgc tttcaagtac ttcgatacaa ccatcgatag gaagagatac 8700
acctctacca aagaagtgct cgatgctacc ctcatccatc agtctatcac tggactctac 8760
gagactagga tcgatctctc acagctcggt ggtgattcaa gggctgatcc taagaagaag 8820
aggaaggttt gacgtcgacg atatgaagat gaagatgaaa tatttggtgt gtcaaataaa 8880
aagcttgtgt gcttaagttt gtgttttttt cttggcttgt tgtgttatga atttgtggct 8940
ttttctaata ttaaatgaat gtaagatcac attataatga ataaacaaat gtttctataa 9000
tccattgtga atgttttgtt ggatctcttc tgcagcatat aactactgta tgtgctatgg 9060
tatggactat ggaatatgat taaagataag ccagagctct ggtgacggac ccatggcttc 9120
gttgaacaac ggaaactcga cttgccttcc gcacaataca tcatttcttc ttagcttttt 9180

-continued

```
ttcttcttct tcgttcatac agttttttt tgtttatcag cttacatttt cttgaaccgt   9240
agctttcgtt ttcttctttt taactttcca ttcggagttt ttgtatcttg tttcatagtt   9300
tgtcccagga ttagaatgat taggcatcga accttcaaga atttgattga ataaaacatc   9360
ttcattctta agatatgaag ataatcttca aaaggcccct gggaatctga aagaagagaa   9420
gcaggcccat ttatatggga aagaacaata gtatttctta tataggccca tttaagttga   9480
aaacaatctt caaaagtccc acatcgctta gataagaaaa cgaagctgag tttatataca   9540
gctagagtcg aagtagtgat tgcctacttg ggctgttgca ggttttagag ctagaaatag   9600
caagttaaaa taaggctagt ccgttatcaa cttgaaaaag tggcaccgag tcggtgcttt   9660
ttttcccggg cgcgccgatc atgagcggag aattaaggga gtcacgttat gacccccgcc   9720
gatgacgcgg gacaagccgt tttacgtttg gaactgacag aaccgcaacg ttgaaggagc   9780
cactcagccg cgggtttctg gagtttaatg agctaagcac atacgtcaga aaccattatt   9840
gcgcgttcaa aagtcgccta aggtcactat cagctagcaa atatttcttg tcaaaaatgc   9900
tccactgacg ttccataaat tcccctcggt atccaattag agtctcatat tcactctcaa   9960
tccaaataat ctgcaccgta cctgcagggt ccgagctagg tcacagaagc gctcaggaag  10020
gccgctgaga tagaggcatg gcggccaatg cgggcggcgg tggagcggga ggaggcagcg  10080
gcagcggcag cgtggctgcg ccggcggtgt gccgccccag cggctcgcgg tggacgccga  10140
cgccggagca gatcaggatg ctgaaggagc tgtactacgg ctgcggcatc cggtcgccca  10200
gctcggagca gatccagcgc atcaccgcca tgctgcggca gcacggcaag atcgagggca  10260
agaacgtctt ctactggttc cagaaccaca aggcccgcga gcgccagaag cgccgcctca  10320
ccagcctcga cgtgaacgtg cccgccgccg gcgcggccga cgccaccacc agccaactcg  10380
gcgtcctctc gctgtcgtcg ccgccgcctt caggcgcggc gcctccctcg cccaccctcg  10440
gcttctacgc cgccggcaat ggcggcggat cggctgtgct gctggacacg agttccgact  10500
ggggcagcag cggcgctgcg atggccaccg agacatgctt cctccaggac tacatgggcg  10560
tgacggacac gggcagctcg tcgcagtggc cacgcttctc gtcgtcggac acgataatgg  10620
cggcggccgc ggcgcgggcg gcgacgacgc gggcgcccga gactctccct ctcttcccga  10680
cctgcggcga cgacggcggc agcggtagca gcagctactt gccgttctgg ggtgccgcgt  10740
ccacaactgc cggcgccact tcttccgttg cgatccagca gcaacaccag ctgcaggagc  10800
agtacagctt ttacagcaac agcaacagca cccagctggc cggcaccggc aaccaagacg  10860
tatcggcaac agcagcagca gccgccgccc tggagctgag cctcagctca tggtgctccc  10920
cttaccctgc tgcagggagt atgtgagagc aacgcgagct gccactgctc ttcacttatg  10980
tctctggaat ggaaggagga ggaagtgagc atagcgttgg tgcgttgctg tcattgtcct  11040
aggttagtag ctagtgccag ttactagtaa gcatcaggca taggagtatg tagtagaagc  11100
atgcacgttg ccggccagcc aggctttaga cgggaaaaga atttggtgca gccggctgca  11160
aaacaggatg tttacagccc ccccctcgag ccctagactt gtccatcttc tggattggcc  11220
aagttaatta atgtatgaaa taaaaggatg cacacatagt gacatgctaa tcactataat  11280
gtgggcatca aagttgtgtg ttatgtgtaa ttactaatta tctgaataag agaaagagat  11340
catccatatt tcttatccta aatgaatgtc acgtgtcttt ataattcttt gatgaaccag  11400
atgcatttta ttaaccaatt ccatatacat ataaatatta atcatatata attaatatca  11460
attgggttag caaaacaaat ctagtctagg tgtgttttgc taattattgg gggatagtgc  11520
aaaaagaaat ctacgttctc aataattcag atagaaaact taataaagtg agataattta  11580
```

-continued

```
catagattgc ttttatcctt tgatatatgt gaaaccatgc atgatataag gaaaatagat  11640
agagaaataa ttttttacat cgttgaatat gtaaacaatt taattcaaga agctaggaat  11700
ataaatattg aggagtttat gattagagct ctcccggcgc gccctatgtc gagctgcagg  11760
tcaacggatc aggatattct tgtttaagat gttgaactct atggaggttt gtatgaactg  11820
atgatctagg accggataag ttcccttctt catagcgaac ttattcaaag aatgttttgt  11880
gtatcattct tgttacattg ttattaatga aaaaatatta ttggtcattg gactgaacac  11940
gagtgttaaa tatggaccag gccccaaata agatccattg atatatgaat taaataacaa  12000
gaataaatcg agtcaccaaa ccacttgcct tttttaacga gacttgttca ccaacttgat  12060
acaaaagtca ttatcctatg caaatcaata atcatacaaa aatatccaat aacactaaaa  12120
aattaaaaga aatggataat ttcacaatat gttatacgat aaagaagtta cttttccaag  12180
aaattcactg attttataag cccacttgca ttagataaat ggcaaaaaaa aacaaaaagg  12240
aaaagaaata aagcacgaag aattctagaa aatacgaaat acgcttcaat gcagtgggac  12300
ccacggttca attattgcca attttcagct ccaccgtata tttaaaaaat aaaacgataa  12360
tgctaaaaaa atataaatcg taacgatcgt taaatctcaa cggctggatc ttatgacgac  12420
cgttagaaat tgtggttgtc gacgagtcag taataaacgg cgtcaaagtg gttgcagccg  12480
gcacacacga gtcgtgttta tcaactcaaa gcacaaatac ttttcctcaa cctaaaaata  12540
aggcaattag ccaaaaacaa ctttgcgtgt aaacaacgct caatacacgt gtcattttat  12600
tattagctat tgcttcaccg ccttagcttt ctcgtgacct agtcgtcctc gtcttttctt  12660
cttcttcttc tataaaacaa tacccaaaga gctcttcttc ttcacaattc agatttcaat  12720
ttctcaaaat cttaaaaact ttctctcaat tctctctacc gtgatcaagg taaatttctg  12780
tgttccttat tctctcaaaa tcttcgattt tgttttcgtt cgatcccaat ttcgtatatg  12840
ttctttggtt tagattctgt taatcttaga tcgaacacga ttttctgggt ttgatcgtta  12900
gatatcatct taattctcga ttagggtttc atagatatca tccgatttgt tcaaataatt  12960
tgagttttgt cgaataatta ctcttcgatt tgtgatttct atctagatct ggtgttagtt  13020
tctagtttgt gcgatcgaat ttgtcgatta atctgagttt ttctgattaa caggcctgca  13080
ggatggaaga cgccaaaaac ataaagaaag gcccggcgcc attctatccg ctggaagatg  13140
gaaccgctgg agagcaactg cataaggcta tgaagagata cgccctggtt cctggaacaa  13200
ttgcttttac agatgcacat atcgaggtgg acatcactta cgctgagtac ttcgaaatgt  13260
ccgttcggtt ggcagaagct atgaaacgat atgggctgaa tacaaatcac agaatcgtcg  13320
tatgcagtga aaactctctt caattcttta tgccggtgtt gggcgcgtta tttatcggag  13380
ttgcagttgc gcccgcgaac gacatttata atgaacgtga attgctcaac agtatgggca  13440
tttcgcagcc taccgtggtg ttcgtttcca aaaaggggtt gcaaaaaatt ttgaacgtgc  13500
aaaaaaagct cccaatcatc caaaaaatta ttatcatgga ttctaaaacg gattaccagg  13560
gatttcagtc gatgtacacg ttcgtcacat ctcatctacc tcccggtttt aatgaatacg  13620
attttgtgcc agagtccttc gatagggaca agacaattgc actgatcatg aactcctctg  13680
gatctactgg tctgcctaaa ggtgtcgctc tgcctcatag aactgcctgc gtgagattct  13740
cgcatgccag agatcctatt tttggcaatc aaatcattcc ggatactgcg attttaagtg  13800
ttgttccatt ccatcacggt tttggaatgt ttactacact cggatatttg atatgtggat  13860
ttcgagtcgt cttaatgtat agatttgaag aagagctgtt tctgaggagc cttcaggatt  13920
```

-continued

```
acaagattca aagtgcgctg ctggtgccaa ccctattctc cttcttcgcc aaaagcactc  13980
tgattgacaa atacgattta tctaatttac acgaaattgc ttctggtggc gctcccctct  14040
ctaaggaagt cggggaagcg gttgccaaga ggttccatct gccaggtatc aggcaaggat  14100
atgggctcac tgagactaca tcagctattc tgattacacc cgagggggat gataaaccgg  14160
gcgcggtcgg taaagttgtt ccattttttg aagcgaaggt tgtggatctg gataccggga  14220
aaacgctggg cgttaatcaa agaggcgaac tgtgtgtgag aggtcctatg attatgtccg  14280
gttatgtaaa caatccggaa gcgaccaacg ccttgattga caaggatgga tggctacatt  14340
ctggagacat agcttactgg gacgaagacg aacacttctt catcgttgac cgcctgaagt  14400
ctctgattaa gtacaaaggc tatcaggtgg ctcccgctga attggaatcc atcttgctcc  14460
aacaccccaa catcttcgac gctggtgtcg caggtcttcc cgacgatgac gccggtgaac  14520
ttcccgccgc cgttgttgtt ttggagcacg gaaagacgat gacggaaaaa gagatcgtgg  14580
attacgtcgc cagtcaagta acaaccgcga aaaagttgcg cggaggagtt gtgtttgtgg  14640
acgaagtacc gaaaggtctt accggaaaac tcgacgcaag aaaaatcaga gagatcctca  14700
taaaggccaa gaagggcgga aagatcgccg tgtgactcga ggttcgagta ttatggcatt  14760
gggaaaactg tttttcttgt accatttgtt gtgcttgtaa tttactgtgt tttttattcg  14820
gttttcgcta tcgaactgtg aaatggaaat ggatggagaa gagttaatga atgatatggt  14880
ccttttgttc attctcaaat taatattatt tgtttttttct cttatttgtt gtgtgttgaa  14940
tttgaaatta taagagatat gcaaacattt tgttttgagt aaaaatgtgt caaatcgtgg  15000
cctctaatga ccgaagttaa tatgaggagt aaaacacttg tagttgtgtt agagctcagt  15060
gtttgatcgc cggcggtacc gagtgtactt caagtcagtg ggaaatcaat aaaatgatta  15120
ttttatgaat atatttcatt gtgcaagtag atagaaatta catatgttac ataacacacg  15180
aaataaacaa aaaaagacaa tccaaaaaca aacaccccaa aaaaaataat cactttagat  15240
aaactcgtat gaggagaggc acgttcagtg actcgacgat tcccgagcaa aaaaagtctc  15300
cccgtcacac atgtagtggg tgacgcaatt atctttaaag taatccttct gttgacttgt  15360
cattgataac atccagtctt cgtcaggatt gcaaagaatt atagaaggga tcccaccttt  15420
tattttcttc ttttttccat atttagggtt gacagtgaaa tcagactggc aacctattaa  15480
ttgcttccac aatgggacga acttgaaggg gatgtcgtcg atgatattat aggtggcgtg  15540
ttcatcgtag ttggtgaaat cgatggtacc gttccaatag ttgtgtcgtc cgagacttct  15600
agcccaggtg gtctttccgg tacgagttgg tccgcagatg tagaggctgg ggtgtcggat  15660
tccattcctt ccattgtcct tgttaaatcg gccatccatt caaggtcaga ttgagcttgt  15720
tggtatgaga caggatgtat gtaagtataa gcgtctatgc ttacatggta tagatgggtt  15780
tccctccagg agtgtagatc ttcgtggcag cgaagatctg attctgtgaa gggcgacaca  15840
tacggttcag gttgtggagg gaataatttg ttggctgaat attccagcca ttgaagcttt  15900
gttgcccatt catgagggaa ttcttccttg atcatgtcaa gatattcctc cttagacgtt  15960
gcagtctgga taatagttct ccatcgtgcg tcagatttgc gaggagaaac cttatgatct  16020
cggaaatctc ctctggtttt aatatctccg tcctttgata tgtaatcaag gacttgttta  16080
gagtttctag ctggctggat attagggtga tttccttcaa aatcgaaaaa agaaggatcc  16140
ctaatacaag gtttttttatc aagctggaga agagcatgat agtgggtagt gccatcttga  16200
tgaagctcag aagcaacacc aaggaagaaa ataagaaaag gtgtgagttt ctcccagaga  16260
aactggaata aatcatctct ttgagatgag cacttgggat aggtaaggaa aacatattta  16320
```

-continued gattggagtc tgaagttctt actagcagaa ggcatgttgt tgtgactccg aggggttgcc 16380
tcaaactcta tcttataacc ggcgtggagg catggaggca ggggtatttt ggtcatttta 16440
atagatagtg gaaaatgacg tggaatttac ttaaagacga agtctttgcg acaagggggg 16500
gcccacgccg aatttaatat taccggcgtg gcccccccctt atcgcgagtg ctttagcacg 16560
agcggtccag atttaaagta gaaaatttcc cgcccactag ggttaaaggt gttcacacta 16620
taaaagcata tacgatgtga tggtatttga tggagcgtat attgtatcag gtatttccgt 16680
tggatacgaa ttattcgtac gaccctcata gtttaaacta tcagtgtttg acaggatata 16740
ttggcgggta aacctaagag aaaagagcgt ttattagaat aacggatatt taaaagggcg 16800
tgaaaaggtt tatccgttcg tccatttgta tgtgcatgcc aaccacaggg ttcccctcgg 16860
gatcaaagta ctttgatcca accccctccgc tgctatagtg cagtcggctt ctgacgttca 16920
gtgcagccgt cttctgaaaa cgacatgtcg cacaagtcct aagttacgcg acaggctgcc 16980
gccctgccct tttcctggcg ttttcttgtc gcgtgtttta gtcgcataaa gtagaatact 17040
tgcgactaga accggagaca ttacgccatg aacaagagcg ccgccgctgg cctgctgggc 17100
tatgcccgcg tcagcaccga cgaccaggac ttgaccaacc aacgggccga actgcacgcg 17160
gccggctgca ccaagctgtt ttccgagaag atcaccggca ccaggcgcga ccgcccggag 17220
ctggccagga tgcttgacca cctacgccct ggcgacgttg tgacagtgac caggctagac 17280
cgcctggccc gcagcacccg cgacctactg gacattgccg agcgcatcca ggaggccggc 17340
gcgggcctgc gtagcctggc agagccgtgg gccgacacca ccacgccggc cggccgcatg 17400
gtgttgaccg tgttcgccgg cattgccgag ttcgagcgtt ccctaatcat cgaccgcacc 17460
cggagcgggc gcgaggccgc caaggcccga ggcgtgaagt ttggcccccg ccctaccctc 17520
accccggcac agatcgcgca cgcccgcgag ctgatcgacc aggaaggccg caccgtgaaa 17580
gaggcggctg cactgcttgg cgtgcatcgc tcgaccctgt accgcgcact tgagcgcagc 17640
gaggaagtga cgcccaccga ggccaggcgg cgcggtgcct tccgtgagga cgcattgacc 17700
gaggccgacg ccctggcggc cgccgagaat gaacgccaag aggaacaagc atgaaaccgc 17760
accaggacgg ccaggacgaa ccgtttttca ttaccgaaga gatcgaggcg gagatgatcg 17820
cggccgggta cgtgttcgag ccgcccgcgc acggctcaac cgtgcggctg catgaaatcc 17880
tggccggttt gtctgatgcc aagctggcgg cctggccggc cagcttggcc gctgaagaaa 17940
ccgagcgccg ccgtctaaaa aggtgatgtg tatttgagta aaacagcttg cgtcatgcgg 18000
tcgctgcgta tatgatgcga tgagtaaata aacaaatacg caaggggaac gcatgaaggt 18060
tatcgctgta cttaaccaga aaggcgggtc aggcaagacg accatcgcaa cccatctagc 18120
ccgcgccctg caactcgccg gggccgatgt tctgttagtc gattccgatc cccagggcag 18180
tgcccgcgat tgggcggccg tgcgggaaga tcaaccgcta accgttgtcg gcatcgaccg 18240
cccgacgatt gaccgcgacg tgaaggccat cggccggcgc gacttcgtag tgatcgacgg 18300
agcgccccag gcggcggact tggctgtgtc cgcgatcaag gcagccgact tcgtgctgat 18360
tccggtgcag ccaagccctt acgacatatg ggccaccgcc gacctggtgg agctggttaa 18420
gcagcgcatt gaggtcacgg atggaaggct acaagcggcc tttgtcgtgt cgcgggcgat 18480
caaaggcacg cgcatcggcg gtgaggttgc cgaggcgctg gccgggtacg agctgcccat 18540
tcttgagtcc cgtatcacgc agcgcgtgag ctacccaggc actgccgccg ccggcacaac 18600
cgttcttgaa tcagaacccg agggcgacgc tgcccgcgag gtccaggcgc tggccgctga 18660

```
aattaaatca aaactcattt gagttaatga ggtaaagaga aaatgagcaa aagcacaaac  18720

acgctaagtg ccggccgtcc gagcgcacgc agcagcaagg ctgcaacgtt ggccagcctg  18780

gcagacacgc cagccatgaa gcgggtcaac tttcagttgc cggcggagga tcacaccaag  18840

ctgaagatgt acgcggtacg ccaaggcaag accattaccg agctgctatc tgaatacatc  18900

gcgcagctac cagagtaaat gagcaaatga ataaatgagt agatgaattt tagcggctaa  18960

aggaggcggc atggaaaatc aagaacaacc aggcaccgac gccgtggaat gccccatgtg  19020

tggaggaacg ggcggttggc caggcgtaag cggctgggtt gtctgccggc cctgcaatgg  19080

cactggaacc cccaagcccg aggaatcggc gtgacggtcg caaaccatcc ggcccggtac  19140

aaatcggcgc ggcgctgggt gatgacctgg tggagaagtt gaaggccgcg caggccgccc  19200

agcggcaacg catcgaggca gaagcacgcc ccggtgaatc gtggcaagcg gccgctgatc  19260

gaatccgcaa agaatcccgg caaccgccgg cagccggtgc gccgtcgatt aggaagccgc  19320

ccaagggcga cgagcaacca gatttttcg ttccgatgct ctatgacgtg ggcacccgcg  19380

atagtcgcag catcatggac gtggccgttt tccgtctgtc gaagcgtgac cgacgagctg  19440

gcgaggtgat ccgctacgag cttccagacg ggcacgtaga ggtttccgca gggccggccg  19500

gcatggccag tgtgtgggat tacgacctgg tactgatggc ggtttcccat ctaaccgaat  19560

ccatgaaccg ataccgggaa gggaagggag acaagcccgg ccgcgtgttc cgtccacacg  19620

ttgcggacgt actcaagttc tgccggcgag ccgatggc                        19658
```

<210> SEQ ID NO 89
<211> LENGTH: 19732
<212> TYPE: DNA
<213> ORGANISM: artificial
<220> FEATURE:
<223> OTHER INFORMATION: synthetic oligonucleotide

<400> SEQUENCE: 89

```
aagacgacct ggtagaaacc tgcattcggt taaacaccac gcacgttgcc atgcagcgta     60

cgaagaaggc caagaacggc cgcctggtga cggtatccga gggtgaagcc ttgattagcc    120

gctacaagat cgtaaagagc gaaaccgggc ggccggagta catcgagatc gagctagctg    180

attggatgta ccgcgagatc acagaaggca agaacccgga cgtgctgacg gttcaccccg    240

attacttttt gatcgatccc ggcatcggcc gttttctcta ccgcctggca cgccgcgccg    300

caggcaaggc agaagccaga tggttgttca agacgatcta cgaacgcagt ggcagcgccg    360

gagagttcaa gaagttctgt ttcaccgtgc gcaagctgat cgggtcaaat gacctgccgg    420

agtacgattt gaaggaggag gcggggcagg ctggcccgat cctagtcatg cgctaccgca    480

acctgatcga gggcgaagca tccgccggtt cctaatgtac ggagcagatg ctagggcaaa    540

ttgccctagc aggggaaaaa ggtcgaaaag gcctctttcc tgtggatagc acgtacattg    600

ggaacccaaa gccgtacatt gggaaccgga acccgtacat tgggaaccca aagccgtaca    660

ttgggaaccg gtcacacatg taagtgactg atataaaaga gaaaaaaggc gatttttccg    720

cctaaaactc tttaaaactt attaaaactc ttaaaacccg cctggcctgt gcataactgt    780

ctggccagcg cacagccgaa gagctgcaaa aagcgcctac ccttcggtcg ctgcgctccc    840

tacgccccgc cgcttcgcgt cggcctatcg cggccgctgg ccgctcaaaa atggctggcc    900

tacggccagg caatctacca gggcgcggac aagccgcgcc gtcgccactc gaccgccggc    960

gcccacatca aggcaccctg cctcgcgcgt ttcggtgatg acggtgaaaa cctctgacac   1020

atgcagctcc cggaaacggt cacagcttgt ctgtaagcgg atgccgggag cagacaagcc   1080
```

-continued

```
cgtcagggcg cgtcagcggg tgttggcggg tgtcggggcg cagccatgac ccagtcacgt   1140
agcgatagcg gagtgtatac tggcttaact atgcggcatc agagcagatt gtactgagag   1200
tgcaccatat gcggtgtgaa ataccgcaca gatgcgtaag gagaaaatac cgcatcaggc   1260
gctcttccgc ttcctcgctc actgactcgc tgcgctcggt cgttcggctg cggcgagcgg   1320
tatcagctca ctcaaaggcg gtaatacggt tatccacaga atcaggggat aacgcaggaa   1380
agaacatgtg agcaaaaggc cagcaaaagg ccaggaaccg taaaaaggcc gcgttgctgg   1440
cgtttttcca taggctccgc ccccctgacg agcatcacaa aaatcgacgc tcaagtcaga   1500
ggtggcgaaa cccgacagga ctataaagat accaggcgtt tccccctgga agctccctcg   1560
tgcgctctcc tgttccgacc ctgccgctta ccggatacct gtccgccttt ctcccttcgg   1620
gaagcgtggc gctttctcat agctcacgct gtaggtatct cagttcggtg taggtcgttc   1680
gctccaagct gggctgtgtg cacgaacccc ccgttcagcc cgaccgctgc gccttatccg   1740
gtaactatcg tcttgagtcc aacccggtaa gacacgactt atcgccactg gcagcagcca   1800
ctggtaacag gattagcaga gcgaggtatg taggcggtgc tacagagttc ttgaagtggt   1860
ggcctaacta cggctacact agaaggacag tatttggtat ctgcgctctg ctgaagccag   1920
ttaccttcgg aaaaagagtt ggtagctctt gatccggcaa acaaaccacc gctggtagcg   1980
gtggtttttt tgtttgcaag cagcagatta cgcgcagaaa aaaaggatct caagaagatc   2040
ctttgatctt ttctacgggg tctgacgctc agtggaacga aaactcacgt taagggattt   2100
tggtcatgca ttctaggtac taaaacaatt catccagtaa aatataatat tttattttct   2160
cccaatcagg cttgatcccc agtaagtcaa aaaatagctc gacatactgt tcttccccga   2220
tatcctccct gatcgaccgg acgcagaagg caatgtcata ccacttgtcc gccctgccgc   2280
ttctcccaag atcaataaag ccacttactt tgccatcttt cacaaagatg ttgctgtctc   2340
ccaggtcgcc gtgggaaaag acaagttcct cttcgggctt ttccgtcttt aaaaaatcat   2400
acagctcgcg cggatcttta aatggagtgt cttcttccca gttttcgcaa tccacatcgg   2460
ccagatcgtt attcagtaag taatccaatt cggctaagcg gctgtctaag ctattcgtat   2520
agggacaatc cgatatgtcg atggagtgaa agagcctgat gcactccgca tacagctcga   2580
taatcttttc agggctttgt tcatcttcat actcttccga gcaaaggacg ccatcggcct   2640
cactcatgag cagattgctc cagccatcat gccgttcaaa gtgcaggacc tttggaacag   2700
gcagctttcc ttccagccat agcatcatgt ccttttcccg ttccacatca taggtggtcc   2760
ctttataccg gctgtccgtc atttttaaat ataggttttc attttctccc accagcttat   2820
ataccttagc aggagacatt ccttccgtat cttttacgca gcggtatttt tcgatcagtt   2880
ttttcaattc cggtgatatt ctcattttag ccatttatta tttccttcct cttttctaca   2940
gtatttaaag ataccccaag aagctaatta taacaagacg aactccaatt cactgttcct   3000
tgcattctaa aaccttaaat accagaaaac agctttttca aagttgtttt caaagttggc   3060
gtataacata gtatcgacgg agccgatttt gaaaccgcgg tgatcacagg cagcaacgct   3120
ctgtcatcgt tacaatcaac atgctaccct ccgcgagatc atccgtgttt caaacccggc   3180
agcttagttg ccgttcttcc gaatagcatc ggtaacatga gcaaagtctg ccgccttaca   3240
acggctctcc cgctgacgcc gtcccggact gatgggctgc ctgtatcgag tggtgatttt   3300
gtgccgagct gccggtcggg gagctgttgg ctggctggtg gcaggatata ttgtggtgta   3360
aacaaattga cgcttagaca acttaataac acattgcgga cgtttttaat gtagagctca   3420
```

-continued

```
aagtttaacg cgttagcaga aggcatgttg ttgtgactcc gaggggttgc ctcaaactct   3480
atcttataac cggcgtggag gcatggaggc aggggtattt tggtcatttt aatagatagt   3540
ggaaaatgac gtggaattta cttaaagacg aagtctttgc gacaaggggg ggcccacgcc   3600
gaatttaata ttaccggcgt ggcccccccct tatcgcgagt gctttagcac gagcggtcca   3660
gatttaaagt agaaaatttc ccgcccacta gggttaaagg tgttcacact ataaaagcat   3720
atacgatgtg atggtatttg atggagcgta tattgtatca ggtatttccg ttggatacga   3780
attattcgta cgaccctcgg taccgatcgg cgcgccagat ttgccttttc aatttcagaa   3840
agaatgctaa cccacagatg gttagagagg cttacgcagc aggtatcatc aagacgatct   3900
acccgagcaa taatctccag gaaatcaaat accttcccaa gaaggttaaa gatgcagtca   3960
aaagattcag gactaactgc atcaagaaca cagagaaaga tatatttctc aagatcagaa   4020
gtactattcc agtatggacg attcaaggct tgcttcacaa accaaggcaa gtaatagaga   4080
ttggagtctc taaaaaggta gttcccactg aatcaaaggc catggagtca aagattcaaa   4140
tagaggacct aacagaactc gccgtaaaga ctggcgaaca gttcatacag agtctcttac   4200
gactcaatga caagaagaaa atcttcgtca acatggtgga gcacgacaca cttgtctact   4260
ccaaaaatat caaagataca gtctcagaag accaaagggc aattgagact tttcaacaaa   4320
gggtaatatc cggaaacctc ctcggattcc attgcccagc tatctgtcac tttattgtga   4380
agatagtgga aaaggaaggt ggctcctaca aatgccatca ttgcgataaa ggaaaggcca   4440
tcgttgaaga tgcctctgcc gacagtggtc ccaaagatgg acccccaccc acgaggagca   4500
tcgtggaaaa agaagacgtt ccaaccacgt cttcaaagca agtggattga tgtgatatct   4560
ccactgacgt aagggatgac gcacaatccc actatccttc gcaagaccct tcctctatat   4620
aaggaagttc atttcatttg gagagaacac gggggactcc tgcaggtaga tcgctcgtcg   4680
acatggataa gaagtactct atcggactcg atatcggaac taactctgtg ggatgggctg   4740
tgatcaccga tgagtacaag gtgccatcta agaagttcaa ggttctcgga aacaccgata   4800
ggcactctat caagaaaaac cttatcggtg ctctcctctt cgattctggt gaaactgctg   4860
aggctaccag actcaagaga accgctagaa gaaggtacac cagaagaaag aacaggatct   4920
gctacctcca agagatcttc tctaacgaga tggctaaagt ggatgattca ttcttccaca   4980
ggctcgaaga gtcattcctc gtggaagaag ataagaagca cgagaggcac cctatcttcg   5040
gaaacatcgt tgatgaggtg gcataccacg agaagtaccc tactatctac cacctcagaa   5100
agaagctcgt tgattctact gataaggctg atctcaggct catctacctc gctctcgctc   5160
acatgatcaa gttcagagga cacttcctca tcgagggtga tctcaaccct gataactctg   5220
atgtggataa gttgttcatc cagctcgtgc agacctacaa ccagcttttc gaagagaacc   5280
ctatcaacgc ttcaggtgtg gatgctaagg ctatcctctc tgctaggctc tctaagtcaa   5340
gaaggcttga gaacctcatt gctcagctcc ctggtgagaa gaagaacgga cttttcggaa   5400
acttgatcgc tctctctctc ggactcaccc ctaacttcaa gtctaacttc gatctcgctg   5460
aggatgcaaa gctccagctc tcaaaggata cctacgatga tgatctcgat aacctcctcg   5520
ctcagatcgg agatcagtac gctgatttgt tcctcgctgc taagaacctc tctgatgcta   5580
tcctcctcag tgatatcctc agagtgaaca ccgagatcac caaggctcca ctctcagctt   5640
ctatgatcaa gagatacgat gagcaccacc aggatctcac acttctcaag gctcttgtta   5700
gacagcagct cccagagaag tacaaagaga ttttcttcga tcagtctaag aacggatacg   5760
ctggttacat cgatggtggt gcatctcaag aagagttcta caagttcatc aagcctatcc   5820
```

-continued

```
tcgagaagat ggatggaacc gaggaactcc tcgtgaagct caatagagag gatcttctca   5880
gaaagcagag gaccttcgat aacggatcta tccctcatca gatccacctc ggagagttgc   5940
acgctatcct tagaaggcaa gaggatttct acccattcct caaggataac agggaaaaga   6000
ttgagaagat tctcaccttc agaatccctt actacgtggg acctctcgct agaggaaact   6060
caagattcgc ttggatgacc agaaagtctg aggaaaccat caccccttgg aacttcgaag   6120
aggtggtgga taagggtgct agtgctcagt ctttcatcga gaggatgacc aacttcgata   6180
agaaccttcc aaacgagaag gtgctcccta agcactcttt gctctacgag tacttcaccg   6240
tgtacaacga gttgaccaag gttaagtacg tgaccgaggg aatgaggaag cctgcttttt   6300
tgtcaggtga gcaaaagaag gctatcgttg atctcttgtt caagaccaac agaaaggtga   6360
ccgtgaagca gctcaaagag gattacttca agaaaatcga gtgcttcgat tcagttgaga   6420
tttctggtgt tgaggatagg ttcaacgcat ctctcggaac ctaccacgat ctcctcaaga   6480
tcattaagga taaggatttc ttggataacg aggaaaacga ggatatcttg gaggatatcg   6540
ttcttaccct caccctcttt gaagatagag agatgattga agaaaggctc aagacctacg   6600
ctcatctctt cgatgataag gtgatgaagc agttgaagag aagaagatac actggttggg   6660
gaaggctctc aagaaagctc attaacggaa tcagggataa gcagtctgga aagacaatcc   6720
ttgatttcct caagtctgat ggattcgcta acagaaactt catgcagctc atccacgatg   6780
attctctcac ctttaaagag gatatccaga aggctcaggt ttcaggacag ggtgatagtc   6840
tccatgagca tatcgctaac ctcgctggat ctcctgcaat caagaaggga atcctccaga   6900
ctgtgaaggt tgtggatgag ttggtgaagg tgatgggaag gcataagcct gagaacatcg   6960
tgatcgaaat ggctagagag aaccagacca ctcagaaggg acagaagaac tctagggaaa   7020
ggatgaagag gatcgaggaa ggtatcaaag agcttggatc tcagatcctc aaagagcacc   7080
ctgttgagaa cactcagctc cagaatgaga agctctacct ctactacctc cagaacggaa   7140
gggatatgta tgtggatcaa gagttggata tcaacaggct ctctgattac gatgttgatc   7200
atatcgtgcc acagtcattc ttgaaggatg attctatcga taacaaggtg ctcaccaggt   7260
ctgataagaa caggggtaag agtgataacg tgccaagtga agaggttgtg aagaaaatga   7320
agaactattg gaggcagctc ctcaacgcta agctcatcac tcagagaaag ttcgataact   7380
tgactaaggc tgagagggga ggactctctg aattggataa ggcaggattc atcaagaggc   7440
agcttgtgga aaccaggcag atcactaagc acgttgcaca gatcctcgat tctaggatga   7500
acaccaagta cgatgagaac gataagttga tcagggaagt gaaggttatc accctcaagt   7560
caaagctcgt gtctgatttc agaaaggatt tccaattcta caaggtgagg gaaatcaaca   7620
actaccacca cgctcacgat gcttacctta acgctgttgt tggaaccgct ctcatcaaga   7680
agtatcctaa gctcgagtca gagttcgtgt acggtgatta caaggtgtac gatgtgagga   7740
agatgatcgc taagtctgag caagagatcg gaaaggctac cgctaagtat ttcttctact   7800
ctaacatcat gaatttcttc aagaccgaga ttaccctcgc taacggtgag atcagaaaga   7860
ggccactcat cgagacaaac ggtgaaacag gtgagatcgt gtgggataag ggaagggatt   7920
tcgctaccgt tagaaaggtg ctctctatgc cacaggtgaa catcgttaag aaaaccgagg   7980
tgcagaccgg tggattctct aaagagtcta tcctccctaa gaggaactct gataagctca   8040
ttgctaggaa gaaggattgg gaccctaaga aatacggtgg tttcgattct cctaccgtgg   8100
cttactctgt tctcgttgtg gctaaggttg agaagggaaa gagtaagaag ctcaagtctg   8160
```

-continued

```
ttaaggaact tctcggaatc actatcatgg aaaggtcatc tttcgagaag aacccaatcg   8220
atttcctcga ggctaaggga tacaaagagg ttaagaagga tctcatcatc aagctcccaa   8280
agtactcact cttcgaactc gagaacggta gaaagaggat gctcgcttct gctggtgagc   8340
ttcaaaaggg aaacgagctt gctctcccat ctaagtacgt taactttctt tacctcgctt   8400
ctcactacga gaagttgaag ggatctccag aagataacga gcagaagcaa cttttcgttg   8460
agcagcacaa gcactacttg gatgagatca tcgagcagat ctctgagttc tctaaaaggg   8520
tgatcctcgc tgatgcaaac ctcgataagg tgttgtctgc ttacaacaag cacagagata   8580
agcctatcag ggaacaggca gagaacatca tccatctctt caccettacc aacctcggtg   8640
ctcctgctgc tttcaagtac ttcgatacaa ccatcgatag gaagagatac acctctacca   8700
aagaagtgct cgatgctacc ctcatccatc agtctatcac tggactctac gagactagga   8760
tcgatctctc acagctcggt ggtgattcaa gggctgatcc taagaagaag aggaaggttt   8820
gacgtcgacg atatgaagat gaagatgaaa tatttggtgt gtcaaataaa aagcttgtgt   8880
gcttaagttt gtgttttttt cttggcttgt tgtgttatga atttgtggct ttttctaata   8940
ttaaatgaat gtaagatcac attataatga ataaacaaat gtttctataa tccattgtga   9000
atgttttgtt ggatctcttc tgcagcatat aactactgta tgtgctatgg tatggactat   9060
ggaatatgat taaagataag ccagagctct ggtgacggac ccatggcttc gttgaacaac   9120
ggaaactcga cttgccttcc gcacaataca tcatttcttc ttagcttttt ttcttcttct   9180
tcgttcatac agtttttttt tgtttatcag cttacatttt cttgaaccgt agctttcgtt   9240
ttcttctttt taactttcca ttcggagttt ttgtatcttg tttcatagtt tgtcccagga   9300
ttagaatgat taggcatcga accttcaaga atttgattga ataaaacatc ttcattctta   9360
agatatgaag ataatcttca aaaggcccct gggaatctga aagaagagaa gcaggcccat   9420
ttatatggga aagaacaata gtatttctta tataggccca tttaagttga aaacaatctt   9480
caaaagtccc acatcgctta gataagaaaa cgaagctgag tttatataca gctagagtcg   9540
aagtagtgat tgcctacttg ggctgttgca ggttttagag ctagaaatag caagttaaaa   9600
taaggctagt ccgttatcaa cttgaaaaag tggcaccgag tcggtgcttt ttttcccggc   9660
gtaatatggc gcgccagatt tgccttttca atttcagaaa gaatgctaac ccacagatgg   9720
ttagagaggc ttacgcagca ggtatcatca agacgatcta cccgagcaat aatctccagg   9780
aaatcaaata ccttcccaag aaggttaaag atgcagtcaa aagattcagg actaactgca   9840
tcaagaacac agagaaagat atatttctca agatcagaag tactattcca gtatggacga   9900
ttcaaggctt gcttcacaaa ccaaggcaag taatagagat tggagtctct aaaaaggtag   9960
ttcccactga atcaaaggcc atggagtcaa agattcaaat agaggaccta acagaactcg  10020
ccgtaaagac tggcgaacag ttcatacaga gtctcttacg actcaatgac aagaagaaaa  10080
tcttcgtcaa catggtggag cacgacacac ttgtctactc caaaaatatc aaagatacag  10140
tctcagaaga ccaaagggca attgagactt ttcaacaaag ggtaatatcc ggaaacctcc  10200
tcggattcca ttgcccagct atctgtcact ttattgtgaa gatagtggaa aaggaaggtg  10260
gctcctacaa atgccatcat tgcgataaag gaaaggccat cgttgaagat gcctctgccg  10320
acagtggtcc caaagatgga cccccaccca cgaggagcat cgtggaaaaa gaagacgttc  10380
caaccacgtc ttcaaagcaa gtggattgat gtgatatctc cactgacgta agggatgacg  10440
cacaatccca ctatccttcg caagaccctt cctctatata aggaagttca tttcatttgg  10500
agagaacacg ggggactcct gcaggatgga tctgcgtcta attttcggtc caacttgcac  10560
```

aggaaagacg tcgaccgcga tacgtcttgc ccagcagact ggccttccag tcctttcgct 10620
cgatcgggtc caatgctgtc ctcaactgtc aaccggaagc ggacgaccaa cagtggaaga 10680
actgaaagga acgacccgtc tataccttga agatcggcct ctggtgaagg gtatcatcgc 10740
agccaagcaa gctcacgaaa ggctgatcgg ggaagtgtac aattatgagg cccacggcgg 10800
gcttattctt gagggaggat ctatctcgtt gctcaggtgc atggcgcaaa gcagttattg 10860
gagtaccgat tttcgttggc atattattcg ccacaagtta gcagacgagg agacattcat 10920
gaacgcggcc aaggccagag ttaggcagat gttgcgccct gctgtaggcc catctattat 10980
tcaagagttg gttcatcttt ggaatgagcc tcggctgagg cccatactga aagagatcga 11040
cggatatcga tatgccatgt tatttgctag ccagaaccag atcacacccg atatgctatt 11100
gcagcttgac ccagatatgg agggtgagtt gattcatgga atcgctcagg agtatctcat 11160
ccatgcgcgc cggcaggagc aggaattccc tccagtgagc gtggtcgctt tcgaaggatt 11220
cgaaggtcca ccgttcggaa tgtgctagct cgagccctag acttgtccat cttctggatt 11280
ggccaagtta attaatgtat gaaataaaag gatgcacaca tagtgacatg ctaatcacta 11340
taatgtgggc atcaaagttg tgtgttatgt gtaattacta attatctgaa taagagaaag 11400
agatcatcca tatttcttat cctaaatgaa tgtcacgtgt ctttataatt ctttgatgaa 11460
ccagatgcat ttattaacc aattccatat acatataaat attaatcata tataattaat 11520
atcaattggg ttagcaaaac aaatctagtc taggtgtgtt ttgctaatta ttgggggata 11580
gtgcaaaaag aaatctacgt tctcaataat tcagatagaa aacttaataa agtgagataa 11640
tttacataga ttgcttttat cctttgatat atgtgaaacc atgcatgata taaggaaaat 11700
agatagagaa ataatttttt acatcgttga atatgtaaac aatttaattc aagaagctag 11760
gaatataaat attgaggagt ttatgattag agctctcccg gcgcgcccta tgtcgagctg 11820
caggtcaacg gatcaggata ttcttgttta agatgttgaa ctctatggag gtttgtatga 11880
actgatgatc taggaccgga taagttccct tcttcatagc gaacttattc aaagaatgtt 11940
ttgtgtatca ttcttgttac attgttatta atgaaaaaat attattggtc attggactga 12000
acacgagtgt taaatatgga ccaggcccca aataagatcc attgatatat gaattaaata 12060
acaagaataa atcgagtcac caaaccactt gcctttttta acgagacttg ttcaccaact 12120
tgatacaaaa gtcattatcc tatgcaaatc aataatcata caaaaatatc caataacact 12180
aaaaaattaa aagaaatgga taatttcaca atatgttata cgataaagaa gttacttttc 12240
caagaaattc actgatttta taagcccact tgcattagat aaatggcaaa aaaaaacaaa 12300
aaggaaaaga aataaagcac gaagaattct agaaaatacg aaatacgctt caatgcagtg 12360
ggacccacgg ttcaattatt gccaattttc agctccaccg tatatttaaa aaataaaacg 12420
ataatgctaa aaaaatataa atcgtaacga tcgttaaatc tcaacggctg gatcttatga 12480
cgaccgttag aaattgtggt tgtcgacgag tcagtaataa acggcgtcaa agtggttgca 12540
gccggcacac acgagtcgtg tttatcaact caaagcacaa atacttttcc tcaacctaaa 12600
aataaggcaa ttagccaaaa acaactttgc gtgtaaacaa cgctcaatac acgtgtcatt 12660
ttattattag ctattgcttc accgccttag ctttctcgtg acctagtcgt cctcgtcttt 12720
tcttcttctt cttctataaa acaataccca aagagctctt cttcttcaca attcagattt 12780
caatttctca aaatcttaaa aactttctct caattctctc taccgtgatc aaggtaaatt 12840
tctgtgttcc ttattctctc aaaatcttcg attttgtttt cgttcgatcc caatttcgta 12900

-continued tatgttcttt ggtttagatt ctgttaatct tagatcgaac acgattttct gggtttgatc 12960
gttagatatc atcttaattc tcgattaggg tttcatagat atcatccgat ttgttcaaat 13020
aatttgagtt ttgtcgaata attactcttc gatttgtgat ttctatctag atctggtgtt 13080
agtttctagt ttgtgcgatc gaatttgtcg attaatctga gtttttctga ttaacaggcc 13140
tgcaggatgg aagacgccaa aaacataaag aaaggcccgg cgccattcta tccgctggaa 13200
gatggaaccg ctggagagca actgcataag gctatgaaga gatacgccct ggttcctgga 13260
acaattgctt ttacagatgc acatatcgag gtggacatca cttacgctga gtacttcgaa 13320
atgtccgttc ggttggcaga agctatgaaa cgatatgggc tgaatacaaa tcacagaatc 13380
gtcgtatgca gtgaaaactc tcttcaattc tttatgccgg tgttgggcgc gttatttatc 13440
ggagttgcag ttgcgcccgc gaacgacatt tataatgaac gtgaattgct caacagtatg 13500
ggcatttcgc agcctaccgt ggtgttcgtt tccaaaaagg ggttgcaaaa aattttgaac 13560
gtgcaaaaaa agctcccaat catccaaaaa attattatca tggattctaa aacggattac 13620
cagggatttc agtcgatgta cacgttcgtc acatctcatc tacctcccgg ttttaatgaa 13680
tacgattttg tgccagagtc cttcgatagg gacaagacaa ttgcactgat catgaactcc 13740
tctggatcta ctggtctgcc taaaggtgtc gctctgcctc atagaactgc ctgcgtgaga 13800
ttctcgcatg ccagagatcc tatttttggc aatcaaatca ttccggatac tgcgatttta 13860
agtgttgttc cattccatca cggttttgga atgtttacta cactcggata tttgatatgt 13920
ggatttcgag tcgtcttaat gtatagattt gaagaagagc tgtttctgag gagccttcag 13980
gattacaaga ttcaaagtgc gctgctggtg ccaaccctat tctccttctt cgccaaaagc 14040
actctgattg acaaatacga tttatctaat ttacacgaaa ttgcttctgg tggcgctccc 14100
ctctctaagg aagtcgggga agcggttgcc aagaggttcc atctgccagg tatcaggcaa 14160
ggatatgggc tcactgagac tacatcagct attctgatta cacccgaggg ggatgataaa 14220
ccgggcgcgg tcggtaaagt tgttccattt tttgaagcga aggttgtgga tctggatacc 14280
gggaaaacgc tgggcgttaa tcaaagaggc gaactgtgtg tgagaggtcc tatgattatg 14340
tccggttatg taaacaatcc ggaagcgacc aacgccttga ttgacaagga tggatggcta 14400
cattctggag acatagctta ctgggacgaa gacgaacact tcttcatcgt tgaccgcctg 14460
aagtctctga ttaagtacaa aggctatcag gtggctcccg ctgaattgga atccatcttg 14520
ctccaacacc ccaacatctt cgacgctggt gtcgcaggtc ttcccgacga tgacgccggt 14580
gaacttcccg ccgccgttgt tgttttggag cacggaaaga cgatgacgga aaaagagatc 14640
gtggattacg tcgccagtca agtaacaacc gcgaaaaagt tgcgcggagg agttgtgttt 14700
gtggacgaag taccgaaagg tcttaccgga aaactcgacg caagaaaaat cagagagatc 14760
ctcataaagg ccaagaaggg cggaaagatc gccgtgtgac tcgaggttcg agtattatgg 14820
cattgggaaa actgtttttc ttgtaccatt tgttgtgctt gtaatttact gtgtttttta 14880
ttcggttttc gctatcgaac tgtgaaatgg aaatggatgg agaagagtta atgaatgata 14940
tggtcctttt gttcattctc aaattaatat tatttgtttt ttctcttatt tgttgtgtgt 15000
tgaatttgaa attataagag atatgcaaac attttgtttt gagtaaaaat gtgtcaaatc 15060
gtggcctcta atgaccgaag ttaatatgag gagtaaaaca cttgtagttg tgttagagct 15120
cagtgtttga tcgccggcgg taccgagtgt acttcaagtc agtgggaaat caataaaatg 15180
attattttat gaatatattt cattgtgcaa gtagatagaa attacatatg ttacataaca 15240
cacgaaataa acaaaaaaag acaatccaaa aacaaacacc ccaaaaaaaa taatcacttt 15300

-continued

```
agataaactc gtatgaggag aggcacgttc agtgactcga cgattcccga gcaaaaaaag  15360
tctccccgtc acacatgtag tgggtgacgc aattatcttt aaagtaatcc ttctgttgac  15420
ttgtcattga taacatccag tcttcgtcag gattgcaaag aattatagaa gggatcccac  15480
cttttatttt cttctttttt ccatatttag ggttgacagt gaaatcagac tggcaaccta  15540
ttaattgctt ccacaatggg acgaacttga aggggatgtc gtcgatgata ttataggtgg  15600
cgtgttcatc gtagttggtg aaatcgatgg taccgttcca atagttgtgt cgtccgagac  15660
ttctagccca ggtggtcttt ccggtacgag ttggtccgca gatgtagagg ctggggtgtc  15720
ggattccatt ccttccattg tccttgttaa atcggccatc cattcaaggt cagattgagc  15780
ttgttggtat gagacaggat gtatgtaagt ataagcgtct atgcttacat ggtatagatg  15840
ggtttccctc caggagtgta gatcttcgtg gcagcgaaga tctgattctg tgaagggcga  15900
cacatacggt tcaggttgtg gagggaataa tttgttggct gaatattcca gccattgaag  15960
ctttgttgcc cattcatgag ggaattcttc cttgatcatg tcaagatatt cctccttaga  16020
cgttgcagtc tggataatag ttctccatcg tgcgtcagat ttgcgaggag aaaccttatg  16080
atctcggaaa tctcctctgg ttttaatatc tccgtccttt gatatgtaat caaggacttg  16140
tttagagttt ctagctggct ggatattagg gtgatttcct tcaaaatcga aaaaagaagg  16200
atccctaata caaggttttt tatcaagctg gagaagagca tgatagtggg tagtgccatc  16260
ttgatgaagc tcagaagcaa caccaaggaa gaaaataaga aaaggtgtga gtttctccca  16320
gagaaactgg aataaatcat ctctttgaga tgagcacttg ggataggtaa ggaaaacata  16380
tttagattgg agtctgaagt tcttactagc agaaggcatg ttgttgtgac tccgaggggt  16440
tgcctcaaac tctatcttat aaccggcgtg gaggcatgga ggcaggggta ttttggtcat  16500
tttaatagat agtggaaaat gacgtggaat ttacttaaag acgaagtctt tgcgacaagg  16560
gggggcccac gccgaattta atattaccgg cgtggccccc ccttatcgcg agtgctttag  16620
cacgagcggt ccagatttaa agtagaaaat ttcccgccca ctagggttaa aggtgttcac  16680
actataaaag catatacgat gtgatggtat ttgatggagc gtatattgta tcaggtattt  16740
ccgttggata cgaattattc gtacgaccct catagtttaa actatcagtg tttgacagga  16800
tatattggcg ggtaaaccta agagaaaaga gcgtttatta gaataacgga tatttaaaag  16860
ggcgtgaaaa ggtttatccg ttcgtccatt tgtatgtgca tgccaaccac agggttcccc  16920
tcgggatcaa agtactttga tccaacccct ccgctgctat agtgcagtcg gcttctgacg  16980
ttcagtgcag ccgtcttctg aaaacgacat gtcgcacaag tcctaagtta cgcgacaggc  17040
tgccgccctg cccttttcct ggcgttttct tgtcgcgtgt tttagtcgca taaagtagaa  17100
tacttgcgac tagaaccgga gacattacgc catgaacaag agcgccgccg ctggcctgct  17160
gggctatgcc cgcgtcagca ccgacgacca ggacttgacc aaccaacggg ccgaactgca  17220
cgcggccggc tgcaccaagc tgttttccga gaagatcacc ggcaccaggc gcgaccgccc  17280
ggagctggcc aggatgcttg accacctacg ccctggcgac gttgtgacag tgaccaggct  17340
agaccgcctg gcccgcagca cccgcgacct actggacatt gccgagcgca tccaggaggc  17400
cggcgcgggc ctgcgtagcc tggcagagcc gtgggccgac accaccacgc cggccggccg  17460
catggtgttg accgtgttcg ccggcattgc cgagttcgag cgttccctaa tcatcgaccg  17520
cacccggagc gggcgcgagg ccgccaaggc ccgaggcgtg aagtttggcc cccgccctac  17580
cctcaccccg gcacagatcg cgcacgcccg cgagctgatc gaccaggaag gccgcaccgt  17640
```

-continued

```
gaaagaggcg gctgcactgc ttggcgtgca tcgctcgacc ctgtaccgcg cacttgagcg  17700
cagcgaggaa gtgacgccca ccgaggccag gcggcgcggt gccttccgtg aggacgcatt  17760
gaccgaggcc gacgccctgg cggccgccga gaatgaacgc caagaggaac aagcatgaaa  17820
ccgcaccagg acggccagga cgaaccgttt ttcattaccg aagagatcga ggcggagatg  17880
atcgcggccg ggtacgtgtt cgagccgccc gcgcacggct caaccgtgcg gctgcatgaa  17940
atcctggccg gtttgtctga tgccaagctg gcggcctggc cggccagctt ggccgctgaa  18000
gaaaccgagc gccgccgtct aaaaaggtga tgtgtatttg agtaaaacag cttgcgtcat  18060
gcggtcgctg cgtatatgat gcgatgagta aataaacaaa tacgcaaggg gaacgcatga  18120
aggttatcgc tgtacttaac cagaaaggcg ggtcaggcaa gacgaccatc gcaacccatc  18180
tagcccgcgc cctgcaactc gccggggccg atgttctgtt agtcgattcc gatccccagg  18240
gcagtgcccg cgattgggcg gccgtgcggg aagatcaacc gctaaccgtt gtcggcatcg  18300
accgcccgac gattgaccgc gacgtgaagg ccatcggccg gcgcgacttc gtagtgatcg  18360
acggagcgcc ccaggcggcg gacttggctg tgtccgcgat caaggcagcc gacttcgtgc  18420
tgattccggt gcagccaagc ccttacgaca tatgggccac cgccgacctg gtggagctgg  18480
ttaagcagcg cattgaggtc acggatggaa ggctacaagc ggcctttgtc gtgtcgcggg  18540
cgatcaaagg cacgcgcatc ggcggtgagg ttgccgaggc gctggccggg tacgagctgc  18600
ccattcttga gtcccgtatc acgcagcgcg tgagctaccc aggcactgcc gccgccggca  18660
caaccgttct tgaatcagaa cccgagggcg acgctgcccg cgaggtccag gcgctggccg  18720
ctgaaattaa atcaaaactc atttgagtta atgaggtaaa gagaaaatga gcaaaagcac  18780
aaacacgcta agtgccggcc gtccgagcgc acgcagcagc aaggctgcaa cgttggccag  18840
cctggcagac acgccagcca tgaagcgggt caactttcag ttgccggcgg aggatcacac  18900
caagctgaag atgtacgcgg tacgccaagg caagaccatt accgagctgc tatctgaata  18960
catcgcgcag ctaccagagt aaatgagcaa atgaataaat gagtagatga attttagcgg  19020
ctaaaggagg cggcatggaa aatcaagaac aaccaggcac cgacgccgtg gaatgcccca  19080
tgtgtggagg aacgggcggt tggccaggcg taagcggctg ggttgtctgc cggccctgca  19140
atggcactgg aacccccaag cccgaggaat cggcgtgacg gtcgcaaacc atccggcccg  19200
gtacaaatcg gcgcggcgct gggtgatgac ctggtggaga agttgaaggc cgcgcaggcc  19260
gcccagcggc aacgcatcga ggcagaagca cgccccggtg aatcgtggca agcggccgct  19320
gatcgaatcc gcaaagaatc ccggcaaccg ccggcagccg gtgcgccgtc gattaggaag  19380
ccgcccaagg gcgacgagca accagatttt ttcgttccga tgctctatga cgtgggcacc  19440
cgcgatagtc gcagcatcat ggacgtggcc gttttccgtc tgtcgaagcg tgaccgacga  19500
gctggcgagg tgatccgcta cgagcttcca gacgggcacg tagaggtttc cgcagggccg  19560
gccggcatgg ccagtgtgtg ggattacgac ctggtactga tggcggtttc ccatctaacc  19620
gaatccatga accgataccg ggaagggaag ggagacaagc ccggccgcgt gttccgtcca  19680
cacgttgcgg acgtactcaa gttctgccgg cgagccgatg gcggaaagca ga          19732
```

<210> SEQ ID NO 90
<211> LENGTH: 21015
<212> TYPE: DNA
<213> ORGANISM: artificial
<220> FEATURE:
<223> OTHER INFORMATION: synthetic oligonucleotide

<400> SEQUENCE: 90

```
accttccaaa cgagaaggtg ctccctaagc actctttgct ctacgagtac ttcaccgtgt     60
acaacgagtt gaccaaggtt aagtacgtga ccgagggaat gaggaagcct gctttttgt    120
caggtgagca aaagaaggct atcgttgatc tcttgttcaa gaccaacaga aaggtgaccg    180
tgaagcagct caaagaggat tacttcaaga aaatcgagtg cttcgattca gttgagattt    240
ctggtgttga ggataggttc aacgcatctc tcggaaccta ccacgatctc ctcaagatca    300
ttaaggataa ggatttcttg gataacgagg aaaacgagga tatcttggag gatatcgttc    360
ttaccctcac cctctttgaa gatagagaga tgattgaaga aaggctcaag acctacgctc    420
atctcttcga tgataaggtg atgaagcagt tgaagagaag aagatacact ggttggggaa    480
ggctctcaag aaagctcatt aacggaatca gggataagca gtctggaaag acaatccttg    540
atttcctcaa gtctgatgga ttcgctaaca gaaacttcat gcagctcatc cacgatgatt    600
ctctcacctt taaagaggat atccagaagg ctcaggtttc aggacagggt gatagtctcc    660
atgagcatat cgctaacctc gctggatctc ctgcaatcaa gaagggaatc ctccagactg    720
tgaaggttgt ggatgagttg gtgaaggtga tgggaaggca taagcctgag aacatcgtga    780
tcgaaatggc tagagagaac cagaccactc agaagggaca gaagaactct agggaaagga    840
tgaagaggat cgaggaaggt atcaaagagc ttggatctca gatcctcaaa gagcaccctg    900
ttgagaacac tcagctccag aatgagaagc tctacctcta ctacctccag aacggaaggg    960
atatgtatgt ggatcaagag ttggatatca acaggctctc tgattacgat gttgatcata   1020
tcgtgccaca gtcattcttg aaggatgatt ctatcgataa caaggtgctc accaggtctg   1080
ataagaacag gggtaagagt gataacgtgc caagtgaaga ggttgtgaag aaaatgaaga   1140
actattggag gcagctcctc aacgctaagc tcatcactca gagaaagttc gataacttga   1200
ctaaggctga gaggggagga ctctctgaat tggataaggc aggattcatc aagaggcagc   1260
ttgtggaaac caggcagatc actaagcacg ttgcacagat cctcgattct aggatgaaca   1320
ccaagtacga tgagaacgat aagttgatca gggaagtgaa ggttatcacc ctcaagtcaa   1380
agctcgtgtc tgatttcaga aaggatttcc aattctacaa ggtgagggaa atcaacaact   1440
accaccacgc tcacgatgct taccttaacg ctgttgttgg aaccgctctc atcaagaagt   1500
atcctaagct cgagtcagag ttcgtgtacg gtgattacaa ggtgtacgat gtgaggaaga   1560
tgatcgctaa gtctgagcaa gagatcggaa aggctaccgc taagtatttc ttctactcta   1620
acatcatgaa tttcttcaag accgagatta ccctcgctaa cggtgagatc agaaagaggc   1680
cactcatcga gacaaacggt gaaacaggtg agatcgtgtg ggataaggga agggatttcg   1740
ctaccgttag aaaggtgctc tctatgccac aggtgaacat cgttaagaaa accgaggtgc   1800
agaccggtgg attctctaaa gagtctatcc tccctaagag gaactctgat aagctcattg   1860
ctaggaagaa ggattgggac cctaagaaat acggtggttt cgattctcct accgtggctt   1920
actctgttct cgttgtggct aaggttgaga agggaaagag taagaagctc aagtctgtta   1980
aggaacttct cggaatcact atcatggaaa ggtcatcttt cgagaagaac ccaatcgatt   2040
tcctcgaggc taagggatac aaagaggtta agaaggatct catcatcaag ctcccaaagt   2100
actcactctt cgaactcgag aacggtagaa agaggatgct cgcttctgct ggtgagcttc   2160
aaaagggaaa cgagcttgct ctcccatcta agtacgttaa ctttctttac ctcgcttctc   2220
actacgagaa gttgaaggga tctccagaag ataacgagca gaagcaactt ttcgttgagc   2280
agcacaagca ctacttggat gagatcatcg agcagatctc tgagttctct aaaagggtga   2340
```

-continued

```
tcctcgctga tgcaaacctc gataaggtgt tgtctgctta caacaagcac agagataagc   2400
ctatcaggga acaggcagag aacatcatcc atctcttcac ccttaccaac ctcggtgctc   2460
ctgctgcttt caagtacttc gatacaacca tcgataggaa gagatacacc tctaccaaag   2520
aagtgctcga tgctaccctc atccatcagt ctatcactgg actctacgag actaggatcg   2580
atctctcaca gctcggtggt gattcaaggg ctgatcctaa gaagaagagg aaggtttgac   2640
gtcgacgata tgaagatgaa gatgaaatat ttggtgtgtc aaataaaaag cttgtgtgct   2700
taagtttgtg ttttttttctt ggcttgttgt gttatgaatt tgtggctttt tctaatatta   2760
aatgaatgta agatcacatt ataatgaata aacaaatgtt tctataatcc attgtgaatg   2820
ttttgttgga tctcttctgc agcatataac tactgtatgt gctatggtat ggactatgga   2880
atatgattaa agataagcca gagctctggt gacggaccca tggcttcgtt gaacaacgga   2940
aactcgactt gccttccgca caatacatca tttcttctta gcttttttttc ttcttcttcg   3000
ttcatacagt ttttttttgt ttatcagctt acattttctt gaaccgtagc tttcgttttc   3060
ttctttttaa ctttccattc ggagtttttg tatcttgttt catagtttgt cccaggatta   3120
gaatgattag gcatcgaacc ttcaagaatt tgattgaata aaacatcttc attcttaaga   3180
tatgaagata atcttcaaaa ggcccctggg aatctgaaag aagagaagca ggcccattta   3240
tatgggaaag aacaatagta tttcttatat aggcccattt aagttgaaaa caatcttcaa   3300
aagtcccaca tcgcttagat aagaaaacga agctgagttt atatacagct agagtcgaag   3360
tagtgattgc ctacttgggc tgttgcaggt tttagagcta gaaatagcaa gttaaaataa   3420
ggctagtccg ttatcaactt gaaaaagtgg caccgagtcg gtgctttttt tcccggggcg   3480
cgccctatgt cgagctgcag gtcaacggat caggatattc ttgtttaaga tgttgaactc   3540
tatggaggtt tgtatgaact gatgatctag gaccggataa gttcccttct tcatagcgaa   3600
cttattcaaa gaatgttttg tgtatcattc ttgttacatt gttattaatg aaaaaatatt   3660
attggtcatt ggactgaaca cgagtgttaa atatggacca ggccccaaat aagatccatt   3720
gatatatgaa ttaaataaca agaataaatc gagtcaccaa accacttgcc tttttaacg   3780
agacttgttc accaacttga tacaaaagtc attatcctat gcaaatcaat aatcatacaa   3840
aaatatccaa taacactaaa aaattaaaag aaatggataa tttcacaata tgttatacga   3900
taaagaagtt actttccaa gaaattcact gattttataa gcccacttgc attagataaa   3960
tggcaaaaaa aaacaaaaag gaaaagaaat aaagcacgaa gaattctaga aaatacgaaa   4020
tacgcttcaa tgcagtggga cccacggttc aattattgcc aattttcagc tccaccgtat   4080
atttaaaaaa taaaacgata atgctaaaaa aatataaatc gtaacgatcg ttaaatctca   4140
acggctggat cttatgacga ccgttagaaa ttgtggttgt cgacgagtca gtaataaacg   4200
gcgtcaaagt ggttgcagcc ggcacacacg agtcgtgttt atcaactcaa agcacaaata   4260
cttttcctca acctaaaaat aaggcaatta gccaaaaaca actttgcgtg taaacaacgc   4320
tcaatacacg tgtcatttta ttattagcta ttgcttcacc gccttagctt tctcgtgacc   4380
tagtcgtcct cgtcttttct tcttcttctt ctataaaaca atacccaaag agctcttctt   4440
cttcacaatt cagatttcaa tttctcaaaa tcttaaaaac tttctctcaa ttctctctac   4500
cgtgatcaag gtaaatttct gtgttcctta ttctctcaaa atcttcgatt ttgttttcgt   4560
tcgatcccaa tttcgtatat gttctttggt ttagattctg ttaatcttag atcgaacacg   4620
attttctggg tttgatcgtt agatatcatc ttaattctcg attagggttt catagatatc   4680
atccgatttg ttcaaataat ttgagttttg tcgaataatt actcttcgat ttgtgatttc   4740
```

```
tatctagatc tggtgttagt ttctagtttg tgcgatcgaa tttgtcgatt aatctgagtt   4800
tttctgatta acaggcctgc aggatggaag acgccaaaaa cataaagaaa ggcccggcgc   4860
cattctatcc gctggaagat ggaaccgctg gagagcaact gcataaggct atgaagagat   4920
acgccctggt tcctggaaca attgctttta cagatgcaca tatcgaggtg gacatcactt   4980
acgctgagta cttcgaaatg tccgttcggt tggcagaagc tatgaaacga tatgggctga   5040
atacaaatca cagaatcgtc gtatgcagtg aaaactctct tcaattcttt atgccggtgt   5100
tgggcgcgtt atttatcgga gttgcagttg cgcccgcgaa cgacatttat aatgaacgtg   5160
aattgctcaa cagtatgggc atttcgcagc ctaccgtggt gttcgtttcc aaaaaggggt   5220
tgcaaaaaat tttgaacgtg caaaaaaagc tcccaatcat ccaaaaaatt attatcatgg   5280
attctaaaac ggattaccag ggatttcagt cgatgtacac gttcgtcaca tctcatctac   5340
ctcccggttt taatgaatac gattttgtgc cagagtcctt cgatagggac aagacaattg   5400
cactgatcat gaactcctct ggatctactg gtctgcctaa aggtgtcgct ctgcctcata   5460
gaactgcctg cgtgagattc tcgcatgcca gagatcctat ttttggcaat caaatcattc   5520
cggatactgc gattttaagt gttgttccat tccatcacgg ttttggaatg tttactacac   5580
tcggatattt gatatgtgga tttcgagtcg tcttaatgta tagatttgaa gaagagctgt   5640
ttctgaggag ccttcaggat tacaagattc aaagtgcgct gctggtgcca accctattct   5700
ccttcttcgc caaaagcact ctgattgaca aatacgattt atctaattta cacgaaattg   5760
cttctggtgg cgctcccctc tctaaggaag tcggggaagc ggttgccaag aggttccatc   5820
tgccaggtat caggcaagga tatgggctca ctgagactac atcagctatt ctgattacac   5880
ccgaggggga tgataaaccg ggcgcggtcg gtaaagttgt tccatttttt gaagcgaagg   5940
ttgtggatct ggataccggg aaaacgctgg gcgttaatca aagaggcgaa ctgtgtgtga   6000
gaggtcctat gattatgtcc ggttatgtaa acaatccgga agcgaccaac gccttgattg   6060
acaaggatgg atggctacat tctggagaca tagcttactg ggacgaagac gaacacttct   6120
tcatcgttga ccgcctgaag tctctgatta agtacaaagg ctatcaggtg gctcccgctg   6180
aattggaatc catcttgctc caacacccca acatcttcga cgctggtgtc gcaggtcttc   6240
ccgacgatga cgccggtgaa cttcccgccg ccgttgttgt tttggagcac ggaaagacga   6300
tgacggaaaa agagatcgtg gattacgtcg ccagtcaagt aacaaccgcg aaaaagttgc   6360
gcggaggagt tgtgtttgtg gacgaagtac cgaaaggtct taccggaaaa ctcgacgcaa   6420
gaaaaatcag agagatcctc ataaaggcca agaagggcgg aaagatcgcc gtgtgactcg   6480
aggttcgagt attatggcat tgggaaaact gtttttcttg taccatttgt tgtgcttgta   6540
atttactgtg tttttattc ggttttcgct atcgaactgt gaaatggaaa tggatggaga   6600
agagttaatg aatgatatgg tccttttgtt cattctcaaa ttaatattat ttgtttttc    6660
tcttatttgt tgtgtgttga atttgaaatt ataagagata tgcaaacatt ttgttttgag   6720
taaaaatgtg tcaaatcgtg gcctctaatg accgaagtta atatgaggag taaaacactt   6780
gtagttgtgt tagagctctc ccgcagattt gccttttcaa tttcagaaag aatgctaacc   6840
cacagatggt tagagaggct tacgcagcag gtatcatcaa gacgatctac ccgagcaata   6900
atctccagga aatcaaatac cttcccaaga aggttaaaga tgcagtcaaa agattcagga   6960
ctaactgcat caagaacaca gagaaagata tatttctcaa gatcagaagt actattccag   7020
tatggacgat tcaaggcttg cttcacaaac caaggcaagt aatagagatt ggagtctcta   7080
```

```
aaaaggtagt tcccactgaa tcaaaggcca tggagtcaaa gattcaaata gaggacctaa   7140
cagaactcgc cgtaaagact ggcgaacagt tcatacagag tctcttacga ctcaatgaca   7200
agaagaaaat cttcgtcaac atggtggagc acgacacact tgtctactcc aaaaatatca   7260
aagatacagt ctcagaagac caaagggcaa ttgagacttt tcaacaaagg gtaatatccg   7320
gaaacctcct cggattccat tgcccagcta tctgtcactt tattgtgaag atagtggaaa   7380
aggaaggtgg ctcctacaaa tgccatcatt gcgataaagg aaaggccatc gttgaagatg   7440
cctctgccga cagtggtccc aaagatggac ccccacccac gaggagcatc gtggaaaaag   7500
aagacgttcc aaccacgtct tcaaagcaag tggattgatg tgatatctcc actgacgtaa   7560
gggatgacgc acaatcccac tatccttcgc aagacccttc ctctatataa ggaagttcat   7620
ttcatttgga gagaacacgg gggactatga tggcttcatt gtcttgtgtt gaagacaaga   7680
tgaaaacaag ttgtttggtt aatggtggag gaactataac aacaacaaca tctcaatcta   7740
ccttgcttga agagatgaag ctgttgaaag accagtcagg tacaagaaag ccggtaataa   7800
actcggagct atggcacgct tgtgcaggcc ctttggtgtg tctccctcaa gttgggagct   7860
tagtgtatta cttctcacaa ggtcatagcg agcaggttgc tgtttcaacc agaagatcag   7920
caacaacaca agttcctaat tatccgaacc ttccatctca gttgatgtgt caagtccata   7980
atgttactct tcatgctgac aaagacagtg acgaaatcta tgctcagatg agtcttcaac   8040
ctgttcactc tgagagagat gtgttccctg taccagactt tggaatgctg agaggaagta   8100
agcacccgac tgagtttttc tgcaaaacac ttactgcaag tgacacaagc acacatggag   8160
gtttctcagt gccacgtaga gctgcagaga agctatttcc accattggac tactcagcac   8220
agccgccaac gcaagagctt gtagttcgag atcttcatga gaatacttgg acatttcgcc   8280
atatctaccg agggcaacca aagagacatc tcctaactac aggatggagt ttgttcgttg   8340
gatcgaagag attgagagct ggggattctg ttttgttcat cagggatgag aagtcacaac   8400
ttatggtcgg tgttaggcgt gccaatcgcc aacaaacagc acttccttca tcagttctct   8460
cagcggatag tatgcacatc ggtgttcttg ctgctgctgc tcacgcaacc gccaaccgta   8520
ctcctttttt gatattctat aatccaagag cttgtccagc agagttcgtg atccctctag   8580
ctaagtaccg taaggcgata tgcgggtctc agctctcagt tggtatgaga tttggaatga   8640
tgtttgaaac tgaagattcc gggaaacgaa ggtacatggg aactattgtt ggaatcagcg   8700
atttggatcc gttgagatgg cctggttcta agtggcgtaa ccttcaggta gaatgggatg   8760
agcctggatg taatgataaa cctactcggg tcagtccatg ggatatcgaa acacctgaaa   8820
gtctcttcat ttttccttct ctgacctcag gactcaaacg tcagctccat ccatcttact   8880
ttgctggtga aactgaatgg ggtagcttga taaaacggcc acttatacgt gttcctgatt   8940
ccgcgaatgg gattatgcca tatgcatctt tccctagtat ggcttcggag cagcttatga   9000
aaatgatgat gaggcctcac aacaaccaaa atgtaccatc tttcatgtct gagatgcagc   9060
agaatattgt aatggggaat ggaggtttgc taggagatat gaagatgcag caaccccctga   9120
tgatgaacca gaaatctgag atggtgcagc cacaaaacaa gctaacagtg aacccatctg   9180
cttctaatac gagtggccaa gaacagaatc tttcacagag tatgagtgct cctgctaaac   9240
ctgagaactc tacactctct ggttgcagct ctggtagagt ccaacatgga cttgagcagt   9300
caatggaaca ggcaagccag gttactacat ccacagtgtg taatgaggaa aaggttaatc   9360
agctacttca gaaaccgggt gcttcgtcgc ctgtacaagc tgatcaatgt cttgacatta   9420
ctcatcagat ttaccaacca cagtctgatc caataaatgg attctctttc ctggaaactg   9480
```

atgagctgac atcacaagtc tcttccttcc agtctcttgc cggatcatac aagcaaccat 9540
tcattctatc ctcccaggat tcttcagctg ttgtgttacc ggattccaca aactcaccgc 9600
tgtttcatga tgtgtgggac actcagttga acggtctcaa gtttgaccag ttcagtccct 9660
tgatgcagca ggacctttat gctagtcaga atatctgtat gagtaatagc acaaccagta 9720
acattctaga tcctccactc tcaaacacag tccttgatga cttctgtgcc atcaaagaca 9780
ctgatttcca gaaccaccct tctggttgtt tggttggaaa caacaacact agctttgctc 9840
aagatgtcca gtcgcagatc acatcagcta gctttgcaga ctcacaggcc ttctctcgcc 9900
aagattttcc agataattct ggaggcactg gtacatcttc aagcaatgtt gattttgatg 9960
attgtagtct gcggcaaaat agtaaaggct catcatggca gaaaattgcg acaccccgcg 10020
tccgaaccta ctcgagtttc tccataataa tgtgtgagta gttcccagat aagggaatta 10080
gggttcctat agggtttcgc tcatgtgttg agcatataag aaacccttag tatgtatttg 10140
tatttgtaaa atacttctat caataaaatt tctaattcct aaaaccaaaa tccagtacta 10200
aaatccagat cccccgaatt aagtgtttga tcgccggcgg taccgagtgt acttcaagtc 10260
agtgggaaat caataaaatg attattttat gaatatattt cattgtgcaa gtagatagaa 10320
attacatatg ttacataaca cacgaaataa acaaaaaaag acaatccaaa aacaaacacc 10380
ccaaaaaaaa taatcacttt agataaactc gtatgaggag aggcacgttc agtgactcga 10440
cgattcccga gcaaaaaaag tctccccgtc acacatgtag tgggtgacgc aattatcttt 10500
aaagtaatcc ttctgttgac ttgtcattga taacatccag tcttcgtcag gattgcaaag 10560
aattatagaa gggatcccac cttttatttt cttctttttt ccatatttag ggttgacagt 10620
gaaatcagac tggcaaccta ttaattgctt ccacaatggg acgaacttga aggggatgtc 10680
gtcgatgata ttataggtgg cgtgttcatc gtagttggtg aaatcgatgg taccgttcca 10740
atagttgtgt cgtccgagac ttctagccca ggtggtcttt ccggtacgag ttggtccgca 10800
gatgtagagg ctggggtgtc ggattccatt ccttccattg tccttgttaa atcggccatc 10860
cattcaaggt cagattgagc ttgttggtat gagacaggat gtatgtaagt ataagcgtct 10920
atgcttacat ggtatagatg ggtttccctc caggagtgta gatcttcgtg gcagcgaaga 10980
tctgattctg tgaagggcga cacatacggt tcaggttgtg gagggaataa tttgttggct 11040
gaatattcca gccattgaag ctttgttgcc cattcatgag ggaattcttc cttgatcatg 11100
tcaagatatt cctccttaga cgttgcagtc tggataatag ttctccatcg tgcgtcagat 11160
ttgcgaggag aaaccttatg atctcggaaa tctcctctgg ttttaatatc tccgtccttt 11220
gatatgtaat caaggacttg tttagagttt ctagctggct ggatattagg gtgatttcct 11280
tcaaaatcga aaaaagaagg atccctaata caaggttttt tatcaagctg gagaagagca 11340
tgatagtggg tagtgccatc ttgatgaagc tcagaagcaa caccaaggaa gaaaataaga 11400
aaaggtgtga gtttctccca gagaaactgg aataaatcat ctctttgaga tgagcacttg 11460
ggataggtaa ggaaaacata tttagattgg agtctgaagt tcttactagc agaaggcatg 11520
ttgttgtgac tccgaggggt tgcctcaaac tctatcttat aaccggcgtg gaggcatgga 11580
ggcaggggta ttttggtcat tttaatagat agtggaaaat gacgtggaat ttacttaaag 11640
acgaagtctt tgcgacaagg gggggcccac gccgaattta atattaccgg cgtggccccc 11700
ccttatcgcg agtgctttag cacgagcggt ccagatttaa agtagaaaat ttcccgccca 11760
ctagggttaa aggtgttcac actataaaag catatacgat gtgatggtat ttgatggagc 11820
gtatattgta tcaggtattt ccgttggata cgaattattc gtacgaccct catagtttaa 11880
actatcagtg tttgacagga tatattggcg ggtaaaccta agagaaaaga gcgtttatta 11940
gaataacgga tatttaaaag ggcgtgaaaa ggtttatccg ttcgtccatt tgtatgtgca 12000
tgccaaccac agggttcccc tcgggatcaa agtactttga tccaacccct ccgctgctat 12060
agtgcagtcg gcttctgacg ttcagtgcag ccgtcttctg aaaacgacat gtcgcacaag 12120
tcctaagtta cgcgacaggc tgccgccctg cccttttcct ggcgttttct tgtcgcgtgt 12180
tttagtcgca taaagtagaa tacttgcgac tagaaccgga gacattacgc catgaacaag 12240
agcgccgccg ctggcctgct gggctatgcc cgcgtcagca ccgacgacca ggacttgacc 12300
aaccaacggg ccgaactgca cgcggccggc tgcaccaagc tgttttccga gaagatcacc 12360
ggcaccaggc gcgaccgccc ggagctggcc aggatgcttg accacctacg ccctggcgac 12420
gttgtgacag tgaccaggct agaccgcctg gcccgcagca cccgcgacct actggacatt 12480
gccgagcgca tccaggaggc cggcgcgggc ctgcgtagcc tggcagagcc gtgggccgac 12540
accaccacgc cggccggccg catggtgttg accgtgttcg ccggcattgc cgagttcgag 12600
cgttccctaa tcatcgaccg cacccggagc gggcgcgagg ccgccaaggc ccgaggcgtg 12660
aagtttggcc cccgccctac cctcaccccg gcacagatcg cgcacgcccg cgagctgatc 12720
gaccaggaag gccgcaccgt gaaagaggcg gctgcactgc ttggcgtgca tcgctcgacc 12780
ctgtaccgcg cacttgagcg cagcgaggaa gtgacgccca ccgaggccag gcggcgcggt 12840
gccttccgtg aggacgcatt gaccgaggcc gacgccctgg cggccgccga gaatgaacgc 12900
caagaggaac aagcatgaaa ccgcaccagg acggccagga cgaaccgttt ttcattaccg 12960
aagagatcga ggcggagatg atcgcggccg ggtacgtgtt cgagccgccc gcgcacggct 13020
caaccgtgcg gctgcatgaa atcctggccg gtttgtctga tgccaagctg gcggcctggc 13080
cggccagctt ggccgctgaa gaaaccgagc gccgccgtct aaaaaggtga tgtgtatttg 13140
agtaaaacag cttgcgtcat gcggtcgctg cgtatatgat gcgatgagta aataaacaaa 13200
tacgcaaggg gaacgcatga aggttatcgc tgtacttaac cagaaaggcg ggtcaggcaa 13260
gacgaccatc gcaacccatc tagcccgcgc cctgcaactc gccggggccg atgttctgtt 13320
agtcgattcc gatccccagg gcagtgcccg cgattgggcg gccgtgcggg aagatcaacc 13380
gctaaccgtt gtcggcatcg accgcccgac gattgaccgc gacgtgaagg ccatcggccg 13440
gcgcgacttc gtagtgatcg acggagcgcc ccaggcggcg gacttggctg tgtccgcgat 13500
caaggcagcc gacttcgtgc tgattccggt gcagccaagc ccttacgaca tatgggccac 13560
cgccgacctg gtggagctgg ttaagcagcg cattgaggtc acggatggaa ggctacaagc 13620
ggcctttgtc gtgtcgcggg cgatcaaagg cacgcgcatc ggcggtgagg ttgccgaggc 13680
gctggccggg tacgagctgc ccattcttga gtcccgtatc acgcagcgcg tgagctaccc 13740
aggcactgcc gccgccggca caaccgttct tgaatcagaa cccgagggcg acgctgcccg 13800
cgaggtccag gcgctggccg ctgaaattaa atcaaaactc atttgagtta atgaggtaaa 13860
gagaaaatga gcaaaagcac aaacacgcta agtgccggcc gtccgagcgc acgcagcagc 13920
aaggctgcaa cgttggccag cctggcagac acgccagcca tgaagcgggt caactttcag 13980
ttgccggcgg aggatcacac caagctgaag atgtacgcgg tacgccaagg caagaccatt 14040
accgagctgc tatctgaata catcgcgcag ctaccagagt aaatgagcaa atgaataaat 14100
gagtagatga attttagcgg ctaaaggagg cggcatggaa aatcaagaac aaccaggcac 14160
cgacgccgtg gaatgcccca tgtgtggagg aacgggcggt tggccaggcg taagcggctg 14220
ggttgtctgc cggccctgca atggcactgg aacccccaag cccgaggaat cggcgtgacg 14280
gtcgcaaacc atccggcccg gtacaaatcg gcgcggcgct gggtgatgac ctggtggaga 14340
agttgaaggc cgcgcaggcc gcccagcggc aacgcatcga ggcagaagca cgccccggtg 14400
aatcgtggca agcggccgct gatcgaatcc gcaaagaatc ccggcaaccg ccggcagccg 14460
gtgcgccgtc gattaggaag ccgcccaagg gcgacgagca accagatttt ttcgttccga 14520
tgctctatga cgtgggcacc cgcgatagtc gcagcatcat ggacgtggcc gttttccgtc 14580
tgtcgaagcg tgaccgacga gctggcgagg tgatccgcta cgagcttcca gacgggcacg 14640
tagaggtttc cgcagggccg gccggcatgg ccagtgtgtg ggattacgac ctggtactga 14700
tggcggtttc ccatctaacc gaatccatga accgataccg ggaagggaag ggagacaagc 14760
ccggccgcgt gttccgtcca cacgttgcgg acgtactcaa gttctgccgg cgagccgatg 14820
gcggaaagca gaaagacgac ctggtagaaa cctgcattcg gttaaacacc acgcacgttg 14880
ccatgcagcg tacgaagaag gccaagaacg gccgcctggt gacggtatcc gagggtgaag 14940
ccttgattag ccgctacaag atcgtaaaga gcgaaaccgg gcggccggag tacatcgaga 15000
tcgagctagc tgattggatg taccgcgaga tcacagaagg caagaacccg gacgtgctga 15060
cggttcaccc cgattacttt ttgatcgatc ccggcatcgg ccgttttctc taccgcctgg 15120
cacgccgcgc cgcaggcaag gcagaagcca gatggttgtt caagacgatc tacgaacgca 15180
gtggcagcgc cggagagttc aagaagttct gtttcaccgt gcgcaagctg atcgggtcaa 15240
atgacctgcc ggagtacgat ttgaaggagg aggcggggca ggctggcccg atcctagtca 15300
tgcgctaccg caacctgatc gagggcgaag catccgccgg ttcctaatgt acggagcaga 15360
tgctagggca aattgcccta gcaggggaaa aaggtcgaaa aggcctcttt cctgtggata 15420
gcacgtacat tgggaaccca aagccgtaca ttgggaaccg gaacccgtac attgggaacc 15480
caaagccgta cattgggaac cggtcacaca tgtaagtgac tgatataaaa gagaaaaaag 15540
gcgatttttc cgcctaaaac tctttaaaac ttattaaaac tcttaaaacc cgcctggcct 15600
gtgcataact gtctggccag cgcacagccg aagagctgca aaaagcgcct acccttcggt 15660
cgctgcgctc cctacgcccc gccgcttcgc gtcggcctat cgcggccgct ggccgctcaa 15720
aaatggctgg cctacggcca ggcaatctac cagggcgcgg acaagccgcg ccgtcgccac 15780
tcgaccgccg gcgcccacat caaggcaccc tgcctcgcgc gtttcggtga tgacggtgaa 15840
aacctctgac acatgcagct cccggaaacg gtcacagctt gtctgtaagc ggatgccggg 15900
agcagacaag cccgtcaggg cgcgtcagcg ggtgttggcg ggtgtcgggg cgcagccatg 15960
acccagtcac gtagcgatag cggagtgtat actggcttaa ctatgcggca tcagagcaga 16020
ttgtactgag agtgcaccat atgcggtgtg aaataccgca cagatgcgta aggagaaaat 16080
accgcatcag gcgctcttcc gcttcctcgc tcactgactc gctgcgctcg gtcgttcggc 16140
tgcggcgagc ggtatcagct cactcaaagg cggtaatacg gttatccaca gaatcagggg 16200
ataacgcagg aaagaacatg tgagcaaaag gccagcaaaa ggccaggaac cgtaaaaagg 16260
ccgcgttgct ggcgtttttc cataggctcc gcccccctga cgagcatcac aaaaatcgac 16320
gctcaagtca gaggtggcga aacccgacag gactataaag ataccaggcg tttccccctg 16380
gaagctccct cgtgcgctct cctgttccga ccctgccgct taccggatac ctgtccgcct 16440
ttctcccttc gggaagcgtg gcgctttctc atagctcacg ctgtaggtat ctcagttcgg 16500
tgtaggtcgt tcgctccaag ctgggctgtg tgcacgaacc ccccgttcag cccgaccgct 16560

-continued

```
gcgccttatc cggtaactat cgtcttgagt ccaacccggt aagacacgac ttatcgccac  16620
tggcagcagc cactggtaac aggattagca gagcgaggta tgtaggcggt gctacagagt  16680
tcttgaagtg gtggcctaac tacggctaca ctagaaggac agtatttggt atctgcgctc  16740
tgctgaagcc agttaccttc ggaaaaagag ttggtagctc ttgatccggc aaacaaacca  16800
ccgctggtag cggtggtttt tttgtttgca agcagcagat tacgcgcaga aaaaaaggat  16860
ctcaagaaga tcctttgatc ttttctacgg ggtctgacgc tcagtggaac gaaaactcac  16920
gttaagggat tttggtcatg cattctaggt actaaaacaa ttcatccagt aaaatataat  16980
attttatttt ctcccaatca ggcttgatcc ccagtaagtc aaaaaatagc tcgacatact  17040
gttcttcccc gatatcctcc ctgatcgacc ggacgcagaa ggcaatgtca taccacttgt  17100
ccgccctgcc gcttctccca agatcaataa agccacttac tttgccatct ttcacaaaga  17160
tgttgctgtc tcccaggtcg ccgtgggaaa agacaagttc ctcttcgggc ttttccgtct  17220
ttaaaaaatc atacagctcg cgcggatctt taaatggagt gtcttcttcc cagttttcgc  17280
aatccacatc ggccagatcg ttattcagta agtaatccaa ttcggctaag cggctgtcta  17340
agctattcgt atagggacaa tccgatatgt cgatggagtg aaagagcctg atgcactccg  17400
catacagctc gataatcttt tcagggcttt gttcatcttc atactcttcc gagcaaagga  17460
cgccatcggc ctcactcatg agcagattgc tccagccatc atgccgttca aagtgcagga  17520
cctttggaac aggcagcttt ccttccagcc atagcatcat gtccttttcc cgttccacat  17580
cataggtggt ccctttatac cggctgtccg tcatttttaa atataggttt tcattttctc  17640
ccaccagctt atataccttta gcaggagaca ttccttccgt atcttttacg cagcggtatt  17700
tttcgatcag ttttttcaat tccggtgata ttctcatttt agccatttat tatttccttc  17760
ctcttttcta cagtatttaa agatacccca agaagctaat tataacaaga cgaactccaa  17820
ttcactgttc cttgcattct aaaaccttaa ataccagaaa acagcttttt caaagttgtt  17880
ttcaaagttg gcgtataaca tagtatcgac ggagccgatt ttgaaaccgc ggtgatcaca  17940
ggcagcaacg ctctgtcatc gttacaatca acatgctacc ctccgcgaga tcatccgtgt  18000
ttcaaacccg gcagcttagt tgccgttctt ccgaatagca tcggtaacat gagcaaagtc  18060
tgccgcctta caacggctct cccgctgacg ccgtcccgga ctgatgggct gcctgtatcg  18120
agtggtgatt ttgtgccgag ctgccggtcg gggagctgtt ggctggctgg tggcaggata  18180
tattgtggtg taaacaaatt gacgcttaga caacttaata acacattgcg gacgttttta  18240
atgtagagct caaagtttaa cgcgttagca gaaggcatgt tgttgtgact ccgaggggtt  18300
gcctcaaact ctatcttata accggcgtgg aggcatggag gcaggggtat tttggtcatt  18360
ttaatagata gtggaaaatg acgtggaatt tacttaaaga cgaagtcttt gcgacaaggg  18420
ggggcccacg ccgaatttaa tattaccggc gtggcccccc cttatcgcga gtgctttagc  18480
acgagcggtc cagatttaaa gtagaaaatt tcccgcccac tagggttaaa ggtgttcaca  18540
ctataaaagc atatacgatg tgatggtatt tgatggagcg tatattgtat caggtatttc  18600
cgttggatac gaattattcg tacgaccctc ggtaccgatc ggcgcgccag atttgccttt  18660
tcaatttcag aaagaatgct aacccacaga tggttagaga ggcttacgca gcaggtatca  18720
tcaagacgat ctacccgagc aataatctcc aggaaatcaa ataccttccc aagaaggtta  18780
aagatgcagt caaaagattc aggactaact gcatcaagaa cacagagaaa gatatatttc  18840
tcaagatcag aagtactatt ccagtatgga cgattcaagg cttgcttcac aaaccaaggc  18900
aagtaataga gattggagtc tctaaaaagg tagttcccac tgaatcaaag gccatggagt  18960
```

caaagattca aatagaggac ctaacagaac tcgccgtaaa gactggcgaa cagttcatac 19020
agagtctctt acgactcaat gacaagaaga aaatcttcgt caacatggtg gagcacgaca 19080
cacttgtcta ctccaaaaat atcaaagata cagtctcaga agaccaaagg gcaattgaga 19140
cttttcaaca aagggtaata tccggaaacc tcctcggatt ccattgccca gctatctgtc 19200
actttattgt gaagatagtg gaaaaggaag gtggctccta caaatgccat cattgcgata 19260
aaggaaaggc catcgttgaa gatgcctctg ccgacagtgg tcccaaagat ggacccccac 19320
ccacgaggag catcgtggaa aaagaagacg ttccaaccac gtcttcaaag caagtggatt 19380
gatgtgatat ctccactgac gtaagggatg acgcacaatc ccactatcct tcgcaagacc 19440
cttcctctat ataaggaagt tcatttcatt tggagagaac acgggggact cctgcaggta 19500
gatcgctcgt cgacatggat aagaagtact ctatcggact cgatatcgga actaactctg 19560
tgggatgggc tgtgatcacc gatgagtaca aggtgccatc taagaagttc aaggttctcg 19620
gaaacaccga taggcactct atcaagaaaa accttatcgg tgctctcctc ttcgattctg 19680
gtgaaactgc tgaggctacc agactcaaga gaaccgctag aagaaggtac accagaagaa 19740
agaacaggat ctgctacctc caagagatct tctctaacga gatggctaaa gtggatgatt 19800
cattcttcca caggctcgaa gagtcattcc tcgtggaaga agataagaag cacgagaggc 19860
accctatctt cggaaacatc gttgatgagg tggcatacca cgagaagtac cctactatct 19920
accacctcag aaagaagctc gttgattcta ctgataaggc tgatctcagg ctcatctacc 19980
tcgctctcgc tcacatgatc aagttcagag gacacttcct catcgagggt gatctcaacc 20040
ctgataactc tgatgtggat aagttgttca tccagctcgt gcagacctac aaccagcttt 20100
tcgaagagaa ccctatcaac gcttcaggtg tggatgctaa ggctatcctc tctgctaggc 20160
tctctaagtc aagaaggctt gagaacctca ttgctcagct ccctggtgag aagaagaacg 20220
gacttttcgg aaacttgatc gctctctctc tcggactcac ccctaacttc aagtctaact 20280
tcgatctcgc tgaggatgca aagctccagc tctcaaagga tacctacgat gatgatctcg 20340
ataacctcct cgctcagatc ggagatcagt acgctgattt gttcctcgct gctaagaacc 20400
tctctgatgc tatcctcctc agtgatatcc tcagagtgaa caccgagatc accaaggctc 20460
cactctcagc ttctatgatc aagagatacg atgagcacca ccaggatctc acacttctca 20520
aggctcttgt tagacagcag ctcccagaga agtacaaaga gattttcttc gatcagtcta 20580
agaacggata cgctggttac atcgatggtg gtgcatctca agaagagttc tacaagttca 20640
tcaagcctat cctcgagaag atggatggaa ccgaggaact cctcgtgaag ctcaatagag 20700
aggatcttct cagaaagcag aggaccttcg ataacggatc tatccctcat cagatccacc 20760
tcggagagtt gcacgctatc cttagaaggc aagaggattt ctacccattc ctcaaggata 20820
acagggaaaa gattgagaag attctcacct tcagaatccc ttactacgtg ggacctctcg 20880
ctagaggaaa ctcaagattc gcttggatga ccagaaagtc tgaggaaacc atcacccctt 20940
ggaacttcga agaggtggtg gataagggtg ctagtgctca gtctttcatc gagaggatga 21000
ccaacttcga taaga 21015

<210> SEQ ID NO 91
<211> LENGTH: 19780
<212> TYPE: DNA
<213> ORGANISM: artificial
<220> FEATURE:
<223> OTHER INFORMATION: synthetic oligonucleotide

<400> SEQUENCE: 91

```
ggcatggcca gtgtgtggga ttacgacctg gtactgatgg cggtttccca tctaaccgaa     60
tccatgaacc gataccggga agggaaggga gacaagcccg gccgcgtgtt ccgtccacac    120
gttgcggacg tactcaagtt ctgccggcga gccgatggcg gaaagcagaa agacgacctg    180
gtagaaacct gcattcggtt aaacaccacg cacgttgcca tgcagcgtac gaagaaggcc    240
aagaacggcc gcctggtgac ggtatccgag ggtgaagcct tgattagccg ctacaagatc    300
gtaaagagcg aaaccgggcg gccggagtac atcgagatcg agctagctga ttggatgtac    360
cgcgagatca cagaaggcaa gaacccggac gtgctgacgg ttcaccccga ttactttttg    420
atcgatcccg gcatcggccg ttttctctac cgcctggcac gccgcgccgc aggcaaggca    480
gaagccagat ggttgttcaa gacgatctac gaacgcagtg gcagcgccgg agagttcaag    540
aagttctgtt tcaccgtgcg caagctgatc gggtcaaatg acctgccgga gtacgatttg    600
aaggaggagg cggggcaggc tggcccgatc ctagtcatgc gctaccgcaa cctgatcgag    660
ggcgaagcat ccgccggttc ctaatgtacg gagcagatgc tagggcaaat tgccctagca    720
ggggaaaaag gtcgaaaagg cctctttcct gtggatagca cgtacattgg gaacccaaag    780
ccgtacattg ggaaccggaa cccgtacatt gggaacccaa agccgtacat tgggaaccgg    840
tcacacatgt aagtgactga tataaaagag aaaaaaggcg atttttccgc ctaaaactct    900
ttaaaactta ttaaaactct taaaacccgc ctggcctgtg cataactgtc tggccagcgc    960
acagccgaag agctgcaaaa agcgcctacc cttcggtcgc tgcgctccct acgccccgcc   1020
gcttcgcgtc ggcctatcgc ggccgctggc cgctcaaaaa tggctggcct acggccaggc   1080
aatctaccag ggcgcggaca agccgcgccg tcgccactcg accgccggcg cccacatcaa   1140
ggcaccctgc ctcgcgcgtt tcggtgatga cggtgaaaac ctctgacaca tgcagctccc   1200
ggaaacggtc acagcttgtc tgtaagcgga tgccgggagc agacaagccc gtcagggcgc   1260
gtcagcgggt gttggcgggt gtcggggcgc agccatgacc cagtcacgta gcgatagcgg   1320
agtgtatact ggcttaacta tgcggcatca gagcagattg tactgagagt gcaccatatg   1380
cggtgtgaaa taccgcacag atgcgtaagg agaaaatacc gcatcaggcg ctcttccgct   1440
tcctcgctca ctgactcgct gcgctcggtc gttcggctgc ggcgagcggt atcagctcac   1500
tcaaaggcgg taatacggtt atccacagaa tcaggggata acgcaggaaa gaacatgtga   1560
gcaaaaggcc agcaaaaggc caggaaccgt aaaaaggccg cgttgctggc gtttttccat   1620
aggctccgcc cccctgacga gcatcacaaa aatcgacgct caagtcagag gtggcgaaac   1680
ccgacaggac tataaagata ccaggcgttt ccccctggaa gctccctcgt gcgctctcct   1740
gttccgaccc tgccgcttac cggatacctg tccgcctttc tcccttcggg aagcgtggcg   1800
ctttctcata gctcacgctg taggtatctc agttcggtgt aggtcgttcg ctccaagctg   1860
ggctgtgtgc acgaaccccc cgttcagccc gaccgctgcg ccttatccgg taactatcgt   1920
cttgagtcca acccggtaag acacgactta tcgccactgg cagcagccac tggtaacagg   1980
attagcagag cgaggtatgt aggcggtgct acagagttct tgaagtggtg gcctaactac   2040
ggctacacta gaaggacagt atttggtatc tgcgctctgc tgaagccagt taccttcgga   2100
aaaagagttg gtagctcttg atccggcaaa caaaccaccg ctggtagcgg tggttttttt   2160
gtttgcaagc agcagattac gcgcagaaaa aaaggatctc aagaagatcc tttgatcttt   2220
tctacggggt ctgacgctca gtggaacgaa aactcacgtt aagggatttt ggtcatgcat   2280
tctaggtact aaaacaattc atccagtaaa atataatatt ttattttctc ccaatcaggc   2340
```

ttgatcccca gtaagtcaaa aaatagctcg acatactgtt cttccccgat atcctccctg 2400
atcgaccgga cgcagaaggc aatgtcatac cacttgtccg ccctgccgct tctcccaaga 2460
tcaataaagc cacttacttt gccatctttc acaaagatgt tgctgtctcc caggtcgccg 2520
tgggaaaaga caagttcctc ttcgggcttt tccgtcttta aaaaatcata cagctcgcgc 2580
ggatctttaa atggagtgtc ttcttcccag ttttcgcaat ccacatcggc cagatcgtta 2640
ttcagtaagt aatccaattc ggctaagcgg ctgtctaagc tattcgtata gggacaatcc 2700
gatatgtcga tggagtgaaa gagcctgatg cactccgcat acagctcgat aatcttttca 2760
gggctttgtt catcttcata ctcttccgag caaaggacgc catcggcctc actcatgagc 2820
agattgctcc agccatcatg ccgttcaaag tgcaggacct ttggaacagg cagctttcct 2880
tccagccata gcatcatgtc cttttcccgt tccacatcat aggtggtccc tttataccgg 2940
ctgtccgtca tttttaaata taggttttca ttttctccca ccagcttata taccttagca 3000
ggagacattc cttccgtatc ttttacgcag cggtattttt cgatcagttt tttcaattcc 3060
ggtgatattc tcattttagc catttattat ttccttcctc ttttctacag tatttaaaga 3120
taccccaaga agctaattat aacaagacga actccaattc actgttcctt gcattctaaa 3180
accttaaata ccagaaaaca gctttttcaa agttgttttc aaagttggcg tataacatag 3240
tatcgacgga gccgattttg aaaccgcggt gatcacaggc agcaacgctc tgtcatcgtt 3300
acaatcaaca tgctaccctc cgcgagatca tccgtgtttc aaacccggca gcttagttgc 3360
cgttcttccg aatagcatcg gtaacatgag caaagtctgc cgccttacaa cggctctccc 3420
gctgacgccg tcccggactg atgggctgcc tgtatcgagt ggtgattttg tgccgagctg 3480
ccggtcgggg agctgttggc tggctggtgg caggatatat tgtggtgtaa acaaattgac 3540
gcttagacaa cttaataaca cattgcggac gtttttaatg tagagctcaa agtttaacgc 3600
gttagcagaa ggcatgttgt tgtgactccg aggggttgcc tcaaactcta tcttataacc 3660
ggcgtggagg catggaggca ggggtatttt ggtcatttta atagatagtg gaaaatgacg 3720
tggaatttac ttaaagacga agtctttgcg acaagggggg gcccacgccg aatttaatat 3780
taccggcgtg gcccccccctt atcgcgagtg ctttagcacg agcggtccag atttaaagta 3840
gaaaatttcc cgcccactag ggttaaaggt gttcacacta taaaagcata tacgatgtga 3900
tggtatttga tggagcgtat attgtatcag gtatttccgt tggatacgaa ttattcgtac 3960
gaccctcggt accgatcggc gcgccagatt tgccttttca atttcagaaa gaatgctaac 4020
ccacagatgg ttagagaggc ttacgcagca ggtatcatca agacgatcta cccgagcaat 4080
aatctccagg aaatcaaata ccttcccaag aaggttaaag atgcagtcaa aagattcagg 4140
actaactgca tcaagaacac agagaaagat atatttctca agatcagaag tactattcca 4200
gtatggacga ttcaaggctt gcttcacaaa ccaaggcaag taatagagat tggagtctct 4260
aaaaaggtag ttcccactga atcaaaggcc atggagtcaa agattcaaat agaggaccta 4320
acagaactcg ccgtaaagac tggcgaacag ttcatacaga gtctcttacg actcaatgac 4380
aagaagaaaa tcttcgtcaa catggtggag cacgacacac ttgtctactc caaaaatatc 4440
aaagatacag tctcagaaga ccaaagggca attgagactt ttcaacaaag ggtaatatcc 4500
ggaaacctcc tcggattcca ttgcccagct atctgtcact ttattgtgaa gatagtggaa 4560
aaggaaggtg gctcctacaa atgccatcat tgcgataaag gaaaggccat cgttgaagat 4620
gcctctgccg acagtggtcc caaagatgga cccccaccca cgaggagcat cgtggaaaaa 4680

-continued

```
gaagacgttc caaccacgtc ttcaaagcaa gtggattgat gtgatatctc cactgacgta   4740
agggatgacg cacaatccca ctatccttcg caagaccctt cctctatata aggaagttca   4800
tttcatttgg agagaacacg ggggactcct gcaggtagat cgctcgtcga catggataag   4860
aagtactcta tcggactcga tatcggaact aactctgtgg gatgggctgt gatcaccgat   4920
gagtacaagg tgccatctaa gaagttcaag gttctcggaa acaccgatag gcactctatc   4980
aagaaaaacc ttatcggtgc tctcctcttc gattctggtg aaactgctga ggctaccaga   5040
ctcaagagaa ccgctagaag aaggtacacc agaagaaaga acaggatctg ctacctccaa   5100
gagatcttct ctaacgagat ggctaaagtg gatgattcat tcttccacag gctcgaagag   5160
tcattcctcg tggaagaaga taagaagcac gagaggcacc ctatcttcgg aaacatcgtt   5220
gatgaggtgg cataccacga gaagtaccct actatctacc acctcagaaa gaagctcgtt   5280
gattctactg ataaggctga tctcaggctc atctacctcg ctctcgctca catgatcaag   5340
ttcagaggac acttcctcat cgagggtgat ctcaaccctg ataactctga tgtggataag   5400
ttgttcatcc agctcgtgca gacctacaac cagcttttcg aagagaaccc tatcaacgct   5460
tcaggtgtgg atgctaaggc tatcctctct gctaggctct ctaagtcaag aaggcttgag   5520
aacctcattg ctcagctccc tggtgagaag aagaacggac ttttcggaaa cttgatcgct   5580
ctctctctcg gactcacccc taacttcaag tctaacttcg atctcgctga ggatgcaaag   5640
ctccagctct caaaggatac ctacgatgat gatctcgata acctcctcgc tcagatcgga   5700
gatcagtacg ctgatttgtt cctcgctgct aagaacctct ctgatgctat cctcctcagt   5760
gatatcctca gagtgaacac cgagatcacc aaggctccac tctcagcttc tatgatcaag   5820
agatacgatg agcaccacca ggatctcaca cttctcaagg ctcttgttag acagcagctc   5880
ccagagaagt acaaagagat tttcttcgat cagtctaaga acggatacgc tggttacatc   5940
gatggtggtg catctcaaga agagttctac aagttcatca agcctatcct cgagaagatg   6000
gatggaaccg aggaactcct cgtgaagctc aatagagagg atcttctcag aaagcagagg   6060
accttcgata acggatctat ccctcatcag atccacctcg gagagttgca cgctatcctt   6120
agaaggcaag aggatttcta cccattcctc aaggataaca gggaaaagat tgagaagatt   6180
ctcaccttca gaatccctta ctacgtggga cctctcgcta gaggaaactc aagattcgct   6240
tggatgacca gaaagtctga ggaaaccatc accccttgga acttcgaaga ggtggtggat   6300
aagggtgcta gtgctcagtc tttcatcgag aggatgacca acttcgataa gaaccttcca   6360
aacgagaagg tgctccctaa gcactctttg ctctacgagt acttcaccgt gtacaacgag   6420
ttgaccaagg ttaagtacgt gaccgaggga atgaggaagc ctgctttttt gtcaggtgag   6480
caaaagaagg ctatcgttga tctcttgttc aagaccaaca gaaaggtgac cgtgaagcag   6540
ctcaaagagg attacttcaa gaaaatcgag tgcttcgatt cagttgagat ttctggtgtt   6600
gaggataggt tcaacgcatc tctcggaacc taccacgatc tcctcaagat cattaaggat   6660
aaggatttct tggataacga ggaaaacgag gatatcttgg aggatatcgt tcttaccctc   6720
accctctttg aagatagaga gatgattgaa gaaaggctca agacctacgc tcatctcttc   6780
gatgataagg tgatgaagca gttgaagaga agaagataca ctggttgggg aaggctctca   6840
agaaagctca ttaacggaat cagggataag cagtctggaa agacaatcct tgatttcctc   6900
aagtctgatg gattcgctaa cagaaacttc atgcagctca tccacgatga ttctctcacc   6960
tttaaagagg atatccagaa ggctcaggtt tcaggacagg gtgatagtct ccatgagcat   7020
atcgctaacc tcgctggatc tcctgcaatc aagaagggaa tcctccagac tgtgaaggtt   7080
```

-continued gtggatgagt tggtgaaggt gatgggaagg cataagcctg agaacatcgt gatcgaaatg 7140
gctagagaga accagaccac tcagaaggga cagaagaact ctagggaaag gatgaagagg 7200
atcgaggaag gtatcaaaga gcttggatct cagatcctca aagagcaccc tgttgagaac 7260
actcagctcc agaatgagaa gctctacctc tactacctcc agaacggaag ggatatgtat 7320
gtggatcaag agttggatat caacaggctc tctgattacg atgttgatca tatcgtgcca 7380
cagtcattct tgaaggatga ttctatcgat aacaaggtgc tcaccaggtc tgataagaac 7440
aggggtaaga gtgataacgt gccaagtgaa gaggttgtga agaaaatgaa gaactattgg 7500
aggcagctcc tcaacgctaa gctcatcact cagagaaagt tcgataactt gactaaggct 7560
gagaggggag gactctctga attggataag gcaggattca tcaagaggca gcttgtggaa 7620
accaggcaga tcactaagca cgttgcacag atcctcgatt ctaggatgaa caccaagtac 7680
gatgagaacg ataagttgat cagggaagtg aaggttatca ccctcaagtc aaagctcgtg 7740
tctgatttca gaaaggattt ccaattctac aaggtgaggg aaatcaacaa ctaccaccac 7800
gctcacgatg cttaccttaa cgctgttgtt ggaaccgctc tcatcaagaa gtatcctaag 7860
ctcgagtcag agttcgtgta cggtgattac aaggtgtacg atgtgaggaa gatgatcgct 7920
aagtctgagc aagagatcgg aaaggctacc gctaagtatt tcttctactc taacatcatg 7980
aatttcttca agaccgagat taccctcgct aacggtgaga tcagaaagag gccactcatc 8040
gagacaaacg gtgaaacagg tgagatcgtg tgggataagg gaagggattt cgctaccgtt 8100
agaaaggtgc tctctatgcc acaggtgaac atcgttaaga aaaccgaggt gcagaccggt 8160
ggattctcta aagagtctat cctccctaag aggaactctg ataagctcat tgctaggaag 8220
aaggattggg accctaagaa atacggtggt ttcgattctc ctaccgtggc ttactctgtt 8280
ctcgttgtgg ctaaggttga gaagggaaag agtaagaagc tcaagtctgt taaggaactt 8340
ctcggaatca ctatcatgga aaggtcatct ttcgagaaga acccaatcga tttcctcgag 8400
gctaagggat acaaagaggt taagaaggat ctcatcatca agctcccaaa gtactcactc 8460
ttcgaactcg agaacggtag aaagaggatg ctcgcttctg ctggtgagct tcaaaaggga 8520
aacgagcttg ctctcccatc taagtacgtt aactttcttt acctcgcttc tcactacgag 8580
aagttgaagg gatctccaga agataacgag cagaagcaac ttttcgttga gcagcacaag 8640
cactacttgg atgagatcat cgagcagatc tctgagttct ctaaaagggt gatcctcgct 8700
gatgcaaacc tcgataaggt gttgtctgct tacaacaagc acagagataa gcctatcagg 8760
gaacaggcag agaacatcat ccatctcttc acccttacca acctcggtgc tcctgctgct 8820
ttcaagtact tcgatacaac catcgatagg aagagataca cctctaccaa agaagtgctc 8880
gatgctaccc tcatccatca gtctatcact ggactctacg agactaggat cgatctctca 8940
cagctcggtg gtgattcaag ggctgatcct aagaagaaga ggaaggtttg acgtcgacga 9000
tatgaagatg aagatgaaat atttggtgtg tcaaataaaa agcttgtgtg cttaagtttg 9060
tgtttttttc ttggcttgtt gtgttatgaa tttgtggctt tttctaatat taaatgaatg 9120
taagatcaca ttataatgaa taaacaaatg tttctataat ccattgtgaa tgttttgttg 9180
gatctcttct gcagcatata actactgtat gtgctatggt atggactatg gaatatgatt 9240
aaagataagc cagagctctg gtgacggacc catggcttcg ttgaacaacg gaaactcgac 9300
ttgccttccg cacaatacat catttcttct tagctttttt tcttcttctt cgttcataca 9360
gttttttttt gtttatcagc ttacattttc ttgaaccgta gctttcgttt tcttcttttt 9420
aactttccat tcggagtttt tgtatcttgt ttcatagttt gtcccaggat tagaatgatt 9480
aggcatcgaa ccttcaagaa tttgattgaa taaaacatct tcattcttaa gatatgaaga 9540
taatcttcaa aaggcccctg ggaatctgaa agaagagaag caggcccatt tatatgggaa 9600
agaacaatag tatttcttat ataggcccat ttaagttgaa aacaatcttc aaaagtccca 9660
catcgcttag ataagaaaac gaagctgagt ttatatacag ctagagtcga agtagtgatt 9720
gcctacttgg gctgttgcag gttttagagc tagaaatagc aagttaaaat aaggctagtc 9780
cgttatcaac ttgaaaaagt ggcaccgagt cggtgctttt tttcccgggg cgcgccctat 9840
gtcgagctgc aggtcaacgg atcaggatat tcttgtttaa gatgttgaac tctatggagg 9900
tttgtatgaa ctgatgatct aggaccggat aagttccctt cttcatagcg aacttattca 9960
aagaatgttt tgtgtatcat tcttgttaca ttgttattaa tgaaaaaata ttattggtca 10020
ttggactgaa cacgagtgtt aaatatggac caggccccaa ataagatcca ttgatatatg 10080
aattaaataa caagaataaa tcgagtcacc aaaccacttg ccttttttaa cgagacttgt 10140
tcaccaactt gatacaaaag tcattatcct atgcaaatca ataatcatac aaaaatatcc 10200
aataacacta aaaaattaaa agaaatggat aatttcacaa tatgttatac gataaagaag 10260
ttacttttcc aagaaattca ctgattttat aagcccactt gcattagata aatggcaaaa 10320
aaaaacaaaa aggaaaagaa ataaagcacg aagaattcta gaaaatacga aatacgcttc 10380
aatgcagtgg gacccacggt tcaattattg ccaattttca gctccaccgt atatttaaaa 10440
aataaaacga taatgctaaa aaaatataaa tcgtaacgat cgttaaatct caacggctgg 10500
atcttatgac gaccgttaga aattgtggtt gtcgacgagt cagtaataaa cggcgtcaaa 10560
gtggttgcag ccggcacaca cgagtcgtgt ttatcaactc aaagcacaaa tacttttcct 10620
caacctaaaa ataaggcaat tagccaaaaa caactttgcg tgtaaacaac gctcaataca 10680
cgtgtcattt tattattagc tattgcttca ccgccttagc tttctcgtga cctagtcgtc 10740
ctcgtctttt cttcttcttc ttctataaaa caatacccaa agagctcttc ttcttcacaa 10800
ttcagatttc aatttctcaa aatcttaaaa actttctctc aattctctct accgtgatca 10860
aggtaaattt ctgtgttcct tattctctca aaatcttcga ttttgttttc gttcgatccc 10920
aatttcgtat atgttctttg gtttagattc tgttaatctt agatcgaaca cgattttctg 10980
ggtttgatcg ttagatatca tcttaattct cgattagggt ttcatagata tcatccgatt 11040
tgttcaaata atttgagttt tgtcgaataa ttactcttcg atttgtgatt tctatctaga 11100
tctggtgtta gtttctagtt tgtgcgatcg aatttgtcga ttaatctgag tttttctgat 11160
taacaggcct gcaggatgga agacgccaaa aacataaaga aaggcccggc gccattctat 11220
ccgctggaag atggaaccgc tggagagcaa ctgcataagg ctatgaagag atacgccctg 11280
gttcctggaa caattgcttt tacagatgca catatcgagg tggacatcac ttacgctgag 11340
tacttcgaaa tgtccgttcg gttggcagaa gctatgaaac gatatgggct gaatacaaat 11400
cacagaatcg tcgtatgcag tgaaaactct cttcaattct ttatgccggt gttgggcgcg 11460
ttatttatcg gagttgcagt tgcgcccgcg aacgacattt ataatgaacg tgaattgctc 11520
aacagtatgg gcatttcgca gcctaccgtg gtgttcgttt ccaaaaaggg gttgcaaaaa 11580
attttgaacg tgcaaaaaaa gctcccaatc atccaaaaaa ttattatcat ggattctaaa 11640
acggattacc agggatttca gtcgatgtac acgttcgtca catctcatct acctcccggt 11700
tttaatgaat acgattttgt gccagagtcc ttcgataggg acaagacaat tgcactgatc 11760
atgaactcct ctggatctac tggtctgcct aaaggtgtcg ctctgcctca tagaactgcc 11820

```
tgcgtgagat tctcgcatgc cagagatcct atttttggca atcaaatcat tccggatact  11880
gcgattttaa gtgttgttcc attccatcac ggttttggaa tgtttactac actcggatat  11940
ttgatatgtg gatttcgagt cgtcttaatg tatagatttg aagaagagct gtttctgagg  12000
agccttcagg attacaagat tcaaagtgcg ctgctggtgc caaccctatt ctccttcttc  12060
gccaaaagca ctctgattga caaatacgat ttatctaatt tacacgaaat tgcttctggt  12120
ggcgctcccc tctctaagga agtcggggaa gcggttgcca agaggttcca tctgccaggt  12180
atcaggcaag gatatgggct cactgagact acatcagcta ttctgattac acccgagggg  12240
gatgataaac cgggcgcggt cggtaaagtt gttccatttt ttgaagcgaa ggttgtggat  12300
ctggataccg ggaaaacgct gggcgttaat caaagaggcg aactgtgtgt gagaggtcct  12360
atgattatgt ccggttatgt aaacaatccg gaagcgacca acgccttgat tgacaaggat  12420
ggatggctac attctggaga catagcttac tgggacgaag acgaacactt cttcatcgtt  12480
gaccgcctga agtctctgat taagtacaaa ggctatcagg tggctcccgc tgaattggaa  12540
tccatcttgc tccaacaccc caacatcttc gacgctggtg tcgcaggtct tcccgacgat  12600
gacgccggtg aacttcccgc cgccgttgtt gttttggagc acggaaagac gatgacggaa  12660
aaagagatcg tggattacgt cgccagtcaa gtaacaaccg cgaaaaagtt gcgcggagga  12720
gttgtgtttg tggacgaagt accgaaaggt cttaccggaa aactcgacgc aagaaaaatc  12780
agagagatcc tcataaaggc caagaagggc ggaaagatcg ccgtgtgact cgaggttcga  12840
gtattatggc attgggaaaa ctgtttttct tgtaccattt gttgtgcttg taatttactg  12900
tgtttttat tcggttttcg ctatcgaact gtgaaatgga aatggatgga gaagagttaa  12960
tgaatgatat ggtccttttg ttcattctca aattaatatt atttgttttt tctcttattt  13020
gttgtgtgtt gaatttgaaa ttataagaga tatgcaaaca ttttgttttg agtaaaaatg  13080
tgtcaaatcg tggcctctaa tgaccgaagt taatatgagg agtaaaacac ttgtagttgt  13140
gttagagctc tcccgcagat ttgccttttc aatttcagaa agaatgctaa cccacagatg  13200
gttagagagg cttacgcagc aggtatcatc aagacgatct acccgagcaa taatctccag  13260
gaaatcaaat accttcccaa gaaggttaaa gatgcagtca aaagattcag gactaactgc  13320
atcaagaaca cagagaaaga tatatttctc aagatcagaa gtactattcc agtatggacg  13380
attcaaggct tgcttcacaa accaaggcaa gtaatagaga ttggagtctc taaaaaggta  13440
gttcccactg aatcaaaggc catggagtca aagattcaaa tagaggacct aacagaactc  13500
gccgtaaaga ctggcgaaca gttcatacag agtctcttac gactcaatga caagaagaaa  13560
atcttcgtca acatggtgga gcacgacaca cttgtctact ccaaaaatat caaagataca  13620
gtctcagaag accaaagggc aattgagact tttcaacaaa gggtaatatc cggaaacctc  13680
ctcggattcc attgcccagc tatctgtcac tttattgtga agatagtgga aaaggaaggt  13740
ggctcctaca aatgccatca ttgcgataaa ggaaaggcca tcgttgaaga tgcctctgcc  13800
gacagtggtc ccaaagatgg acccccaccc acgaggagca tcgtggaaaa agaagacgtt  13860
ccaaccacgt cttcaaagca agtggattga tgtgatatct ccactgacgt aagggatgac  13920
gcacaatccc actatccttc gcaagaccct tcctctatat aaggaagttc atttcatttg  13980
gagagaacac gggggactat ggagagtggt tccaacagca cttcttgtcc aatggctttt  14040
gccggggata atagtgatgg tccgatgtgt cctatgatga tgatgatgcc gcccatcatg  14100
acatcacatc aacatcatgg tcatgatcat caacatcaac aacaagaaca tgatggttat  14160
```

```
gcatatcagt cacaccacca acaaagtagt tccctttttc ttcaatcact agctcctccc  14220
caaggaacta agaacaaagt tgcttcttct tcttctcctt cctcttgtgc tcctgcctat  14280
tctctaatgg agatccatca taacgaaatc gttgcaggag gaatcaaccc ttgctcctct  14340
tcctcttctt cagcctctgt caaggccaag atcatggctc atcctcacta ccaccgcctc  14400
ttggccgctt atgtcaattg tcagaaggtt ggagcaccac cggaggttgt ggcgaggcta  14460
gaggaggcat gctcgtctgc cgcagccgct gccgcatcta tgggaccaac aggatgtcta  14520
ggtgaagatc cagggcttga tcaattcatg gaagcttact gtgaaatgct cgttaagtat  14580
gagcaagagc tctccaaacc tttcaaggaa gctatggtct tccttcaacg tgtcgagtgt  14640
caattcaaat ccctctctct atcctcacct tcctctttct ccggttatgg agagacagca  14700
attgatagga acaataatgg gtcatccgag gaagaagtcg atatgaacaa tgaatttgta  14760
gatccacaag ctgaggatag agagcttaaa ggacagctct tgcgcaagta cagtggttac  14820
ttagggagcc tcaagcaaga gttcatgaag aagaggaaga aaggaaagct ccctaaagaa  14880
gctcgtcaac aactgcttga ttggtggagc cgtcactaca aatggcctta cccttcggag  14940
caacaaaagc tcgcccttgc ggaatcaacg gggctggacc agaaacagat aaacaattgg  15000
ttcataaacc agaggaaacg gcattggaag ccgtcggagg acatgcagtt tgtagtaatg  15060
gacgcaacac atcctcacca ttacttcatg gataatgtct tgggcaatcc tttcccaatg  15120
gatcacatct cctccaccat gctttgactc gagtttctcc ataataatgt gtgagtagtt  15180
cccagataag ggaattaggg ttcctatagg gtttcgctca tgtgttgagc atataagaaa  15240
cccttagtat gtatttgtat ttgtaaaata cttctatcaa taaaatttct aattcctaaa  15300
accaaaatcc agtactaaaa tccagatccc ccgaattaag tgtttgatcg ccggcggtac  15360
cgagtgtact tcaagtcagt gggaaatcaa taaaatgatt attttatgaa tatatttcat  15420
tgtgcaagta gatagaaatt acatatgtta cataacacac gaaataaaca aaaaaagaca  15480
atccaaaaac aaacacccca aaaaaaataa tcactttaga taaactcgta tgaggagagg  15540
cacgttcagt gactcgacga ttcccgagca aaaaaagtct ccccgtcaca catgtagtgg  15600
gtgacgcaat tatctttaaa gtaatccttc tgttgacttg tcattgataa catccagtct  15660
tcgtcaggat tgcaaagaat tatagaaggg atcccacctt ttattttctt cttttttcca  15720
tatttagggt tgacagtgaa atcagactgg caacctatta attgcttcca caatgggacg  15780
aacttgaagg ggatgtcgtc gatgatatta taggtggcgt gttcatcgta gttggtgaaa  15840
tcgatggtac cgttccaata gttgtgtcgt ccgagacttc tagcccaggt ggtctttccg  15900
gtacgagttg gtccgcagat gtagaggctg gggtgtcgga ttccattcct tccattgtcc  15960
ttgttaaatc ggccatccat tcaaggtcag attgagcttg ttggtatgag acaggatgta  16020
tgtaagtata agcgtctatg cttacatggt atagatgggt ttccctccag gagtgtagat  16080
cttcgtggca gcgaagatct gattctgtga agggcgacac atacggttca ggttgtggag  16140
ggaataattt gttggctgaa tattccagcc attgaagctt tgttgcccat tcatgaggga  16200
attcttcctt gatcatgtca agatattcct ccttagacgt tgcagtctgg ataatagttc  16260
tccatcgtgc gtcagatttg cgaggagaaa ccttatgatc tcggaaatct cctctggttt  16320
taatatctcc gtcctttgat atgtaatcaa ggacttgttt agagtttcta gctggctgga  16380
tattagggtg atttccttca aaatcgaaaa aagaaggatc cctaatacaa ggttttttat  16440
caagctggag aagagcatga tagtgggtag tgccatcttg atgaagctca gaagcaacac  16500
caaggaagaa aataagaaaa ggtgtgagtt tctcccagag aaactggaat aaatcatctc  16560
```

tttgagatga gcacttggga taggtaagga aaacatattt agattggagt ctgaagttct 16620
tactagcaga aggcatgttg ttgtgactcc gaggggttgc ctcaaactct atcttataac 16680
cggcgtggag gcatggaggc aggggtattt tggtcatttt aatagatagt ggaaaatgac 16740
gtggaattta cttaaagacg aagtctttgc gacaaggggg ggcccacgcc gaatttaata 16800
ttaccggcgt ggcccccccct tatcgcgagt gctttagcac gagcggtcca gatttaaagt 16860
agaaaatttc ccgcccacta gggttaaagg tgttcacact ataaaagcat atacgatgtg 16920
atggtatttg atggagcgta tattgtatca ggtatttccg ttggatacga attattcgta 16980
cgaccctcat agtttaaact atcagtgttt gacaggatat attggcgggt aaacctaaga 17040
gaaaagagcg tttattagaa taacggatat ttaaaagggc gtgaaaaggt ttatccgttc 17100
gtccatttgt atgtgcatgc caaccacagg gttcccctcg ggatcaaagt actttgatcc 17160
aacccctccg ctgctatagt gcagtcggct tctgacgttc agtgcagccg tcttctgaaa 17220
acgacatgtc gcacaagtcc taagttacgc gacaggctgc cgccctgccc ttttcctggc 17280
gttttcttgt cgcgtgtttt agtcgcataa agtagaatac ttgcgactag aaccggagac 17340
attacgccat gaacaagagc gccgccgctg gcctgctggg ctatgcccgc gtcagcaccg 17400
acgaccagga cttgaccaac caacgggccg aactgcacgc ggccggctgc accaagctgt 17460
tttccgagaa gatcaccggc accaggcgcg accgcccgga gctggccagg atgcttgacc 17520
acctacgccc tggcgacgtt gtgacagtga ccaggctaga ccgcctggcc cgcagcaccc 17580
gcgacctact ggacattgcc gagcgcatcc aggaggccgg cgcgggcctg cgtagcctgg 17640
cagagccgtg ggccgacacc accacgccgg ccggccgcat ggtgttgacc gtgttcgccg 17700
gcattgccga gttcgagcgt tccctaatca tcgaccgcac ccggagcggg cgcgaggccg 17760
ccaaggcccg aggcgtgaag tttggccccc gccctaccct caccccggca cagatcgcgc 17820
acgcccgcga gctgatcgac caggaaggcc gcaccgtgaa agaggcggct gcactgcttg 17880
gcgtgcatcg ctcgaccctg taccgcgcac ttgagcgcag cgaggaagtg acgcccaccg 17940
aggccaggcg gcgcggtgcc ttccgtgagg acgcattgac cgaggccgac gccctggcgg 18000
ccgccgagaa tgaacgccaa gaggaacaag catgaaaccg caccaggacg gccaggacga 18060
accgtttttc attaccgaag agatcgaggc ggagatgatc gcggccgggt acgtgttcga 18120
gccgcccgcg cacggctcaa ccgtgcggct gcatgaaatc ctggccggtt tgtctgatgc 18180
caagctggcg gcctggccgg ccagcttggc cgctgaagaa accgagcgcc gccgtctaaa 18240
aaggtgatgt gtatttgagt aaaacagctt gcgtcatgcg gtcgctgcgt atatgatgcg 18300
atgagtaaat aaacaaatac gcaaggggaa cgcatgaagg ttatcgctgt acttaaccag 18360
aaaggcgggt caggcaagac gaccatcgca acccatctag cccgcgccct gcaactcgcc 18420
ggggccgatg ttctgttagt cgattccgat ccccagggca gtgcccgcga ttgggcggcc 18480
gtgcgggaag atcaaccgct aaccgttgtc ggcatcgacc gcccgacgat tgaccgcgac 18540
gtgaaggcca tcggccggcg cgacttcgta gtgatcgacg gagcgcccca ggcggcggac 18600
ttggctgtgt ccgcgatcaa ggcagccgac ttcgtgctga ttccggtgca gccaagccct 18660
tacgacatat gggccaccgc cgacctggtg gagctggtta agcagcgcat tgaggtcacg 18720
gatggaaggc tacaagcggc ctttgtcgtg tcgcgggcga tcaaaggcac gcgcatcggc 18780
ggtgaggttg ccgaggcgct ggccgggtac gagctgccca ttcttgagtc ccgtatcacg 18840
cagcgcgtga gctacccagg cactgccgcc gccggcacaa ccgttcttga atcagaaccc 18900
gagggcgacg ctgcccgcga ggtccaggcg ctggccgctg aaattaaatc aaaactcatt 18960
tgagttaatg aggtaaagag aaaatgagca aaagcacaaa cacgctaagt gccggccgtc 19020
cgagcgcacg cagcagcaag gctgcaacgt tggccagcct ggcagacacg ccagccatga 19080
agcgggtcaa ctttcagttg ccggcggagg atcacaccaa gctgaagatg tacgcggtac 19140
gccaaggcaa gaccattacc gagctgctat ctgaatacat cgcgcagcta ccagagtaaa 19200
tgagcaaatg aataaatgag tagatgaatt ttagcggcta aaggaggcgg catggaaaat 19260
caagaacaac caggcaccga cgccgtggaa tgccccatgt gtggaggaac gggcggttgg 19320
ccaggcgtaa gcggctgggt tgtctgccgg ccctgcaatg gcactggaac ccccaagccc 19380
gaggaatcgg cgtgacggtc gcaaaccatc cggcccggta caaatcggcg cggcgctggg 19440
tgatgacctg gtggagaagt tgaaggccgc gcaggccgcc cagcggcaac gcatcgaggc 19500
agaagcacgc cccggtgaat cgtggcaagc ggccgctgat cgaatccgca aagaatcccg 19560
gcaaccgccg gcagccggtg cgccgtcgat taggaagccg cccaagggcg acgagcaacc 19620
agattttttc gttccgatgc tctatgacgt gggcacccgc gatagtcgca gcatcatgga 19680
cgtggccgtt ttccgtctgt cgaagcgtga ccgacgagct ggcgaggtga tccgctacga 19740
gcttccagac gggcacgtag aggtttccgc agggccggcc 19780

<210> SEQ ID NO 92
<211> LENGTH: 20871
<212> TYPE: DNA
<213> ORGANISM: artificial
<220> FEATURE:
<223> OTHER INFORMATION: synthetic oligonucleotide

<400> SEQUENCE: 92
gatccgctac gagcttccag acgggcacgt agaggtttcc gcagggccgg ccggcatggc 60
cagtgtgtgg gattacgacc tggtactgat ggcggtttcc catctaaccg aatccatgaa 120
ccgataccgg gaagggaagg gagacaagcc cggccgcgtg ttccgtccac acgttgcgga 180
cgtactcaag ttctgccggc gagccgatgg cggaaagcag aaagacgacc tggtagaaac 240
ctgcattcgg ttaaacacca cgcacgttgc catgcagcgt acgaagaagg ccaagaacgg 300
ccgcctggtg acggtatccg agggtgaagc cttgattagc cgctacaaga tcgtaaagag 360
cgaaaccggg cggccggagt acatcgagat cgagctagct gattggatgt accgcgagat 420
cacagaaggc aagaacccgg acgtgctgac ggttcacccc gattactttt tgatcgatcc 480
cggcatcggc cgttttctct accgcctggc acgccgcgcc gcaggcaagg cagaagccag 540
atggttgttc aagacgatct acgaacgcag tggcagcgcc ggagagttca agaagttctg 600
tttcaccgtg cgcaagctga tcgggtcaaa tgacctgccg gagtacgatt tgaaggagga 660
ggcggggcag gctggcccga tcctagtcat gcgctaccgc aacctgatcg agggcgaagc 720
atccgccggt tcctaatgta cggagcagat gctagggcaa attgccctag caggggaaaa 780
aggtcgaaaa ggcctctttc ctgtggatag cacgtacatt gggaacccaa agccgtacat 840
tgggaaccgg aacccgtaca ttgggaaccc aaagccgtac attgggaacc ggtcacacat 900
gtaagtgact gatataaaag agaaaaaagg cgatttttcc gcctaaaact ctttaaaact 960
tattaaaact cttaaaaccc gcctggcctg tgcataactg tctggccagc gcacagccga 1020
agagctgcaa aaagcgccta cccttcggtc gctgcgctcc ctacgccccg ccgcttcgcg 1080
tcggcctatc gcggccgctg gccgctcaaa aatggctggc ctacggccag gcaatctacc 1140
agggcgcgga caagccgcgc cgtcgccact cgaccgccgg cgcccacatc aaggcaccct 1200

-continued

```
gcctcgcgcg tttcggtgat gacggtgaaa acctctgaca catgcagctc ccggaaacgg   1260
tcacagcttg tctgtaagcg gatgccggga gcagacaagc ccgtcagggc gcgtcagcgg   1320
gtgttggcgg gtgtcggggc gcagccatga cccagtcacg tagcgatagc ggagtgtata   1380
ctggcttaac tatgcggcat cagagcagat tgtactgaga gtgcaccata tgcggtgtga   1440
aataccgcac agatgcgtaa ggagaaaata ccgcatcagg cgctcttccg cttcctcgct   1500
cactgactcg ctgcgctcgg tcgttcggct gcggcgagcg gtatcagctc actcaaaggc   1560
ggtaatacgg ttatccacag aatcagggga taacgcagga aagaacatgt gagcaaaagg   1620
ccagcaaaag gccaggaacc gtaaaaaggc cgcgttgctg gcgtttttcc ataggctccg   1680
cccccctgac gagcatcaca aaaatcgacg ctcaagtcag aggtggcgaa acccgacagg   1740
actataaaga taccaggcgt ttccccctgg aagctccctc gtgcgctctc ctgttccgac   1800
cctgccgctt accggatacc tgtccgcctt tctcccttcg ggaagcgtgg cgctttctca   1860
tagctcacgc tgtaggtatc tcagttcggt gtaggtcgtt cgctccaagc tgggctgtgt   1920
gcacgaaccc cccgttcagc ccgaccgctg cgccttatcc ggtaactatc gtcttgagtc   1980
caacccggta agacacgact tatcgccact ggcagcagcc actggtaaca ggattagcag   2040
agcgaggtat gtaggcggtg ctacagagtt cttgaagtgg tggcctaact acggctacac   2100
tagaaggaca gtatttggta tctgcgctct gctgaagcca gttaccttcg gaaaaagagt   2160
tggtagctct tgatccggca aacaaaccac cgctggtagc ggtggttttt ttgtttgcaa   2220
gcagcagatt acgcgcagaa aaaaaggatc tcaagaagat cctttgatct tttctacggg   2280
gtctgacgct cagtggaacg aaaactcacg ttaagggatt ttggtcatgc attctaggta   2340
ctaaaacaat tcatccagta aaatataata ttttattttc tcccaatcag gcttgatccc   2400
cagtaagtca aaaaatagct cgacatactg ttcttccccg atatcctccc tgatcgaccg   2460
gacgcagaag gcaatgtcat accacttgtc cgccctgccg cttctcccaa gatcaataaa   2520
gccacttact ttgccatctt tcacaaagat gttgctgtct cccaggtcgc cgtgggaaaa   2580
gacaagttcc tcttcgggct tttccgtctt taaaaaatca tacagctcgc gcggatcttt   2640
aaatggagtg tcttcttccc agttttcgca atccacatcg gccagatcgt tattcagtaa   2700
gtaatccaat tcggctaagc ggctgtctaa gctattcgta tagggacaat ccgatatgtc   2760
gatggagtga aagagcctga tgcactccgc atacagctcg ataatctttt cagggctttg   2820
ttcatcttca tactcttccg agcaaaggac gccatcggcc tcactcatga gcagattgct   2880
ccagccatca tgccgttcaa agtgcaggac ctttggaaca ggcagctttc cttccagcca   2940
tagcatcatg tccttttccc gttccacatc ataggtggtc cctttatacc ggctgtccgt   3000
catttttaaa tataggtttt cattttctcc caccagctta tataccttag caggagacat   3060
tccttccgta tcttttacgc agcggtattt ttcgatcagt tttttcaatt ccggtgatat   3120
tctcatttta gccatttatt atttccttcc tcttttctac agtatttaaa gataccccaa   3180
gaagctaatt ataacaagac gaactccaat tcactgttcc ttgcattcta aaaccttaaa   3240
taccagaaaa cagctttttc aaagttgttt tcaaagttgg cgtataacat agtatcgacg   3300
gagccgattt tgaaaccgcg gtgatcacag gcagcaacgc tctgtcatcg ttacaatcaa   3360
catgctaccc tccgcgagat catccgtgtt tcaaacccgg cagcttagtt gccgttcttc   3420
cgaatagcat cggtaacatg agcaaagtct gccgccttac aacggctctc ccgctgacgc   3480
cgtcccggac tgatgggctg cctgtatcga gtggtgattt tgtgccgagc tgccggtcgg   3540
```

-continued

```
ggagctgttg gctggctggt ggcaggatat attgtggtgt aaacaaattg acgcttagac   3600
aacttaataa cacattgcgg acgtttttaa tgtagagctc aaagtttaac gcgttagcag   3660
aaggcatgtt gttgtgactc cgaggggttg cctcaaactc tatcttataa ccggcgtgga   3720
ggcatggagg caggggtatt ttggtcattt taatagatag tggaaaatga cgtggaattt   3780
acttaaagac gaagtctttg cgacaagggg gggcccacgc cgaatttaat attaccggcg   3840
tggccccccc ttatcgcgag tgctttagca cgagcggtcc agatttaaag tagaaaattt   3900
cccgcccact agggttaaag gtgttcacac tataaaagca tatacgatgt gatggtattt   3960
gatggagcgt atattgtatc aggtatttcc gttggatacg aattattcgt acgaccctcg   4020
gtaccgatcg gcgcgccaga tttgcctttt caatttcaga aagaatgcta acccacagat   4080
ggttagagag gcttacgcag caggtatcat caagacgatc tacccgagca ataatctcca   4140
ggaaatcaaa taccttccca agaaggttaa agatgcagtc aaaagattca ggactaactg   4200
catcaagaac acagagaaag atatatttct caagatcaga agtactattc cagtatggac   4260
gattcaaggc ttgcttcaca aaccaaggca agtaatagag attggagtct ctaaaaaggt   4320
agttcccact gaatcaaagg ccatggagtc aaagattcaa atagaggacc taacagaact   4380
cgccgtaaag actggcgaac agttcataca gagtctctta cgactcaatg acaagaagaa   4440
aatcttcgtc aacatggtgg agcacgacac acttgtctac tccaaaaata tcaaagatac   4500
agtctcagaa gaccaaaggg caattgagac ttttcaacaa agggtaatat ccggaaacct   4560
cctcggattc cattgcccag ctatctgtca ctttattgtg aagatagtgg aaaaggaagg   4620
tggctcctac aaatgccatc attgcgataa aggaaaggcc atcgttgaag atgcctctgc   4680
cgacagtggt cccaaagatg gacccccacc cacgaggagc atcgtggaaa aagaagacgt   4740
tccaaccacg tcttcaaagc aagtggattg atgtgatatc tccactgacg taagggatga   4800
cgcacaatcc cactatcctt cgcaagaccc ttcctctata taaggaagtt catttcattt   4860
ggagagaaca cgggggactc ctgcaggtag atcgctcgtc gacatggata agaagtactc   4920
tatcggactc gatatcggaa ctaactctgt gggatgggct gtgatcaccg atgagtacaa   4980
ggtgccatct aagaagttca aggttctcgg aaacaccgat aggcactcta tcaagaaaaa   5040
ccttatcggt gctctcctct tcgattctgg tgaaactgct gaggctacca gactcaagag   5100
aaccgctaga agaaggtaca ccagaagaaa gaacaggatc tgctacctcc aagagatctt   5160
ctctaacgag atggctaaag tggatgattc attcttccac aggctcgaag agtcattcct   5220
cgtggaagaa gataagaagc acgagaggca ccctatcttc ggaaacatcg ttgatgaggt   5280
ggcataccac gagaagtacc ctactatcta ccacctcaga aagaagctcg ttgattctac   5340
tgataaggct gatctcaggc tcatctacct cgctctcgct cacatgatca agttcagagg   5400
acacttcctc atcgagggtg atctcaaccc tgataactct gatgtggata agttgttcat   5460
ccagctcgtg cagacctaca accagctttt cgaagagaac cctatcaacg cttcaggtgt   5520
ggatgctaag gctatcctct ctgctaggct ctctaagtca agaaggcttg agaacctcat   5580
tgctcagctc cctggtgaga agaagaacgg acttttcgga aacttgatcg ctctctctct   5640
cggactcacc cctaacttca agtctaactt cgatctcgct gaggatgcaa agctccagct   5700
ctcaaaggat acctacgatg atgatctcga taacctcctc gctcagatcg gagatcagta   5760
cgctgatttg ttcctcgctg ctaagaacct ctctgatgct atcctcctca gtgatatcct   5820
cagagtgaac accgagatca ccaaggctcc actctcagct tctatgatca agagatacga   5880
tgagcaccac caggatctca cacttctcaa ggctcttgtt agacagcagc tcccagagaa   5940
```

gtacaaagag attttcttcg atcagtctaa gaacggatac gctggttaca tcgatggtgg 6000
tgcatctcaa gaagagttct acaagttcat caagcctatc ctcgagaaga tggatggaac 6060
cgaggaactc ctcgtgaagc tcaatagaga ggatcttctc agaaagcaga ggaccttcga 6120
taacggatct atccctcatc agatccacct cggagagttg cacgctatcc ttagaaggca 6180
agaggatttc tacccattcc tcaaggataa cagggaaaag attgagaaga ttctcacctt 6240
cagaatccct tactacgtgg gacctctcgc tagaggaaac tcaagattcg cttggatgac 6300
cagaaagtct gaggaaacca tcaccccttg gaacttcgaa gaggtggtgg ataagggtgc 6360
tagtgctcag tctttcatcg agaggatgac caacttcgat aagaaccttc caaacgagaa 6420
ggtgctccct aagcactctt tgctctacga gtacttcacc gtgtacaacg agttgaccaa 6480
ggttaagtac gtgaccgagg gaatgaggaa gcctgctttt ttgtcaggtg agcaaaagaa 6540
ggctatcgtt gatctcttgt tcaagaccaa cagaaaggtg accgtgaagc agctcaaaga 6600
ggattacttc aagaaaatcg agtgcttcga ttcagttgag atttctggtg ttgaggatag 6660
gttcaacgca tctctcggaa cctaccacga tctcctcaag atcattaagg ataaggattt 6720
cttggataac gaggaaaacg aggatatctt ggaggatatc gttcttaccc tcaccctctt 6780
tgaagataga gagatgattg aagaaaggct caagacctac gctcatctct tcgatgataa 6840
ggtgatgaag cagttgaaga gaagaagata cactggttgg ggaaggctct caagaaagct 6900
cattaacgga atcagggata agcagtctgg aaagacaatc cttgatttcc tcaagtctga 6960
tggattcgct aacagaaact tcatgcagct catccacgat gattctctca cctttaaaga 7020
ggatatccag aaggctcagg tttcaggaca gggtgatagt ctccatgagc atatcgctaa 7080
cctcgctgga tctcctgcaa tcaagaaggg aatcctccag actgtgaagg ttgtggatga 7140
gttggtgaag gtgatgggaa ggcataagcc tgagaacatc gtgatcgaaa tggctagaga 7200
gaaccagacc actcagaagg gacagaagaa ctctagggaa aggatgaaga ggatcgagga 7260
aggtatcaaa gagcttggat ctcagatcct caaagagcac cctgttgaga acactcagct 7320
ccagaatgag aagctctacc tctactacct ccagaacgga agggatatgt atgtggatca 7380
agagttggat atcaacaggc tctctgatta cgatgttgat catatcgtgc cacagtcatt 7440
cttgaaggat gattctatcg ataacaaggt gctcaccagg tctgataaga acaggggtaa 7500
gagtgataac gtgccaagtg aagaggttgt gaagaaaatg aagaactatt ggaggcagct 7560
cctcaacgct aagctcatca ctcagagaaa gttcgataac ttgactaagg ctgagagggg 7620
aggactctct gaattggata aggcaggatt catcaagagg cagcttgtgg aaaccaggca 7680
gatcactaag cacgttgcac agatcctcga ttctaggatg aacaccaagt acgatgagaa 7740
cgataagttg atcagggaag tgaaggttat caccctcaag tcaaagctcg tgtctgattt 7800
cagaaaggat ttccaattct acaaggtgag ggaaatcaac aactaccacc acgctcacga 7860
tgcttacctt aacgctgttg ttggaaccgc tctcatcaag aagtatccta agctcgagtc 7920
agagttcgtg tacggtgatt acaaggtgta cgatgtgagg aagatgatcg ctaagtctga 7980
gcaagagatc ggaaaggcta ccgctaagta tttcttctac tctaacatca tgaatttctt 8040
caagaccgag attaccctcg ctaacggtga gatcagaaag aggccactca tcgagacaaa 8100
cggtgaaaca ggtgagatcg tgtgggataa gggaagggat ttcgctaccg ttagaaaggt 8160
gctctctatg ccacaggtga acatcgttaa gaaaaccgag gtgcagaccg gtggattctc 8220
taaagagtct atcctcccta agaggaactc tgataagctc attgctagga agaaggattg 8280

-continued

```
ggaccctaag aaatacggtg gtttcgattc tcctaccgtg gcttactctg ttctcgttgt   8340
ggctaaggtt gagaagggaa agagtaagaa gctcaagtct gttaaggaac ttctcggaat   8400
cactatcatg gaaaggtcat ctttcgagaa gaacccaatc gatttcctcg aggctaaggg   8460
atacaaagag gttaagaagg atctcatcat caagctccca aagtactcac tcttcgaact   8520
cgagaacggt agaaagagga tgctcgcttc tgctggtgag cttcaaaagg gaaacgagct   8580
tgctctccca tctaagtacg ttaactttct ttacctcgct tctcactacg agaagttgaa   8640
gggatctcca gaagataacg agcagaagca acttttcgtt gagcagcaca agcactactt   8700
ggatgagatc atcgagcaga tctctgagtt ctctaaaagg gtgatcctcg ctgatgcaaa   8760
cctcgataag gtgttgtctg cttacaacaa gcacagagat aagcctatca gggaacaggc   8820
agagaacatc atccatctct tcacccttac caacctcggt gctcctgctg ctttcaagta   8880
cttcgataca accatcgata ggaagagata cacctctacc aaagaagtgc tcgatgctac   8940
cctcatccat cagtctatca ctggactcta cgagactagg atcgatctct cacagctcgg   9000
tggtgattca agggctgatc ctaagaagaa gaggaaggtt tgacgtcgac gatatgaaga   9060
tgaagatgaa atatttggtg tgtcaaataa aaagcttgtg tgcttaagtt tgtgtttttt   9120
tcttggcttg ttgtgttatg aatttgtggc tttttctaat attaaatgaa tgtaagatca   9180
cattataatg aataaacaaa tgtttctata atccattgtg aatgttttgt tggatctctt   9240
ctgcagcata taactactgt atgtgctatg gtatggacta tggaatatga ttaaagataa   9300
gccagagctc tggtgacgga cccatggctt cgttgaacaa cggaaactcg acttgccttc   9360
cgcacaatac atcatttctt cttagctttt tttcttcttc ttcgttcata cagttttttt   9420
ttgtttatca gcttacattt tcttgaaccg tagctttcgt ttcttctttt ttaactttcc   9480
attcggagtt tttgtatctt gtttcatagt ttgtcccagg attagaatga ttaggcatcg   9540
aaccttcaag aatttgattg aataaaacat cttcattctt aagatatgaa gataatcttc   9600
aaaaggcccc tgggaatctg aaagaagaga agcaggccca tttatatggg aaagaacaat   9660
agtatttctt atataggccc atttaagttg aaaacaatct tcaaaagtcc cacatcgctt   9720
agataagaaa acgaagctga gtttatatac agctagagtc gaagtagtga ttgcctactt   9780
gggctgttgc aggttttaga gctagaaata gcaagttaaa ataaggctag tccgttatca   9840
acttgaaaaa gtggcaccga gtcggtgctt tttttcccgg ggcgcgccct atgtcgagct   9900
gcaggtcaac ggatcaggat attcttgttt aagatgttga actctatgga ggtttgtatg   9960
aactgatgat ctaggaccgg ataagttccc ttcttcatag cgaacttatt caaagaatgt  10020
tttgtgtatc attcttgtta cattgttatt aatgaaaaaa tattattggt cattggactg  10080
aacacgagtg ttaaatatgg accaggcccc aaataagatc cattgatata tgaattaaat  10140
aacaagaata aatcgagtca ccaaaccact tgcctttttt aacgagactt gttcaccaac  10200
ttgatacaaa agtcattatc ctatgcaaat caataatcat acaaaaatat ccaataacac  10260
taaaaaatta aaagaaatgg ataatttcac aatatgttat acgataaaga agttactttt  10320
ccaagaaatt cactgatttt ataagcccac ttgcattaga taaatggcaa aaaaaaacaa  10380
aaaggaaaag aaataaagca cgaagaattc tagaaaatac gaaatacgct tcaatgcagt  10440
gggacccacg gttcaattat tgccaatttt cagctccacc gtatatttaa aaaataaaac  10500
gataatgcta aaaaaatata aatcgtaacg atcgttaaat ctcaacggct ggatcttatg  10560
acgaccgtta gaaattgtgg ttgtcgacga gtcagtaata aacggcgtca aagtggttgc  10620
agccggcaca cacgagtcgt gtttatcaac tcaaagcaca aatacttttc ctcaacctaa  10680
```

aaataaggca attagccaaa aacaactttg cgtgtaaaca acgctcaata cacgtgtcat 10740
tttattatta gctattgctt caccgcctta gctttctcgt gacctagtcg tcctcgtctt 10800
ttcttcttct tcttctataa aacaataccc aaagagctct tcttcttcac aattcagatt 10860
tcaatttctc aaaatcttaa aaactttctc tcaattctct ctaccgtgat caaggtaaat 10920
ttctgtgttc cttattctct caaaatcttc gattttgttt tcgttcgatc ccaatttcgt 10980
atatgttctt tggtttagat tctgttaatc ttagatcgaa cacgattttc tgggtttgat 11040
cgttagatat catcttaatt ctcgattagg gtttcataga tatcatccga tttgttcaaa 11100
taatttgagt tttgtcgaat aattactctt cgatttgtga tttctatcta gatctggtgt 11160
tagtttctag tttgtgcgat cgaatttgtc gattaatctg agtttttctg attaacaggc 11220
ctgcaggatg gaagacgcca aaaacataaa gaaaggcccg gcgccattct atccgctgga 11280
agatggaacc gctggagagc aactgcataa ggctatgaag agatacgccc tggttcctgg 11340
aacaattgct tttacagatg cacatatcga ggtggacatc acttacgctg agtacttcga 11400
aatgtccgtt cggttggcag aagctatgaa acgatatggg ctgaatacaa atcacagaat 11460
cgtcgtatgc agtgaaaact ctcttcaatt ctttatgccg gtgttgggcg cgttatttat 11520
cggagttgca gttgcgcccg cgaacgacat ttataatgaa cgtgaattgc tcaacagtat 11580
gggcatttcg cagcctaccg tggtgttcgt ttccaaaaag gggttgcaaa aaattttgaa 11640
cgtgcaaaaa aagctcccaa tcatccaaaa aattattatc atggattcta aaacggatta 11700
ccagggattt cagtcgatgt acacgttcgt cacatctcat ctacctcccg gttttaatga 11760
atacgatttt gtgccagagt ccttcgatag ggacaagaca attgcactga tcatgaactc 11820
ctctggatct actggtctgc ctaaaggtgt cgctctgcct catagaactg cctgcgtgag 11880
attctcgcat gccagagatc ctatttttgg caatcaaatc attccggata ctgcgatttt 11940
aagtgttgtt ccattccatc acggttttgg aatgtttact acactcggat atttgatatg 12000
tggatttcga gtcgtcttaa tgtatagatt tgaagaagag ctgtttctga ggagccttca 12060
ggattacaag attcaaagtg cgctgctggt gccaacccta ttctccttct tcgccaaaag 12120
cactctgatt gacaaatacg atttatctaa tttacacgaa attgcttctg gtggcgctcc 12180
cctctctaag gaagtcgggg aagcggttgc caagaggttc catctgccag gtatcaggca 12240
aggatatggg ctcactgaga ctacatcagc tattctgatt acacccgagg gggatgataa 12300
accgggcgcg gtcggtaaag ttgttccatt ttttgaagcg aaggttgtgg atctggatac 12360
cgggaaaacg ctgggcgtta atcaaagagg cgaactgtgt gtgagaggtc ctatgattat 12420
gtccggttat gtaaacaatc cggaagcgac caacgccttg attgacaagg atggatggct 12480
acattctgga gacatagctt actgggacga agacgaacac ttcttcatcg ttgaccgcct 12540
gaagtctctg attaagtaca aaggctatca ggtggctccc gctgaattgg aatccatctt 12600
gctccaacac cccaacatct tcgacgctgg tgtcgcaggt cttcccgacg atgacgccgg 12660
tgaacttccc gccgccgttg ttgttttgga gcacggaaag acgatgacgg aaaaagagat 12720
cgtggattac gtcgccagtc aagtaacaac cgcgaaaaag ttgcgcggag gagttgtgtt 12780
tgtggacgaa gtaccgaaag gtcttaccgg aaaactcgac gcaagaaaaa tcagagagat 12840
cctcataaag gccaagaagg gcggaaagat cgccgtgtga ctcgaggttc gagtattatg 12900
gcattgggaa aactgttttt cttgtaccat ttgttgtgct tgtaatttac tgtgtttttt 12960
attcggtttt cgctatcgaa ctgtgaaatg gaaatggatg gagaagagtt aatgaatgat 13020

-continued

```
atggtccttt tgttcattct caaattaata ttatttgttt tttctcttat ttgttgtgtg  13080
ttgaatttga aattataaga gatatgcaaa cattttgttt tgagtaaaaa tgtgtcaaat  13140
cgtggcctct aatgaccgaa gttaatatga ggagtaaaac acttgtagtt gtgttagagc  13200
tctcccgcgt cgagctgcag gtcaacggat caggatattc ttgtttaaga tgttgaactc  13260
tatggaggtt tgtatgaact gatgatctag gaccggataa gttcccttct tcatagcgaa  13320
cttattcaaa gaatgttttg tgtatcattc ttgttacatt gttattaatg aaaaaatatt  13380
attggtcatt ggactgaaca cgagtgttaa atatggacca ggccccaaat aagatccatt  13440
gatatatgaa ttaaataaca agaataaatc gagtcaccaa accacttgcc ttttttaacg  13500
agacttgttc accaacttga tacaaaagtc attatcctat gcaaatcaat aatcatacaa  13560
aaatatccaa taacactaaa aaattaaaag aaatggataa tttcacaata tgttatacga  13620
taaagaagtt acttttccaa gaaattcact gattttataa gcccacttgc attagataaa  13680
tggcaaaaaa aaacaaaaag gaaaagaaat aaagcacgaa gaattctaga aaatacgaaa  13740
tacgcttcaa tgcagtggga cccacggttc aattattgcc aattttcagc tccaccgtat  13800
atttaaaaaa taaaacgata atgctaaaaa aatataaatc gtaacgatcg ttaaatctca  13860
acggctggat cttatgacga ccgttagaaa ttgtggttgt cgacgagtca gtaataaacg  13920
gcgtcaaagt ggttgcagcc ggcacacacg agtcgtgttt atcaactcaa agcacaaata  13980
cttttcctca acctaaaaat aaggcaatta gccaaaaaca actttgcgtg taaacaacgc  14040
tcaatacacg tgtcatttta ttattagcta ttgcttcacc gccttagctt tctcgtgacc  14100
tagtcgtcct cgtcttttct tcttcttctt ctataaaaca atacccaaag agctcttctt  14160
cttcacaatt cagatttcaa tttctcaaaa tcttaaaaac tttctctcaa ttctctctac  14220
cgtgatcaag gtaaatttct gtgttcctta ttctctcaaa atcttcgatt ttgttttcgt  14280
tcgatcccaa tttcgtatat gttctttggt ttagattctg ttaatcttag atcgaacacg  14340
attttctggg tttgatcgtt agatatcatc ttaattctcg attagggttt catagatatc  14400
atccgatttg ttcaaataat ttgagttttg tcgaataatt actcttcgat ttgtgatttc  14460
tatctagatc tggtgttagt ttctagtttg tgcgatcgaa tttgtcgatt aatctgagtt  14520
tttctgatta acagggatga actcgatgaa taactggtta ggcttctctc tctctcctca  14580
tgatcaaaat catcaccgta cggatgttga ctcctccacc accagaaccg ccgtagatgt  14640
tgccggaggg tactgttttg atctggccgc tccctccgat gaatcttctg ccgttcaaac  14700
atcttttctt tctcctttcg gtgtcaccct cgaagctttc accagagaca ataatagtca  14760
ctcccgagat tgggacatca atggtggtgc atgcaataac attaacaata acgaacaaaa  14820
tggaccaaag cttgagaatt tcctcggccg caccaccacg atttacaata ccaacgagac  14880
cgttgtagat ggaaatggcg attgtggagg aggagacggt ggtggtggcg gctcactagg  14940
cctttcgatg ataaaaacat ggctgagtaa tcattcggtt gctaatgcta atcatcaaga  15000
caatggtaac ggtgcacgag gcttgtccct ctctatgaat tcatctacta gtgatagcaa  15060
caactacaac aacaatgatg atgtcgtcca agagaagact attgttgatg tcgtagaaac  15120
tacaccgaag aaaactattg agagttttgg acaaaggacg tctatatacc gcggtgttac  15180
aaggcatcgg tggacaggta gatacgaggc acatttatgg gacaatagtt gcaaaagaga  15240
aggccagact cgcaaaggaa gacaagttta tctgggaggt tatgacaaag aagaaaaagc  15300
agctagggct tacgatttag ccgcactaaa gtattgggga accaccacta ctactaactt  15360
ccccttgagt gaatatgaga aagaggtaga agagatgaag cacatgacga ggcaagagta  15420
```

tgttgcctct ctgcgcagga aaagtagtgg tttctctcgt ggtgcatcga tttatcgagg 15480
agtaacaagg catcaccaac atggaaggtg gcaagctagg atcggaagag tcgccggtaa 15540
caaagacctc tacttgggaa ctttcggcac acaggaagag gctgctgagg cttatgacat 15600
tgcagccatt aaattcagag gattaagcgc agtgactaac ttcgacatga acagatacaa 15660
tgttaaagca atcctcgaga gcccgagtct acctattggt agttctgcga aacgtctcaa 15720
ggacgttaat aatccggttc cagctatgat gattagtaat aacgtttcag agagtgcaaa 15780
taatgttagc ggttggcaaa acactgcgtt tcagcatcat cagggaatgg atttgagctt 15840
attgcagcaa cagcaggaga ggtacgttgg ttattacaat ggaggaaact tgtctaccga 15900
gagtactagg gtttgtttca aacaagagga ggaacaacaa cacttcttga gaaactcgcc 15960
gagtcacatg actaatgttg atcatcatag ctcgacctct gatgattctg ttaccgtttg 16020
tggaaatgtt gttagttatg gtggttatca aggattcgca atccctgttg gaacatcggt 16080
taattacgat ccctttactg ctgctgagat tgcttacaac gcaagaaatc attattacta 16140
tgctcagcat cagcaacaac agcagattca gcagtcgccg ggaggagatt ttccggtggc 16200
gatttcgaat aaccatagct ctaacatgta ctttcacggg gaaggtggtg gagaaggggc 16260
tccaacgttt tcagtttgga acgacactta gctcgagttt ctccataata atgtgtgagt 16320
agttcccaga taagggaatt agggttccta tagggtttcg ctcatgtgtt gagcatataa 16380
gaaaccctta gtatgtattt gtatttgtaa aatacttcta tcaataaaat ttctaattcc 16440
taaaaccaaa atccagtact aaaatccaga tcccccgaat aagtgtttga tcgccggcgg 16500
taccgagtgt acttcaagtc agtgggaaat caataaaatg attattttat gaatatattt 16560
cattgtgcaa gtagatagaa attacatatg ttacataaca cacgaaataa acaaaaaaag 16620
acaatccaaa aacaaacacc ccaaaaaaaa taatcacttt agataaactc gtatgaggag 16680
aggcacgttc agtgactcga cgattcccga gcaaaaaaag tctccccgtc acacatgtag 16740
tgggtgacgc aattatcttt aaagtaatcc ttctgttgac ttgtcattga taacatccag 16800
tcttcgtcag gattgcaaag aattatagaa gggatcccac cttttatttt cttctttttt 16860
ccatatttag ggttgacagt gaaatcagac tggcaaccta ttaattgctt ccacaatggg 16920
acgaacttga aggggatgtc gtcgatgata ttataggtgg cgtgttcatc gtagttggtg 16980
aaatcgatgg taccgttcca atagttgtgt cgtccgagac ttctagccca ggtggtcttt 17040
ccggtacgag ttggtccgca gatgtagagg ctggggtgtc ggattccatt ccttccattg 17100
tccttgttaa atcggccatc cattcaaggt cagattgagc ttgttggtat gagacaggat 17160
gtatgtaagt ataagcgtct atgcttacat ggtatagatg ggtttccctc caggagtgta 17220
gatcttcgtg gcagcgaaga tctgattctg tgaagggcga cacatacggt tcaggttgtg 17280
gagggaataa tttgttggct gaatattcca gccattgaag ctttgttgcc cattcatgag 17340
ggaattcttc cttgatcatg tcaagatatt cctccttaga cgttgcagtc tggataatag 17400
ttctccatcg tgcgtcagat ttgcgaggag aaaccttatg atctcggaaa tctcctctgg 17460
ttttaatatc tccgtccttt gatatgtaat caaggacttg tttagagttt ctagctggct 17520
ggatattagg gtgatttcct tcaaaatcga aaaaagaagg atccctaata caaggttttt 17580
tatcaagctg gagaagagca tgatagtggg tagtgccatc ttgatgaagc tcagaagcaa 17640
caccaaggaa gaaaataaga aaaggtgtga gtttctccca gagaaactgg aataaatcat 17700
ctctttgaga tgagcacttg ggataggtaa ggaaaacata tttagattgg agtctgaagt 17760

-continued

```
tcttactagc agaaggcatg ttgttgtgac tccgaggggt tgcctcaaac tctatcttat  17820
aaccggcgtg gaggcatgga ggcaggggta ttttggtcat tttaatagat agtggaaaat  17880
gacgtggaat ttacttaaag acgaagtctt tgcgacaagg gggggcccac gccgaattta  17940
atattaccgg cgtggccccc ccttatcgcg agtgctttag cacgagcggt ccagatttaa  18000
agtagaaaat ttcccgccca ctagggttaa aggtgttcac actataaaag catatacgat  18060
gtgatggtat ttgatggagc gtatattgta tcaggtattt ccgttggata cgaattattc  18120
gtacgaccct catagtttaa actatcagtg tttgacagga tatattggcg ggtaaaccta  18180
agagaaaaga gcgtttatta gaataacgga tatttaaaag ggcgtgaaaa ggtttatccg  18240
ttcgtccatt tgtatgtgca tgccaaccac agggttcccc tcgggatcaa agtactttga  18300
tccaacccct ccgctgctat agtgcagtcg gcttctgacg ttcagtgcag ccgtcttctg  18360
aaaacgacat gtcgcacaag tcctaagtta cgcgacaggc tgccgccctg cccttttcct  18420
ggcgttttct tgtcgcgtgt tttagtcgca taaagtagaa tacttgcgac tagaaccgga  18480
gacattacgc catgaacaag agcgccgccg ctggcctgct gggctatgcc cgcgtcagca  18540
ccgacgacca ggacttgacc aaccaacggg ccgaactgca cgcggccggc tgcaccaagc  18600
tgttttccga gaagatcacc ggcaccaggc gcgaccgccc ggagctggcc aggatgcttg  18660
accacctacg ccctggcgac gttgtgacag tgaccaggct agaccgcctg gcccgcagca  18720
cccgcgacct actggacatt gccgagcgca tccaggaggc cggcgcgggc ctgcgtagcc  18780
tggcagagcc gtgggccgac accaccacgc cggccggccg catggtgttg accgtgttcg  18840
ccggcattgc cgagttcgag cgttccctaa tcatcgaccg cacccggagc gggcgcgagg  18900
ccgccaaggc ccgaggcgtg aagtttggcc cccgccctac cctcaccccg gcacagatcg  18960
cgcacgcccg cgagctgatc gaccaggaag gccgcaccgt gaaagaggcg gctgcactgc  19020
ttggcgtgca tcgctcgacc ctgtaccgcg cacttgagcg cagcgaggaa gtgacgccca  19080
ccgaggccag gcggcgcggt gccttccgtg aggacgcatt gaccgaggcc gacgccctgg  19140
cggccgccga gaatgaacgc caagaggaac aagcatgaaa ccgcaccagg acggccagga  19200
cgaaccgttt ttcattaccg aagagatcga ggcggagatg atcgcggccg ggtacgtgtt  19260
cgagccgccc gcgcacggct caaccgtgcg gctgcatgaa atcctggccg gtttgtctga  19320
tgccaagctg gcggcctggc cggccagctt ggccgctgaa gaaaccgagc gccgccgtct  19380
aaaaaggtga tgtgtatttg agtaaaacag cttgcgtcat gcggtcgctg cgtatatgat  19440
gcgatgagta aataaacaaa tacgcaaggg gaacgcatga aggttatcgc tgtacttaac  19500
cagaaaggcg ggtcaggcaa gacgaccatc gcaacccatc tagcccgcgc cctgcaactc  19560
gccggggccg atgttctgtt agtcgattcc gatccccagg gcagtgcccg cgattgggcg  19620
gccgtgcggg aagatcaacc gctaaccgtt gtcggcatcg accgcccgac gattgaccgc  19680
gacgtgaagg ccatcggccg gcgcgacttc gtagtgatcg acggagcgcc ccaggcggcg  19740
gacttggctg tgtccgcgat caaggcagcc gacttcgtgc tgattccggt gcagccaagc  19800
ccttacgaca tatgggccac cgccgacctg gtggagctgg ttaagcagcg cattgaggtc  19860
acggatggaa ggctacaagc ggcctttgtc gtgtcgcggg cgatcaaagg cacgcgcatc  19920
ggcggtgagg ttgccgaggc gctggccggg tacgagctgc ccattcttga gtcccgtatc  19980
acgcagcgcg tgagctaccc aggcactgcc gccgccggca caaccgttct tgaatcagaa  20040
cccgagggcg acgctgcccg cgaggtccag gcgctggccg ctgaaattaa atcaaaactc  20100
atttgagtta atgaggtaaa gagaaaatga gcaaaagcac aaacacgcta agtgccggcc  20160
```

gtccgagcgc acgcagcagc aaggctgcaa cgttggccag cctggcagac acgccagcca 20220
tgaagcgggt caactttcag ttgccggcgg aggatcacac caagctgaag atgtacgcgg 20280
tacgccaagg caagaccatt accgagctgc tatctgaata catcgcgcag ctaccagagt 20340
aaatgagcaa atgaataaat gagtagatga attttagcgg ctaaaggagg cggcatggaa 20400
aatcaagaac aaccaggcac cgacgccgtg gaatgcccca tgtgtggagg aacgggcggt 20460
tggccaggcg taagcggctg ggttgtctgc cggccctgca atggcactgg aacccccaag 20520
cccgaggaat cggcgtgacg gtcgcaaacc atccggcccg gtacaaatcg gcgcggcgct 20580
gggtgatgac ctggtggaga agttgaaggc cgcgcaggcc gcccagcggc aacgcatcga 20640
ggcagaagca cgccccggtg aatcgtggca agcggccgct gatcgaatcc gcaaagaatc 20700
ccggcaaccg ccggcagccg gtgcgccgtc gattaggaag ccgcccaagg gcgacgagca 20760
accagatttt ttcgttccga tgctctatga cgtgggcacc cgcgatagtc gcagcatcat 20820
ggacgtggcc gttttccgtc tgtcgaagcg tgaccgacga gctggcgagg t 20871

<210> SEQ ID NO 93
<211> LENGTH: 17616
<212> TYPE: DNA
<213> ORGANISM: artificial
<220> FEATURE:
<223> OTHER INFORMATION: synthetic oligonucleotide

<400> SEQUENCE: 93
tgcagcgtac gaagaaggcc aagaacggcc gcctggtgac ggtatccgag ggtgaagcct 60
tgattagccg ctacaagatc gtaaagagcg aaaccgggcg gccggagtac atcgagatcg 120
agctagctga ttggatgtac cgcgagatca cagaaggcaa gaacccggac gtgctgacgg 180
ttcaccccga ttactttttg atcgatcccg gcatcggccg ttttctctac cgcctggcac 240
gccgcgccgc aggcaaggca gaagccagat ggttgttcaa gacgatctac gaacgcagtg 300
gcagcgccgg agagttcaag aagttctgtt tcaccgtgcg caagctgatc gggtcaaatg 360
acctgccgga gtacgatttg aaggaggagg cggggcaggc tggcccgatc ctagtcatgc 420
gctaccgcaa cctgatcgag ggcgaagcat ccgccggttc ctaatgtacg gagcagatgc 480
tagggcaaat tgccctagca ggggaaaaag gtcgaaaagg cctctttcct gtggatagca 540
cgtacattgg gaacccaaag ccgtacattg ggaaccggaa cccgtacatt gggaacccaa 600
agccgtacat tgggaaccgg tcacacatgt aagtgactga tataaaagag aaaaaaggcg 660
atttttccgc ctaaaactct ttaaaactta ttaaaactct taaaacccgc ctggcctgtg 720
cataactgtc tggccagcgc acagccgaag agctgcaaaa agcgcctacc cttcggtcgc 780
tgcgctccct acgccccgcc gcttcgcgtc ggcctatcgc ggccgctggc cgctcaaaaa 840
tggctggcct acggccaggc aatctaccag ggcgcggaca agccgcgccg tcgccactcg 900
accgccggcg cccacatcaa ggcaccctgc ctcgcgcgtt tcggtgatga cggtgaaaac 960
ctctgacaca tgcagctccc ggaaacggtc acagcttgtc tgtaagcgga tgccgggagc 1020
agacaagccc gtcagggcgc gtcagcgggt gttggcgggt gtcggggcgc agccatgacc 1080
cagtcacgta gcgatagcgg agtgtatact ggcttaacta tgcggcatca gagcagattg 1140
tactgagagt gcaccatatg cggtgtgaaa taccgcacag atgcgtaagg agaaaatacc 1200
gcatcaggcg ctcttccgct tcctcgctca ctgactcgct gcgctcggtc gttcggctgc 1260
ggcgagcggt atcagctcac tcaaaggcgg taatacggtt atccacagaa tcaggggata 1320

```
acgcaggaaa gaacatgtga gcaaaaggcc agcaaaaggc caggaaccgt aaaaaggccg   1380
cgttgctggc gtttttccat aggctccgcc cccctgacga gcatcacaaa aatcgacgct   1440
caagtcagag gtggcgaaac ccgacaggac tataaagata ccaggcgttt ccccctggaa   1500
gctccctcgt gcgctctcct gttccgaccc tgccgcttac cggatacctg tccgcctttc   1560
tcccttcggg aagcgtggcg ctttctcata gctcacgctg taggtatctc agttcggtgt   1620
aggtcgttcg ctccaagctg ggctgtgtgc acgaaccccc cgttcagccc gaccgctgcg   1680
ccttatccgg taactatcgt cttgagtcca acccggtaag acacgactta tcgccactgg   1740
cagcagccac tggtaacagg attagcagag cgaggtatgt aggcggtgct acagagttct   1800
tgaagtggtg gcctaactac ggctacacta gaaggacagt atttggtatc tgcgctctgc   1860
tgaagccagt taccttcgga aaaagagttg gtagctcttg atccggcaaa caaaccaccg   1920
ctggtagcgg tggttttttt gtttgcaagc agcagattac gcgcagaaaa aaaggatctc   1980
aagaagatcc tttgatcttt tctacggggt ctgacgctca gtggaacgaa aactcacgtt   2040
aagggatttt ggtcatgcat tctaggtact aaaacaattc atccagtaaa atataatatt   2100
ttattttctc ccaatcaggc ttgatcccca gtaagtcaaa aaatagctcg acatactgtt   2160
cttccccgat atcctccctg atcgaccgga cgcagaaggc aatgtcatac cacttgtccg   2220
ccctgccgct tctcccaaga tcaataaagc cacttacttt gccatctttc acaaagatgt   2280
tgctgtctcc caggtcgccg tgggaaaaga caagttcctc ttcgggcttt tccgtcttta   2340
aaaaatcata cagctcgcgc ggatctttaa atggagtgtc ttcttcccag ttttcgcaat   2400
ccacatcggc cagatcgtta ttcagtaagt aatccaattc ggctaagcgg ctgtctaagc   2460
tattcgtata gggacaatcc gatatgtcga tggagtgaaa gagcctgatg cactccgcat   2520
acagctcgat aatcttttca gggctttgtt catcttcata ctcttccgag caaaggacgc   2580
catcggcctc actcatgagc agattgctcc agccatcatg ccgttcaaag tgcaggacct   2640
ttggaacagg cagctttcct tccagccata gcatcatgtc cttttcccgt tccacatcat   2700
aggtggtccc tttataccgg ctgtccgtca tttttaaata taggttttca ttttctccca   2760
ccagcttata taccttagca ggagacattc cttccgtatc ttttacgcag cggtattttt   2820
cgatcagttt tttcaattcc ggtgatattc tcattttagc catttattat ttccttcctc   2880
ttttctacag tatttaaaga taccccaaga agctaattat aacaagacga actccaattc   2940
actgttcctt gcattctaaa accttaaata ccagaaaaca gctttttcaa agttgttttc   3000
aaagttggcg tataacatag tatcgacgga gccgattttg aaaccgcggt gatcacaggc   3060
agcaacgctc tgtcatcgtt acaatcaaca tgctaccctc cgcgagatca tccgtgtttc   3120
aaacccggca gcttagttgc cgttcttccg aatagcatcg gtaacatgag caaagtctgc   3180
cgccttacaa cggctctccc gctgacgccg tcccggactg atgggctgcc tgtatcgagt   3240
ggtgattttg tgccgagctg ccggtcgggg agctgttggc tggctggtgg caggatatat   3300
tgtggtgtaa acaaattgac gcttagacaa cttaataaca cattgcggac gtttttaatg   3360
tagagctcaa agtttaacgc gttagcagaa ggcatgttgt tgtgactccg aggggttgcc   3420
tcaaactcta tcttataacc ggcgtggagg catggaggca ggggtatttt ggtcatttta   3480
atagatagtg gaaaatgacg tggaatttac ttaaagacga agtctttgcg acaagggggg   3540
gcccacgccg aatttaatat taccggcgtg gcccccccct atcgcgagtg ctttagcacg   3600
agcggtccag atttaaagta gaaaatttcc cgcccactag ggttaaaggt gttcacacta   3660
taaaagcata tacgatgtga tggtatttga tggagcgtat attgtatcag gtatttccgt   3720
```

-continued

```
tggatacgaa ttattcgtac gaccctcggt accgatcggc gcgccagatt tgccttttca   3780
atttcagaaa gaatgctaac ccacagatgg ttagagaggc ttacgcagca ggtatcatca   3840
agacgatcta cccgagcaat aatctccagg aaatcaaata ccttcccaag aaggttaaag   3900
atgcagtcaa aagattcagg actaactgca tcaagaacac agagaaagat atatttctca   3960
agatcagaag tactattcca gtatggacga ttcaaggctt gcttcacaaa ccaaggcaag   4020
taatagagat tggagtctct aaaaaggtag ttcccactga atcaaaggcc atggagtcaa   4080
agattcaaat agaggaccta acagaactcg ccgtaaagac tggcgaacag ttcatacaga   4140
gtctcttacg actcaatgac aagaagaaaa tcttcgtcaa catggtggag cacgacacac   4200
ttgtctactc caaaaatatc aaagatacag tctcagaaga ccaaagggca attgagactt   4260
ttcaacaaag ggtaatatcc ggaaacctcc tcggattcca ttgcccagct atctgtcact   4320
ttattgtgaa gatagtggaa aaggaaggtg gctcctacaa atgccatcat tgcgataaag   4380
gaaaggccat cgttgaagat gcctctgccg acagtggtcc caaagatgga cccccaccca   4440
cgaggagcat cgtggaaaaa gaagacgttc caaccacgtc ttcaaagcaa gtggattgat   4500
gtgatatctc cactgacgta agggatgacg cacaatccca ctatccttcg caagaccctt   4560
cctctatata aggaagttca tttcatttgg agagaacacg ggggactcct gcaggtagat   4620
cgctcgtcga catggataag aagtactcta tcggactcga tatcggaact aactctgtgg   4680
gatgggctgt gatcaccgat gagtacaagg tgccatctaa gaagttcaag gttctcggaa   4740
acaccgatag gcactctatc aagaaaaacc ttatcggtgc tctcctcttc gattctggtg   4800
aaactgctga ggctaccaga ctcaagagaa ccgctagaag aaggtacacc agaagaaaga   4860
acaggatctg ctacctccaa gagatcttct ctaacgagat ggctaaagtg gatgattcat   4920
tcttccacag gctcgaagag tcattcctcg tggaagaaga taagaagcac gagaggcacc   4980
ctatcttcgg aaacatcgtt gatgaggtgg cataccacga gaagtaccct actatctacc   5040
acctcagaaa gaagctcgtt gattctactg ataaggctga tctcaggctc atctacctcg   5100
ctctcgctca catgatcaag ttcagaggac acttcctcat cgagggtgat ctcaaccctg   5160
ataactctga tgtggataag ttgttcatcc agctcgtgca gacctacaac cagcttttcg   5220
aagagaaccc tatcaacgct tcaggtgtgg atgctaaggc tatcctctct gctaggctct   5280
ctaagtcaag aaggcttgag aacctcattg ctcagctccc tggtgagaag aagaacggac   5340
ttttcggaaa cttgatcgct ctctctctcg gactcacccc taacttcaag tctaacttcg   5400
atctcgctga ggatgcaaag ctccagctct caaaggatac ctacgatgat gatctcgata   5460
acctcctcgc tcagatcgga gatcagtacg ctgatttgtt cctcgctgct aagaacctct   5520
ctgatgctat cctcctcagt gatatcctca gagtgaacac cgagatcacc aaggctccac   5580
tctcagcttc tatgatcaag agatacgatg agcaccacca ggatctcaca cttctcaagg   5640
ctcttgttag acagcagctc ccagagaagt acaaagagat tttcttcgat cagtctaaga   5700
acggatacgc tggttacatc gatggtggtg catctcaaga agagttctac aagttcatca   5760
agcctatcct cgagaagatg gatggaaccg aggaactcct cgtgaagctc aatagagagg   5820
atcttctcag aaagcagagg accttcgata acggatctat ccctcatcag atccacctcg   5880
gagagttgca cgctatcctt agaaggcaag aggatttcta cccattcctc aaggataaca   5940
gggaaaagat tgagaagatt ctcaccttca gaatccctta ctacgtggga cctctcgcta   6000
gaggaaactc aagattcgct tggatgacca gaaagtctga ggaaaccatc accccttgga   6060
```

acttcgaaga ggtggtggat aagggtgcta gtgctcagtc tttcatcgag aggatgacca 6120
acttcgataa gaaccttcca aacgagaagg tgctccctaa gcactctttg ctctacgagt 6180
acttcaccgt gtacaacgag ttgaccaagg ttaagtacgt gaccgaggga atgaggaagc 6240
ctgctttttt gtcaggtgag caaaagaagg ctatcgttga tctcttgttc aagaccaaca 6300
gaaaggtgac cgtgaagcag ctcaaagagg attacttcaa gaaaatcgag tgcttcgatt 6360
cagttgagat ttctggtgtt gaggataggt tcaacgcatc tctcggaacc taccacgatc 6420
tcctcaagat cattaaggat aaggatttct tggataacga ggaaaacgag gatatcttgg 6480
aggatatcgt tcttaccctc accctctttg aagatagaga gatgattgaa gaaaggctca 6540
agacctacgc tcatctcttc gatgataagg tgatgaagca gttgaagaga agaagataca 6600
ctggttgggg aaggctctca agaaagctca ttaacggaat cagggataag cagtctggaa 6660
agacaatcct tgatttcctc aagtctgatg gattcgctaa cagaaacttc atgcagctca 6720
tccacgatga ttctctcacc tttaaagagg atatccagaa ggctcaggtt tcaggacagg 6780
gtgatagtct ccatgagcat atcgctaacc tcgctggatc tcctgcaatc aagaagggaa 6840
tcctccagac tgtgaaggtt gtggatgagt tggtgaaggt gatgggaagg cataagcctg 6900
agaacatcgt gatcgaaatg gctagagaga accagaccac tcagaaggga cagaagaact 6960
ctagggaaag gatgaagagg atcgaggaag gtatcaaaga gcttggatct cagatcctca 7020
aagagcaccc tgttgagaac actcagctcc agaatgagaa gctctacctc tactacctcc 7080
agaacggaag ggatatgtat gtggatcaag agttggatat caacaggctc tctgattacg 7140
atgttgatca tatcgtgcca cagtcattct tgaaggatga ttctatcgat aacaaggtgc 7200
tcaccaggtc tgataagaac aggggtaaga gtgataacgt gccaagtgaa gaggttgtga 7260
agaaaatgaa gaactattgg aggcagctcc tcaacgctaa gctcatcact cagagaaagt 7320
tcgataactt gactaaggct gagaggggag gactctctga attggataag gcaggattca 7380
tcaagaggca gcttgtggaa accaggcaga tcactaagca cgttgcacag atcctcgatt 7440
ctaggatgaa caccaagtac gatgagaacg ataagttgat cagggaagtg aaggttatca 7500
ccctcaagtc aaagctcgtg tctgatttca gaaaggattt ccaattctac aaggtgaggg 7560
aaatcaacaa ctaccaccac gctcacgatg cttaccttaa cgctgttgtt ggaaccgctc 7620
tcatcaagaa gtatcctaag ctcgagtcag agttcgtgta cggtgattac aaggtgtacg 7680
atgtgaggaa gatgatcgct aagtctgagc aagagatcgg aaaggctacc gctaagtatt 7740
tcttctactc taacatcatg aatttcttca agaccgagat taccctcgct aacggtgaga 7800
tcagaaagag gccactcatc gagacaaacg gtgaaacagg tgagatcgtg tgggataagg 7860
gaagggattt cgctaccgtt agaaaggtgc tctctatgcc acaggtgaac atcgttaaga 7920
aaaccgaggt gcagaccggt ggattctcta aagagtctat cctccctaag aggaactctg 7980
ataagctcat tgctaggaag aaggattggg accctaagaa atacggtggt ttcgattctc 8040
ctaccgtggc ttactctgtt ctcgttgtgg ctaaggttga gaagggaaag agtaagaagc 8100
tcaagtctgt taaggaactt ctcggaatca ctatcatgga aaggtcatct ttcgagaaga 8160
acccaatcga tttcctcgag gctaagggat acaaagaggt taagaaggat ctcatcatca 8220
agctcccaaa gtactcactc ttcgaactcg agaacggtag aaagaggatg ctcgcttctg 8280
ctggtgagct tcaaaaggga aacgagcttg ctctcccatc taagtacgtt aactttcttt 8340
acctcgcttc tcactacgag aagttgaagg gatctccaga agataacgag cagaagcaac 8400
ttttcgttga gcagcacaag cactacttgg atgagatcat cgagcagatc tctgagttct 8460
ctaaaagggt gatcctcgct gatgcaaacc tcgataaggt gttgtctgct tacaacaagc 8520
acagagataa gcctatcagg gaacaggcag agaacatcat ccatctcttc acccttacca 8580
acctcggtgc tcctgctgct ttcaagtact tcgatacaac catcgatagg aagagataca 8640
cctctaccaa agaagtgctc gatgctaccc tcatccatca gtctatcact ggactctacg 8700
agactaggat cgatctctca cagctcggtg gtgattcaag ggctgatcct aagaagaaga 8760
ggaaggtttg acgtcgacga tatgaagatg aagatgaaat atttggtgtg tcaaataaaa 8820
agcttgtgtg cttaagtttg tgtttttttc ttggcttgtt gtgttatgaa tttgtggctt 8880
tttctaatat taaatgaatg taagatcaca ttataatgaa taaacaaatg tttctataat 8940
ccattgtgaa tgttttgttg gatctcttct gcagcatata actactgtat gtgctatggt 9000
atggactatg gaatatgatt aaagataagc cagagctctg gtgacggacc catggcttcg 9060
ttgaacaacg gaaactcgac ttgccttccg cacaatacat catttcttct tagctttttt 9120
tcttcttctt cgttcataca gttttttttt gtttatcagc ttacattttc ttgaaccgta 9180
gctttcgttt tcttcttttt aactttccat tcggagtttt tgtatcttgt ttcatagttt 9240
gtcccaggat tagaatgatt aggcatcgaa ccttcaagaa tttgattgaa taaaacatct 9300
tcattcttaa gatatgaaga taatcttcaa aaggcccctg ggaatctgaa agaagagaag 9360
caggcccatt tatatgggaa agaacaatag tatttcttat ataggcccat ttaagttgaa 9420
aacaatcttc aaaagtccca catcgcttag ataagaaaac gaagctgagt ttatatacag 9480
ctagagtcga agtagtgatt gcctacttgg gctgttgcag gttttagagc tagaaatagc 9540
aagttaaaat aaggctagtc cgttatcaac ttgaaaaagt ggcaccgagt cggtgctttt 9600
tttcccgggg cgcgccctat gtcgagctgc aggtcaacgg atcaggatat tcttgtttaa 9660
gatgttgaac tctatggagg tttgtatgaa ctgatgatct aggaccggat aagttccctt 9720
cttcatagcg aacttattca aagaatgttt tgtgtatcat tcttgttaca ttgttattaa 9780
tgaaaaaata ttattggtca ttggactgaa cacgagtgtt aaatatggac caggccccaa 9840
ataagatcca ttgatatatg aattaaataa caagaataaa tcgagtcacc aaaccacttg 9900
cctttttttaa cgagacttgt tcaccaactt gatacaaaag tcattatcct atgcaaatca 9960
ataatcatac aaaaatatcc aataacacta aaaaattaaa agaaatggat aatttcacaa 10020
tatgttatac gataaagaag ttacttttcc aagaaattca ctgattttat aagcccactt 10080
gcattagata aatggcaaaa aaaaacaaaa aggaaaagaa ataaagcacg aagaattcta 10140
gaaaatacga aatacgcttc aatgcagtgg gacccacggt tcaattattg ccaattttca 10200
gctccaccgt atatttaaaa aataaaacga taatgctaaa aaaatataaa tcgtaacgat 10260
cgttaaatct caacggctgg atcttatgac gaccgttaga aattgtggtt gtcgacgagt 10320
cagtaataaa cggcgtcaaa gtggttgcag ccggcacaca cgagtcgtgt ttatcaactc 10380
aaagcacaaa tacttttcct caacctaaaa ataaggcaat tagccaaaaa caactttgcg 10440
tgtaaacaac gctcaataca cgtgtcattt tattattagc tattgcttca ccgccttagc 10500
tttctcgtga cctagtcgtc ctcgtctttt cttcttcttc ttctataaaa caatacccaa 10560
agagctcttc ttcttcacaa ttcagatttc aatttctcaa aatcttaaaa actttctctc 10620
aattctctct accgtgatca aggtaaattt ctgtgttcct tattctctca aaatcttcga 10680
ttttgttttc gttcgatccc aatttcgtat atgttctttg gtttagattc tgttaatctt 10740
agatcgaaca cgattttctg ggtttgatcg ttagatatca tcttaattct cgattagggt 10800

-continued

```
ttcatagata tcatccgatt tgttcaaata atttgagttt tgtcgaataa ttactcttcg  10860
atttgtgatt tctatctaga tctggtgtta gtttctagtt tgtgcgatcg aatttgtcga  10920
ttaatctgag tttttctgat taacaggcct gcaggatgga agacgccaaa aacataaaga  10980
aaggcccggc gccattctat ccgctggaag atggaaccgc tggagagcaa ctgcataagg  11040
ctatgaagag atacgccctg gttcctggaa caattgcttt tacagatgca catatcgagg  11100
tggacatcac ttacgctgag tacttcgaaa tgtccgttcg gttggcagaa gctatgaaac  11160
gatatgggct gaatacaaat cacagaatcg tcgtatgcag tgaaaactct cttcaattct  11220
ttatgccggt gttgggcgcg ttatttatcg gagttgcagt tgcgcccgcg aacgacattt  11280
ataatgaacg tgaattgctc aacagtatgg gcatttcgca gcctaccgtg gtgttcgttt  11340
ccaaaaaggg gttgcaaaaa attttgaacg tgcaaaaaaa gctcccaatc atccaaaaaa  11400
ttattatcat ggattctaaa acggattacc agggatttca gtcgatgtac acgttcgtca  11460
catctcatct acctcccggt tttaatgaat acgattttgt gccagagtcc ttcgataggg  11520
acaagacaat tgcactgatc atgaactcct ctggatctac tggtctgcct aaaggtgtcg  11580
ctctgcctca tagaactgcc tgcgtgagat tctcgcatgc cagagatcct atttttggca  11640
atcaaatcat tccggatact gcgattttaa gtgttgttcc attccatcac ggttttggaa  11700
tgtttactac actcggatat ttgatatgtg gatttcgagt cgtcttaatg tatagatttg  11760
aagaagagct gtttctgagg agccttcagg attacaagat tcaaagtgcg ctgctggtgc  11820
caaccctatt ctccttcttc gccaaaagca ctctgattga caaatacgat ttatctaatt  11880
tacacgaaat tgcttctggt ggcgctcccc tctctaagga agtcggggaa gcggttgcca  11940
agaggttcca tctgccaggt atcaggcaag gatatgggct cactgagact acatcagcta  12000
ttctgattac acccgagggg gatgataaac cgggcgcggt cggtaaagtt gttccatttt  12060
ttgaagcgaa ggttgtggat ctggataccg ggaaaacgct gggcgttaat caaagaggcg  12120
aactgtgtgt gagaggtcct atgattatgt ccggttatgt aaacaatccg gaagcgacca  12180
acgccttgat tgacaaggat ggatggctac attctggaga catagcttac tgggacgaag  12240
acgaacactt cttcatcgtt gaccgcctga agtctctgat taagtacaaa ggctatcagg  12300
tggctcccgc tgaattggaa tccatcttgc tccaacaccc caacatcttc gacgctggtg  12360
tcgcaggtct tcccgacgat gacgccggtg aacttcccgc cgccgttgtt gttttggagc  12420
acggaaagac gatgacggaa aaagagatcg tggattacgt cgccagtcaa gtaacaaccg  12480
cgaaaaagtt gcgcggagga gttgtgtttg tggacgaagt accgaaaggt cttaccggaa  12540
aactcgacgc aagaaaaatc agagagatcc tcataaaggc caagaagggc ggaaagatcg  12600
ccgtgtgact cgaggttcga gtattatggc attgggaaaa ctgtttttct tgtaccattt  12660
gttgtgcttg taatttactg tgttttttat tcggttttcg ctatcgaact gtgaaatgga  12720
aatggatgga gaagagttaa tgaatgatat ggtccttttg ttcattctca aattaatatt  12780
atttgttttt tctcttattt gttgtgtgtt gaatttgaaa ttataagaga tatgcaaaca  12840
ttttgttttg agtaaaaatg tgtcaaatcg tggcctctaa tgaccgaagt taatatgagg  12900
agtaaaacac ttgtagttgt gttagagctc tcccggcgcg ccgatatcga gctcagtgtt  12960
tgatcgccgg cggtaccgag tgtacttcaa gtcagtggga aatcaataaa atgattattt  13020
tatgaatata tttcattgtg caagtagata gaaattacat atgttacata acacacgaaa  13080
taaacaaaaa aagacaatcc aaaaacaaac accccaaaaa aaataatcac tttagataaa  13140
ctcgtatgag gagaggcacg ttcagtgact cgacgattcc cgagcaaaaa aagtctcccc  13200
```

```
gtcacacatg tagtgggtga cgcaattatc tttaaagtaa tccttctgtt gacttgtcat  13260
tgataacatc cagtcttcgt caggattgca aagaattata gaagggatcc caccttttat  13320
tttcttcttt tttccatatt tagggttgac agtgaaatca gactggcaac ctattaattg  13380
cttccacaat gggacgaact tgaaggggat gtcgtcgatg atattatagg tggcgtgttc  13440
atcgtagttg gtgaaatcga tggtaccgtt ccaatagttg tgtcgtccga gacttctagc  13500
ccaggtggtc tttccggtac gagttggtcc gcagatgtag aggctggggt gtcggattcc  13560
attccttcca ttgtccttgt taaatcggcc atccattcaa ggtcagattg agcttgttgg  13620
tatgagacag gatgtatgta agtataagcg tctatgctta catggtatag atgggtttcc  13680
ctccaggagt gtagatcttc gtggcagcga agatctgatt ctgtgaaggg cgacacatac  13740
ggttcaggtt gtggagggaa taatttgttg gctgaatatt ccagccattg aagctttgtt  13800
gcccattcat gagggaattc ttccttgatc atgtcaagat attcctcctt agacgttgca  13860
gtctggataa tagttctcca tcgtgcgtca gatttgcgag gagaaacctt atgatctcgg  13920
aaatctcctc tggttttaat atctccgtcc tttgatatgt aatcaaggac ttgtttagag  13980
tttctagctg gctggatatt agggtgattt ccttcaaaat cgaaaaaaga aggatcccta  14040
atacaaggtt ttttatcaag ctggagaaga gcatgatagt gggtagtgcc atcttgatga  14100
agctcagaag caacaccaag gaagaaaata agaaaaggtg tgagtttctc ccagagaaac  14160
tggaataaat catctctttg agatgagcac ttgggatagg taaggaaaac atatttagat  14220
tggagtctga agttcttact agcagaaggc atgttgttgt gactccgagg ggttgcctca  14280
aactctatct tataaccggc gtggaggcat ggaggcaggg gtattttggt cattttaata  14340
gatagtggaa aatgacgtgg aatttactta aagacgaagt ctttgcgaca aggggggggcc  14400
cacgccgaat ttaatattac cggcgtggcc ccccccttatc gcgagtgctt tagcacgagc  14460
ggtccagatt taaagtagaa aatttcccgc ccactagggt taaaggtgtt cacactataa  14520
aagcatatac gatgtgatgg tatttgatgg agcgtatatt gtatcaggta tttccgttgg  14580
atacgaatta ttcgtacgac cctcatagtt taaactatca gtgtttgaca ggatatattg  14640
gcgggtaaac ctaagagaaa agagcgttta ttagaataac ggatatttaa aagggcgtga  14700
aaaggtttat ccgttcgtcc atttgtatgt gcatgccaac cacagggttc ccctcgggat  14760
caaagtactt tgatccaacc cctccgctgc tatagtgcag tcggcttctg acgttcagtg  14820
cagccgtctt ctgaaaacga catgtcgcac aagtcctaag ttacgcgaca ggctgccgcc  14880
ctgccctttt cctggcgttt tcttgtcgcg tgttttagtc gcataaagta gaatacttgc  14940
gactagaacc ggagacatta cgccatgaac aagagcgccg ccgctggcct gctgggctat  15000
gcccgcgtca gcaccgacga ccaggacttg accaaccaac gggccgaact gcacgcggcc  15060
ggctgcacca agctgttttc cgagaagatc accggcacca ggcgcgaccg cccggagctg  15120
gccaggatgc ttgaccacct acgccctggc gacgttgtga cagtgaccag gctagaccgc  15180
ctggcccgca gcacccgcga cctactggac attgccgagc gcatccagga ggccggcgcg  15240
ggcctgcgta gcctggcaga gccgtgggcc gacaccacca cgccggccgg ccgcatggtg  15300
ttgaccgtgt tcgccggcat tgccgagttc gagcgttccc taatcatcga ccgcacccgg  15360
agcgggcgcg aggccgccaa ggcccgaggc gtgaagtttg gcccccgccc taccctcacc  15420
ccggcacaga tcgcgcacgc ccgcgagctg atcgaccagg aaggccgcac cgtgaaagag  15480
gcggctgcac tgcttggcgt gcatcgctcg accctgtacc gcgcacttga gcgcagcgag  15540
```

gaagtgacgc ccaccgaggc caggcggcgc ggtgccttcc gtgaggacgc attgaccgag 15600
gccgacgccc tggcggccgc cgagaatgaa cgccaagagg aacaagcatg aaaccgcacc 15660
aggacggcca ggacgaaccg tttttcatta ccgaagagat cgaggcggag atgatcgcgg 15720
ccgggtacgt gttcgagccg cccgcgcacg gctcaaccgt gcggctgcat gaaatcctgg 15780
ccggtttgtc tgatgccaag ctggcggcct ggccggccag cttggccgct gaagaaaccg 15840
agcgccgccg tctaaaaagg tgatgtgtat ttgagtaaaa cagcttgcgt catgcggtcg 15900
ctgcgtatat gatgcgatga gtaaataaac aaatacgcaa ggggaacgca tgaaggttat 15960
cgctgtactt aaccagaaag gcgggtcagg caagacgacc atcgcaaccc atctagcccg 16020
cgccctgcaa ctcgccgggg ccgatgttct gttagtcgat tccgatcccc agggcagtgc 16080
ccgcgattgg gcggccgtgc gggaagatca accgctaacc gttgtcggca tcgaccgccc 16140
gacgattgac cgcgacgtga aggccatcgg ccggcgcgac ttcgtagtga tcgacggagc 16200
gccccaggcg gcggacttgg ctgtgtccgc gatcaaggca gccgacttcg tgctgattcc 16260
ggtgcagcca agcccttacg acatatgggc caccgccgac ctggtggagc tggttaagca 16320
gcgcattgag gtcacggatg gaaggctaca agcggccttt gtcgtgtcgc gggcgatcaa 16380
aggcacgcgc atcggcggtg aggttgccga ggcgctggcc gggtacgagc tgcccattct 16440
tgagtcccgt atcacgcagc gcgtgagcta cccaggcact gccgccgccg gcacaaccgt 16500
tcttgaatca gaacccgagg gcgacgctgc ccgcgaggtc caggcgctgg ccgctgaaat 16560
taaatcaaaa ctcatttgag ttaatgaggt aaagagaaaa tgagcaaaag cacaaacacg 16620
ctaagtgccg gccgtccgag cgcacgcagc agcaaggctg caacgttggc cagcctggca 16680
gacacgccag ccatgaagcg ggtcaacttt cagttgccgg cggaggatca caccaagctg 16740
aagatgtacg cggtacgcca aggcaagacc attaccgagc tgctatctga atacatcgcg 16800
cagctaccag agtaaatgag caaatgaata aatgagtaga tgaattttag cggctaaagg 16860
aggcggcatg gaaaatcaag aacaaccagg caccgacgcc gtggaatgcc ccatgtgtgg 16920
aggaacgggc ggttggccag gcgtaagcgg ctgggttgtc tgccggccct gcaatggcac 16980
tggaaccccc aagcccgagg aatcggcgtg acggtcgcaa accatccggc ccggtacaaa 17040
tcggcgcggc gctgggtgat gacctggtgg agaagttgaa ggccgcgcag gccgcccagc 17100
ggcaacgcat cgaggcagaa gcacgccccg gtgaatcgtg gcaagcggcc gctgatcgaa 17160
tccgcaaaga atcccggcaa ccgccggcag ccggtgcgcc gtcgattagg aagccgccca 17220
agggcgacga gcaaccagat tttttcgttc cgatgctcta tgacgtgggc acccgcgata 17280
gtcgcagcat catggacgtg gccgttttcc gtctgtcgaa gcgtgaccga cgagctggcg 17340
aggtgatccg ctacgagctt ccagacgggc acgtagaggt ttccgcaggg ccggccggca 17400
tggccagtgt gtgggattac gacctggtac tgatggcggt ttcccatcta accgaatcca 17460
tgaaccgata ccgggaaggg aagggagaca agcccggccg cgtgttccgt ccacacgttg 17520
cggacgtact caagttctgc cggcgagccg atggcggaaa gcagaaagac gacctggtag 17580
aaacctgcat tcggttaaac accacgcacg ttgcca 17616

<210> SEQ ID NO 94
<211> LENGTH: 15986
<212> TYPE: DNA
<213> ORGANISM: artificial
<220> FEATURE:
<223> OTHER INFORMATION: synthetic oligonucleotide

<400> SEQUENCE: 94

-continued

```
tttgatcgcc ggcggtaccg agtgtacttc aagtcagtgg gaaatcaata aaatgattat     60
tttatgaata tatttcattg tgcaagtaga tagaaattac atatgttaca taacacacga    120
aataaacaaa aaaagacaat ccaaaaacaa acaccccaaa aaaaataatc actttagata    180
aactcgtatg aggagaggca cgttcagtga ctcgacgatt cccgagcaaa aaaagtctcc    240
ccgtcacaca tgtagtgggt gacgcaatta tctttaaagt aatccttctg ttgacttgtc    300
attgataaca tccagtcttc gtcaggattg caaagaatta tagaagggat cccacctttt    360
attttcttct tttttccata tttagggttg acagtgaaat cagactggca acctattaat    420
tgcttccaca atgggacgaa cttgaagggg atgtcgtcga tgatattata ggtggcgtgt    480
tcatcgtagt tggtgaaatc gatggtaccg ttccaatagt tgtgtcgtcc gagacttcta    540
gcccaggtgg tctttccggt acgagttggt ccgcagatgt agaggctggg gtgtcggatt    600
ccattccttc cattgtcctt gttaaatcgg ccatccattc aaggtcagat tgagcttgtt    660
ggtatgagac aggatgtatg taagtataag cgtctatgct tacatggtat agatgggttt    720
ccctccagga gtgtagatct tcgtggcagc gaagatctga ttctgtgaag ggcgacacat    780
acggttcagg ttgtggaggg aataatttgt tggctgaata ttccagccat tgaagctttg    840
ttgcccattc atgagggaat tcttccttga tcatgtcaag atattcctcc ttagacgttg    900
cagtctggat aatagttctc catcgtgcgt cagatttgcg aggagaaacc ttatgatctc    960
ggaaatctcc tctggtttta atatctccgt cctttgatat gtaatcaagg acttgtttag   1020
agtttctagc tggctggata ttagggtgat ttccttcaaa atcgaaaaaa gaaggatccc   1080
taatacaagg ttttttatca agctggagaa gagcatgata gtgggtagtg ccatcttgat   1140
gaagctcaga agcaacacca aggaagaaaa taagaaaagg tgtgagtttc tcccagagaa   1200
actggaataa atcatctctt tgagatgagc acttgggata ggtaaggaaa acatatttag   1260
attggagtct gaagttctta ctagcagaag gcatgttgtt gtgactccga ggggttgcct   1320
caaactctat cttataaccg gcgtggaggc atggaggcag gggtattttg gtcattttaa   1380
tagatagtgg aaaatgacgt ggaatttact taaagacgaa gtctttgcga caaggggggg   1440
cccacgccga atttaatatt accggcgtgg cccccccta tcgcgagtgc tttagcacga   1500
gcggtccaga tttaaagtag aaaatttccc gcccactagg gttaaaggtg ttcacactat   1560
aaaagcatat acgatgtgat ggtatttgat ggagcgtata ttgtatcagg tatttccgtt   1620
ggatacgaat tattcgtacg accctcatag tttaaactat cagtgtttga caggatatat   1680
tggcgggtaa acctaagaga aaagagcgtt tattagaata acggatattt aaaagggcgt   1740
gaaaaggttt atccgttcgt ccatttgtat gtgcatgcca accacagggt tcccctcggg   1800
atcaaagtac tttgatccaa cccctccgct gctatagtgc agtcggcttc tgacgttcag   1860
tgcagccgtc ttctgaaaac gacatgtcgc acaagtccta agttacgcga caggctgccg   1920
ccctgccctt ttcctggcgt tttcttgtcg cgtgttttag tcgcataaag tagaatactt   1980
gcgactagaa ccggagacat tacgccatga acaagagcgc cgccgctggc ctgctgggct   2040
atgcccgcgt cagcaccgac gaccaggact tgaccaacca acgggccgaa ctgcacgcgg   2100
ccggctgcac caagctgttt tccgagaaga tcaccggcac caggcgcgac cgcccggagc   2160
tggccaggat gcttgaccac ctacgccctg gcgacgttgt gacagtgacc aggctagacc   2220
gcctggcccg cagcacccgc gacctactgg acattgccga gcgcatccag gaggccggcg   2280
cgggcctgcg tagcctggca gagccgtggg ccgacaccac cacgccggcc ggccgcatgg   2340
```

```
tgttgaccgt gttcgccggc attgccgagt tcgagcgttc cctaatcatc gaccgcaccc   2400
ggagcgggcg cgaggccgcc aaggcccgag gcgtgaagtt tggcccccgc cctaccctca   2460
ccccggcaca gatcgcgcac gcccgcgagc tgatcgacca ggaaggccgc accgtgaaag   2520
aggcggctgc actgcttggc gtgcatcgct cgaccctgta ccgcgcactt gagcgcagcg   2580
aggaagtgac gcccaccgag gccaggcggc gcggtgcctt ccgtgaggac gcattgaccg   2640
aggccgacgc cctggcggcc gccgagaatg aacgccaaga ggaacaagca tgaaaccgca   2700
ccaggacggc caggacgaac cgtttttcat taccgaagag atcgaggcgg agatgatcgc   2760
ggccgggtac gtgttcgagc cgcccgcgca cggctcaacc gtgcggctgc atgaaatcct   2820
ggccggtttg tctgatgcca agctggcggc ctggccggcc agcttggccg ctgaagaaac   2880
cgagcgccgc cgtctaaaaa ggtgatgtgt atttgagtaa aacagcttgc gtcatgcggt   2940
cgctgcgtat atgatgcgat gagtaaataa acaaatacgc aaggggaacg catgaaggtt   3000
atcgctgtac ttaaccagaa aggcgggtca ggcaagacga ccatcgcaac ccatctagcc   3060
cgcgccctgc aactcgccgg ggccgatgtt ctgttagtcg attccgatcc ccagggcagt   3120
gcccgcgatt gggcggccgt gcgggaagat caaccgctaa ccgttgtcgg catcgaccgc   3180
ccgacgattg accgcgacgt gaaggccatc ggccggcgcg acttcgtagt gatcgacgga   3240
gcgccccagg cggcggactt ggctgtgtcc gcgatcaagg cagccgactt cgtgctgatt   3300
ccggtgcagc caagccctta cgacatatgg gccaccgccg acctggtgga gctggttaag   3360
cagcgcattg aggtcacgga tggaaggcta caagcggcct ttgtcgtgtc gcgggcgatc   3420
aaaggcacgc gcatcggcgg tgaggttgcc gaggcgctgg ccgggtacga gctgcccatt   3480
cttgagtccc gtatcacgca gcgcgtgagc tacccaggca ctgccgccgc cggcacaacc   3540
gttcttgaat cagaacccga gggcgacgct gcccgcgagg tccaggcgct ggccgctgaa   3600
attaaatcaa aactcatttg agttaatgag gtaaagagaa aatgagcaaa agcacaaaca   3660
cgctaagtgc cggccgtccg agcgcacgca gcagcaaggc tgcaacgttg gccagcctgg   3720
cagacacgcc agccatgaag cgggtcaact ttcagttgcc ggcggaggat cacaccaagc   3780
tgaagatgta cgcggtacgc caaggcaaga ccattaccga gctgctatct gaatacatcg   3840
cgcagctacc agagtaaatg agcaaatgaa taaatgagta gatgaatttt agcggctaaa   3900
ggaggcggca tggaaaatca agaacaacca ggcaccgacg ccgtggaatg ccccatgtgt   3960
ggaggaacgg gcggttggcc aggcgtaagc ggctgggttg tctgccggcc ctgcaatggc   4020
actggaaccc ccaagcccga ggaatcggcg tgacggtcgc aaaccatccg gcccggtaca   4080
aatcggcgcg gcgctgggtg atgacctggt ggagaagttg aaggccgcgc aggccgccca   4140
gcggcaacgc atcgaggcag aagcacgccc cggtgaatcg tggcaagcgg ccgctgatcg   4200
aatccgcaaa gaatcccggc aaccgccggc agccggtgcg ccgtcgatta ggaagccgcc   4260
caagggcgac gagcaaccag atttttttcgt tccgatgctc tatgacgtgg gcacccgcga   4320
tagtcgcagc atcatggacg tggccgtttt ccgtctgtcg aagcgtgacc gacgagctgg   4380
cgaggtgatc cgctacgagc ttccagacgg gcacgtagag gtttccgcag ggccggccgg   4440
catggccagt gtgtgggatt acgacctggt actgatggcg gtttcccatc taaccgaatc   4500
catgaaccga taccgggaag ggaagggaga caagcccggc cgcgtgttcc gtccacacgt   4560
tgcggacgta ctcaagttct gccggcgagc cgatggcgga aagcagaaag acgacctggt   4620
agaaacctgc attcggttaa acaccacgca cgttgccatg cagcgtacga agaaggccaa   4680
gaacggccgc ctggtgacgg tatccgaggg tgaagccttg attagccgct acaagatcgt   4740
```

```
aaagagcgaa accgggcggc cggagtacat cgagatcgag ctagctgatt ggatgtaccg   4800
cgagatcaca gaaggcaaga acccggacgt gctgacggtt caccccgatt actttttgat   4860
cgatcccggc atcggccgtt ttctctaccg cctggcacgc cgcgccgcag gcaaggcaga   4920
agccagatgg ttgttcaaga cgatctacga acgcagtggc agcgccggag agttcaagaa   4980
gttctgtttc accgtgcgca agctgatcgg gtcaaatgac ctgccggagt acgatttgaa   5040
ggaggaggcg gggcaggctg gcccgatcct agtcatgcgc taccgcaacc tgatcgaggg   5100
cgaagcatcc gccggttcct aatgtacgga gcagatgcta gggcaaattg ccctagcagg   5160
ggaaaaaggt cgaaaaggcc tctttcctgt ggatagcacg tacattggga acccaaagcc   5220
gtacattggg aaccggaacc cgtacattgg gaacccaaag ccgtacattg ggaaccggtc   5280
acacatgtaa gtgactgata taaaagagaa aaaaggcgat tttccgcct aaaactcttt    5340
aaaacttatt aaaactctta aaacccgcct ggcctgtgca taactgtctg gccagcgcac   5400
agccgaagag ctgcaaaaag cgcctaccct tcggtcgctg cgctccctac gccccgccgc   5460
ttcgcgtcgg cctatcgcgg ccgctggccg ctcaaaaatg gctggcctac ggccaggcaa   5520
tctaccaggg cgcggacaag ccgcgccgtc gccactcgac cgccggcgcc cacatcaagg   5580
caccctgcct cgcgcgtttc ggtgatgacg gtgaaaacct ctgacacatg cagctcccgg   5640
aaacggtcac agcttgtctg taagcggatg ccgggagcag acaagcccgt cagggcgcgt   5700
cagcgggtgt tggcgggtgt cggggcgcag ccatgaccca gtcacgtagc gatagcggag   5760
tgtatactgg cttaactatg cggcatcaga gcagattgta ctgagagtgc accatatgcg   5820
gtgtgaaata ccgcacagat gcgtaaggag aaaataccgc atcaggcgct cttccgcttc   5880
ctcgctcact gactcgctgc gctcggtcgt tcggctgcgg cgagcggtat cagctcactc   5940
aaaggcggta atacggttat ccacagaatc aggggataac gcaggaaaga acatgtgagc   6000
aaaaggccag caaaaggcca ggaaccgtaa aaaggccgcg ttgctggcgt ttttccatag   6060
gctccgcccc cctgacgagc atcacaaaaa tcgacgctca agtcagaggt ggcgaaaccc   6120
gacaggacta taaagatacc aggcgtttcc ccctggaagc tccctcgtgc gctctcctgt   6180
tccgaccctg ccgcttaccg gatacctgtc cgcctttctc ccttcgggaa gcgtggcgct   6240
ttctcatagc tcacgctgta ggtatctcag ttcggtgtag gtcgttcgct ccaagctggg   6300
ctgtgtgcac gaaccccccg ttcagcccga ccgctgcgcc ttatccggta actatcgtct   6360
tgagtccaac ccggtaagac acgacttatc gccactggca gcagccactg gtaacaggat   6420
tagcagagcg aggtatgtag gcggtgctac agagttcttg aagtggtggc ctaactacgg   6480
ctacactaga aggacagtat ttggtatctg cgctctgctg aagccagtta ccttcggaaa   6540
aagagttggt agctcttgat ccggcaaaca aaccaccgct ggtagcggtg gtttttttgt   6600
ttgcaagcag cagattacgc gcagaaaaaa aggatctcaa gaagatcctt tgatcttttc   6660
tacggggtct gacgctcagt ggaacgaaaa ctcacgttaa gggattttgg tcatgcattc   6720
taggtactaa aacaattcat ccagtaaaat ataatatttt attttctccc aatcaggctt   6780
gatccccagt aagtcaaaaa atagctcgac atactgttct tccccgatat cctccctgat   6840
cgaccggacg cagaaggcaa tgtcatacca cttgtccgcc ctgccgcttc tcccaagatc   6900
aataaagcca cttactttgc catctttcac aaagatgttg ctgtctccca ggtcgccgtg   6960
ggaaaagaca agttcctctt cgggcttttc cgtctttaaa aaatcataca gctcgcgcgg   7020
atctttaaat ggagtgtctt cttcccagtt ttcgcaatcc acatcggcca gatcgttatt   7080
```

-continued

```
cagtaagtaa tccaattcgg ctaagcggct gtctaagcta ttcgtatagg gacaatccga   7140
tatgtcgatg gagtgaaaga gcctgatgca ctccgcatac agctcgataa tcttttcagg   7200
gctttgttca tcttcatact cttccgagca aaggacgcca tcggcctcac tcatgagcag   7260
attgctccag ccatcatgcc gttcaaagtg caggaccttt ggaacaggca gctttccttc   7320
cagccatagc atcatgtcct tttcccgttc cacatcatag gtggtccctt tataccggct   7380
gtccgtcatt tttaaatata ggttttcatt ttctcccacc agcttatata ccttagcagg   7440
agacattcct tccgtatctt ttacgcagcg gtatttttcg atcagttttt tcaattccgg   7500
tgatattctc attttagcca tttattattt ccttcctctt ttctacagta tttaaagata   7560
ccccaagaag ctaattataa caagacgaac tccaattcac tgttccttgc attctaaaac   7620
cttaaatacc agaaaacagc tttttcaaag ttgttttcaa agttggcgta taacatagta   7680
tcgacggagc cgattttgaa accgcggtga tcacaggcag caacgctctg tcatcgttac   7740
aatcaacatg ctaccctccg cgagatcatc cgtgtttcaa acccggcagc ttagttgccg   7800
ttcttccgaa tagcatcggt aacatgagca aagtctgccg ccttacaacg gctctcccgc   7860
tgacgccgtc ccggactgat gggctgcctg tatcgagtgg tgattttgtg ccgagctgcc   7920
ggtcggggag ctgttggctg gctggtggca ggatatattg tggtgtaaac aaattgacgc   7980
ttagacaact taataacaca ttgcggacgt ttttaatgta gagctcaaag tttaacgcgt   8040
tagcagaagg catgttgttg tgactccgag gggttgcctc aaactctatc ttataaccgg   8100
cgtggaggca tggaggcagg ggtattttgg tcattttaat agatagtgga aaatgacgtg   8160
gaatttactt aaagacgaag tctttgcgac aagggggggc ccacgccgaa tttaatatta   8220
ccggcgtggc cccccctat cgcgagtgct ttagcacgag cggtccagat ttaaagtaga   8280
aaatttcccg cccactaggg ttaaaggtgt tcacactata aaagcatata cgatgtgatg   8340
gtatttgatg gagcgtatat tgtatcaggt atttccgttg gatacgaatt attcgtacga   8400
ccctcggtac cgatcggcgc gcgcggccgc acagagattt aaatagctcc ggtgacggac   8460
ggcgcgccct atgtcgagct gcaggtcaac ggatcaggat attcttgttt aagatgttga   8520
actctatgga ggtttgtatg aactgatgat ctaggaccgg ataagttccc ttcttcatag   8580
cgaacttatt caaagaatgt tttgtgtatc attcttgtta cattgttatt aatgaaaaaa   8640
tattattggt cattggactg aacacgagtg ttaaatatgg accaggcccc aaataagatc   8700
cattgatata tgaattaaat aacaagaata aatcgagtca ccaaaccact tgcctttttt   8760
aacgagactt gttcaccaac ttgatacaaa agtcattatc ctatgcaaat caataatcat   8820
acaaaaatat ccaataacac taaaaaatta aaagaaatgg ataatttcac aatatgttat   8880
acgataaaga agttactttt ccaagaaatt cactgatttt ataagcccac ttgcattaga   8940
taaatggcaa aaaaaaacaa aaaggaaaag aaataaagca cgaagaattc tagaaaatac   9000
gaaatacgct tcaatgcagt gggacccacg gttcaattat tgccaatttt cagctccacc   9060
gtatatttaa aaaataaaac gataatgcta aaaaaatata aatcgtaacg atcgttaaat   9120
ctcaacggct ggatcttatg acgaccgtta gaaattgtgg ttgtcgacga gtcagtaata   9180
aacggcgtca aagtggttgc agccggcaca cacgagtcgt gtttatcaac tcaaagcaca   9240
aatacttttc ctcaacctaa aaataaggca attagccaaa aacaactttg cgtgtaaaca   9300
acgctcaata cacgtgtcat tttattatta gctattgctt caccgcctta gctttctcgt   9360
gacctagtcg tcctcgtctt ttcttcttct tcttctataa aacaataccc aaagagctct   9420
tcttcttcac aattcagatt tcaatttctc aaaatcttaa aaactttctc tcaattctct   9480
```

```
ctaccgtgat caaggtaaat ttctgtgttc cttattctct caaaatcttc gattttgttt   9540
tcgttcgatc ccaatttcgt atatgttctt tggtttagat tctgttaatc ttagatcgaa   9600
cacgattttc tgggtttgat cgttagatat catcttaatt ctcgattagg gtttcataga   9660
tatcatccga tttgttcaaa taatttgagt tttgtcgaat aattactctt cgatttgtga   9720
tttctatcta gatctggtgt tagtttctag tttgtgcgat cgaatttgtc gattaatctg   9780
agtttttctg attaacaggc ctgcaggatg gaagacgcca aaaacataaa gaaaggcccg   9840
gcgccattct atccgctgga agatggaacc gctggagagc aactgcataa ggctatgaag   9900
agatacgccc tggttcctgg aacaattgct tttacagatg cacatatcga ggtggacatc   9960
acttacgctg agtacttcga aatgtccgtt cggttggcag aagctatgaa acgatatggg  10020
ctgaatacaa atcacagaat cgtcgtatgc agtgaaaact ctcttcaatt ctttatgccg  10080
gtgttgggcg cgttatttat cggagttgca gttgcgcccg cgaacgacat ttataatgaa  10140
cgtgaattgc tcaacagtat gggcatttcg cagcctaccg tggtgttcgt ttccaaaaag  10200
gggttgcaaa aaattttgaa cgtgcaaaaa aagctcccaa tcatccaaaa aattattatc  10260
atggattcta aaacggatta ccagggattt cagtcgatgt acacgttcgt cacatctcat  10320
ctacctcccg gttttaatga atacgatttt gtgccagagt ccttcgatag ggacaagaca  10380
attgcactga tcatgaactc ctctggatct actggtctgc ctaaaggtgt cgctctgcct  10440
catagaactg cctgcgtgag attctcgcat gccagagatc ctatttttgg caatcaaatc  10500
attccggata ctgcgatttt aagtgttgtt ccattccatc acggttttgg aatgtttact  10560
acactcggat atttgatatg tggatttcga gtcgtcttaa tgtatagatt tgaagaagag  10620
ctgtttctga ggagccttca ggattacaag attcaaagtg cgctgctggt gccaacccta  10680
ttctccttct tcgccaaaag cactctgatt gacaaatacg atttatctaa tttacacgaa  10740
attgcttctg gtggcgctcc cctctctaag gaagtcgggg aagcggttgc caagaggttc  10800
catctgccag gtatcaggca aggatatggg ctcactgaga ctacatcagc tattctgatt  10860
acacccgagg gggatgataa accgggcgcg gtcggtaaag ttgttccatt ttttgaagcg  10920
aaggttgtgg atctggatac cgggaaaacg ctgggcgtta atcaaagagg cgaactgtgt  10980
gtgagaggtc ctatgattat gtccggttat gtaaacaatc cggaagcgac caacgccttg  11040
attgacaagg atggatggct acattctgga gacatagctt actgggacga agacgaacac  11100
ttcttcatcg ttgaccgcct gaagtctctg attaagtaca aaggctatca ggtggctccc  11160
gctgaattgg aatccatctt gctccaacac cccaacatct tcgacgctgg tgtcgcaggt  11220
cttcccgacg atgacgccgg tgaacttccc gccgccgttg ttgttttgga gcacggaaag  11280
acgatgacgg aaaaagagat cgtggattac gtcgccagtc aagtaacaac cgcgaaaaag  11340
ttgcgcggag gagttgtgtt tgtggacgaa gtaccgaaag gtcttaccgg aaaactcgac  11400
gcaagaaaaa tcagagagat cctcataaag gccaagaagg gcggaaagat cgccgtgtga  11460
cgtcgacggt tcgagtatta tggcattggg aaaactgttt ttcttgtacc atttgttgtg  11520
cttgtaattt actgtgtttt ttattcggtt ttcgctatcg aactgtgaaa tggaaatgga  11580
tggagaagag ttaatgaatg atatggtcct tttgttcatt ctcaaattaa tattatttgt  11640
tttttctctt atttgttgtg tgttgaattt gaaattataa gagatatgca aacattttgt  11700
tttgagtaaa aatgtgtcaa atcgtggcct ctaatgaccg aagttaatat gaggagtaaa  11760
acacttgtag ttgtgttaga gctcccgggc gcgccgatca tgagcggaga attaagggag  11820
```

tcacgttatg acccccgccg atgacgcggg acaagccgtt ttacgtttgg aactgacaga 11880
accgcaacgt tgaaggagcc actcagccgc gggtttctgg agtttaatga gctaagcaca 11940
tacgtcagaa accattattg cgcgttcaaa agtcgcctaa ggtcactatc agctagcaaa 12000
tatttcttgt caaaaatgct ccactgacgt tccataaatt cccctcggta tccaattaga 12060
gtctcatatt cactctcaat ccaaataatc tgcaccgtac ctgcagggtc cgagctaggt 12120
cacagaagcg ctcaggaagg ccgctgagat agaggcatgg cggccaatgc gggcggcggt 12180
ggagcgggag gaggcagcgg cagcggcagc gtggctgcgc cggcggtgtg ccgccccagc 12240
ggctcgcggt ggacgccgac gccggagcag atcaggatgc tgaaggagct gtactacggc 12300
tgcggcatcc ggtcgcccag ctcggagcag atccagcgca tcaccgccat gctgcggcag 12360
cacggcaaga tcgagggcaa gaacgtcttc tactggttcc agaaccacaa ggcccgcgag 12420
cgccagaagc gccgcctcac cagcctcgac gtgaacgtgc ccgccgccgg cgcggccgac 12480
gccaccacca gccaactcgg cgtcctctcg ctgtcgtcgc cgccgccttc aggcgcggcg 12540
cctccctcgc ccaccctcgg cttctacgcc gccggcaatg gcggcggatc ggctgtgctg 12600
ctggacacga gttccgactg gggcagcagc ggcgctgcga tggccaccga gacatgcttc 12660
ctccaggact acatgggcgt gacggacacg ggcagctcgt cgcagtggcc acgcttctcg 12720
tcgtcggaca cgataatggc ggcggccgcg gcgcgggcgg cgacgacgcg ggcgcccgag 12780
actctccctc tcttcccgac ctgcggcgac gacggcggca gcggtagcag cagctacttg 12840
ccgttctggg gtgccgcgtc cacaactgcc ggcgccactt cttccgttgc gatccagcag 12900
caacaccagc tgcaggagca gtacagcttt tacagcaaca gcaacagcac ccagctggcc 12960
ggcaccggca accaagacgt atcggcaaca gcagcagcag ccgccgccct ggagctgagc 13020
ctcagctcat ggtgctcccc ttaccctgct gcagggagta tgtgagagca acgcgagctg 13080
ccactgctct tcacttatgt ctctggaatg gaaggaggag gaagtgagca tagcgttggt 13140
gcgttgctgt cattgtccta ggttagtagc tagtgccagt tactagtaag catcaggcat 13200
aggagtatgt agtagaagca tgcacgttgc cggccagcca ggctttagac gggaaaagaa 13260
tttggtgcag ccggctgcaa aacaggatgt ttacagcccc cccctcgagc cctagacttg 13320
tccatcttct ggattggcca agttaattaa tgtatgaaat aaaaggatgc acacatagtg 13380
acatgctaat cactataatg tgggcatcaa agttgtgtgt tatgtgtaat tactaattat 13440
ctgaataaga gaaagagatc atccatattt cttatcctaa atgaatgtca cgtgtcttta 13500
taattctttg atgaaccaga tgcattttat taaccaattc catatacata taaatattaa 13560
tcatatataa ttaatatcaa ttgggttagc aaaacaaatc tagtctaggt gtgttttgct 13620
aattattggg ggatagtgca aaaagaaatc tacgttctca ataattcaga tagaaaactt 13680
aataaagtga gataatttac atagattgct tttatccttt gatatatgtg aaaccatgca 13740
tgatataagg aaaatagata gagaaataat tttttacatc gttgaatatg taaacaattt 13800
aattcaagaa gctaggaata taaatattga ggagtttatg attagagctc tcccggcgcg 13860
ccagatttgc cttttcaatt tcagaaagaa tgctaaccca cagatggtta gagaggctta 13920
cgcagcaggt atcatcaaga cgatctaccc gagcaataat ctccaggaaa tcaaatacct 13980
tcccaagaag gttaaagatg cagtcaaaag attcaggact aactgcatca agaacacaga 14040
gaaagatata tttctcaaga tcagaagtac tattccagta tggacgattc aaggcttgct 14100
tcacaaacca aggcaagtaa tagagattgg agtctctaaa aaggtagttc ccactgaatc 14160
aaaggccatg gagtcaaaga ttcaaataga ggacctaaca gaactcgccg taaagactgg 14220
cgaacagttc atacagagtc tcttacgact caatgacaag aagaaaatct tcgtcaacat 14280
ggtggagcac gacacacttg tctactccaa aaatatcaaa gatacagtct cagaagacca 14340
aagggcaatt gagacttttc aacaaagggt aatatccgga aacctcctcg gattccattg 14400
cccagctatc tgtcacttta ttgtgaagat agtggaaaag gaaggtggct cctacaaatg 14460
ccatcattgc gataaaggaa aggccatcgt tgaagatgcc tctgccgaca gtggtcccaa 14520
agatggaccc ccacccacga ggagcatcgt ggaaaaagaa gacgttccaa ccacgtcttc 14580
aaagcaagtg gattgatgtg atatctccac tgacgtaagg gatgacgcac aatcccacta 14640
tccttcgcaa gacccttcct ctatataagg aagttcattt catttggaga gaacacgggg 14700
gactcctgca ggatggatct gcgtctaatt ttcggtccaa cttgcacagg aaagacgtcg 14760
accgcgatac gtcttgccca gcagactggc cttccagtcc tttcgctcga tcgggtccaa 14820
tgctgtcctc aactgtcaac cggaagcgga cgaccaacag tggaagaact gaaaggaacg 14880
acccgtctat accttgaaga tcggcctctg gtgaagggta tcatcgcagc caagcaagct 14940
cacgaaaggc tgatcgggga agtgtacaat tatgaggccc acggcgggct tattcttgag 15000
ggaggatcta tctcgttgct caggtgcatg gcgcaaagca gttattggag taccgatttt 15060
cgttggcata ttattcgcca caagttagca gacgaggaga cattcatgaa cgcggccaag 15120
gccagagtta ggcagatgtt gcgccctgct gtaggcccat ctattattca agagttggtt 15180
catctttgga atgagcctcg gctgaggccc atactgaaag agatcgacgg atatcgatat 15240
gccatgttat ttgctagcca gaaccagatc acacccgata tgctattgca gcttgaccca 15300
gatatggagg gtgagttgat tcatggaatc gctcaggagt atctcatcca tgcgcgccgg 15360
caggagcagg aattccctcc agtgagcgtg gtcgctttcg aaggattcga aggtccaccg 15420
ttcggaatgt gctagctcga gccctagact tgtccatctt ctggattggc caagttaatt 15480
aatgtatgaa ataaaaggat gcacacatag tgacatgcta atcactataa tgtgggcatc 15540
aaagttgtgt gttatgtgta attactaatt atctgaataa gagaaagaga tcatccatat 15600
ttcttatcct aaatgaatgt cacgtgtctt tataattctt tgatgaacca gatgcatttt 15660
attaaccaat tccatataca tataaatatt aatcatatat aattaatatc aattgggtta 15720
gcaaaacaaa tctagtctag gtgtgttttg ctaattattg ggggatagtg caaaaagaaa 15780
tctacgttct caataattca gatagaaaac ttaataaagt gagataattt acatagattg 15840
cttttatcct ttgatatatg tgaaaccatg catgatataa ggaaaataga tagagaaata 15900
attttttaca tcgttgaata tgtaaacaat ttaattcaag aagctaggaa tataaatatt 15960
gaggagttta tgattagagc tcagtg 15986

<210> SEQ ID NO 95
<211> LENGTH: 15986
<212> TYPE: DNA
<213> ORGANISM: artificial
<220> FEATURE:
<223> OTHER INFORMATION: synthetic oligonucleotide

<400> SEQUENCE: 95
cagctcgata atcttttcag ggctttgttc atcttcatac tcttccgagc aaaggacgcc 60
atcggcctca ctcatgagca gattgctcca gccatcatgc cgttcaaagt gcaggacctt 120
tggaacaggc agctttcctt ccagccatag catcatgtcc ttttcccgtt ccacatcata 180
ggtggtccct ttataccggc tgtccgtcat ttttaaatat aggttttcat tttctcccac 240

```
cagcttatat accttagcag gagacattcc ttccgtatct tttacgcagc ggtatttttc    300
gatcagtttt ttcaattccg gtgatattct cattttagcc atttattatt tccttcctct    360
tttctacagt atttaaagat accccaagaa gctaattata acaagacgaa ctccaattca    420
ctgttccttg cattctaaaa ccttaaatac cagaaaacag ctttttcaaa gttgttttca    480
aagttggcgt ataacatagt atcgacggag ccgattttga aaccgcggtg atcacaggca    540
gcaacgctct gtcatcgtta caatcaacat gctaccctcc gcgagatcat ccgtgtttca    600
aacccggcag cttagttgcc gttcttccga atagcatcgg taacatgagc aaagtctgcc    660
gccttacaac ggctctcccg ctgacgccgt cccggactga tgggctgcct gtatcgagtg    720
gtgattttgt gccgagctgc cggtcgggga gctgttggct ggctggtggc aggatatatt    780
gtggtgtaaa caaattgacg cttagacaac ttaataacac attgcggacg tttttaatgt    840
agagctcaaa gtttaacgcg ttagcagaag gcatgttgtt gtgactccga ggggttgcct    900
caaactctat cttataaccg gcgtggaggc atggaggcag ggtattttgg gtcattttaa    960
tagatagtgg aaaatgacgt ggaatttact taaagacgaa gtctttgcga caaggggggg   1020
cccacgccga atttaatatt accggcgtgg ccccccctta tcgcgagtgc tttagcacga   1080
gcggtccaga tttaaagtag aaaatttccc gcccactagg gttaaaggtg ttcacactat   1140
aaaagcatat acgatgtgat ggtatttgat ggagcgtata ttgtatcagg tatttccgtt   1200
ggatacgaat tattcgtacg accctcggta ccgatcggcg cgcgcggccg cacagagatt   1260
taaatagctc cggtgacgga cggcgcgccc tatgtcgagc tgcaggtcaa cggatcagga   1320
tattcttgtt taagatgttg aactctatgg aggtttgtat gaactgatga tctaggaccg   1380
gataagttcc cttcttcata gcgaacttat tcaaagaatg ttttgtgtat cattcttgtt   1440
acattgttat taatgaaaaa atattattgg tcattggact gaacacgagt gttaaatatg   1500
gaccaggccc caaataagat ccattgatat atgaattaaa taacaagaat aaatcgagtc   1560
accaaaccac ttgccttttt taacgagact tgttcaccaa cttgatacaa aagtcattat   1620
cctatgcaaa tcaataatca tacaaaaata tccaataaca ctaaaaaatt aaaagaaatg   1680
gataatttca caatatgtta tacgataaag aagttacttt tccaagaaat tcactgattt   1740
tataagccca cttgcattag ataaatggca aaaaaaaaca aaaaggaaaa gaaataaagc   1800
acgaagaatt ctagaaaata cgaaatacgc ttcaatgcag tgggacccac ggttcaatta   1860
ttgccaattt tcagctccac cgtatattta aaaaataaaa cgataatgct aaaaaaatat   1920
aaatcgtaac gatcgttaaa tctcaacggc tggatcttat gacgaccgtt agaaattgtg   1980
gttgtcgacg agtcagtaat aaacggcgtc aaagtggttg cagccggcac acacgagtcg   2040
tgtttatcaa ctcaaagcac aaatactttt cctcaaccta aaaataaggc aattagccaa   2100
aaacaacttt gcgtgtaaac aacgctcaat acacgtgtca ttttattatt agctattgct   2160
tcaccgcctt agctttctcg tgacctagtc gtcctcgtct tttcttcttc ttcttctata   2220
aaacaatacc caaagagctc ttcttcttca caattcagat ttcaatttct caaaatctta   2280
aaaactttct ctcaattctc tctaccgtga tcaaggtaaa tttctgtgtt ccttattctc   2340
tcaaaatctt cgattttgtt ttcgttcgat cccaatttcg tatatgttct ttggtttaga   2400
ttctgttaat cttagatcga acacgatttt ctgggtttga tcgttagata tcatcttaat   2460
tctcgattag ggtttcatag atatcatccg atttgttcaa ataatttgag ttttgtcgaa   2520
taattactct tcgatttgtg atttctatct agatctggtg ttagtttcta gtttgtgcga   2580
tcgaatttgt cgattaatct gagtttttct gattaacagg cctgcaggat ggaagacgcc   2640
```

-continued

```
aaaaacataa agaaaggccc ggcgccattc tatccgctgg aagatggaac cgctggagag   2700
caactgcata aggctatgaa gagatacgcc ctggttcctg gaacaattgc ttttacagat   2760
gcacatatcg aggtggacat cacttacgct gagtacttcg aaatgtccgt tcggttggca   2820
gaagctatga aacgatatgg gctgaataca aatcacagaa tcgtcgtatg cagtgaaaac   2880
tctcttcaat tctttatgcc ggtgttgggc gcgttattta tcggagttgc agttgcgccc   2940
gcgaacgaca tttataatga acgtgaattg ctcaacagta tgggcatttc gcagcctacc   3000
gtggtgttcg tttccaaaaa ggggttgcaa aaaattttga acgtgcaaaa aaagctccca   3060
atcatccaaa aaattattat catggattct aaaacggatt accagggatt tcagtcgatg   3120
tacacgttcg tcacatctca tctacctccc ggttttaatg aatacgattt tgtgccagag   3180
tccttcgata gggacaagac aattgcactg atcatgaact cctctggatc tactggtctg   3240
cctaaaggtg tcgctctgcc tcatagaact gcctgcgtga gattctcgca tgccagagat   3300
cctatttttg gcaatcaaat cattccggat actgcgattt taagtgttgt tccattccat   3360
cacggttttg gaatgtttac tacactcgga tatttgatat gtggatttcg agtcgtctta   3420
atgtatagat ttgaagaaga gctgtttctg aggagccttc aggattacaa gattcaaagt   3480
gcgctgctgg tgccaaccct attctccttc ttcgccaaaa gcactctgat tgacaaatac   3540
gatttatcta atttacacga aattgcttct ggtggcgctc ccctctctaa ggaagtcggg   3600
gaagcggttg ccaagaggtt ccatctgcca ggtatcaggc aaggatatgg gctcactgag   3660
actacatcag ctattctgat tacacccgag ggggatgata aaccgggcgc ggtcggtaaa   3720
gttgttccat tttttgaagc gaaggttgtg gatctggata ccgggaaaac gctgggcgtt   3780
aatcaaagag gcgaactgtg tgtgagaggt cctatgatta tgtccggtta tgtaaacaat   3840
ccggaagcga ccaacgcctt gattgacaag gatggatggc tacattctgg agacatagct   3900
tactgggacg aagacgaaca cttcttcatc gttgaccgcc tgaagtctct gattaagtac   3960
aaaggctatc aggtggctcc cgctgaattg gaatccatct tgctccaaca ccccaacatc   4020
ttcgacgctg gtgtcgcagg tcttcccgac gatgacgccg gtgaacttcc cgccgccgtt   4080
gttgttttgg agcacggaaa gacgatgacg gaaaaagaga tcgtggatta cgtcgccagt   4140
caagtaacaa ccgcgaaaaa gttgcgcgga ggagttgtgt ttgtggacga agtaccgaaa   4200
ggtcttaccg gaaaactcga cgcaagaaaa atcagagaga tcctcataaa ggccaagaag   4260
ggcggaaaga tcgccgtgtg acgtcgacgg ttcgagtatt atggcattgg gaaaactgtt   4320
tttcttgtac catttgttgt gcttgtaatt tactgtgttt tttattcggt tttcgctatc   4380
gaactgtgaa atggaaatgg atggagaaga gttaatgaat gatatggtcc ttttgttcat   4440
tctcaaatta atattatttg ttttttctct tatttgttgt gtgttgaatt tgaaattata   4500
agagatatgc aaacattttg ttttgagtaa aaatgtgtca aatcgtggcc tctaatgacc   4560
gaagttaata tgaggagtaa aacacttgta gttgtgttag agctcccggg cgcgccgatc   4620
atgagcggag aattaaggga gtcacgttat gacccccgcc gatgacgcgg gacaagccgt   4680
tttacgtttg gaactgacag aaccgcaacg ttgaaggagc cactcagccg cgggtttctg   4740
gagtttaatg agctaagcac atacgtcaga aaccattatt gcgcgttcaa aagtcgccta   4800
aggtcactat cagctagcaa atatttcttg tcaaaaatgc tccactgacg ttccataaat   4860
tcccctcggt atccaattag agtctcatat tcactctcaa tccaaataat ctgcaccgta   4920
cctgcagggt ccgagctagg tcacagaagc gctcaggaag gccgctgaga tagaggcatg   4980
```

gcggccaatg cgggcggcgg tggagcggga ggaggcagcg gcagcggcag cgtggctgcg 5040
ccggcggtgt gccgccccag cggctcgcgg tggacgccga cgccggagca gatcaggatg 5100
ctgaaggagc tgtactacgg ctgcggcatc cggtcgccca gctcggagca gatccagcgc 5160
atcaccgcca tgctgcggca gcacggcaag atcgagggca agaacgtctt ctactggttc 5220
cagaaccaca aggcccgcga gcgccagaag cgccgcctca ccagcctcga cgtgaacgtg 5280
cccgccgccg gcgcggccga cgccaccacc agccaactcg gcgtcctctc gctgtcgtcg 5340
ccgccgcctt caggcgcggc gcctccctcg cccaccctcg gcttctacgc cgccggcaat 5400
ggcggcggat cggctgtgct gctggacacg agttccgact ggggcagcag cggcgctgcg 5460
atggccaccg agacatgctt cctccaggac tacatgggcg tgacggacac gggcagctcg 5520
tcgcagtggc cacgcttctc gtcgtcggac acgataatgg cggcggccgc ggcgcgggcg 5580
gcgacgacgc gggcgcccga gactctccct ctcttcccga cctgcggcga cgacggcggc 5640
agcggtagca gcagctactt gccgttctgg ggtgccgcgt ccacaactgc cggcgccact 5700
tcttccgttg cgatccagca gcaacaccag ctgcaggagc agtacagctt ttacagcaac 5760
agcaacagca cccagctggc cggcaccggc aaccaagacg tatcggcaac agcagcagca 5820
gccgccgccc tggagctgag cctcagctca tggtgctccc cttaccctgc tgcaggggagt 5880
atgtgagagc aacgcgagct gccactgctc ttcacttatg tctctggaat ggaaggagga 5940
ggaagtgagc atagcgttgg tgcgttgctg tcattgtcct aggttagtag ctagtgccag 6000
ttactagtaa gcatcaggca taggagtatg tagtagaagc atgcacgttg ccggccagcc 6060
aggctttaga cgggaaaaga atttggtgca gccggctgca aaacaggatg tttacagccc 6120
ccccctcgag ccctagactt gtccatcttc tggattggcc aagttaatta atgtatgaaa 6180
taaaaggatg cacacatagt gacatgctaa tcactataat gtgggcatca aagttgtgtg 6240
ttatgtgtaa ttactaatta tctgaataag agaaagagat catccatatt tcttatccta 6300
aatgaatgtc acgtgtcttt ataattcttt gatgaaccag atgcatttta ttaaccaatt 6360
ccatatacat ataaatatta atcatatata attaatatca attgggttag caaaacaaat 6420
ctagtctagg tgtgttttgc taattattgg gggatagtgc aaaaagaaat ctacgttctc 6480
aataattcag atagaaaact taataaagtg agataattta catagattgc ttttatcctt 6540
tgatatatgt gaaaccatgc atgatataag gaaaatagat agagaaataa ttttttacat 6600
cgttgaatat gtaaacaatt taattcaaga agctaggaat ataaatattg aggagtttat 6660
gattagagct ctcccggcgc gccagatttg ccttttcaat ttcagaaaga atgctaaccc 6720
acagatggtt agagaggctt acgcagcagg tatcatcaag acgatctacc cgagcaataa 6780
tctccaggaa atcaaatacc ttcccaagaa ggttaaagat gcagtcaaaa gattcaggac 6840
taactgcatc aagaacacag agaaagatat atttctcaag atcagaagta ctattccagt 6900
atggacgatt caaggcttgc ttcacaaacc aaggcaagta atagagattg gagtctctaa 6960
aaaggtagtt cccactgaat caaaggccat ggagtcaaag attcaaatag aggacctaac 7020
agaactcgcc gtaaagactg gcgaacagtt catacagagt ctcttacgac tcaatgacaa 7080
gaagaaaatc ttcgtcaaca tggtggagca cgacacactt gtctactcca aaaatatcaa 7140
agatacagtc tcagaagacc aaagggcaat tgagactttt caacaaaggg taatatccgg 7200
aaacctcctc ggattccatt gcccagctat ctgtcacttt attgtgaaga tagtggaaaa 7260
ggaaggtggc tcctacaaat gccatcattg cgataaagga aaggccatcg ttgaagatgc 7320
ctctgccgac agtggtccca aagatggacc cccacccacg aggagcatcg tggaaaaaga 7380

-continued

```
agacgttcca accacgtctt caaagcaagt ggattgatgt gatatctcca ctgacgtaag   7440
ggatgacgca caatcccact atccttcgca agacccttcc tctatataag gaagttcatt   7500
tcatttggag agaacacggg ggactcctgc aggatggatc tgcgtctaat tttcggtcca   7560
acttgcacag gaaagacgtc gaccgcgata cgtcttgccc agcagactgg ccttccagtc   7620
ctttcgctcg atcgggtcca atgctgtcct caactgtcaa ccggaagcgg acgaccaaca   7680
gtggaagaac tgaaaggaac gacccgtcta taccttgaag atcggcctct ggtgaagggt   7740
atcatcgcag ccaagcaagc tcacgaaagg ctgatcgggg aagtgtacaa ttatgaggcc   7800
cacggcgggc ttattcttga gggaggatct atctcgttgc tcaggtgcat ggcgcaaagc   7860
agttattgga gtaccgattt tcgttggcat attattcgcc acaagttagc agacgaggag   7920
acattcatga acgcggccaa ggccagagtt aggcagatgt tgcgccctgc tgtaggccca   7980
tctattattc aagagttggt tcatctttgg aatgagcctc ggctgaggcc catactgaaa   8040
gagatcgacg gatatcgata tgccatgtta tttgctagcc agaaccagat cacacccgat   8100
atgctattgc agcttgaccc agatatggag ggtgagttga ttcatggaat cgctcaggag   8160
tatctcatcc atgcgcgccg gcaggagcag gaattccctc cagtgagcgt ggtcgctttc   8220
gaaggattcg aaggtccacc gttcggaatg tgctagctcg agccctagac ttgtccatct   8280
tctggattgg ccaagttaat taatgtatga aataaaagga tgcacacata gtgacatgct   8340
aatcactata atgtgggcat caaagttgtg tgttatgtgt aattactaat tatctgaata   8400
agagaaagag atcatccata tttcttatcc taaatgaatg tcacgtgtct ttataattct   8460
ttgatgaacc agatgcattt tattaaccaa ttccatatac atataaatat taatcatata   8520
taattaatat caattgggtt agcaaaacaa atctagtcta ggtgtgtttt gctaattatt   8580
gggggatagt gcaaaaagaa atctacgttc tcaataattc agatagaaaa cttaataaag   8640
tgagataatt tacatagatt gcttttatcc tttgatatat gtgaaaccat gcatgatata   8700
aggaaaatag atagagaaat aattttttac atcgttgaat atgtaaacaa tttaattcaa   8760
gaagctagga atataaatat tgaggagttt atgattagag ctcagtgttt gatcgccggc   8820
ggtaccgagt gtacttcaag tcagtgggaa atcaataaaa tgattatttt atgaatatat   8880
ttcattgtgc aagtagatag aaattacata tgttacataa cacacgaaat aaacaaaaaa   8940
agacaatcca aaaacaaaca ccccaaaaaa aataatcact ttagataaac tcgtatgagg   9000
agaggcacgt tcagtgactc gacgattccc gagcaaaaaa agtctccccg tcacacatgt   9060
agtgggtgac gcaattatct ttaaagtaat ccttctgttg acttgtcatt gataacatcc   9120
agtcttcgtc aggattgcaa agaattatag aagggatccc accttttatt ttcttctttt   9180
ttccatattt agggttgaca gtgaaatcag actggcaacc tattaattgc ttccacaatg   9240
ggacgaactt gaaggggatg tcgtcgatga tattataggt ggcgtgttca tcgtagttgg   9300
tgaaatcgat ggtaccgttc caatagttgt gtcgtccgag acttctagcc caggtggtct   9360
ttccggtacg agttggtccg cagatgtaga ggctggggtg tcggattcca ttccttccat   9420
tgtccttgtt aaatcggcca tccattcaag gtcagattga gcttgttggt atgagacagg   9480
atgtatgtaa gtataagcgt ctatgcttac atggtataga tgggtttccc tccaggagtg   9540
tagatcttcg tggcagcgaa gatctgattc tgtgaagggc gacacatacg gttcaggttg   9600
tggagggaat aatttgttgg ctgaatattc cagccattga agctttgttg cccattcatg   9660
agggaattct tccttgatca tgtcaagata ttcctcctta gacgttgcag tctggataat   9720
```

-continued

```
agttctccat cgtgcgtcag atttgcgagg agaaacctta tgatctcgga aatctcctct   9780
ggttttaata tctccgtcct ttgatatgta atcaaggact tgtttagagt ttctagctgg   9840
ctggatatta gggtgatttc cttcaaaatc gaaaaaagaa ggatccctaa tacaaggttt   9900
tttatcaagc tggagaagag catgatagtg ggtagtgcca tcttgatgaa gctcagaagc   9960
aacaccaagg aagaaaataa gaaaaggtgt gagtttctcc cagagaaact ggaataaatc  10020
atctctttga gatgagcact tgggataggt aaggaaaaca tatttagatt ggagtctgaa  10080
gttcttacta gcagaaggca tgttgttgtg actccgaggg gttgcctcaa actctatctt  10140
ataaccggcg tggaggcatg gaggcagggg tattttggtc attttaatag atagtggaaa  10200
atgacgtgga atttacttaa agacgaagtc tttgcgacaa gggggggccc acgccgaatt  10260
taatattacc ggcgtggccc ccccttatcg cgagtgcttt agcacgagcg gtccagattt  10320
aaagtagaaa atttcccgcc cactagggtt aaaggtgttc acactataaa agcatatacg  10380
atgtgatggt atttgatgga gcgtatattg tatcaggtat ttccgttgga tacgaattat  10440
tcgtacgacc ctcatagttt aaactatcag tgtttgacag gatatattgg cgggtaaacc  10500
taagagaaaa gagcgtttat tagaataacg gatatttaaa agggcgtgaa aaggtttatc  10560
cgttcgtcca tttgtatgtg catgccaacc acagggttcc cctcgggatc aaagtacttt  10620
gatccaaccc ctccgctgct atagtgcagt cggcttctga cgttcagtgc agccgtcttc  10680
tgaaaacgac atgtcgcaca agtcctaagt tacgcgacag gctgccgccc tgcccttttc  10740
ctggcgtttt cttgtcgcgt gttttagtcg cataaagtag aatacttgcg actagaaccg  10800
gagacattac gccatgaaca agagcgccgc cgctggcctg ctgggctatg cccgcgtcag  10860
caccgacgac caggacttga ccaaccaacg ggccgaactg cacgcggccg gctgcaccaa  10920
gctgttttcc gagaagatca ccggcaccag gcgcgaccgc ccggagctgg ccaggatgct  10980
tgaccaccta cgccctggcg acgttgtgac agtgaccagg ctagaccgcc tggcccgcag  11040
cacccgcgac ctactggaca ttgccgagcg catccaggag gccggcgcgg gcctgcgtag  11100
cctggcagag ccgtgggccg acaccaccac gccggccggc cgcatggtgt tgaccgtgtt  11160
cgccggcatt gccgagttcg agcgttccct aatcatcgac cgcacccgga gcgggcgcga  11220
ggccgccaag gcccgaggcg tgaagtttgg cccccgccct accctcaccc cggcacagat  11280
cgcgcacgcc cgcgagctga tcgaccagga aggccgcacc gtgaaagagg cggctgcact  11340
gcttggcgtg catcgctcga ccctgtaccg cgcacttgag cgcagcgagg aagtgacgcc  11400
caccgaggcc aggcggcgcg gtgccttccg tgaggacgca ttgaccgagg ccgacgccct  11460
ggcggccgcc gagaatgaac gccaagagga acaagcatga aaccgcacca ggacggccag  11520
gacgaaccgt ttttcattac cgaagagatc gaggcggaga tgatcgcggc cgggtacgtg  11580
ttcgagccgc ccgcgcacgg ctcaaccgtg cggctgcatg aaatcctggc cggtttgtct  11640
gatgccaagc tggcggcctg gccggccagc ttggccgctg aagaaaccga gcgccgccgt  11700
ctaaaaaggt gatgtgtatt tgagtaaaac agcttgcgtc atgcggtcgc tgcgtatatg  11760
atgcgatgag taaataaaca aatacgcaag gggaacgcat gaaggttatc gctgtactta  11820
accagaaagg cgggtcaggc aagacgacca tcgcaaccca tctagcccgc gccctgcaac  11880
tcgccggggc cgatgttctg ttagtcgatt ccgatcccca gggcagtgcc cgcgattggg  11940
cggccgtgcg ggaagatcaa ccgctaaccg ttgtcggcat cgaccgcccg acgattgacc  12000
gcgacgtgaa ggccatcggc cggcgcgact tcgtagtgat cgacggagcg ccccaggcgg  12060
cggacttggc tgtgtccgcg atcaaggcag ccgacttcgt gctgattccg gtgcagccaa  12120
```

-continued gcccttacga catatgggcc accgccgacc tggtggagct ggttaagcag cgcattgagg 12180
tcacggatgg aaggctacaa gcggcctttg tcgtgtcgcg ggcgatcaaa ggcacgcgca 12240
tcggcggtga ggttgccgag gcgctggccg ggtacgagct gcccattctt gagtcccgta 12300
tcacgcagcg cgtgagctac ccaggcactg ccgccgccgg cacaaccgtt cttgaatcag 12360
aacccgaggg cgacgctgcc cgcgaggtcc aggcgctggc cgctgaaatt aaatcaaaac 12420
tcatttgagt taatgaggta aagagaaaat gagcaaaagc acaaacacgc taagtgccgg 12480
ccgtccgagc gcacgcagca gcaaggctgc aacgttggcc agcctggcag acacgccagc 12540
catgaagcgg gtcaactttc agttgccggc ggaggatcac accaagctga agatgtacgc 12600
ggtacgccaa ggcaagacca ttaccgagct gctatctgaa tacatcgcgc agctaccaga 12660
gtaaatgagc aaatgaataa atgagtagat gaattttagc ggctaaagga ggcggcatgg 12720
aaaatcaaga acaaccaggc accgacgccg tggaatgccc catgtgtgga ggaacgggcg 12780
gttggccagg cgtaagcggc tgggttgtct gccggccctg caatggcact ggaaccccca 12840
agcccgagga atcggcgtga cggtcgcaaa ccatccggcc cggtacaaat cggcgcggcg 12900
ctgggtgatg acctggtgga gaagttgaag gccgcgcagg ccgcccagcg gcaacgcatc 12960
gaggcagaag cacgccccgg tgaatcgtgg caagcggccg ctgatcgaat ccgcaaagaa 13020
tcccggcaac cgccggcagc cggtgcgccg tcgattagga agccgcccaa gggcgacgag 13080
caaccagatt ttttcgttcc gatgctctat gacgtgggca cccgcgatag tcgcagcatc 13140
atggacgtgg ccgttttccg tctgtcgaag cgtgaccgac gagctggcga ggtgatccgc 13200
tacgagcttc cagacgggca cgtagaggtt tccgcagggc cggccggcat ggccagtgtg 13260
tgggattacg acctggtact gatggcggtt tcccatctaa ccgaatccat gaaccgatac 13320
cgggaaggga agggagacaa gcccggccgc gtgttccgtc cacacgttgc ggacgtactc 13380
aagttctgcc ggcgagccga tggcggaaag cagaaagacg acctggtaga aacctgcatt 13440
cggttaaaca ccacgcacgt tgccatgcag cgtacgaaga aggccaagaa cggccgcctg 13500
gtgacggtat ccgagggtga agccttgatt agccgctaca agatcgtaaa gagcgaaacc 13560
gggcggccgg agtacatcga gatcgagcta gctgattgga tgtaccgcga gatcacagaa 13620
ggcaagaacc cggacgtgct gacggttcac cccgattact ttttgatcga tcccggcatc 13680
ggccgttttc tctaccgcct ggcacgccgc gccgcaggca aggcagaagc cagatggttg 13740
ttcaagacga tctacgaacg cagtggcagc gccggagagt tcaagaagtt ctgtttcacc 13800
gtgcgcaagc tgatcgggtc aaatgacctg ccggagtacg atttgaagga ggaggcgggg 13860
caggctggcc cgatcctagt catgcgctac cgcaacctga tcgagggcga agcatccgcc 13920
ggttcctaat gtacggagca gatgctaggg caaattgccc tagcagggga aaaaggtcga 13980
aaaggcctct ttcctgtgga tagcacgtac attgggaacc caaagccgta cattgggaac 14040
cggaacccgt acattgggaa cccaaagccg tacattggga accggtcaca catgtaagtg 14100
actgatataa aagagaaaaa aggcgatttt tccgcctaaa actctttaaa acttattaaa 14160
actcttaaaa cccgcctggc ctgtgcataa ctgtctggcc agcgcacagc cgaagagctg 14220
caaaaagcgc ctacccttcg gtcgctgcgc tccctacgcc ccgccgcttc gcgtcggcct 14280
atcgcggccg ctggccgctc aaaaatggct ggcctacggc caggcaatct accagggcgc 14340
ggacaagccg cgccgtcgcc actcgaccgc cggcgcccac atcaaggcac cctgcctcgc 14400
gcgtttcggt gatgacggtg aaaacctctg acacatgcag ctcccggaaa cggtcacagc 14460

```
ttgtctgtaa gcggatgccg ggagcagaca agcccgtcag ggcgcgtcag cgggtgttgg  14520

cgggtgtcgg ggcgcagcca tgacccagtc acgtagcgat agcggagtgt atactggctt  14580

aactatgcgg catcagagca gattgtactg agagtgcacc atatgcggtg tgaaataccg  14640

cacagatgcg taaggagaaa ataccgcatc aggcgctctt ccgcttcctc gctcactgac  14700

tcgctgcgct cggtcgttcg gctgcggcga gcggtatcag ctcactcaaa ggcggtaata  14760

cggttatcca cagaatcagg ggataacgca ggaaagaaca tgtgagcaaa aggccagcaa  14820

aaggccagga accgtaaaaa ggccgcgttg ctggcgtttt tccataggct ccgcccccct  14880

gacgagcatc acaaaaatcg acgctcaagt cagaggtggc gaaacccgac aggactataa  14940

agataccagg cgtttccccc tggaagctcc ctcgtgcgct ctcctgttcc gaccctgccg  15000

cttaccggat acctgtccgc ctttctccct tcgggaagcg tggcgctttc tcatagctca  15060

cgctgtaggt atctcagttc ggtgtaggtc gttcgctcca agctgggctg tgtgcacgaa  15120

ccccccgttc agcccgaccg ctgcgcctta tccggtaact atcgtcttga gtccaacccg  15180

gtaagacacg acttatcgcc actggcagca gccactggta acaggattag cagagcgagg  15240

tatgtaggcg gtgctacaga gttcttgaag tggtggccta actacggcta cactagaagg  15300

acagtatttg gtatctgcgc tctgctgaag ccagttacct tcggaaaaag agttggtagc  15360

tcttgatccg gcaaacaaac caccgctggt agcggtggtt tttttgtttg caagcagcag  15420

attacgcgca gaaaaaaagg atctcaagaa gatcctttga tcttttctac ggggtctgac  15480

gctcagtgga acgaaaactc acgttaaggg attttggtca tgcattctag gtactaaaac  15540

aattcatcca gtaaaatata atattttatt ttctcccaat caggcttgat ccccagtaag  15600

tcaaaaaata gctcgacata ctgttcttcc ccgatatcct ccctgatcga ccggacgcag  15660

aaggcaatgt cataccactt gtccgccctg ccgcttctcc caagatcaat aaagccactt  15720

actttgccat ctttcacaaa gatgttgctg tctcccaggt cgccgtggga aaagacaagt  15780

tcctcttcgg gcttttccgt ctttaaaaaa tcatacagct cgcgcggatc tttaaatgga  15840

gtgtcttctt cccagttttc gcaatccaca tcggccagat cgttattcag taagtaatcc  15900

aattcggcta agcggctgtc taagctattc gtatagggac aatccgatat gtcgatggag  15960

tgaaagagcc tgatgcactc cgcata                                      15986
```

```
<210> SEQ ID NO 96
<211> LENGTH: 13942
<212> TYPE: DNA
<213> ORGANISM: artificial
<220> FEATURE:
<223> OTHER INFORMATION: synthetic oligonucleotide

<400> SEQUENCE: 96

cggtaatacg gttatccaca gaatcagggg ataacgcagg aaagaacatg tgagcaaaag     60

gccagcaaaa ggccaggaac cgtaaaaagg ccgcgttgct ggcgtttttc cataggctcc    120

gcccccctga cgagcatcac aaaaatcgac gctcaagtca gaggtggcga aacccgacag    180

gactataaag ataccaggcg tttccccctg gaagctccct cgtgcgctct cctgttccga    240

ccctgccgct taccggatac ctgtccgcct ttctcccttc gggaagcgtg gcgctttctc    300

atagctcacg ctgtaggtat ctcagttcgg tgtaggtcgt tcgctccaag ctgggctgtg    360

tgcacgaacc ccccgttcag cccgaccgct gcgccttatc cggtaactat cgtcttgagt    420

ccaacccggt aagacacgac ttatcgccac tggcagcagc cactggtaac aggattagca    480

gagcgaggta tgtaggcggt gctacagagt tcttgaagtg gtggcctaac tacggctaca    540
```

ctagaaggac agtatttggt atctgcgctc tgctgaagcc agttaccttc ggaaaaagag 600
ttggtagctc ttgatccggc aaacaaacca ccgctggtag cggtggtttt tttgtttgca 660
agcagcagat tacgcgcaga aaaaaaggat ctcaagaaga tcctttgatc ttttctacgg 720
ggtctgacgc tcagtggaac gaaaactcac gttaagggat tttggtcatg cattctaggt 780
actaaaacaa ttcatccagt aaaatataat attttatttt ctcccaatca ggcttgatcc 840
ccagtaagtc aaaaaatagc tcgacatact gttcttcccc gatatcctcc ctgatcgacc 900
ggacgcagaa ggcaatgtca taccacttgt ccgccctgcc gcttctccca agatcaataa 960
agccacttac tttgccatct ttcacaaaga tgttgctgtc tcccaggtcg ccgtgggaaa 1020
agacaagttc ctcttcgggc ttttccgtct ttaaaaaatc atacagctcg cgcggatctt 1080
taaatggagt gtcttcttcc cagttttcgc aatccacatc ggccagatcg ttattcagta 1140
agtaatccaa ttcggctaag cggctgtcta agctattcgt atagggacaa tccgatatgt 1200
cgatggagtg aaagagcctg atgcactccg catacagctc gataatcttt tcagggcttt 1260
gttcatcttc atactcttcc gagcaaagga cgccatcggc ctcactcatg agcagattgc 1320
tccagccatc atgccgttca aagtgcagga cctttggaac aggcagcttt ccttccagcc 1380
atagcatcat gtccttttcc cgttccacat cataggtggt ccctttatac cggctgtccg 1440
tcatttttaa atataggttt tcattttctc ccaccagctt atataccttta gcaggagaca 1500
ttccttccgt atcttttacg cagcggtatt tttcgatcag tttttcaat tccggtgata 1560
ttctcatttt agccatttat tatttccttc ctcttttcta cagtatttaa agatacccca 1620
agaagctaat tataacaaga cgaactccaa ttcactgttc cttgcattct aaaaccttaa 1680
ataccagaaa acagcttttt caaagttgtt ttcaaagttg gcgtataaca tagtatcgac 1740
ggagccgatt ttgaaaccgc ggtgatcaca ggcagcaacg ctctgtcatc gttacaatca 1800
acatgctacc ctccgcgaga tcatccgtgt ttcaaacccg gcagcttagt tgccgttctt 1860
ccgaatagca tcggtaacat gagcaaagtc tgccgcctta caacggctct cccgctgacg 1920
ccgtcccgga ctgatgggct gcctgtatcg agtggtgatt ttgtgccgag ctgccggtcg 1980
gggagctgtt ggctggctgg tggcaggata tattgtggtg taaacaaatt gacgcttaga 2040
caacttaata acacattgcg gacgttttta atgtagagct caaagtttaa cgcgttagca 2100
gaaggcatgt tgttgtgact ccgaggggtt gcctcaaact ctatcttata accggcgtgg 2160
aggcatggag gcaggggtat tttggtcatt ttaatagata gtggaaaatg acgtggaatt 2220
tacttaaaga cgaagtcttt gcgacaaggg ggggcccacg ccgaatttaa tattaccggc 2280
gtggcccccc cttatcgcga gtgctttagc acgagcggtc cagatttaaa gtagaaaatt 2340
tcccgcccac tagggttaaa ggtgttcaca ctataaaagc atatacgatg tgatggtatt 2400
tgatggagcg tatattgtat caggtatttc cgttggatac gaattattcg tacgaccctc 2460
ggtaccgatc ggcgcgcgcg gccgcacaga gatttaaata gctccggtga cggacggcgc 2520
gccctatgtc gagctgcagg tcaacggatc aggatattct tgtttaagat gttgaactct 2580
atggaggttt gtatgaactg atgatctagg accggataag ttcccttctt catagcgaac 2640
ttattcaaag aatgttttgt gtatcattct tgttacattg ttattaatga aaaaatatta 2700
ttggtcattg gactgaacac gagtgttaaa tatggaccag gccccaaata agatccattg 2760
atatatgaat taaataacaa gaataaatcg agtcaccaaa ccacttgcct tttttaacga 2820
gacttgttca ccaacttgat acaaaagtca ttatcctatg caaatcaata atcatacaaa 2880

-continued

```
aatatccaat aacactaaaa aattaaaaga aatggataat ttcacaatat gttatacgat   2940
aaagaagtta cttttccaag aaattcactg attttataag cccacttgca ttagataaat   3000
ggcaaaaaaa aacaaaaagg aaaagaaata aagcacgaag aattctagaa aatacgaaat   3060
acgcttcaat gcagtgggac ccacggttca attattgcca attttcagct ccaccgtata   3120
tttaaaaaat aaaacgataa tgctaaaaaa atataaatcg taacgatcgt taaatctcaa   3180
cggctggatc ttatgacgac cgttagaaat tgtggttgtc gacgagtcag taataaacgg   3240
cgtcaaagtg gttgcagccg gcacacacga gtcgtgttta tcaactcaaa gcacaaatac   3300
ttttcctcaa cctaaaaata aggcaattag ccaaaaacaa ctttgcgtgt aaacaacgct   3360
caatacacgt gtcattttat tattagctat tgcttcaccg ccttagcttt ctcgtgacct   3420
agtcgtcctc gtcttttctt cttcttcttc tataaaacaa tacccaaaga gctcttcttc   3480
ttcacaattc agatttcaat ttctcaaaat cttaaaaact ttctctcaat tctctctacc   3540
gtgatcaagg taaatttctg tgttccttat tctctcaaaa tcttcgattt tgttttcgtt   3600
cgatcccaat ttcgtatatg ttctttggtt tagattctgt taatcttaga tcgaacacga   3660
ttttctgggt ttgatcgtta gatatcatct taattctcga ttagggtttc atagatatca   3720
tccgatttgt tcaaataatt tgagttttgt cgaataatta ctcttcgatt tgtgatttct   3780
atctagatct ggtgttagtt tctagtttgt gcgatcgaat ttgtcgatta atctgagttt   3840
ttctgattaa caggcctgca ggatggaaga cgccaaaaac ataaagaaag gcccggcgcc   3900
attctatccg ctggaagatg gaaccgctgg agagcaactg cataaggcta tgaagagata   3960
cgccctggtt cctggaacaa ttgcttttac agatgcacat atcgaggtgg acatcactta   4020
cgctgagtac ttcgaaatgt ccgttcggtt ggcagaagct atgaaacgat atgggctgaa   4080
tacaaatcac agaatcgtcg tatgcagtga aaactctctt caattcttta tgccggtgtt   4140
gggcgcgtta tttatcggag ttgcagttgc gcccgcgaac gacatttata atgaacgtga   4200
attgctcaac agtatgggca tttcgcagcc taccgtggtg ttcgtttcca aaaaggggtt   4260
gcaaaaaatt ttgaacgtgc aaaaaaagct cccaatcatc caaaaaatta ttatcatgga   4320
ttctaaaacg gattaccagg gatttcagtc gatgtacacg ttcgtcacat ctcatctacc   4380
tcccggtttt aatgaatacg attttgtgcc agagtccttc gatagggaca agacaattgc   4440
actgatcatg aactcctctg gatctactgg tctgcctaaa ggtgtcgctc tgcctcatag   4500
aactgcctgc gtgagattct cgcatgccag agatcctatt tttggcaatc aaatcattcc   4560
ggatactgcg attttaagtg ttgttccatt ccatcacggt tttggaatgt ttactacact   4620
cggatatttg atatgtggat ttcgagtcgt cttaatgtat agatttgaag aagagctgtt   4680
tctgaggagc cttcaggatt acaagattca aagtgcgctg ctggtgccaa ccctattctc   4740
cttcttcgcc aaaagcactc tgattgacaa atacgattta tctaatttac acgaaattgc   4800
ttctggtggc gctcccctct ctaaggaagt cggggaagcg gttgccaaga ggttccatct   4860
gccaggtatc aggcaaggat atgggctcac tgagactaca tcagctattc tgattacacc   4920
cgagggggat gataaaccgg gcgcggtcgg taaagttgtt ccattttttg aagcgaaggt   4980
tgtggatctg gataccggga aaacgctggg cgttaatcaa agaggcgaac tgtgtgtgag   5040
aggtcctatg attatgtccg gttatgtaaa caatccggaa gcgaccaacg ccttgattga   5100
caaggatgga tggctacatt ctggagacat agcttactgg gacgaagacg aacacttctt   5160
catcgttgac cgcctgaagt ctctgattaa gtacaaaggc tatcaggtgg ctcccgctga   5220
attggaatcc atcttgctcc aacaccccaa catcttcgac gctggtgtcg caggtcttcc   5280
```

cgacgatgac gccggtgaac ttcccgccgc cgttgttgtt ttggagcacg gaaagacgat 5340
gacggaaaaa gagatcgtgg attacgtcgc cagtcaagta acaaccgcga aaaagttgcg 5400
cggaggagtt gtgtttgtgg acgaagtacc gaaaggtctt accggaaaac tcgacgcaag 5460
aaaaatcaga gagatcctca taaaggccaa gaagggcgga aagatcgccg tgtgactcga 5520
ggttcgagta ttatggcatt gggaaaactg tttttcttgt accatttgtt gtgcttgtaa 5580
tttactgtgt tttttattcg gttttcgcta tcgaactgtg aaatggaaat ggatggagaa 5640
gagttaatga atgatatggt ccttttgttc attctcaaat taatattatt tgttttttct 5700
cttatttgtt gtgtgttgaa tttgaaatta taagagatat gcaaacattt tgttttgagt 5760
aaaaatgtgt caaatcgtgg cctctaatga ccgaagttaa tatgaggagt aaaacacttg 5820
tagttgtgtt agagctcccg gggcgcgccg atatcgagct ctcccggcgc gccagatttg 5880
ccttttcaat ttcagaaaga atgctaaccc acagatggtt agagaggctt acgcagcagg 5940
tatcatcaag acgatctacc cgagcaataa tctccaggaa atcaaatacc ttcccaagaa 6000
ggttaaagat gcagtcaaaa gattcaggac taactgcatc aagaacacag agaaagatat 6060
atttctcaag atcagaagta ctattccagt atggacgatt caaggcttgc ttcacaaacc 6120
aaggcaagta atagagattg gagtctctaa aaaggtagtt cccactgaat caaaggccat 6180
ggagtcaaag attcaaatag aggacctaac agaactcgcc gtaaagactg gcgaacagtt 6240
catacagagt ctcttacgac tcaatgacaa gaagaaaatc ttcgtcaaca tggtggagca 6300
cgacacactt gtctactcca aaaatatcaa agatacagtc tcagaagacc aaagggcaat 6360
tgagactttt caacaaaggg taatatccgg aaacctcctc ggattccatt gcccagctat 6420
ctgtcacttt attgtgaaga tagtggaaaa ggaaggtggc tcctacaaat gccatcattg 6480
cgataaagga aaggccatcg ttgaagatgc ctctgccgac agtggtccca aagatggacc 6540
cccacccacg aggagcatcg tggaaaaaga agacgttcca accacgtctt caaagcaagt 6600
ggattgatgt gatatctcca ctgacgtaag ggatgacgca caatcccact atccttcgca 6660
agacccttcc tctatataag gaagttcatt tcatttggag agaacacggg ggactcctgc 6720
aggatggatc tgcgtctaat tttcggtcca acttgcacag gaaagacgtc gaccgcgata 6780
cgtcttgccc agcagactgg ccttccagtc ctttcgctcg atcgggtcca atgctgtcct 6840
caactgtcaa ccggaagcgg acgaccaaca gtggaagaac tgaaaggaac gacccgtcta 6900
taccttgaag atcggcctct ggtgaagggt atcatcgcag ccaagcaagc tcacgaaagg 6960
ctgatcgggg aagtgtacaa ttatgaggcc cacggcgggc ttattcttga gggaggatct 7020
atctcgttgc tcaggtgcat ggcgcaaagc agttattgga gtaccgattt tcgttggcat 7080
attattcgcc acaagttagc agacgaggag acattcatga acgcggccaa ggccagagtt 7140
aggcagatgt tgcgccctgc tgtaggccca tctattattc aagagttggt tcatctttgg 7200
aatgagcctc ggctgaggcc catactgaaa gagatcgacg gatatcgata tgccatgtta 7260
tttgctagcc agaaccagat cacacccgat atgctattgc agcttgaccc agatatggag 7320
ggtgagttga ttcatggaat cgctcaggag tatctcatcc atgcgcgccg gcaggagcag 7380
gaattccctc cagtgagcgt ggtcgctttc gaaggattcg aaggtccacc gttcggaatg 7440
tgctagctcg agccctagac ttgtccatct tctggattgg ccaagttaat taatgtatga 7500
aataaaagga tgcacacata gtgacatgct aatcactata atgtgggcat caaagttgtg 7560
tgttatgtgt aattactaat tatctgaata agagaaagag atcatccata tttcttatcc 7620
taaatgaatg tcacgtgtct ttataattct ttgatgaacc agatgcattt tattaaccaa 7680
ttccatatac atataaatat taatcatata taattaatat caattgggtt agcaaaacaa 7740
atctagtcta ggtgtgtttt gctaattatt gggggatagt gcaaaaagaa atctacgttc 7800
tcaataattc agatagaaaa cttaataaag tgagataatt tacatagatt gcttttatcc 7860
tttgatatat gtgaaaccat gcatgatata aggaaaatag atagagaaat aattttttac 7920
atcgttgaat atgtaaacaa tttaattcaa gaagctagga atataaatat tgaggagttt 7980
atgattagag ctcagtgttt gatcgccggc ggtaccgagt gtacttcaag tcagtgggaa 8040
atcaataaaa tgattatttt atgaatatat ttcattgtgc aagtagatag aaattacata 8100
tgttacataa cacacgaaat aaacaaaaaa agacaatcca aaaacaaaca ccccaaaaaa 8160
aataatcact ttagataaac tcgtatgagg agaggcacgt tcagtgactc gacgattccc 8220
gagcaaaaaa agtctccccg tcacacatgt agtgggtgac gcaattatct ttaaagtaat 8280
ccttctgttg acttgtcatt gataacatcc agtcttcgtc aggattgcaa agaattatag 8340
aagggatccc accttttatt ttcttctttt ttccatattt agggttgaca gtgaaatcag 8400
actggcaacc tattaattgc ttccacaatg ggacgaactt gaaggggatg tcgtcgatga 8460
tattataggt ggcgtgttca tcgtagttgg tgaaatcgat ggtaccgttc caatagttgt 8520
gtcgtccgag acttctagcc caggtggtct ttccggtacg agttggtccg cagatgtaga 8580
ggctggggtg tcggattcca ttccttccat tgtccttgtt aaatcggcca tccattcaag 8640
gtcagattga gcttgttggt atgagacagg atgtatgtaa gtataagcgt ctatgcttac 8700
atggtataga tgggtttccc tccaggagtg tagatcttcg tggcagcgaa gatctgattc 8760
tgtgaagggc gacacatacg gttcaggttg tggagggaat aatttgttgg ctgaatattc 8820
cagccattga agctttgttg cccattcatg agggaattct tccttgatca tgtcaagata 8880
ttcctcctta gacgttgcag tctggataat agttctccat cgtgcgtcag atttgcgagg 8940
agaaacctta tgatctcgga aatctcctct ggttttaata tctccgtcct ttgatatgta 9000
atcaaggact tgtttagagt ttctagctgg ctggatatta gggtgatttc cttcaaaatc 9060
gaaaaaagaa ggatccctaa tacaaggttt tttatcaagc tggagaagag catgatagtg 9120
ggtagtgcca tcttgatgaa gctcagaagc aacaccaagg aagaaaataa gaaaaggtgt 9180
gagtttctcc cagagaaact ggaataaatc atctctttga gatgagcact tgggataggt 9240
aaggaaaaca tatttagatt ggagtctgaa gttcttacta gcagaaggca tgttgttgtg 9300
actccgaggg gttgcctcaa actctatctt ataaccggcg tggaggcatg gaggcagggg 9360
tattttggtc attttaatag atagtggaaa atgacgtgga atttacttaa agacgaagtc 9420
tttgcgacaa gggggggccc acgccgaatt taatattacc ggcgtggccc cccttatcg 9480
cgagtgcttt agcacgagcg gtccagattt aaagtagaaa atttcccgcc cactagggtt 9540
aaaggtgttc acactataaa agcatatacg atgtgatggt atttgatgga gcgtatattg 9600
tatcaggtat ttccgttgga tacgaattat tcgtacgacc ctcatagttt aaactatcag 9660
tgtttgacag gatatattgg cgggtaaacc taagagaaaa gagcgtttat tagaataacg 9720
gatatttaaa agggcgtgaa aaggtttatc cgttcgtcca tttgtatgtg catgccaacc 9780
acagggttcc cctcgggatc aaagtacttt gatccaaccc ctccgctgct atagtgcagt 9840
cggcttctga cgttcagtgc agccgtcttc tgaaaacgac atgtcgcaca agtcctaagt 9900
tacgcgacag gctgccgccc tgccctttc ctggcgtttt cttgtcgcgt gttttagtcg 9960
cataaagtag aatacttgcg actagaaccg gagacattac gccatgaaca agagcgccgc 10020

-continued

```
cgctggcctg ctgggctatg cccgcgtcag caccgacgac caggacttga ccaaccaacg  10080
ggccgaactg cacgcggccg gctgcaccaa gctgttttcc gagaagatca ccggcaccag  10140
gcgcgaccgc ccggagctgg ccaggatgct tgaccaccta cgccctggcg acgttgtgac  10200
agtgaccagg ctagaccgcc tggcccgcag cacccgcgac ctactggaca ttgccgagcg  10260
catccaggag gccggcgcgg gcctgcgtag cctggcagag ccgtgggccg acaccaccac  10320
gccggccggc cgcatggtgt tgaccgtgtt cgccggcatt gccgagttcg agcgttccct  10380
aatcatcgac cgcacccgga gcgggcgcga ggccgccaag gcccgaggcg tgaagtttgg  10440
cccccgccct accctcaccc cggcacagat cgcgcacgcc cgcgagctga tcgaccagga  10500
aggccgcacc gtgaaagagg cggctgcact gcttggcgtg catcgctcga ccctgtaccg  10560
cgcacttgag cgcagcgagg aagtgacgcc caccgaggcc aggcggcgcg gtgccttccg  10620
tgaggacgca ttgaccgagg ccgacgccct ggcggccgcc gagaatgaac gccaagagga  10680
acaagcatga aaccgcacca ggacggccag gacgaaccgt ttttcattac cgaagagatc  10740
gaggcggaga tgatcgcggc cgggtacgtg ttcgagccgc ccgcgcacgg ctcaaccgtg  10800
cggctgcatg aaatcctggc cggtttgtct gatgccaagc tggcggcctg gccggccagc  10860
ttggccgctg aagaaaccga gcgccgccgt ctaaaaaggt gatgtgtatt tgagtaaaac  10920
agcttgcgtc atgcggtcgc tgcgtatatg atgcgatgag taaataaaca aatacgcaag  10980
gggaacgcat gaaggttatc gctgtactta accagaaagg cgggtcaggc aagacgacca  11040
tcgcaaccca tctagcccgc gccctgcaac tcgccggggc cgatgttctg ttagtcgatt  11100
ccgatcccca gggcagtgcc cgcgattggg cggccgtgcg ggaagatcaa ccgctaaccg  11160
ttgtcggcat cgaccgcccg acgattgacc gcgacgtgaa ggccatcggc cggcgcgact  11220
tcgtagtgat cgacggagcg ccccaggcgg cggacttggc tgtgtccgcg atcaaggcag  11280
ccgacttcgt gctgattccg gtgcagccaa gcccttacga catatgggcc accgccgacc  11340
tggtggagct ggttaagcag cgcattgagg tcacggatgg aaggctacaa gcggcctttg  11400
tcgtgtcgcg ggcgatcaaa ggcacgcgca tcggcggtga ggttgccgag gcgctggccg  11460
ggtacgagct gcccattctt gagtcccgta tcacgcagcg cgtgagctac ccaggcactg  11520
ccgccgccgg cacaaccgtt cttgaatcag aacccgaggg cgacgctgcc cgcgaggtcc  11580
aggcgctggc cgctgaaatt aaatcaaaac tcatttgagt taatgaggta aagagaaaat  11640
gagcaaaagc acaaacacgc taagtgccgg ccgtccgagc gcacgcagca gcaaggctgc  11700
aacgttggcc agcctggcag acacgccagc catgaagcgg gtcaactttc agttgccggc  11760
ggaggatcac accaagctga agatgtacgc ggtacgccaa ggcaagacca ttaccgagct  11820
gctatctgaa tacatcgcgc agctaccaga gtaaatgagc aaatgaataa atgagtagat  11880
gaattttagc ggctaaagga ggcggcatgg aaaatcaaga acaaccaggc accgacgccg  11940
tggaatgccc catgtgtgga ggaacgggcg gttggccagg cgtaagcggc tgggttgtct  12000
gccggccctg caatggcact ggaaccccca agcccgagga atcggcgtga cggtcgcaaa  12060
ccatccggcc cggtacaaat cggcgcggcg ctgggtgatg acctggtgga gaagttgaag  12120
gccgcgcagg ccgcccagcg gcaacgcatc gaggcagaag cacgccccgg tgaatcgtgg  12180
caagcggccg ctgatcgaat ccgcaaagaa tcccggcaac cgccggcagc cggtgcgccg  12240
tcgattagga agccgcccaa gggcgacgag caaccagatt ttttcgttcc gatgctctat  12300
gacgtgggca cccgcgatag tcgcagcatc atggacgtgg ccgttttccg tctgtcgaag  12360
```

-continued

```
cgtgaccgac gagctggcga ggtgatccgc tacgagcttc cagacgggca cgtagaggtt  12420

tccgcagggc cggccggcat ggccagtgtg tgggattacg acctggtact gatggcggtt  12480

tcccatctaa ccgaatccat gaaccgatac cgggaaggga agggagacaa gcccggccgc  12540

gtgttccgtc cacacgttgc ggacgtactc aagttctgcc ggcgagccga tggcggaaag  12600

cagaaagacg acctggtaga aacctgcatt cggttaaaca ccacgcacgt tgccatgcag  12660

cgtacgaaga aggccaagaa cggccgcctg gtgacggtat ccgagggtga agccttgatt  12720

agccgctaca agatcgtaaa gagcgaaacc gggcggccgg agtacatcga gatcgagcta  12780

gctgattgga tgtaccgcga gatcacagaa ggcaagaacc cggacgtgct gacggttcac  12840

cccgattact ttttgatcga tcccggcatc ggccgttttc tctaccgcct ggcacgccgc  12900

gccgcaggca aggcagaagc cagatggttg ttcaagacga tctacgaacg cagtggcagc  12960

gccggagagt tcaagaagtt ctgtttcacc gtgcgcaagc tgatcgggtc aaatgacctg  13020

ccggagtacg atttgaagga ggaggcgggg caggctggcc cgatcctagt catgcgctac  13080

cgcaacctga tcgagggcga agcatccgcc ggttcctaat gtacggagca gatgctaggg  13140

caaattgccc tagcagggga aaaaggtcga aaaggcctct ttcctgtgga tagcacgtac  13200

attgggaacc caaagccgta cattgggaac cggaacccgt acattgggaa cccaaagccg  13260

tacattggga accggtcaca catgtaagtg actgatataa aagagaaaaa aggcgatttt  13320

tccgcctaaa actctttaaa acttattaaa actcttaaaa cccgcctggc ctgtgcataa  13380

ctgtctggcc agcgcacagc cgaagagctg caaaaagcgc ctacccttcg gtcgctgcgc  13440

tccctacgcc ccgccgcttc gcgtcggcct atcgcggccg ctggccgctc aaaaatggct  13500

ggcctacggc caggcaatct accagggcgc ggacaagccg cgccgtcgcc actcgaccgc  13560

cggcgcccac atcaaggcac cctgcctcgc gcgtttcggt gatgacggtg aaaacctctg  13620

acacatgcag ctcccggaaa cggtcacagc ttgtctgtaa gcggatgccg ggagcagaca  13680

agcccgtcag ggcgcgtcag cgggtgttgg cgggtgtcgg ggcgcagcca tgacccagtc  13740

acgtagcgat agcggagtgt atactggctt aactatgcgg catcagagca gattgtactg  13800

agagtgcacc atatgcggtg tgaaataccg cacagatgcg taaggagaaa ataccgcatc  13860

aggcgctctt ccgcttcctc gctcactgac tcgctgcgct cggtcgttcg gctgcggcga  13920

gcggtatcag ctcactcaaa gg                                           13942
```

<210> SEQ ID NO 97
<211> LENGTH: 11836
<212> TYPE: DNA
<213> ORGANISM: artificial
<220> FEATURE:
<223> OTHER INFORMATION: synthetic oligonucleotide

<400> SEQUENCE: 97

```
tcgaggcaga agcacgcccc ggtgaatcgt ggcaagcggc cgctgatcga atccgcaaag     60

aatcccggca accgccggca gccggtgcgc cgtcgattag gaagccgccc aagggcgacg    120

agcaaccaga tttttttcgtt ccgatgctct atgacgtggg cacccgcgat agtcgcagca    180

tcatggacgt ggccgttttc cgtctgtcga agcgtgaccg acgagctggc gaggtgatcc    240

gctacgagct tccagacggg cacgtagagg tttccgcagg gccggccggc atggccagtg    300

tgtgggatta cgacctggta ctgatggcgg tttcccatct aaccgaatcc atgaaccgat    360

accgggaagg gaagggagac aagcccggcc gcgtgttccg tccacacgtt gcggacgtac    420

tcaagttctg ccggcgagcc gatggcggaa agcagaaaga cgacctggta gaaacctgca    480
```

```
ttcggttaaa caccacgcac gttgccatgc agcgtacgaa gaaggccaag aacggccgcc    540

tggtgacggt atccgagggt gaagccttga ttagccgcta caagatcgta aagagcgaaa    600

ccgggcggcc ggagtacatc gagatcgagc tagctgattg gatgtaccgc gagatcacag    660

aaggcaagaa cccggacgtg ctgacggttc accccgatta ctttttgatc gatcccggca    720

tcggccgttt tctctaccgc ctggcacgcc gcgccgcagg caaggcagaa gccagatggt    780

tgttcaagac gatctacgaa cgcagtggca gcgccggaga gttcaagaag ttctgtttca    840

ccgtgcgcaa gctgatcggg tcaaatgacc tgccggagta cgatttgaag gaggaggcgg    900

ggcaggctgg cccgatccta gtcatgcgct accgcaacct gatcgagggc gaagcatccg    960

ccggttccta atgtacggag cagatgctag ggcaaattgc cctagcaggg gaaaaaggtc   1020

gaaaaggcct ctttcctgtg gatagcacgt acattgggaa cccaaagccg tacattggga   1080

accggaaccc gtacattggg aacccaaagc cgtacattgg gaaccggtca cacatgtaag   1140

tgactgatat aaaagagaaa aaaggcgatt tttccgccta aaactcttta aaacttatta   1200

aaactcttaa aacccgcctg gcctgtgcat aactgtctgg ccagcgcaca gccgaagagc   1260

tgcaaaaagc gcctaccctt cggtcgctgc gctccctacg ccccgccgct tcgcgtcggc   1320

ctatcgcggc cgctggccgc tcaaaaatgg ctggcctacg gccaggcaat ctaccagggc   1380

gcggacaagc cgcgccgtcg ccactcgacc gccggcgccc acatcaaggc accctgcctc   1440

gcgcgtttcg gtgatgacgg tgaaaacctc tgacacatgc agctcccgga aacggtcaca   1500

gcttgtctgt aagcggatgc cgggagcaga caagcccgtc agggcgcgtc agcgggtgtt   1560

ggcgggtgtc ggggcgcagc catgacccag tcacgtagcg atagcggagt gtatactggc   1620

ttaactatgc ggcatcagag cagattgtac tgagagtgca ccatatgcgg tgtgaaatac   1680

cgcacagatg cgtaaggaga aaataccgca tcaggcgctc ttccgcttcc tcgctcactg   1740

actcgctgcg ctcggtcgtt cggctgcggc gagcggtatc agctcactca aaggcggtaa   1800

tacggttatc cacagaatca ggggataacg caggaaagaa catgtgagca aaaggccagc   1860

aaaaggccag gaaccgtaaa aaggccgcgt tgctggcgtt tttccatagg ctccgccccc   1920

ctgacgagca tcacaaaaat cgacgctcaa gtcagaggtg gcgaaacccg acaggactat   1980

aaagatacca ggcgtttccc cctggaagct ccctcgtgcg ctctcctgtt ccgaccctgc   2040

cgcttaccgg atacctgtcc gcctttctcc cttcgggaag cgtggcgctt tctcatagct   2100

cacgctgtag gtatctcagt tcggtgtagg tcgttcgctc caagctgggc tgtgtgcacg   2160

aaccccccgt tcagcccgac cgctgcgcct tatccggtaa ctatcgtctt gagtccaacc   2220

cggtaagaca cgacttatcg ccactggcag cagccactgg taacaggatt agcagagcga   2280

ggtatgtagg cggtgctaca gagttcttga agtggtggcc taactacggc tacactagaa   2340

ggacagtatt tggtatctgc gctctgctga agccagttac cttcggaaaa agagttggta   2400

gctcttgatc cggcaaacaa accaccgctg gtagcggtgg tttttttgtt tgcaagcagc   2460

agattacgcg cagaaaaaaa ggatctcaag aagatccttt gatcttttct acggggtctg   2520

acgctcagtg gaacgaaaac tcacgttaag ggattttggt catgcattct aggtactaaa   2580

acaattcatc cagtaaaata taatatttta ttttctccca atcaggcttg atccccagta   2640

agtcaaaaaa tagctcgaca tactgttctt ccccgatatc ctccctgatc gaccggacgc   2700

agaaggcaat gtcataccac ttgtccgccc tgccgcttct cccaagatca ataaagccac   2760

ttactttgcc atctttcaca aagatgttgc tgtctcccag gtcgccgtgg gaaaagacaa   2820
```

-continued

```
gttcctcttc gggcttttcc gtctttaaaa aatcatacag ctcgcgcgga tctttaaatg   2880
gagtgtcttc ttcccagttt tcgcaatcca catcggccag atcgttattc agtaagtaat   2940
ccaattcggc taagcggctg tctaagctat tcgtataggg acaatccgat atgtcgatgg   3000
agtgaaagag cctgatgcac tccgcataca gctcgataat cttttcaggg ctttgttcat   3060
cttcatactc ttccgagcaa aggacgccat cggcctcact catgagcaga ttgctccagc   3120
catcatgccg ttcaaagtgc aggacctttg gaacaggcag ctttccttcc agccatagca   3180
tcatgtcctt ttcccgttcc acatcatagg tggtcccttt ataccggctg tccgtcattt   3240
ttaaatatag gttttcattt tctcccacca gcttatatac cttagcagga gacattcctt   3300
ccgtatcttt tacgcagcgg tatttttcga tcagtttttt caattccggt gatattctca   3360
ttttagccat ttattatttc cttcctcttt tctacagtat ttaaagatac cccaagaagc   3420
taattataac aagacgaact ccaattcact gttccttgca ttctaaaacc ttaaatacca   3480
gaaaacagct ttttcaaagt tgttttcaaa gttggcgtat aacatagtat cgacggagcc   3540
gattttgaaa ccgcggtgat cacaggcagc aacgctctgt catcgttaca atcaacatgc   3600
taccctccgc gagatcatcc gtgtttcaaa cccggcagct tagttgccgt tcttccgaat   3660
agcatcggta acatgagcaa agtctgccgc cttacaacgg ctctcccgct gacgccgtcc   3720
cggactgatg ggctgcctgt atcgagtggt gattttgtgc cgagctgccg gtcggggagc   3780
tgttggctgg ctggtggcag gatatattgt ggtgtaaaca aattgacgct tagacaactt   3840
aataacacat tgcggacgtt tttaatgtag agctcaaagt ttaacgcgtt agcagaaggc   3900
atgttgttgt gactccgagg ggttgcctca aactctatct tataaccggc gtggaggcat   3960
ggaggcaggg gtattttggt cattttaata gatagtggaa aatgacgtgg aatttactta   4020
aagacgaagt ctttgcgaca aggggggggcc cacgccgaat ttaatattac cggcgtggcc   4080
ccccccttatc gcgagtgctt tagcacgagc ggtccagatt taaagtagaa aatttcccgc   4140
ccactagggt taaaggtgtt cacactataa aagcatatac gatgtgatgg tatttgatgg   4200
agcgtatatt gtatcaggta tttccgttgg atacgaatta ttcgtacgac cctcggtacc   4260
gatcggcgcg cgcggccgca cagagattta aatagctccg gtgacggacg gcgcgcccta   4320
tgtcgagctg caggtcaacg gatcaggata ttcttgttta agatgttgaa ctctatggag   4380
gtttgtatga actgatgatc taggaccgga taagttccct tcttcatagc gaacttattc   4440
aaagaatgtt ttgtgtatca ttcttgttac attgttatta atgaaaaaat attattggtc   4500
attggactga acacgagtgt taaatatgga ccaggcccca aataagatcc attgatatat   4560
gaattaaata acaagaataa atcgagtcac caaaccactt gcctttttta acgagacttg   4620
ttcaccaact tgatacaaaa gtcattatcc tatgcaaatc aataatcata caaaaatatc   4680
caataacact aaaaaattaa aagaaatgga taatttcaca atatgttata cgataaagaa   4740
gttacttttc caagaaattc actgatttta taagcccact tgcattagat aaatggcaaa   4800
aaaaaacaaa aaggaaaaga aataaagcac gaagaattct agaaaatacg aaatacgctt   4860
caatgcagtg ggacccacgg ttcaattatt gccaattttc agctccaccg tatatttaaa   4920
aaataaaacg ataatgctaa aaaaatataa atcgtaacga tcgttaaatc tcaacggctg   4980
gatcttatga cgaccgttag aaattgtggt tgtcgacgag tcagtaataa acggcgtcaa   5040
agtggttgca gccggcacac acgagtcgtg tttatcaact caaagcacaa atacttttcc   5100
tcaacctaaa aataaggcaa ttagccaaaa acaactttgc gtgtaaacaa cgctcaatac   5160
acgtgtcatt ttattattag ctattgcttc accgccttag ctttctcgtg acctagtcgt   5220
```

```
cctcgtcttt tcttcttctt cttctataaa acaataccca aagagctctt cttcttcaca   5280
attcagattt caatttctca aaatcttaaa aactttctct caattctctc taccgtgatc   5340
aaggtaaatt tctgtgttcc ttattctctc aaaatcttcg attttgtttt cgttcgatcc   5400
caatttcgta tatgttcttt ggtttagatt ctgttaatct tagatcgaac acgattttct   5460
gggtttgatc gttagatatc atcttaattc tcgattaggg tttcatagat atcatccgat   5520
ttgttcaaat aatttgagtt ttgtcgaata attactcttc gatttgtgat ttctatctag   5580
atctggtgtt agtttctagt ttgtgcgatc gaatttgtcg attaatctga gtttttctga   5640
ttaacaggcc tgcaggatgg aagacgccaa aaacataaag aaaggcccgg cgccattcta   5700
tccgctggaa gatggaaccg ctggagagca actgcataag gctatgaaga gatacgccct   5760
ggttcctgga acaattgctt ttacagatgc acatatcgag gtggacatca cttacgctga   5820
gtacttcgaa atgtccgttc ggttggcaga agctatgaaa cgatatgggc tgaatacaaa   5880
tcacagaatc gtcgtatgca gtgaaaactc tcttcaattc tttatgccgg tgttgggcgc   5940
gttatttatc ggagttgcag ttgcgcccgc gaacgacatt tataatgaac gtgaattgct   6000
caacagtatg ggcatttcgc agcctaccgt ggtgttcgtt tccaaaaagg ggttgcaaaa   6060
aattttgaac gtgcaaaaaa agctcccaat catccaaaaa attattatca tggattctaa   6120
aacggattac cagggatttc agtcgatgta cacgttcgtc acatctcatc tacctcccgg   6180
ttttaatgaa tacgattttg tgccagagtc cttcgatagg gacaagacaa ttgcactgat   6240
catgaactcc tctggatcta ctggtctgcc taaaggtgtc gctctgcctc atagaactgc   6300
ctgcgtgaga ttctcgcatg ccagagatcc tatttttggc aatcaaatca ttccggatac   6360
tgcgatttta agtgttgttc cattccatca cggttttgga atgtttacta cactcggata   6420
tttgatatgt ggatttcgag tcgtcttaat gtatagattt gaagaagagc tgtttctgag   6480
gagccttcag gattacaaga ttcaaagtgc gctgctggtg ccaaccctat tctccttctt   6540
cgccaaaagc actctgattg acaaatacga tttatctaat ttacacgaaa ttgcttctgg   6600
tggcgctccc ctctctaagg aagtcgggga agcggttgcc aagaggttcc atctgccagg   6660
tatcaggcaa ggatatgggc tcactgagac tacatcagct attctgatta cacccgaggg   6720
ggatgataaa ccgggcgcgg tcggtaaagt tgttccattt tttgaagcga aggttgtgga   6780
tctggatacc gggaaaacgc tgggcgttaa tcaaagaggc gaactgtgtg tgagaggtcc   6840
tatgattatg tccggttatg taaacaatcc ggaagcgacc aacgccttga ttgacaagga   6900
tggatggcta cattctggag acatagctta ctgggacgaa gacgaacact tcttcatcgt   6960
tgaccgcctg aagtctctga ttaagtacaa aggctatcag gtggctcccg ctgaattgga   7020
atccatcttg ctccaacacc ccaacatctt cgacgctggt gtcgcaggtc ttcccgacga   7080
tgacgccggt gaacttcccg ccgccgttgt tgttttggag cacggaaaga cgatgacgga   7140
aaaagagatc gtggattacg tcgccagtca agtaacaacc gcgaaaaagt tgcgcggagg   7200
agttgtgttt gtggacgaag taccgaaagg tcttaccgga aaactcgacg caagaaaaat   7260
cagagagatc ctcataaagg ccaagaaggg cggaaagatc gccgtgtgac gtcgacggtt   7320
cgagtattat ggcattggga aaactgtttt tcttgtacca tttgttgtgc ttgtaattta   7380
ctgtgttttt tattcggttt tcgctatcga actgtgaaat ggaaatggat ggagaagagt   7440
taatgaatga tatggtcctt ttgttcattc tcaaattaat attatttgtt ttttctctta   7500
tttgttgtgt gttgaatttg aaattataag agatatgcaa acattttgtt ttgagtaaaa   7560
```

-continued

```
atgtgtcaaa tcgtggcctc taatgaccga agttaatatg aggagtaaaa cacttgtagt    7620
tgtgttagag ctcccggggc gcgccgatat cgagctctcc cggcgcgccg atatcgagct    7680
cagtgtttga tcgccggcgg taccgagtgt acttcaagtc agtgggaaat caataaaatg    7740
attattttat gaatatattt cattgtgcaa gtagatagaa attacatatg ttacataaca    7800
cacgaaataa acaaaaaaag acaatccaaa aacaaacacc ccaaaaaaaa taatcacttt    7860
agataaactc gtatgaggag aggcacgttc agtgactcga cgattcccga gcaaaaaaag    7920
tctccccgtc acacatgtag tgggtgacgc aattatcttt aaagtaatcc ttctgttgac    7980
ttgtcattga taacatccag tcttcgtcag gattgcaaag aattatagaa gggatcccac    8040
cttttatttt cttctttttt ccatatttag ggttgacagt gaaatcagac tggcaaccta    8100
ttaattgctt ccacaatggg acgaacttga aggggatgtc gtcgatgata ttataggtgg    8160
cgtgttcatc gtagttggtg aaatcgatgg taccgttcca atagttgtgt cgtccgagac    8220
ttctagccca ggtggtcttt ccggtacgag ttggtccgca gatgtagagg ctggggtgtc    8280
ggattccatt ccttccattg tccttgttaa atcggccatc cattcaaggt cagattgagc    8340
ttgttggtat gagacaggat gtatgtaagt ataagcgtct atgcttacat ggtatagatg    8400
ggtttccctc caggagtgta gatcttcgtg gcagcgaaga tctgattctg tgaagggcga    8460
cacatacggt tcaggttgtg gagggaataa tttgttggct gaatattcca gccattgaag    8520
ctttgttgcc cattcatgag ggaattcttc cttgatcatg tcaagatatt cctccttaga    8580
cgttgcagtc tggataatag ttctccatcg tgcgtcagat ttgcgaggag aaaccttatg    8640
atctcggaaa tctcctctgg ttttaatatc tccgtccttt gatatgtaat caaggacttg    8700
tttagagttt ctagctggct ggatattagg gtgatttcct tcaaaatcga aaaaagaagg    8760
atccctaata caaggttttt tatcaagctg gagaagagca tgatagtggg tagtgccatc    8820
ttgatgaagc tcagaagcaa caccaaggaa gaaaataaga aaaggtgtga gtttctccca    8880
gagaaactgg aataaatcat ctctttgaga tgagcacttg ggataggtaa ggaaaacata    8940
tttagattgg agtctgaagt tcttactagc agaaggcatg ttgttgtgac tccgaggggt    9000
tgcctcaaac tctatcttat aaccggcgtg gaggcatgga ggcaggggta ttttggtcat    9060
tttaatagat agtggaaaat gacgtggaat ttacttaaag acgaagtctt tgcgacaagg    9120
gggggcccac gccgaattta atattaccgg cgtggccccc ccttatcgcg agtgctttag    9180
cacgagcggt ccagatttaa agtagaaaat ttcccgccca ctagggttaa aggtgttcac    9240
actataaaag catatacgat gtgatggtat ttgatggagc gtatattgta tcaggtattt    9300
ccgttggata cgaattattc gtacgaccct catagtttaa actatcagtg tttgacagga    9360
tatattggcg ggtaaaccta agagaaaaga gcgtttatta gaataacgga tatttaaaag    9420
ggcgtgaaaa ggtttatccg ttcgtccatt tgtatgtgca tgccaaccac agggttcccc    9480
tcgggatcaa agtactttga tccaacccct ccgctgctat agtgcagtcg gcttctgacg    9540
ttcagtgcag ccgtcttctg aaaacgacat gtcgcacaag tcctaagtta cgcgacaggc    9600
tgccgccctg cccttttcct ggcgttttct tgtcgcgtgt tttagtcgca taaagtagaa    9660
tacttgcgac tagaaccgga gacattacgc catgaacaag agcgccgccg ctggcctgct    9720
gggctatgcc cgcgtcagca ccgacgacca ggacttgacc aaccaacggg ccgaactgca    9780
cgcggccggc tgcaccaagc tgttttccga gaagatcacc ggcaccaggc gcgaccgccc    9840
ggagctggcc aggatgcttg accacctacg ccctggcgac gttgtgacag tgaccaggct    9900
agaccgcctg gcccgcagca cccgcgacct actggacatt gccgagcgca tccaggaggc    9960
```

cggcgcgggc ctgcgtagcc tggcagagcc gtgggccgac accaccacgc cggccggccg 10020
catggtgttg accgtgttcg ccggcattgc cgagttcgag cgttccctaa tcatcgaccg 10080
cacccggagc gggcgcgagg ccgccaaggc ccgaggcgtg aagtttggcc cccgccctac 10140
cctcaccccg gcacagatcg cgcacgcccg cgagctgatc gaccaggaag gccgcaccgt 10200
gaaagaggcg gctgcactgc ttggcgtgca tcgctcgacc ctgtaccgcg cacttgagcg 10260
cagcgaggaa gtgacgccca ccgaggccag gcggcgcggt gccttccgtg aggacgcatt 10320
gaccgaggcc gacgccctgg cggccgccga gaatgaacgc caagaggaac aagcatgaaa 10380
ccgcaccagg acggccagga cgaaccgttt ttcattaccg aagagatcga ggcggagatg 10440
atcgcggccg ggtacgtgtt cgagccgccc gcgcacggct caaccgtgcg gctgcatgaa 10500
atcctggccg gtttgtctga tgccaagctg gcggcctggc cggccagctt ggccgctgaa 10560
gaaaccgagc gccgccgtct aaaaaggtga tgtgtatttg agtaaaacag cttgcgtcat 10620
gcggtcgctg cgtatatgat gcgatgagta aataaacaaa tacgcaaggg gaacgcatga 10680
aggttatcgc tgtacttaac cagaaaggcg ggtcaggcaa gacgaccatc gcaacccatc 10740
tagcccgcgc cctgcaactc gccggggccg atgttctgtt agtcgattcc gatccccagg 10800
gcagtgcccg cgattgggcg gccgtgcggg aagatcaacc gctaaccgtt gtcggcatcg 10860
accgcccgac gattgaccgc gacgtgaagg ccatcggccg gcgcgacttc gtagtgatcg 10920
acggagcgcc ccaggcggcg gacttggctg tgtccgcgat caaggcagcc gacttcgtgc 10980
tgattccggt gcagccaagc ccttacgaca tatgggccac cgccgacctg gtggagctgg 11040
ttaagcagcg cattgaggtc acggatggaa ggctacaagc ggcctttgtc gtgtcgcggg 11100
cgatcaaagg cacgcgcatc ggcggtgagg ttgccgaggc gctggccggg tacgagctgc 11160
ccattcttga gtcccgtatc acgcagcgcg tgagctaccc aggcactgcc gccgccggca 11220
caaccgttct tgaatcagaa cccgagggcg acgctgcccg cgaggtccag gcgctggccg 11280
ctgaaattaa atcaaaactc atttgagtta atgaggtaaa gagaaaatga gcaaaagcac 11340
aaacacgcta agtgccggcc gtccgagcgc acgcagcagc aaggctgcaa cgttggccag 11400
cctggcagac acgccagcca tgaagcgggt caactttcag ttgccggcgg aggatcacac 11460
caagctgaag atgtacgcgg tacgccaagg caagaccatt accgagctgc tatctgaata 11520
catcgcgcag ctaccagagt aaatgagcaa atgaataaat gagtagatga attttagcgg 11580
ctaaaggagg cggcatggaa aatcaagaac aaccaggcac cgacgccgtg gaatgcccca 11640
tgtgtggagg aacgggcggt tggccaggcg taagcggctg ggttgtctgc cggccctgca 11700
atggcactgg aacccccaag cccgaggaat cggcgtgacg gtcgcaaacc atccggcccg 11760
gtacaaatcg gcgcggcgct gggtgatgac ctggtggaga agttgaaggc cgcgcaggcc 11820
gcccagcggc aacgca 11836

<210> SEQ ID NO 98
<211> LENGTH: 11812
<212> TYPE: DNA
<213> ORGANISM: artificial
<220> FEATURE:
<223> OTHER INFORMATION: synthetic oligonucleotide

<400> SEQUENCE: 98
ccttttattt tcttcttttt tccatattta gggttgacag tgaaatcaga ctggcaacct 60
attaattgct tccacaatgg gacgaacttg aaggggatgt cgtcgatgat attataggtg 120

-continued

```
gcgtgttcat cgtagttggt gaaatcgatg gtaccgttcc aatagttgtg tcgtccgaga    180
cttctagccc aggtggtctt tccggtacga gttggtccgc agatgtagag gctggggtgt    240
cggattccat tccttccatt gtccttgtta aatcggccat ccattcaagg tcagattgag    300
cttgttggta tgagacagga tgtatgtaag tataagcgtc tatgcttaca tggtatagat    360
gggtttccct ccaggagtgt agatcttcgt ggcagcgaag atctgattct gtgaagggcg    420
acacatacgg ttcaggttgt ggagggaata atttgttggc tgaatattcc agccattgaa    480
gctttgttgc ccattcatga gggaattctt ccttgatcat gtcaagatat tcctccttag    540
acgttgcagt ctggataata gttctccatc gtgcgtcaga tttgcgagga gaaaccttat    600
gatctcggaa atctcctctg gttttaatat ctccgtcctt tgatatgtaa tcaaggactt    660
gtttagagtt tctagctggc tggatattag ggtgatttcc ttcaaaatcg aaaaaagaag    720
gatccctaat acaaggtttt ttatcaagct ggagaagagc atgatagtgg gtagtgccat    780
cttgatgaag ctcagaagca acaccaagga agaaaataag aaaaggtgtg agtttctccc    840
agagaaactg gaataaatca tctctttgag atgagcactt gggataggta aggaaaacat    900
atttagattg gagtctgaag ttcttactag cagaaggcat gttgttgtga ctccgagggg    960
ttgcctcaaa ctctatctta taaccggcgt ggaggcatgg aggcaggggt attttggtca   1020
ttttaataga tagtggaaaa tgacgtggaa tttacttaaa gacgaagtct ttgcgacaag   1080
ggggggccca cgccgaattt aatattaccg gcgtggcccc cccttatcgc gagtgcttta   1140
gcacgagcgg tccagattta aagtagaaaa tttcccgccc actagggtta aaggtgttca   1200
cactataaaa gcatatacga tgtgatggta tttgatggag cgtatattgt atcaggtatt   1260
tccgttggat acgaattatt cgtacgaccc tcatagttta aactatcagt gtttgacagg   1320
atatattggc gggtaaacct aagagaaaag agcgtttatt agaataacgg atatttaaaa   1380
gggcgtgaaa aggtttatcc gttcgtccat ttgtatgtgc atgccaacca caggggttccc   1440
ctcgggatca aagtactttg atccaacccc tccgctgcta tagtgcagtc ggcttctgac   1500
gttcagtgca gccgtcttct gaaaacgaca tgtcgcacaa gtcctaagtt acgcgacagg   1560
ctgccgccct gccctttttcc tggcgttttc ttgtcgcgtg ttttagtcgc ataaagtaga   1620
atacttgcga ctagaaccgg agacattacg ccatgaacaa gagcgccgcc gctggcctgc   1680
tgggctatgc ccgcgtcagc accgacgacc aggacttgac caaccaacgg gccgaactgc   1740
acgcggccgg ctgcaccaag ctgttttccg agaagatcac cggcaccagg cgcgaccgcc   1800
cggagctggc caggatgctt gaccacctac gccctggcga cgttgtgaca gtgaccaggc   1860
tagaccgcct ggcccgcagc acccgcgacc tactggacat tgccgagcgc atccaggagg   1920
ccggcgcggg cctgcgtagc ctggcagagc cgtgggccga caccaccacg ccggccggcc   1980
gcatggtgtt gaccgtgttc gccggcattg ccgagttcga gcgttcccta atcatcgacc   2040
gcacccggag cgggcgcgag gccgccaagg cccgaggcgt gaagtttggc ccccgcccta   2100
ccctcacccc ggcacagatc gcgcacgccc gcgagctgat cgaccaggaa ggccgcaccg   2160
tgaaagaggc ggctgcactg cttggcgtgc atcgctcgac cctgtaccgc gcacttgagc   2220
gcagcgagga agtgacgccc accgaggcca ggcggcgcgg tgccttccgt gaggacgcat   2280
tgaccgaggc cgacgccctg gcggccgccg agaatgaacg ccaagaggaa caagcatgaa   2340
accgcaccag gacggccagg acgaaccgtt tttcattacc gaagagatcg aggcggagat   2400
gatcgcggcc gggtacgtgt tcgagccgcc cgcgcacggc tcaaccgtgc ggctgcatga   2460
aatcctggcc ggtttgtctg atgccaagct ggcggcctgg ccggccagct tggccgctga   2520
```

```
agaaaccgag cgccgccgtc taaaaaggtg atgtgtattt gagtaaaaca gcttgcgtca   2580
tgcggtcgct gcgtatatga tgcgatgagt aaataaacaa atacgcaagg ggaacgcatg   2640
aaggttatcg ctgtacttaa ccagaaaggc gggtcaggca agacgaccat cgcaacccat   2700
ctagcccgcg ccctgcaact cgccggggcc gatgttctgt tagtcgattc cgatccccag   2760
ggcagtgccc gcgattgggc ggccgtgcgg gaagatcaac cgctaaccgt tgtcggcatc   2820
gaccgcccga cgattgaccg cgacgtgaag gccatcggcc ggcgcgactt cgtagtgatc   2880
gacggagcgc cccaggcggc ggacttggct gtgtccgcga tcaaggcagc cgacttcgtg   2940
ctgattccgg tgcagccaag cccttacgac atatgggcca ccgccgacct ggtggagctg   3000
gttaagcagc gcattgaggt cacggatgga aggctacaag cggcctttgt cgtgtcgcgg   3060
gcgatcaaag gcacgcgcat cggcggtgag gttgccgagg cgctggccgg gtacgagctg   3120
cccattcttg agtcccgtat cacgcagcgc gtgagctacc caggcactgc cgccgccggc   3180
acaaccgttc ttgaatcaga acccgagggc gacgctgccc gcgaggtcca ggcgctggcc   3240
gctgaaatta aatcaaaact catttgagtt aatgaggtaa agagaaaatg agcaaaagca   3300
caaacacgct aagtgccggc cgtccgagcg cacgcagcag caaggctgca acgttggcca   3360
gcctggcaga cacgccagcc atgaagcggg tcaactttca gttgccggcg gaggatcaca   3420
ccaagctgaa gatgtacgcg gtacgccaag gcaagaccat taccgagctg ctatctgaat   3480
acatcgcgca gctaccagag taaatgagca aatgaataaa tgagtagatg aattttagcg   3540
gctaaaggag gcggcatgga aaatcaagaa caaccaggca ccgacgccgt ggaatgcccc   3600
atgtgtggag gaacgggcgg ttggccaggc gtaagcggct gggttgtctg ccggccctgc   3660
aatggcactg gaacccccaa gcccgaggaa tcggcgtgac ggtcgcaaac catccggccc   3720
ggtacaaatc ggcgcggcgc tgggtgatga cctggtggag aagttgaagg ccgcgcaggc   3780
cgcccagcgg caacgcatcg aggcagaagc acgccccggt gaatcgtggc aagcggccgc   3840
tgatcgaatc cgcaaagaat cccggcaacc gccggcagcc ggtgcgccgt cgattaggaa   3900
gccgcccaag ggcgacgagc aaccagattt tttcgttccg atgctctatg acgtgggcac   3960
ccgcgatagt cgcagcatca tggacgtggc cgttttccgt ctgtcgaagc gtgaccgacg   4020
agctggcgag gtgatccgct acgagcttcc agacgggcac gtagaggttt ccgcagggcc   4080
ggccggcatg gccagtgtgt gggattacga cctggtactg atggcggttt cccatctaac   4140
cgaatccatg aaccgatacc gggaagggaa gggagacaag cccggccgcg tgttccgtcc   4200
acacgttgcg gacgtactca agttctgccg gcgagccgat ggcggaaagc agaaagacga   4260
cctggtagaa acctgcattc ggttaaacac cacgcacgtt gccatgcagc gtacgaagaa   4320
ggccaagaac ggccgcctgg tgacggtatc cgagggtgaa gccttgatta gccgctacaa   4380
gatcgtaaag agcgaaaccg ggcggccgga gtacatcgag atcgagctag ctgattggat   4440
gtaccgcgag atcacagaag gcaagaaccc ggacgtgctg acggttcacc ccgattactt   4500
tttgatcgat cccggcatcg gccgttttct ctaccgcctg gcacgccgcg ccgcaggcaa   4560
ggcagaagcc agatggttgt tcaagacgat ctacgaacgc agtggcagcg ccggagagtt   4620
caagaagttc tgtttcaccg tgcgcaagct gatcgggtca aatgacctgc cggagtacga   4680
tttgaaggag gaggcggggc aggctggccc gatcctagtc atgcgctacc gcaacctgat   4740
cgagggcgaa gcatccgccg gttcctaatg tacggagcag atgctagggc aaattgccct   4800
agcaggggaa aaaggtcgaa aaggcctctt tcctgtggat agcacgtaca ttgggaaccc   4860
```

-continued

```
aaagccgtac attgggaacc ggaacccgta cattgggaac ccaaagccgt acattgggaa   4920
ccggtcacac atgtaagtga ctgatataaa agagaaaaaa ggcgattttt ccgcctaaaa   4980
ctctttaaaa cttattaaaa ctcttaaaac ccgcctggcc tgtgcataac tgtctggcca   5040
gcgcacagcc gaagagctgc aaaaagcgcc tacccttcgg tcgctgcgct ccctacgccc   5100
cgccgcttcg cgtcggccta tcgcggccgc tggccgctca aaaatggctg gcctacggcc   5160
aggcaatcta ccagggcgcg gacaagccgc gccgtcgcca ctcgaccgcc ggcgcccaca   5220
tcaaggcacc ctgcctcgcg cgtttcggtg atgacggtga aaacctctga cacatgcagc   5280
tcccggaaac ggtcacagct tgtctgtaag cggatgccgg gagcagacaa gcccgtcagg   5340
gcgcgtcagc gggtgttggc gggtgtcggg gcgcagccat gacccagtca cgtagcgata   5400
gcggagtgta tactggctta actatgcggc atcagagcag attgtactga gagtgcacca   5460
tatgcggtgt gaaataccgc acagatgcgt aaggagaaaa taccgcatca ggcgctcttc   5520
cgcttcctcg ctcactgact cgctgcgctc ggtcgttcgg ctgcggcgag cggtatcagc   5580
tcactcaaag gcggtaatac ggttatccac agaatcaggg gataacgcag gaaagaacat   5640
gtgagcaaaa ggccagcaaa aggccaggaa ccgtaaaaag gccgcgttgc tggcgttttt   5700
ccataggctc cgcccccctg acgagcatca caaaaatcga cgctcaagtc agaggtggcg   5760
aaacccgaca ggactataaa gataccaggc gtttccccct ggaagctccc tcgtgcgctc   5820
tcctgttccg accctgccgc ttaccggata cctgtccgcc tttctccctt cgggaagcgt   5880
ggcgctttct catagctcac gctgtaggta tctcagttcg gtgtaggtcg ttcgctccaa   5940
gctgggctgt gtgcacgaac cccccgttca gcccgaccgc tgcgccttat ccggtaacta   6000
tcgtcttgag tccaacccgg taagacacga cttatcgcca ctggcagcag ccactggtaa   6060
caggattagc agagcgaggt atgtaggcgg tgctacagag ttcttgaagt ggtggcctaa   6120
ctacggctac actagaagga cagtatttgg tatctgcgct ctgctgaagc cagttacctt   6180
cggaaaaaga gttggtagct cttgatccgg caaacaaacc accgctggta gcggtggttt   6240
ttttgtttgc aagcagcaga ttacgcgcag aaaaaaagga tctcaagaag atcctttgat   6300
cttttctacg gggtctgacg ctcagtggaa cgaaaactca cgttaaggga ttttggtcat   6360
gcattctagg tactaaaaca attcatccag taaaatataa tattttattt tctcccaatc   6420
aggcttgatc cccagtaagt caaaaaatag ctcgacatac tgttcttccc cgatatcctc   6480
cctgatcgac cggacgcaga aggcaatgtc ataccacttg tccgccctgc cgcttctccc   6540
aagatcaata aagccactta ctttgccatc tttcacaaag atgttgctgt ctcccaggtc   6600
gccgtgggaa aagacaagtt cctcttcggg cttttccgtc tttaaaaaat catacagctc   6660
gcgcggatct ttaaatggag tgtcttcttc ccagttttcg caatccacat cggccagatc   6720
gttattcagt aagtaatcca attcggctaa gcggctgtct aagctattcg tatagggaca   6780
atccgatatg tcgatggagt gaaagagcct gatgcactcc gcatacagct cgataatctt   6840
ttcagggctt tgttcatctt catactcttc cgagcaaagg acgccatcgg cctcactcat   6900
gagcagattg ctccagccat catgccgttc aaagtgcagg acctttggaa caggcagctt   6960
tccttccagc catagcatca tgtccttttc ccgttccaca tcataggtgg tccctttata   7020
ccggctgtcc gtcattttta aatataggtt ttcattttct cccaccagct tatatacctt   7080
agcaggagac attccttccg tatcttttac gcagcggtat ttttcgatca gtttttttcaa  7140
ttccggtgat attctcattt tagccattta ttatttcctt cctcttttct acagtattta   7200
aagatacccc aagaagctaa ttataacaag acgaactcca attcactgtt ccttgcattc   7260
```

taaaacctta aataccagaa aacagctttt tcaaagttgt tttcaaagtt ggcgtataac 7320
atagtatcga cggagccgat tttgaaaccg cggtgatcac aggcagcaac gctctgtcat 7380
cgttacaatc aacatgctac cctccgcgag atcatccgtg tttcaaaccc ggcagcttag 7440
ttgccgttct tccgaatagc atcggtaaca tgagcaaagt ctgccgcctt acaacggctc 7500
tcccgctgac gccgtcccgg actgatgggc tgcctgtatc gagtggtgat tttgtgccga 7560
gctgccggtc ggggagctgt tggctggctg gtggcaggat atattgtggt gtaaacaaat 7620
tgacgcttag acaacttaat aacacattgc ggacgttttt aatgtagagc tcaaagttta 7680
acgcgttagc agaaggcatg ttgttgtgac tccgaggggt tgcctcaaac tctatcttat 7740
aaccggcgtg gaggcatgga ggcaggggta ttttggtcat tttaatagat agtggaaaat 7800
gacgtggaat ttacttaaag acgaagtctt tgcgacaagg gggggcccac gccgaattta 7860
atattaccgg cgtggccccc ccttatcgcg agtgctttag cacgagcggt ccagatttaa 7920
agtagaaaat ttcccgccca ctagggttaa aggtgttcac actataaaag catatacgat 7980
gtgatggtat ttgatggagc gtatattgta tcaggtattt ccgttggata cgaattattc 8040
gtacgaccct cggtaccgat cggcgcgcca gatttgcctt ttcaatttca gaaagaatgc 8100
taacccacag atggttagag aggcttacgc agcaggtatc atcaagacga tctacccgag 8160
caataatctc caggaaatca aataccttcc caagaaggtt aaagatgcag tcaaaagatt 8220
caggactaac tgcatcaaga acacagagaa agatatattt ctcaagatca gaagtactat 8280
tccagtatgg acgattcaag gcttgcttca caaaccaagg caagtaatag agattggagt 8340
ctctaaaaag gtagttccca ctgaatcaaa ggccatggag tcaaagattc aaatagagga 8400
cctaacagaa ctcgccgtaa agactggcga acagttcata cagagtctct tacgactcaa 8460
tgacaagaag aaaatcttcg tcaacatggt ggagcacgac acacttgtct actccaaaaa 8520
tatcaaagat acagtctcag aagaccaaag ggcaattgag acttttcaac aaagggtaat 8580
atccggaaac ctcctcggat tccattgccc agctatctgt cactttattg tgaagatagt 8640
ggaaaaggaa ggtggctcct acaaatgcca tcattgcgat aaaggaaagg ccatcgttga 8700
agatgcctct gccgacagtg gtcccaaaga tggaccccca cccacgagga gcatcgtgga 8760
aaaagaagac gttccaacca cgtcttcaaa gcaagtggat tgatgtgata tctccactga 8820
cgtaagggat gacgcacaat cccactatcc ttcgcaagac ccttcctcta tataaggaag 8880
ttcatttcat ttggagagaa cacgggggac tcctgcagga tggaagacgc caaaaacata 8940
aagaaaggcc cggcgccatt ctatccgctg gaagatggaa ccgctggaga gcaactgcat 9000
aaggctatga agagatacgc cctggttcct ggaacaattg cttttacaga tgcacatatc 9060
gaggtggaca tcacttacgc tgagtacttc gaaatgtccg ttcggttggc agaagctatg 9120
aaacgatatg ggctgaatac aaatcacaga atcgtcgtat gcagtgaaaa ctctcttcaa 9180
ttctttatgc cggtgttggg cgcgttattt atcggagttg cagttgcgcc cgcgaacgac 9240
atttataatg aacgtgaatt gctcaacagt atgggcattt cgcagcctac cgtggtgttc 9300
gtttccaaaa aggggttgca aaaaattttg aacgtgcaaa aaaagctccc aatcatccaa 9360
aaaattatta tcatggattc taaaacggat taccagggat ttcagtcgat gtacacgttc 9420
gtcacatctc atctacctcc cggttttaat gaatacgatt ttgtgccaga gtccttcgat 9480
agggacaaga caattgcact gatcatgaac tcctctggat ctactggtct gcctaaaggt 9540
gtcgctctgc ctcatagaac tgcctgcgtg agattctcgc atgccagaga tcctattttt 9600

-continued

```
ggcaatcaaa tcattccgga tactgcgatt ttaagtgttg ttccattcca tcacggtttt   9660
ggaatgttta ctacactcgg atatttgata tgtggatttc gagtcgtctt aatgtataga   9720
tttgaagaag agctgtttct gaggagcctt caggattaca agattcaaag tgcgctgctg   9780
gtgccaaccc tattctcctt cttcgccaaa agcactctga ttgacaaata cgatttatct   9840
aatttacacg aaattgcttc tggtggcgct cccctctcta aggaagtcgg ggaagcggtt   9900
gccaagaggt tccatctgcc aggtatcagg caaggatatg ggctcactga gactacatca   9960
gctattctga ttacacccga gggggatgat aaaccgggcg cggtcggtaa agttgttcca  10020
tttttgaag cgaaggttgt ggatctggat accgggaaaa cgctgggcgt taatcaaaga  10080
ggcgaactgt gtgtgagagg tcctatgatt atgtccggtt atgtaaacaa tccggaagcg  10140
accaacgcct tgattgacaa ggatggatgg ctacattctg gagacatagc ttactgggac  10200
gaagacgaac acttcttcat cgttgaccgc ctgaagtctc tgattaagta caaaggctat  10260
caggtggctc ccgctgaatt ggaatccatc ttgctccaac accccaacat cttcgacgct  10320
ggtgtcgcag gtcttcccga cgatgacgcc ggtgaacttc ccgccgccgt tgttgttttg  10380
gagcacggaa agacgatgac ggaaaaagag atcgtggatt acgtcgccag tcaagtaaca  10440
accgcgaaaa agttgcgcgg aggagttgtg tttgtggacg aagtaccgaa aggtcttacc  10500
ggaaaactcg acgcaagaaa aatcagagag atcctcataa aggccaagaa gggcggaaag  10560
atcgccgtgt gacgtcgacg atatgaagat gaagatgaaa tatttggtgt gtcaaataaa  10620
aagcttgtgt gcttaagttt gtgttttttt cttggcttgt tgtgttatga atttgtggct  10680
ttttctaata ttaaatgaat gtaagatcac attataatga ataaacaaat gtttctataa  10740
tccattgtga atgttttgtt ggatctcttc tgcagcatat aactactgta tgtgctatgg  10800
tatggactat ggaatatgat taaagataag ccagagctct ggtgacggac ccatggcttc  10860
gttgaacaac ggaaactcga cttgccttcc gcacaataca tcatttcttc ttagcttttt  10920
ttcttcttct tcgttcatac agtttttttt tgtttatcag cttacatttt cttgaaccgt  10980
agctttcgtt ttcttctttt taactttcca ttcggagttt ttgtatcttg tttcatagtt  11040
tgtcccagga ttagaatgat taggcatcga accttcaaga atttgattga ataaaacatc  11100
ttcattctta agatatgaag ataatcttca aaaggcccct gggaatctga aagaagagaa  11160
gcaggcccat ttatatggga aagaacaata gtatttctta tataggccca tttaagttga  11220
aaacaatctt caaaagtccc acatcgctta gataagaaaa cgaagctgag tttatataca  11280
gctagagtcg aagtagtgat tgttggtagt agcgactcca tggttttaga gctagaaata  11340
gcaagttaaa ataaggctag tccgttatca acttgaaaaa gtggcaccga gtcggtgctt  11400
tttttcccgg ggcgcgccga tatcgagctc tcccggcgcg ccgatatcga gctcagtgtt  11460
tgatcgccgg cggtaccgag tgtacttcaa gtcagtggga aatcaataaa atgattattt  11520
tatgaatata tttcattgtg caagtagata gaaattacat atgttacata acacacgaaa  11580
taaacaaaaa aagacaatcc aaaaacaaac accccaaaaa aaataatcac tttagataaa  11640
ctcgtatgag gagaggcacg ttcagtgact cgacgattcc cgagcaaaaa aagtctcccc  11700
gtcacacatg tagtgggtga cgcaattatc tttaaagtaa tccttctgtt gacttgtcat  11760
tgataacatc cagtcttcgt caggattgca aagaattata gaagggatcc ca          11812
```

<210> SEQ ID NO 99
<211> LENGTH: 62
<212> TYPE: DNA
<213> ORGANISM: Nicotiana benthamiana

<400> SEQUENCE: 99
ggaatttgtt atgttttggt agtagcgact ccatggggca taagtttaga attcgtactc 60
cc 62

<210> SEQ ID NO 100
<211> LENGTH: 61
<212> TYPE: DNA
<213> ORGANISM: artificial
<220> FEATURE:
<223> OTHER INFORMATION: synthetic oligonucleotide

<400> SEQUENCE: 100
ggaatttgtt atgttttggt agtagcgact catggggcat aagtttagaa ttcgtactcc 60
c 61

<210> SEQ ID NO 101
<211> LENGTH: 52
<212> TYPE: DNA
<213> ORGANISM: artificial
<220> FEATURE:
<223> OTHER INFORMATION: synthetic oligonucleotide

<400> SEQUENCE: 101
ggaatttgtt atgttttggt agatggggca taagtttaga attcgtactc cc 52

<210> SEQ ID NO 102
<211> LENGTH: 33
<212> TYPE: DNA
<213> ORGANISM: artificial
<220> FEATURE:
<223> OTHER INFORMATION: synthetic oligonucleotide

<400> SEQUENCE: 102
ggaatttgtt atgttttggt agtagcgact ccc 33

<210> SEQ ID NO 103
<211> LENGTH: 59
<212> TYPE: DNA
<213> ORGANISM: artificial
<220> FEATURE:
<223> OTHER INFORMATION: synthetic oligonucleotide

<400> SEQUENCE: 103
ggaatttgtt atgttttggt agtagcgaca tggggcataa gtttagaatt cgtactccc 59

<210> SEQ ID NO 104
<211> LENGTH: 59
<212> TYPE: DNA
<213> ORGANISM: artificial
<220> FEATURE:
<223> OTHER INFORMATION: synthetic oligonucleotide

<400> SEQUENCE: 104
ggaatttgtt atgttttggt agtagcgaca tggggcataa gtttagaatt cgtactccc 59

<210> SEQ ID NO 105
<211> LENGTH: 63
<212> TYPE: DNA
<213> ORGANISM: artificial
<220> FEATURE:
<223> OTHER INFORMATION: synthetic oligonucleotide

<400> SEQUENCE: 105
ggaatttgtt atgttttggt agtagcgact cccatggggc ataagtttag aattcgtact 60
ccc 63

<210> SEQ ID NO 106
<211> LENGTH: 58
<212> TYPE: DNA
<213> ORGANISM: artificial
<220> FEATURE:
<223> OTHER INFORMATION: synthetic oligonucleotide

<400> SEQUENCE: 106
ggaatttgtt atgttttggt agtagcgaat ggggcataag tttagaattc gtactccc 58

<210> SEQ ID NO 107
<211> LENGTH: 56
<212> TYPE: DNA
<213> ORGANISM: artificial
<220> FEATURE:
<223> OTHER INFORMATION: synthetic oligonucleotide

<400> SEQUENCE: 107
ggaatttgtt atgttttggt agtagcatgg ggcataagtt tagaattcgt actccc 56

<210> SEQ ID NO 108
<211> LENGTH: 33
<212> TYPE: DNA
<213> ORGANISM: artificial
<220> FEATURE:
<223> OTHER INFORMATION: synthetic oligonucleotide

<400> SEQUENCE: 108
ggaatttgtt atgttttggt agtagcgact ccc 33

<210> SEQ ID NO 109
<211> LENGTH: 50
<212> TYPE: DNA
<213> ORGANISM: artificial
<220> FEATURE:
<223> OTHER INFORMATION: synthetic oligonucleotide

<400> SEQUENCE: 109
ggaatttgtt atgttttggt atggggcata agtttagaat tcgtactccc 50

<210> SEQ ID NO 110
<211> LENGTH: 53
<212> TYPE: DNA
<213> ORGANISM: artificial
<220> FEATURE:
<223> OTHER INFORMATION: synthetic oligonucleotide

<400> SEQUENCE: 110
ggaatttgtt atgttttggt agtatggggc ataagtttag aattcgtact ccc 53

<210> SEQ ID NO 111
<211> LENGTH: 55
<212> TYPE: DNA
<213> ORGANISM: artificial
<220> FEATURE:
<223> OTHER INFORMATION: synthetic oligonucleotide

<400> SEQUENCE: 111
ggaatttgtt atgttttggt agtagatggg gcataagttt agaattcgta ctccc 55

<210> SEQ ID NO 112
<211> LENGTH: 51

<212> TYPE: DNA
<213> ORGANISM: artificial
<220> FEATURE:
<223> OTHER INFORMATION: synthetic oligonucleotide

<400> SEQUENCE: 112
ggaatttgtt atgttttggt agtagggcat aagtttagaa ttcgtactcc c 51

<210> SEQ ID NO 113
<211> LENGTH: 30
<212> TYPE: DNA
<213> ORGANISM: artificial
<220> FEATURE:
<223> OTHER INFORMATION: synthetic oligonucleotide

<400> SEQUENCE: 113
atggggcata agtttagaat tcgtactccc 30

<210> SEQ ID NO 114
<211> LENGTH: 40
<212> TYPE: DNA
<213> ORGANISM: Nicotiana benthamiana

<400> SEQUENCE: 114
ggaatttgtt atgttttggt agtagcgact ccatggggca 40

<210> SEQ ID NO 115
<211> LENGTH: 41
<212> TYPE: DNA
<213> ORGANISM: artificial
<220> FEATURE:
<223> OTHER INFORMATION: synthetic oligonucleotide

<400> SEQUENCE: 115
ggaatttgtt atgttttggt agtagcgact cccatggggc a 41

<210> SEQ ID NO 116
<211> LENGTH: 38
<212> TYPE: DNA
<213> ORGANISM: artificial
<220> FEATURE:
<223> OTHER INFORMATION: synthetic oligonucleotide

<400> SEQUENCE: 116
ggaatttgtt atgttttggt agtagcgacc atggggca 38

<210> SEQ ID NO 117
<211> LENGTH: 39
<212> TYPE: DNA
<213> ORGANISM: artificial
<220> FEATURE:
<223> OTHER INFORMATION: synthetic oligonucleotide

<400> SEQUENCE: 117
ggaatttgtt atgttttggt agtagcgact catggggca 39

<210> SEQ ID NO 118
<211> LENGTH: 302
<212> TYPE: PRT
<213> ORGANISM: Zea maize

<400> SEQUENCE: 118

Met Ala Ala Asn Ala Gly Gly Gly Gly Ala Gly Gly Gly Ser Gly Ser
1 5 10 15

Gly Ser Val Ala Ala Pro Ala Val Cys Arg Pro Ser Gly Ser Arg Trp

```
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Pro Ser Gly Ala Ala
        115                 120                 125

Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190

Ile Met Ala Ala Ala Ala Ala Arg Ala Ala Thr Thr Arg Ala Pro Glu
        195                 200                 205

Thr Leu Pro Leu Phe Pro Thr Cys Gly Asp Asp Gly Gly Ser Gly Ser
    210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
            260                 265                 270

Gln Asp Val Ser Ala Thr Ala Ala Ala Ala Ala Ala Leu Glu Leu Ser
        275                 280                 285

Leu Ser Ser Trp Cys Ser Pro Tyr Pro Ala Ala Gly Ser Met
    290                 295                 300


<210> SEQ ID NO 119
<211> LENGTH: 382
<212> TYPE: PRT
<213> ORGANISM: Arabidopsis thaliana

<400> SEQUENCE: 119

Met Glu Ser Gly Ser Asn Ser Thr Ser Cys Pro Met Ala Phe Ala Gly
1               5                   10                  15

Asp Asn Ser Asp Gly Pro Met Cys Pro Met Met Met Met Met Pro Pro
            20                  25                  30

Ile Met Thr Ser His Gln His His Gly His Asp His Gln His Gln Gln
        35                  40                  45

Gln Glu His Asp Gly Tyr Ala Tyr Gln Ser His His Gln Gln Ser Ser
    50                  55                  60

Ser Leu Phe Leu Gln Ser Leu Ala Pro Pro Gln Gly Thr Lys Asn Lys
65                  70                  75                  80

Val Ala Ser Ser Ser Ser Pro Ser Ser Cys Ala Pro Ala Tyr Ser Leu
                85                  90                  95
```

```
Met Glu Ile His His Asn Glu Ile Val Ala Gly Gly Ile Asn Pro Cys
            100                 105                 110

Ser Ser Ser Ser Ser Ser Ala Ser Val Lys Ala Lys Ile Met Ala His
        115                 120                 125

Pro His Tyr His Arg Leu Leu Ala Ala Tyr Val Asn Cys Gln Lys Val
    130                 135                 140

Gly Ala Pro Pro Glu Val Val Ala Arg Leu Glu Glu Ala Cys Ser Ser
145                 150                 155                 160

Ala Ala Ala Ala Ala Ala Ser Met Gly Pro Thr Gly Cys Leu Gly Glu
                165                 170                 175

Asp Pro Gly Leu Asp Gln Phe Met Glu Ala Tyr Cys Glu Met Leu Val
            180                 185                 190

Lys Tyr Glu Gln Glu Leu Ser Lys Pro Phe Lys Glu Ala Met Val Phe
        195                 200                 205

Leu Gln Arg Val Glu Cys Gln Phe Lys Ser Leu Ser Leu Ser Ser Pro
    210                 215                 220

Ser Ser Phe Ser Gly Tyr Gly Glu Thr Ala Ile Asp Arg Asn Asn Asn
225                 230                 235                 240

Gly Ser Ser Glu Glu Glu Val Asp Met Asn Asn Glu Phe Val Asp Pro
                245                 250                 255

Gln Ala Glu Asp Arg Glu Leu Lys Gly Gln Leu Leu Arg Lys Tyr Ser
            260                 265                 270

Gly Tyr Leu Gly Ser Leu Lys Gln Glu Phe Met Lys Lys Arg Lys Lys
        275                 280                 285

Gly Lys Leu Pro Lys Glu Ala Arg Gln Gln Leu Leu Asp Trp Trp Ser
    290                 295                 300

Arg His Tyr Lys Trp Pro Tyr Pro Ser Glu Gln Gln Lys Leu Ala Leu
305                 310                 315                 320

Ala Glu Ser Thr Gly Leu Asp Gln Lys Gln Ile Asn Asn Trp Phe Ile
                325                 330                 335

Asn Gln Arg Lys Arg His Trp Lys Pro Ser Glu Asp Met Gln Phe Val
            340                 345                 350

Val Met Asp Ala Thr His Pro His His Tyr Phe Met Asp Asn Val Leu
        355                 360                 365

Gly Asn Pro Phe Pro Met Asp His Ile Ser Ser Thr Met Leu
    370                 375                 380


<210> SEQ ID NO 120
<211> LENGTH: 794
<212> TYPE: PRT
<213> ORGANISM: Arabidopsis thaliana

<400> SEQUENCE: 120

Met Met Ala Ser Leu Ser Cys Val Glu Asp Lys Met Lys Thr Ser Cys
1               5                   10                  15

Leu Val Asn Gly Gly Gly Thr Ile Thr Thr Thr Thr Ser Gln Ser Thr
            20                  25                  30

Leu Leu Glu Glu Met Lys Leu Leu Lys Asp Gln Ser Gly Thr Arg Lys
        35                  40                  45

Pro Val Ile Asn Ser Glu Leu Trp His Ala Cys Ala Gly Pro Leu Val
    50                  55                  60

Cys Leu Pro Gln Val Gly Ser Leu Val Tyr Tyr Phe Ser Gln Gly His
65                  70                  75                  80

Ser Glu Gln Val Ala Val Ser Thr Arg Arg Ser Ala Thr Thr Gln Val
                85                  90                  95
```

-continued

```
Pro Asn Tyr Pro Asn Leu Pro Ser Gln Leu Met Cys Gln Val His Asn
            100                 105                 110

Val Thr Leu His Ala Asp Lys Asp Ser Asp Glu Ile Tyr Ala Gln Met
        115                 120                 125

Ser Leu Gln Pro Val His Ser Glu Arg Asp Val Phe Pro Val Pro Asp
    130                 135                 140

Phe Gly Met Leu Arg Gly Ser Lys His Pro Thr Glu Phe Phe Cys Lys
145                 150                 155                 160

Thr Leu Thr Ala Ser Asp Thr Ser Thr His Gly Gly Phe Ser Val Pro
                165                 170                 175

Arg Arg Ala Ala Glu Lys Leu Phe Pro Pro Leu Asp Tyr Ser Ala Gln
            180                 185                 190

Pro Pro Thr Gln Glu Leu Val Val Arg Asp Leu His Glu Asn Thr Trp
        195                 200                 205

Thr Phe Arg His Ile Tyr Arg Gly Gln Pro Lys Arg His Leu Leu Thr
    210                 215                 220

Thr Gly Trp Ser Leu Phe Val Gly Ser Lys Arg Leu Arg Ala Gly Asp
225                 230                 235                 240

Ser Val Leu Phe Ile Arg Asp Glu Lys Ser Gln Leu Met Val Gly Val
                245                 250                 255

Arg Arg Ala Asn Arg Gln Gln Thr Ala Leu Pro Ser Ser Val Leu Ser
            260                 265                 270

Ala Asp Ser Met His Ile Gly Val Leu Ala Ala Ala Ala His Ala Thr
        275                 280                 285

Ala Asn Arg Thr Pro Phe Leu Ile Phe Tyr Asn Pro Arg Ala Cys Pro
    290                 295                 300

Ala Glu Phe Val Ile Pro Leu Ala Lys Tyr Arg Lys Ala Ile Cys Gly
305                 310                 315                 320

Ser Gln Leu Ser Val Gly Met Arg Phe Gly Met Met Phe Glu Thr Glu
                325                 330                 335

Asp Ser Gly Lys Arg Arg Tyr Met Gly Thr Ile Val Gly Ile Ser Asp
            340                 345                 350

Leu Asp Pro Leu Arg Trp Pro Gly Ser Lys Trp Arg Asn Leu Gln Val
        355                 360                 365

Glu Trp Asp Glu Pro Gly Cys Asn Asp Lys Pro Thr Arg Val Ser Pro
    370                 375                 380

Trp Asp Ile Glu Thr Pro Glu Ser Leu Phe Ile Phe Pro Ser Leu Thr
385                 390                 395                 400

Ser Gly Leu Lys Arg Gln Leu His Pro Ser Tyr Phe Ala Gly Glu Thr
                405                 410                 415

Glu Trp Gly Ser Leu Ile Lys Arg Pro Leu Ile Arg Val Pro Asp Ser
            420                 425                 430

Ala Asn Gly Ile Met Pro Tyr Ala Ser Phe Pro Ser Met Ala Ser Glu
        435                 440                 445

Gln Leu Met Lys Met Met Met Arg Pro His Asn Asn Gln Asn Val Pro
    450                 455                 460

Ser Phe Met Ser Glu Met Gln Gln Asn Ile Val Met Gly Asn Gly Gly
465                 470                 475                 480

Leu Leu Gly Asp Met Lys Met Gln Gln Pro Leu Met Met Asn Gln Lys
                485                 490                 495

Ser Glu Met Val Gln Pro Gln Asn Lys Leu Thr Val Asn Pro Ser Ala
            500                 505                 510
```

```
Ser Asn Thr Ser Gly Gln Glu Gln Asn Leu Ser Gln Ser Met Ser Ala
        515                 520                 525

Pro Ala Lys Pro Glu Asn Ser Thr Leu Ser Gly Cys Ser Ser Gly Arg
    530                 535                 540

Val Gln His Gly Leu Glu Gln Ser Met Glu Gln Ala Ser Gln Val Thr
545                 550                 555                 560

Thr Ser Thr Val Cys Asn Glu Glu Lys Val Asn Gln Leu Leu Gln Lys
                565                 570                 575

Pro Gly Ala Ser Ser Pro Val Gln Ala Asp Gln Cys Leu Asp Ile Thr
            580                 585                 590

His Gln Ile Tyr Gln Pro Gln Ser Asp Pro Ile Asn Gly Phe Ser Phe
        595                 600                 605

Leu Glu Thr Asp Glu Leu Thr Ser Gln Val Ser Ser Phe Gln Ser Leu
    610                 615                 620

Ala Gly Ser Tyr Lys Gln Pro Phe Ile Leu Ser Ser Gln Asp Ser Ser
625                 630                 635                 640

Ala Val Val Leu Pro Asp Ser Thr Asn Ser Pro Leu Phe His Asp Val
                645                 650                 655

Trp Asp Thr Gln Leu Asn Gly Leu Lys Phe Asp Gln Phe Ser Pro Leu
            660                 665                 670

Met Gln Gln Asp Leu Tyr Ala Ser Gln Asn Ile Cys Met Ser Asn Ser
        675                 680                 685

Thr Thr Ser Asn Ile Leu Asp Pro Pro Leu Ser Asn Thr Val Leu Asp
    690                 695                 700

Asp Phe Cys Ala Ile Lys Asp Thr Asp Phe Gln Asn His Pro Ser Gly
705                 710                 715                 720

Cys Leu Val Gly Asn Asn Asn Thr Ser Phe Ala Gln Asp Val Gln Ser
                725                 730                 735

Gln Ile Thr Ser Ala Ser Phe Ala Asp Ser Gln Ala Phe Ser Arg Gln
            740                 745                 750

Asp Phe Pro Asp Asn Ser Gly Gly Thr Gly Thr Ser Ser Ser Asn Val
        755                 760                 765

Asp Phe Asp Asp Cys Ser Leu Arg Gln Asn Ser Lys Gly Ser Ser Trp
    770                 775                 780

Gln Lys Ile Ala Thr Pro Arg Val Arg Thr
785                 790


<210> SEQ ID NO 121
<211> LENGTH: 584
<212> TYPE: PRT
<213> ORGANISM: Arabidopsis thaliana

<400> SEQUENCE: 121

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Asn Glu Gln Asn Gly
                85                  90                  95
```

```
Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
        115                 120                 125

Gly Gly Gly Gly Ser Leu Gly Leu Ser Met Ile Lys Thr Trp Leu Ser
    130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Leu Ser Glu Tyr Glu Lys Glu Val Glu Glu Met Lys
        275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Ser Ala Val Thr Asn
        355                 360                 365

Phe Asp Met Asn Arg Tyr Asn Val Lys Ala Ile Leu Glu Ser Pro Ser
    370                 375                 380

Leu Pro Ile Gly Ser Ser Ala Lys Arg Leu Lys Asp Val Asn Asn Pro
385                 390                 395                 400

Val Pro Ala Met Met Ile Ser Asn Asn Val Ser Glu Ser Ala Asn Asn
                405                 410                 415

Val Ser Gly Trp Gln Asn Thr Ala Phe Gln His His Gln Gly Met Asp
            420                 425                 430

Leu Ser Leu Leu Gln Gln Gln Gln Glu Arg Tyr Val Gly Tyr Tyr Asn
        435                 440                 445

Gly Gly Asn Leu Ser Thr Glu Ser Thr Arg Val Cys Phe Lys Gln Glu
    450                 455                 460

Glu Glu Gln Gln His Phe Leu Arg Asn Ser Pro Ser His Met Thr Asn
465                 470                 475                 480

Val Asp His His Ser Ser Thr Ser Asp Asp Ser Val Thr Val Cys Gly
                485                 490                 495

Asn Val Val Ser Tyr Gly Gly Tyr Gln Gly Phe Ala Ile Pro Val Gly
            500                 505                 510
```

-continued

```
Thr Ser Val Asn Tyr Asp Pro Phe Thr Ala Ala Glu Ile Ala Tyr Asn
        515                 520                 525

Ala Arg Asn His Tyr Tyr Tyr Ala Gln His Gln Gln Gln Gln Gln Ile
    530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Gly Glu Gly Ala Pro
                565                 570                 575

Thr Phe Ser Val Trp Asn Asp Thr
            580


<210> SEQ ID NO 122
<211> LENGTH: 240
<212> TYPE: PRT
<213> ORGANISM: Agrobacterium tumefaciens

<400> SEQUENCE: 122

Met Asp Leu Arg Leu Ile Phe Gly Pro Thr Cys Thr Gly Lys Thr Ser
1               5                   10                  15

Thr Ala Ile Arg Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Glu Asp Arg
    50                  55                  60

Pro Leu Val Lys Gly Ile Ile Ala Ala Lys Gln Ala His Glu Arg Leu
65                  70                  75                  80

Ile Gly Glu Val Tyr Asn Tyr Glu Ala His Gly Gly Leu Ile Leu Glu
                85                  90                  95

Gly Gly Ser Ile Ser Leu Leu Arg Cys Met Ala Gln Ser Ser Tyr Trp
            100                 105                 110

Ser Thr Asp Phe Arg Trp His Ile Ile Arg His Lys Leu Ala Asp Glu
        115                 120                 125

Glu Thr Phe Met Asn Ala Ala Lys Ala Arg Val Arg Gln Met Leu Arg
    130                 135                 140

Pro Ala Val Gly Pro Ser Ile Ile Gln Glu Leu Val His Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Pro Asp Met Leu Leu
            180                 185                 190

Gln Leu Asp Pro Asp Met Glu Gly Glu Leu Ile His Gly Ile Ala Gln
        195                 200                 205

Glu Tyr Leu Ile His Ala Arg Arg Gln Glu Gln Glu Phe Pro Pro Val
    210                 215                 220

Ser Val Val Ala Phe Glu Gly Phe Glu Gly Pro Pro Phe Gly Met Cys
225                 230                 235                 240
```

DELIVERY OF DEVELOPMENTAL REGULATORS TO PLANTS FOR THE INDUCTION OF MERISTEMATIC TISSUE WITH GENETIC ALTERATIONS

CROSS-REFERENCE TO RELATED APPLICATIONS

This application is a National Stage application under 35 U.S.C. § 371 of International Application No. PCT/US2019/039297 having an International Filing Date of Jun. 26, 2019, which claims priority from U.S. Provisional Application Ser. No. 62/690,165, filed Jun. 26, 2018. The disclosure of the prior applications are considered part of (and are incorporated by reference in) the disclosure of this application.

STATEMENT OF FEDERALLY SPONSORED RESEARCH

This invention was made with government support under IOS-1339209 awarded by the National Science Foundation. The government has certain rights in the invention.

TECHNICAL FIELD

This document relates to materials and methods for inducing genetic alterations in meristematic plant tissue.

BACKGROUND

The ability to generate plants with a desired genetic makeup, whether commercially or for basic research, is limited by two facets—the delivery of genetic engineering (GE) reagents and the subsequent generation of edited tissues. Procedures for delivery of GE reagents typically utilize the gene transferring bacterium *Agrobacterium tumefaciens*, or physical means such as particle bombardment. After delivery of reagents, many protocols require subsequent regeneration of the edited somatic tissue into whole plants. Transformed somatic tissue often is pushed to de-differentiate (into callus) and then re-differentiate using tissue culture media containing specific hormone ratios required to drive shoot or root formation. Tissue culture techniques can be complicated by the fact that a majority of agriculturally relevant crop lines are recalcitrant to tissue culture regeneration. Additionally, this process can be time consuming and technically demanding, requires sterile conditions, and may be subject to undesired genetic alterations due to prolonged exposure to hormones. Efforts also may be confounded because resulting tissues can present non-specific chimerism for the transgene, requiring more than one generation to fix the genetic event of interest. All of these limitations render current practices for plant genetic engineering non-ideal for large scale generation of edited plants in a high throughput manner.

Developmental regulatory genes have been employed to generate tissues with modifications of interest. For example, controlled expression of the maize regulatory genes WUSCHEL (WUS) and BABY BOOM (BBM) induced somatic embryogenesis from immature maize embryos, as well as other somatic tissues (Lowe et al., *Plant Cell* 28(9):1998-2015, 2016; and Mookkan et al., *Plant Cell Reports* 36(9): 1477-1491, 2017). Hundreds of plantlets were recovered from these somatic embryos even in lines previously recalcitrant to tissue culture, and the generated somatic embryos were capable of developing into full plants with the transgene cassette of interest. Despite this improvement to standard monocot regeneration practices, however, the generation of full plants still required tissue culture steps, sterile technique, and explant handling. In addition, these techniques were only demonstrated in monocot species and have not been implemented in any dicot species.

SUMMARY

This document provides new techniques that avoid the constraints noted above and provide a boon for both basic research and commercial germplasm production. The combination of developmental regulators WUS and SHOOT MERISTEMLESS (STM), as well as other regulator combinations, can have an impact on patterning and formation of shoot meristems (Gallois et al., *Development* 129:3207-3217, 2002), and these developmental regulators have been ectopically expressed in *Arabidopsis thaliana* and other species to create meristem-like tissue. The methods described herein are based, at least in part, on the discovery that such genes can be combined with GE reagents to promote the formation of edited meristematic tissue that can flower and produce seed. The resultant seed is derived from a single meristematic cell, and therefore represents a clonal genetic editing event that provides an abundance of edited seed after one generation. The direct delivery method described herein also provides the advantage of avoiding tissue culture, which reduces the time needed to regenerate tissues and considerably simplifies the process of generating GE events. Thus, the methods described herein can circumvent the limitations of current plant regeneration protocols, and greatly enhance the potential for development of GE plant lines for both commercial use and basic research.

Thus, this document is based, at least in part, on the development of methods for delivery of developmental regulators to whole plants to induce the transdifferentiation of somatic plant cells in vivo for the production of meristems. These meristems can carry transgenic insertions or genetic editing events to the next generation, creating seed with a GE event of interest in a fraction of the time needed using current standard protocols. The techniques described herein can simplify protocols for transformation, remove requirements for tissue culture, and be accessible to labs with diverse skill sets.

In a first aspect, this document features a method for generating plant tissue having one or more genetic modifications of interest. The method can include (a) introducing into plant cells (i) nucleic acid encoding one or more developmental regulators that, when expressed in the plant cells, induce meristem formation from the plant cells, and (ii) nucleic acid comprising one or more sequences that, when expressed, modify a plant cell to achieve one or more genetic modifications of interest; and (b) deriving de novo tissue from plant cells identified as having the one or more genetic modifications of interest. The one or more developmental regulators can include one or more of Baby Boom, Isopentenyl Transferase, Irrepressible Variants of Monopteros, Shoot Meristemless, and Wuschel. The introducing can be by *Agrobacterium*, and the nucleic acid encoding one or more developmental regulators and the nucleic acid comprising one or more sequences that modify a plant cell can be included on the same T-DNA or on separate T-DNAs. The method can include introducing nucleic acid encoding two or more developmental regulators into the plant cells by *Agrobacterium*, where the two or more developmental regulators are encoded by a single T-DNA or are encoded by separate T-DNAs. The method can include introducing nucleic acid encoding two or more developmental regulators into the plant cells by *Agrobacterium*, where the two or more developmental regulators are encoded by two or more strains of *Agrobacterium*. The introducing can include electroporation, biolistics, particle bombardment, chemical transfection, nanoparticle delivery, or viral infection. The introducing can include transient transformation or stable transgenesis. The plant cells into which the nucleic acids are introduced can be within a differentiated tissue, within an undifferentiated tissue, within a whole plant, within a germinating seedling, or within a plant part taken from a plant. The plant cells can be cells of a monocotyledonous plant, or cells of a dicotyledonous plant. The one or more sequences that modify a plant cell can include a transgene that, when expressed in the plant cells, achieves an agriculturally relevant trait (e.g., herbicide tolerance). The one or more sequences that modify a plant cell can include a transgene that, when expressed, edits the plant DNA. For example, the one or more sequences that modify a plant cell can include a nucleotide sequence encoding a targeted endonuclease (e.g., a meganuclease, zinc finger nuclease, transcription activator-like effector nuclease, or Clustered Regularly-Interspaced Short Palindromic Repeats-associated nuclease). The one or more sequences that modify a plant cell can encode a targeted enzyme that modifies plant DNA (e.g., a cytosine deaminase or an adenosine deaminase, such as BE3 or ABE). The one or more sequences that modify a plant cell can encode a targeted endonuclease and can include a repair template to introduce one or more specific modifications into the plant genome. The de novo tissue can be meristematic and can be capable of deriving new tissue carrying the one or more genetic modifications of interest. The new tissue can include a branch, a flower, or a root.

In some cases, the method can include (a) using *Agrobacterium*, introducing into cells of a germinating seedling or a portion thereof nucleic acid encoding the one or more developmental regulators, wherein expression of the one or more developmental regulators induces meristem formation in the germinating seedling or portion thereof; (b) introducing into the cells, via the *Agrobacterium*, the nucleic acid comprising one or more sequences that, when expressed, modify the cells to achieve the one or more genetic modifications of interest; and (c) culturing the meristem induced by the one or more developmental regulators, to obtain modified plant tissue comprising the one or more genetic modifications of interest. The method can include introducing nucleic acid encoding two or more developmental regulators, wherein the two or more developmental regulators are encoded by one T-DNA or by separate T-DNAs. The method can include introducing nucleic acid encoding two or more developmental regulators, where the two or more developmental regulators are encoded by separate strains of *Agrobacterium*. The germinating seedling or portion thereof can be from a monocotyledonous plant or from a dicotyledonous plant. The one or more genetic modifications can include insertion of a transgene that, when expressed, achieves an agriculturally relevant trait (e.g., herbicide tolerance). The one or more genetic modifications can include insertion of a transgene that, when expressed, edits the plant cell DNA. The nucleic acid that modifies a plant cell can encode a targeted endonuclease (e.g., a meganuclease, zinc finger nuclease, transcription activator-like effector nuclease, or Clustered Regularly-Interspaced Short Palindromic Repeats-associated nuclease). The nucleic acid that modifies a plant cell can encode a targeted enzyme that modifies plant DNA (e.g., a cytosine deaminase or an adenosine deaminase, such as BE3 or ABE). The nucleic acid that modifies a plant cell can encode a targeted endonuclease and can include a repair template to introduce a specific modification into the genetic material of the plant cell. The method can further include assaying the meristem induced by the one or more developmental regulators for the one or more genetic modifications of interest, and subsequently generating a whole plant from the meristem induced by the one or more developmental regulators. The method also can include placing the meristem induced by the one or more developmental regulators directly into culture and inducing the meristem in culture to form a plant.

In another aspect, this document features a method for generating plant tissue containing one or more genetic modifications of interest. The method can include (a) using *Agrobacterium*, introducing into cells of a germinating seedling or a portion thereof nucleic acid encoding one or more developmental regulators, wherein expression of the one or more developmental regulators induces meristem formation in the germinating seedling or portion thereof; (b) simultaneously introducing into the cells, via the *Agrobacterium*, nucleic acid that modifies genetic material within the cells to achieve one or more targeted genetic modifications of interest; and (c) culturing the meristem induced by the one or more developmental regulators, to obtain modified plant tissue containing the one or more genetic modifications of interest. The one or more developmental regulators can include, for example, one or more of Baby Boom, Isopentenyl Transferase, Irrepressible Variants of Monopteros, Shoot Meristemless, and Wuschel. The method can include introducing two or more developmental regulators into cells of the germinating seedling or portion thereof, where the two or more developmental regulators are encoded by one T-DNA, or where the two or more developmental regulators are encoded on separate T-DNAs. The method can include introducing two or more developmental regulators into cells of the germinating seedling or portion thereof, where the two or more developmental regulators are encoded by two or more strains of *Agrobacterium.*

The germinating seedling or portion thereof can be from a monocotyledonous plant or from a dicotyledonous plant. The one or more targeted genetic modifications can include insertion of a transgene that, when expressed, achieves an agriculturally relevant trait (e.g., herbicide tolerance). The one or more targeted genetic modifications can include insertion of a transgene that, when expressed, edits the plant cell DNA. The nucleic acid that modifies a plant cell can encode a targeted endonuclease, such as a meganuclease, zinc finger nuclease (ZFN), transcription activator-like effector (TALE) nuclease, or clustered regularly-interspaced short palindromic repeats (CRISPR)/CRISPR associated (Cas) nuclease. The nucleic acid that modifies a plant cell can encode a targeted enzyme that modifies plant DNA. The targeted enzyme can be a cytosine deaminase or an adenosine deaminase (e.g., BE3 or ABE). The nucleic acid that modifies a plant cell can encode a targeted endonuclease and can contain a repair template to introduce a specific modification into the genetic material of the plant cell. The method can further include assaying meristem induced by the one or more developmental regulators for the one or more genetic modifications of interest, and subsequently generating a whole plant from the meristem induced by the one or more developmental regulators. The method can further include placing the meristem induced by the one or more developmental regulators directly into culture and inducing the meristem in culture to form a plant.

In another aspect, this document features a method for generating plant tissue containing one or more genetic modifications of interest. The method can include (a) introducing into plant cells (i) nucleic acid encoding one or more developmental regulators that, when expressed in the plant cells, induce meristem formation from the plant cells, and (ii) nucleic acid comprising one or more sequences that modify a plant cell to achieve one or more genetic modifications of interest; and (b) deriving de novo tissue from plant cells identified as having the one or more genetic modifications of interest. The one or more developmental regulators can include one or more of Baby Boom, Isopentenyl Transferase, Irrepressible Variants of Monopteros, Shoot Meristemless, and Wuschel. The introducing can be by *Agrobacterium*, and the nucleic acid encoding one or more developmental regulators and the nucleic acid comprising one or more sequences that modify a plant cell can be included on the same T-DNA. Alternatively, the nucleic acid encoding one or more developmental regulators and the nucleic acid comprising one or more sequences that modify a plant cell can be included on separate T-DNAs. The method can include introducing nucleic acid encoding two or more developmental regulators into the plant cells by *Agrobacterium*, where the two or more developmental regulators are encoded by a single T-DNA, or where the two or more developmental regulators are encoded by separate T-DNAs. The method can include introducing nucleic acid encoding two or more developmental regulators into the plant cells by *Agrobacterium*, where the two or more developmental regulators are encoded by two or more strains of *Agrobacterium*. The introducing can include electroporation, nanoparticle delivery, biolistics, particle bombardment, chemical transfection, or viral infection. The method can include transient delivery of the one or more developmental regulators or stable integration of genes encoding the one or more developmental regulators into the plant genome by any of the above means of delivery.

The plant cells into which the nucleic acids are introduced can be within a differentiated tissue, or within an undifferentiated tissue. The plant cells into which the nucleic acids are introduced can be within a whole plant, or within a plant part taken from a plant. The plant cells can be of a monocotyledonous plant or a dicotyledonous plant.

The one or more sequences that modify a plant cell can include a transgene that, when expressed in the plant cells, achieves an agriculturally relevant trait (e.g., herbicide tolerance). The one or more sequences that modify a plant cell can include a transgene that, when expressed, edits the plant DNA. The one or more sequences that modify a plant cell can include a nucleotide sequence encoding a targeted endonuclease, such as a meganuclease, ZFN, TALE nuclease, or CRISPR/Cas nuclease. The one or more sequences that modify a plant cell can encode a targeted enzyme that modifies plant DNA (e.g., a cytosine deaminase or an adenosine deaminase, such as BE3 or ABE). The one or more sequences that modify a plant cell can encode a targeted endonuclease and can include a repair template to introduce one or more specific modifications into the plant genome. The de novo tissue can be meristematic and capable of deriving new tissue carrying the one or more genetic modifications of interest. The new tissue can include a branch, a flower, or a root.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A, 2B, 2C, and 2D are representative of induced de novo growth observed for multiple plants. FIGS. 2E and 2F are images providing visual confirmation that in some cases, newly formed tissues contained the reporter gene, as evidenced by imaging in bright field (FIG. 2E) and bioluminescence (FIG. 2F).

FIGS. 3A to 3G show the results of molecular analyses to assess the delivery of developmental regulators and editing of de novo tissue. *Agrobacterium* was used to deliver a T-DNA containing sequences encoding developmental regulators, a luciferase reporter gene, and a guide RNA (gRNA) targeting an endogenous site in the genome of *N. benthamiana* plants transgenic for 35S:Cas9. The *Agrobacterium* solution was delivered to somatic tissues by injection (FIGS. 3C and 3F; injection sites are indicated by boxes). Sample tissues were harvested at distal sites of tissue generated from the injection sites (FIGS. 3C and 3F; harvest sites are indicated by circles). Tissue samples were treated with luciferin and imaged for bioluminescence (FIGS. 3A and 3D, bright field; FIGS. 3B and 3E, luminescence). Genomic DNA was isolated from the harvested tissue by cetyl trimethylammonium bromide (CTAB) extraction, and the genomic region targeted by the gRNA was amplified by PCR and subjected to NcoI endonuclease digestion prior to electrophoresis (FIG. 3G). The Cas9 endonuclease could induce mutations to destroy the NcoI site at the gRNA target. Thus, the WT "un-edited" genomic sequence produced a lower molecular weight band upon NcoI digestion (FIG. 3G, solid arrow), while undigested "edited" DNA produces a higher molecular weight band (dashed arrow). Samples 114-2 and 155-1 showed complete cutting (lanes 3 and 5) and therefore do not have induced mutations. Samples 114-1 and 115-2

(lanes 1 and 7) demonstrated incomplete cutting by NcoI, denoting gRNA-induced mutations. The positive control (Pos) was obtained by leaf infiltration followed by leaf DNA isolation 7 days post infection.

Figure 4C:
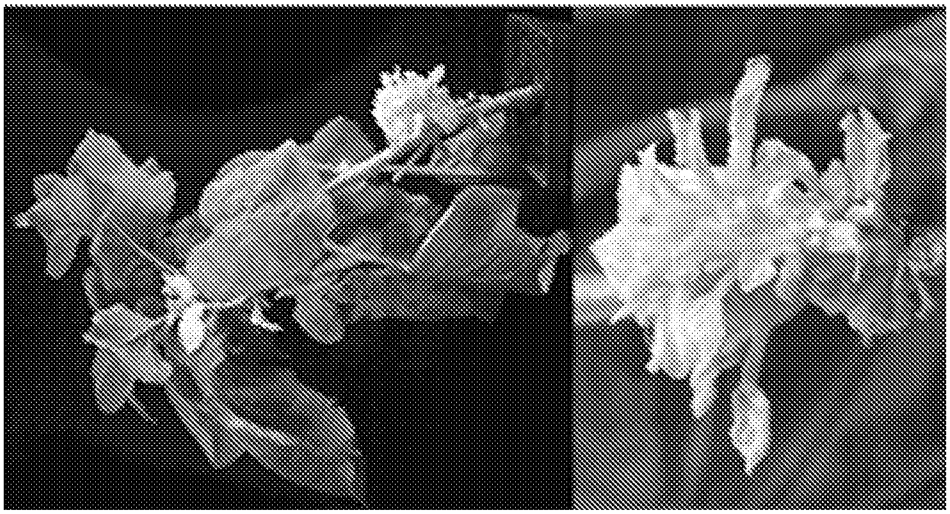
Figure 4B:
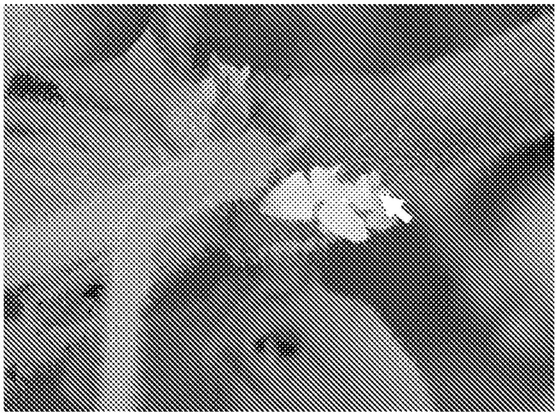
Figure 4A:
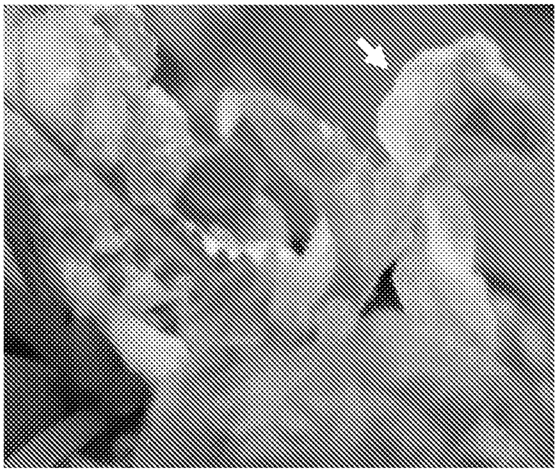
Figure 4D:
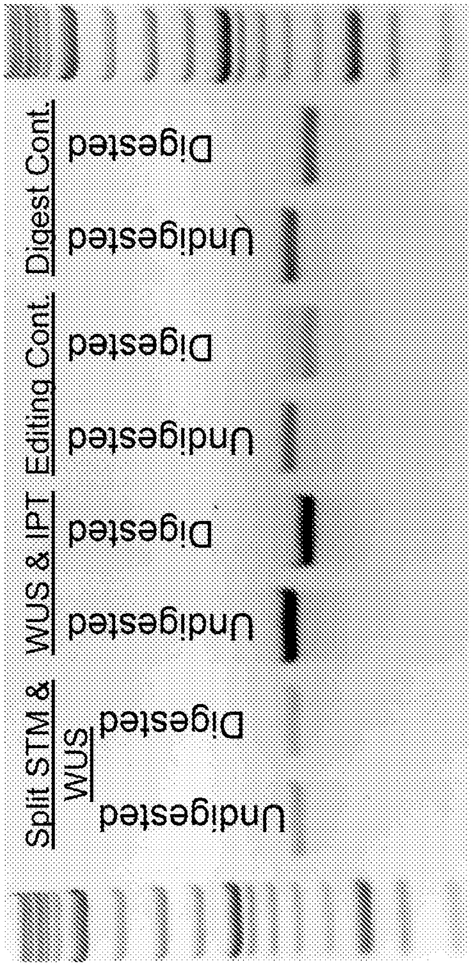
Figure 4E:
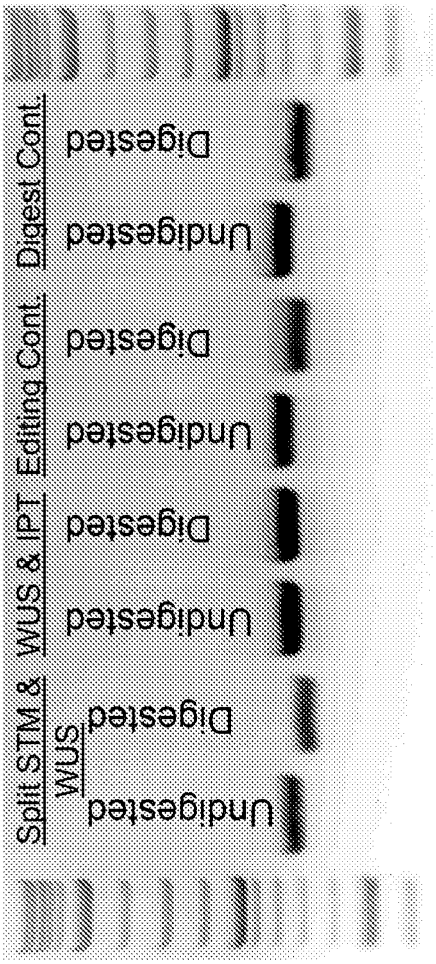

FIGS. 4A to 4G show that edited shoots are discernable by phenotype due to targeted editing. Transgenic *N. benthamiana* plants expressing 35S:Cas9 were exposed to developmental regulators to induce de novo tissue formation. The developmental regulators were delivered either as a coinfection of *Agrobacterium* strains containing WUS or STM on separate T-DNA vectors (FIG. 4A) or as a single T-DNA vector containing WUS and IPT (FIG. 4B). All vectors included a gRNA targeting both NbPDS homologs present in the genome (SEQ ID NOS:16 and 17). A PDS knock-out phenotype was observed as white sectoring (FIG. 4A) or as completely white de novo meristems (FIGS. 4B and 4C) formed from the injection site. To molecularly characterize targeted mutation of both PDS homologs, genomic DNA was isolated from select tissues (white arrows), and was amplified by PCR and visualized for induced mutations at the gRNA target sites. As two homologs of the NbPDS gene exist in the *N. benthamiana* genome, primers were used that selectively amplify either homolog 1 (Niben101Scf14708g00023.1; FIG. 4D) or homolog 2 (Niben101Scf01283g02002.1; FIG. 4E). Incomplete digestion of PCR amplicons by the restriction enzyme NcoI denoted a mutation within the restriction recognition site. Amplification of Scf14708g00023.1 provided a band of 712 bp, while a NcoI digested band was visible at 648 bp. Amplification of Scf01283g02002.1 provided a band of 755 bp, and a corresponding cleaved 691 bp band after NcoI digest. Tissue samples assayed for the split vector system were completely modified at the Scf14708g00023.1 locus as observed by undigested restriction bands in the digest assay (FIG. 4D, lane 2), but appeared unedited (completely digested) at the Scf01283g02002.1 locus (FIG. 4E, lane 2). This pattern was reversed for the combination vector. Positive control ("Editing Cont.") was acquired by infiltrating vectors into leaf tissue and harvesting DNA 7 days post infection, and was expected to demonstrate chimerism (both cleaved and uncleaved bands; FIGS. 4D and 4E, lane 6). Negative control ("Digest Cont.") utilized genomic DNA isolated from an uninoculated plant (FIGS. 4D and 4E, lane 8). While restriction digest assays did not show editing for some samples (FIG. 4D, lane 4; FIG. 4E, lane 2), Illumina sequencing performed on genomic amplifications of Scf14708g00023.1 validated the presence of genomic edits when WUS or STM were delivered on separate T-DNA vectors (FIG. 4F; from top to bottom, SEQ ID NOS:38, 39, 40, and 38) or when WUS and IPT were delivered via a single T-DNA vector (FIG. 4G; from top to bottom, SEQ ID NOS:38, 40, and 39). The frequency of edits inferred the tissues present were non-chimeric as compared to negative controls. In addition, edits that could not be visualized by restriction digest were confirmed as edited for both alleles of both homologs of PDS (targeted mutations involved a 'C' insertion that did not destroy the CCATGG NcoI site).

FIGS. 5A and 5B further demonstrate the ability to create targeted mutations in the *N. benthamiana* PDS2 locus (SEQ ID NO:17). Constructs introduced included a single vector containing WUS and STM (WUS/STM, SEQ ID NO:30) a single vector containing WUS and IPT (WUS/IPT; SEQ ID NO:31) a combination of co-inoculated vectors each containing a single DR (STM, IPT, WUS, MPA, and BBM; SEQ ID NOS:33, 34, 35, 36, and 37, respectively). FIG. 5A is a table providing results from these studies. Derived shoots were given individual designators to facilitate tracking of samples (FIG. 5A, column 2). Purified genomic DNA was amplified for the PDS2 locus. Amplicons were pooled and submitted for next generation sequencing. The observed number of sequences containing the expected forward and reverse barcodes (column 3), the number of sequences observed to have non-specific DNA insertions at the sgRNA target site (column 4), the number of sequences observed to have targeted mutations at the sgRNA target site (column 5), and the total number of sequences that were observed to have targeted modifications (column 6) are provided. Mutations observed at a frequency >30% of the total are denoted in column 7. "Seed produced" (column 8) indicates whether sampled shoots were identified that produced seed. It was observed that one sample (5-14-1-08) produced seed capable of transmitting genomic modifications to the next generation. FIG. 5B shows the sequences of mutations observed by next generation sequencing for plants listed in FIG. 5A.

Figure 6:
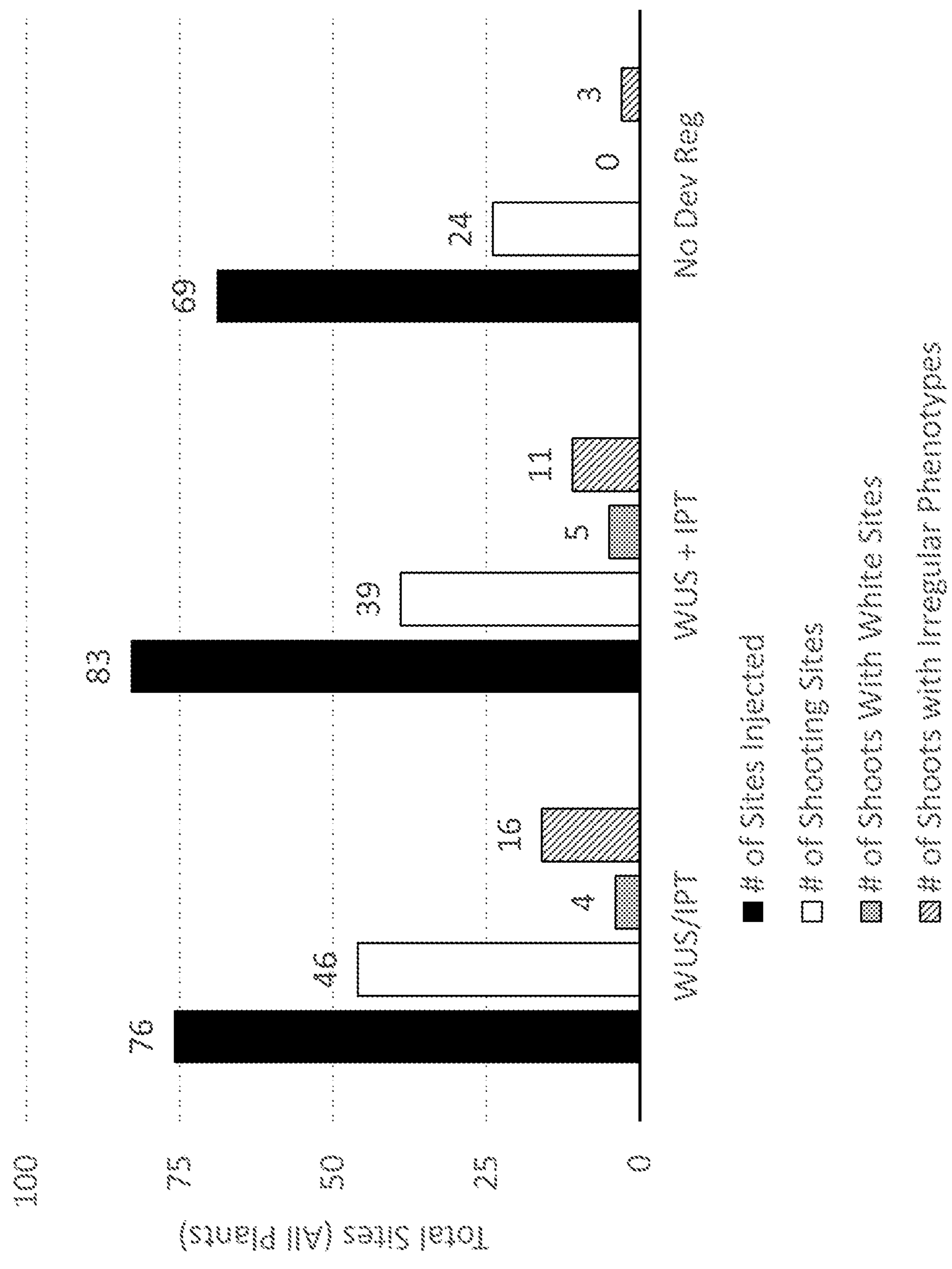

FIG. 6 is a graph plotting results from an injection study in *N. benthamiana*. Constructs introduced included WUS and IPT as either a single vector (WUS/IPT; SEQ ID NO:31), or a combination of co-inoculated vectors each containing a single DR (SEQ ID NOS:34 and 35), or a vector containing editing reagents but no DRs (No Dev Reg, SEQ ID NO:98). The total number of sites injected, as well as the number of shooting sites, was monitored across all plants within each group. Groups were additionally observed for the number of shoots with distorted morphology, likely induced by developmental regulators, and photobleaching due to simultaneous targeted mutations in both PDS homologs.

Figure 7:
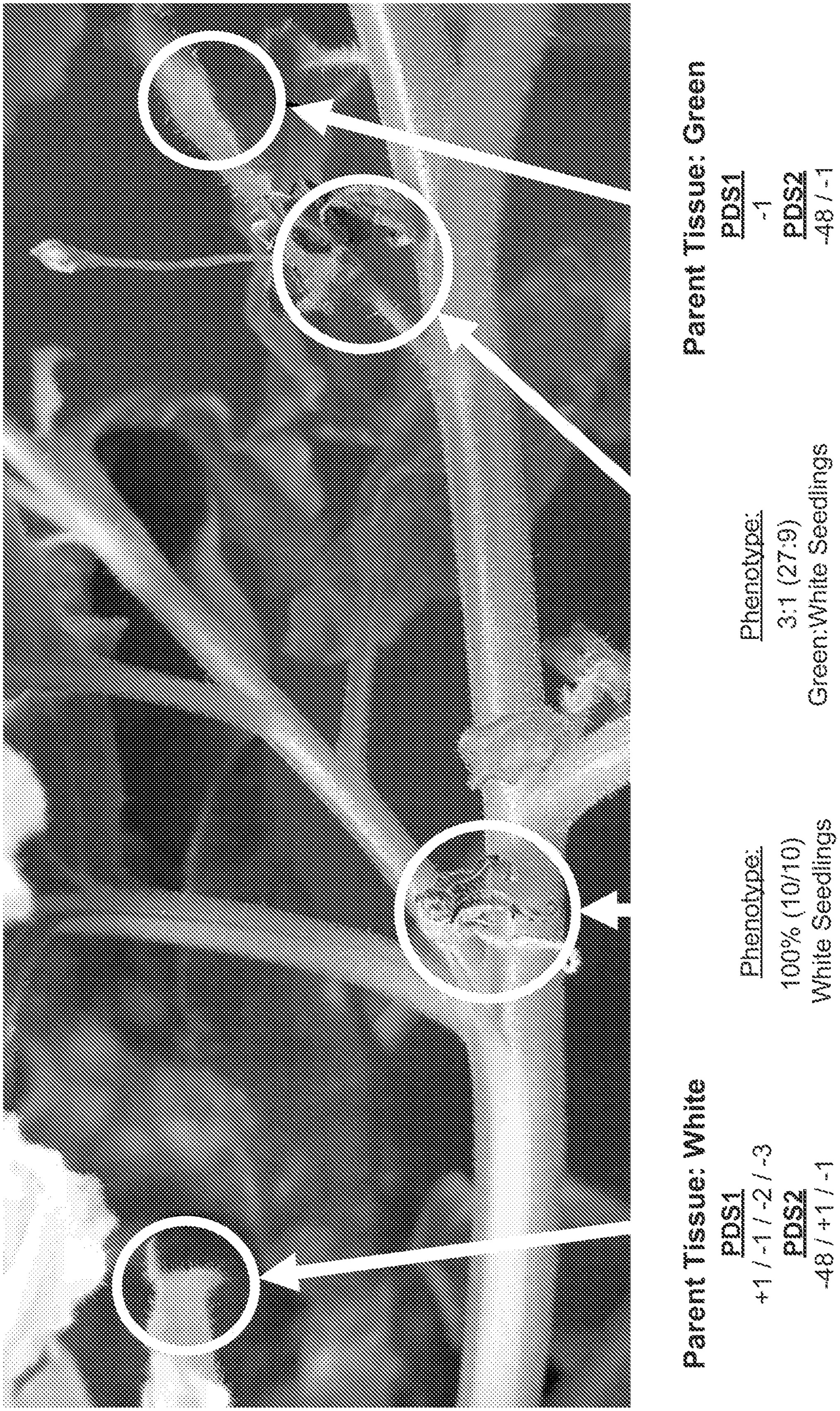

FIG. 7 is a representative image of an induced chimeric shoot with a WT growth pattern and sectored green and photobleached tissue, both of which produced seed (inner two circles). Below the image are the genotypes of the parental green and white tissues (outer two circles) observed by Tracking of Indels by Decomposition (TIDE) analysis of Sanger sequencing and phenotypes of the resulting progeny (see, also, FIGS. 8A and 10A for the resulting genotypes of individual seedlings). The −48 bp mutation constituted an in-frame deletion that may have maintained a functional PDS protein, retaining the green phenotype for green sectors.

Figure 8B:
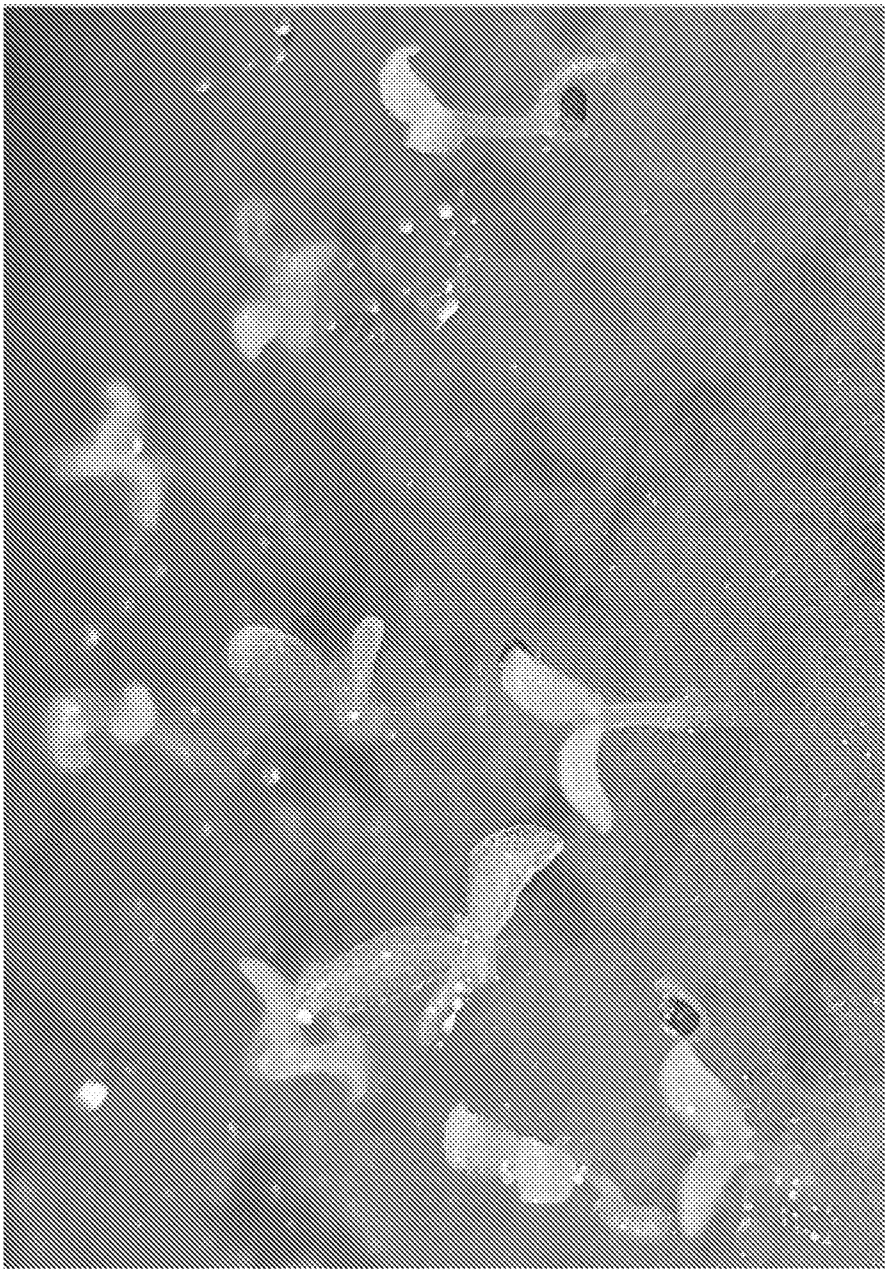

FIG. 8A is a table listing observed mutations for white tissues shown in FIG. 7 and for the resulting progeny. Genomic DNA was extracted from parental tissue and seedlings and submitted for Sanger sequencing. Sequences were assessed for mutations by TIDE sequence trace analysis. FIG. 8B is an image showing seedlings exhibiting the PDS KO phenotype.

Figure 9:
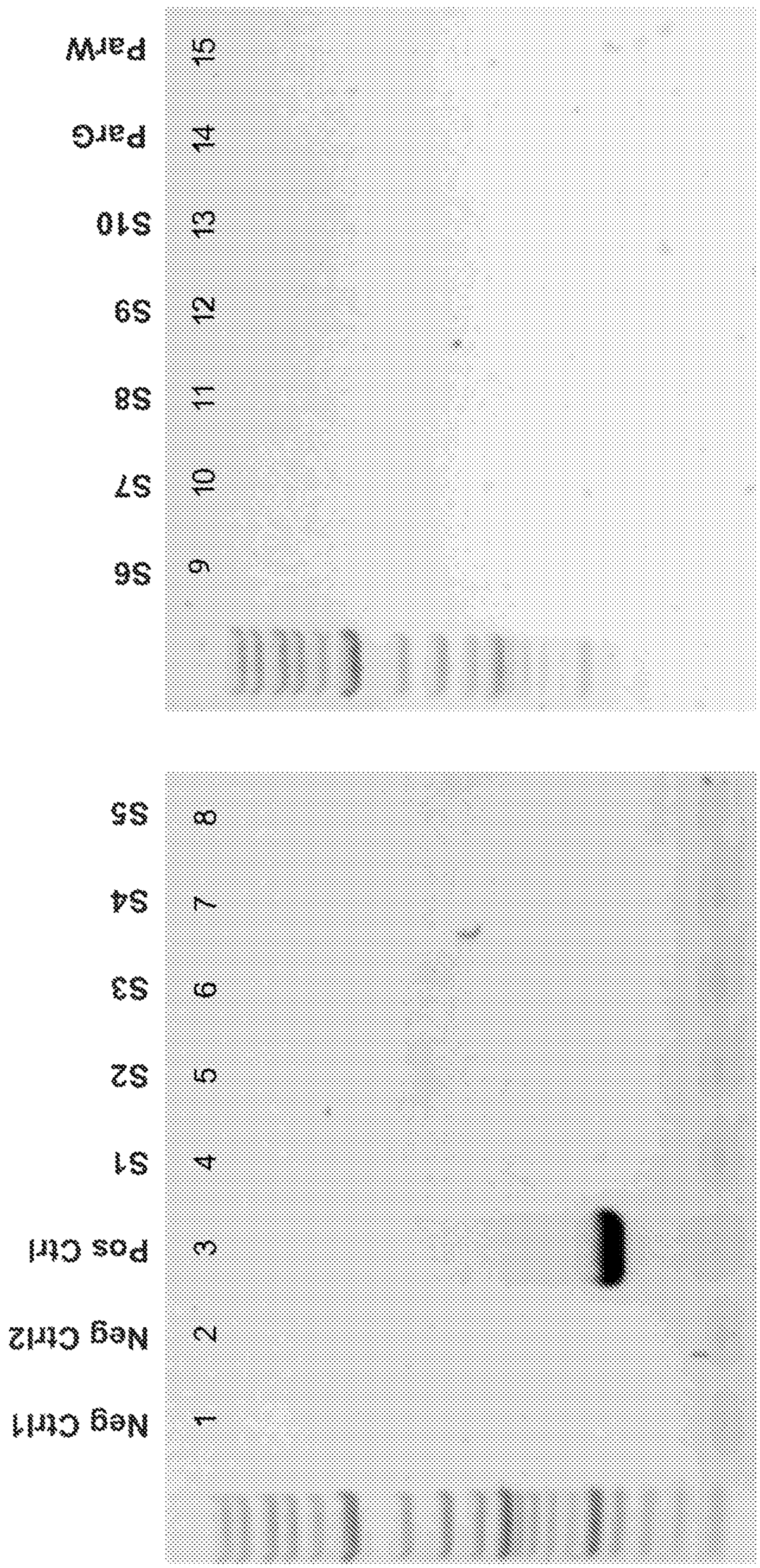

FIG. 9 is a pair of images confirming that the plants shown FIGS. 7 and 8B were transgene-free. Genomic DNA (gDNA) was extracted from parental white (ParW) and green (ParG) tissues of a plant demonstrating targeted editing (shown in FIG. 7), as well as from ten seedlings derived from the white flower (S1-S10; FIG. 8A). Genomic DNA also was extracted from plants that did not receive the vector (Neg Ctrl1 and Neg Ctrl2), as well as from leaf tissue infiltrated with the target vector (Pos Ctrl). DNA was amplified using primers specific to the U6 promoter present on the T-DNA (expected 448 bp). Ladder=NEB 2 log.

Figure 10B:

FIG. 10A is a table listing observed mutations for green tissues shown in FIG. 7 and the resulting progeny. Genomic DNA was extracted from parental tissue and seedlings and submitted for Sanger sequencing. Sequences were assessed for mutations by TIDE sequence trace analysis. FIG. 10B is an image demonstrating segregation of the PDS KO phenotype in a 3:1 ratio observed for the seedlings listed in FIG. 8A.

FIG. 11 is a table listing observed phenotypes and genotypes for PDS mutations in a TO plant (plant designator 5-14-1-08; FIGS. 5A and 5B) induced to form meristems and next generation progeny. The parent plant was trimmed and co-inoculated with *agrobacterium* strains individually carrying T-DNAs harboring DRs STM (pMM131; SEQ ID NO:33), IPT (pMM134; SEQ ID NO:34), WUS (pMM135; SEQ ID NO:35), (pMM136; SEQ ID NO:36), or BBM (pMM146; SEQ ID NO:37). Resulting induced de novo shoots were screened for PDS phenotype and genotype. Shoots were allowed to flower and set seed. Next generation progeny seed was germinated and assessed for phenotype and genotype. FIG. 11 provides information for parental shoot tissue from 5-14-1-8 and ten screened seedlings. The parent tissue was observed to harbor a −3 bp mutation in PDS1 in a heterozygous state. Progeny from this event were observed to segregate this −3 bp mutation.

Figures 12A, 12B, 12C, 12D, 12E, 12F, 12G:
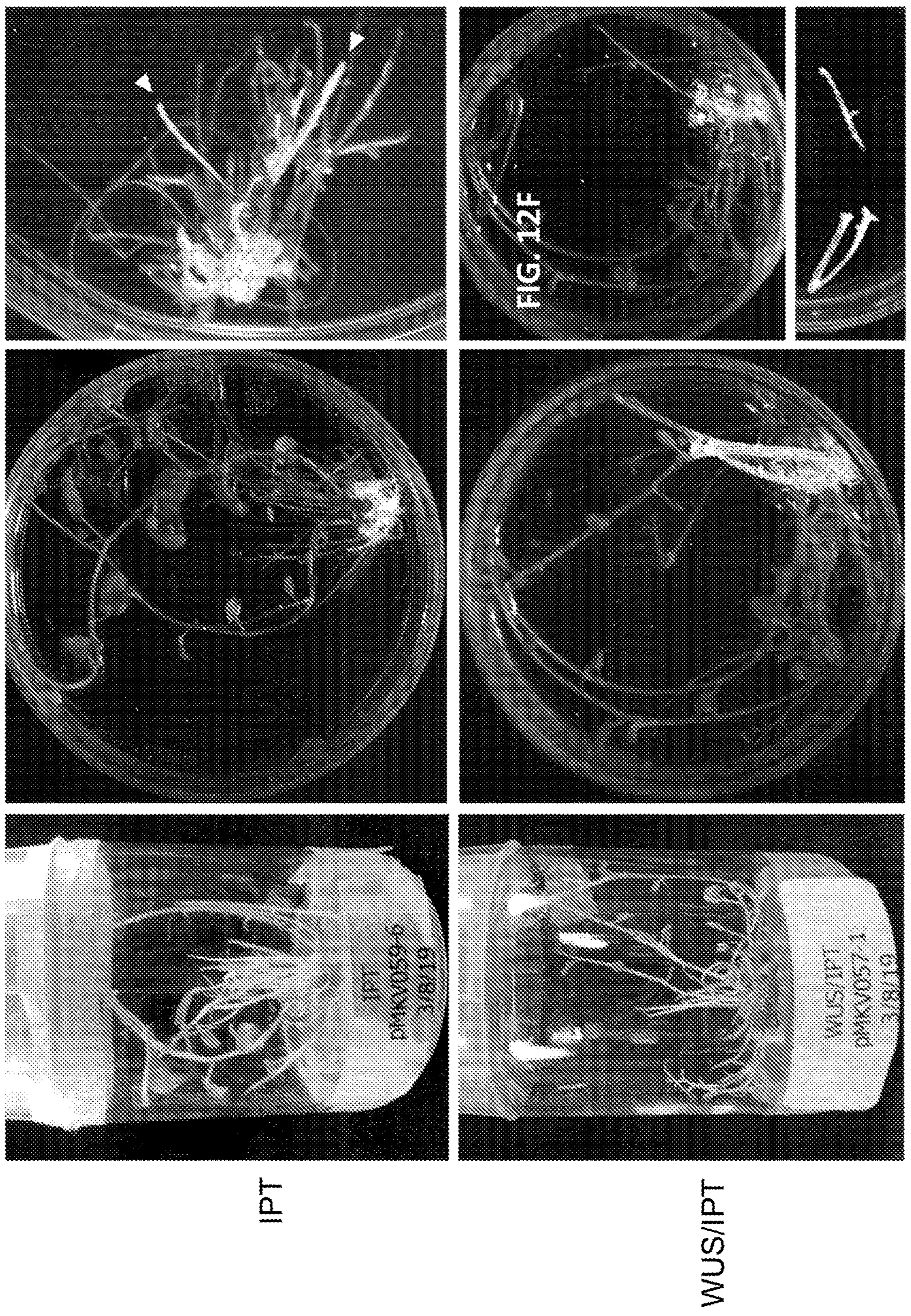
Figure 12I:
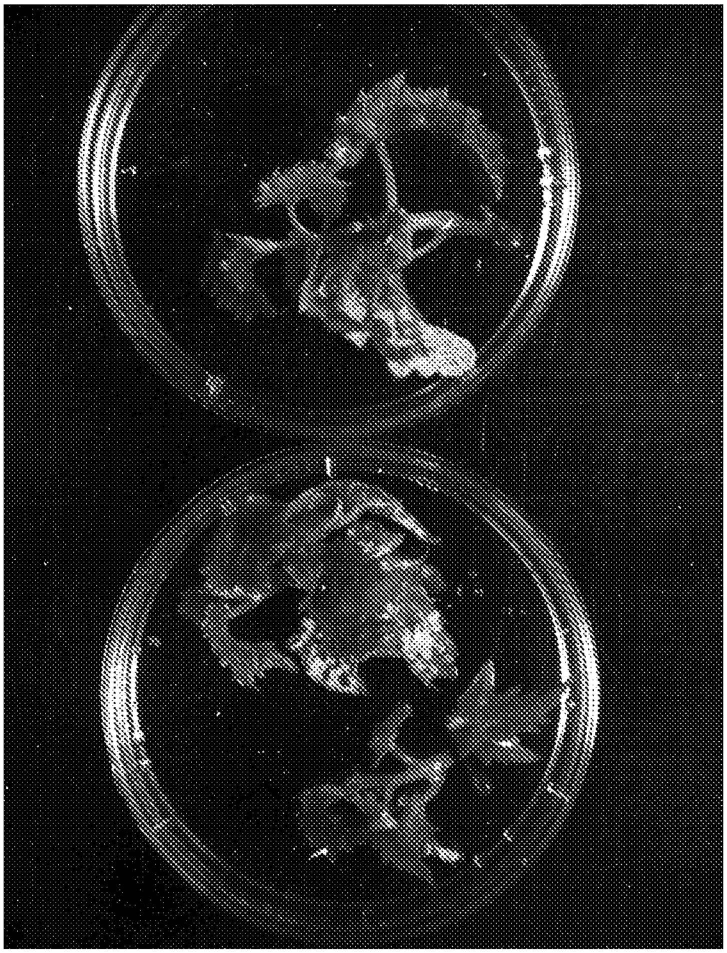
Figure 12H:
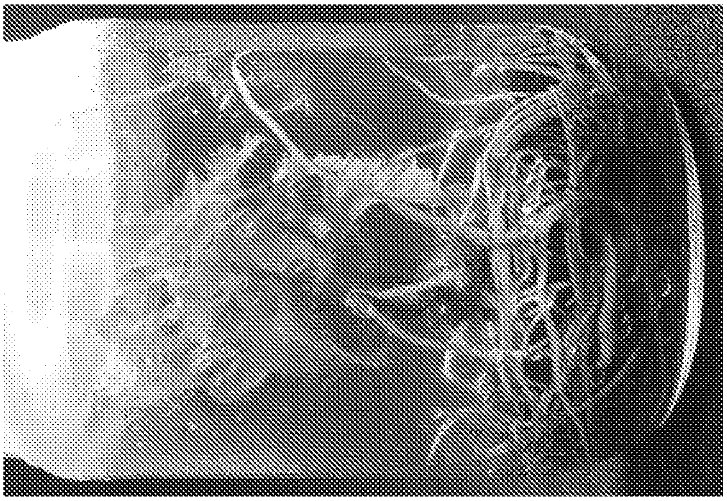

FIGS. 12A-12I depict induced transgenic shooting for vectors containing a luciferase reporter in *Solanum tuberosum* (potato) and *Vitis vinifera* (grape). *Agrobacterium* strains expressing either IPT (FIGS. 12A, 12B, and 12C; SEQ ID NO:96) or co-expressing WUS and IPT (FIGS. 12D, 12E, 12F, and 12G; SEQ ID NO:94) were delivered to potato plants along with a luciferase expression cassette (SEQ ID NO:14). FIGS. 12A and 12D show abnormal shooting phenotypes induced by DRs 95 days post infection (p.i.). Transgenic shoot formation was confirmed by imaging bioluminescence of de novo shoots formed after injection (FIGS. 12B, 12C, 12E, 12F, and 12G) at 97 days p.i. Fully transgenic shoots were detected upon trimming away several wild-type shoots (FIGS. 12C and 12G), signifying stable T-DNA integration in those induced shoots (highlighted in FIG. 12C by white arrowheads). FIGS. 12H and 12I demonstrate that delivery of DRs to grape plants (Pixie Pinnot cultivar) induced transgenic shoot formation with normal growth phenotypes. FIG. 12H is an image showing an exemplary grape plant 40 days after co-inoculation of *agrobacterium* strains individually carrying T-DNA vectors with DRs (WUS, IPT, MPA, STM, and BBM; SEQ ID NOs:88, 89, 90, 91, and 92, respectively). Newly formed shoots were generated at *Agrobacterium* inoculation sites. FIG. 12I shows that newly formed shoots removed from the grape plant of FIG. 12H panel were transgenic, as determined by a bioluminescence assay. Shoots were removed, exposed to luciferin substrate, and imaged for bioluminescence. The presence of bioluminescent-positive tissues indicated that the newly formed tissues were transgenic and expressed the luciferase reporter.

Figure 13:
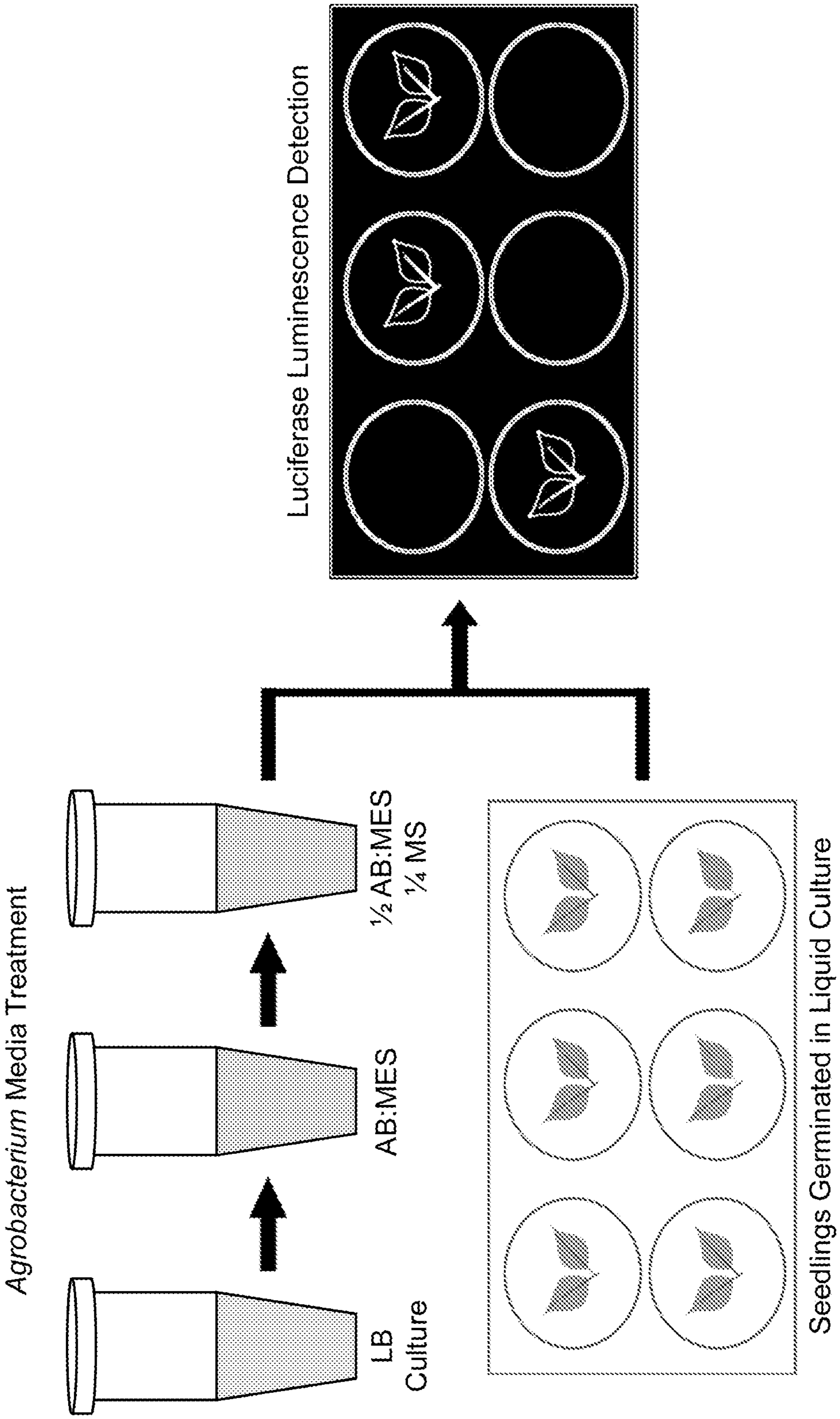

FIG. 13 is a diagram showing the steps of a Fast-TrACC delivery method as provided herein. As depicted, Fast-TrACC delivery involves three days of treatment with an *Agrobacterium tumefaciens* culture of interest, where the Agrobacteria contain one or more T-DNAs that encode one, two, or more developmental regulators, and also contain nucleic acid sequences that can result in a genetic change within a plant. The T-DNA also can include a reporter such as a luciferase gene. In the first step, Agrobacteria cultures are grown overnight to achieve confluency. Next, cultures are resuspended in AB:MES salts to increase the expression of vir genes, and grown overnight again. The final treatment involves combining AB:MES salts with plant growth media (½ MS) to promote the activity of both the bacteria and the seedlings being co-cultured. After the final treatment, the Agrobacteria are combined with seedlings roughly 2-3 days post germination. The co-culture is incubated for two days before the seedlings are washed free of the Agrobacteria. The washed seedlings are returned to liquid ½ MS containing the antibiotic Timentin to kill off any residual Agrobacteria. Using a reporter such as luciferase, seedlings can be analyzed for delivery of the T-DNA construct.

Figure 14A:
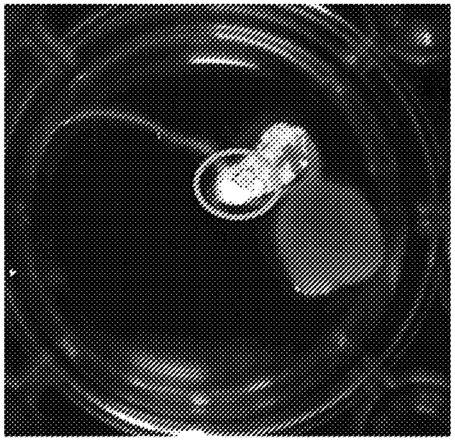
Figure 14B:
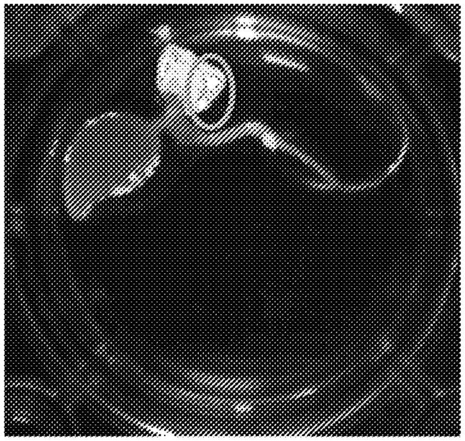
Figure 14C:
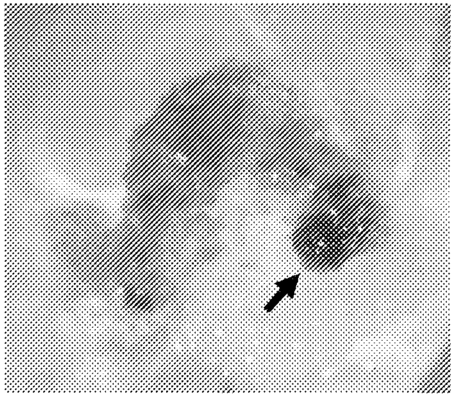
Figure 14D:
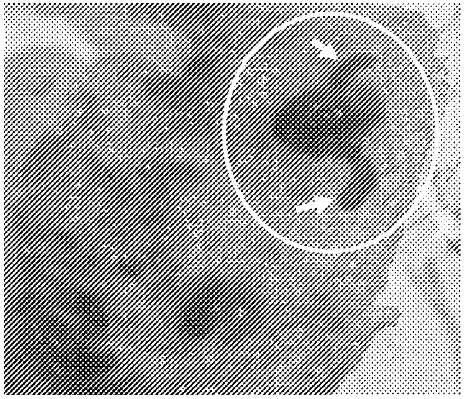

FIGS. 14A to 14D illustrate the generation of growths from sites of delivery for the Fast-TrACC method. T-DNAs with GVRs containing luciferase and the developmental regulators WUS and STM were incorporated into *N. benthamiana* seedlings. The sites of delivery were approximated by observing luminescence from the luciferase reporter (FIGS. 14A and 14B). De novo tissue growth occurred from the sites with the highest expression of luciferase (circles in FIGS. 14A and 14B). This presumably was due to high levels of developmental regulator expression coinciding with the reporter expression. The de novo tissues that were generated developed into different tissue types. Many remained in an undifferentiated callus-like state (FIG. 14C, arrow), while others progressed into meristem-like tissues (FIG. 14D, circle). The meristem-like growths developed defined structures such as leaflets (FIG. 14D, arrows).

Figure 15A:
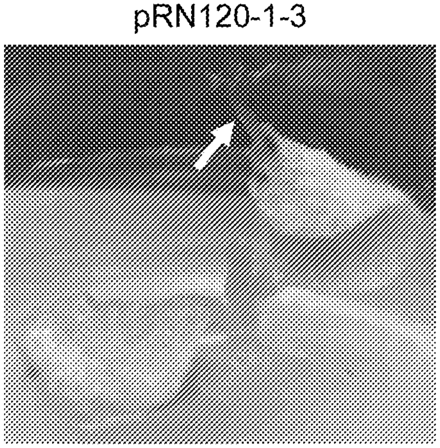
Figure 15B:
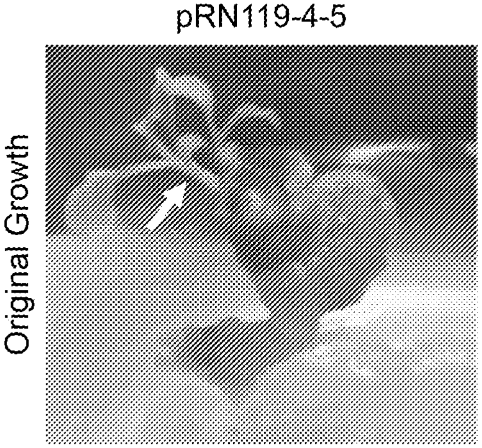
Figure 15C:
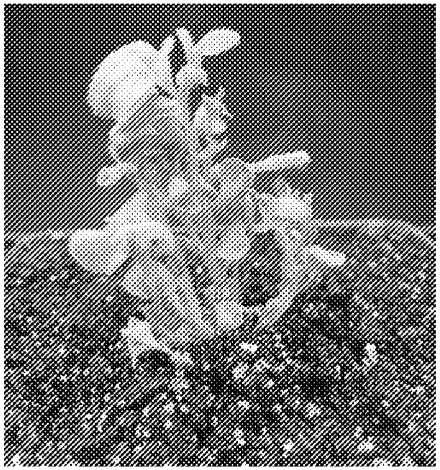

FIGS. 15A to 15E show regeneration of plantlets from developmental regulator derived shoots. Using the developmental regulator combination WUS and STM, shoot-like growths (FIGS. 15A and 15B) were formed on the cotyledons of *N. benthamiana* seedlings. These growths were transferred to auxin-rich rooting media to promote root system formation. Once full plantlets were generated, they were moved to soil (FIGS. 15C and 15D) to promote further growth. The generated plantlets exhibited a variety of whole plant phenotypes. For example, certain plantlets exhibited close to wild type appearance (FIG. 15D) while others had a far more disorganized phenotype (FIG. 15C). Three leaves from each of six generated plantlets were tested for expression of luciferase (FIG. 15E) from the original delivered T-DNA. Five of the six tested plantlets were luciferase positive in at least one leaf sample, indicating some chimeric level of transgene integration and maintenance.

Figure 16A:
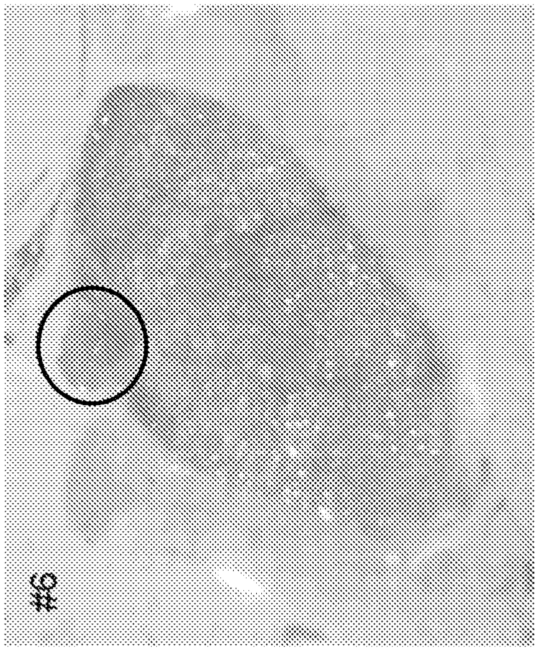
Figure 16B:
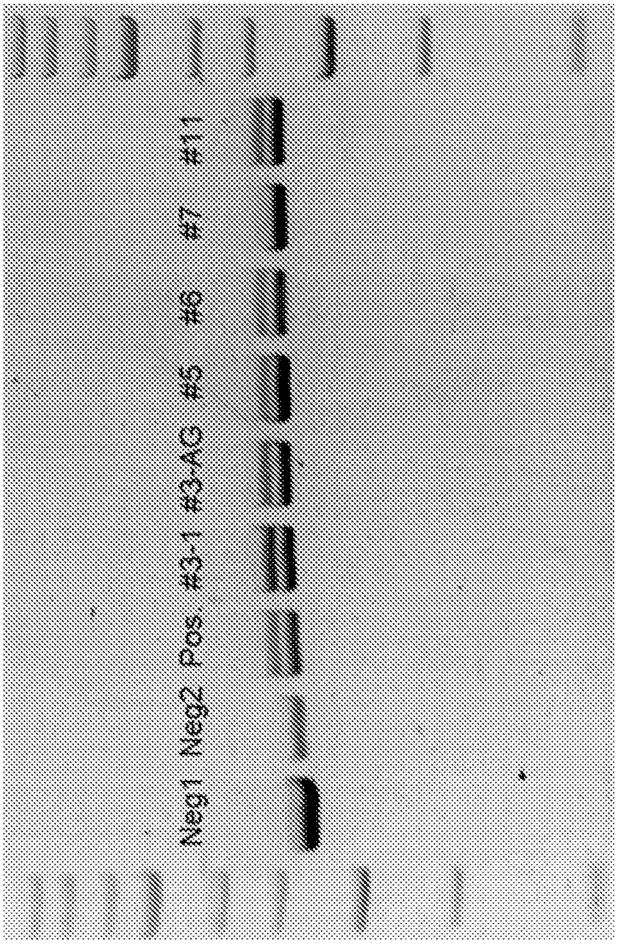
Figure 16C:
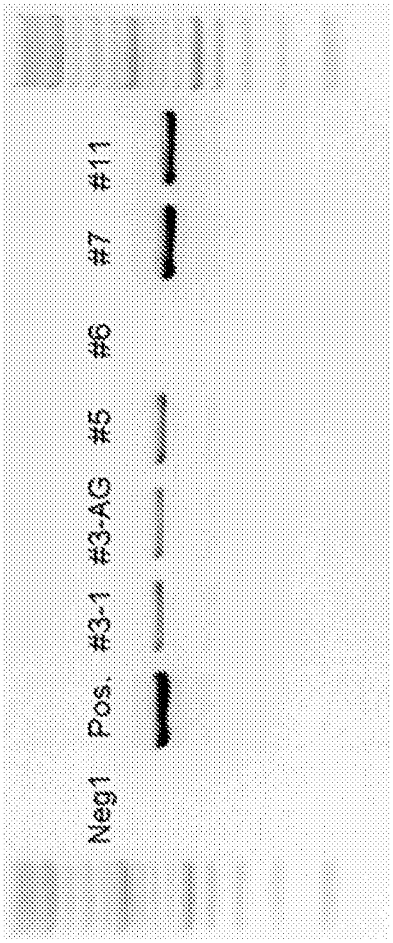
Figure 16D:
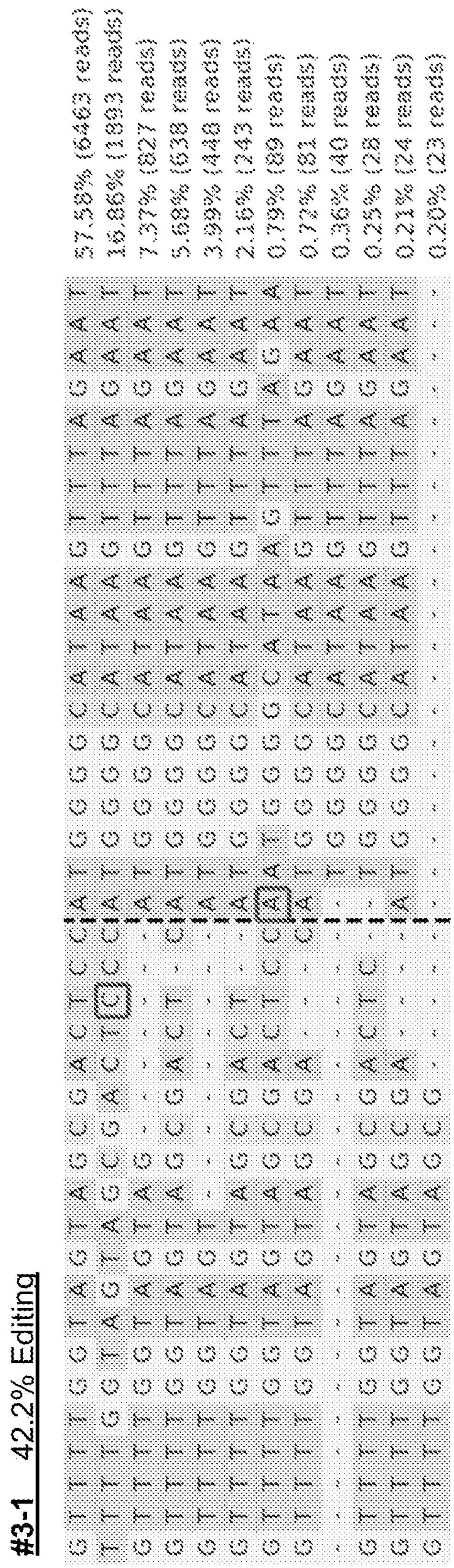
Figure 16E:
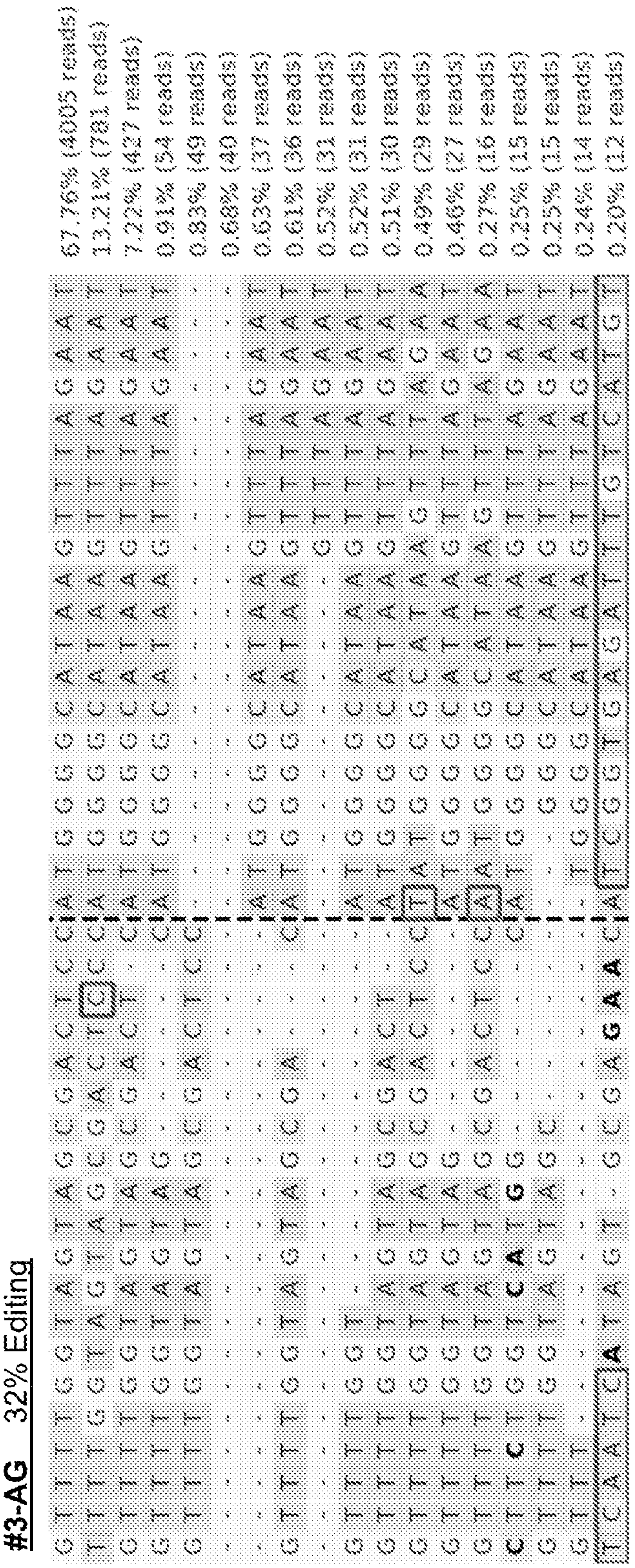
Figure 16F:
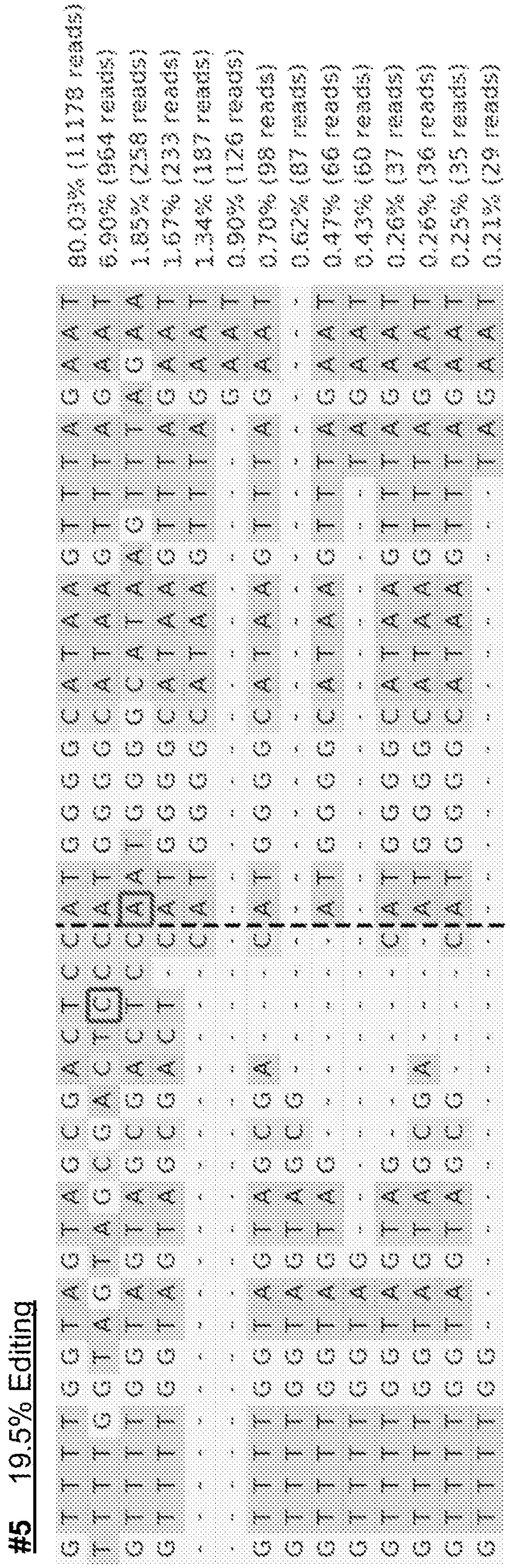
Figure 16G:
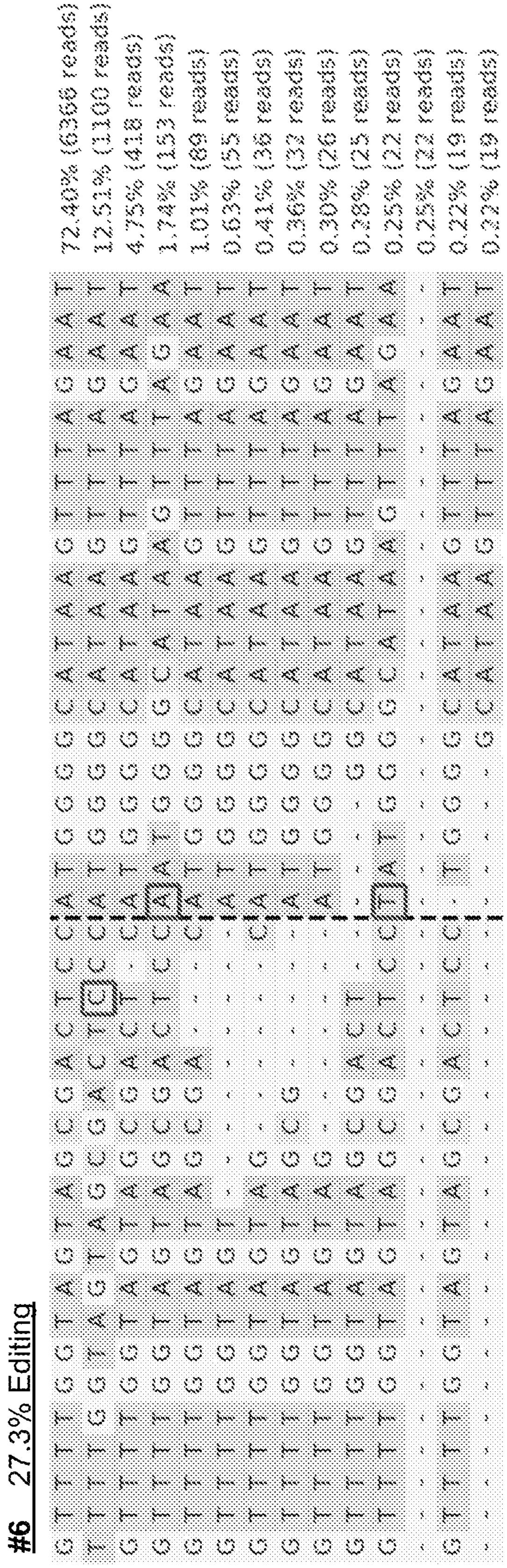
Figure 16H:
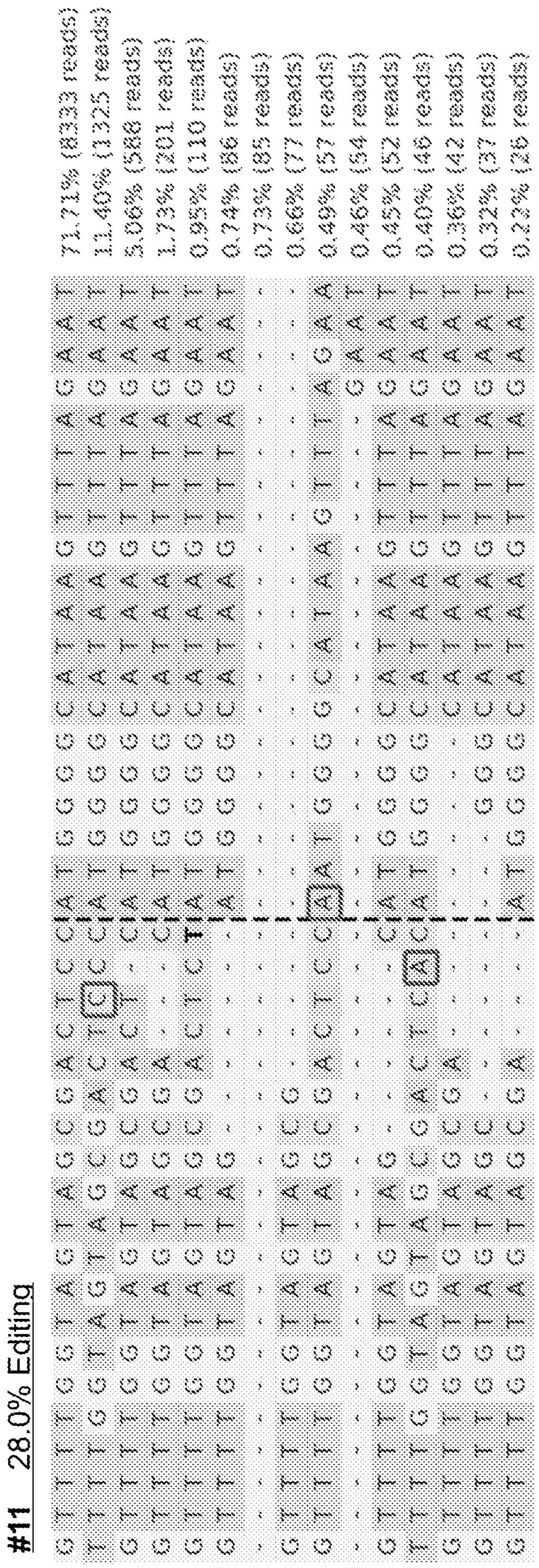

FIGS. 16A to 16H show confirmation of editing occurring in generated growths. Using the Fast-TrACC method, gene editing reagents were delivered along with the developmental regulators WUS and STM to promote the formation of edited growths. Five out of twenty-four seedlings had growths (FIG. 16A) that were candidates for molecular analysis. Using primers in NbPDS (Niben101Scf14708g00023.1), the target locus was amplified and tested for edits via a RFLP assay (FIG. 16B). The growths also were tested for amplification of Rep (FIG. 16C) to indicate the presence of the T-DNA. The isolated DNA samples were submitted for next generation sequencing (NGS; FIGS. 16D to 16H) for the NbPDS locus of interest to determine the frequency and scope of edits made. A variety of different edits were detected at the target site, with a single cytosine insertion and a single base deletion being the most consistently observed edits. Sequences that likely were the product of PCR induced mutation (asterisks) also were observed; these are not likely to have been caused by the delivered editing reagents. FIG. 16D, top to bottom: SEQ ID NOS:38, 40, 41, 39, 42, 43, 44, 45, 46, 47, 48, and 49. FIG. 16E, top to bottom: SEQ ID NOS:38, 40, 39, 50, 51, N/A, 52, 45, N/A, 53, 43, 54, 41, 44, 55, 56, 57, and 58. FIG. 16F, top to bottom: SEQ ID NOS:38, 40, 44, 39, 59, N/A, 45, 49, 41, 60, 50, 48, 61, and 62. FIG. 16G, top to bottom: SEQ ID NOS:38, 40, 39, 44, 45, 42, 50, 63, 41, 64, 54, N/A, 65, and 66. FIG. 16H, top to bottom: SEQ ID NOS:38, 40, 39, 45, 67, 41, N/A, 49, 44, N/A, 50, 68, 69, 57, and 48. N/A, no sequence identifier if less than 10 nucleotides in length.

Figure 17C:
Figure 17B:
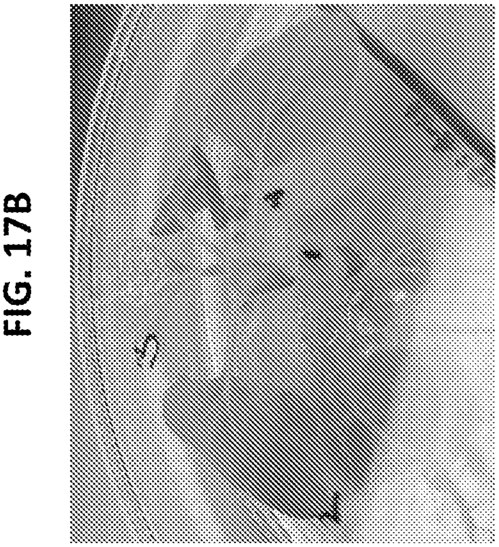
Figure 17A:
Figure 17D:
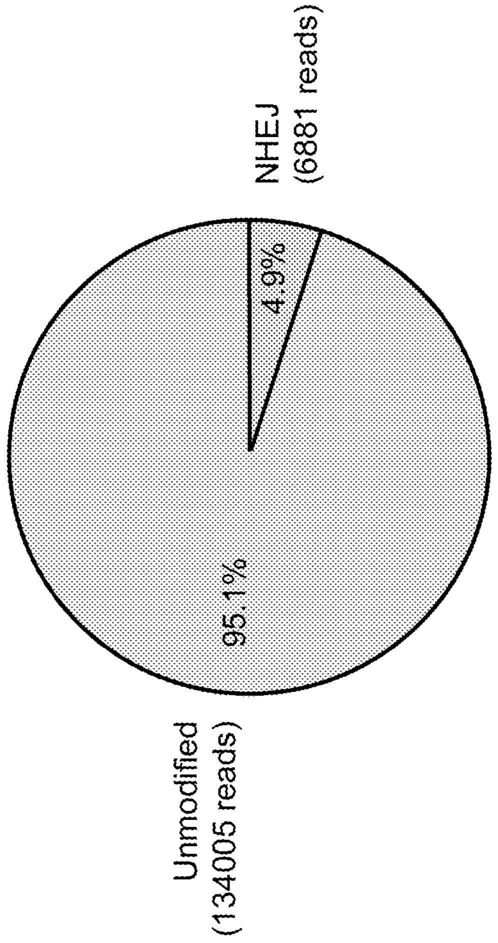
Figure 17E:
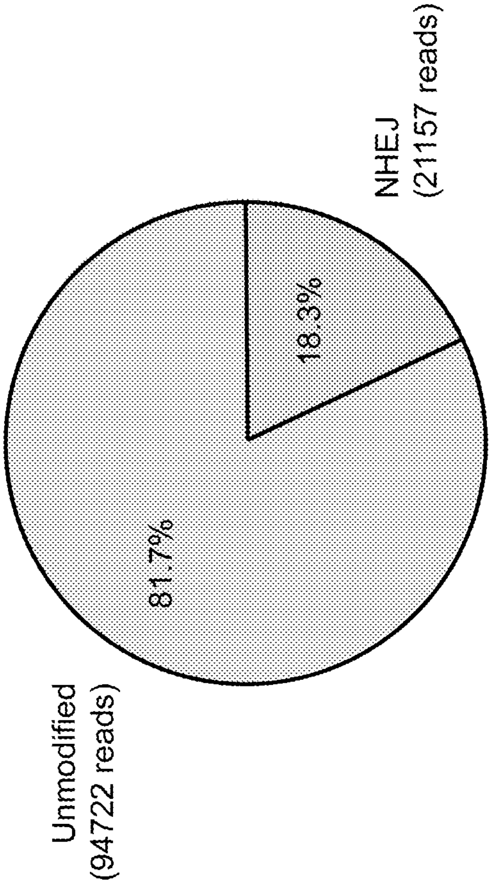
Figure 17F:
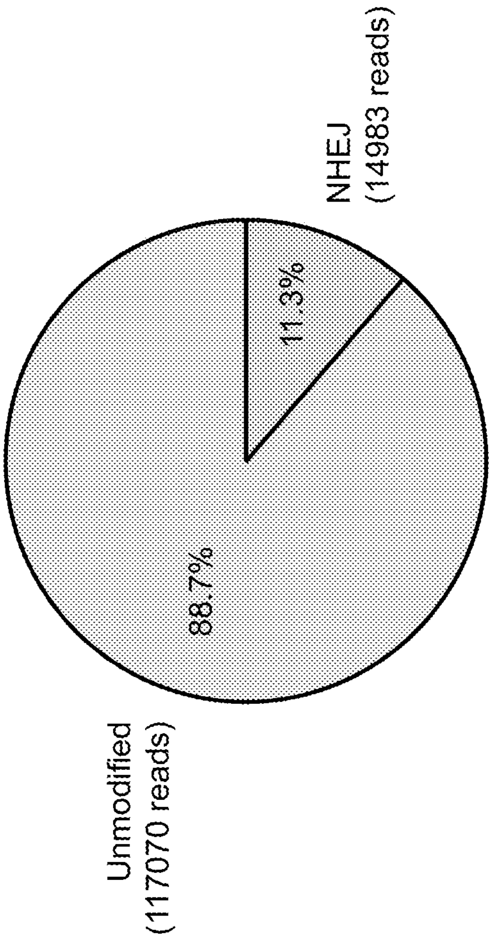
Figure 17G:
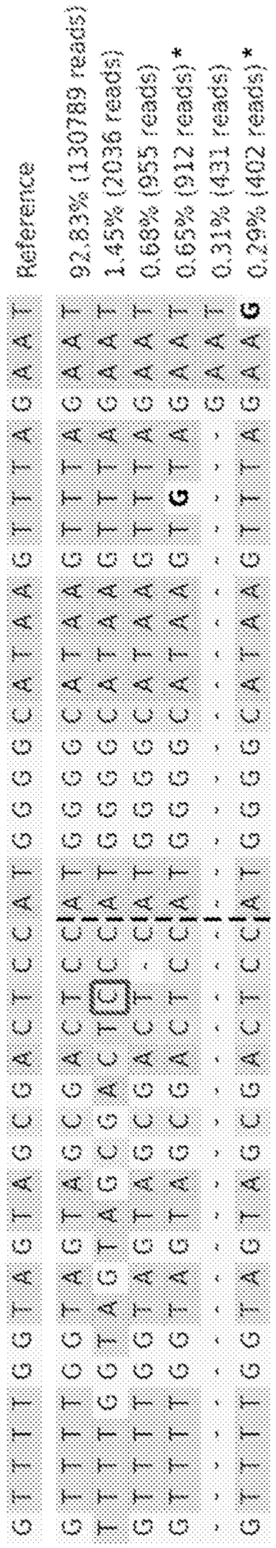
Figure 17H:
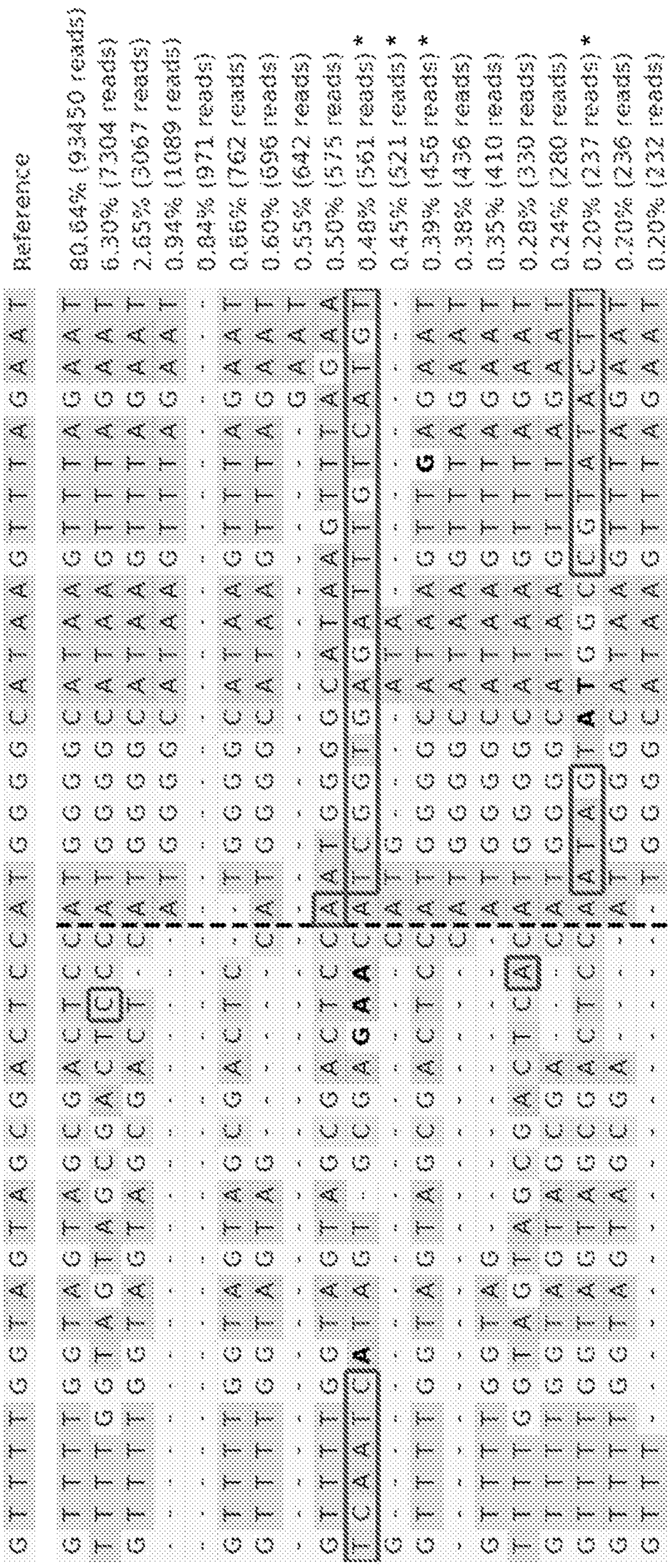
Figure 17I:
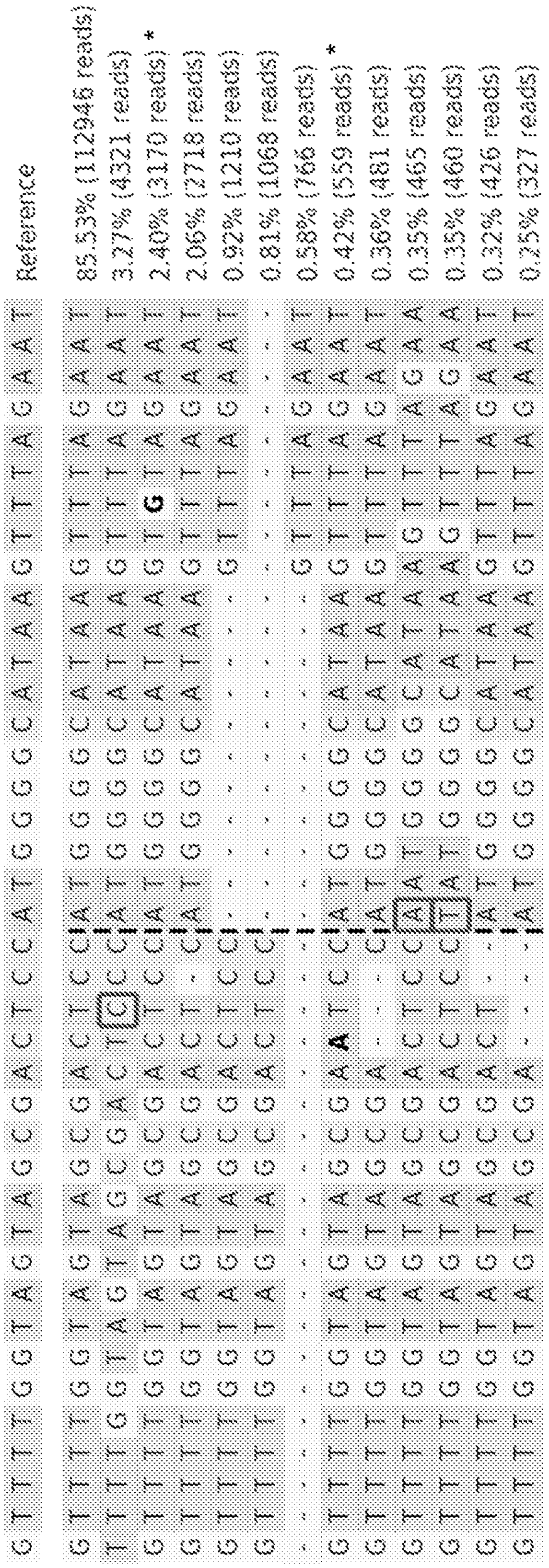

FIGS. 17A to 17I show results for mosaic plantlets derived from growths. Plantlets were regenerated from developmental regulator derived growths that received gene editing components (Cas9 and NbPDS gRNA). These plantlets exhibited a range of phenotypes, with individuals that appeared mostly wild type (FIGS. 17A and 17B) as well as individuals exhibiting abnormal leaf or branch phenotypes (FIG. 17C), or generally disorganized states. DNA isolated from leaves using CTAB was pooled and submitted for NGS sequencing at the NbPDS (Niben101Scf14708g00023.1) locus. The resulting spectrum of edited reads indicated that the derived plantlets were mosaics of different edits. The proportion of reads isolated that contained edits was fairly low (FIGS. 17D, 17E, and 17F), but clearly detectable. The most commonly induced mutations of those observed (FIGS. 17G, 17H, and 17I) were single base insertions and deletions, as expected. FIG. 17G, top to bottom: SEQ ID NOS:38, 38, 40, 39, 70, N/A, and 71. FIG. 17H, top to bottom: SEQ ID NOS:38, 38, 40, 39, 52, N/A, 47, 50, N/A, 44, 58, N/A, 72, 60, 73, 68, 45, 74, 48, and 75. FIG. 17I, top to bottom: SEQ ID NOS:38, 38, 40, 71, 39, 76, 51, N/A, 77, 45, 44, 54, 43, and 48. N/A, no sequence identifier if less than 10 nucleotides in length.

Figure 18B:
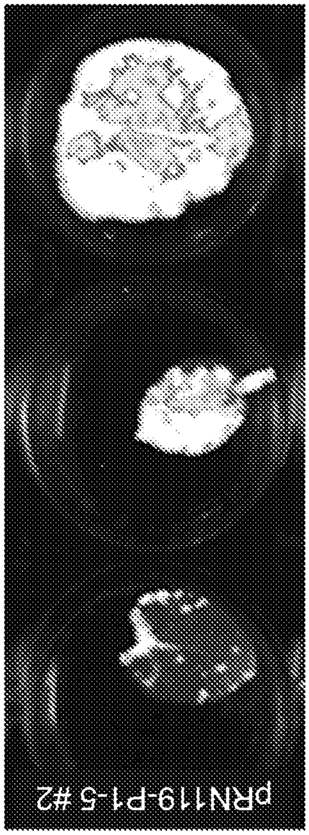
Figure 18C:
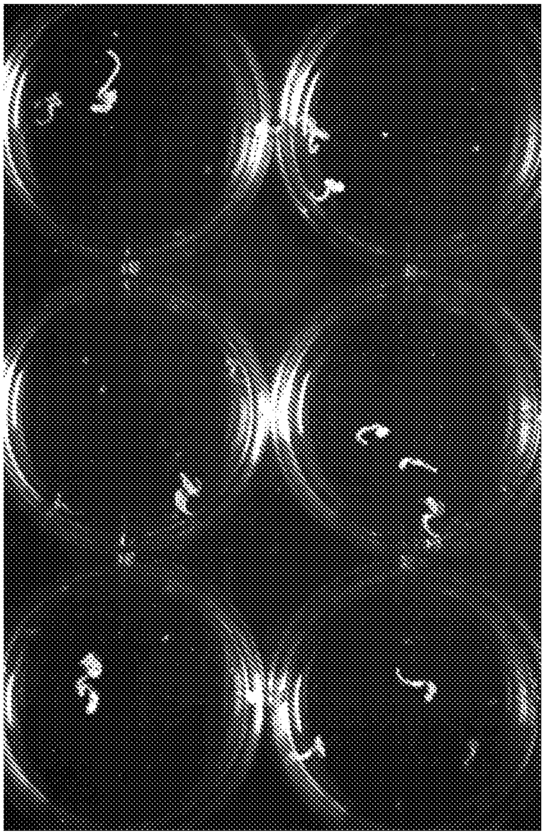
Figure 18A:
Figure 18D:
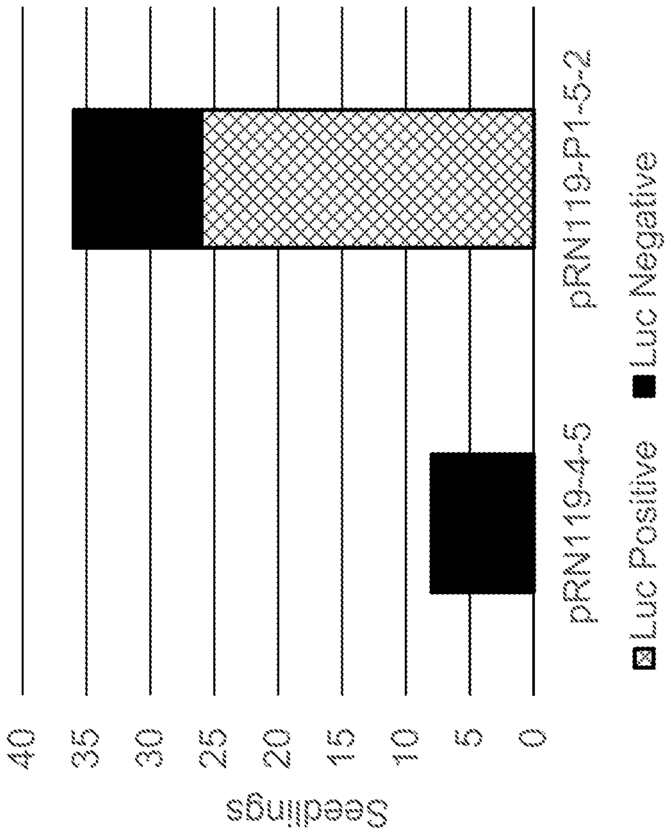

FIGS. 18A to 18D show vertical transmission of integrated T-DNA. Plants were derived after delivery of developmental regulators using the Fast-TrACC method. The original construct delivered to the progenitor plant via *Agrobacterium* contained 35S:Luciferase, Nos:WUS, and CmYLCV:STM on the T-DNA (pRN119, SEQ ID NO:27). Candidate plants (FIG. 18A) exhibiting high luciferase expression from leaf punches (FIG. 18B) were monitored for vertical transmission; after the plants flowered and set seed, the seeds themselves were tested for luminescence. The seedlings were found to maintain high levels of reporter expression (FIG. 18C), and luminescence was observed in the positive seedlings at a Mendelian ratio, consistent with inheritance from a heterozygote (FIG. 18D, 119-P1-5-2).

Figure 19B:
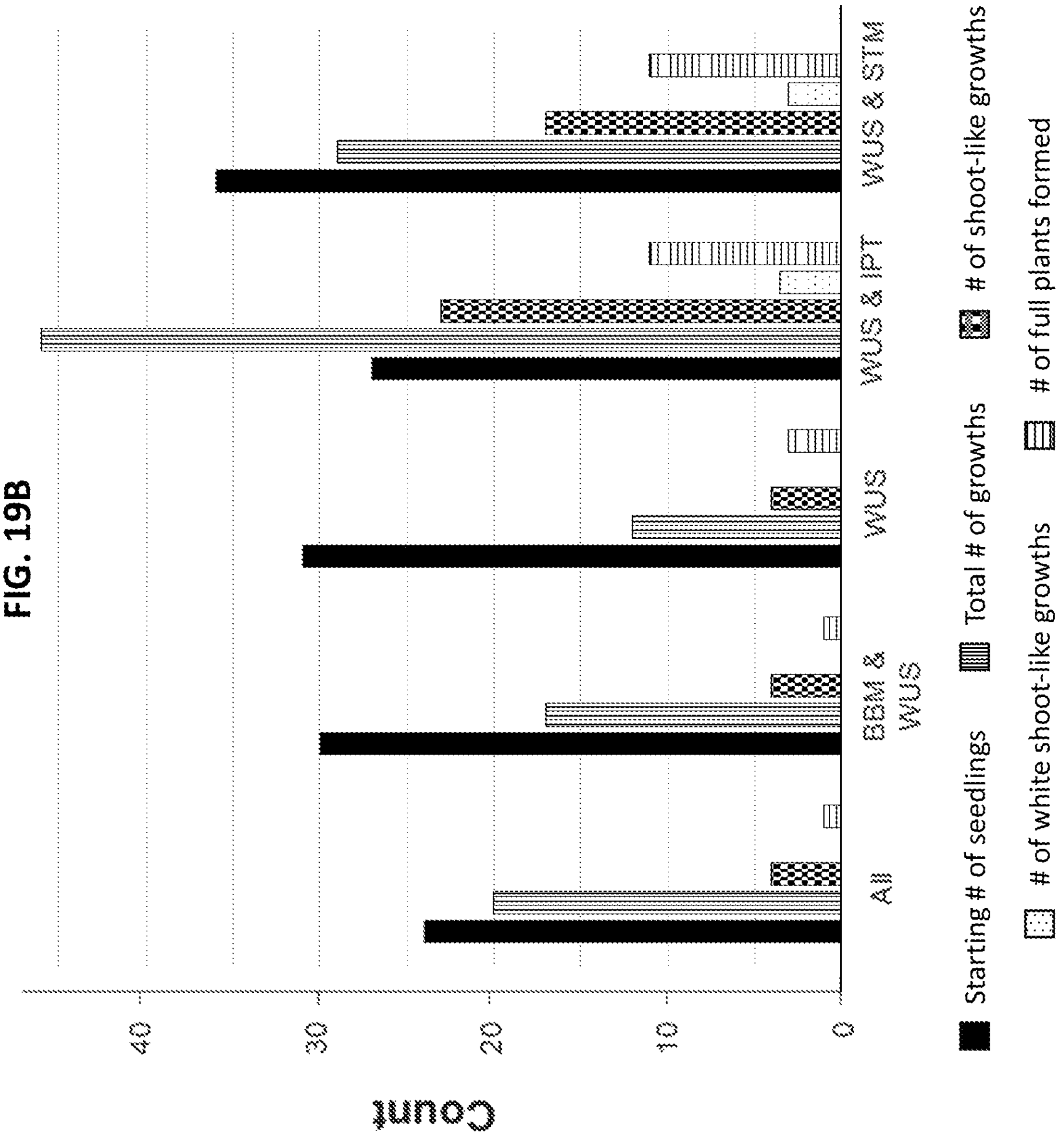

FIG. 19A is a table listing characteristics for plants that received various combinations of DRs. To determine combinations of DRs that were most effective in creating de novo meristems, *A. tumefaciens* strains each carrying a single DR delivered individually or in various pools to *N. benthamiana* seedlings, which were monitored for de novo growth formation. Out of twelve tested options, five combinations produced de novo meristems and subsequent plants. The number of seedlings, growths, shoot-like growths, white shoot-like growths, and full plants for these five combinations are plotted in FIG. 19B.

Figure 20:
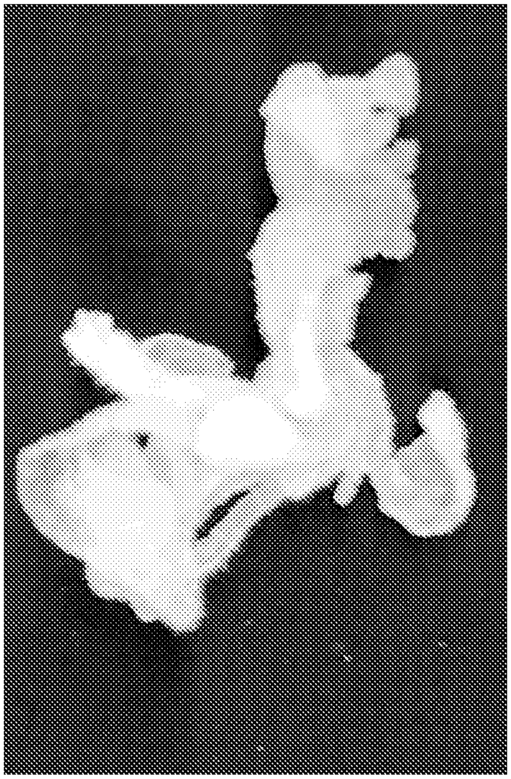

FIG. 20 is an image showing a seedling that resulted from Fast-TrACC delivery of T-DNAs with developmental regulators and a gRNA that targeted the two homologs of phytoene desaturase (PDS1 and PDS2) to *N. benthamiana* seedlings constitutively expressing Cas9. When the alleles of both homologs are fully knocked-out, plants exhibited a white phenotype due to photobleaching. About 15% of the shoots were white, but could not be grown into full plants due to lack of chlorophyll.

Figure 21A:
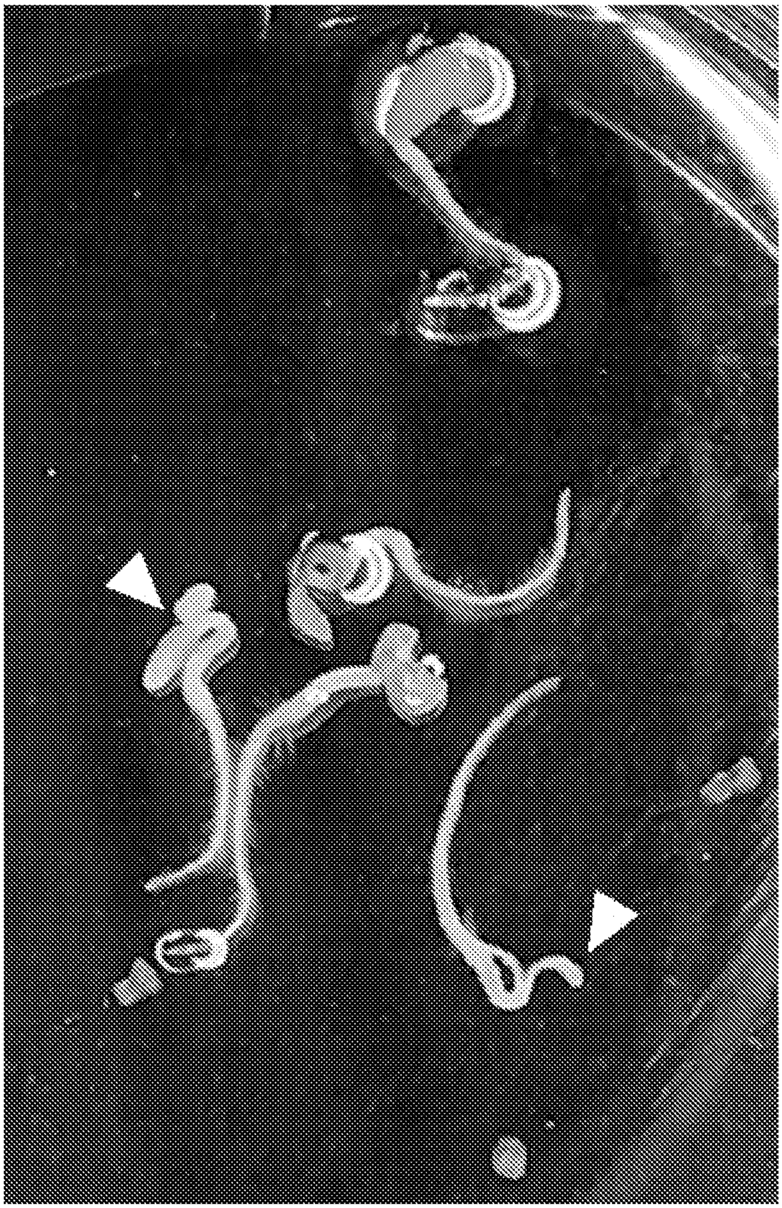

FIG. 21A is an image showing green plants that were chimeric for edits at the PDS loci. Seedlings derived from some of these plants possessed the expected white phenotype (arrowheads). In plant 1-7, two separate flowers (designated as F4 and F6) produced white seedlings. Mutations were observed in the alleles of both PDS loci, and are listed in FIG. 21B. The sgRNA sequence is underlined, and the predicted cut site is represented as a vertical line.

Figure 22A:
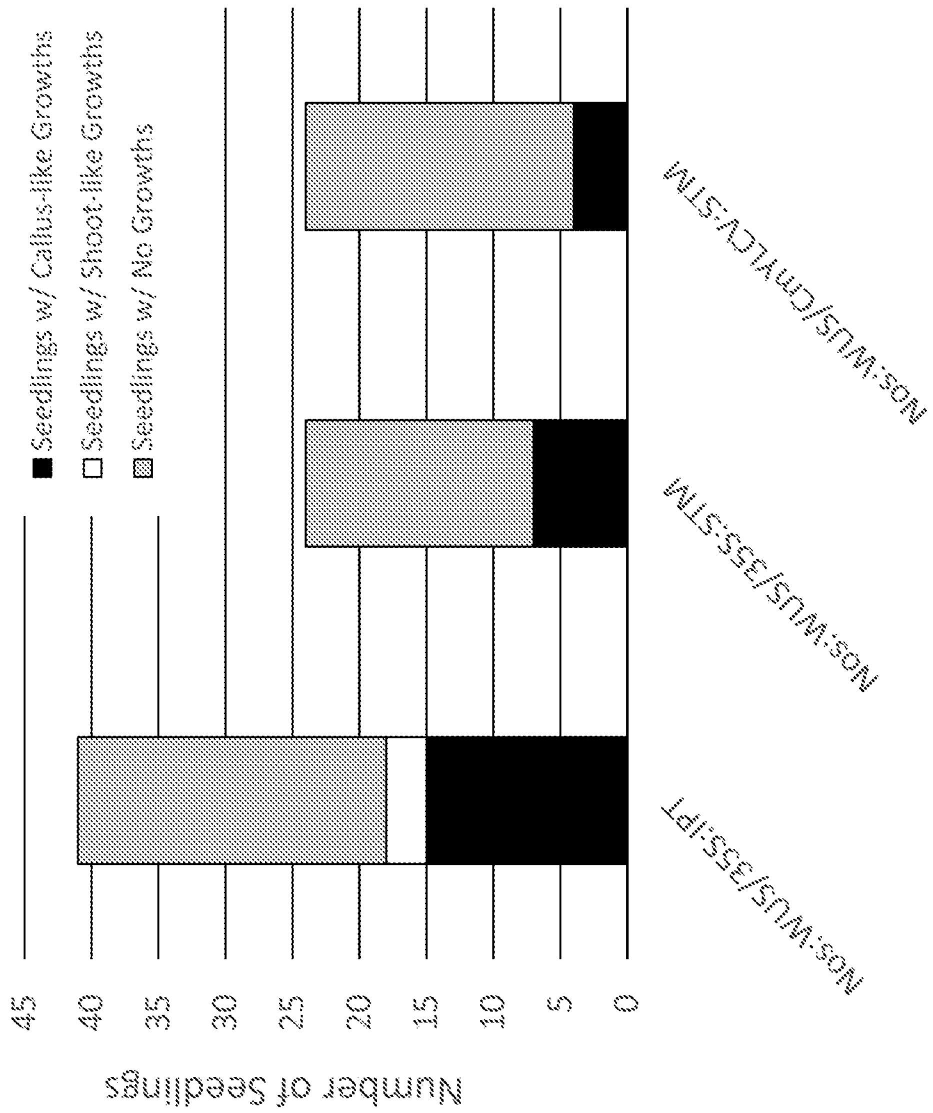
Figure 22B:
Figure 22D:
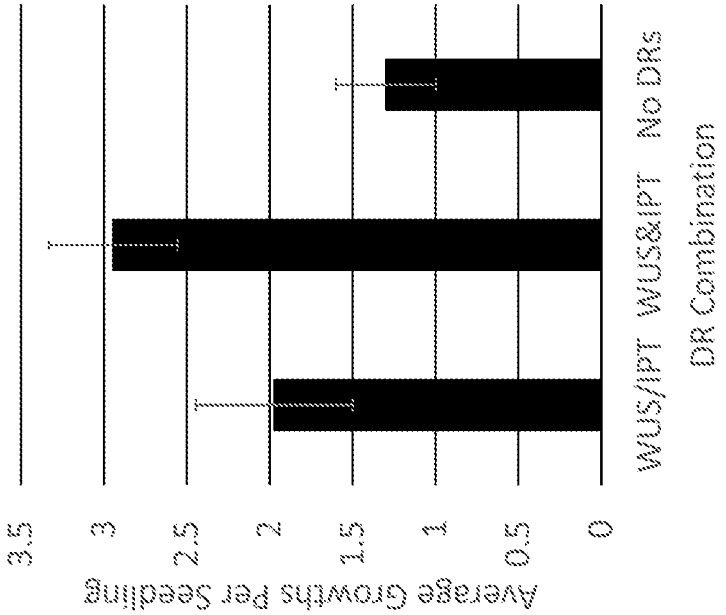
Figure 22E:
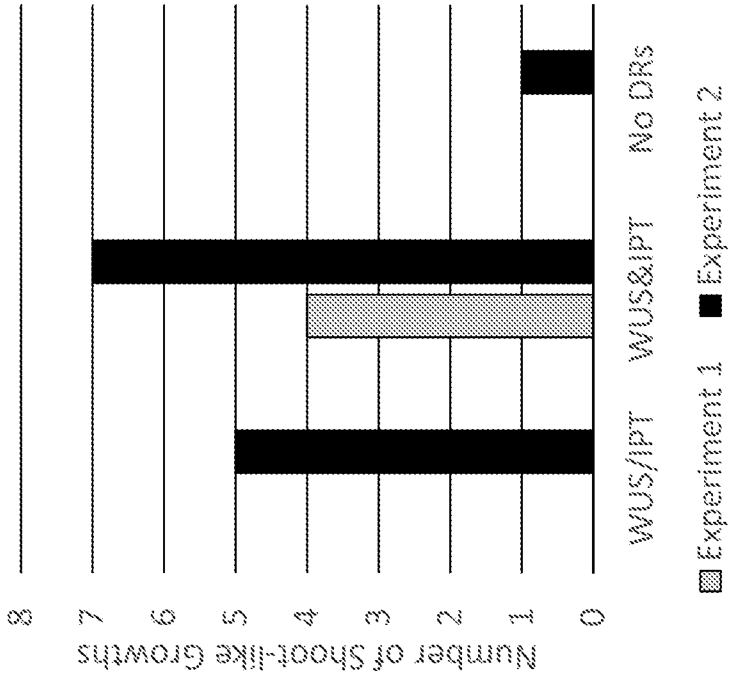
Figure 22G:
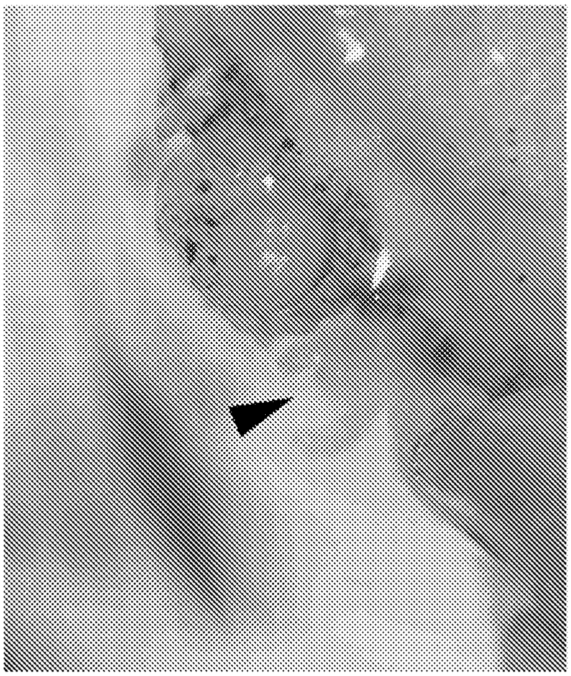
Figure 22F:
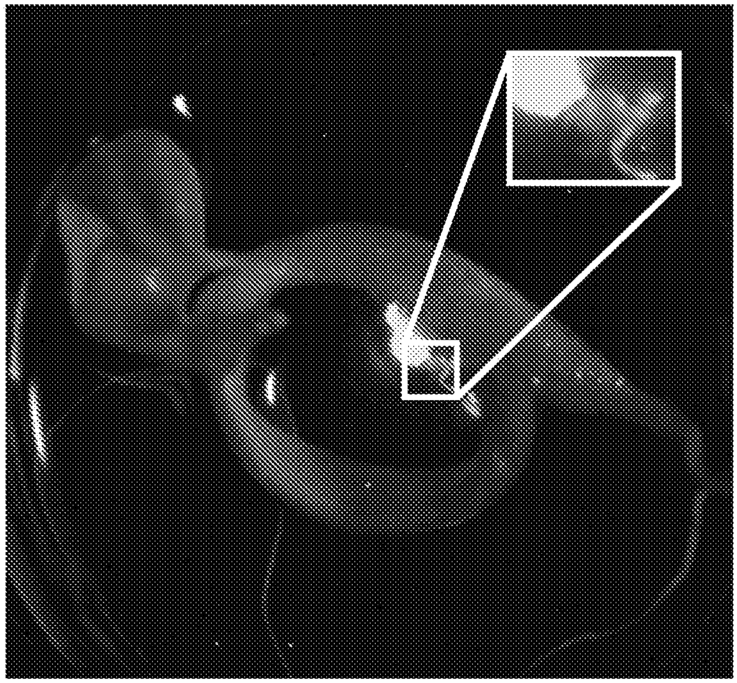
Figure 22I:
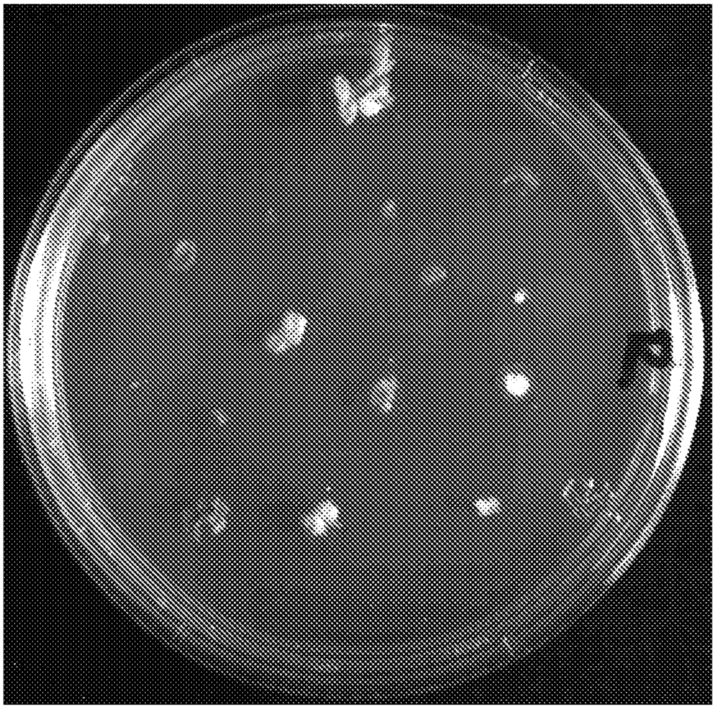
Figure 22H:
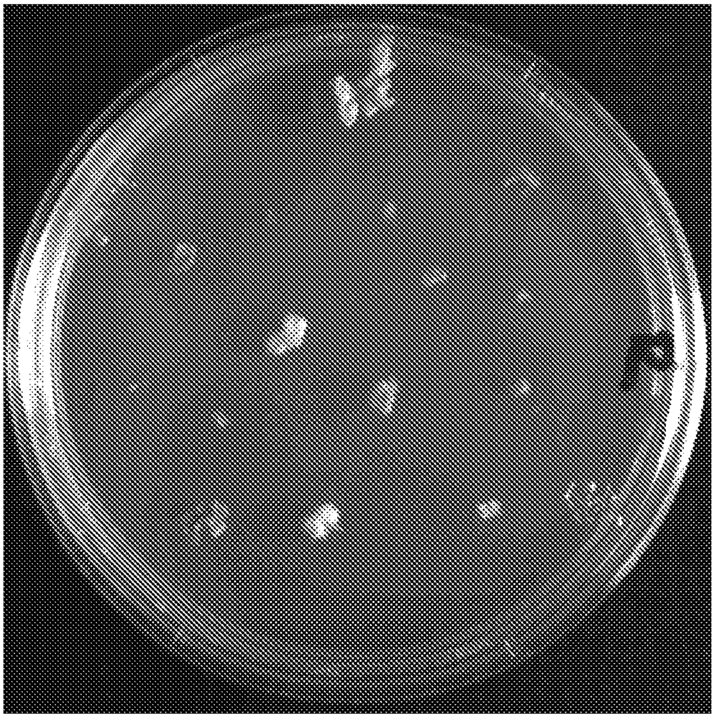

FIGS. 22A-22J demonstrate results for tomato. To induce de novo meristems in tomato, combinations of developmental regulators that effectively induced meristems in *N. benthamiana* were tested (WUS+IPT and two combinations of WUS+STM). For both combinations of WUS and STM, no shoot-like growths were formed (FIGS. 21A and 21C), and substantial tissue necrosis was observed after delivery. In contrast, the combination of WUS and IPT promoted shoot-like growths (FIGS. 21A and 21C), which ultimately formed fully rooted plants (FIG. 21B). WUS and IPT were then delivered to tomato seedlings on either a single vector (WUS/IPT) or on separate vectors in two different *Agrobacterium* strains (WUS&IPT). Both WUS/IPT and WUS&IPT showed an increase in the frequency of average growths per plant over the background level of growths that developed on plants that did not receive developmental regulators (FIGS. 22D and 22J). Shoot-like growths form from the WUS and IPT derived growths (FIGS. 22E and 22J), and luciferase positive, meristem-like structures were observed (FIGS. 22F (boxed) and 22G, arrowhead). These structures progressed to form shoot-like growths (FIG. 22H) that were excised and assessed for luminescence (FIG. 22I). Four out of 15 shoot-like growths showed evidence of luminescence (FIGS. 22I and 22J).

DETAILED DESCRIPTION

A principle goal of GE techniques is the creation of an editing event in the germline of an organism so that the modification can be transmitted to the next generation. For plants, the germline is produced by reproductive tissues derived from the meristem, instead of from isolated gametophyte cells. Plant meristems are the developmental centers of the plant from which all ensuing plant growth is derived. If these stem cells are edited, all tissues subsequently derived from the meristem should contain the GE event(s) of interest, leading to transmission to the next generation. Direct modification of existing meristematic tissue has proven challenging, as it is a highly regulated tissue type that has historically been recalcitrant to genetic modification. This little understood barrier, among other factors, has necessitated the use of suboptimal tissue culture procedures for most agriculturally relevant crops.

The present document is based, at least in part, on the discovery that developmental regulators can be combined with GE reagents to promote the formation of edited meristematic tissue that can flower and produce seed. The methods described herein include steps for delivery of developmental regulators to whole plants to induce the transdifferentiation of somatic plant cells in vivo, leading to the production of meristems. These meristems can carry transgenic insertions or genetic editing events to the next generation, creating seed with a GE event of interest in a fraction of the time needed using current standard protocols. Because the seed is derived from a single meristematic cell, it represents a clonal genetic editing event that provides an abundance of edited seed after a single generation. The direct delivery methods described herein also provide the advantage of avoiding tissue culture, which can reduce the time needed to regenerate tissues and considerably simplifies the process of generating GE events. Thus, the methods provided herein can circumvent the limitations of current plant regeneration protocols, and greatly enhance the potential for development of GE plant lines for both commercial use and basic research.

Figure 1:
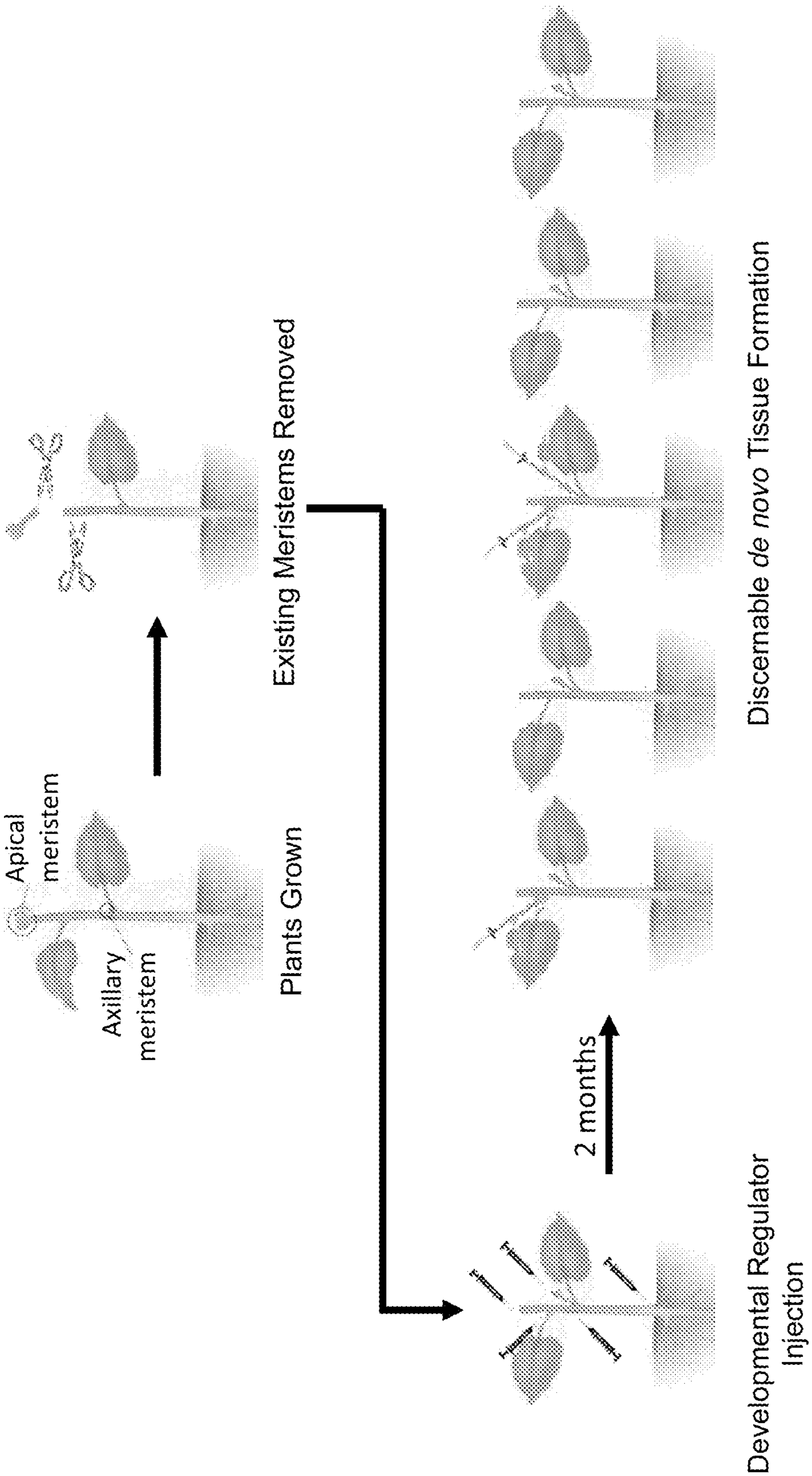
FIG. 1 is a diagram depicting an experimental procedure for a direct injection method as provided herein. Plants can be grown to a developmental stage at which axillary shoot meristems are visualized. Removal of existing shoot meristem tissue (shoot apical meristem and axillary meristems) can be performed to increase the potential for de novo shoot formation. Reagents to create a genetic change and to stimulate growth of de novo tissue can be delivered to plant tissues by various means, including direct injection as depicted in FIG. 1. The delivered reagents can result in induction of de novo shoots, as well as other somatic tissues, and the newly formed tissue(s) can contain the genetic change of interest.
Figures 2A, 2B, 2C, 2D, 2E, 2F:
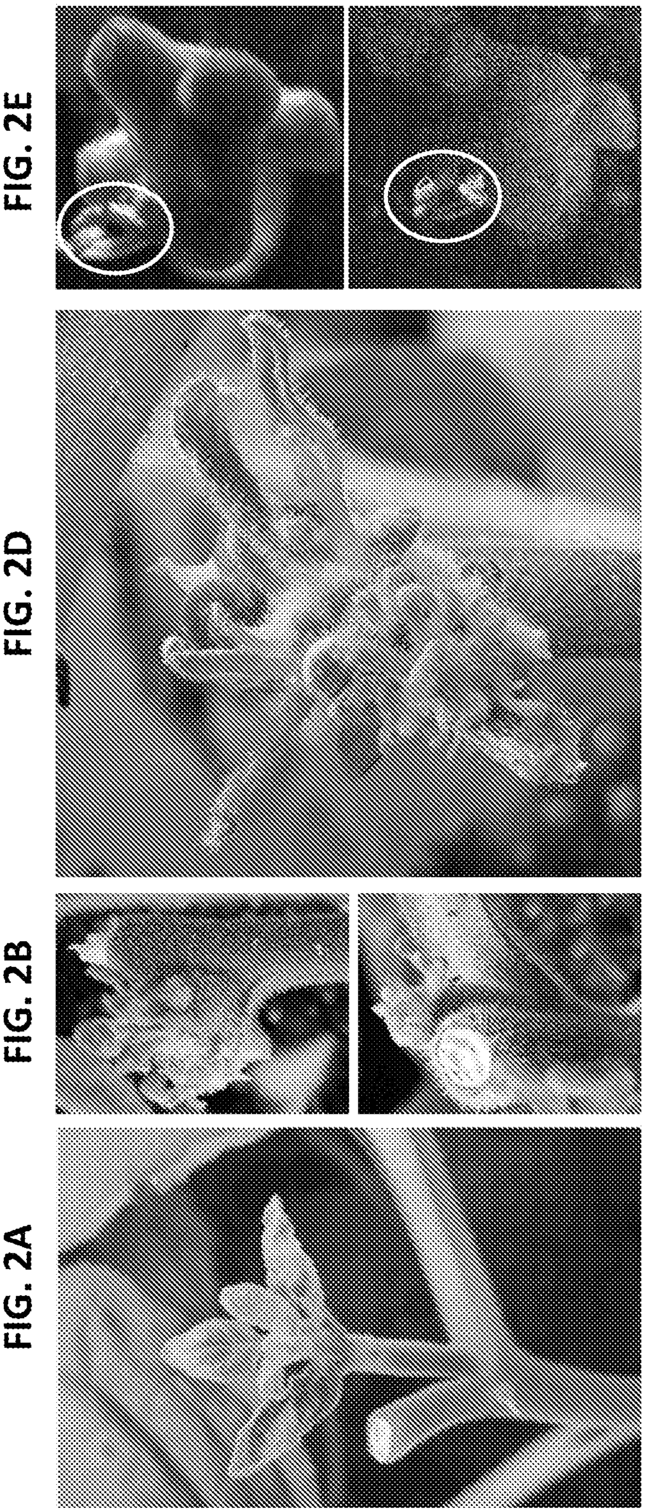
FIGS. 2A-2F show the generation of de novo tissues from injection sites. Reagents for the induction of de novo shoot meristems were delivered to *Nicotiana benthamiana* as outlined in FIG. 1. For this experiment, *Agrobacterium* was injected into somatic tissues. The delivered T-DNA contained a geminiviral replicon (GVR) designed to circularize and replicate within a plant cell. The replicon contained a luciferase reporter (SEQ ID NO:14) for visualization of vector presence, as well as the developmental regulators WUS (SEQ ID NO:6) and STM (SEQ ID NO:7).

In some embodiments, this document provides methods in which plants can be grown to a desired stage in either sterile or non-sterile conditions (e.g., soil). In these methods, one or more developmental regulators can be delivered to select tissues, either by *Agrobacterium* or through ectopic means such as direct injection, electroporation, particle bombardment, biolistics, chemical transfection, viral infection, nanoparticle delivery, or any other suitable means for transient transfection or stable integration (exemplified in FIG. 1). In some cases, pre-existing meristems can be removed prior to delivery of the one or more developmental regulators. The tissues can summarily be induced to produce meristematic tissues containing a GE event of interest. Importantly, this method can obviate the need for sterile tissue culture and advanced equipment, significantly reducing the cost and level of expertise necessary to carry out experiments.

Non-limiting examples of developmental regulators that can be used in the methods provided herein are listed in TABLE 1. As used herein, a "developmental regulator" (DR) is an agent (e.g., a transcription factor, an enzyme, or a hormone) that directs or influences a plant's development, and may guide the differentiation of plant cells, organs, or tissues. For example, a DR can be a transcription factor (e.g., Baby Boom, Irrepressible Variants of Monopteros, Shoot Meristemless, or Wuschel) that can stimulate plant hormone biosynthesis or plant susceptibility to/sensing of cytokinins or other plant hormones that affect plant development and lead to de novo meristem development. In some cases, a DR can lead to increased cytokinin levels. Therefore, a DR also can be a means of increasing one or more cytokinins through ectopic application or through endogenous biogenesis, such as by increasing the expression of one or more enzymes involved in the synthesis of plant hormones. Thus, in some cases, a DR can be an enzyme involved in synthesis of plant hormones, such as Isopentenyl Transferase, which is in the cytokinin biosynthesis pathway. Other examples of enzymes that can lead to increased cytokinin levels and may be useful as DRs include, without limitation, tRNA-isopentenyltransferase, cytochrome P450 monooxygenase, LONELY GUY, adenosine kinase, and adenine phosphoribosyltransferase. A nucleic acid encoding a DR also is considered to be a DR for the purposes of this document, since the nucleic acid can be delivered to plant cells (e.g., in a whole plant or plant part) in order to increase the level of the encoded DR. The DR coding sequence can be operably linked to a promoter (e.g., Nos, 35S, CmYLCV, AtUBQ10, or any other appropriate promoter) that drives expression of the DR in plant cells. Moreover, in some cases, a DR can be a means of increasing expression of genes downstream of the DRs listed in TABLE 1.

Thus, in some embodiments of the methods provided herein, one or more of the DRs listed in TABLE 1 can be delivered to a plant or a plant part.

TABLE 1

| Developmental Regulators | |
|---|---|
| Name | Abbreviation |
| Baby Boom | BBM |
| Isopentenyl Transferase | IPT |
| Irrepressible Variants of Monopteros | MPΔ |
| Shoot Meristemless | STM |
| Wuschel | WUS |
| Leafy Cotyledon 1 | LEC1 |
| Wound Induced Dedifferentiation 1 | WIND1 |

Exemplary sequences for at least some of the above-referenced DRs and promoters are provided in the attached sequence listing. It is to be noted, however, that homologs of these DRs exist in numerous plant species, and the methods provided herein are not limited to use of the listed DRs or to DRs having 100% identity to the provided sequences. In some cases, for example, a DR coding sequence can have at least 80% (e.g., at least 85%, at least 90%, or at least 95%) identity to the WUS sequence set forth in SEQ ID NO:6, the STM sequence set forth in SEQ ID NO:7, the MPΔ sequence set forth in SEQ ID NO:8, the BBM sequence set forth in SEQ ID NO:9 or SEQ ID NO:10, or the IPT sequence set forth in SEQ ID NO:11. Further, in some cases, a DR can have an amino acid sequence that is at least 80% (e.g., at least 85%, at least 90%, or at least 95%) identical to the WUS sequence set forth in SEQ ID NO:118, the STM sequence set forth in SEQ ID NO:119, the MPΔ sequence set forth in SEQ ID NO:120, the BBM sequence set forth in SEQ ID NO:121, or the IPT sequence set forth in SEQ ID NO:122.

The terms "percent identity" or "identity" in the context of two or more nucleic acids or polypeptides refer to two or more sequences that are the same or have a specified percentage of nucleotides or amino acid residues that are the same. The percent identity can be measured using sequence comparison software or algorithms or by visual inspection.

In general, percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. With regard to DR sequences, the total number of aligned nucleotides or amino acids refers to the minimum number of DR nucleotides or amino acids that are necessary to align the second sequence, and does not include alignment (e.g., forced alignment) with non-DR sequences. The total number of aligned nucleotides or amino acids may correspond to the entire DR sequence or may correspond to fragments of a full-length DR sequence.

Sequences can be aligned using the algorithm described by Altschul et al. (*Nucleic Acids Res,* 25:3389-3402, 1997) as incorporated into BLAST® (basic local alignment search tool) programs, available at ncbi.nlm.nih.gov on the World Wide Web. BLAST® searches or alignments can be performed to determine percent sequence identity between a DR nucleic acid or amino acid sequence and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST® programs to calculate the percent identity between a NOTCH sequence and another sequence, the default parameters of the respective programs are used.

This document also provides methods that are referred to herein as "Fast-TrACC" (Treated *Agrobacterium* Co-Culture) methods (exemplified in FIG. 13). Fast-TrACC methods involve the co-culture of germinating seedlings with treated *Agrobacterium* to deliver gene cassettes encoding developmental regulators. The developmental regulators can be broadly delivered to somatic cells in a variety of tissue types within the germinating seedlings. Cells expressing the developmental regulators, and their surrounding neighbors, can then be induced into a meristematic growth pattern that subsequently derives plant tissues of interest (e.g., shoots). In addition to the cassettes encoding the developmental regulators that promote shoot formation, one or more transgenes can be co-delivered. In some cases, the one or more transgenes themselves can create a GE event of interest. Alternatively, the transgene(s) can encode one or more gene editing reagents that can make precise alterations to the developing meristem, or to somatic cells prior to transdifferentiation, to create the desired GE event.

Both types of methods described herein can offer new and broadly applicable approaches to solve current bottlenecks in delivery of GE reagents, as well as the regeneration of tissues carrying GE events of interest. Inherently, in vivo delivery of developmental regulators provides a means to easily deliver reagents to somatic tissues, and also provides positive selection for cells receiving GE reagents. By inducing transdifferentiation of somatic cells and subsequent growth on existing tissues, the significant periods of time that otherwise would be necessary for regeneration and development of whole plant tissues can be avoided. Additionally, as these developmental regulators are evolutionarily conserved, these method are amenable to use across a variety of species. Finally, the methods may avoid regulatory hurdles in the development of agricultural crops, as there is potential for transient delivery of reagents and subsequent recovery of non-transgenic progeny carrying a GE event of interest.

Thus, in some embodiments, this document provides methods for generating plant cells, plant parts, plant tissues, or plants that contain one or more genetic modifications of interest, where the methods can include removing existing meristems from a plant, and then introducing nucleic acids into cells of the remaining plant. The introduced nucleic acid sequences can (1) encode one or more (e.g., two, three, four, or more) developmental regulators such as WUS, BBM, IPT, MPA, and/or STM to induce meristem formation, and (2) edit endogenous sequences within the plant cells, or encode polypeptides that act to edit endogenous sequences within the plant cells, to result in a genetic modification of interest. As a result of introducing these nucleic acid sequences, de novo tissue subsequently derived from the plant can carry the genetic modification of interest. In some cases, the de novo tissue can be meristematic, and capable of deriving new tissue (e.g., branch, flower, or root tissue) carrying the genetic modification(s) of interest.

The nucleic acids provided to the plant (e.g., after removal of existing meristems) can be delivered by any suitable method, including by *Agrobacterium*—in which case the developmental regulator(s) and the editing sequence(s) can be delivered on the same T-DNA or on separate T-DNAs. In some cases, the nucleic acids can be delivered by direct injection, electroporation, biolistics, nanoparticle delivery, particle bombardment, chemical transfection, viral infection, or any other useful method that can result in transient expression or stable integration of the delivered nucleic acid sequences. When two or more developmental regulators are delivered by *Agrobacterium*, they can be present on the same T-DNA or on separate T-DNAs. In some cases, different strains of *Agrobacterium* can be used to deliver the developmental regulator(s) and the gene editing component(s). In addition, it is to be noted that the T-DNA(s) used in the methods provided herein can include any suitable replicon. In some cases, for example, a T-DNA can include a viral replicon (e.g., a geminivirus replicon), which can include any appropriate virus component (e.g., RepA) to enable the generation of meristems.

In some embodiments, this document also provides methods for generating plant cells, plant parts, plant tissues, or plants that contain a genetic modifications of interest, where the methods include using *Agrobacterium* to introduce nucleic acids into germinating seedlings. The nucleic acids can (1) encode one or more (e.g., two, three, four, or more) developmental regulators such as WUS, BBM, IPT, MPΔ, and/or STM to induce meristem formation in the germinating seedling, and (2) edit endogenous sequences within cells of the seedlings, or encode polypeptides that act to edit endogenous sequences within cells of the seedlings, to result in a genetic modification of interest. The methods can further include culturing meristem generated as a result of expression of the developmental regulator(s), to yield modified plant cells, plant tissue, plant parts, and/or plants that contain the genetic modification of interest.

The developmental regulator(s) and the editing nucleic acid(s) can be introduced into the seedling via the same T-DNA or via separate T-DNAs, or even via different strains of *Agrobacterium*. Similarly, when two or more developmental regulators are used, they can be introduced into the seedling via the same T-DNA, or via separate T-DNAs or different strains of *Agrobacterium.*

The methods provided herein can be used with monocotyledonous plants, plant cells, plant tissues, and plant parts (e.g., banana, grasses such as *Brachypodium distachyon*), wheat, oats, barley, maize, *Haynaldia villosa*, millet, palms, orchids, onions, pineapple, rice, rye, sorghum, and sugarcane) and dicotyledonous plants, plant cells, plant tissues, and plant parts (e.g., alfalfa, amaranth, *Arabidopsis*, beans, *Brassica*, carnations, chrysanthemums, citrus plants, coffee, cotton, *eucalyptus*, grape, *impatiens*, melons, peanuts, peas, peppers, *Petunia*, poplars, potatoes, rapeseed, roses, safflower, soybeans, squash, strawberry, sugar beets, sunflower, tobacco, tomatoes, and woody tree species).

In some cases, the methods provided herein can be used to obtain plants, plant tissues, plant parts, and plant cells having a desired trait, such as an agriculturally relevant trait. Agriculturally relevant traits can include, without limitation, herbicide tolerance, resistance to diseases and pests, growth rate, size, shape, color, and flavor of harvested products. For example, the methods provided herein can be used to insert a transgene into the genomic sequence of a plant cell, where expression of the transgene yields the desired trait. In some cases, expression of an inserted transgene can produce a polypeptide that edits the plant DNA. Examples of such polypeptides include targeted rare-cutting endonucleases (e.g., meganucleases, zinc finger nucleases (ZFNs), transcription activator-like effector (TALE) endonucleases, and RNA-guided endonucleases such as clustered regularly-interspaced short palindromic repeats (CRISPR)/CRISPR associated (Cas) endonucleases), as well as targeted cytosine or adenosine deaminases (e.g., apolipoprotein B mRNA editing enzyme, catalytic polypeptide-like (APOBEC)-CRISPR/Cas fusions such as BE3, and ABE). Methods for making and using such targeted DNA modifying enzymes are described elsewhere. See, e.g., Sander et al., *Nature Methods,* 8:67-69, 2011; Jacoby et al., *Nucl. Acids Res.,* 10.1093/nar/gkr1303, 2012); Christian et al., Genetics, 186: 757-761, 2010; U.S. Publication No. 2011/0145940; Cong et al., Science 339:819-823, 2013; and Mali et al., *Science* 339:823-826, 2013. For example, CRISPR/Cas systems use RNA base pairing to direct DNA or RNA cleavage by a Cas endonuclease. CRISPR RNA (crRNA) and transactivating crRNA (tracrRNA) sequences direct the Cas enzyme to a specific target DNA sequence (Makarova et al., *Nat Rev Microbiol,* 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas9 cleavage activity (Jinek et al., *Science,* 337(6096):816-821, 2012).

In some embodiments, a repair template also can be delivered to plant cells along with a targeted endonuclease. When the endonuclease cleaves the plant cell DNA, the repair template can become integrated into the plant cell's genomic DNA, thus introducing a specific modification into the plant genome.

The methods provided herein also can include culturing the meristem induced by the developmental regulator(s) to give rise to a plant. In some cases, before a plant is generated from the new meristem, de novo derived tissue resulting from expression of the developmental regulator(s) can be assessed to determine whether it includes the genetic modification of interest. For example, DNA from newly derived tissue can be isolated and assessed by restriction digest, hybridization methods (e.g., Southern blotting), or sequencing to determine whether a genetic modification has occurred at the target site. In some embodiments, the expression of a reporter delivered with the developmental regulator(s) and the editing sequence(s) can first be detected, to identify tissues that are likely to carry the genetic modification.

The invention will be further described in the following examples, which do not limit the scope of the invention described in the claims.

EXAMPLES

Example 1—Vectors for Expressing Developmental Regulators

To facilitate the expression of developmental regulators in plants, T-DNA vectors encoding different arrangements of developmental regulators were generated (SEQ ID NOS:6-11. These T-DNA vectors were designed to have two developmental regulators combined on one T-DNA (SEQ ID NOS:26-32) or to contain a single developmental regulator (SEQ ID NOS:33-37). Construct descriptions are provided in TABLE 2. Developmental regulators were expressed using the 35S (SEQ ID NO:1), CmYLCV (SEQ ID NO:3), AtUBQ10 (SEQ ID NO:2), or Nos (SEQ ID NO:5) promoter. For Fast-TrACC experiments, these vectors often coexpressed the RNA guided endonuclease Cas9 (SEQ ID NO:24) driven by the 35S promoter. For many of the experiments, a gRNA was expressed under the control of an AtU6 promoter (SEQ ID NO:4) targeting both of the duplicated PDS1 homologs (Niben101Scf14708g00023.1, SEQ ID NO:16; and Niben101Scf01283g02002.1, SEQ ID NO:17) in the *N. benthamiana* genome. A luciferase reporter gene (SEQ ID NO:14) driven by either the 35S or the CmYLCV promoter was used as a visual confirmation of construct delivery. These constructs were cloned into the T-DNA backbone of pTRANS_201 (SEQ ID NO:18) or pTRANS_221 (SEQ ID NO:19) as described elsewhere (Cermak et al., *Plant Cell* 29(6):1196-1217, 2017). This *Agrobacterium* vector was designed to deliver a T-DNA containing a modified bean yellow dwarf virus (BeYDV) capable of circularization and replication upon delivery and expression of the encoded replication protein (Rep; SEQ ID NO:25) in vivo. Replication of the replicon can enable an increased copy number of the vector, and consequently high levels of gene expression. Additionally, this vector has the potential to replicate regardless of whether it integrates into the genome, enabling transient high copy delivery of vector constructs.

| Construct | Promoter: Reporter | Promoter: RNA | Promoter: $1^{st}$ DR | Promoter: $2^{nd}$ DR | Base Vector | SEQ ID: |
|---|---|---|---|---|---|---|
| pRN114 | 35S:Luc+ | — | Nos:WUS | CmCLYV:STM | T-DNA w/ BeYDV Replicon, Kan Resistance | 26 |
| pRN119 | CmYLCV:Luc+ | — | Nos:WUS | 35S:STM | T-DNA w/ BeYDV Replicon, Kan Resistance | 27 |
| pRN120 | CmYLCV:Luc+ | — | Nos:WUS | AtUBQ10:STM | T-DNA w/ BeYDV Replicon, Kan Resistance | 28 |
| pRN227 | 35S:Cas9 | AtU6: NbPDS gRNA1 | Nos:WUS | CmCLYV:STM | T-DNA w/ BeYDV Replicon, Kan Resistance | 29 |
| pMM113 | 35S:Luc+ | AtU6: NbPDS gRNA1 | Nos:WUS | CmCLYV:STM | T-DNA w/ BeYDV Replicon, Kan Resistance | 30 |
| pMM114 | CmYLCV:Luc+ | AtU6: NbPDS gRNA1 | Nos:WUS | 35S:IPT | T-DNA w/ BeYDV Replicon, Kan Resistance | 31 |
| pMM115 | CmYLCV:Luc+ | AtU6: NbPDS gRNA1 | Nos:WUS | 35S:MPΔ | T-DNA w/ BeYDV Replicon, Kan Resistance | 32 |
| pMM131 | 35S:Luc+ | AtU6: NbPDS gRNA1 | — | CmCLYV:STM | T-DNA w/ BeYDV Replicon | 33 |
| pMM134 | CmYLCV:Luc+ | AtU6: NbPDS gRNA1 | 35S:IPT | — | T-DNA w/ BeYDV Replicon | 34 |
| pMM135 | CmYLCV:Luc+ | AtU6: NbPDS gRNA1 | Nos:WUS | — | T-DNA w/ BeYDV Replicon | 35 |
| pMM136 | CmYLCV:Luc+ | AtU6: NbPDS gRNA1 | — | 35S:MPΔ | T-DNA w/ BeYDV Replicon | 36 |
| pMM146 | CmYLCV:Luc+ | AtU6: NbPDS gRNA1 | — | Ubi1:BBM | T-DNA w/ BeYDV Replicon | 37 |
| pMM230 | 35S:AtCas9 | AtU6:gRNA (VvMLO) | Nos:ZmWUS2 | AtUbi10:LUC | pCambia T-DNA w/ BeYDV Replicon, Kan Resisance | 88 |
| pMM231 | 35S:AtCas9 | AtU6:gRNA (VvMLO) | 35S:IPT | AtUbi10:LUC | pCambia T-DNA w/ BeYDV Replicon, Kan Resisance | 89 |
| pMM232 | 35S:AtCas9 | AtU6:gRNA (VvMLO) | AtUbi10:LUC | 35S:MPΔ | pCambia T-DNA w/ BeYDV Replicon, Kan Resisance | 90 |
| pMM233 | 35S:AtCas9 | AtU6:gRNA (VvMLO) | AtUbi10:LUC | 35S:STM | pCambia T-DNA w/ BeYDV Replicon, Kan Resisance | 91 |
| pMM234 | 35S:AtCas9 | AtU6:gRNA (VvMLO) | AtUbi10:LUC | AtUbi10:BBM | pCambia T-DNA w/ BeYDV Replicon, Kan Resisance | 92 |
| pMM235 | 35S:AtCas9 | AtU6:gRNA (VvMLO) | AtUbi10:LUC | — | pCambia T-DNA w/ BeYDV Replicon, Kan Resisance | 93 |
| pMVK057 | — | AtUbi10:Luc | Nos:ZmWUS2 | 35S:IPT | pCambia T-DNA w/ BeYDV Replicon, Kan Resisance | 94 |
| pMVK058 | — | AtUbi10:Luc | Nos:ZmWUS2 | — | pCambia T-DNA w/ BeYDV Replicon, Kan Resisance | 95 |

| Construct | Promoter: Reporter | Promoter: RNA | Promoter: 1st DR | Promoter: 2nd DR | Base Vector | SEQ ID: |
|---|---|---|---|---|---|---|
| pMVK059 | — | AtUbi10:Luc | — | 35S:IPT | pCambia T-DNA w/ BeYDV Replicon, Kan Resisance | 96 |
| pMVK060 | — | AtUbi10:Luc | — | — | pCambia T-DNA w/ BeYDV Replicon, Kan Resisance | 97 |

Example 2—Generation of Transgenic Branches from Direct Injection

Plant cells are inherently totipotent and can be transdifferentiated into other cell types. Thus, studies were conducted to determine whether de novo meristems could be induced in vivo by ectopically expressing DRs in plant somatic cells, and by co-delivering gene editing reagents with the DRs, whether it might be possible to create edited meristems that ultimately produce seed and transmit induced genetic changes to the next generation.

Young (10-12 week-old) transgenic *N. benthamiana* plants that constitutively expressed Cas9 were pruned to remove all visibly discernible shoot meristems (FIG. 1). *Agrobacterium* strains with vectors encoding various DR combinations and a luciferase reporter were grown overnight and resuspended in infiltration buffer (150 µM acetosyringone, 10 mM MgCl$_2$, pH 5.6) to an OD600 of 0.2. Selected meristematic tissues (shoot apical and axillary) were removed from plants using a razor blade. *Agrobacterium* cultures were injected into wound sites created by the removal of meristematic tissue, and also into other tissues such as nodes and internodes. Plants were monitored for 2 weeks to remove residual unerupted premature axillary meristems, as well as those that spontaneously developed from the stem base. After 3-5 weeks, various tissue types developed. Some shoots appeared phenotypically normal (FIGS. 2A and 3F), whereas others displayed abnormal and/or adverse phenotypes, such as an abundance of leaves or other developmental abnormalities, likely due to persistent expression of the DRs (FIGS. 2B-2D and 3C).

To demonstrate that transgenic tissues were generated de novo from injected tissues, samples were visualized for luciferase activity. Tissues were isolated from newly formed shoots arising from *Agrobacterium* injection sites. To visualize luciferase expression, tissues were immersed in water containing 5 mM luciferin for 5 minutes prior to bright field imaging or imaging in the dark using a CCD camera. Some tissues demonstrated luciferase expression, indicating that the newly formed tissues were derived from cells that had received the T-DNA from *Agrobacterium* (FIGS. 2E, and 2F, 3A, 3B, 3D, and 3E). Thus, direct injection of *Agrobacterium* strains delivering DRs was able to induce transgenic shoots.

In subsequent studies, transgenic shoots are allowed to develop and produce flowers. At some frequency, transgenes are transmitted to progeny, thereby creating stably transgenic plants.

Example 3—Generation of Tissues with Gene Edits from Direct Injection

Figure 3G:
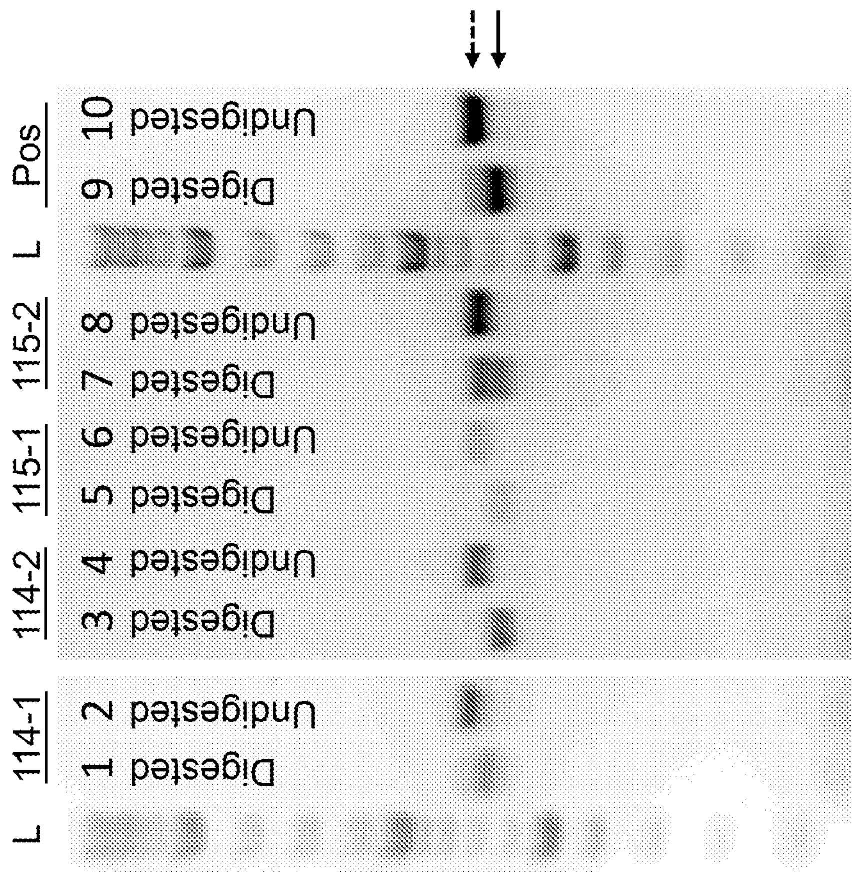

The T-DNA delivered to the transgenic Cas9 plants also expressed a gRNA targeting *N. benthamiana* phytoene desaturase (PDS) genes. There are two PDS homologs in *N. benthamiana* (NbPDS1; Niben101Scf14708g00023.1 and NbPDS2; Niben101Scf01283g02002.1). The gRNA was selected to target conserved sequences in both genes. In the absence of PDS, photobleaching occurs due to lack of photoprotective carotenoids, giving rise to a readily discernible phenotype (Qin et al., Cell Res 17:471-482, 2007). A subset of the shoots that emerged in the experiments described in Example 2 were white, suggesting biallelic inactivation of the two PDS homologs (FIGS. 4A-4C). To assess gene editing, genomic DNA was isolated from white tissue samples, amplified by PCR, and analyzed for NHEJ induced mutations at the gRNA target sites. Primers were used to selectively amplify either gene: TGGGAACTGAAAGTCAAGATGGTC (oCS1200; SEQ ID NO:20) and ACAATAAATGGGATGGGCCTGG (oCS1202; SEQ ID NO:21) for Niben101Scf14708g00023.1, and TGGGAACTGAAAGTCAAGATGTTT (oMM299; SEQ ID NO:22) and CAAAAGCTAGCTTATGAGGTGAAGC (oMM300; SEQ ID NO:23) for Niben101Scf01283g02002.1). Incomplete digestion of PCR amplicons by the restriction enzyme NcoI indicated that mutations had occurred within the restriction recognition site as a result of gRNA-directed cutting and error prone NHEJ mediated repair (FIGS. 3G, 4D, and 4E). These results indicated that de novo derived tissues received the expression cassettes containing the developmental regulators and gene editing reagents.

To confirm the creation of non-chimeric, genetically modified de novo tissue, genomic DNA was isolated from tissues exhibiting the PDS phenotype. NGS primers specific to the Scf14708g00023.1 homolog (NbPDS1, SEQ ID NOS: 78-87) were used to amplify the locus in the genomic DNA sample, and the resulting amplicon was submitted for Illumina sequencing. The results demonstrated a mutation profile consistent with a single editing event at the target locus as compared to negative controls (FIGS. 4F and 4G). Thus, the activity of developmental regulators strongly increased the potential for deriving editing events in de novo meristems.

Example 4—Vertical Transmission of GE from De Novo Derived Tissues

It was desired to determine whether GE in induced shoots could transmit the edits to the next generation. However, none of the shoots with developmental abnormalities or the PDS phenotype set seed. Because all shoots were molecularly surveyed for mutations at the PDS targets, however, one green shoot that produced viable seed and had a 3 bp deletion in one PDS allele was identified (FIG. 5A, shaded row; FIG. 5B). To determine if additional gene edited shoots could be obtained, a second experiment was performed in which WUS and IPT were delivered on the same T-DNA or on separate T-DNAs (again, a mixed infection with separate strains). Rather than monitoring the total number of shoots produced, the number of shoots that emerged from each injection site was monitored. Previous experiments had suggested that initial shoots were often not transgenic and, as such, shoots appearing in the first 20 days were removed and discarded. Abundant shoots emerged regardless of whether the developmental regulators were on the same T-DNA or on T-DNAs in different strains (FIG. 6). When on the same T-DNA, for example, 46 shoots were recovered from 76 injection sites. Of these, 16 shoots had a distorted phenotype and four were white or had white sectors, indicative of transgene overexpression and PDS targeting, respectively. In contrast, the negative control produced no white shoots, although some shoots were initially distorted due to trimming but then progressed with a WT growth pattern.

One shoot emerged that was chimeric for white and green tissue, but otherwise was phenotypically normal and non-bioluminescent (FIG. 7). From the white tissue, a flower was produced that set seed, which produced completely white seedlings when germinated (FIGS. 8A and 8B). The seedlings had biallelic mutations in both PDS homologs, and the frameshift mutations transmitted to the progeny were present in the parental white tissue. Neither the parental tissues nor the seedlings were transgenic, as indicated by the lack of luciferase expression and the inability to detect the transgene cassette by PCR (FIG. 9). Seed and tissue also were harvested from the associated green chimeric sector. Germinated seed segregated in an approximately 3:1 ratio for the PDS phenotype (FIGS. 10A and 10B). The mutations in the seedlings were the same as those observed in the parental green tissue, but they were distinct from those observed in white sectors. The green shoot that was produced in the initial experiment also was shown to transmit mutations to progeny (FIG. 11). Thus, in three independent studies, non-transgenic tissues were produced in *N. benthamiana* with multiple targeted mutations and within a single generation, without the use of plant selection. Importantly, gene edited plants that lacked a transgene were recovered, obviating the need to segregate away the transgene in subsequent generations.

Example 5—Generation of Transgenic Tissues in Grape and Potato after Direct Injection of Developmental Regulators To determine if de novo meristems could be induced on agronomically important species, additional experiments were performed in *Vitis vinifera* (grape) and *Solanum tuberosum* (potato). Cuttings from asexually propagated potato (FIGS. 12A and 12D) and grape (FIG. 12H) were injected in sterile culture jars with *Agrobacterium* strains delivering individual or a combination of DRs. Vectors in both experiments contained a luciferase reporter. For both grape and potato, a subset of plants produced bioluminescent shoots (FIGS. 12B, 12C, 12E, 12F, 12G, and 12I). In grape, the shoots were produced after combined delivery of vectors expressing WUS, IPT, STM, MPΔ, and BBM (pMM230 through 234), as well as after individual delivery of *Agrobacterium* expressing IPT (pMM231). In potato, shoots were induced after delivery of WUS and IPT (pMKV057) or IPT alone (pMVK059). These results demonstrated that DRs can induce transgenic shoots on diverse dicot species.

In further studies, transgenic shoots are created in potato, grape, or other species that express Cas9 and a gRNA targeting an endogenous gene. Cas9 and the gRNA create mutations in somatic cells, which are induced by the DRs to form meristems and shoots. Some shoots have edited genes that produce flowers and transmit gene edits to the next generation. Other shoots have edited genes but lack the transgene and produce edited, transgene-free progeny (as described in Example 4 for *N. benthamiana*, for example).

Example 6—Generation of Growths from Sites of Delivery after Fast-TrACC

Examples 1-5 describe studies using methods to generate de novo meristems in whole plants that either carry transgenes or have GE events. This Example and the following Examples describe studies showing that de novo meristem-like tissue can be generated out of somatic tissue via Fast-TrACC delivery of developmental regulators (FIG. 13).

Fast-TrACC involves treating *A. tumefaciens* cultures (GV3101 was used in the studies described herein, but any other suitable strain can be used) for three days prior to a two day co-culture with newly germinated seedlings. The first step is to grow the cultures overnight (8-12 hours) at 28° C. Next, cells are harvested by centrifugation and re-suspended to an $OD_{600}$ of 0.3 in AB:MES salts (17.2 mM $K_2HPO_4$, 8.3 mM $NaH_2PO_4$, 18.7 mM $NH_4Cl$, 2 mM KCl, 1.25 mM $MgSO_4$, 100 μM CaCl2, 10 μM $FeSO_4$, 50 mM MES, 2% glucose (w/v), 200 μM acetosyringone, pH 5.5) (Wu et al., Plant Methods 10:19, 2014), with the intent to increase the expression of vir genes, and then grown overnight. The culture is again centrifuged and resuspended to $OD_{600}$ within the range of 0.10 to 0.18 in a 50:50 (v/v) mix of AB:MES salts and ½ MS liquid plant growth medium (½ MS salt supplemented with 0.5% sucrose (w/v), pH 5.5). The *A. tumefaciens* culture is now ready for incubating with seedlings.

Seeds are sterilized using 70% ethanol for 1 minute and 50% bleach (v/v) for 5 minutes. The seeds are then rinsed 5 times with sterile water, and transferred to 6-well plates (~5 seeds per well in 2 mL ½ MS), where they are subsequently germinated and maintained in growth chambers for 2-3 days at 24° C. under a 16 hour/8 hour light/dark cycle. *A. tumefaciens* is added and the co-culture is incubated for two days before the seedlings are washed free of *A. tumefaciens* using sterile water. The washed seedlings are returned to liquid ½ MS containing 100 μM of antibiotic timentin to effectively counter-select against residual *A. tumefaciens.*

The Fast-TrACC method was used to deliver *Agrobacterium tumefaciens* T-DNA constructs (SEQ ID NOS:26 and 27) encoding developmental regulators into the cotyledons of *N. benthamiana* seedlings. These constructs contained a luciferase reporter (CmYLCV:Luc, SEQ ID NO:3:SEQ ID NO:14) and the developmental regulators WUS (Nos:WUS, SEQ ID NO:5:SEQ ID NO:6) and STM (SEQ ID NO:7). STM was expressed using three different promoters (35S, SEQ ID NO:1; AtUBQ10, SEQ ID NO:2; and CmYLCV, SEQ ID NO:3) to determine if one had optimal meristem patterning potential. All three promoters formed growths but at slightly different frequencies.

Using the luciferase reporter expression as a proxy for T-DNA delivery, sectors of the plant that received the developmental regulators were identified. From regions exhibiting high levels of localized luciferase expression (FIGS. 14A and 14B, circled) developmental regulator-derived growths were formed. The derived growths appeared to be of two types: one subset included globular callus-like growths (FIG. 14C, arrow), while others formed into meristem-like structures (FIG. 14D, circled). The globular growths continued as undifferentiated tissue, but the meristem-like growths formed structures such as leaflets (FIG. 14D, arrows) that indicated differentiation of the tissue. Observing de novo formation of meristem-like tissues suggested that developmental regulators can be implemented to generate new plant tissues out of entirely separate tissue types, which allows for the potential to be used for the generation of whole plants.

Example 7—Generation of Transgenic Plants from Fast-TrACC Treatment

Figure 15D:
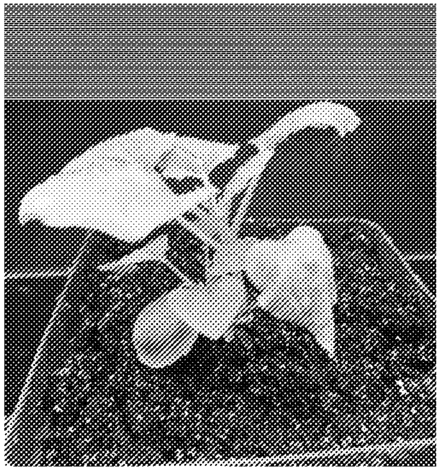
Figure 15E:
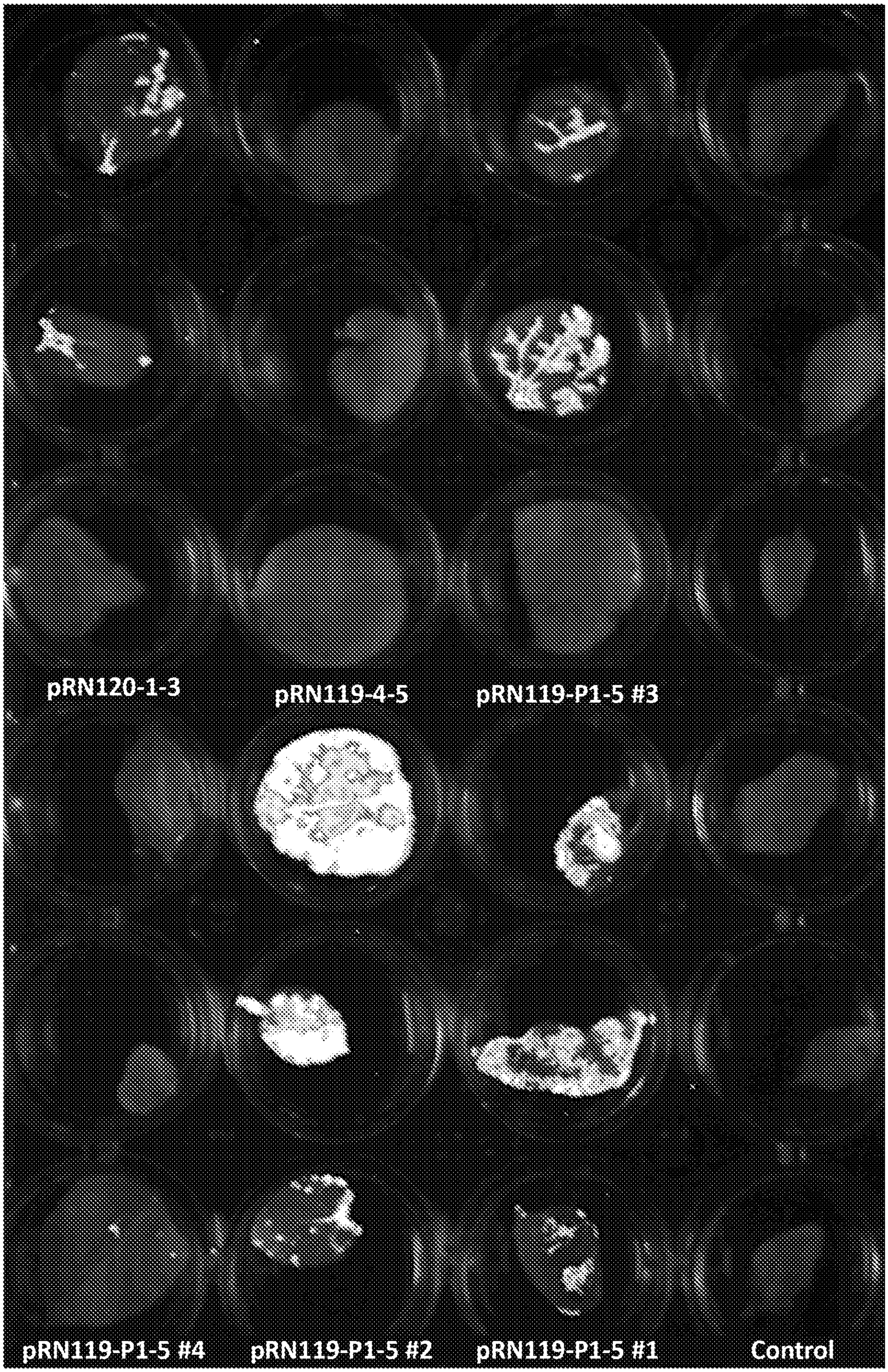

To determine the ability to produce plants from de novo growths, *N. benthamiana* seedlings with meristem-like growths were selected as candidates for the generation of transgenic plants. The meristem-like growths were derived using the developmental regulator combination WUS and STM. Efforts were made to ensure that the newly formed meristem-like tissue could be propagated. The meristem-like tissues were grown for about 3 weeks, until they started to form secondary leaves (FIGS. 15A and 15B). The shoot-like growths were then transferred to auxin-rich media to establish a root network. Once roots formed (about 1.5 weeks later), the plantlets were transferred to soil (FIGS. 15C and 15D). Among the derived plants, some looked essentially wild type (FIG. 15D), some exhibited excessive shooting and slight leaf abnormalities (FIG. 15C), and others were completely disfigured (not shown). To assess transgenesis, leaf punches were taken from each recovered plant and tested for luciferase expression (FIG. 15E). Varying levels of luciferase expression were observed, ranging from completely luciferase positive to specific sectoring of expression, to overall absence of luciferase.

One purpose of generating transgenic plants, whether of mosaic or uniform genetic constitution, was to produce flowers. These flowers can be derived from the same tissues that lead to the formation of luciferase positive leaves, implying that at some frequency, the flowers have the T-DNA and therefore will be transgenic themselves. The transgenic flowers will produce seed, some of which will be transgenic. Seeds from transgene-positive plants can be collected and tested for luciferase expression (i.e., presence of the transgene) and for the presence of GE events. Demonstration of heritable transmission of transgenes is described below in Example 10; demonstration of heritable transmission of GE events is described below in Example 12.

Example 8—Confirmation of Gene Editing in Developmental Regulator-Derived Growths To demonstrate that GE events can occur in de novo growths, gene editing reagents were combined with developmental regulators and delivered to seedlings. The construct that was used (SEQ ID NO:29) contained 35S:Cas9 (SEQ ID NO:1:SEQ ID NO:24), AtU6:gRNA (SEQ ID NO:4:SEQ ID NO:12), Nos:WUS (SEQ ID NO:5:SEQ ID NO:6), and CmYLCV:STM (SEQ ID NO:3:SEQ ID NO:7). Limits on construct size prevented the inclusion of luciferase as a delivery reporter. Seedlings were screened for production of growths. Out of twenty-four seedlings, five seedlings exhibited growth formations (FIG. 16A) suitable to test for edits.

The growths were excised and DNA was isolated from each. From the isolated DNA, the target region in NbPDS1 was PCR amplified. The gRNA used in these studies targeted a locus with a NcoI restriction site that, when edited, will not allow for digestion in a RFLP assay. Four of the five tested samples contained the “protected” band indicative of editing (FIG. 16B). These same samples contained the T-DNA, as indicated by the presence of Rep (FIG. 16C). The samples were then submitted for NGS. The resulting sequences (FIGS. 16D-16H) indicated that the tissues were considerably edited, with as high as 42% of reads from a given growth being edited. This observation indicated that the delivery of gene editing reagents with developmental regulators allowed for editing within the tissues generated by developmental regulators.

Example 9—Generation of Edited Plants after Fast-TrACC Treatment

To illustrate the capability to regenerate edited plants in a fashion similar to the generation of transgenic plants, whole plants were derived from edited growths. The same construct (SEQ ID NO:29) used to generate edits within undifferentiated growths was used to promote the formation of plantlets with edits. A new set of growths were developed on *N. benthamiana* cotyledons that then formed meristem-like growths. Once the growths established a shoot-like structure, they were transferred to rooting medium to initiate a root network. Full plants were considered formed once the root system was established (FIGS. 17A-17C), and the plants were subsequently moved to soil.

Leaf tissue samples were taken from the generated plants and submitted for NGS. The sequencing results from individual tissue samples resulted in a small proportion of edited reads (FIGS. 17D-17F), revealing that the generated plantlets were chimeric but did contain edits derived from the gene editing reagents. Since the plants were chimeric, a variety of different mutations were isolated from the NGS reads (FIGS. 17G-17I). The most common mutations were single base insertions or deletions. Reads that were likely due to aberrant mutations from PCR amplification (denoted with asterisks) were also isolated, indicating that the overall editing frequencies highlighted (FIGS. 17D-17F) were over estimates. The amount of mosaicism differed between plants, with the presence of the most common two edits ranging from 9% (FIG. 17H) to as low as 2% (FIG. 17G).

Ideally, these chimeric plants will contain mutations within a floral meristem, which would cause the flower to produce edited seeds at some frequency. As described below in Example 12, plants are grown and seeds are collected and tested for gene editing. The isolation of edited plants derived from these seeds demonstrates that edited plants can be obtained in a single generation through the creation of developmental regulator-derived plants.

Example 10—Vertical Transmission of Transgenes from Fast-TrACC Derived Plants The ultimate goal for DR-based plant generation is to create genetic changes that can be transmitted to subsequent generations. Several of the DR-derived *N. benthamiana* plants grew seed-bearing flowers. These plants were created using the constructs pRN114, pRN119 and pRN120 (SEQ ID NOS:26-28) and exhibited different levels of luciferase expression (FIG. 15E). Seeds from the most luciferase-positive plant, RN119-P1-5-2 (FIG. 18A), were collected and tested for luminescence (FIG. 18B). A large proportion of the seeds from this plant were positive for luciferase (FIG. 18C). The inheritance pattern of luciferase (~75% of seedlings) was in line with the expected Mendelian inheritance pattern of a hemizygous transgene insertion (FIG. 18D). Not all plants tested had a luciferase-positive signal in their derived seeds (FIG. 18D, RN119-4-5), which could be due to mosaicism in the parent, segregation of the transgene, or silencing of the T-DNA. It also is possible that transient delivery of the developmental regulators primed a microenvironment that promoted meristem formation without transgene integration. Regardless, the observation that transgenes could be transmitted to the next generation demonstrated that a heritable transgenic event was created through de novo induction of a meristem.

Example 11—Optimizing Combinations of Developmental Regulators for Meristem Induction and the Recovery of Plants Fast-TrACC was used to test different combinations of developmental regulators in order to identify those that could best induce growths that give rise to full plants. Separate *A. tumefaciens* strains, each carrying expression cassettes for a unique DR, were pooled for seedling co-culture. Twelve combinations of DRs were tested, and five of those combinations resulted in growths from which plants could be derived (FIGS. 19A and 19B). Two combinations, WUS & STM and WUS & IPT, produced up to five times as many shoot-like growths and roughly four times more full plants than the other treatments. Thus, Fast-TrACC can be used to determine the best combination of developmental regulators for meristem induction in a given plant species.

Example 12—Vertical Transmission of GE Events from Fast-TrACC Derived Plants Studies were conducted to determine if Fast-TrACC could be used to generate meristems with gene edits and subsequently plants that transmit mutations to progeny. In the experiment described in Example 11, transgenic *N. benthamiana* seedlings constitutively expressing Cas9 were treated with Fast-TrACC. In addition to a DR, the T-DNAs carried a cassette that expressed a gRNA targeting NbPDS1 and NbPDS2. Biallelic knockouts of both PDS homologs are expected to result in a white phenotype due to chlorophyll photobleaching (Qin et al., supra). About 15% of the generated shoots showed evidence of photobleaching, but these shoots did not form full plants; they were likely compromised by lack of chlorophyll (FIG. 20). Nonetheless, white shoots were evaluated molecularly and found to have biallelic mutations in both PDS homologs. Thus Fast-TrACC can generate meristems with gene edits.

Of 27 total plants recovered in the experiment described in Example 11, five phenotypically normal green plants were found to show considerable amounts of editing in somatic cells (FIG. 19A). For one of these plants, seed collected from two flowers (F4 and F6) produced green and white seedlings (FIG. 21A). gRNA target sites for both PDS homologs were assessed molecularly for two white seedlings derived from each flower, and mutations were observed in both alleles of each PDS gene (FIG. 21B). Based on this data, it was concluded that co-delivery of DRs and gene editing reagents can produce shoots with mutations, and these shoots can transmit mutations to the next generation.

Example 13—Generation of Transgenic Tomato Shoots Using Fast-TrACC

As DRs are evolutionarily conserved, studies were conducted to determine whether the approach for seedling transformation would be applicable to other plant species. Combinations of DRs that generated de novo meristems on *N. benthamiana* seedlings were therefore tested to determine whether they could induce shoots on other dicots, such as tomato. In particular, Fast-TrACC was used to deliver three combinations of developmental regulators (Nos:WUS&35S:STM, Nos:WUS&CmYLCV:STM, and Nos:WUS&35S:IPT) to tomato seedlings. For both combinations of WUS & STM, no shoot-like growths formed (FIGS. 22A and 22C). In contrast, WUS & IPT promoted shoot-like growths (FIGS. 22A and 22C), which ultimately formed fully rooted plants (FIG. 22B).

Next, WUS and IPT were delivered to tomato seedlings on either a single vector (WUS/IPT) or on separate vectors in two different *Agrobacterium* strains (WUS&IPT). Both WUS/IPT and WUS&IPT showed an increase in the frequency of average growths per plant over the background level of callus-like growths that developed on plants that did not receive developmental regulators (FIG. 22D). From the WUS and IPT derived growths, shoot-like growths formed that were luciferase positive (FIGS. 22E, 22F, and 22G). These structures progressed to form shoots (FIG. 22H), which were excised and assessed for luminescence (FIG. 22I). Four out of 15 shoots showed evidence of luminescence (FIG. 22J). Thus FAST-TrACC can be used to determine the optimal combination of developmental regulators for meristem induction in other plant species, which indicates that Fast-TrACC has utility outside of the *N. benthamiana* model to induce transgenic shoots.

In subsequent experiments, transgenic shoots are placed on root-inducing medium to promote root formation. Resulting plantlets are transferred to soil where they continue to grow, flower, and produce fruit and seed. Progeny are assessed to for transmission of the transgene, as demonstrated in Example 10. Gene edited tomato plants are generated and assessed through an approach similar to that described in detail in Example 12 for *N. benthamiana.*

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating plant tissue comprising one or more genetic modifications of interest, the method comprising:

(a) introducing into plant cells (i) a nucleic acid construct encoding one or more developmental regulators that, when expressed in the plant cells, induce meristem formation from the plant cells, and (ii) a nucleic acid construct comprising one or more sequences that, when expressed, edit the plant cell DNA to introduce one or more genetic modifications of interest;

(b) incubating the plant cells such that the one or more developmental regulators and the one or more sequences that edit the plant cell DNA are expressed;

(c) identifying plant cells having the one or more genetic modifications of interest; and (d) deriving de novo tissue from the plant cells identified as having the one or more genetic modifications of interest.

2. The method of claim 1, wherein the one or more developmental regulators comprise one or more of Baby Boom, Isopentenyl Transferase, Irrepressible Variants of Monopteros, Shoot Meristemless, and Wuschel.

3. The method of claim 1, wherein the introducing is by *Agrobacterium.*

4. The method of claim 1, comprising introducing a nucleic acid construct encoding two or more developmental regulators into the plant cells by *Agrobacterium.*

5. The method of claim 1, wherein the plant cells into which the nucleic acid constructs are introduced are within a differentiated tissue.

6. The method of claim 1, wherein the plant cells into which the nucleic acid constructs are introduced are within an undifferentiated tissue.

7. The method of claim 1, wherein the plant cells into which the nucleic acid constructs are introduced are within a whole plant.

8. The method of claim 1, wherein the plant cells into which the nucleic acid constructs are introduced are within a germinating seedling.

9. The method of claim 1, wherein the plant cells into which the nucleic acid constructs are introduced are within a plant part.

10. The method of claim 1, wherein the one or more sequences that edit the plant cell DNA comprise a nucleotide sequence encoding a targeted endonuclease, and wherein the targeted endonuclease comprises a meganuclease, zinc finger nuclease, transcription activator-like effector nuclease, or Clustered Regularly-Interspaced Short Palindromic Repeats-associated nuclease that, when expressed, edits the plant DNA.

11. The method of claim 1, wherein the one or more sequences that edit the plant cell DNA comprise a nucleotide sequence encoding a targeted enzyme that, when expressed, edits plant DNA, and wherein the targeted enzyme is a cytosine deaminase or an adenosine deaminase.

12. The method of claim 1, wherein the one or more sequences that edit the plant cell DNA comprise (1) a nucleotide sequence encoding a targeted endonuclease and (2) a repair template.

13. The method of claim 1, wherein the de novo tissue is meristematic and is capable of deriving new tissue carrying the one or more genetic modifications of interest.

14. The method of claim 1, comprising:

using *Agrobacterium*, introducing into cells of a germinating seedling or a portion thereof the nucleic acid construct encoding the one or more developmental regulators, wherein expression of the one or more developmental regulators induces meristem formation in the germinating seedling or portion thereof;

introducing into the cells, via the *Agrobacterium*, the nucleic acid construct comprising the one or more sequences that, when expressed, edit the plant cell DNA to introduce the one or more genetic modifications of interest; and culturing the meristem induced by the one or more developmental regulators, to obtain modified plant tissue comprising the one or more genetic modifications of interest.

15. The method of claim 14, wherein the nucleic acid construct encoding one or more developmental regulators encodes two or more developmental regulators.

16. The method of claim 14, wherein the one or more sequences that edit the plant cell DNA comprise a nucleotide sequence encoding a targeted endonuclease, and wherein the targeted endonuclease comprises a meganuclease, zinc finger nuclease, transcription activator-like effector nuclease, or Clustered Regularly-Interspaced Short Palindromic Repeats-associated nuclease that, when expressed, edits the plant cell DNA.

17. The method of claim 14, wherein the one or more sequences that edit the plant cell DNA comprise a nucleotide sequence encoding a targeted enzyme that, when expressed, edits plant DNA, and wherein the targeted enzyme is a cytosine deaminase or an adenosine deaminase.

18. The method of claim 14, wherein the one or more sequences that edit the plant cell DNA comprise (1) a nucleotide sequence encoding a targeted endonuclease and (2) a repair template.

19. The method of claim 14, further comprising assaying the meristem induced by the one or more developmental regulators for the one or more genetic modifications of interest, and subsequently generating a whole plant from the meristem induced by the one or more developmental regulators.

20. The method of claim 14, comprising placing the meristem induced by the one or more developmental regulators directly into culture and inducing the meristem in culture to form a plant.

* * * * *